US012678502B2

(12) United States Patent (10) Patent No.: US 12,678,502 B2
Brew et al. (45) Date of Patent: *Jul. 14, 2026

(54) COMPOSITIONS HAVING IMPROVED BIOAVAILABILITY OF THERAPEUTICS

(71) Applicant: TRx Biosciences Limited, London (GB)

(72) Inventors: John Brew, St. Albans (GB); Daniel Gooding, Cambridge (GB); Robin M. Bannister, Saffron Walden (GB)

(73) Assignee: TRx Biosciences Limited, London (GB)

( * ) Notice: Subject to any disclaimer, the term of this patent is extended or adjusted under 35 U.S.C. 154(b) by 1082 days.

This patent is subject to a terminal disclaimer.

(21) Appl. No.: 17/656,702

(22) Filed: Mar. 28, 2022

(65) Prior Publication Data

US 2022/0305125 A1 Sep. 29, 2022

Related U.S. Application Data

(60) Provisional application No. 63/269,330, filed on Mar. 14, 2022, provisional application No. 63/166,995, filed on Mar. 27, 2021.

(51) Int. Cl.

| | |
|---|---|
| *A61K 47/14* | (2017.01) |
| *A61K 31/00* | (2006.01) |
| *A61K 31/12* | (2006.01) |
| *A61K 31/192* | (2006.01) |
| *A61K 31/196* | (2006.01) |
| *A61K 31/216* | (2006.01) |
| *A61K 31/4025* | (2006.01) |
| *A61K 31/4184* | (2006.01) |
| *A61K 31/436* | (2006.01) |
| *A61K 31/44* | (2006.01) |
| *A61K 31/4418* | (2006.01) |
| *A61K 31/4453* | (2006.01) |
| *A61K 31/496* | (2006.01) |
| *A61K 31/502* | (2006.01) |
| *A61K 31/5377* | (2006.01) |
| *A61K 31/553* | (2006.01) |
| *A61K 31/58* | (2006.01) |
| *A61K 31/7135* | (2006.01) |
| *A61K 38/12* | (2006.01) |
| *A61K 47/12* | (2006.01) |
| *A61K 47/28* | (2006.01) |

(52) U.S. Cl.
CPC .............. *A61K 47/14* (2013.01); *A61K 31/12* (2013.01); *A61K 31/192* (2013.01); *A61K 31/196* (2013.01); *A61K 31/216* (2013.01); *A61K 31/4025* (2013.01); *A61K 31/4184* (2013.01); *A61K 31/436* (2013.01); *A61K 31/44* (2013.01); *A61K 31/4418* (2013.01); *A61K 31/4453* (2013.01); *A61K 31/496* (2013.01); *A61K 31/502* (2013.01); *A61K*

*31/5377* (2013.01); *A61K 31/553* (2013.01); *A61K 31/58* (2013.01); *A61K 31/658* (2023.05); *A61K 31/7135* (2013.01); *A61K 38/12* (2013.01); *A61K 47/28* (2013.01)

(58) Field of Classification Search
None
See application file for complete search history.

(56) References Cited

U.S. PATENT DOCUMENTS

| | | | |
|---|---|---|---|
| 5,082,667 A | 1/1992 | Van | |
| 5,885,486 A | 3/1999 | Westesen et al. | |
| 6,063,768 A | 5/2000 | First | |
| 6,294,192 B1 | 9/2001 | Patel et al. | |
| 6,451,339 B2 | 9/2002 | Patel et al. | |
| 6,569,463 B2 | 5/2003 | Patel et al. | |
| 6,719,999 B2 | 4/2004 | Liu et al. | |
| 6,720,001 B2 | 4/2004 | Chen et al. | |
| 6,762,203 B2 * | 7/2004 | Koike ..................... | A23L 27/60 |
| | | | 514/546 |
| 6,764,708 B2 * | 7/2004 | Suzuki ................... | A23K 50/40 |
| | | | 426/805 |

(Continued)

FOREIGN PATENT DOCUMENTS

| | | | |
|---|---|---|---|
| CN | 101366697 A | * | 2/2009 |
| CN | 101507707 A | | 8/2009 |

(Continued)

OTHER PUBLICATIONS

Voelker, D. R. "Glycerolipid structure, function, and synthesis in eukaryotes." (2013): 412-418. (Year: 2013).*

(Continued)

*Primary Examiner* — Bethany P Barham

*Assistant Examiner* — Peter Anthopolos

(74) *Attorney, Agent, or Firm* — UltimatEdge IP Law Group, P.C.; Dean G. Stathakis

(57) ABSTRACT

The present specification discloses pharmaceutical composition disclosed herein comprises one or more therapeutic compounds, one or more glycerolipids, and one or more digestion enhancers. The disclosed glycerolipids comprise one or more hard fats and one or more liquid fats. The disclosed digestion enhancers comprise one or more bile acids, one or more phospholipids, one or more free $C_{14-24}$ fatty acids, one or more free $C_{14-24}$ fatty acid surfactants, or any combination thereof. The present specification also discloses methods and procedures to formulate the disclosed one or more therapeutic compounds into the disclosed pharmaceutical compositions.

21 Claims, 20 Drawing Sheets

(56) References Cited

U.S. PATENT DOCUMENTS

| | | | | |
|---|---|---|---|---|
| 6,982,281 | B1 | 1/2006 | Chen et al. | |
| 7,374,779 | B2 * | 5/2008 | Chen | A61K 38/13 |
| | | | | 424/455 |
| 9,339,553 | B2 | 5/2016 | Zhang et al. | |
| 9,861,602 | B2 | 1/2018 | Chen et al. | |
| 2002/0028813 | A1 | 3/2002 | Jackson et al. | |
| 2006/0138059 | A1 | 6/2006 | Vair, Jr. et al. | |
| 2011/0092583 | A1 * | 4/2011 | Murty | A61K 47/44 |
| | | | | 514/454 |
| 2011/0195993 | A1 | 8/2011 | Masson et al. | |
| 2014/0357708 | A1 * | 12/2014 | Murty | A61K 47/14 |
| | | | | 514/454 |
| 2015/0150881 | A1 | 6/2015 | Di Paolo et al. | |
| 2018/0251422 | A1 | 9/2018 | Martinez et al. | |
| 2020/0368159 | A1 | 11/2020 | Chen et al. | |
| 2021/0346302 | A1 | 11/2021 | Malhotra et al. | |

FOREIGN PATENT DOCUMENTS

| | | | |
|---|---|---|---|
| CN | 102813639 | A | 12/2012 |
| CN | 113546045 | A | 10/2021 |
| EP | 2220073 | B1 | 9/2014 |
| JP | 2015508099 | A | 3/2015 |
| WO | 2005053612 | A2 | 6/2005 |
| WO | 2006017692 | A2 | 2/2006 |
| WO | 2010041051 | A1 | 4/2010 |
| WO | 2010075065 | A2 | 7/2010 |
| WO | 2012104654 | A1 | 8/2012 |
| WO | 2012104655 | A2 | 8/2012 |
| WO | 2013126132 | A1 | 8/2013 |
| WO | 2014108569 | A1 | 7/2014 |
| WO | 2014108572 | A1 | 7/2014 |
| WO | 2014108573 | A1 | 7/2014 |
| WO | 2014108574 | A1 | 7/2014 |
| WO | 2014117999 | A1 | 8/2014 |
| WO | 2017025517 | A1 | 2/2017 |
| WO | 2020217235 | A1 | 10/2020 |
| WO | 2022207580 | A2 | 10/2022 |

OTHER PUBLICATIONS

Shi, Feng, et al. "Formulation design, preparation, and in vitro and in vivo characterizations of β-elemene-loaded nanostructured lipid carriers." International Journal of Nanomedicine (2013): 2533-2541. (Year: 2013).*

Zhang, Cong, et al. "Nanostructured lipid carriers as a novel oral delivery system for triptolide: induced changes in pharmacokinetics profile associated with reduced toxicity in male rats." International journal of nanomedicine (2014): 1049-1063. (Year: 2014).*

Moghimipour, Eskandar, Abdulghani Ameri, and Somayeh Handali. "Absorption-enhancing effects of bile salts." Molecules 20.8 (2015): 14451-14473. (Year: 2015).*

Kaur, Sarabjot, et al. "Nanostructure lipid carrier (NLC): the new generation of lipid nanoparticles." Asian Pac J Health Sci 2.2 (2015): 76-93. (Year: 2015).*

Zhang, Xingwang, et al. "Pharmaceutical dispersion techniques for dissolution and bioavailability enhancement of poorly water-soluble drugs." Pharmaceutics 10.3 (2018): 74. (Year: 2018).*

Esmaeli, et al., Preferential PPAR-α Activation Reduces Neuroinflammation, and Blocks Neurodegeneration in vivo, Hum. Mol. Genet. 25(2): 317-327 (2016).

Metibemu, et al., Exploring receptor tyrosine kinases-inhibitors in Cancer treatments, Egypt. J. Med. Hum. Genet. 20 (35): 1-16 (2019).

Pavlovic, et al., Bile Acids and Their Derivatives as Potential Modifiers of Drug Release and Pharmacokinetic Profiles, Front. Pharmacol. 9(1283): 1-23 (2018).

Sarjoj, et al., Current Trends in Lipid Based Delivery Systems and its Application in Drug Delivery, Asian J. Pharm. Clin. Res. 5(3): 4-9 (2012).

Shi, et al., Formulation Design, Preparation, and in vitro and in vivo Characterizations of ß-Elemene-Loaded Nanostructured Lipid Carriers, Int. J. Nanomed. 8: 2533-2541 (2013).

Tsume, et al., The Biopharmaceutics Classification System: Subclasses for in vivo Predictive Dissolution (IPD) Methodology and IVIVC, Eur. J. Pharm. Sci. 57: 152-163 (2014).

Voelker, Glycerolipid Structure, Function, and Synthesis in Eukaryotes, Encyclopedia BioChem. pp. 412-418 (2013).

Yousaf, et al., Enhanced Oral Bioavailability of Fenofibrate using Polymeric Nanoparticulated Systems: Physicochemical Characterization and in vivo Investigation, Int. J. Nanomed. 10: 1819-1830 (2015).

"Zhang, et al., Nanostructured Lipid Carriers as a Novel Oral Delivery System for Triptolide: Induced Changesin Pharmacokinetics Profile Associated with Reduced Toxicity in Male Rats, Int. J. Nanomed. 9: 1049-1063 (2014)."

WIPO, PCT Form ISA210, International Search Report for International Patent Application Serial No. PCT/EP2023/056491, pp. 5 (Jun. 15, 2023).

WIPO, PCT Form ISA237, Written Opinion for International Patent Application Serial No. PCT/EP2023/056491, pp. 8 (Jun. 15, 2023).

WIPO, PCT Form ISA210, International Search Report for International Patent Application Serial No. PCT/EP2023/056506, pp. 12 (Sep. 28, 2023).

WIPO, PCT Form ISA237, Written Opinion for International Patent Application Serial No. PCT/EP2023/056506, pp. 25 (Sep. 28, 2023).

WIPO, PCT Form IB373, International Preliminary Report on Patentability for International Patent Application Serial No. PCT/EP2022/058180, pp. 9 (Oct. 3, 2023).

WIPO, PCT Form ISA210, International Search Report for International Patent Application Serial No. PCT/EP2022/058180, pp. 5 (Nov. 17, 2022).

WIPO, PCT ISA 237, Written Opinion for International Patent Application Serial No. PCT/EP2022/058180, pp. 11 (Nov. 17, 2022).

* cited by examiner

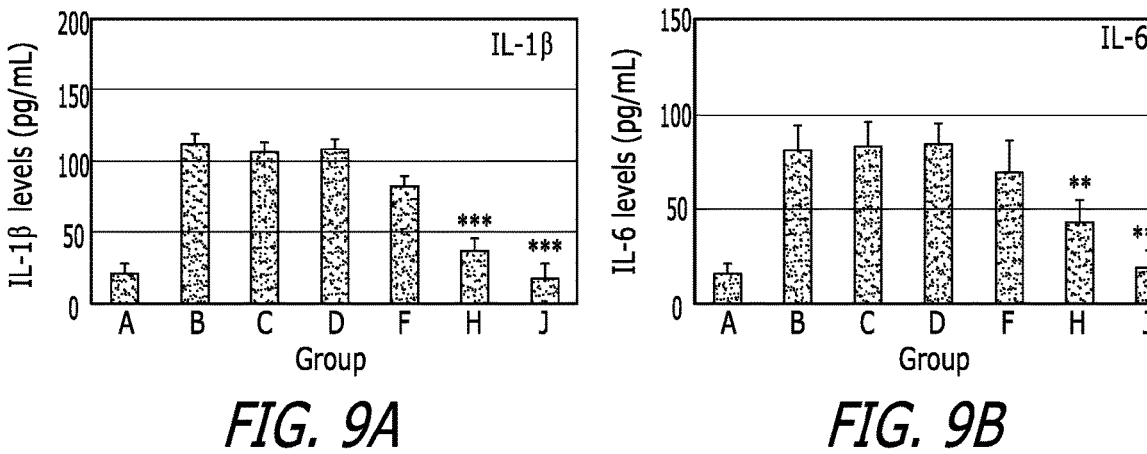
FIG. 9A
FIG. 9B
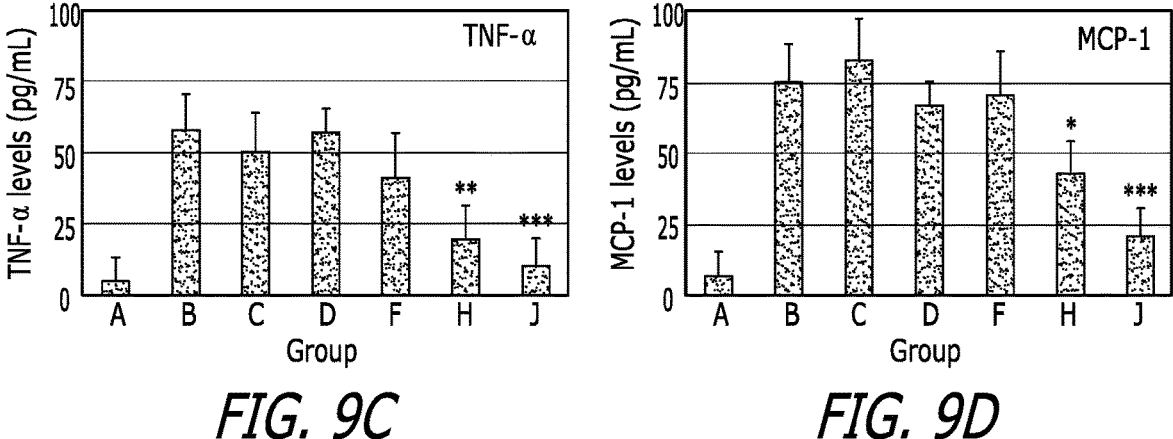
FIG. 9C
FIG. 9D
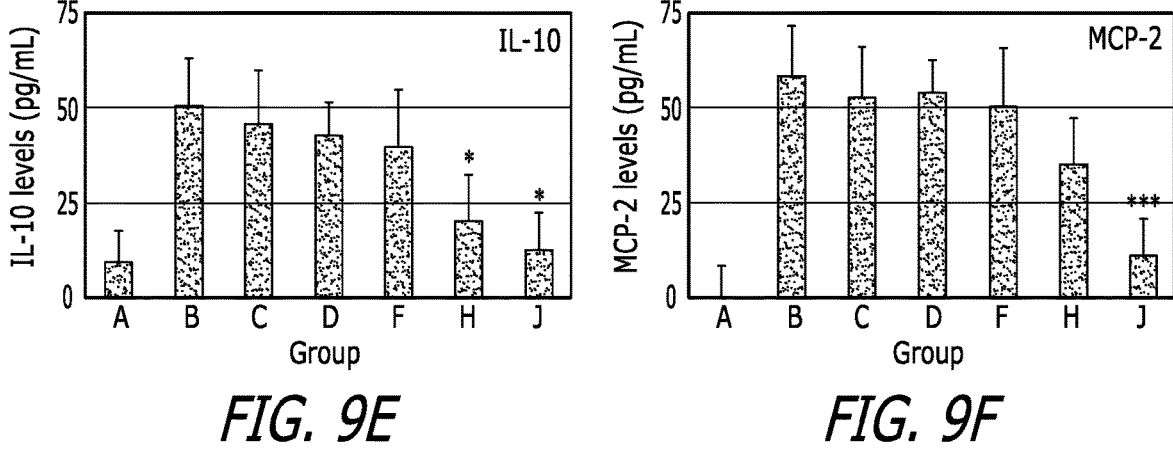
FIG. 9E
FIG. 9F

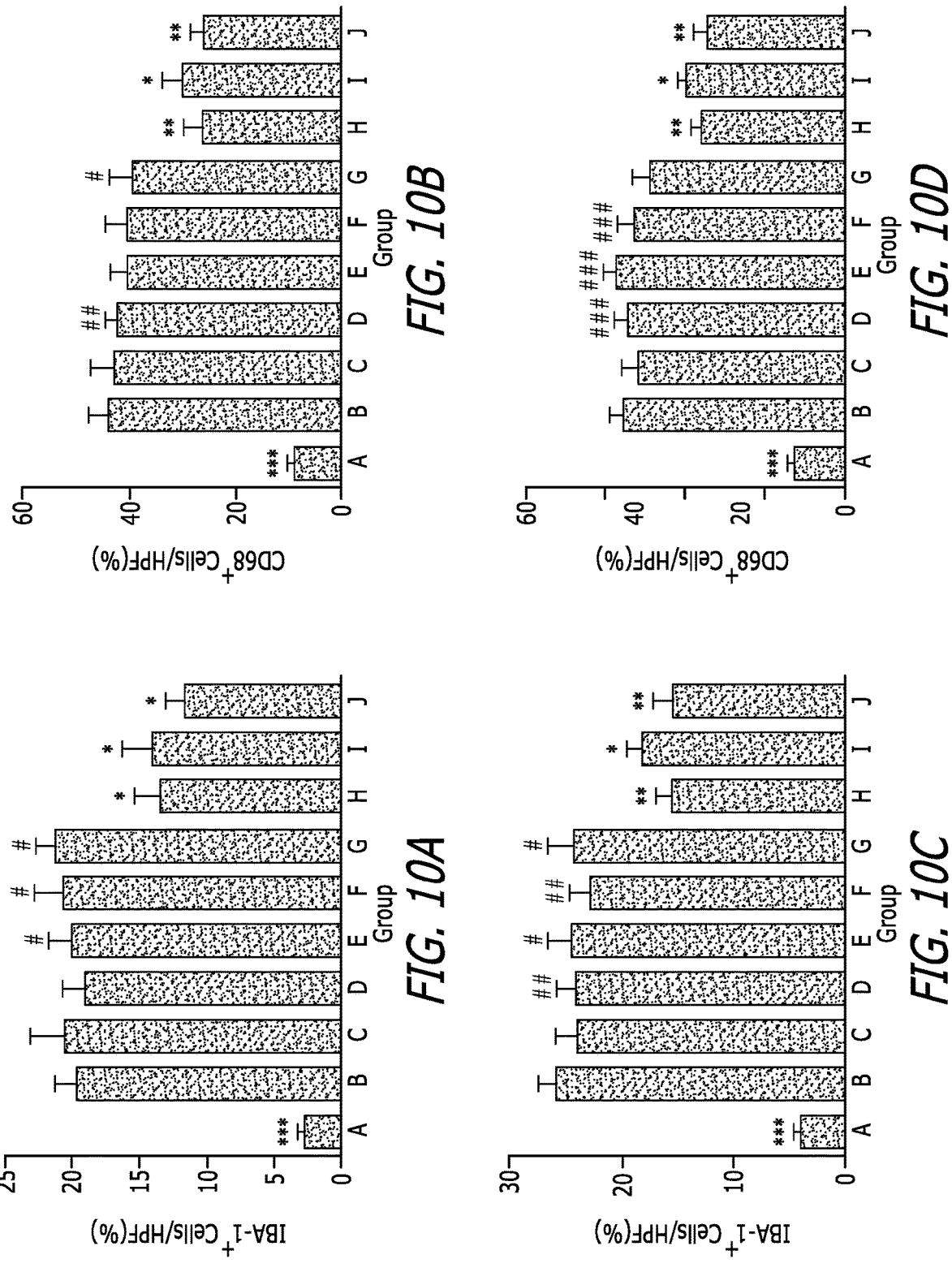

COMPOSITIONS HAVING IMPROVED BIOAVAILABILITY OF THERAPEUTICS

This application is a 35 U.S.C. § 111 patent application that claims the benefit of priority and is entitled to the filing date pursuant to 35 U.S.C. § 119(e) of U.S. Provisional Patent Application 63/269,330, filed Mar. 14, 2022 and U.S. Provisional Patent Application 63/166,995, filed Mar. 27, 2021, the content of which is hereby incorporated by reference in its entirety.

Oral delivery of a therapeutic compound is the most preferred route of administration and account for eighty percent of all the pharmaceutical compositions on the market. The underlying premise of traditional oral delivery is that the therapeutic compound must first be released from the composition into the gastrointestinal fluids being absorbed by capillaries lining the duodenum of the small intestine and then distributed systemically by the bloodstream. However, the effectiveness of oral delivery typically relies on the pharmacokinetic properties of the pharmaceutical composition and the therapeutic compound formulated therein, with the amount of therapeutic compound released from the pharmaceutical composition (dissolution rate) and the amount of the therapeutic compound absorbed into systemic circulation and made available to the body (or bioavailability) being two primary critical factors.

Poorly water soluble or hydrophobic therapeutic compounds both present particularly difficult oral delivery challenges due to their poor aqueous solubility and slow dissolution rate in the aqueous gastrointestinal environment. To solve these problems, the pharmaceutical industry has traditional focused on optimizing the formulation of a pharmaceutical composition in a manner that 1) improves the dissolution rate of a hydrophobic therapeutic compound within the formulation to increase the amount released into the gastrointestinal tract; and/or 2) improves the bioavailability of the hydrophobic therapeutic compound to increase the amount systemically delivered to the body.

For hydrophilic therapeutic compounds, the formulation challenges are different. Although these compounds are readily soluble in the aqueous gastrointestinal environment, many are poorly absorbed, due to poor membrane permeability and/or enzymatic degradation. Many solid dosage formulations of hydrophilic therapeutic compounds exhibit poor or no absorption of the therapeutic compounds.

One approach to improve the pharmacokinetics of a pharmaceutical composition comprising hydrophobic therapeutic compound has been the requirement to ingest the pharmaceutical composition with a high fat content meal to facilitate absorption in the small intestine and thus increase its bioavailability. Ingestion of the meal triggers the digestive process in the stomach which includes release of bile from the gall bladder into the duodenum, where it breaks down and absorbs fats from food. Although such meals do not generally influence dissolution rates, the absorption of the therapeutic compound that is released is enters the systemic circulation in higher amounts due to the concomitant absorption of fats from the meal.

Another approach to improve the pharmacokinetics of a pharmaceutical composition comprising hydrophobic therapeutic compound has been the use of phospholipid-based formulations, including macroemulsion, microemulsion, self-emulsifying drug delivery systems (SEDDS), self-microemulsifying drug delivery systems (SMEDDS), self-nanoemulsifying drug delivery systems (SNEDDS), solid-lipid nanoparticle (SLN), liposomes and lipoplexes. These surfactant-based formulations create oily emulsions with the therapeutic compound which facilitates its absorption by the small intestine into systemic circulation, and thus increases bioavailability of the therapeutic compound. However, besides not generally affecting dissolution rates, such surfactant-based formulations also destabilize membrane lining in the stomach causing irritation. Additional limitations associated with this approach include, e.g., in vivo drug precipitation, formulation handling issues, limited lymphatic uptake, lack of predictive in vitro tests and oxidation of unsaturated fatty acids, which restrict their potential usage. Accordingly, wide variability of the bioavailability of therapeutic compounds remains a daunting hurdle.

The present specification provides an alternative approach where pharmaceutical compositions disclosed herein are formulated to rely on physiological lipid digestion and absorption systems to achieve absorption and enhanced efficacy and increase bioavailability of therapeutic compounds to better facilitate treatment of a disease or disorder. In addition, such formulations are not only applicable to highly lipophilic therapeutic compounds but also provide a means to increase the solubility of therapeutic compounds that are generally less soluble in both aqueous and lipid matrices.

SUMMARY

Aspects of the present specification disclose, in part, a pharmaceutic composition comprising a) one or more therapeutic compounds, b) one or more glycerolipids, and c) one or more digestion enhancers. A therapeutic compound disclosed herein can be a hydrophilic therapeutic compound, a hydrophobic therapeutic compound, or a pharmaceutical active agent or ingredient, a diagnostic agent or ingredient, a cosmeceutical active agent or ingredient, or a nutraceutical active agent or ingredient. A glycerolipid disclosed herein includes hard fats and liquid fats. A hard fat is a glycerolipid that is solid at 18° C. and includes triglycerides. A liquid fat is a glycerolipid that is liquid at 18° C. and also includes partially hydrolyzed glycerolipids and monoglycerides. Digestion enhancers disclosed herein include one or more bile acids, one or more phospholipids, one or more free $C_{14-24}$ fatty acid surfactants, one or more fatty acid salts, one or more fatty acid derivatives with a polyhydroxylated head group, one or more steroidal surfactants, or any combination thereof. A composition disclosed herein may further comprise one or more pharmaceutically-acceptable stabilizing agents.

Other aspects of the present specification disclose a method of treating an individual with a disease or disorder, the method comprising the step of administering to the individual in need thereof a composition disclosed herein, wherein administration results in a reduction in a symptom associated with the disease or disorder, thereby treating the individual. Other aspects of the present specification disclose a use of a composition disclosed herein in the manufacture of a medicament for the treatment of a disease or disorder. Other aspects of the present specification disclose a composition disclosed herein for use in the treatment of a disease or disorder.

BRIEF DESCRIPTION OF THE DRAWINGS

The accompanying drawings, which are incorporated in and constitute a part of this specification, illustrate aspects of the disclosed subject matter in at least one of its exemplary embodiments, which are further defined in detail in the following description. Features, elements, and aspects of the disclosure are referenced by numerals with like numerals in different drawings representing the same, equivalent, or similar features, elements, or aspects, in accordance with one or more embodiments. The drawings are not necessarily to scale, emphasis instead being placed upon illustrating the principles herein described and provided by exemplary embodiments of the invention. In such drawings:

FIG. 1B showing a representative PXRD spectra of a cholic acid standard; FIG. 1C showing a representative PXRD spectra of a fenofibrate standard; FIG. 1D showing a representative PXRD spectra of a Vehicle standard; FIG. 1E showing a representative PXRD spectra of a disclosed pharmaceutical composition comprising fenofibrate standard; FIG. 1F showing a representative PXRD spectra of a fenofibrate standard superimposed over a representative PXRD spectra of a disclosed pharmaceutical composition comprising fenofibrate standard with asterisks above peak indicating relevant peak overlap;

FIG. 1G showing a representative PXRD spectra of a cholic acid standard superimposed over a representative PXRD spectra of a Vehicle standard with asterisks above peak indicating relevant peak overlap; and FIG. 1H showing a representative PXRD spectra of a cholic acid standard superimposed over a disclosed pharmaceutical composition comprising fenofibrate standard with asterisks above peak indicating relevant peak overlap;

FIG. 2B showing a representative PXRD spectra of a cholic acid standard; FIG. 2C showing a representative PXRD spectra of an aprepitant standard; FIG. 2D showing a representative PXRD spectra of a Vehicle standard; FIG. 2E showing a representative PXRD spectra of a disclosed pharmaceutical composition comprising aprepitant standard; FIG. 2F showing a representative PXRD spectra of a aprepitant standard superimposed over a representative PXRD spectra of a disclosed pharmaceutical composition comprising aprepitant standard with asterisks above peak indicating relevant peak overlap; FIG. 2G showing a representative PXRD spectra of a cholic acid standard superimposed over a representative PXRD spectra of a Vehicle standard; and FIG. 2H showing a representative PXRD spectra of a cholic acid standard superimposed over a disclosed pharmaceutical composition comprising aprepitant standard;

FIG. 3B shows a UHPLC tracing of fenofibric acid levels in brain after oral administration of 30 mg/kg of disclosed pharmaceutical compositions comprising fenofibrate;

FIG. 4B shows a UHPLC tracing of fenofibric acid levels in brain after oral administration of 30 mg/kg of disclosed pharmaceutical compositions comprising fenofibrate;

FIG. 6B showing IL-6 levels; FIG. 6C showing TNFα levels; FIG. 6D showing MCP-1 levels; FIG. 6E showing IL-10 levels; and FIG. 6F showing MCP-2 levels. A is saline, B is non-lipid Vehicle control, C is lipid vehicle control, D is 30 mg/Kg CMF2, E is 100 mg/Kg CMF2, F is FENF4, and G is 3 mg/kg Dexamethasone (*=$p < 0.05$, =$p < 0.01$; *=$p < 0.001$ versus vehicle control);

FIG. 7B showing IL-6 levels; FIG. 7C showing TNFα levels; FIG. 7D showing MCP-1 levels; FIG. 7E showing IL-10 levels; and FIG. 7F showing MCP-2 levels (bars represent the SEM,*=$p < 0.05$, =$p < 0.01$; *=$p < 0.001$ versus vehicle control);

FIG. 8B showing IL-6 levels; FIG. 8C showing TNFα levels; FIG. 8D showing MCP-1 levels; FIG. 8E showing IL-10 levels; and FIG. 8F showing MCP-2 levels (bars represent the SEM,*=$p < 0.05$, =$p < 0.01$; *=$p < 0.001$ versus vehicle control);

FIGS. 9A-9F show bar graphs of brain cytokine levels in animals undergoing 5 days of pre-treatment before 5 days of an LPS challenge with FIG. 9A showing IL-1β levels; FIG. 9B showing IL-6 levels; FIG. 9C showing TNFα levels; FIG. 9D showing MCP-1 levels; FIG. 9E showing IL-10 levels; and FIG. 9F showing MCP-2 levels (bars represent the SEM,*=$p < 0.05$, =$p < 0.01$; *=$p < 0.001$ versus vehicle control);

FIGS. 10A-10D show bar graphs representing percent levels of IBA-1$^+$ cells and CD-68$^+$ cells per high power field (HPF, ×400) in hippocampal and cortex slices in the brain with FIG. 10A showing percent levels of cells present in a hippocampal slice stained with anti-IBA-1 antibodies; FIG. 10B showing percent levels of cells present in a hippocampal slice stained with anti-CD-68 antibodies; FIG. 10C showing percent levels of cells present in a cortical slice stained with anti-IBA-1 antibodies; FIG. 10D showing percent levels of cells present in a cortical slice stained with anti-CD-68 antibodies (bars represent the SEM,*=$p < 0.05$, =$p < 0.01$; *=$p < 0.001$ versus vehicle control, #=$p < 0.05$, ##=$p < 0.01$; ###=$p < 0.001$ versus CMF2).

FIG. 11B shows a UHPLC tracing of cannabidiol levels in brain after oral administration of 30 mg/kg of disclosed pharmaceutical compositions comprising cannabidiol.

DETAILED DESCRIPTION

Figure 1A:
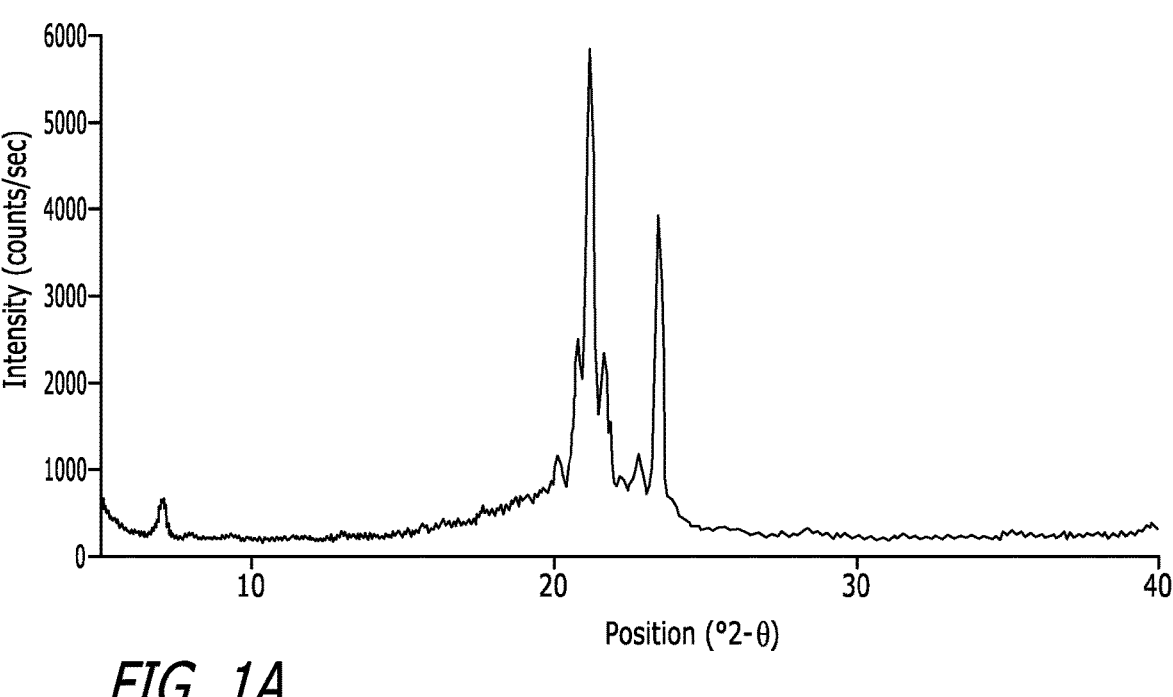
FIGS. 1A-1H show representative PXRD spectra analyzing a disclosed pharmaceutical composition comprising fenofibrate with FIG. 1A showing a representative PXRD spectra of a GELCURE® 43/01 standard.

The present specification discloses pharmaceutical compositions formulated for oral delivery in a manner where the therapeutic compound present in the pharmaceutical composition is preferentially taken up into the lymphatic system. The pharmaceutical compositions disclosed herein comprises one or more therapeutic compounds, one or more glycerolipids, and one or more digestion enhancers. A glycerolipid disclosed herein facilitates dissolvement of a therapeutic compound disclosed herein into solution and/or acts as a stabilizing agent that prevents a disclosed therapeutic compound from precipitating out of the pharmaceutical composition. A digestion enhancer disclosed herein increases the solubility of the one or more therapeutic compounds in the glycerolipid matrix, in conjunction with the glycerolipids, increases absorption of these compounds into the lymphatic system, and increases availability of these compounds to their therapeutic target. As shown herein, a disclosed pharmaceutical composition formulated using one or more glycerolipids and one or more digestion enhancers disclosed herein increases bioavailability of a therapeutic compound minimally by maintaining higher levels of the therapeutic compound over extended time period as well as increasing the directed bio-distribution of the therapeutic compound to its therapeutic target. Furthermore, besides achieving the greatest amount of therapeutic compound exposure over time to its therapeutic target, in many cases, a disclosed pharmaceutical composition enables a therapeutic compound to also reach its maximum concentration in the shortest period of time. Overall, a disclosed pharmaceutical composition exhibits a superior pharmacokinetic and pharmacodynamic profiles over current formulations of the same therapeutic compound making the disclosed pharmaceutical compositions more effective and efficacious for its intended use.

The majority of the digestion of dietary organic macromolecules and almost all absorption of the resulting breakdown products, occurs in the small intestine. The luminal wall of the small intestine is lined with many projections called villi, each of which comprises intestinal cells called enterocytes. Enterocytes not only secrete enzymes that digest proteins (polypeptides), carbohydrates (polysaccharides), and fats (lipids) but these cells also absorbed the amino acids, monosaccharides and fatty acid breakdown products. Interestingly, however, enterocytes process these breakdown products differently with amino acids and monosaccharides being taken up by capillaries and transported systemically by the blood system and fatty acids being taken up by blind ended lymphatic vessels called lacteal and then transported systemically by the lymphatic system. The disclosed pharmaceutical compositions take advantage of this differential processing by formulating therapeutic compounds that are preferentially processed by enterocytes in a manner where these compounds are taken up and transported into the lymphatic system.

Dietary lipids typically consumed by a mammal comprise 90% triglycerides as well as small amounts of cholesterol esters and phospholipids. Unlike proteins and carbohydrates, dietary lipids are hydrophobic molecules that cannot dissolve in the fluids present in the lumen of the small intestine and instead aggregate together to form fat globules. Pancreatic lipase is a water-soluble enzyme that cleaves ester bonds and breaks down lipid triglycerides into fatty acids and glycerol. However, due to its hydrophilic character lipase remain in the intestinal fluids, are unable to dissolve into fat globules and as such can only access and cleave triglycerides located at the surface where fat globules and intestinal fluids interface. In order to increase efficiency and cleavage rate at which lipase can breakdown lipids in the small intestine, the liver produces a fluid called bile. Bile contains amphipathic molecules such as bile salts including sodium cholate and sodium chenodeoxycholate, phospholipids including lecithin, as well as the hydrophobic steroid cholesterol. When bile is excreted into the small intestine it mixes with the fat globules in a manner where bile salts and phospholipids intercalate with and break apart these structures into smaller units called emulsion droplets as well as recruits an amphipathic molecule called colipase. Colipase is a protein co-enzyme that binds lipase to the emulsion droplets and stabilizes the enzyme in its active conformation, As such, emulsification greatly increases the surface area of which lipases can act upon triglycerides as well as increases its efficiency and catalytic rate thereby enabling sufficient amounts of lipid digestion to occur in the small intestine.

As lipid triglyceride digestion proceeds, the resulting free fatty acids, which are also hydrophobic and insoluble in the intestinal fluids, associate with the phospholipids from the bile to form tiny droplets called mixed micelles having a phospholipid and bile salt composition which encapsulates the free fatty acids. Mixed micelles, which are about 200 to 500 times smaller in size than emulsion droplets, fuse with the membranes of enterocytes where the free fatty acids enter the cytosol of these cells. Once inside the enterocytes, the free fatty acids are transported to the lumen of smooth endoplasmic reticulum and are transformed back into triglycerides are assembled with cholesterol and phospholipids into spherical lipid structures. These lipid structures are transported to the rough endoplasmic reticulum where apo-protein Apo B-48 is attached to the surface to form large lipoproteins called chylomicrons. Chylomicrons are then packaged is the Golgi apparatus and exit the basolateral side of the enterocytes via exocytosis. Since chylomicrons are too larger to be taken up by blood capillaries, these lipoproteins enter the lymphatic system via the lacteal in a process that depends on Apo B-48. The chylomicrons then circulate through the lymph vessels and drain into the blood system via the thoracic duct bypassing the liver circulation. Once chylomicrons are in the blood system, these lipoproteins travel to various extrahepatic tissues where their triglycerides are hydrolyzed by the activity of the lipoprotein lipase, allowing the released free fatty acids and glycerol to be absorbed by the tissues. When a large portion of the triglycerides has been hydrolyzed, chylomicron remnants are formed and are taken up by the liver, thereby also transferring dietary fat to this organ.

Natural digestion processes rely upon the secretion of bile onto the ingested gut contents and rely upon their mixing with the gut contents to initiate emulsification and access to other digestion processes such as the activity of lipases. These processes must be completed for the drug to be absorbed. A full gall bladder response in relation to the ingestion of lipids will secrete up to 50-60 mL of bile into the duodenum. The present invention relies upon the intimate mixing of digestion enhancers with the therapeutic compound in the preparation of a pharmaceutical composition disclosed herein that can then be taken orally by the patient. The therapeutic compound is then presented to the gut lumen in a form that is immediately ready for uptake. This process is highly efficient as the digestion enhancers are intimately mixed with the formulation lipid excipients. Without wishing to be limited by any theory, the pharmaceutical compositions disclosed herein employ components that are the products of triglyceride digestion to mimic the conditions created by a high fat meal. There formulations enable the one or more therapeutic compounds contained therein to be bundled along with the free fatty acids into micelles and absorbed by the enterocytes which then package the one or more therapeutic compounds into chylomicrons. The therapeutic compound loaded chylomicrons are then transported by the lymphatic system to their target cells where the therapeutic compounds are taken up by these cells to exert their beneficial effects. In essence, the chylomicrons are being co-opted as a drug delivery system for the one or more therapeutic compounds contain in a pharmaceutical composition disclosed herein. By controlling the components and amounts of the one or more glycerolipids and one or more digestion enhancers, the disclosed pharmaceutical compositions provide a more consistent and predictable bioavailability of the one or more therapeutic compounds disclosed herein that could ever be achieved by reliance on a high fat meal.

The pharmaceutical compositions disclosed herein are advantageous for several reasons all of which ultimately increase the bioavailability and efficacy of the one or more therapeutic compounds contained therein. For example, a pharmaceutical composition disclosed herein delivers its therapeutic compounds via the lymphatic system. The use of the lymphatic system to deliver therapeutic compounds is beneficial for several reasons. First, the lymphatic system avoids pre-systemic metabolism that reduces the bioavailability of many therapeutic compounds administered using a traditional oral delivery approach. Also called first pass effect or first-pass metabolism, a therapeutic compound absorbed by the digestive system must first enter the hepatic portal system before reaching systemic circulation. While in the hepatic portal system, a therapeutic compound can be metabolized by hepatic enzymes of the liver which reduce the amount of therapeutic compound that enters systemic circulation. As such, delivery of therapeutic compounds via the lymphatic system acts as a bypass to the hepatic portal system for therapeutic compounds susceptible to hepatic metabolism. The lymphatic uptake system represents an attractive opportunity for the preferential delivery of drugs. However, small water-soluble molecules that obey the rules for paracellular absorption (such as Lipinski's Rules) are not ideal substrates for lymphatic uptake. Additional highly lipophilic molecules which are often poorly and variably bioavailable even when absorbed by lymphatic uptake. This invention, uses a wide family of digestion enhancers in a lipidic delivery system, to allow both the small molecule Lipinski compliant drugs and the highly lipophilic drugs to be effectively delivered through the lymphatic uptake route.

Additionally, the lymphatic route of administration can aid delivery of therapeutic compounds directly to its target cells, thereby increasing its bioavailability and decreasing its clearance rate. For example, therapeutic compound loaded chylomicrons transported into the lymphatic system would drain into the thoracic artery and circulate throughout the body via the arterial system until reaching a capillary bed where the therapeutic compound loaded chylomicrons extracavates into the surrounding tissue to be taken up by target cell. Therapeutic compound loaded chylomicrons not taken up by target cells and cleared from the extracellular environment by interstitial fluid where they are taken up by lacteals, transported by the lymphatic system, and drained into the thoracic artery where the therapeutic compound loaded chylomicrons would once again be systemically recirculated throughout the body. Such lymphatic-based administration results in more therapeutic compound being delivered to the various systems, organs and tissues due to the avoidance of the hepatic portal system discussed above. Additionally, since more therapeutic compound enters the general circulatory system, its elimination, i.e., metabolism and excretion, is prolonged, thereby decreasing the clearance rate of the therapeutic compound which effectively increases its half-life.

Another advantage of the disclosed pharmaceutical compositions is the use of chylomicrons to selectively biodistribute the one or more therapeutic compounds contained therein to immune cells such as, e.g., macrophages and dendritic cells. For example, there are several processes whereby macrophages can take up chylomicrons. First, macrophages circulating in the lymph and blood secrete lipoprotein lipase and chylomicrons are substrates for this enzymatic activity resulting in the uptake of chylomicron proteins and lipids, and by extension any therapeutic compounds contained within the chylomicrons. Additionally, the exogenous lipoprotein metabolism pathway through a series of processing events converts chylomicrons to LDL particles which become oxidized by ROS to create oxidized LDL particles. FAT/CD36 scavenger receptor located on membrane of macrophages bind to and endocytose these oxidized LDL particles including any therapeutic compounds contained therein. Ultimately, these therapeutic compound-loaded macrophages will be directed to cells undergoing pathologic distress where the therapeutic compounds can be delivered to these distressed cells.

Additionally, when processed in the small intestine into micelles, components of the disclosed pharmaceutical compositions are believed to mimic pathogen-associated molecular patterns (PAMPs). Absorption of these micelles by gut-associated lymphoid tissue (GALT) of the small intestine result in the subsequent the subsequent uptake by immune cells like macrophages and dendritic cells by a pattern recognition receptor-mediated process. It is also suspected that since these micelles share structural similarities to chylomicrons, these micelles can also be taken up via the macrophage lipoprotein lipase process discussed above.

The disclosed pharmaceutical compositions are also advantageous because the components used for its formulation mimic the signals that trigger bile and pancreatic lipoprotein lipase secretion, enhance the rate of micellular formation, and increase the enterocyte absorption rate of micelle above that achieved with the use of the digestion enhancers in the formulation alone. Such characteristics increase the speed and amount of therapeutic compound entering the lymphatic system and thus its bioavailability.

Besides the preferential uptake into the lymphatic system and selective biodistribution to immune cells, the disclosed pharmaceutical compositions have several additional advantages. For example, a pharmaceutical composition disclosed herein can be used to formulate a wide range of poorly water soluble or hydrophobic therapeutic compounds that heretofore have proven difficult to formulate in a therapeutically effective manner due to, e.g., their insolubility or instability in solution resulting in precipitation. Additionally, it has surprisingly be found that significantly higher concentrations of poorly water soluble or hydrophobic therapeutic compounds can be formulated in a pharmaceutical composition disclosed herein relative to currently known formulations. In addition, a pharmaceutical composition disclosed herein are also useful to formulate a wide range of hydrophilic therapeutic compounds as such formulations dramatically increase the dissolution rate and bioavailability of these hydrophilic compounds.

Yet another advantage of the disclosed pharmaceutical compositions is enhanced specificity for the cellular targets of the one or more therapeutic compounds. Chylomicrons comprise membrane-bound proteins which function as ligands which associate with their cognate receptors located on the membrane surface of cells. One such ligand of these large lipoprotein particles are proteins that interact with lipid transport proteins. As therapeutic compound-loaded chylomicrons are shed for absorption, cells that express high levels of lipid transport proteins on the cellular membrane preferentially bind and internalize these lipoprotein particles. For example, the brain has high levels of lipid transport proteins on the cellular membrane allowing passage across the blood brain barrier, and other epithelial tissue such as the choroid plexus. This mechanism thereby increases the efficacy of these compounds. Other cells that express high levels of lipid transport proteins on the cellular membrane include, immune, heart, adipose, hepatic, and cancer cells. Heart cells express high levels of lipid transport proteins on their surface and we may therefore anticipate an increased cardiotoxicity for therapeutic compounds delivered through the lymphatic pathway. However, cardiotoxicity of therapeutic compounds is commonly caused through a high $C_{max}$ concentrations of free compound, resulting in GPCR or ion channel related pathologies. Surprisingly therefore lipid delivery of therapeutic compounds can result in lower-than-expected cardiotoxicity as these targets are protected from high concentrations of free compounds, as they are only slowly released from the chylomicron phase. Thus, the use of a pharmaceutical composition disclosed herein can also be associated with reduce cardiac side effects and diminished toxicity. In addition, upon ingestion, therapeutic compounds remain embedded in the oily/fatty excipients, limiting opportunity for the compounds to become solubilized in the aqueous gut contents, thereby avoiding contact toxicities such as gastric erosion and other localized damage or harm. As well as avoiding first pass metabolism and local toxicities, the enhanced uptake through the lymphatic pathway also minimizes the contact and availability of free therapeutic compound further down the alimentary canal. In this way interaction and disruption of the gut microbiome can be minimized. This is a particular benefit in using the technology with antimicrobial agents. Furthermore, due to the anatomy of the lymphatic system, the lungs can be effectively targeted with appropriate medications. For example, anti-inflammatory, antifibrotic, antimicrobial and bronchodilatory medications can be considered ling targeting through lymphatic delivery, using this technology.

Furthermore, the disclosed pharmaceutical compositions are unlike current surfactant-based formulations, such as, e.g., macroemulsion, microemulsion, self-emulsifying drug delivery systems (SEDDS), self-microemulsifying drug delivery systems (SMEDDS), self-nanoemulsifying drug delivery systems (SNEDDS), solid-lipid nanoparticle (SLN), liposomes and lipoplexes. The disclosed pharmaceutical compositions are not emulsions or self-emulsifying compositions, and as such avoid the side-effects associated with these formulations like destabilizing the membranes lining in the stomach causing irritation. Additionally, the disclosed pharmaceutical compositions avoid the manufacturing issues associated with current surfactant-based formulations, such as, e.g., formulation handling issues and no predictive in vitro testing. The disclosed pharmaceutical compositions also avoid the problems associated with current surfactant-based formulations include, e.g., in vivo drug precipitation, limited lymphatic uptake, and lack of and oxidation of unsaturated fatty acids. Surprisingly, by mimicking the microenvironment of a mixed micelle, the disclosed pharmaceutical compositions completely bypass the dissolution phase of drug uptake resulting in significantly greater bioavailability of one or more therapeutic compounds contained therein. Unlike the self emulsifying systems above the formulations disclosed herein are designed to avoid the formation of stable emulsions and when added to water, do not undergo spontaneous emulsification (exhibit the Ouzo Effect). Rather, when added to water these materials are clearly immiscible.

Pharmaceutical Composition

Aspects of the present specification disclose, in part, a composition. A composition disclosed herein is generally administered as a pharmaceutical acceptable composition. As used herein, the term "pharmaceutically acceptable" refers any molecular entity or composition refers any molecular entity or composition useful in preparing a pharmaceutical composition that is generally safe, non-toxic, and neither biologically nor otherwise undesirable and includes that which is acceptable for veterinary use as well as human pharmaceutical use. As used herein, the term "pharmaceutically acceptable composition" is synonymous with "pharmaceutical composition" and means the combination of one or more therapeutic compounds disclosed herein that are combined with one or more glycerolipids, one or more digestion enhances, and other components disclosed herein to form the product that is administered to an individual. A pharmaceutical composition disclosed herein is useful for medical and veterinary applications. A pharmaceutical composition may be administered to an individual alone, or in combination with other supplementary active ingredients, agents, drugs or hormones.

The present specification discloses pharmaceutical compositions useful to formulate a wide variety of therapeutic compounds. In some embodiments, a pharmaceutical composition disclosed herein comprises a) one or more therapeutic compounds, b) one or more glycerolipids, and c) one or more digestion enhancers. In some embodiments, a pharmaceutical composition disclosed herein comprises a) one or more therapeutic compounds, b) one or more glycerolipids, c) one or more bile acids and/or one or more bile salts, one or more phospholipids, one or more free $C_{14-24}$ fatty acid surfactants, or any combination thereof. In some embodiments, a pharmaceutical composition disclosed herein comprises a) one or more therapeutic compounds, b) one or more glycerolipids, c) one or more bile acids and/or one or more bile salts; and d) one or more phospholipids. In some embodiments, a pharmaceutical composition disclosed herein comprises a) one or more therapeutic compounds, b) one or more glycerolipids, c) one or more bile acids and/or one or more bile salts; d) one or more phospholipids; and e) one or more free $C_{14-24}$ fatty acid surfactants. In all the above embodiments, one or more therapeutic compounds disclosed herein can comprise one or more hydrophilic therapeutic compounds, one or more poorly water soluble or hydrophobic therapeutic compounds, or any combination thereof.

In some embodiments, a pharmaceutical composition disclosed herein comprises a) one or more therapeutic compounds, b) one or more triglycerides, one or more partially hydrolyzed glycerolipids including a mixture of mono-, di- and triglycerides, or a combination of one or more triglycerides and one or more partially hydrolyzed glycerolipids, and c) one or more digestion enhancers. In some embodiments, a pharmaceutical composition disclosed herein comprises a) one or more therapeutic compounds, b) one or more triglycerides, one or more partially hydrolyzed glycerolipids including a mixture of mono-, di- and triglycerides, or a combination of one or more triglycerides and one or more partially hydrolyzed glycerolipids, c) one or more bile acids and/or one or more bile salts, one or more phospholipids, one or more free $C_{14-24}$ fatty acid surfactants, or any combination thereof. In some embodiments, a pharmaceutical composition disclosed herein comprises a) one or more therapeutic compounds, b) one or more triglycerides, one or more partially hydrolyzed glycerolipids including a mixture of mono-, di- and triglycerides, or a combination of one or more triglycerides and one or more partially hydrolyzed glycerolipids, c) one or more bile acids and/or one or more bile salts; and d) one or more phospholipids. In some embodiments, a pharmaceutical composition disclosed herein comprises a) one or more therapeutic compounds, b) one or more triglycerides, one or more partially hydrolyzed glycerolipids including a mixture of mono-, di- and triglycerides, or a combination of one or more triglycerides and one or more partially hydrolyzed glycerolipids, c) one or more bile acids and/or one or more bile salts; d) one or more phospholipids; and e) one or more free $C_{14-24}$ fatty acid surfactants. In all the above embodiments, one or more therapeutic compounds disclosed herein can comprise one or more hydrophilic therapeutic compounds, one or more poorly water soluble or hydrophobic therapeutic compounds, or any combination thereof.

In some embodiments, a pharmaceutical composition disclosed herein comprises a) one or more therapeutic compounds, b) one or more triglycerides, one or more monoglycerides, or a combination of one or more triglycerides and one or more monoglycerides, and c) one or more digestion enhancers. In some embodiments, a pharmaceutical composition disclosed herein comprises a) one or more therapeutic compounds, b) one or more triglycerides, one or more monoglycerides, or a combination of one or more triglycerides and one or more monoglycerides, c) one or more bile acids and/or one or more bile salts, one or more phospholipids, one or more free $C_{14-24}$ fatty acid surfactants, or any combination thereof. In some embodiments, a pharmaceutical composition disclosed herein comprises a) one or more therapeutic compounds, b) one or more triglycerides, one or more monoglycerides, or a combination of one or more triglycerides and one or more monoglycerides, c) one or more bile acids and/or one or more bile salts; and d) one or more phospholipids. In some embodiments, a pharmaceutical composition disclosed herein comprises a) one or more therapeutic compounds, b) one or more triglycerides, one or more monoglycerides, or a combination of one or more triglycerides and one or more monoglycerides, c) one or more bile acids and/or one or more bile salts; d) one or more phospholipids; and e) one or more free $C_{14-24}$ fatty acid surfactants. In all the above embodiments, one or more therapeutic compounds disclosed herein can comprise one or more hydrophilic therapeutic compounds, one or more poorly water soluble or hydrophobic therapeutic compounds, or any combination thereof.

A pharmaceutical composition disclosed herein is formulated as an anhydrous solid, a solid dispersion, or a molecular dispersion. As such, the formulations of the disclosed pharmaceutical compositions lack any water. In addition, as discussed above, the disclosed pharmaceutical compositions are not emulsions or self-emulsifying compositions. As such, a pharmaceutical composition disclosed herein will maintain its hydrophobilc lipid characteristics when in an aqueous environment, behaving just like fats and oils and requiring the lipid digestive process to be broken down for absorption. Only when exposed to pancreatic juices from the small intestine will emulsification occur. One reason is that the one or more glycerolipids and the one or more digestion enhancers used are not sufficiently amphiphilic to initiate emulsification and require the action of bile secreted by the gall bladder during the digestion process in order for these components to contribute to the formation of micellar structures. Another reason is that the bile acid, fatty acid surfactants, phospholipids, and any other digestion enhancer are all individually and in combination below the critical micellar concentration necessary for emulsification to occur.

Therapeutic Compound

Aspects of the present specification disclose, in part, a therapeutic compound. A therapeutic compound is a compound that provides pharmacological activity or other direct effect in the diagnosis, cure, mitigation, treatment, or prevention of disease, or to affect the structure or any function of the body of man or animals. A therapeutic compound includes both a small molecule therapeutic compound that is synthesized and a synthetic peptide, a biologic therapeutic compound manufactured in, extracted from, or semi synthesized from biological sources including vaccines, whole blood, blood components, allergenics, somatic cells, gene therapies, tissues, recombinant therapeutic protein, and living medicines used in cell therapy. Non-limiting examples of a biologic include a blood factors like Factor VIII and Factor IX, a thrombolytic agents like tissue plasminogen activator, a hormones like insulin, glucagon, growth hormone, gonadotrophins, a hematopoietic growth factor like Erythropoietin, colony-stimulating factors, an immunotherapeutic, an interferon like Interferon-$\alpha$, Interferon-$\beta$, and Interferon-$\gamma$, an interleukin-based product like Interleukin-2, a vaccine, like an influenza vaccine, a SAR-CoV-2 vaccine, an HIV vaccine, a hepatitis B vaccine, a hepatitis C vaccine, and a malaria vaccine, a monoclonal antibody, a tumour necrosis factor, and a therapeutic enzyme.

Non-limiting examples of a therapeutic compound include, a pharmaceutical active agent or ingredient, a diagnostic agent or ingredient, a cosmeceutical active agent or ingredient, and a nutraceutical active agent or ingredient. A therapeutic compound disclosed herein may be used in the form of a pharmaceutically acceptable salt, solvate, or solvate of a salt, e.g. the hydrochloride. Additionally, therapeutic compound disclosed herein may be provided as racemates, or as individual enantiomers, including the R- or S-enantiomer. Thus, the therapeutic compound disclosed herein may comprise a R-enantiomer only, a S-enantiomer only, or a combination of both a R-enantiomer and a S-enantiomer of a therapeutic compound. A therapeutic compound disclosed herein can be a hydrophilic therapeutic compound or a hydrophobic therapeutic compound.

A pharmaceutical composition disclosed herein may comprises one or more therapeutic compounds based on Biopharmaceutics Classification System (BCS) Class I-IV drugs. The BCS is a scientific framework for classifying drug substances based on based on its minimum aqueous solubility in the pH range of 1 to 7.5, dose and human fraction absorbed or intestinal membrane permeability, see U.S. Department of Health and Human Services Food and Drug Administration Center for Evaluation and Research (CDER), *Waiver of in vivo Bioavailability and Bioequiva-*

*lence Studies for Immediate-Release Solid Oral Dosage Forms Based on a Biopharmaceutics Classification System, Guidance for Industry* (2017), which is hereby incorporated by reference in its entirety. When combined with the dissolution of the drug product, the BCS takes into account three major factors that govern the rate and extent of drug absorption from IR solid oral dosage forms: (1) dissolution, (2) solubility, and (3) intestinal permeability. This system categorizes drugs into four classes according to their permeability and solubility. BCS Class I drugs are therapeutic compounds that have high solubility and high permeable and are generally absorbed completely. BCS Class II drugs are therapeutic compounds that have low solubility and high permeable and would be absorbed completely, if in solution. BCS Class III drugs are therapeutic compounds that have high solubility and low permeable and have difficulty being absorbed completely, even though the agent is in solution (high dissolution rate). BCS Class IV drugs are therapeutic compounds that have low solubility and low permeable and are difficult to get in solution and once in solution are difficult to get absorbed. Subclassification shave also been proposed based on whether a therapeutic compound from BCS Class I or III is an acid, a base or neutral, see Tsume, et al., *The Biopharmaceutics Classification System: Subclasses for in vivo predictive dissolution (IPD) methodology and IVIVC, Eur. J. Pharm. Sci.* 57: 152-163 (2014), which is hereby incorporated by reference in its entirety.

In some embodiments, a pharmaceutical composition disclosed herein may comprises one or more BCS Class I therapeutic compounds, BCS Class II therapeutic compounds, BCS Class III therapeutic compounds, BCS Class IV therapeutic compounds, or any combination thereof. In aspects of these embodiments, a pharmaceutical composition disclosed herein may comprises one or more BCS Class I therapeutic compounds. In aspects of these embodiments, a pharmaceutical composition disclosed herein may comprises one or more BCS Class II therapeutic compounds. In aspects of these embodiments, a pharmaceutical composition disclosed herein may comprises one or more BCS Class III therapeutic compounds. In aspects of these embodiments, a pharmaceutical composition disclosed herein may comprises one or more BCS Class IV therapeutic compounds.

A pharmaceutical composition disclosed herein may comprises one or more hydrophilic therapeutic compounds. A hydrophilic therapeutic compound disclosed herein includes amphipathic therapeutic compound, and are water soluble compounds with appreciable or substantial water solubility. In some embodiments, a hydrophilic therapeutic compound disclosed herein has an intrinsic water solubility (i.e., water solubility of the unionized form) of, e.g., at least 0.1% by weight, at least 0.5% by weight, at least 1% by weight or, and more typically at least 10% by weight.

A pharmaceutical composition disclosed herein may comprises one or more hydrophobic therapeutic compounds. A hydrophobic therapeutic compound disclosed herein includes lipophilic therapeutic compounds, and are poorly water-soluble compounds having little or no water solubility. In some embodiments, a poorly water soluble or hydrophobic therapeutic compound disclosed herein has an intrinsic water solubility (i.e., water solubility of the unionized form) of, e.g., at most 1% by weight, at most 0.5% by weight, at most 0.1% by weight, and more typically at most 0.01% by weight.

A therapeutic compound disclosed herein may have a log P value greater than zero. As used herein, the term "log P value" refers to the logarithm (base 10) of the partition coefficient (P) for a compound and is a measure of lipophilicity. Typically, P is defined as the ratio of concentrations of a unionized compound in the two phases of a mixture of two immiscible solvents at equilibrium. Thus, log P=Log 10 (P), where P=[solute in immiscible solvent 1]/[solute in immiscible solvent 2]. With regard to organic and aqueous phases, the log P value of a compound is constant for any given pair of solvents, and its value can be determined empirically by one of several phase-partitioning methods known to one skilled in the art including, e.g., a shake flask assay, a HPLC assay, and an interface between two immiscible electrolyte solutions (ITIES) assay.

In some embodiments, a therapeutic compound disclosed herein may have a log P value indicating that the compound is substantially soluble in a formulation of a pharmaceutical composition disclosed herein. In one embodiment, a therapeutic compound disclosed herein may have a log P value indicating that the compound is, e.g., at least 50% soluble, at least 60% soluble, at least 70% soluble, at least 80% soluble, or at least 90% soluble in a formulation of a pharmaceutical composition disclosed herein. In one embodiment, a therapeutic compound disclosed herein may have a log P value indicating that the compound is between, e.g., about 50% to about 100% soluble, about 60% to about 100% soluble, about 70% to about 100% soluble, about 80% to about 100% soluble, or about 90% to about 100% soluble in a formulation of a pharmaceutical composition disclosed herein.

In one embodiment, a therapeutic compound disclosed herein may have a log P value of, e.g., at least 1.1, at least 1.2, at least 1.4, at least 1.6, at least 1.8, at least 2.0, at least 2.2, at least 2.4, at least 2.6, at least 2.8, at least 3.0, at least 3.2, at least 3.4, or at least 3.6. In one embodiment, a therapeutic compound disclosed herein may have a log P value of, e.g., at most 1.1, at most 1.2, at most 1.4, at most 1.6, at most 1.8, at most 2.0, at most 2.2, at most 2.4, at most 2.6, at most 2.8, at most 3.0, at most 3.2, at most 3.4, or at most 3.6. In one embodiment, a therapeutic compound disclosed herein may have a log P value in the range of, e.g., between 1.0 and 4.0, between 1.1 and 4.0, between 1.2 and 4.0, or between 1.3 and 4.0, between 1.4 and 4.0, between 1.5 and 4.0, between 1.6 and 4.0, between 1.8 and 4.0, between 2.0 and 4.0, between 2.1 and 4.0, between 2.2 and 4.0, or between 2.3 and 4.0, between 2.4 and 4.0, between 2.5 and 4.0, between 2.6 and 4.0, between 2.8 and 4.0, between 3.0 and 4.0, or between 3.1 and 4.0, between 3.2 and 4.0, between 3.3 and 4.0, between 3.4 and 4.0, between 3.5 and 4.0, or between 3.6 and 4.0. In one embodiment, a therapeutic compound disclosed herein may have a log P value in the range of, e.g., between 1.0 and 3.0, between 1.1 and 3.0, between 1.2 and 3.0, or between 1.3 and 3.0, between 1.4 and 3.0, between 1.5 and 3.0, between 1.6 and 3.0, between 1.8 and 3.0, between 2.0 and 3.0, between 2.1 and 3.0, between 2.2 and 3.0, or between 2.3 and 3.0, between 2.4 and 3.0, between 2.5 and 3.0, between 2.6 and 3.0, or between 2.8 and 3.0. In one embodiment, a therapeutic compound disclosed herein may have a log P value in the range of, e.g., between 1.0 and 2.0, between 1.1 and 2.0, between 1.2 and 2.0, or between 1.3 and 2.0, between 1.4 and 2.0, between 1.5 and 2.0, between 1.6 and 2.0, or between 1.8 and 2.0.

A therapeutic compound disclosed herein may have a polar surface area that is hydrophobic. As used herein, the term "polar surface area" refers to the surface sum over all of the polar atoms in the structure of a compound and is a measure of hydrophobicity. Typically, these polar atoms include, e.g., oxygen, nitrogen, and their attached hydrogens. In one embodiment, a therapeutic compound disclosed herein may have a polar surface area of, e.g., less than 8.0 nm$^2$, less than 7.0 nm$^2$, less than 6.0 nm$^2$, less than 5.0 nm$^2$, less than 4.0 nm$^2$, or less than 3.0 nm$^2$. In one embodiment, a therapeutic compound disclosed herein may have a polar surface area in the range of, e.g., between 3.0 nm$^2$ and 6.5 nm$^2$, between 3.0 nm$^2$ and 6.0 nm$^2$, between 3.0 nm$^2$ and 5.5 nm$^2$, between 3.0 nm$^2$ and 5.0 nm$^2$, between 3.0 nm$^2$ and 4.5 nm$^2$, between 3.5 nm$^2$ and 6.5 nm$^2$, between 3.5 nm$^2$ and 6.0 nm$^2$, between 3.5 nm$^2$ and 5.5 nm$^2$, between 3.5 nm$^2$ and 5.0 nm$^2$, between 3.5 nm$^2$ and 4.5 nm$^2$, between 4.0 nm$^2$ and 6.5 nm$^2$, between 4.0 nm$^2$ and 6.0 nm$^2$, between 4.0 nm$^2$ and 5.5 nm$^2$, or between 4.0 nm$^2$ and 5.0 nm$^2$, between 4.0 nm$^2$ and 4.5 nm$^2$, or between 4.5 nm$^2$ and 5.5 nm$^2$. In one embodiment, poorly water soluble or hydrophobic therapeutic compound disclosed herein may have a polar surface area in the range of, e.g., between 2.0 nm$^2$ and 6.5 nm$^2$, between 2.0 nm$^2$ and 6.0 nm$^2$, between 2.0 nm$^2$ and 5.5 nm$^2$, between 2.0 nm$^2$ and 5.0 nm$^2$, between 2.0 nm$^2$ and 4.5 nm$^2$, between 2.5 nm$^2$ and 6.5 nm$^2$, between 2.5 nm$^2$ and 6.0 nm$^2$, between 2.5 nm$^2$ and 5.5 nm$^2$, between 2.5 nm$^2$ and 5.0 nm$^2$, or between 2.5 nm$^2$ and 4.5 nm$^2$.

In some embodiments, a therapeutic compound disclosed herein is a therapeutic compound comprising an organic acid functional group, such as, e.g., a carboxylic acid functional group or sulfonic acid functional group. Examples of a disclosed therapeutic compound comprising an organic acid functional group include a free acid form of a therapeutic compound (i.e., a therapeutic compound having a free organic acid) and a salt form of a therapeutic compound (i.e., a therapeutic compound having an organic acid salt). An organic acid salt form of a therapeutic compound includes any therapeutic compound associated with an alkali metal, such as, e.g., lithium (Li), sodium (Na), potassium (K), rubidium (Rb), cesium (Cs), and francium (Fr), or alkaline earth metal, such as, e.g., beryllium (Be), magnesium (Mg), calcium (Ca), strontium (Sr), barium (Ba), and radium (Ra).

In some embodiments, a therapeutic compound disclosed herein is a therapeutic compound comprising an organic base functional group, such as, e.g. an amine functional group. Examples of a disclosed therapeutic compound comprising an organic base functional group include a therapeutic compound containing an organic base functional group capable of donating ions. In some embodiments, a therapeutic compound containing an organic base functional group capable of donating ions is a therapeutic compound containing an amine functional group capable of donating ions including, without limitation, a primary amine, a secondary amine, a tertiary amine, amide, amidine, amido, amino, imidate, imide, imine, imino, aminohydroxy, and a quaternary salt.

Non-limiting examples of a therapeutic compound include those classified by the United States Pharmacopea (USP) including analgesics (including opioids and non-opioids), anesthetics, antibacterials (including antibiotics), anticonvulsants, antidementia agents, antidepressants, antidotes and antitoxins, antiemetics, antifungals, anti-inflammatory agents (including corticosteroids, disease-modifying antirheumatic drugs (DMARDs), and nonsteroidal anti-inflammatory drugs (NSAIDs)), antimigraine agents, antimyasthenic agents, antimycobacterials, antineoplastics, antiparasitics, antiparkinson agents, antipsychotics, antivirals (including HIV antiretrovirals and direct-acting hepatitis C drugs), anxiolytic (anti-anxiety) agents, bipolar agents, blood glucose regulators (including insulin and other diabetes medications), blood products (including anticoagulants), cardiovascular agents (including beta-blockers. ACE inhibitors, and lipid management drugs such as statins and PPAR agonists), central nervous system agents (including amphetamines), dental and oral agents, dermatological (skin) agents, enzyme replacement agent, gastrointestinal agents (including H2 blockers and proton pump inhibitors), genitourinary (genital and urinary tract) agents, hormonal agents (adrenal, pituitary, prostaglandins, sex hormones, including estrogen, testosterone, and anabolic steroids, and thyroid), hormone suppressant (adrenal, parathyroid, pituitary, sex hormones, and thyroid), immunological agents, inflammatory bowel disease agents, metabolic bone disease agents, nootropic agents, ophthalmic agents, otic agents, respiratory tract agents (including antihistamines and bronchodilators), sedatives and hypnotics, skeletal muscle relaxants, and therapeutic nutrients, minerals, and electrolytes.

Non-limiting examples of a therapeutic compound include those classified as 5-alpha-reductase inhibitors, 5-aminosalicylates, 5HT3 receptor antagonists, adamantane, adrenal cortical steroids, adrenal corticosteroid inhibitors, agents for hypertensive emergencies, agents for pulmonary hypertension, aldosterone receptor antagonists, alkylating agents, allergenics, alpha-glucosidase inhibitors, alternative medicines, amebicides, aminoglycosides, aminopenicillins, aminosalicylates, amphetamines, AMPA receptor antagonists, amylin analogs, analgesics, androgens, anabolic steroids, Angiotensin Converting Enzyme (ACE) inhibitors, angiotensin II inhibitors, angiotensin receptor blockers, anorexiants, antacids, antiadrenergic agents, antiandrogens, antianginal agents, antiarrhythmic agents, antiasthmatic agents, antianxiety agents, antibiotics, anticholinergic agents, anticoagulants, anticoagulant reversal agents, anticonvulsants, antidepressants, antidiabetic agents, antidiarrheals, antidotes, antiemetic agents, antifungals, antigonadotropic agents, antigout agents, antihelmintic agents, antihistamines, antihyperlipidemic agents, antihypertensive agents, antihyperuricemic agents, anti infective agents, antimalarial agents, antimanic agents, antimetabolites, antimigraine agents, antineoplastic agents, antineoplastic detoxifying agents, antineoplastic interferons, antiparkinson agents, antiplatelet agents, antipseudomonal penicillins, antipsoriatics, antipsychotics, antirheumatics, antirosacea agents, antiseptic and germicides, antispasmodics, antithyroid agents, antitoxins and antivenins, antituberculosis agents, antitussive agents, antivertigo agents, antiviral agents, antiviral boosters, anxiolytics, sedatives, and hypnotics, aromatase inhibitors, astringents, atypical antipsychotics, azole, barbiturates, BCR-ABL tyrosine kinase inhibitors, benzodiazepines, beta blockers, beta-adrenergic blocking agents, beta-lactamase inhibitors, bile acid sequestrants, bisphosphonates, bone morphogenetic proteins, bone resorption inhibitors, bronchodilator combinations, bronchodilators, BTK inhibitors, calcimimetics, calcineurin inhibitors, calcitonin, calcium channel blocking agents, carbapenems, carbonic anhydrase inhibitors, cardiac stressing agents, cardioselective beta blockers, cardiovascular agents, catecholamines, CDK 4/6 inhibitors, central nervous system agents, cephalosporins, cerumenolytics, CFTR potentiators, CGRP inhibitors, chelating agents, chemokine receptor antagonist, chloride channel activators, cholesterol absorption inhibitors, cholinergic agonists, cholinergic muscle stimulants, cholinesterase inhibitors, chronotropic agents, CNS stimulants, coagulation modifiers, colony stimulating factors, corticosteroids, corticotropin, coumarins and indandiones, cox-2 inhibitors, decongestants, diarylquinolines, dibenzazepine, diagnostic dyes, dipeptidyl peptidase 4 inhibitors, disease-modifying antirheumatic drugs (DMARDs), diuretics, echinocandins, EGFR inhibitors, erythropoiesis agents, estrogen receptor antagonists, estrogens, expectorants, factor Xa inhibitors, fibric acid derivatives, first generation cephalosporins, fourth generation cephalosporins, functional bowel disorder agents, gallstone solubilizing agents, gamma-aminobutyric acid analogs, gamma-aminobutyric acid reuptake inhibitors. gastrointestinal agents, genitourinary tract agents, GI stimulants, glucocorticoids, glucose elevating agents, glycoprotein platelet inhibitors, glycylcyclines, gonadotropin releasing hormones, gonadotropin-releasing hormone antagonists, gonadotropins, group I antiarrhythmics, group II antiarrhythmics, group III antiarrhythmics, group IV antiarrhythmics, group V antiarrhythmics, growth hormone receptor blockers, growth hormones, guanylate cyclase-C agonists, *H. pylori* eradication agents, H2 antagonists, hedgehog pathway inhibitors, hematopoietic stem cell mobilizer, heparin antagonists, heparins, HER2 inhibitors, herbal products, histone deacetylase inhibitors, hormones, hydantoin, hydrazide derivatives, immunologic agents, immunostimulants, immunosuppressive agents, impotence agents, incretin mimetics, inotropic agents, insulin, insulin-like growth factors, integrase strand transfer inhibitor, interferons, interleukin inhibitors, interleukins, intravenous nutritional products, investigational drugs, iodinated contrast media, iron products, ketolides, leprostatics, leukotriene modifiers, lincomycin derivatives, local injectable anesthetics, lymphatic staining agents, macrolide derivatives, macrolides, magnetic resonance imaging contrast media, malignancy photosensitizers, mast cell stabilizers, meglitinides, melanocortin receptor agonists, metabolic agents, methylxanthines, mineralocorticoids, minerals and electrolytes, mitotic inhibitors, monoamine oxidase inhibitors, mTOR inhibitors, mucolytics, multikinase inhibitors, muscle relaxants, mydriatics, neprilysin inhibitors, neuraminidase inhibitors, neuromuscular blocking agents, neuronal potassium channel openers, NHE3 inhibitors, nicotinic acid derivatives, NK1 receptor antagonists, non-opioids, NNRTIs, non-cardioselective beta blockers, non-sulfonylureas, nonsteroidal anti-inflammatory drugs, nootropic agents, NS5A inhibitors, nucleoside reverse transcriptase inhibitors (NRTIs), nutraceutical products, nutritional products, ophthalmic agents, opioids, otic agents, oxazolidinedione, parathyroid hormone and analogs, PARP inhibitors, PCSK9 inhibitors, penicillins, peripheral opioid receptor antagonists, peripheral opioid receptor mixed agonists/antagonists, peripheral vasodilators, peripherally acting antiobesity agents, phenothiazine, phenylpiperazine, phosphate binders, PI3K inhibitors, plasma expanders, platelet aggregation inhibitors, platelet-stimulating agents, polyenes, probiotics, progesterone receptor modulators, progestins, prolactin inhibitors, prostaglandin D2 antagonists, protease inhibitors, protease-activated receptor-1 antagonists, proteasome inhibitors, proton pump inhibitors, PPAR agonists, psoralens, psychotherapeutic agents, purine nucleosides, pyrrolidine, quinolones, radiocontrast agents, radiologic adjuncts, radiologic agents, radiologic conjugating agents, radiopharmaceuticals, renal replacement solutions, renin inhibitors, respiratory agents, rifamycin derivatives, salicylates, sclerosing agents, second generation cephalosporins, selective estrogen receptor modulators, selective immunosuppressants, selective phosphodiesterase-4 inhibitors, selective serotonin reuptake inhibitors, serotonin-norepinephrine reuptake inhibitors, serotoninergic neuroenteric modulators, sex hormones, SGLT-2 inhibitors, skeletal muscle relaxants, smoking cessation agents, somatostatin and somatostatin analogs, spermicides, statins, streptogramins, *streptomyces* derivatives, succinimide, sulfonamides, sulfonylureas, sympathomimetic amines, synthetic ovulation stimulants, tetracyclines, therapeutic radiopharmaceuticals, thiazide, thiazolidinediones, thioxanthenes, third generation cephalosporins, thrombin inhibitors, thrombolytics, thyroid drugs, TNFα inhibitors, tocolytic agents, transthyretin stabilizers, triazines, urea cycle disorder agents, urinary pH modifiers, uterotonic agents, vasodilators, vasopressin antagonists, vasopressors, VEGF/VEGFR inhibitors, viscosupplementation agents, vitamin, and VMAT2 inhibitors.

A therapeutic compound disclosed herein may be a non-steroidal anti-inflammatory drug (NSAID). NSAIDs are a large group of therapeutic compounds with analgesic, anti-pain, and anti-pyretic properties. NSAIDs may be classified based on their chemical structure or mechanism of action. A NSAID can be a non-selective cyclo-oxygenase (COX) inhibitor, a selective cyclooxygenase 1 (COX 1) inhibitor, or a selective cyclooxygenase 2 (COX 2) inhibitor. Non-limiting examples of NSAIDs include an acetate derivative NSAID, an enolicate derivative NSAID, a fenamate derivative NSAID, a propionate derivative NSAID, a pyrazolone derivative NSAID, a salicylate derivative NSAID, A NSAID may be a profen.

Examples of a suitable acetic acid derivative NSAID include, without limitation, aceclofenac, acemetacin, aclofenac, amfenac, alclofenac, bendazac, bromfenac, bufexamac, bumadizone, cinmetacin, clometacin, diclofenac, difenpiramide, etodolac, felbinac, fenclofenac, fentiazac, glucametacin, indometacin (indomethacin), indometacin farnesil, ketorolac, lonazolac, mofezolac, nabumetone, oxametacin, oxindanac, proglumetacin, sulindac, sulindac sulfide, tolmetin, zidometacin, and zomepirac. Examples of a suitable enolic acid (oxicam) derivative NSAID include, without limitation, ampiroxicam, droxicam, isoxicam, lornoxicam, meloxicam, piroxicam, and tenoxicam. Examples of a suitable fenamic acid derivative NSAID include, without limitation, etofenamic acid (etofenamate), floctafenic acid (floctafenate), flufenamic acid (flufenamate), meclofenamic acid (meclofenamate), mefenamic acid (mefenamate), morniflumic acid (morniflumate), niflumic acid (niflumate), talinflumic acid (talinflumate), tolfenamic acid (tolfenamate). Examples of a suitable propionate derivative NSAID include, without limitation, alminoprofen, benoxaprofen, bucloxic acid (blucloxate), butibufen, carprofen, dexibuprofen, dexindoprofen, dexketoprofen, fenbufen, fenoprofen, flunoxaprofen, flurbiprofen, ibuprofen, ibuproxam, indoprofen, ketoprofen, loxoprofen, miroprofen, naproxen, naproxcinod, oxaprozin, pirprofen, pranoprofen, suprofen, tarenflurbil, tepoxalin, tiaprofenic acid (tiaprofenate), and vedaprofen. Examples of a suitable pyrazolone derivative NSAID include, without limitation, aminophenazone, ampyrone, metamizole (dipyrone), nifenazone, phenoazone, and propyphenazone. Examples of a suitable salicylate derivative NSAID include, without limitation, acetylsalicylic acid (asprin), aloxiprin, benorilate (benorylate), carbasalate calcium, diflusinal, dipyrocetyl, ethenzamide, guacetisal, magnesium salicylate, mesalazine (5-aminosalicylic acid), methyl salicylate, salacetamide, salicin, salicylamide, salicylate (salicylic acid), salsalate, sodium salicylate, and triflusal. Examples of a suitable selective COX-2 inhibitors include, without limitation, celecoxib, etoricoxib, firocoxib, lumiracoxib, meloxicam, parecoxib, rofecoxib, and valdecoxib.

A therapeutic compound disclosed herein may be a paracetamol-type therapeutic compound. Examples of a suitable paracetamol-type therapeutic compound include, without limitation, acetanilide, bucetin, butacetin, paracetamol (acetaminophen), parapropamol, phenacetin, and propacetamol.

A therapeutic compound disclosed herein may be a peroxisome proliferator-activated receptor (PPAR) agonist. Examples of a suitable PPAR agonist include, without limitation, a PPARα agonist, a PPARγ agonist, a PPARδ agonist, a duel PPAR-α/γ agonist (or glitazar).

A therapeutic compound disclosed herein may be a PPARα agonist. Examples of a suitable PPARα agonist include, without limitation, 15-H-eicosatetraenoic acid, 15-hydroperoxy-eicosatetraenoic acid, aleglitazar, aluminium clofibrate, arachidonic acid, bezafibrate, clofibrate, CP-775146, daidzein, DHEA (prasterone), elafibranor, etomoxir, fenofibrate, genistein, gemfibrozil, GW-7647, lanifibranor, leukotriene B4, LG-101506, LG-100754, lobeglitazone, muraglitazar, oleylethanolamide, palmitoylethanolamide, pemafibrate, perfluorononanoic acid, perfluorooctanoic acid, pioglitazone, saroglitazar, sodelglitazar, tesaglitazar, tetradecylthioacetic acid, troglitazone, and WY-14643.

A therapeutic compound disclosed herein may be a PPARγ agonist. Examples of a suitable PPARγ agonist include, without limitation, 5-oxo-eicosatetraenoic acid, 5-oxo-15-hydroxy-eicosatetraenoic acid, 15-deoxy-Δ12,14-prostaglandin J2, 15-eicosatetraenoic acid, 15-hydroperoxy-eicosatetraenoic acid, aleglitazar, arachidonic acid, balaglitazone, berberine, bezafibrate, cannabidiol, cevoglitazar, ciglitazone, daidzein, darglitazone, edaglitazone, efatutazone, englitazone, etalocib, farglitazar, genistein, GW-1929, ibuprofen, imiglitazar, indeglitazar, lanifibranor, LG-100268, LG-100754, LG-101506, lobeglitazone, muraglitazar (muroglitazar), nTZDpa, naveglitazar, netoglitazone, oxeglitazar, peliglitazar, pemaglitazar, perfluorononanoic acid, pioglitazone, prostaglandin J2, ragaglitazar, reglitazar, rivoglitazone, rosiglitazone,-5444, saroglitazar, sipoglitazar, sodelglitazar, telmisartan, tesaglitazar, and troglitazone. Other suitable PPARγ agonists are described in Masson and Caumont-Bertrand, *PPAR Agonist Compounds, Preparation and Uses*, US 2011/0195993, which is hereby incorporated by reference in its entirety.

A therapeutic compound disclosed herein may be a PPARδ agonist. Examples of a suitable PPARδ agonist include, without limitation, 15-H-eicosatetraenoic acid, 15-hydroperoxy-eicosatetraenoic acid, arachidonic acid, bezafibrate, daidzein, elafibranor, fonadelpar, genistein, GW-0742, GW-501516, L-165,041, ianifibranor, LG-101506, seladelpar, sodelglitazar, and tetradecylthioacetic acid.

A therapeutic compound disclosed herein may be a duel PPAR-α/γ agonist. Examples of a suitable duel PPAR-α/γ agonist include, without limitation, aleglitazar, muraglitazar, saroglitazar, and tesaglitazar.

A therapeutic compound disclosed herein may be a PPAR-13 agonist. In another embodiment, a PPAR-13 agonist is, without limitation, endurobol and/or GW0742.

A therapeutic compound disclosed herein may be a cancer drug. Examples of a suitable cancer drug include, without limitation, an alkylating agent, an anti-metabolite, a plant alkaloid and terpenoid, a topoisomerase inhibitor and a cytotoxic antibiotic. An alkylating agent incudes carboplatin, chlorambucil, cisplatin, cyclophosphamide, ifosfamide, oxaliplatin, and mechlorethamine. An anti-metabolite includes Azathioprine and Mercaptopurine. A plant alkaloid and terpenoid include a *vinca* alkaloid like vincristine, vinblastine, vinorelbine, and vindesine, a podophyllotoxin like etoposide and teniposide, and a taxane like docetaxel and ortataxel. A topoisomerase inhibitor includes a type i topoisomerase inhibitor like a camptothecins, such as, e.g., exatecan, irinotecan, lurtotecan, topotecan, BNP 1350, CKD 602, DB 67 (AR67), and ST 1481, and a type ii inhibitor like an epipodophyllotoxin such as, e.g., amsacrine, etoposid, etoposide phosphate, and teniposide. A cytotoxic antibiotic includes an actinomycin like actinomycin d, bacitracin, colistin (polymyxin E), and polymyxin b, an anthracenedione like mitoxantrone and pixantrone, and a anthracycline like bleomycin, doxorubicin (adriamycin), daunorubicin (daunomycin), epirubicin, idarubicin, mitomycin, plicamycin, and valrubicin. PARP inhibitors, kinase inhibitors and repurposed drugs including mebendazole, beta blockers, aminocoumarin antibiotics such as novobiocin, antirheumatic drugs such as methotrexate and auranofin A therapeutic compound disclosed herein may be a sympathomimetic amine. Sympathomimetic amines are a class of therapeutic compounds that mimic the effects of transmitter substances of the sympathetic nervous system such as catecholamines, epinephrine (adrenaline), norepinephrine (noradrenaline), and/or dopamine. A sympathomimetic amine may act as an α-adrenergic agonist, a β-adrenergic agonist, a dopaminergic agonist, a monoamine oxidase (MAO) inhibitor, and a COMT inhibitor. Such therapeutic compounds, among other things, are used to treat cardiac arrest, low blood pressure, or even delay premature labor. Examples of a suitable sympathomimetic amine include, without limitation, clenbuterol, salbutamol, ephedrine, pseudoephedrine, methamphetamine, amphetamine, phenylephrine, isoproterenol, dobutamine, methylphenidate, lisdexamfetamine, cathine, cathinone, methcathinone, cocaine, benzylpiperazine (BZP), methylenedioxypyrovalerone (MDPV), 4-methylaminorex, pemoline, phenmetrazine, and propylhexedrine. An α-adrenergic agonist includes Phenylephrine, Propylhexedrine, and Pseudoephedrine. A β-adrenergic agonist includes clenbuterol, dobutamine, eephedrine, isoproterenol, and salbutamol. A Dopaminergic/Norepinephrinergic agonist includes cocaine (DA/NE reuptake inhibitor), lisdexamfetamine (5HT/DA/NE reuptake inhibitor), methylphenidate (DA/NE reuptake inhibitor), and methylenedioxypyrovalerone (DA/NE reuptake inhibitor). A neurotransmitter releasing agent includes amphetamine (DA/NE releasing agent), benzylpiperazine (DA/NE releasing agent), Cathine (DA/NE releasing agent), cathinone (DA/NE releasing agent), methamphetamine (DA/NE releasing agent), methcathinone (DA/NE releasing agent), 4-methylaminorex (DA/NE releasing agent), pemoline, phenmetrazine (DA/NE releasing agent), and phenethylamine (DA/NE releasing agent).

A therapeutic compound disclosed herein may be a nootropic agent. Examples of a suitable sympathomimetic amine include, without limitation, aniracetam, cacao, caffeine, choline, choline bitartrate, choline citrate, citicoline, CDP-choline, coluracetam, 5-HTP, melatonin, methyphenidate, modafinil, nefiracetam, nicotine, noopept, oxiracetam, phenibut, phenylpiracetam, piracetam, pramiracetam, and vinpocetine.

A therapeutic compound disclosed herein may be a CNS agent. Examples of a suitable CNS agent include, without limitation, amphetamines, anticholinergic agents, anticonvulsant agents, antidementia agents, antidepressant agents, antispasticity agents, antiemetic agents, anti migraine agents, anti-obesity agents, antiparkinson agents, antipsychotic agents, anxiolytic agents, attention deficit hyperactivity disorder agents, benzodiazepines, bipolar agents, calcitonin gene-related peptide (CGRP) receptor antagonists, calcium channel modifying agents, cholinesterase inhibitors, dopamine agonists, dopamine precursors and/or I-amino acid decarboxylase inhibitors, emetogenic therapy adjuncts, ergot alkaloids, fibromyalgia agents, gamma-aminobutyric acid (GABA) augmenting agents, monoamine oxidase inhibitors, monoamine oxidase B inhibitors, multiple sclerosis agents, N-methyl-D-aspartate (NMDA) receptor antagonist, selective serotonin reuptake inhibitors/serotonin and norepinephrine reuptake inhibitors (SSRI/SNRI), serotonin (5-HT) receptor agonists, sleep disorder agents, sleep promoting agents, sodium channel modifying agents, tricyclic agents, and wakefulness promoting agents. Other CNS therapeutic compounds include, without limitation, amifampridine, deutetrabenazine, dextromethorphan, edaravone, quinidine, riluzole, tetrabenazine, and valbenazine.

Anticonvulsants agents include, without limitation, brivaracetam, cannabidiol, cenobamate, divalproex, ethosuximide, felbamate, fenfluramine, lamotrigine, levetiracetam, methsuximide perampanel, topiramate, and valproic acid. Antidepressant agents include, without limitation, amitriptyline, aripiprazole, buproprion, chlordiazepoxide, esketamine, fluoxetine, isocarboxazid, ketamine, maprotiline, mirtazapine, olanzapine, perphenazine, phenelzine sulfate, quetiapine fumarate, selegiline, and tranylcypromine sulfate. Antidementia agents include, without limitation, donepezil, ergoloid, galantamine, memantine, rivastigmine, and rivastigmine. Antiemetic agent include, without limitation, aprepitant, amisulpride, chlorpromazine, diphenhydramine, doxylamine, dronabinol, fosnetupitant, granisetron, hydroxyzine, meclizine, metoclopramide, nabilone, netupitant, ondansetron, ondansetron, palonosetron, perphenazine, prochlorperazine edisylate, prochlorperazine, promethazine, pyridoxine, rolapitant, scopolamine, and trimethobenzamide. Antimigraine agents include, without limitation, caffeine, dihydroergotamine, divalproex, ergotamine, propranolol, timolol, topiramate, and valproic acid. Anti-obesity agents include, without limitation, benzphetamine, bupropion, diethylpropion, liraglutide, methamphetamine, naltrexone, phendimetrazine, phentermine, and topiramate. Antiparkinson agents include, without limitation, amantadine, benztropine, carbidopa, diphenhydramine, entacapone, istradefylline, levodopa, opicapone, trihexyphenidyl, and tolcapone. Antipsychotic agents include, without limitation, aripiprazole, asenapine, brexpiprazole, cariprazine, chlorpromazine, clozapine, fluphenazine, fluphenazine, haloperidol, iloperidone, loxapine, lurasidone, olanzapine, paliperidone, perphenazine, pimavanserin, pimozide, prochlorperazine, quetiapine, risperidone, thioridazine, thiothixene, trifluoperazine, and ziprasidone. Antispasticity agents include, without limitation, baclofen, dantrolene, and tizanidine. Anxiolytic agents include, without limitation, buspirone, doxepin, duloxetine, escitalopram, meprobamate, paroxetine, sertraline, and venlafaxine hydroxyzine. Attention deficit hyperactivity disorder agents include, without limitation, atomoxetine, clonidine, dexmethylphenidate, dextroamphetamine, guanfacine, methylphenidate, lisdexamfetamine, and methamphetamine. Bipolar agents include, without limitation, aripiprazole, asenapine, carbamazepine, divalproex, lamotrigine, lithium, lurasidone, olanzapine, quetiapine, risperidone, valproic acid, and ziprasidone. Benzodiazepines include, without limitation, alprazolam, chlordiazepoxide, clonazepam, clorazepate, diazepam, lorazepam, and oxazepam. CGRP receptor antagonists include, without limitation, eptinezumab, erenumab, fremanezumab, galcanezumab, rimegepant, and ubrogepant. Dopamine agonists include, without limitation, apomorphine, bromocriptine, pramipexole Di, ropinirole, and rotigotine. Dopamine Precursors and/or L-Amino Acid Decarboxylase Inhibitors include, without limitation, carbidopa, carbidopa, and levodopa. Fibromyalgia agents include, without limitation, duloxetine, milnacipran, and pregabalin. GABA Augmenting Agents include, without limitation, clobazam, clonazepam, clorazepate, diazepam, gabapentin, lorazepam, pregabalin, phenobarbital, primidone, tiagabine, and vigabatrin. Monoamine oxidase B inhibitors include, without limitation, rasagiline, safinamide, and selegiline. Multiple Sclerosis agents include, without limitation, alemtuzumab, cladribine, dalfampridine, dimethyl fumarate, diroximel fumarate, fingolimod, glatiramer, interferon β-1a, interferon β-1b, mitoxantrone, monomethyl fumarate, natalizumab, ocrelizumab, ozanimod, peginterferon β-1a, siponimod, and teriflunomide. NMDA receptor antagonist include, without limitation, memantine. Serotonin (5-HT) receptor agonists include, without limitation, almotriptan, eletriptan, frovatriptan, lasmiditan, naratriptan, naproxen, rizatriptan benzoate, sumatriptan, sumatriptan, and zolmitriptan. Sodium channel agents include, without limitation, carbamazepine, eslicarbazepine, ethotoin, fosphenytoin, lacosamide, oxcarbazepine, phenytoin, phenytoin, rufinamide, and zonisamide. SSRIs/SNRIs include, without limitation, citalopram, desvenlafaxine, desvenlafaxine, duloxetine, escitalopram oxalate, fluoxetine, fluvoxamine, levomilnacipran, nefazodone, paroxetine, sertraline, trazodone, venlafaxine, vilazodone, and vortioxetine. Sleep Promoting agents include, without limitation, doxepin, estazolam, eszopiclone, flurazepam, lemborexant, quazepam, ramelteon, suvorexant, tasimelteon, temazepam, triazolam, zaleplon, zopiclone, and zolpidem. Wakefulness Promoting agents include, without limitation, armodafinil, modafinil, calcium/magnesium/potassium/sodium oxybates, pitolisant, and solriamfetol. Tricyclic agents include, without limitation, amitriptyline, amoxapine, clomipramine, desipramine, doxepin, imipramine, imipramine pamoate, nortriptyline, protriptyline, and trimipramine.

A therapeutic compound disclosed herein may be an anti-hyperlipidemic agent. There are several classes of anti-hyperlipidemic agents (also known as hypolipidemic agents). They may differ in both their impact on the cholesterol profile and adverse effects. For example, some may lower low density lipoprotein (LDL), while others may preferentially increase high density lipoprotein (HDL). Clinically, the choice of an agent will depend on the cholesterol profile of an individual, cardiovascular risk of an individual, and/or the liver and kidney functions of an individual. Examples of a suitable anti-hyperlipidemic agent include, without limitation, a fibrate, a statin, a tocotrienol, a niacin, a bile acid sequestrants (resin), a cholesterol absorption inhibitor, a pancreatic lipase inhibitor, and a sympathomimetic amine.

A therapeutic compound disclosed herein may be a fibrate. Fibrates are a class of amphipathic carboxylic acids with lipid level modifying properties. These therapeutic compounds are used for a range of metabolic disorders. One non-limiting use is as an anti-hyperlipidemic agent where it may lower levels of, e.g., triglycerides and LDL as well as increase levels of HDL. Examples of a suitable fibrate include, without limitation, a bezafibrate, a ciprofibrate, clinofibrate, clofibrate, clofibride, etofibrate, fenofibrate, fenofibric acid, gemfibrozil, nafenopin, ronifibrate, and simfibrate.

A therapeutic compound disclosed herein may be a statin. Statins (or HMG-CoA reductase inhibitors) are a class of therapeutic compounds used to lower LDL and/or cholesterol levels by inhibiting the enzyme HMG-CoA reductase, which plays a central role in the production of cholesterol in the liver. To compensate for the decreased cholesterol availability, synthesis of hepatic LDL receptors is increased, resulting in an increased clearance of LDL particles from the blood. Examples of a suitable statin include, without limitation, atorvastatin, fluvastatin, lovastatin, pitavastatin, pravastatin, rosuvastatin, and simvastatin.

A therapeutic compound disclosed herein may be a tocotrienol. Tocotrienols are another class of HMG-CoA reductase inhibitors and may be used to lower LDL and/or cholesterol levels by inducing hepatic LDL receptor up-regulation and/or decreasing plasma LDL levels. Examples of a suitable tocotrienol include, without limitation, a γ-tocotrienol and a δ-tocotrienol.

A therapeutic compound disclosed herein may be a niacin. Niacins are a class of therapeutic compounds with lipid level modifying properties. For example, a niacin may lower LDL by selectively inhibiting hepatic diacyglycerol acyltransferase 2, reduce triglyceride synthesis, and VLDL secretion through a receptor HM74 and HM74A or GPR109A. These therapeutic compounds are used for a range of metabolic disorders. One non-limiting use is as an anti-hyperlipidemic agent where it may inhibit the breakdown of fats in adipose tissue. Because a niacin blocks the breakdown of fats, it causes a decrease in free fatty acids in the blood and, as a consequence, decreases the secretion of very-low-density lipoproteins (VLDL) and cholesterol by the liver. By lowering VLDL levels, a niacin may also increase the level of HDL in blood. Examples of a suitable niacin include, without limitation, acipimox, niacin, nicotinamide, and vitamin B3.

A therapeutic compound disclosed herein may be a bile acid sequestrant. Bile acid sequestrants (also known as resins) are a class of therapeutic compounds used to bind certain components of bile in the gastrointestinal tract. They disrupt the enterohepatic circulation of bile acids by sequestering them and preventing their reabsorption from the gut. Bile acid sequestrants are particularly effective for lowering LDL and cholesterol by sequestering the cholesterol-containing bile acids released into the intestine and preventing their reabsorption from the intestine. In addition, a bile acid sequestrant may also raise HDL levels. Examples of a suitable bile acid sequestrant include, without limitation, cholestyramine, colesevelam, and colestipol.

A therapeutic compound disclosed herein may be a cholesterol absorption inhibitor. Cholesterol absorption inhibitors are a class of therapeutic compounds that inhibits the absorption of cholesterol from the intestine. Decreased cholesterol absorption leads to an upregulation of LDL-receptors on the surface of cells and an increased LDL-cholesterol uptake into these cells, thus decreasing levels of LDL in the blood plasma. Examples of a suitable cholesterol absorption inhibitor include, without limitation, Ezetimibe, a phytosterol, a sterol and a stanol.

A therapeutic compound disclosed herein may be a fat absorption inhibitor. Fat absorption inhibitors are a class of therapeutic compounds that inhibits the absorption of fat from the intestine. Decreased fat absorption reduces caloric intake. In one aspect, a fat absorption inhibitor inhibits pancreatic lipase, an enzyme that breaks down triglycerides in the intestine. Examples of a suitable fat absorption inhibitor include, without limitation, orlistat.

A therapeutic compound disclosed herein may be an antihelminthic. An antihelmintic (also known as an antihelminthic agent or helminthic) a group of antiparasitic drugs that expel parasitic worms (helminths) and other internal parasites from the body by either stunning or killing them and without causing significant damage to the host. They may also be called vermifuges (those that stun) or vermicides (those that kill). Non-limiting examples of an antihelmintic include an aminoacetonitrile derivative, an artemisinin, an avermectin, a benzimidazole, a milbemycin, an octadepsipeptide, a spiroindole, diethylcarbamazine, levamisole, monepantel, niclosamide, nitazoxanide, phosphoric acid (metrifonate), praziquantel, pyrantel pamoate, salicylanilide, suramin, or any combination thereof. In aspects of this embodiment, an artemisinin includes, without limitation, artelinic acid, artemether, artemotil (β-arteether), artenimol, arterolane, artesunate, dihydroartemisinin, a butyrate ester of dihydroartemesinin, or any combination thereof. In aspects of this embodiment, an avermectin includes, without limitation, abamectin, doramectin, emamectin, ivermectin, selamectin, or any combination thereof. In aspects of this embodiment, a benzimidazole includes, without limitation, albendazole, ciclobendazole, fenbendazole, flubendazole, mebendazole, thiabendazole, triclabendazole, or any combination thereof. In aspects of this embodiment, a milbemycin includes, without limitation, moxidectin, milbemycin oxime, or any combination thereof. In aspects of this embodiment, an octadepsipeptide includes, without limitation, emodepside. In aspects of this embodiment, a spiroindole includes, without limitation, dequantel.

A therapeutic compound disclosed herein may be a retinoid. The retinoids are a class of chemical compounds that are vitamers of vitamin A or are chemically related to it. Non-limiting examples of a retinoid include a first generation retinoid like alitretinoin, isotretinoin retinol, retinal, and tretinoin (retinoic acid); a second generation retinoid like etretinate and its metabolite acitretin; a third generation retinoid like adapalene, bexarotene, and tazarotene; and a fourth generation retinoid like trifarotene.

A therapeutic compound disclosed herein may be a vitamin. Non-limiting examples of a retinoid include vitamin A, vitamin D, vitamin E and vitamin K. A vitamin A includes, without limitation, α-carotene, β-carotene, retinol, and tretinoin. A vitamin D includes, without limitation, A vitamin $D_2$ like ergosterol and ergocalciferol, a vitamin $D_3$ like 7-dehydrocholesterol, previtamin $D_3$, cholecalciferol, 25-hydroxycholecalciferol, calcitriol (1,2,5-dihydroxycholecalciferol), and calcitroic acid, a vitamin $D_4$ like dihydroergocalciferol, a vitamin $D_5$, and vitamin D analogues like alfacalcidol, dihydrotachysterol, calcipotriol, tacalcitol, and paricalcitol. A vitamin E includes, without limitation, α-tocopherol, β-tocopherol, γ-tocopherol, δ-tocopherol, α-tocotrienol, β-tocotrienol, γ-tocotrienol, δ-tocotrienol, and tocofersolan. A vitamin K includes, without limitation, Naphthoquinone, a vitamin $K_1$ like Phylloquinone, a vitamin $K_2$ like Menaquinones, a vitamin $K_3$ like Menadione, a vitamin $K_4$, a vitamin $K_5$ like 4-Amino-2-methyl-1-naphthol, a vitamin $K_6$ like 2-Methylnaphthalene-1,4-diamine, and a vitamin $K_7$ like 4-Amino-3-methyl-1-naphthol.

A therapeutic compound disclosed herein may be a cannabinoid. Examples of a suitable cannabinoid drug include, without limitation, a phytocannabinoid, an endocannabinoid, and a synthetic cannabinoid. A phytocannabinoid includes a tetrahydrocannabinol (such as, e.g., delta-9-tetrahydrocannabinol (Δ9-THC, THC), and delta-8-tetrahydrocannabinol (Δ8-THC)), a cannabidiol, a cannabinol, a cannabigerol, a tetrahydrocannabivarin, a cannabidivarin, and a cannabichromene. An endocannabinoid includes arachidonoylethanolamine (anandamide or AEA), 2-arachidonoyl glycerol (2-AG), 2-arachidonyl glyceryl ether (noladin ether), N-arachidonoyl-dopamine (NADA), virodhamine (OAE), and lysophosphatidylinositol (LPI). A synthetic cannabinoid includes dronabinol (Marinol), nabilone (Cesamet), sativex, rimonabant (SR141716), JWH-018, JWH- 073, CP-55940, dimethylheptylpyran, HU-210, HU-331, SR144528, WIN 55,212-2, JWH-133, levonantradol (Nantrodolum), and AM-2201.

A therapeutic compound disclosed herein may be a cannabinoid receptor modulator. A cannabinoid receptor modulator includes, without limitation, a CB1 agonist, a CB1 antagonist, a CB2 agonist, a CB2 antagonist, a GPR18 (NAGly) agonist, a GPR18 (NAGly) antagonist, a GPR55 agonist, a GPR55 antagonist, a GPR119 agonist, a GPR119 antagonist, a eCBT inhibitor, a FAAH activator, a FAAH inhibitor, a MAGL inhibitor, a ABHD6 inhibitor, a ABHD6 inhibitor, and a ABHD12 inhibitor.

A therapeutic compound disclosed herein may be an antiemetic. Non-limiting examples of an antiemetic include a 5-HT3 serotonin ion channel antagonist, a 5-HT serotonin G-protein receptor antagonist, a CB1 agonist, a D2/D3 antagonist, a H1 antagonist, a mACh antagonist, a NK1 antagonist, cerium oxalate, dexamethasone, lorazepam, midazolam, and propofol. A 5-HT3 serotonin ion channel antagonist includes, without limitation, alosetron, azasetron, bemesetron, cilansetron, clozapine, dazopride, dolasetron, granisetron, lerisetron, metoclopramide, mianserin, mirtazapine, olanzapine, ondansetron, palonosetron, quetiapine, ramosetron, ricasetron, tropisetron and zatosetron. A 5-HT serotonin G-protein receptor antagonist includes, without limitation, clozapine, cyproheptadine, hydroxyzine, olanzapine, risperidone and ziprasidone. A CB1 agonist (or cannabinoid) includes, without limitation, dronabinol, nabilone, tetrahydrocannabinol (*cannabis*). A D2/D3 antagonist includes, without limitation, alizapride, bromopride, chlorpromazine, clebopride, domperidone, haloperidol, hydroxyzineltopride, metoclopramide, metopimazine, prochlorperazine, thiethylperazine, and trimethobenzamide. A H1 antagonist (antihistamine) includes, without limitation, cyclizine, dimenhydrinate, diphenhydramine, hydroxyzine, meclizine, and promethazine. A mACh antagonist (anticholinergics) includes, without limitation, atropine, diphenhydramine, hydroxyzine, hyoscyamine, and scopolamine. A NK1 antagonist includes, without limitation, aprepitant, casopitant, ezlopitant, fosaprepitant, maropitant, netupitant, rolapitant, and vestipitant.

A therapeutic compound disclosed herein may be one shown in Table 1.

TABLE 1

| Therapeutic Compound | Log P | BCS | USPC | Functionality | MOA |
|---|---|---|---|---|---|
| | | | Therapeutic Compounds | | |
| Abiraterone | >1 | IV | Antiandrogen | Androgen biosynthesis inhibitor | Enzyme inhibitor |
| Amitriptyline | >1 | I | Antidepressant agent | Tricyclic antidepressant | Serotonin transporter (SERT) blocker; Norepinephrine transporter (NET) blocker |
| Amlexanox | >1 | ND | Kinase inhibitor Anti-inflammatory antiallergic immunomodulator | Histamine and leukotriene inhibitor | Noncanonical IkB kinase IKKε and TANK-binding kinase 1 (TBK1) inhibitor |
| Aprepitant | >1 | IV | Antiemetic | G protein-coupled receptor inhibitor | Neurokinin-1 (NK1) receptor antagonist |
| Atorvastatin | >1 | II | Dyslipidemic, Anti-hyperlipidemic agent | Statin | HMG co-A reductase inhibitor |
| Auranofin | >1 | ND | Anti-inflammatory agent | DMARD | Thioredoxin reductase inhibitor |
| BX-471 | <1 | ND | Anti-inflammatory agent | DMARD | Chemokine receptor CCR1 antagonist |
| CBD | >1 | II | Anticonvulsant agent | Phytocannabinoid | CB1 and CB2 agonist |
| CCT3833 | >1 | ND | Antineoplastic agent | Raf-mediated signal transduction inhibitor | Pan-RAF kinase inhibitor |
| Clodronic acid | | | Anti-inflammatory agent | Bisphosphonate | Pyrophosphate-dependent enzyme inhibitor |
| Curcumin | >1 | IV | Anti-inflammatory agent | Phyto-polyphenol; Curcuminoid | Reactive oxygen scavenger |
| Eliglustat | >1 | I or III | Enzyme Inhibitor | Glucocerebroside inhibitor | Glucosylceramide synthase inhibitor |
| Estrogen | | | Hormonal agent | Estrogen receptor modulator | Estrogen receptor agonist |
| Fenofibrate | >1 | II | Dyslipidemic, Anti-hyperlipidemic agent | Fibrate | PPARα agonist |
| Flavonoid Gemfibrozil | >1 | II | Dyslipidemic, Anti-hyperlipidemic agents | Fibrate | PPARα agonist |
| Icatibant | | | Hematological agent | Peptide-based hormone | Brakyokinin 2 antagonist |
| ICI188-551 | ND | ND | | | β2 adrenoceptor antagonist |

TABLE 1-continued

Therapeutic Compounds

| Therapeutic Compound | Log P | BCS | USPC | Functionality | MOA |
|---|---|---|---|---|---|
| Ketamine Lipid soluble nuclear receptor molecule | >1 | ND | Analgesic; anesthetic | Arylcyclohexylamine | NMDA antagonist |
| Mebendazole | >1 | II | Anthelmintic agent | Microtubule synthesis inhibitor | Benzimidazole |
| Metformin | <1 | I | Antidiabetic Agents | Biguanide | Mitochondrial complex I inhibitor; AMP-activated protein kinase (AMPK) activator; cAMP inhibitor |
| Midostaurin | >1 | II | Enzyme Inhibitor | Cytokine receptor modulator | Kinase inhibitor |
| Miglustat | | | Enzyme Inhibitor | Glucocerebroside inhibitor | glucosylceramide synthase inhibitor |
| Niacin | <1 | I | Dyslipidemic, Anti-hyperlipidemic agent | Pyridinecarboxylic acid | G protein-coupled receptor activator; Triglyceride synthesis inhibitor |
| Nintedanib | >1 | II or IV | Respiratory tract agent; antineoplastic agent | Tyrosine protein kinase inhibitor | Nonreceptor tyrosine kinase (nRTK) inhibitor; Receptor tyrosine kinase (RTK) inhibitor |
| Novobiocin | >1 | ND | Antibiotic | Aminocoumarin | DNA gyrase inhibitor; POL-Theta inhibitor. |
| Olaparib | >1 | IV | Antineoplastic agent | Enzyme inhibitor | Poly ADP ribose polymerase (PARP) inhibitor |
| Orlistat | | | Anti-obesity agent | Enzyme inhibitor | Lipase inhibitor |
| Omeprazole | >1 | II | Gastrointestinal agent | Pregnane X receptor (PXR) antagonist | Proton pump inhibitor |
| Pirfenidone | >1 | I | Antifibrotic agent; anti-inflammatory agent | IPF treatment | Fibroblast proliferation inhibitor; Collagen synthesis inhibitor; Fibrogenic mediator synthesis inhibitor; inflammatory mediator sythesis inhibitor |
| Pitolisant | >1 | I | Anti-dyssomnia agent | Lipophilic ether | Histamine 3 (H3) receptor antagonist/inverse agonist |
| Praziquantel | >1 | II | Anthelmintic agent | Antitrematodal agent | Calcium ion channel ligand; Adenosine uptake inhibitor |
| Progesterone | >1 | II | Hormonal agent | Progestogen receptor modulator | Progesterone receptor agonist |
| Propranolol | >1 | I | Cardiovascular agent | β-Receptor modulator | β-Receptor antagonist |
| Psilocin | >1 | ND | Antidepressant agent | Tryptamine; Phospholipase A2 activator | Serotonin 2A, 2C and 1A agonist or partial agonist. |
| Rebamipide | >1 | IV | Gastrointestinal agent | | COX-2 agonist |
| Raloxifene | >1 | II | Hormonal agent | Estrogen receptor modulator | Selective estrogen receptor modulator (SERM) |
| Resversatol | >1 | II | Cardiovascular agent | Phyto-polyphenol | Stilbenoid, |
| Retinoic acid | >1 | IV | Antineoplastic agent | Retinoid receptor modulator | RAR nuclear receptor agonists; RXR nuclear receptor agonists |
| Sapropterin | <1 | I | Metabolic agent | Neurotransmitter synthesis cofactor | Biotin H4 cofactor |
| Simvastatin | >1 | II | Dyslipidemic, Anti-hyperlipidemic agents | Statin | HMG co-A reductase inhibitor |

TABLE 1-continued

Therapeutic Compounds

| Therapeutic Compound | Log P | BCS | USPC | Functionality | MOA |
|---|---|---|---|---|---|
| Serotonin | <1 | III | | | |
| THC | >1 | II | Antiemetic agent | Phytocannabinoid | CB1 and CB2 agonist |
| Tryptophan | <1 | ND | | | |
| Verapamil | >1 | II | Antiarrhythmic | Ion channel blocking agent | L-type calcium channel blocker |
| Vitamin A | >1 | II | Antiinflammatory agent | Vitamin A vitamer | RAR nuclear receptor agonists; RXR nuclear receptor agonists |
| Vitamin D | >1 | II | Antiinflammatory agent | Vitamin D vitamer | Vitamins D nuclear receptor agonist |
| Vitamin E | >1 | II | Antioxidant | Vitamin A vitamer; tocopherol and tocotrienol | Vitamins E nuclear receptor agonist |
| Vitamin K | >1 | II | | Vitamin K vitamer | Vitamins K nuclear receptor agonist |

In one embodiment, a pharmaceutical composition disclosed herein comprises one or more therapeutic compounds in an amount of, e.g., about 0.05%, about 0.1%, about 1%, about 2.5%, about 5%, about 7.5%, about 10%, about 12.5%, about 15%, about 17.5%, about 20%, about 22.5%, about 25%, about 30%, about 35%, about 40%, about 45%, or about 50% by weight. In one embodiment, a pharmaceutical composition disclosed herein comprises one or more therapeutic compounds in an amount of, e.g., at least 0.05%, at least 0.1%, at least 1%, at least 2.5%, at least 5%, at least 7.5%, at least 10%, at least 12.5%, at least 15%, at least 17.5%, at least 20%, at least 22.5%, at least 25%, at least 30%, at least 35%, at least 40%, at least 45%, or at least 50% by weight. In one embodiment, a pharmaceutical composition disclosed herein comprises one or more therapeutic compounds in an amount of, e.g., at most 0.05%, at most 0.1%, at most 1%, at most 2.5%, at most 5%, at most 7.5%, at most 10%, at most 12.5%, at most 15%, at most 17.5%, at most 20%, at most 22.5%, at most 25%, at most 30%, at most 35%, at most 40%, at most 45%, or at most 50% by weight.

In one embodiment, a pharmaceutical composition disclosed herein comprises one or more therapeutic compounds disclosed herein in an amount of, e.g., about 0.05% to about 1%, about 0.05% to about 2.5%, about 0.05% to about 5%, about 0.05% to about 7.5%, about 0.05% to about 10%, about 0.05% to about 12.5%, about 0.05% to about 15%, about 0.05% to about 17.5%, about 0.05% to about 20%, about 0.05% to about 22.5%, about 0.05% to about 25%, about 0.05% to about 30%, about 0.05% to about 40%, about 0.05% to about 50%, about 0.1% to about 1%, about 0.1% to about 2.5%, about 0.1% to about 5%, about 0.1% to about 7.5%, about 0.1% to about 10%, about 0.1% to about 12.5%, about 0.1% to about 15%, about 0.1% to about 17.5%, about 0.1% to about 20%, about 0.1% to about 22.5%, about 0.1% to about 25%, about 0.1% to about 30%, about 0.1% to about 40%, about 0.1% to about 50%, about 1% to about 2.5%, about 1% to about 5%, about 1% to about 7.5%, about 1% to about 10%, about 1% to about 12.5%, about 1% to about 15%, about 1% to about 17.5%, about 1% to about 20%, about 1% to about 22.5%, about 1% to about 25%, about 1% to about 30%, about 1% to about 40%, about 1% to about 50%, about 5% to about 10%, about 5% to about 20%, about 5% to about 30%, about 5% to about 40%, about 5% to about 50%, about 5% to about 60%, about 5% to about 70%, about 5% to about 80%, about 5% to about 90%, about 10% to about 20%, about 10% to about 30%, about 10% to about 40%, about 10% to about 50%, about 10% to about 60%, about 10% to about 70%, about 10% to about 80%, about 10% to about 90%, about 20% to about 30%, about 20% to about 40%, about 20% to about 50%, about 20% to about 60%, about 20% to about 70%, about 20% to about 80%, about 20% to about 90%, about 30% to about 40%, about 30% to about 50%, about 30% to about 60%, about 30% to about 70%, about 30% to about 80%, about 30% to about 90%, about 40% to about 50%, about 40% to about 60%, about 40% to about 70%, about 40% to about 80%, about 40% to about 90%, about 50% to about 60%, about 50% to about 70%, about 50% to about 80%, about 50% to about 90%, about 60% to about 70%, about 60% to about 80%, about 60% to about 90%, about 70% to about 80%, about 70% to about 90%, or about 80% to about 90% by weight.

In one embodiment, a pharmaceutical composition disclosed herein comprises one or more therapeutic compounds in a concentration of, e.g., about 25 mg/mL, about 30 mg/mL, about 35 mg/mL, about 40 mg/mL, about 45 mg/mL, about 50 mg/mL, about 60 mg/mL, about 65 mg/mL, about 70 mg/mL, about 75 mg/mL, about 100 mg/mL, about 125 mg/mL, about 150 mg/mL, about 175 mg/mL, about 200 mg/mL, about 225 mg/mL, about 250 mg/mL, about 275 mg/mL, about 300 mg/mL, about 325 mg/mL, about 350 mg/mL, about 375 mg/mL, about 400 mg/mL, about 425 mg/mL, about 450 mg/mL, about 475 mg/mL, about 500 mg/mL, about 525 mg/mL, about 550 mg/mL, about 575 mg/mL, or about 600 mg/mL. In one embodiment, a pharmaceutical composition disclosed herein comprises one or more therapeutic compounds in a concentration of, e.g., at least 25 mg/mL, at least 30 mg/mL, at least 35 mg/mL, at least 40 mg/mL, at least 45 mg/mL, at least 50 mg/mL, at least 60 mg/mL, at least 65 mg/mL, at least 70 mg/mL, at least 75 mg/mL, at least 100 mg/mL, at least 125 mg/mL, at least 150 mg/mL, at least 175 mg/mL, at least 200 mg/mL, at least 225 mg/mL, at least 250 mg/mL, at least 275 mg/mL, at least 300 mg/mL, at least 325 mg/mL, at least 350 mg/mL, at least 375 mg/mL, at least 400 mg/mL, at least 425 mg/mL, at least 450 mg/mL, at least 475 mg/mL, at least 500 mg/mL, at least 525 mg/mL, at least 550 mg/mL, at least 575 mg/mL, or at least 600 mg/mL. In one embodiment, a pharmaceutical composition disclosed herein comprises one or more therapeutic compounds in a concentration of, e.g., at most 25 mg/mL, at most 30 mg/mL, at most 35 mg/mL, at most 40 mg/mL, at most 45 mg/mL, at most 50 mg/mL, at most 60 mg/mL, at most 65 mg/mL, at most 70 mg/mL, at most 75 mg/mL, at most 100 mg/mL, at most 125 mg/mL, at most 150 mg/mL, at most 175 mg/mL, at most 200 mg/mL, at most 225 mg/mL, at most 250 mg/mL, at most 275 mg/mL, at most 300 mg/mL, at most 325 mg/mL, at most 350 mg/mL, at most 375 mg/mL, at most 400 mg/mL, at most 425 mg/mL, at most 450 mg/mL, at most 475 mg/mL, at most 500 mg/mL, at most 525 mg/mL, at most 550 mg/mL, at most 575 mg/mL, or at most 600 mg/mL.

In one embodiment, a pharmaceutical composition disclosed herein comprises one or more therapeutic compounds in a concentration of, e.g., about 25 mg/mL to about 50 mg/mL, about 25 mg/mL to about 75 mg/mL, about 25 mg/mL to about 100 mg/mL, about 25 mg/mL to about 125 mg/mL, about 25 mg/mL to about 150 mg/mL, about 25 mg/mL to about 200 mg/mL, about 25 mg/mL to about 250 mg/mL, about 25 mg/mL to about 300 mg/mL, about 25 mg/mL to about 350 mg/mL, about 25 mg/mL to about 400 mg/mL, about 25 mg/mL to about 450 mg/mL, about 25 mg/mL to about 500 mg/mL, about 25 mg/mL to about 550 mg/mL, about 25 mg/mL to about 600 mg/mL, about 50 mg/mL to about 100 mg/mL, about 50 mg/mL to about 150 mg/mL, about 50 mg/mL to about 200 mg/mL, about 50 mg/mL to about 250 mg/mL, about 50 mg/mL to about 300 mg/mL, about 50 mg/mL to about 350 mg/mL, about 50 mg/mL to about 400 mg/mL, about 50 mg/mL to about 450 mg/mL, about 50 mg/mL to about 500 mg/mL, about 50 mg/mL to about 550 mg/mL, about 50 mg/mL to about 600 mg/mL, about 75 mg/mL to about 100 mg/mL, about 75 mg/mL to about 150 mg/mL, about 75 mg/mL to about 200 mg/mL, about 75 mg/mL to about 250 mg/mL, about 75 mg/mL to about 300 mg/mL, about 75 mg/mL to about 350 mg/mL, about 75 mg/mL to about 400 mg/mL, about 75 mg/mL to about 450 mg/mL, about 75 mg/mL to about 500 mg/mL, about 75 mg/mL to about 550 mg/mL, about 75 mg/mL to about 600 mg/mL, about 100 mg/mL to about 150 mg/mL, about 100 mg/mL to about 200 mg/mL, about 100 mg/mL to about 250 mg/mL, about 100 mg/mL to about 300 mg/mL, about 100 mg/mL to about 350 mg/mL, about 100 mg/mL to about 400 mg/mL, about 100 mg/mL to about 450 mg/mL, about 100 mg/mL to about 500 mg/mL, about 100 mg/mL to about 550 mg/mL, about 100 mg/mL to about 600 mg/mL, about 150 mg/mL to about 200 mg/mL, about 150 mg/mL to about 250 mg/mL, about 150 mg/mL to about 300 mg/mL, about 150 mg/mL to about 350 mg/mL, about 150 mg/mL to about 400 mg/mL, about 150 mg/mL to about 450 mg/mL, about 150 mg/mL to about 500 mg/mL, about 150 mg/mL to about 550 mg/mL, about 150 mg/mL to about 600 mg/mL, about 200 mg/mL to about 250 mg/mL, about 200 mg/mL to about 300 mg/mL, about 200 mg/mL to about 350 mg/mL, about 200 mg/mL to about 400 mg/mL, about 200 mg/mL to about 450 mg/mL, about 200 mg/mL to about 500 mg/mL, about 200 mg/mL to about 550 mg/mL, about 200 mg/mL to about 600 mg/mL, about 250 mg/mL to about 300 mg/mL, about 250 mg/mL to about 350 mg/mL, about 250 mg/mL to about 400 mg/mL, about 250 mg/mL to about 450 mg/mL, about 250 mg/mL to about 500 mg/mL, about 250 mg/mL to about 550 mg/mL, about 250 mg/mL to about 600 mg/mL, about 300 mg/mL to about 350 mg/mL, about 300 mg/mL to about 400 mg/mL, about 300 mg/mL to about 450 mg/mL, about 300 mg/mL to about 500 mg/mL, about 300 mg/mL to about 550 mg/mL, about 300 mg/mL to about 600 mg/mL, about 350 mg/mL to about 400 mg/mL, about 350 mg/mL to about 450 mg/mL, about 350 mg/mL to about 500 mg/mL, about 350 mg/mL to about 550 mg/mL, about 350 mg/mL to about 600 mg/mL, about 400 mg/mL to about 450 mg/mL, about 400 mg/mL to about 500 mg/mL, about 400 mg/mL to about 550 mg/mL, about 400 mg/mL to about 600 mg/mL, about 450 mg/mL to about 500 mg/mL, about 450 mg/mL to about 550 mg/mL, about 450 mg/mL to about 600 mg/mL, about 500 mg/mL to about 550 mg/mL, about 500 mg/mL to about 600 mg/mL, and about 550 mg/mL to about 600 mg/mL.

Glycerolipids

A pharmaceutical composition disclosed herein may comprises one or more glycerolipids. Glycerolipids are composed mainly of mono-, di-, and tri-substituted glycerols and are hydrophobic molecules having an HLB of less than 4. One group of glycerolipids is the glycerides, where one, two, or all three hydroxyl groups of glycerol are each esterified using a fatty acid to produce monoglycerides, diglycerides, and triglycerides, respectively. In these compounds, each hydroxyl groups of glycerol may be esterified by the same fatty acid or different fatty acids. In some embodiments, a monoglyceride disclosed herein may include a saturated or unsaturated fatty acid having a carbon length of $C_{12}$-$C_{24}$. In some embodiments, a diglyceride disclosed herein may include one saturated or unsaturated fatty acid having a carbon length of $C_{12}$-$C_{24}$, or two saturated or unsaturated fatty acids each having a carbon length of $C_{12}$-$C_{24}$. In some embodiments, a triglyceride disclosed herein may include one saturated or unsaturated fatty acid having a carbon length of $C_{12}$-$C_{24}$, two saturated or unsaturated fatty acids each having a carbon length of $C_{12}$-$C_{24}$, or three saturated or unsaturated fatty acids each having a carbon length of $C_{12}$-$C_{24}$.

Two types of glycerolipids are used in formulating one or more therapeutic compounds disclosed herein to produce a pharmaceutical composition disclosed herein. One type is hard fats, namely glycerolipids that are solid at 18° C. A disclosed hard fat or glycerolipid that is solid at 18° C. has several purposes. During the formulation process of a pharmaceutical composition disclosed herein, a hard fat complexes with a therapeutic compound disclosed herein, stabilizes it in a glycerolipid matrix that prevents the compound from precipitating out. Additionally, during administration of a pharmaceutical composition disclosed herein, a hard fat disclosed herein triggers the lipid digestion process stimulating the release of bile from the gallbladder to enhance the emulsification of the administered pharmaceutical composition. Furthermore, the hard fats present in the pharmaceutical composition serve as substrates for pancreatic lipase which breaks down these hard fats into glycerol and free fatty acids. The presence of these digested lipid molecules triggers their absorption, along with the associated therapeutic compound, by the enterocytes lining the lumen of the duodenum of the small intestine. Once internalized, the enterocytes subsequent process and distribute the free fatty acid/therapeutic compound mixture into the lymphatic system. A disclosed hard fat or glycerolipid that is solid at 18° C. do not have emulsion forming properties since these lipids does not exhibit a critical micelle concentration. As such, another purpose of a disclosed hard fat or glycerolipid that is solid at 18° C. is to prevent formulary components that do possess a critical micelle concentration from initiating emulsification by diluting these components to below their critical micelle concentration and providing an anhydrous environment that reduces the necessary interaction of these components to initiate emulsification.

The other type of glycerolipid used in formulating one or more therapeutic compounds disclosed herein is liquid fats or oils, namely glycerolipids that are liquid at 18° C. The primary purposes of a disclosed liquid fat or glycerolipid that is liquid at 18° C. is as a solvent that facilitates dissolvement of a therapeutic compound disclosed herein as well as a stabilizing agent that prevents a disclosed therapeutic compound from precipitating out of the glycerolipid matrix. A disclosed liquid fat or glycerolipid that is liquid at 18° C. do not have emulsion forming properties since these lipids does not exhibit a critical micelle concentration. As such, another purpose of a disclosed liquid fat or glycerolipid that is liquid at 18° C. is to prevent formulary components that do possess a critical micelle concentration from initiating emulsification by diluting these components to below their critical micelle concentration and providing an anhydrous environment that reduces the necessary interaction of these components to initiate emulsification.

In some embodiments, a pharmaceutical composition disclosed herein may include one or more glycerolipids in an amount of, e.g., about 20% by weight, about 25% by weight, about 30% by weight, about 35% by weight, about 40% by weight, about 45% by weight, about 50% by weight, about 55% by weight, about 60% by weight, about 65% by weight, about 70% by weight, about 75% by weight, about 80% by weight, about 85% by weight, about 90% by weight, or about 95% by weight. In some embodiments, a pharmaceutical composition disclosed herein may include one or more glycerolipids in an amount of, e.g., at least 20% by weight, at least 25% by weight, at least 30% by weight, at least 35% by weight, at least 40% by weight, at least 45% by weight, at least 50% by weight, at least 55% by weight, at least 60% by weight, at least 65% by weight, at least 70% by weight, at least 75% by weight, at least 80% by weight, at least 85% by weight, at least 90% by weight, or at least 95% by weight. In some embodiments, a pharmaceutical composition disclosed herein may include one or more glycerolipids in an amount of, e.g., at most 20% by weight, at most 25% by weight, at most 30% by weight, at most 35% by weight, at most 40% by weight, at most 45% by weight, at most 50% by weight, at most 55% by weight, at most 60% by weight, at most 65% by weight, at most 70% by weight, at most 75% by weight, at most 80% by weight, at most 85% by weight, at most 90% by weight, at most 95% by weight, or at most 99% by weight.

In some embodiments, a pharmaceutical composition disclosed herein may include one or more glycerolipids in an amount of, e.g., about 20% to about 30%, about 20% to about 40%, about 20% to about 50%, about 20% to about 55%, about 20% to about 60%, about 20% to about 70%, about 20% to about 80%, about 20% to about 90%, about 25% to about 30%, about 25% to about 40%, about 25% to about 50%, about 25% to about 55%, about 25% to about 60%, about 25% to about 70%, about 25% to about 80%, about 25% to about 90%, about 30% to about 40%, about 30% to about 50%, about 30% to about 55%, about 30% to about 60%, about 30% to about 70%, about 30% to about 80%, about 30% to about 90%, about 40% to about 50%, about 40% to about 55%, about 40% to about 60%, about 40% to about 65%, about 40% to about 70%, about 40% to about 75%, about 40% to about 80%, about 40% to about 85%, about 40% to about 90%, about 40% to about 95%, about 45% to about 55%, about 45% to about 60%, about 45% to about 65%, about 45% to about 70%, about 45% to about 75%, about 45% to about 80%, about 45% to about 85%, about 45% to about 90%, about 45% to about 95%, about 50% to about 55%, about 50% to about 60%, about 50% to about 65%, about 50% to about 70%, about 50% to about 75%, about 50% to about 80%, about 50% to about 85%, about 50% to about 90%, about 50% to about 95%, about 55% to about 60%, about 55% to about 65%, about 55% to about 70%, about 55% to about 75%, about 55% to about 80%, about 55% to about 85%, about 55% to about 90%, about 55% to about 95%, about 60% to about 65%, about 60% to about 70%, about 60% to about 75%, about 60% to about 80%, about 60% to about 85%, about 60% to about 90%, about 60% to about 95%, about 65% to about 70%, about 65% to about 75%, about 65% to about 80%, about 65% to about 85%, about 65% to about 90%, about 65% to about 95%, about 70% to about 75%, about 70% to about 80%, about 70% to about 85%, about 70% to about 90%, about 70% to about 95%, about 75% to about 80%, about 75% to about 85%, about 75% to about 90%, about 75% to about 95%, about 80% to about 85%, about 80% to about 90%, about 80% to about 95%, about 80% to about 99%, about 85% to about 90%, about 85% to about 95%, about 85% to about 99%, about 90% to about 95%, or about 90% to about 99% by weight.

In some embodiments, pharmaceutical composition disclosed herein may include one or more hard fats or glycerolipids that are solid at 18° C. comprising, or consisting essentially of or consisting of a mixture of saturated $C_{10}$-$C_{18}$ triglycerides, a mixture of saturated $C_{10}$-$C_{20}$ triglycerides, a mixture of saturated $C_{10}$-$C_{22}$ triglycerides, a mixture of saturated $C_{10}$-$C_{24}$ triglycerides, a mixture of saturated $C_{12}$-$C_{18}$ triglycerides, a mixture of saturated $C_{12}$-$C_{20}$ triglycerides, a mixture of saturated $C_{12}$-$C_{22}$ triglycerides, a mixture of saturated $C_{12}$-$C_{24}$ triglycerides, a mixture of saturated $C_{14}$-$C_{18}$ triglycerides, a mixture of saturated $C_{14}$-$C_{20}$ triglycerides, a mixture of saturated $C_{14}$-$C_{22}$ triglycerides, a mixture of saturated $C_{14}$-$C_{24}$ triglycerides, a mixture of saturated $C_{16}$-$C_{18}$ triglycerides, a mixture of saturated $C_{16}$-$C_{20}$ triglycerides, a mixture of saturated $C_{16}$-$C_{22}$ triglycerides, a mixture of saturated $C_{16}$-$C_{24}$ triglycerides, a mixture of saturated $C_{18}$-$C_{20}$ triglycerides, a mixture of saturated $C_{18}$-$C_{22}$ triglycerides, a mixture of saturated $C_{18}$-$C_{24}$ triglycerides, a mixture of saturated $C_{20}$-$C_{22}$ triglycerides, or a mixture of saturated $C_{22}$-$C_{24}$ triglycerides.

In some embodiments, pharmaceutical composition disclosed herein may include one or more hard fats or glycerolipids that are solid at 18° C. comprising, or consisting essentially of or consisting of a mixture of unsaturated $C_{10}$-$C_{18}$ triglycerides, a mixture of unsaturated $C_{10}$-$C_{20}$ triglycerides, a mixture of unsaturated $C_{10}$-$C_{22}$ triglycerides, a mixture of unsaturated $C_{10}$-$C_{24}$ triglycerides, a mixture of unsaturated $C_{12}$-$C_{18}$ triglycerides, a mixture of unsaturated $C_{12}$-$C_{20}$ triglycerides, a mixture of unsaturated $C_{12}$-$C_{22}$ triglycerides, a mixture of unsaturated $C_{12}$-$C_{24}$ triglycerides, a mixture of unsaturated $C_{14}$-$C_{18}$ triglycerides, a mixture of unsaturated $C_{14}$-$C_{20}$ triglycerides, a mixture of unsaturated $C_{14}$-$C_{22}$ triglycerides, a mixture of unsaturated $C_{14}$-$C_{24}$ triglycerides, a mixture of unsaturated $C_{16}$-$C_{18}$ triglycerides, a mixture of unsaturated $C_{16}$-$C_{20}$ triglycerides, a mixture of unsaturated $C_{16}$-$C_{22}$ triglycerides, a mixture of unsaturated $C_{16}$-$C_{24}$ triglycerides, a mixture of unsaturated $C_{18}$-$C_{20}$ triglycerides, a mixture of unsaturated $C_{18}$-$C_{22}$ triglycerides, a mixture of unsaturated $C_{18}$-$C_{24}$ triglycerides, a mixture of unsaturated $C_{20}$-$C_{22}$ triglycerides, or a mixture of unsaturated $C_{22}$-$C_{24}$ triglycerides.

In some embodiments, pharmaceutical composition disclosed herein may include one or more hard fats or glycerolipids that are solid at 18° C. comprising, or consisting essentially of or consisting of a mixture of saturated and unsaturated $C_{10}$-$C_{18}$ triglycerides, a mixture of saturated and unsaturated $C_{10}$-$C_{20}$ triglycerides, a mixture of saturated and unsaturated $C_{10}$-$C_{22}$ triglycerides, a mixture of saturated and unsaturated $C_{10}$-$C_{24}$ triglycerides, a mixture of saturated and unsaturated $C_{12}$-$C_{18}$ triglycerides, a mixture of saturated and unsaturated $C_{12}$-$C_{20}$ triglycerides, a mixture of saturated and unsaturated $C_{12}$-$C_{22}$ triglycerides, a mixture of saturated and unsaturated $C_{12}$-$C_{24}$ triglycerides, a mixture of saturated and unsaturated $C_{14}$-$C_{18}$ triglycerides, a mixture of saturated and unsaturated $C_{14}$-$C_{20}$ triglycerides, a mixture of saturated and unsaturated $C_{14}$-$C_{22}$ triglycerides, a mixture of saturated and unsaturated $C_{14}$-$C_{24}$ triglycerides, a mixture of saturated and unsaturated $C_{16}$-$C_{18}$ triglycerides, a mixture of saturated and unsaturated $C_{16}$-$C_{20}$ triglycerides, a mixture of saturated and unsaturated $C_{16}$-$C_{22}$ triglycerides, a mixture of saturated and unsaturated $C_{16}$-$C_{24}$ triglycerides, a mixture of saturated and unsaturated $C_{18}$-$C_{20}$ triglycerides, a mixture of saturated and unsaturated $C_{18}$-$C_{22}$ triglycerides, a mixture of saturated and unsaturated $C_{18}$-$C_{24}$ triglycerides, a mixture of saturated and unsaturated $C_{20}$-$C_{22}$ triglycerides, or a mixture of saturated and unsaturated $C_{22}$-$C_{24}$ triglycerides.

In some embodiments, a pharmaceutical composition disclosed herein may include one or more hard fats or glycerolipids that are solid at 18° C. comprising, or consisting essentially of or consisting of a mixture of triglycerides having a melting point of, e.g., about 25° C., about 26° C., about 27° C., about 28° C., about 29° C., about 30° C., about 31° C., about 32° C., about 33° C., about 34° C., about 35° C., about 36° C., about 37° C., about 38° C., about 39° C., about 40° C., about 41° C., about 43° C., about 43° C., about 44° C., about 45° C., about 45° C., about 47° C., about 48° C., about 49° C., or about 50° C. In some embodiments, a pharmaceutical composition disclosed herein may include one or more hard fats or glycerolipids that are solid at 18° C. comprising, or consisting essentially of or consisting of a mixture of triglycerides having a melting point of, e.g., at least 25° C., at least 26° C., at least 27° C., at least 28° C., at least 29° C., at least 30° C., at least 31° C., at least 32° C., at least 33° C., at least 34° C., at least 35° C., at least 36° C., at least 37° C., at least 38° C., at least 39° C., at least 40° C., at least 41° C., at least 43° C., at least 43° C., at least 44° C., at least 45° C., at least 45° C., at least 47° C., at least 48° C., at least 49° C., or at least 50° C. In some embodiments, a pharmaceutical composition disclosed herein may include one or more hard fats or glycerolipids that are solid at 18° C. comprising, or consisting essentially of or consisting of a mixture of triglycerides having a melting point of, e.g., at most 25° C., at most 26° C., at most 27° C., at most 28° C., at most 29° C., at most 30° C., at most 31° C., at most 32° C., at most 33° C., at most 34° C., at most 35° C., at most 36° C., at most 37° C., at most 38° C., at most 39° C., at most 40° C., at most 41° C., at most 43° C., at most 43° C., at most 44° C., at most 45° C., at most 45° C., at most 47° C., at most 48° C., at most 49° C., or at most 50° C.

In some embodiment, a pharmaceutical composition disclosed herein may include one or more hard fats or glycerolipids that are solid at 18° C. comprising, or consisting essentially of or consisting of a mixture of triglycerides having a melting point of, e.g., about 25° C. to about 37° C., about 25° C. to about 38° C., about 25° C. to about 39° C., about 25° C. to about 40° C., about 25° C. to about 41° C., about 25° C. to about 42° C., about 25° C. to about 43° C., about 25° C. to about 44° C., about 25° C. to about 45° C., about 25° C. to about 46° C., about 25° C. to about 47° C., about 25° C. to about 48° C., about 25° C. to about 49° C., about 25° C. to about 50° C., about 28° C. to about 37° C., about 28° C. to about 38° C., about 28° C. to about 39° C., about 28° C. to about 40° C., about 28° C. to about 41° C., about 28° C. to about 42° C., about 28° C. to about 43° C., about 28° C. to about 44° C., about 28° C. to about 45° C., about 28° C. to about 46° C., about 28° C. to about 47° C., about 28° C. to about 48° C., about 28° C. to about 49° C., about 28° C. to about 50° C., about 30° C. to about 37° C., about 30° C. to about 38° C., about 30° C. to about 39° C., about 30° C. to about 40° C., about 30° C. to about 41° C., about 30° C. to about 42° C., about 30° C. to about 43° C., about 30° C. to about 44° C., about 30° C. to about 45° C., about 30° C. to about 46° C., about 30° C. to about 47° C., about 30° C. to about 48° C., about 30° C. to about 49° C., about 30° C. to about 50° C., about 32° C. to about 44° C., about 32° C. to about 45° C., about 32° C. to about 46° C., about 32° C. to about 47° C., about 32° C. to about 48° C., about 32° C. to about 49° C., about 32° C. to about 50° C., about 34° C. to about 44° C., about 34° C. to about 45° C., about 34° C. to about 46° C., about 34° C. to about 47° C., about 34° C. to about 48° C., about 34° C. to about 49° C., about 34° C. to about 50° C., about 36° C. to about 44° C., about 36° C. to about 45° C., about 36° C. to about 46° C., about 36° C. to about 47° C., about 36° C. to about 48° C., about 36° C. to about 49° C., about 36° C. to about 50° C., about 38° C. to about 44° C., about 38° C. to about 45° C., about 38° C. to about 46° C., about 38° C. to about 47° C., about 38° C. to about 48° C., about 38° C. to about 49° C., about 38° C. to about 50° C., about 40° C. to about 44° C., about 40° C. to about 45° C., about 40° C. to about 46° C., about 40° C. to about 47° C., about 40° C. to about 48° C., about 40° C. to about 49° C., about 40° C. to about 50° C., about 42° C. to about 44° C., about 42° C. to about 45° C., about 42° C. to about 46° C., about 42° C. to about 47° C., about 42° C. to about 48° C., about 42° C. to about 49° C., or about 42° C. to about 50° C.

In some embodiments, a pharmaceutical composition disclosed herein may include one or more hard fats or glycerolipids that are solid at 18° C. comprising, or consisting essentially of or consisting of a mixture of triglycerides in an amount of, e.g., about 10% by weight, about 15% by weight, about 20% by weight, about 25% by weight, about 30% by weight, about 35% by weight, about 40% by weight, about 45% by weight, about 50% by weight, about 55% by weight, about 60% by weight, about 65% by weight, about 70% by weight, or about 75% by weight. In some embodiments, a pharmaceutical composition disclosed herein may include one or more hard fats or glycerolipids that are solid at 18° C. comprising, or consisting essentially of or consisting of a mixture of triglycerides in an amount of, e.g., at least 10% by weight, at least 15% by weight, at least 20% by weight, at least 25% by weight, at least 30% by weight, at least 35% by weight, at least 40% by weight, at least 45% by weight, at least 50% by weight, at least 55% by weight, at least 60% by weight, at least 65% by weight, at least 70% by weight, or at least 75% by weight. In some embodiments, a pharmaceutical composition disclosed herein may include one or more hard fats or glycerolipids that are solid at 18° C. comprising, or consisting essentially of or consisting of a mixture of triglycerides in an amount of, e.g., at most 10% by weight, at most 15% by weight, at most 20% by weight, at most 25% by weight, at most 30% by weight, at most 35% by weight, at most 40% by weight, at most 45% by weight, at most 50% by weight, at most 55% by weight, at most 60% by weight, at most 65% by weight, at most 70% by weight, at most 75% by weight, at most 80% by weight, at most 85% by weight, at most 90% by weight, at most 95% by weight, or at most 99% by weight.

In some embodiments, a pharmaceutical composition disclosed herein may include one or more hard fats or glycerolipids that are solid at 18° C. comprising, or consisting essentially of or consisting of a mixture of triglycerides in an amount of, e.g., about 10% to about 20%, about 10% to about 25%, about 10% to about 30%, about 10% to about 35%, about 10% to about 40%, about 10% to about 45%, about 10% to about 50%, about 10% to about 55%, about 10% to about 60%, about 10% to about 65%, about 10% to about 70%, about 15% to about 20%, about 15% to about 25%, about 15% to about 30%, about 15% to about 35%, about 15% to about 40%, about 15% to about 45%, about 15% to about 50%, about 15% to about 55%, about 15% to about 60%, about 15% to about 65%, about 15% to about 70%, about 20% to about 25%, about 20% to about 30%, about 20% to about 35%, about 20% to about 40%, about 20% to about 45%, about 20% to about 50%, about 20% to about 55%, about 20% to about 60%, about 20% to about 65%, about 20% to about 70%, about 25% to about 30%, about 25% to about 35%, about 25% to about 40%, about 25% to about 45%, about 25% to about 50%, about 25% to about 55%, about 25% to about 60%, about 25% to about 65%, about 25% to about 70%, about 30% to about 35%, about 30% to about 40%, about 30% to about 45%, about 30% to about 50%, about 30% to about 55%, about 30% to about 60%, about 30% to about 65%, about 30% to about 70%, about 35% to about 40%, about 35% to about 45%, about 35% to about 50%, about 35% to about 55%, about 35% to about 60%, about 35% to about 65%, about 35% to about 70%, about 40% to about 45%, about 40% to about 50%, about 40% to about 55%, about 40% to about 60%, about 40% to about 65%, about 40% to about 70%, about 45% to about 50%, about 45% to about 55%, about 45% to about 60%, about 45% to about 65%, about 45% to about 70%, about 50% to about 55%, about 50% to about 60%, about 50% to about 65%, about 50% to about 70%, about 55% to about 60%, about 55% to about 65%, about 55% to about 70%, about 60% to about 65%, about 60% to about 70%, or about 65% to about 70% by weight.

In some embodiments, a pharmaceutical composition disclosed herein may include one or more liquid fats or glycerolipids that are liquid at 18° C. comprising, or consisting essentially of or consisting of a mixture of mono-, di- and triglycerides. In some embodiments, pharmaceutical composition disclosed herein may include one or more liquid fats or glycerolipids that are liquid at 18° C. comprising, or consisting essentially of or consisting of a mixture of unsaturated $C_{10}$-$C_{18}$ monoglycerides, $C_{10}$-$C_{18}$ diglycerides, and triglycerides, a mixture of unsaturated $C_{10}$-$C_{20}$ monoglycerides, $C_{10}$-$C_{20}$ diglycerides, and $C_{10}$-$C_{20}$ triglycerides, a mixture of unsaturated $C_{10}$-$C_{22}$ monoglycerides, $C_{10}$-$C_{22}$ diglycerides, and $C_{10}$-$C_{22}$ triglycerides, a mixture of unsaturated $C_{10}$-$C_{24}$ monoglycerides, $C_{10}$-$C_{24}$ diglycerides, and $C_{10}$-$C_{24}$ triglycerides, a mixture of unsaturated $C_{12}$-$C_{18}$ monoglycerides, $C_{12}$-$C_{18}$ diglycerides, and $C_{12}$-$C_{18}$ triglycerides, a mixture of unsaturated $C_{12}$-$C_{20}$ monoglycerides, $C_{12}$-$C_{20}$ diglycerides, and $C_{12}$-$C_{20}$ triglycerides, a mixture of unsaturated $C_{12}$-$C_{22}$ monoglycerides, $C_{12}$-$C_{22}$ diglycerides, and $C_{12}$-$C_{22}$ triglycerides, a mixture of unsaturated $C_{12}$-$C_{24}$ monoglycerides, $C_{12}$-$C_{24}$ diglycerides, and $C_{12}$-$C_{24}$ triglycerides, a mixture of unsaturated $C_{14}$-$C_{18}$ monoglycerides, $C_{14}$-$C_{18}$ diglycerides, and $C_{14}$-$C_{18}$ triglycerides, a mixture of unsaturated $C_{14}$-$C_{20}$ monoglycerides, $C_{14}$-$C_{20}$ diglycerides, and $C_{14}$-$C_{20}$ triglycerides, a mixture of unsaturated $C_{14}$-$C_{22}$ monoglycerides, $C_{14}$-$C_{22}$ diglycerides, and $C_{14}$-$C_{22}$ triglycerides, a mixture of unsaturated $C_{14}$-$C_{24}$ monoglycerides, $C_{14}$-$C_{24}$ diglycerides, and $C_{14}$-$C_{24}$ triglycerides, a mixture of unsaturated $C_{16}$-$C_{18}$ monoglycerides, $C_{16}$-$C_{18}$ diglycerides, and $C_{16}$-$C_{18}$ triglycerides, a mixture of unsaturated $C_{16}$-$C_{20}$ monoglycerides, $C_{16}$-$C_{20}$ diglycerides, and $C_{16}$-$C_{20}$ triglycerides, a mixture of unsaturated $C_{16}$-$C_{22}$ monoglycerides, $C_{16}$-$C_{22}$ diglycerides, and $C_{16}$-$C_{22}$ triglycerides, a mixture of unsaturated $C_{16}$-$C_{24}$ monoglycerides, $C_{16}$-$C_{24}$ diglycerides, and $C_{16}$-$C_{24}$ triglycerides, a mixture of unsaturated $C_{18}$-$C_{20}$ monoglycerides, $C_{18}$-$C_{20}$ diglycerides, and $C_{18}$-$C_{20}$ triglycerides, a mixture of unsaturated $C_{18}$-$C_{22}$ monoglycerides, $C_{18}$-$C_{22}$ diglycerides, and $C_{18}$-$C_{22}$ triglycerides, a mixture of unsaturated $C_{18}$-$C_{24}$ monoglycerides, $C_{18}$-$C_{24}$ diglycerides, and $C_{18}$-$C_{24}$ triglycerides, a mixture of unsaturated $C_{20}$-$C_{22}$ monoglycerides, $C_{20}$-$C_{22}$ diglycerides, $C_{20}$-$C_{22}$ triglycerides, or a mixture of unsaturated $C_{22}$-$C_{24}$ monoglycerides, $C_{22}$-$C_{24}$ diglycerides, and $C_{22}$-$C_{24}$ triglycerides.

In some embodiments, a pharmaceutical composition disclosed herein may include one or more liquid fats or glycerolipids that are liquid at 18° C. comprising, or consisting essentially of or consisting of a mixture of saturated $C_{10}$-$C_{18}$ monoglycerides, $C_{10}$-$C_{20}$ diglycerides, and $C_{10}$-$C_{18}$ triglycerides, a mixture of saturated $C_{10}$-$C_{20}$ monoglycerides, $C_{10}$-$C_{20}$ diglycerides, and $C_{10}$-$C_{20}$ triglycerides, a mixture of saturated $C_{10}$-$C_{22}$ monoglycerides, $C_{10}$-$C_{22}$ diglycerides, and $C_{10}$-$C_{22}$ triglycerides, a mixture of saturated $C_{10}$-$C_{24}$ monoglycerides, $C_{10}$-$C_{24}$ diglycerides, and $C_{10}$-$C_{24}$ triglycerides, a mixture of saturated $C_{12}$-$C_{18}$ monoglycerides, $C_{12}$-$C_{18}$ diglycerides, and $C_{12}$-$C_{18}$ triglycerides, a mixture of saturated $C_{12}$-$C_{20}$ monoglycerides, $C_{12}$-$C_{20}$ diglycerides, and $C_{12}$-$C_{20}$ triglycerides, a mixture of saturated $C_{12}$-$C_{22}$ monoglycerides, $C_{12}$-$C_{22}$ diglycerides, and $C_{12}$-$C_{22}$ triglycerides, a mixture of saturated $C_{12}$-$C_{24}$ monoglycerides, $C_{12}$-$C_{24}$ diglycerides, and $C_{12}$-$C_{24}$ triglycerides, a mixture of saturated $C_{14}$-$C_{18}$ monoglycerides, $C_{14}$-$C_{18}$ diglycerides, and $C_{14}$-$C_{18}$ triglycerides, a mixture of saturated $C_{14}$-$C_{20}$ monoglycerides, $C_{14}$-$C_{20}$ diglycerides, and $C_{14}$-$C_{20}$ triglycerides, a mixture of saturated $C_{14}$-$C_{22}$ monoglycerides, $C_{14}$-$C_{22}$ diglycerides, and $C_{14}$-$C_{22}$ triglycerides, a mixture of saturated $C_{14}$-$C_{24}$ monoglycerides, $C_{14}$-$C_{24}$ diglycerides, and $C_{14}$-$C_{24}$ triglycerides, a mixture of saturated $C_{16}$-$C_{18}$ monoglycerides, $C_{16}$-$C_{18}$ diglycerides, and $C_{16}$-$C_{18}$ triglycerides, a mixture of saturated $C_{16}$-$C_{20}$ monoglycerides, $C_{16}$-$C_{20}$ diglycerides, and $C_{16}$-$C_{20}$ triglycerides, a mixture of saturated $C_{16}$-$C_{22}$ monoglycerides, $C_{16}$-$C_{22}$ diglycerides, and $C_{16}$-$C_{22}$ triglycerides, a mixture of saturated $C_{16}$-$C_{24}$ monoglycerides, $C_{16}$-$C_{24}$ diglycerides, and $C_{16}$-$C_{24}$ triglycerides, a mixture of saturated $C_{18}$-$C_{20}$ monoglycerides, $C_{18}$-$C_{20}$ diglycerides, and $C_{18}$-$C_{20}$ triglycerides, a mixture of saturated $C_{18}$-$C_{22}$ monoglycerides, $C_{18}$-$C_{22}$ diglycerides, and $C_{18}$-$C_{22}$ triglycerides, a mixture of saturated $C_{18}$-$C_{24}$ monoglycerides, $C_{18}$-$C_{24}$ diglycerides, and $C_{18}$-$C_{24}$ triglycerides, a mixture of saturated $C_{20}$-$C_{22}$ monoglycerides, $C_{20}$-$C_{22}$ diglycerides, $C_{20}$-$C_{22}$ triglycerides, or a mixture of saturated $C_{22}$-$C_{24}$ monoglycerides, $C_{22}$-$C_{24}$ diglycerides, and $C_{22}$-$C_{24}$ triglycerides.

In some embodiments, a pharmaceutical composition disclosed herein may include one or more liquid fats or glycerolipids that are liquid at 18° C. comprising, or consisting essentially of or consisting of a mixture of saturated and unsaturated $C_{10}$-$C_{18}$ monoglycerides, $C_{10}$-$C_{18}$ diglycerides, and $C_{10}$-$C_{18}$ triglycerides, a mixture of saturated and unsaturated $C_{10}$-$C_{20}$ monoglycerides, $C_{10}$-$C_{20}$ diglycerides, and $C_{10}$-$C_{20}$ triglycerides, a mixture of saturated and unsaturated $C_{10}$-$C_{22}$ monoglycerides, $C_{10}$-$C_{22}$ diglycerides, and $C_{10}$-$C_{22}$ triglycerides, a mixture of saturated and unsaturated $C_{10}$-$C_{24}$ monoglycerides, $C_{10}$-$C_{24}$ diglycerides, and $C_{10}$-$C_{24}$ triglycerides, a mixture of saturated and unsaturated $C_{12}$-$C_{18}$ monoglycerides, $C_{12}$-$C_{18}$ diglycerides, and $C_{12}$-$C_{18}$ triglycerides, a mixture of saturated and unsaturated $C_{12}$-$C_{20}$ monoglycerides, $C_{12}$-$C_{20}$ diglycerides, and $C_{12}$-$C_{20}$ triglycerides, a mixture of saturated and unsaturated $C_{12}$-$C_{22}$ monoglycerides, $C_{12}$-$C_{22}$ diglycerides, and $C_{12}$-$C_{22}$ triglycerides, a mixture of saturated and unsaturated $C_{12}$-$C_{24}$ monoglycerides, $C_{12}$-$C_{24}$ diglycerides, and $C_{12}$-$C_{24}$ triglycerides, a mixture of saturated and unsaturated $C_{14}$-$C_{18}$ monoglycerides, $C_{14}$-$C_{18}$ diglycerides, and $C_{14}$-$C_{18}$ triglycerides, a mixture of saturated and unsaturated $C_{14}$-$C_{20}$ monoglycerides, $C_{14}$-$C_{20}$ diglycerides, and $C_{14}$-$C_{20}$ triglycerides, a mixture of saturated and unsaturated $C_{14}$-$C_{22}$ monoglycerides, $C_{14}$-$C_{22}$ diglycerides, and $C_{14}$-$C_{22}$ triglycerides, a mixture of saturated and unsaturated $C_{14}$-$C_{24}$ monoglycerides, $C_{14}$-$C_{24}$ diglycerides, and $C_{14}$-$C_{24}$ triglycerides, a mixture of saturated and unsaturated $C_{16}$-$C_{18}$ monoglycerides, $C_{16}$-$C_{18}$ diglycerides, and $C_{16}$-$C_{18}$ triglycerides, a mixture of saturated and unsaturated $C_{16}$-$C_{20}$ monoglycerides, $C_{16}$-$C_{20}$ diglycerides, and $C_{16}$-$C_{20}$ triglycerides, a mixture of saturated and unsaturated $C_{16}$-$C_{22}$ monoglycerides, $C_{16}$-$C_{22}$ diglycerides, and $C_{16}$-$C_{22}$ triglycerides, a mixture of saturated and unsaturated $C_{16}$-$C_{24}$ monoglycerides, $C_{16}$-$C_{24}$ diglycerides, and $C_{16}$-$C_{24}$ triglycerides, a mixture of saturated and unsaturated $C_{18}$-$C_{20}$ monoglycerides, $C_{18}$-$C_{20}$ diglycerides, and $C_{18}$-$C_{20}$ triglycerides, a mixture of saturated and unsaturated $C_{18}$-$C_{22}$ monoglycerides, $C_{18}$-$C_{22}$ diglycerides, and $C_{18}$-$C_{22}$ triglycerides, a mixture of saturated and unsaturated $C_{18}$-$C_{24}$ monoglycerides, $C_{18}$-$C_{24}$ diglycerides, and $C_{18}$-$C_{24}$ triglycerides, a mixture of saturated and unsaturated $C_{20}$-$C_{22}$ monoglycerides, $C_{20}$-$C_{22}$ diglycerides, $C_{20}$-$C_{22}$ triglycerides, or a mixture of saturated and unsaturated $C_{22}$-$C_{24}$ monoglycerides, $C_{22}$-$C_{24}$ diglycerides, and $C_{22}$-$C_{24}$ triglycerides.

In some embodiments, a pharmaceutical composition disclosed herein may include one or more liquid fats or glycerolipids that are liquid at 18° C. comprising, or consisting essentially of or consisting of a mixture of mono-, di- and triglycerides having a melting point of, e.g., at most 15° C., at most 16° C., at most 17° C., at most 18° C., at most 19° C., or at most 20° C. In some embodiments, a pharmaceutical composition disclosed herein may include one or more liquid fats or glycerolipids that are liquid at 18° C. comprising, or consisting essentially of or consisting of a mixture of mono-, di- and triglycerides having a melting point between, e.g., about 0° C. to about 5° C., about 0° C. to about 10° C., about 0° C. to about 15° C., about 0° C. to about 20° C., about 0° C. to about 22° C., about 0° C. to about 25° C., about 5° C. to about 10° C., about 5° C. to about 15° C., about 5° C. to about 20° C., about 5° C. to about 22° C., about 5° C. to about 25° C., about 10° C. to about 15° C., about 10° C. to about 20° C., about 10° C. to about 22° C., about 10° C. to about 25° C., about 15° C. to about 20° C., about 15° C. to about 22° C., or about 15° C. to about 25° C.

In some embodiments, a pharmaceutical composition disclosed herein may include one or more liquid fats or glycerolipids that are liquid at 18° C. comprising or consisting essentially of or consisting of a mixture of mono-, di-, and/or triglycerides in an amount of, e.g., about 10% by weight, about 15% by weight, about 20% by weight, about 25% by weight, about 30% by weight, about 35% by weight, about 40% by weight, about 45% by weight, about 50% by weight, about 55% by weight, about 60% by weight, about 65% by weight, about 70% by weight, or about 75% by weight by weight. In some embodiments, a pharmaceutical composition disclosed herein may include one or more liquid fats or glycerolipids that are liquid at 18° C. comprising or consisting essentially of or consisting of a mixture of mono-, di-, and/or triglycerides in an amount of, e.g., at least 10% by weight, at least 15% by weight, at least 20% by weight, at least 25% by weight, at least 30% by weight, at least 35% by weight, at least 40% by weight, at least 45% by weight, at least 50% by weight, at least 55% by weight, at least 60% by weight, at least 65% by weight, at least 70% by weight, or at least 75% by weight. In some embodiments, a pharmaceutical composition disclosed herein may include one or more liquid fats or glycerolipids that are liquid at 18° C. comprising or consisting essentially of or consisting of a mixture of mono-, di-, and/or triglycerides in an amount of, e.g., at most 10% by weight, at most 15% by weight, at most 20% by weight, at most 25% by weight, at most 30% by weight, at most 35% by weight, at most 40% by weight, at most 45% by weight, at most 50% by weight, at most 55% by weight, at most 60% by weight, at most 65% by weight, at most 70% by weight, or at most 75% by weigh.

In some embodiments, a pharmaceutical composition disclosed herein may include one or more liquid fats or glycerolipids that are liquid at 18° C. comprising or consisting essentially of or consisting of a mixture of mono-, di-, and/or triglycerides in an amount of, e.g., about 10% to about 20%, about 10% to about 25%, about 10% to about 30%, about 10% to about 35%, about 10% to about 40%, about 10% to about 45%, about 10% to about 50%, about 10% to about 55%, about 10% to about 60%, about 10% to about 65%, about 10% to about 70%, about 15% to about 20%, about 15% to about 25%, about 15% to about 30%, about 15% to about 35%, about 15% to about 40%, about 15% to about 45%, about 15% to about 50%, about 15% to about 55%, about 15% to about 60%, about 15% to about 65%, about 15% to about 70%, about 20% to about 25%, about 20% to about 30%, about 20% to about 35%, about 20% to about 40%, about 20% to about 45%, about 20% to about 50%, about 20% to about 55%, about 20% to about 60%, about 20% to about 65%, about 20% to about 70%, about 25% to about 30%, about 25% to about 35%, about 25% to about 40%, about 25% to about 45%, about 25% to about 50%, about 25% to about 55%, about 25% to about 60%, about 25% to about 65%, about 25% to about 70%, about 30% to about 35%, about 30% to about 40%, about 30% to about 45%, about 30% to about 50%, about 30% to about 55%, about 30% to about 60%, about 30% to about 65%, about 30% to about 70%, about 35% to about 40%, about 35% to about 45%, about 35% to about 50%, about 35% to about 55%, about 35% to about 60%, about 35% to about 65%, about 35% to about 70%, about 40% to about 45%, about 40% to about 50%, about 40% to about 55%, about 40% to about 60%, about 40% to about 65%, about 40% to about 70%, about 45% to about 50%, about 45% to about 55%, about 45% to about 60%, about 45% to about 65%, about 45% to about 70%, about 50% to about 55%, about 50% to about 60%, about 50% to about 65%, about 50% to about 70%, about 55% to about 60%, about 55% to about 65%, about 55% to about 70%, about 60% to about 65%, about 60% to about 70%, or about 65% to about 70% by weight.

In some embodiments, pharmaceutical composition disclosed herein may include one or more liquid fats or glycerolipids that are liquid at 18° C. comprising, or consisting essentially of or consisting of one or more monoglycerides. A monoglyceride includes, without limitation, glycerol monomyristoleate, glycerol monopalmitoleate, glycerol monosapienate, glycerol monooleate, glycerol monoelaidate, glycerol monovaccenate, glycerol monolinoleate, glycerol monolinoelaidate, glycerol monolinolenate, glycerol monostearidonate, glycerol monoeicosenoate, glycerol monomeadate, glycerol monoarachidonate, glycerol monoeicosapentaenoate, glycerol monoerucate, glycerol monodocosahexaenoate, and glycerol mononervonate.

In some embodiments, pharmaceutical composition disclosed herein may include one or more liquid fats or glycerolipids that are liquid at 18° C. comprising, or consisting essentially of or consisting of unsaturated $C_{10}$-$C_{18}$ monoglycerides, unsaturated $C_{10}$-$C_{20}$ monoglycerides, unsaturated $C_{10}$-$C_{22}$ monoglycerides, unsaturated $C_{10}$-$C_{24}$ monoglycerides, unsaturated $C_{12}$-$C_{18}$ monoglycerides, unsaturated $C_{12}$-$C_{20}$ monoglycerides, unsaturated $C_{12}$-$C_{22}$ monoglycerides, unsaturated $C_{12}$-$C_{24}$ monoglycerides, unsaturated $C_{14}$-$C_{18}$ monoglycerides, unsaturated $C_{14}$-$C_{20}$ monoglycerides, unsaturated $C_{14}$-$C_{22}$ monoglycerides, unsaturated $C_{14}$-$C_{24}$ monoglycerides, unsaturated $C_{16}$-$C_{18}$ monoglycerides, unsaturated $C_{16}$-$C_{20}$ monoglycerides, unsaturated $C_{16}$-$C_{22}$ monoglycerides, unsaturated $C_{16}$-$C_{24}$ monoglycerides, unsaturated $C_{18}$-$C_{20}$ monoglycerides, unsaturated $C_{18}$-$C_{22}$ monoglycerides, unsaturated $C_{18}$-$C_{24}$ monoglycerides, unsaturated $C_{20}$-$C_{22}$ monoglycerides, or unsaturated $C_{22}$-$C_{24}$ monoglycerides.

In some embodiments, pharmaceutical composition disclosed herein may include one or more liquid fats or glycerolipids that are liquid at 18° C. comprising, or consisting essentially of or consisting of saturated $C_{10}$-$C_{18}$ monoglycerides, saturated $C_{10}$-$C_{20}$ monoglycerides, saturated $C_{10}$-$C_{22}$ monoglycerides, saturated $C_{10}$-$C_{24}$ monoglycerides, saturated $C_{12}$-$C_{18}$ monoglycerides, saturated $C_{12}$-$C_{20}$ monoglycerides, saturated $C_{12}$-$C_{22}$ monoglycerides, saturated $C_{12}$-$C_{24}$ monoglycerides, saturated $C_{14}$-$C_{18}$ monoglycerides, saturated $C_{14}$-$C_{20}$ monoglycerides, saturated $C_{14}$-$C_{22}$ monoglycerides, saturated $C_{14}$-$C_{24}$ monoglycerides, saturated $C_{16}$-$C_{18}$ monoglycerides, saturated $C_{16}$-$C_{20}$ monoglycerides, saturated $C_{16}$-$C_{22}$ monoglycerides, saturated $C_{16}$-$C_{24}$ monoglycerides, saturated $C_{18}$-$C_{20}$ monoglycerides, saturated $C_{18}$-$C_{22}$ monoglycerides, saturated $C_{18}$-$C_{24}$ monoglycerides, saturated $C_{20}$-$C_{22}$ monoglycerides, or saturated $C_{22}$-$C_{24}$ monoglycerides.

In some embodiments, a pharmaceutical composition disclosed herein may include one or more liquid fats or glycerolipids that are liquid at 18° C. comprising, or consisting essentially of or consisting of a mixture of saturated and unsaturated $C_{10}$-$C_{18}$ monoglycerides, a mixture of saturated and unsaturated $C_{10}$-$C_{20}$ monoglycerides, a mixture of saturated and unsaturated $C_{10}$-$C_{22}$ monoglycerides, a mixture of saturated and unsaturated $C_{10}$-$C_{24}$ monoglycerides, a mixture of saturated and unsaturated $C_{12}$-$C_{18}$ monoglycerides, a mixture of saturated and unsaturated $C_{12}$-$C_{20}$ monoglycerides, a mixture of saturated and unsaturated $C_{12}$-$C_{22}$ monoglycerides, a mixture of saturated and unsaturated $C_{12}$-$C_{24}$ monoglycerides, a mixture of saturated and unsaturated $C_{14}$-$C_{18}$ monoglycerides, a mixture of saturated and unsaturated $C_{14}$-$C_{20}$ monoglycerides, a mixture of saturated and unsaturated $C_{14}$-$C_{22}$ monoglycerides, a mixture of saturated and unsaturated $C_{14}$-$C_{24}$ monoglycerides, a mixture of saturated and unsaturated $C_{16}$-$C_{18}$ monoglycerides, a mixture of saturated and unsaturated $C_{16}$-$C_{20}$ monoglycerides, a mixture of saturated and unsaturated $C_{16}$-$C_{22}$ monoglycerides, a mixture of saturated and unsaturated $C_{16}$-$C_{24}$ monoglycerides, a mixture of saturated and unsaturated $C_{18}$-$C_{20}$ monoglycerides, a mixture of saturated and unsaturated $C_{18}$-$C_{22}$ monoglycerides, a mixture of saturated and unsaturated $C_{18}$-$C_{24}$ monoglycerides, a mixture of saturated and unsaturated $C_{20}$-$C_{22}$ monoglycerides, or a mixture of saturated and unsaturated $C_{22}$-$C_{24}$ monoglycerides.

In some embodiments, a pharmaceutical composition disclosed herein may include one or more liquid fats or glycerolipids that are liquid at 18° C. comprising, or consisting essentially of or consisting of a monoglyceride having a melting point of, e.g., at most 15° C., at most 16° C., at most 17° C., at most 18° C., at most 19° C., or at most 20° C. In some embodiments, a pharmaceutical composition disclosed herein may include one or more liquid fats or glycerolipids that are liquid at 18° C. comprising, or consisting essentially of or consisting of a monoglyceride having a melting point between, e.g., about 0° C. to about 5° C., about 0° C. to about 10° C., about 0° C. to about 15° C., about 0° C. to about 20° C., about 0° C. to about 22° C., about 0° C. to about 25° C., about 5° C. to about 10° C., about 5° C. to about 15° C., about 5° C. to about 20° C., about 5° C. to about 22° C., about 5° C. to about 25° C., about 10° C. to about 15° C., about 10° C. to about 20° C., about 10° C. to about 22° C., about 10° C. to about 25° C., about 15° C. to about 20° C., about 15° C. to about 22° C., or about 15° C. to about 25° C.

In some embodiments, a pharmaceutical composition disclosed herein may include one or more liquid fats or glycerolipids that are liquid at 18° C. comprising or consisting essentially of or consisting of one or more monoglycerides in an amount of, e.g., about 10% by weight, about 15% by weight, about 20% by weight, about 25% by weight, about 30% by weight, about 35% by weight, about 40% by weight, about 45% by weight, about 50% by weight, about 55% by weight, about 60% by weight, about 65% by weight, about 70% by weight, or about 75% by weight. In some embodiments, a pharmaceutical composition disclosed herein may include one or more liquid fats or glycerolipids that are liquid at 18° C. comprising or consisting essentially of or consisting of one or more monoglycerides in an amount of, e.g. at least 10% by weight, at least 15% by weight, at least 20% by weight, at least 25% by weight, at least 30% by weight, at least 35% by weight, at least 40% by weight, at least 45% by weight, at least 50% by weight, at least 55% by weight, at least 60% by weight, at least 65% by weight, at least 70% by weight, or at least 75% by weight. In some embodiments, a pharmaceutical composition disclosed herein may include one or more liquid fats or glycerolipids that are liquid at 18° C. comprising or consisting essentially of or consisting of one or more monoglycerides in an amount of, e.g., at most 10% by weight, at most 15% by weight, at most 20% by weight, at most 25% by weight, at most 30% by weight, at most 35% by weight, at most 40% by weight, at most 45% by weight, at most 50% by weight, at most 55% by weight, at most 60% by weight, at most 65% by weight, at most 70% by weight, or at most 75% by weight.

In some embodiments, a pharmaceutical composition disclosed herein may include one or more liquid fats or glycerolipids that are liquid at 18° C. comprising or consisting essentially of or consisting of one or more monoglycerides in an amount of, e.g., about 10% to about 20%, about 10% to about 25%, about 10% to about 30%, about 10% to about 35%, about 10% to about 40%, about 10% to about 45%, about 10% to about 50%, about 10% to about 55%, about 10% to about 60%, about 10% to about 65%, about 10% to about 70%, about 15% to about 20%, about 15% to about 25%, about 15% to about 30%, about 15% to about 35%, about 15% to about 40%, about 15% to about 45%, about 15% to about 50%, about 15% to about 55%, about 15% to about 60%, about 15% to about 65%, about 15% to about 70%, about 20% to about 25%, about 20% to about 30%, about 20% to about 35%, about 20% to about 40%, about 20% to about 45%, about 20% to about 50%, about 20% to about 55%, about 20% to about 60%, about 20% to about 65%, about 20% to about 70%, about 25% to about 30%, about 25% to about 35%, about 25% to about 40%, about 25% to about 45%, about 25% to about 50%, about 25% to about 55%, about 25% to about 60%, about 25% to about 65%, about 25% to about 70%, about 30% to about 35%, about 30% to about 40%, about 30% to about 45%, about 30% to about 50%, about 30% to about 55%, about 30% to about 60%, about 30% to about 65%, about 30% to about 70%, about 35% to about 40%, about 35% to about 45%, about 35% to about 50%, about 35% to about 55%, about 35% to about 60%, about 35% to about 65%, about 35% to about 70%, about 40% to about 45%, about 40% to about 50%, about 40% to about 55%, about 40% to about 60%, about 40% to about 65%, about 40% to about 70%, about 45% to about 50%, about 45% to about 55%, about 45% to about 60%, about 45% to about 65%, about 45% to about 70%, about 50% to about 55%, about 50% to about 60%, about 50% to about 65%, about 50% to about 70%, about 55% to about 60%, about 55% to about 65%, about 55% to about 70%, about 60% to about 65%, about 60% to about 70%, or about 65% to about 70% by weight.

Commercially available hard fats or glycerolipids that are solid at 18° C. include, without limitation, Cocoa butter, mixtures of saturated $C_{10}$-$C_{18}$ triglycerides having a melting point around 33° C. (GELUCIRE® 33/01), mixtures of saturated $C_{10}$-$C_{18}$ triglycerides having a melting point around 39° C. (GELUCIRE® 39/01), and mixtures of saturated $C_{10}$-$C_{18}$ triglycerides having a melting point around 43° C. (GELUCIRE® 43/01), Commercially available liquid fats or glycerolipids that are liquid at 18° C. include, without limitation, a hydrolyzed corn oil including glycerol monolinoleate (MAISINE™ 35-1, MAISINE™ CC). In some embodiments, a hydrolyzed corn oil including glycerol monolinoleate (MAISINE™ 35-1, MAISINE™ CC) comprises about 32% to 52% monoglycerides including glycerol monolinoleate, about 40% to 50% diglycerides, and about 5% to 30% triglycerides.

A pharmaceutical composition disclosed herein comprises any ratio of hard fats or glycerolipids that are solid at 18° C. to liquid fats or glycerolipids that are liquid at 18° C. that stabilizes one or more therapeutic compounds disclosed herein in a manner that prevents precipitation of the one or more therapeutic compounds. In some embodiments, a pharmaceutical composition disclosed herein comprises a hard fats or glycerolipids that are solid at 18° C. to a liquid fats or glycerolipids that are liquid at 18° C. ratio of, e.g., about 5:1, about 4:1, about 3:1, about 2:1, or about 1:1. In some embodiments, a pharmaceutical composition disclosed herein comprises a hard fats or glycerolipids that are solid at 18° C. to a liquid fats or glycerolipids that are liquid at 18° C. ratio of, e.g., about 5:1 to about 4:1, about 5:1 to about 3:1, about 5:1 to about 2:1, about 5:1 to about 1:1, about 4:1 to about 3:1, about 4:1 to about 2:1, about 4:1 to about 1:1, about 3:1 to about 2:1, about 3:1 to about 1:1, or about 2:1 to about 1:1.

In some embodiments, a pharmaceutical composition disclosed herein comprises a hard fats or glycerolipids that are solid at 18° C. to a liquid fats or glycerolipids that are liquid at 18° C. ratio of, e.g., about 1:5, about 1:4, about 1:3, or about 1:2. In some embodiments, a pharmaceutical composition disclosed herein comprises a hard fats or glycerolipids that are solid at 18° C. to a liquid fats or glycerolipids that are liquid at 18° C. ratio of, e.g., about 1:5 to about 1:4, about 1:5 to about 1:3, about 1:5 to about 1:2, about 1:5 to about 1:1, about 1:4 to about 1:3, about 1:4 to about 1:2, about 1:4 to about 1:1, about 1:3 to about 1:2, about 1:3 to about 1:1, or about 1:2 to about 1:1.

Hydrophilic Protic Solvent

A pharmaceutical composition disclosed herein may comprises one or more hydrophilic protic solvents. The primary purpose of hydrophilic protic solvents is to enhance solubility of a biologic therapeutic compound within the glycerolipid admixture. A hydrophilic protic solvent disclosed herein must be anhydrous and miscible in non-polar compounds such as the one or more glycerolipids and one or more $C_{14\text{-}24}$ fatty acids disclosed herein. On example of a suitable hydrophilic protic solvent is a carboxylic acid. A carboxylic acid is an organic acid that contains a carboxyl group (C(=O)OH) attached to an R-group. The general formula of a carboxylic acid is R—COOH or R—$CO_2H$, with R referring to the alkyl, alkenyl, aryl, or other group. Non-limiting examples of a carboxylic acid include methanoic acid (formic acid), ethanoic acid (acetic acid), propanoic acid (propionic acid), butanoic acid (butyric acid), pentanoic acid (valeric acid), hexanoic acid (caproic acid), heptanoic acid (enanthic acid), and octanoic acid (caprylic acid).

The amount of one or more hydrophilic protic solvents useful in a pharmaceutical composition disclosed herein is an amount necessary to sufficiently dissolve a biologic therapeutic compound. In some embodiments, a pharmaceutical composition disclosed herein may comprising or consisting essentially of or consisting of one or more hydrophilic protic solvents in an amount of, e.g., about 0.01%, about 0.05%, about 0.1%, about 0.5%, about 1% by weight, about 1.5% by weight, about 2% by weight, about 2.5% by weight, about 3% by weight, about 4% by weight, about 5% by weight, about 7.5% by weight, or about 10% by weight. In some embodiments, a pharmaceutical composition disclosed herein may comprising or consisting essentially of or consisting of one or more hydrophilic protic solvents in an amount of, e.g., at least 0.01%, at least 0.05%, at least 0.1%, at least 0.5%, at least 1% by weight, at least 1.5% by weight, at least 2% by weight, at least 2.5% by weight, at least 3% by weight, at least 4% by weight, at least 5% by weight, at least 7.5% by weight, or at least 10% by weight. In some embodiments, a pharmaceutical composition disclosed herein may comprising or consisting essentially of or consisting of one or more hydrophilic protic solvents in an amount of, e.g., at least 0.01%, at most 0.05%, at most 0.1%, at most 0.5%, at most 1% by weight, at most 1.5% by weight, at most 2% by weight, at most 1% by weight, at most 1.5% by weight, at most 2% by weight, at most 2.5% by weight, at most 3% by weight, at most 4% by weight, at most 5% by weight, at most 7.5% by weight, or at most 10% by weight.

In some embodiments, a pharmaceutical composition disclosed herein may comprising or consisting essentially of or consisting of one or more hydrophilic protic solvents in an amount of, e.g., about 0.1% to about 1% by weight, about 0.1% to about 1.5% by weight, about 0.1% to about 2% by weight, about 0.1% to about 2.5% by weight, about 0.1% to about 5% by weight, about 0.1% to about 7.5% by weight, about 0.1% to about 10% by weight, about 0.5% to about 1% by weight, about 0.5% to about 1.5% by weight, about 0.5% to about 2% by weight, about 0.5% to about 2.5% by weight, about 0.5% to about 5% by weight, about 0.5% to about 7.5% by weight, about 0.5% to about 10% by weight, about 1% to about 1.5% by weight, about 1% to about 2% by weight, about 1% to about 2.5% by weight, about 1% to about 5% by weight, about 1% to about 7.5% by weight, or about 1% to about 10% by weight.

Digestion Enhancers

A pharmaceutical composition disclosed herein may comprises one or more digestion enhancers. The primary purposes of the one or more digestion enhancers are to enhance solubility of a therapeutic compound disclosed herein with the glycerolipid admixture, to enhance absorption of a therapeutic compound disclosed herein thereby improving the pharmacokinetics of the compound, and/or to improve availability and facilitate selected bio-distribution of a therapeutic compound disclosed herein thereby improving the pharmacodynamics of the compound. These improved properties are achieved by the one or more digestion enhancers by creating a pre-lipid digestion formulation of a therapeutic compound disclosed herein which facilitates and enhances the processing of the one or more glycerolipids disclosed herein when a pharmaceutical composition disclosed herein enters the duodenum region of the small intestine. Such glycerolipid processing enables the one or more therapeutic compounds contained in the pharmaceutical composition to be absorbed by enterocytes along with the digested glycerolipids and subsequently processed and transported into the lymphatic system. In some embodiments, a pharmaceutical composition disclosed comprises one or more digestion enhancers that includes one or more bile acids. In some embodiments, a pharmaceutical composition disclosed comprises one or more digestion enhancers that includes cholic acid. In some embodiments, a pharmaceutical composition disclosed comprises one or more digestion enhancers that includes one or more $C_{14}$-$C_{24}$ free fatty acids. In some embodiments, a pharmaceutical composition disclosed comprises one or more digestion enhancers that includes one or more $C_{14}$-$C_{20}$ free fatty acids. In some embodiments, a pharmaceutical composition disclosed comprises one or more digestion enhancers that includes an oleic acid, a steric acid, or a linoleic acid. In some embodiments, a pharmaceutical composition disclosed comprises one or more digestion enhancers that includes one or more $C_{14}$-$C_{24}$ free fatty acid surfactants. In some embodiments, a pharmaceutical composition disclosed comprises one or more digestion enhancers that includes one or more $C_{14}$-$C_{20}$ free fatty acid surfactants. In some embodiments, a pharmaceutical composition disclosed comprises one or more digestion enhancers that includes a sodium oleate, a sodium stearate, and/or a sodium linoleate.

In some embodiments, a pharmaceutical composition disclosed comprises one or more digestion enhancers that includes 1) one or more bile acids disclosed herein; and 2) one or more $C_{14}$-$C_{24}$ free fatty acids disclosed herein. In some embodiments, a pharmaceutical composition disclosed comprises one or more digestion enhancers that includes 1) a cholic acid disclosed herein; and 2) one or more $C_{14}$-$C_{20}$ free fatty acids disclosed herein. In some embodiments, a pharmaceutical composition disclosed comprises one or more digestion enhancers that includes 1) a cholic acid disclosed herein; and 2) an oleic acid, a steric acid, or a linoleic acid.

In some embodiments, a pharmaceutical composition disclosed comprises one or more digestion enhancers that includes 1) one or more bile acids disclosed herein; 2) one or more $C_{14}$-$C_{24}$ free fatty acids disclosed herein; and 3) one or more $C_{14}$-$C_{24}$ free fatty acid surfactants disclosed herein. In some embodiments, a pharmaceutical composition disclosed comprises one or more digestion enhancers that includes 1) a cholic acid disclosed herein; 2) one or more $C_{14}$-$C_{20}$ free fatty acids disclosed herein; and 3) one or more $C_{14}$-$C_{20}$ free fatty acid surfactants disclosed herein. In some embodiments, a pharmaceutical composition disclosed comprises one or more digestion enhancers that includes 1) a cholic acid disclosed herein; 2) an oleic acid, a steric acid, and/or a linoleic acid; and 3) a sodium oleate, a sodium stearate, and/or a sodium linoleate.

In some embodiments, a pharmaceutical composition disclosed comprises one or more digestion enhancers that includes 1) one or more bile acids disclosed herein; and 2) one or more phospholipids disclosed herein. In some embodiments, a pharmaceutical composition disclosed comprises one or more digestion enhancers that includes 1) a cholic acid disclosed herein; and 2) one or more phospholipids disclosed herein.

In some embodiments, a pharmaceutical composition disclosed comprises one or more digestion enhancers that includes 1) one or more $C_{14}$-$C_{24}$ free fatty acids disclosed herein; and 2) one or more phospholipids disclosed herein. In some embodiments, a pharmaceutical composition disclosed comprises one or more digestion enhancers that includes 1) one or more $C_{14}$-$C_{20}$ free fatty acids disclosed herein; and 2) one or more phospholipids disclosed herein. In some embodiments, a pharmaceutical composition disclosed comprises one or more digestion enhancers that includes 1) an oleic acid, a steric acid, and/or a linoleic acid; and 2) one or more phospholipids disclosed herein.

In some embodiments, a pharmaceutical composition disclosed comprises one or more digestion enhancers that includes 1) one or more bile acids disclosed herein; 2) one or more $C_{14}$-$C_{24}$ free fatty acids disclosed herein; and 3) one or more phospholipids disclosed herein. In some embodiments, a pharmaceutical composition disclosed comprises one or more digestion enhancers that includes 1) one or more bile acids disclosed herein; 2) one or more $C_{14}$-$C_{20}$ free fatty acids disclosed herein; and 3) one or more phospholipids disclosed herein. In some embodiments, a pharmaceutical composition disclosed comprises one or more digestion enhancers that includes 1) a cholic acid disclosed herein; 2) an oleic acid, a steric acid, and/or a linoleic acid; and 3) one or more phospholipids disclosed herein.

In some embodiments, a pharmaceutical composition disclosed comprises one or more digestion enhancers that includes 1) one or more bile acids disclosed herein; 2) one or more phospholipids disclosed herein; and 3) one or more $C_{14}$-$C_{24}$ free fatty acid surfactants disclosed herein. In some embodiments, a pharmaceutical composition disclosed comprises one or more digestion enhancers that includes 1) a cholic acid disclosed herein; 2) one or more phospholipids disclosed herein; and 3) one or more $C_{14}$-$C_{20}$ free fatty acid surfactants disclosed herein. In some embodiments, a pharmaceutical composition disclosed comprises one or more digestion enhancers that includes 1) a cholic acid disclosed herein; 2) one or more phospholipids disclosed herein; and 3) a sodium $C_{14}$-$C_{20}$ free fatty acid disclosed herein. In some embodiments, a pharmaceutical composition disclosed comprises one or more digestion enhancers that includes 1) a cholic acid disclosed herein; 2) one or more phospholipids disclosed herein; and 3) a sodium oleate, a sodium stearate, and/or a sodium linoleate.

In some embodiments, a pharmaceutical composition disclosed comprises one or more digestion enhancers that includes 1) one or more $C_{14}$-$C_{24}$ free fatty acids disclosed herein; 2) one or more phospholipids disclosed herein; and 3) one or more $C_{14}$-$C_{24}$ free fatty acid surfactants disclosed herein. In some embodiments, a pharmaceutical composition disclosed comprises one or more digestion enhancers that includes 1) one or more $C_{14}$-$C_{20}$ free fatty acids disclosed herein; 2) one or more phospholipids disclosed herein; and 3) one or more $C_{14}$-$C_{20}$ free fatty acid surfactants disclosed herein. In some embodiments, a pharmaceutical composition disclosed comprises one or more digestion enhancers that includes 1) an oleic acid, a steric acid, and/or a linoleic acid; 2) one or more phospholipids disclosed herein; and 3) one or more sodium $C_{14}$-$C_{20}$ free fatty acid surfactants disclosed herein. In some embodiments, a pharmaceutical composition disclosed comprises one or more digestion enhancers that includes 1) an oleic acid, a steric acid, and/or a linoleic acid; 2) one or more phospholipids disclosed herein; and 3) a sodium oleate, a sodium stearate, and/or a sodium linoleate.

In some embodiments, a pharmaceutical composition disclosed comprises one or more digestion enhancers that includes 1) one or more bile acids disclosed herein; 2) one or more $C_{14}$-$C_{24}$ free fatty acids disclosed herein; 3) one or more phospholipids disclosed herein; and 4) one or more $C_{14}$-$C_{24}$ free fatty acid surfactants disclosed herein. In some embodiments, a pharmaceutical composition disclosed comprises one or more digestion enhancers that includes 1) one or more bile acids disclosed herein; 2) one or more $C_{14}$-$C_{20}$ free fatty acids disclosed herein; 3) one or more phospholipids disclosed herein; and 4) one or more $C_{14}$-$C_{20}$ free fatty acid surfactants disclosed herein. In some embodiments, a pharmaceutical composition disclosed comprises one or more digestion enhancers that includes 1) a cholic acid disclosed herein; 2) an oleic acid, a steric acid, and/or a linoleic acid; 3) one or more phospholipids disclosed herein; and 4) one or more sodium $C_{14}$-$C_{20}$ free fatty acid surfactants disclosed herein. In some embodiments, a pharmaceutical composition disclosed comprises one or more digestion enhancers that includes 1) a cholic acid disclosed herein; 2) an oleic acid, a steric acid, and/or a linoleic acid; 3) one or more phospholipids disclosed herein; and 4) a sodium oleate, a sodium stearate, and/or a sodium linoleate.

In some embodiments, a pharmaceutical composition disclosed herein may comprising or consisting essentially of or consisting of one or more digestion enhancers in an amount of, e.g., about 1% by weight, about 2.5% by weight, about 5% by weight, about 7.5% by weight, about 10% by weight, about 12.5% by weight, about 15% by weight, about 17.5% by weight, about 20% by weight, about 22.5% by weight, about 25% by weight, about 30% by weight, about 35% by weight, about 40% by weight, about 45% by weight, about 50% by weight, about 55% by weight, about 60% by weight, about 65% by weight, about 70% by weight, about 75% by weight, or about 80% by weight. In some embodiments, a pharmaceutical composition disclosed herein may comprising or consisting essentially of or consisting of one or more digestion enhancers in an amount of, e.g., at least 1% by weight, at least 2.5% by weight, at least 5% by weight, at least 7.5% by weight, at least 10% by weight, at least 12.5% by weight, at least 15% by weight, at least 17.5% by weight, at least 20% by weight, at least 22.5% by weight, at least 25% by weight, at least 30% by weight, at least 35% by weight, at least 40% by weight, at least 45% by weight, at least 50% by weight, at least 55% by weight, at least 60% by weight, at least 65% by weight, at least 70% by weight, at least 75% by weight, or at least 75% by weight. In some embodiments, a pharmaceutical composition disclosed herein may comprising or consisting essentially of or consisting of one or more digestion enhancers in an amount of, e.g., at most 1% by weight, at most 2.5% by weight, at most 5% by weight, at most 7.5% by weight, at most 10% by weight, at most 12.5% by weight, at most 15% by weight, at most 17.5% by weight, at most 20% by weight, at most 22.5% by weight, at most 25% by weight, at most 30% by weight, at most 35% by weight, at most 40% by weight, at most 45% by weight, at most 50% by weight, at most 55% by weight, at most 60% by weight, at most 65% by weight, at most 70% by weight, at most 75% by weight, or at most 80% by weight.

In some embodiments, a pharmaceutical composition disclosed herein may comprising or consisting essentially of or consisting of one or more digestion enhancers in an amount of, e.g., about 1% to about 2.5% by weight, about 1% to about 5% by weight, about 1% to about 10% by weight, about 1% to about 15% by weight, about 1% to about 20% by weight, about 1% to about 25% by weight, about 2.5% to about 5% by weight, about 2.5% to about 10% by weight, about 2.5% to about 15% by weight, about 2.5% to about 20% by weight, about 2.5% to about 25% by weight, about 5% to about 10% by weight, about 5% to about 15% by weight, about 5% to about 20% by weight, about 5% to about 25% by weight, about 10% to about 20%, about 10% to about 25%, about 10% to about 30%, about 10% to about 35%, about 10% to about 40%, about 10% to about 45%, about 10% to about 50%, about 10% to about 55%, about 10% to about 60%, about 10% to about 65%, about 10% to about 70%, about 15% to about 20%, about 15% to about 25%, about 15% to about 30%, about 15% to about 35%, about 15% to about 40%, about 15% to about 45%, about 15% to about 50%, about 15% to about 55%, about 15% to about 60%, about 15% to about 65%, about 15% to about 70%, about 20% to about 25%, about 20% to about 30%, about 20% to about 35%, about 20% to about 40%, about 20% to about 45%, about 20% to about 50%, about 20% to about 55%, about 20% to about 60%, about 20% to about 65%, about 20% to about 70%, about 25% to about 30%, about 25% to about 35%, about 25% to about 40%, about 25% to about 45%, about 25% to about 50%, about 25% to about 55%, about 25% to about 60%, about 25% to about 65%, about 25% to about 70%, about 30% to about 35%, about 30% to about 40%, about 30% to about 45%, about 30% to about 50%, about 30% to about 55%, about 30% to about 60%, about 30% to about 65%, about 30% to about 70%, about 35% to about 40%, about 35% to about 45%, about 35% to about 50%, about 35% to about 55%, about 35% to about 60%, about 35% to about 65%, about 35% to about 70%, about 40% to about 45%, about 40% to about 50%, about 40% to about 55%, about 40% to about 60%, about 40% to about 65%, about 40% to about 70%, about 40% to about 75%, about 40% to about 80%, about 45% to about 50%, about 45% to about 55%, about 45% to about 60%, about 45% to about 65%, about 45% to about 70%, about 45% to about 75%, about 45% to about 80%, about 50% to about 55%, about 50% to about 60%, about 50% to about 65%, about 50% to about 70%, about 50% to about 75%, about 50% to about 80%, about 55% to about 60%, about 55% to about 65%, about 55% to about 70%, about 55% to about 75%, about 55% to about 80%, about 60% to about 65%, about 60% to about 70%, about 60% to about 75%, about 60% to about 80%, about 65% to about 70% by weight, about 65% to about 75%, about 65% to about 80%, about 70% to about 75%, about 70% to about 80%, or about 75% to about 80%.

Bile Acids

A pharmaceutical composition disclosed herein may comprises one or more bile acids. The primary purpose of bile acids are to enhance solubility of a therapeutic compound disclosed herein within the glycerolipid admixture, to enhance absorption of a therapeutic compound disclosed herein thereby improving the pharmacokinetics of the compound, and/or to improve availability and facilitate selected bio-distribution of a therapeutic compound disclosed herein thereby improving the pharmacodynamics of the compound.

In addition, as disclosed in Example 2, a bile acid disclosed herein improves the solubility of a therapeutic compound disclosed herein within one or more glycerolipid and/or one or more free $C_{14-24}$ fatty acids disclosed herein. The improved solubility properties are achieved by the bile acids by preventing the recrystallization of a therapeutic compound during solidification when the molton pharmaceutical composition cools to room temperature (18° C. to 20° C.). The improved pharmacokinetic properties are achieved by the bile acids by breaking apart the lipid component of a pharmaceutical composition disclosed herein via its surfactant properties into smaller lipid structures that mimic emulsion droplets, thereby facilitating the emulsification process. The "emulsion droplets" recruit colipase and create a greater surface area for which pancreatic lipase can digest the hard fat glycerolipids present there within which ultimately enhances enterocyte absorption and subsequent chylomicron formation. Bile acids are involved in signaling for the initiation of chylomicron formation. Hence the inclusion of bile acids in the lipid formulation will maximise this signaling pathway and the production of chylomicrons, As a result, the improved pharmacodynamic properties provided by bile acids are produced by increasing the availability of a therapeutic compound by increasing its content within chylomicrons prior to entering the circulatory system and subsequently facilitating the delivery of the therapeutic compound to compartments such as the brain passing across membranes such as the blood-brain barrier and the choroid plexus.

Amphipathic molecules having an HLB of greater than 12, bile acids have a specific chemical structure, different from ordinary aliphatic surfactants, due to the presence of a large, rigid, and planar hydrophobic moiety of a steroid nucleus carrying 2-4 hydroxyl groups. Specifically, bile acids comprise the following basic components: (1) 4 rings, (2) a 5-/8-carbon side chain that ends with a carboxylic acid, and (3) a number of hydroxyl groups (whose position/number changes among the various salts). The rings are ascribed the letters A, B, C, and D based on their distance from the side chain with the —COOH group, the D ring being the most distant (as well as being 1 C smaller than the other rings), as discussed below. Beta hydroxyl groups face up/out, alpha groups down, and every bile acid has a 3-hydroxyl group that originates from their cholesterol precursor. The chemical structure of bile salts results in this emulsification pathway being useful in accordance with the teachings of the disclosure, and accordingly, synthetic surfactants will not work.

Examples of bile acids include, without limitation, chenodeoxycholic acid, cholic acid, dafachronic acid, deoxycholic acid, glycocholic acid, glycohenodeoxycholic acid, lithocholic acid, taurochenodeoxycholic acid, taurocholic acid, and any stereoisomer thereof. cholic acid and chenodeoxycholic acid are referred to as primary bile acids while deoxycholic acid (which is converted from cholic acid) and lithocholic acid (which is converted from chenodeoxycholic acid) are referred to as secondary bile acids. Taurocholic acid and glycocholic acid (derivatives of cholic acid) and taurochenodeoxycholic acid and glycochenodeoxycholic acid (derivatives of chenodeoxycholic acid) are the major bile acids that serve as the basis for the bile salts found in bile.

There is a direct correlation between the amount of a bile acid present in a pharmaceutical composition disclosed herein and the improved properties observed. As such, the more bile acid present in a pharmaceutical composition disclosed herein the greater the improvement in solubility, absorption, and availability of the therapeutic composition. In addition, the upper limit of bile acid including in a pharmaceutical composition disclosed herein is not limited to the solution point of a bile acid. As such, a pharmaceutical composition disclosed herein can include supersaturating amounts of a bile acid. As such, the upper limit of bile acid that can be included in a pharmaceutical composition disclosed herein is its critical micellar concentration (CMC). Besides the above-mentioned improved properties, an additional advantage of supersaturating amounts of a bile acid is the presence of the resulting nanoparticle formation of crystalline bile acid in a pharmaceutical composition disclosed herein. Without wishing to be limited by a one theory, bile acid nanoparticles can serve as a reservoir that upon exposure to the alkaline environment of the small intestine dissolve and form bile salts which in turn further enhances the emulsification process of the pharmaceutical composition disclosed herein.

The amount of a bile acid useful in a pharmaceutical composition disclosed herein is an amount below its CMC. In some embodiments, the amount of a bile acid useful in a pharmaceutical composition disclosed herein is an amount below its CMC and one that is supersaturating. In some embodiments, a pharmaceutical composition disclosed herein may comprising or consisting essentially of or consisting of one or more bile acids in an amount of, e.g., about 0.1% by weight, about 0.5% by weight, about 1.0% by weight, about 1.0% by weight, about 1.5% by weight, about 2.0% by weight, about 2.5% by weight, about 3.0% by weight, about 3.5% by weight, about 4.0% by weight, about 4.5% by weight, about 5.0% by weight, about 5.5% by weight, about 6.0% by weight, about 6.5% by weight, about 7.0% by weight, about 7.5% by weight, about 8.0% by weight, about 8.5% by weight, about 9.0% by weight, about 9.5% by weight, or about 10.0% by weight. In some embodiments, a pharmaceutical composition disclosed herein may comprising or consisting essentially of or consisting of one or more bile acids in an amount of, e.g., at least 0.1% by weight, at least 0.5% by weight, at least 1.0% by weight, at least 1.5% by weight, at least 2.0% by weight, at least 2.5% by weight, at least 3.0% by weight, at least 3.5% by weight, at least 4.0% by weight, at least 4.5% by weight, at least 5.0% by weight, at least 5.5% by weight, at least 6.0% by weight, at least 6.5% by weight, at least 7.0% by weight, at least 7.5% by weight, at least 8.0% by weight, at least 8.5% by weight, at least 9.0% by weight, at least 9.5% by weight, or at least 10.0% by weight. In some embodiments, a pharmaceutical composition disclosed herein may comprising or consisting essentially of or consisting of one or more bile acids in an amount of, e.g., at most 0.1% by weight, at most 0.5% by weight, at most 1.0% by weight, at most 1.5% by weight, at most 2.0% by weight, at most 2.5% by weight, at most 3.0% by weight, at most 3.5% by weight, at most 4.0% by weight, at most 4.5% by weight, at most 5.0% by weight, at most 5.5% by weight, at most 6.0% by weight, at most 6.5% by weight, at most 7.0% by weight, at most 7.5% by weight, at most 8.0% by weight, at most 8.5% by weight, at most 9.0% by weight, at most 9.5% by weight, or at most 10.0% by weight.

In some embodiments, a pharmaceutical composition disclosed herein may comprising or consisting essentially of or consisting of one or more bile acids in an amount of, e.g., about 0.1% to about 0.5%, about 0.1% to about 1.0%, about 0.1% to about 2.0%, about 0.1% to about 3.0%, about 0.1% to about 4.0%, about 0.1% to about 5.0%, about 0.1% to about 6.0%, about 0.1% to about 7.0%, about 0.1% to about 8.0%, about 0.1% to about 9.0%, about 0.1% to about 10.0%, about 0.5% to about 1.0%, about 0.5% to about 2.0%, about 0.5% to about 3.0%, about 0.5% to about 4.0%, about 0.5% to about 5.0%, about 0.5% to about 6.0%, about 0.5% to about 7.0%, about 0.5% to about 8.0%, about 0.5% to about 9.0%, about 0.5% to about 10.0%, about 1.0% to about 2.0%, about 1.0% to about 3.0%, about 1.0% to about 4.0%, about 1.0% to about 5.0%, about 1.0% to about 6.0%, about 1.0% to about 7.0%, about 1.0% to about 8.0%, about 1.0% to about 9.0%, about 1.0% to about 10.0%, about 2.0% to about 3.0%, about 2.0% to about 4.0%, about 2.0% to about 5.0%, about 2.0% to about 6.0%, about 2.0% to about 7.0%, about 2.0% to about 8.0%, about 2.0% to about 9.0%, about 2.0% to about 10.0%, about 3.0% to about 4.0%, about 3.0% to about 5.0%, about 3.0% to about 6.0%, about 3.0% to about 7.0%, about 3.0% to about 8.0%, about 3.0% to about 9.0%, about 3.0% to about 10.0%, about 4.0% to about 5.0%, about 4.0% to about 6.0%, about 4.0% to about 7.0%, about 4.0% to about 8.0%, about 4.0% to about 9.0%, about 4.0% to about 10.0%, about 5.0% to about 6.0%, about 5.0% to about 7.0%, about 5.0% to about 8.0%, about 5.0% to about 9.0%, about 5.0% to about 10.0%, about 6.0% to about 7.0%, about 6.0% to about 8.0%, about 6.0% to about 9.0%, about 6.0% to about 10.0%, about 7.0% to about 8.0%, about 7.0% to about 9.0%, about 7.0% to about 10.0%, about 8.0% to about 9.0%, about 8.0% to about 10.0%, or about 9.0% to about 10.0% by weight.

In some embodiments, a pharmaceutical composition disclosed herein may comprising or consisting essentially of or consisting of one or more bile acids in a concentration of, e.g., at most 0.01 mM, at most 0.025 mM, at most 0.05 mM, at most 0.075 mM, at most 0.1 mM, at most 0.25 mM, at most 0.5 mM, at most 0.75 mM, at most 1 mM, or at most 5 mM. In some embodiments, a pharmaceutical composition disclosed herein may comprising or consisting essentially of or consisting of one or more bile acids in a concentration of, e.g., about 0.01 mM to about 0.05 mM, about 0.01 mM to about 0.1 mM, about 0.01 mM to about 0.5 mM, about 0.01 mM to about 1 mM, about 0.01 mM to about 5 mM, about 0.05 mM to about 0.1 mM, about 0.05 mM to about 0.5 mM, about 0.05 mM to about 1 mM, about 0.05 mM to about 5 mM, about 0.1 mM to about 0.5 mM, about 0.1 mM to about 1 mM, about 0.1 mM to about 5 mM, or about 1 mM to about 5 mM.

$C_{14-24}$ Fatty Acids

A pharmaceutical composition disclosed herein may comprises one or more free $C_{14-24}$ fatty acids. A fatty acid comprises a carboxylic acid with a long unbranched hydrocarbon chain which may be either saturated or unsaturated and are hydrophobic molecules having an HLB of less than 4. The primary purpose of free $C_{14-24}$ fatty acids are to enhance solubility of a therapeutic compound disclosed herein within the glycerolipid admixture and to enhance absorption of a therapeutic compound disclosed herein thereby improving the pharmacokinetics of the compound. The improved solubility properties are achieved by the free $C_{14-24}$ fatty acids due to their properties of being a solvent that facilitates dissolvement of a therapeutic compound disclosed herein. The improved absorption properties are achieved by the free $C_{14-24}$ fatty acids by facilitating and increasing the formation of micelles by breaking up larger emulsion droplets, thereby mimicking the lipid digestion products of triglycerides, namely free fatty acids. As such, a $C_{14-24}$ fatty acid disclosed herein increases the uptake of micelles comprising one or more therapeutic compounds into enterocytes. In addition, as disclosed in Example 2, a free $C_{14-24}$ fatty acids disclosed herein improves the solubility of a bile salt disclosed herein.

In some embodiments, pharmaceutical composition disclosed herein may include one or more free $C_{14-24}$ fatty acids comprising, or consisting essentially of or consisting of unsaturated free $C_{14}$-$C_{16}$ fatty acids, unsaturated free $C_{14}$-$C_{18}$ fatty acids, unsaturated free $C_{14}$-$C_{20}$ fatty acids, unsaturated free $C_{14}$-$C_{22}$ fatty acids, unsaturated free $C_{14}$-$C_{24}$ fatty acids, unsaturated free $C_{16}$-$C_{18}$ fatty acids, unsaturated free $C_{16}$-$C_{20}$ fatty acids, unsaturated free $C_{16}$-$C_{22}$ fatty acids, unsaturated free $C_{16}$-$C_{24}$ fatty acids, unsaturated free $C_{18}$-$C_{20}$ fatty acids, unsaturated free $C_{18}$-$C_{22}$ fatty acids, unsaturated free $C_{18}$-$C_{24}$ fatty acids, unsaturated free $C_{20}$-$C_{22}$ fatty acids, or unsaturated free $C_{22}$-$C_{24}$ fatty acids. In some embodiments, pharmaceutical composition disclosed herein may include one or more free $C_{14-24}$ fatty acids comprising, or consisting essentially of or consisting of ω-3 unsaturated free $C_{18}$-$C_{22}$ fatty acids, ω-5 unsaturated free $C_{18}$-$C_{22}$ fatty acids, ω-6 unsaturated free $C_{18}$-$C_{22}$ fatty acids, ω-7 unsaturated free $C_{18}$-$C_{22}$ fatty acids, ω-9 unsaturated free $C_{18}$-$C_{22}$ fatty acids, ω-10 unsaturated free $C_{18}$-$C_{22}$ fatty acids, ω-11 unsaturated free $C_{18}$-$C_{22}$ fatty acids, or ω-12 unsaturated free $C_{18}$-$C_{22}$ fatty acids.

In some embodiments, pharmaceutical composition disclosed herein may include one or more free $C_{14-24}$ fatty acids comprising, or consisting essentially of or consisting of saturated free $C_{14}$-$C_{16}$ fatty acids, saturated free $C_{14}$-$C_{18}$ fatty acids, saturated free $C_{14}$-$C_{20}$ fatty acids, saturated free $C_{14}$-$C_{22}$ fatty acids, saturated free $C_{14}$-$C_{24}$ fatty acids, saturated free $C_{16}$-$C_{18}$ fatty acids, saturated free $C_{16}$-$C_{20}$ fatty acids, saturated free $C_{16}$-$C_{22}$ fatty acids, saturated free $C_{16}$-$C_{24}$ fatty acids, saturated free $C_{18}$-$C_{20}$ fatty acids, saturated free $C_{18}$-$C_{22}$ fatty acids, saturated free $C_{18}$-$C_{24}$ fatty acids, saturated free $C_{20}$-$C_{22}$ fatty acids, or saturated free $C_{22}$-$C_{24}$ fatty acids.

In some embodiments, a pharmaceutical composition disclosed herein may include one or more free $C_{14-24}$ fatty acids comprising, or consisting essentially of or consisting of a mixture of saturated and unsaturated free $C_{14}$-$C_{16}$ fatty acids, a mixture of saturated and unsaturated free $C_{14}$-$C_{18}$ fatty acids, a mixture of saturated and unsaturated free $C_{14}$-$C_{20}$ fatty acids, a mixture of saturated and unsaturated free $C_{14}$-$C_{22}$ fatty acids, a mixture of saturated and unsaturated free $C_{14}$-$C_{24}$ fatty acids, a mixture of saturated and unsaturated free $C_{16}$-$C_{18}$ fatty acids, a mixture of saturated and unsaturated free $C_{16}$-$C_{20}$ fatty acids, a mixture of saturated and unsaturated free $C_{16}$-$C_{22}$ fatty acids, a mixture of saturated and unsaturated free $C_{16}$-$C_{24}$ fatty acids, a mixture of saturated and unsaturated free $C_{18}$-$C_{20}$ fatty acids, a mixture of saturated and unsaturated free $C_{18}$-$C_{22}$ fatty acids, a mixture of saturated and unsaturated free $C_{18}$-$C_{24}$ fatty acids, a mixture of saturated and unsaturated free $C_{20}$-$C_{22}$ fatty acids, or a mixture of saturated and unsaturated free $C_{22}$-$C_{24}$ fatty acids.

Non-limiting examples of a free $C_{14-24}$ fatty acid include palmitic acid (hexadecenoic acid), palmitolinolenic acid, palmitidonic acid, palmitovaccenic acid, palmitoleic acid, sapienic acid, 4-Hexadecenoic acid, stearic acid (octadecenoic acid), α-linolenic acid, stearidonic acid, α-eleostearic acid, β-eleostearic acid, pumicic acid, 7,10,13-octadecatrienoic acid, 12-octadecenoic acid, linoleic acid, linolelaidic acid, γ-linolenic acid, calendic acid, pinolenic acid, vaccinic acid, ruminic acid, oleic acid, elaidic acid, petroselinic acid, arachidic acid (eicosanoic acid), dihomo-α-linolenic acid, eicosic acidtraenoic acid, eicosapentaenoic acid, 9,12,15-eicosatrienoic acid, β-eicosic acidtraenoic acid, dihomo-linoleic acid, dihomo-γ-linolenic acid, arachidonic acid, paullinic acid, 7,10,13-eicosatrienoic acid, gondoic acid, 8,11-eicosadienoic acid, meadic acid, gadoleic acid, 8-eicosenoic acid, behenic acid (docosanoic acid), clupanodonic acid, docosahexaenoic acid, adrenic acid, osbondic acid, erucic acid, lignoceric acid (tetracosanoic acid), 9,12,15,18, 21-Tetracosapentaenoic acid, 6,9,12,15,18,21-Tetracosahexaenoic acid, and nervonic acid.

The amount of a free $C_{14-24}$ fatty acid useful in a pharmaceutical composition disclosed herein is an amount that does not adversely affect the pharmacokinetics of a therapeutic compound it is being formulated with. In some embodiments, a pharmaceutical composition disclosed herein may comprising or consisting essentially of or consisting of one or more free $C_{14-24}$ fatty acids in an amount of, e.g., about 1% by weight, about 2.5% by weight, about 5% by weight, about 7.5% by weight, about 10% by weight, about 12.5% by weight, about 15% by weight, about 17.5% by weight, about 20% by weight, about 22.5% by weight, about 25% by weight, about 35% by weight, about 30% by weight, about 40% by weight, about 50% by weight, about 60% by weight, about 70% by weight, or about 75% by weight. In some embodiments, a pharmaceutical composition disclosed herein may comprising or consisting essentially of or consisting of one or more free $C_{14-24}$ fatty acids in an amount of, e.g., at least 1% by weight, at least 2.5% by weight, at least 5% by weight, at least 7.5% by weight, at least 10% by weight, at least 12.5% by weight, at least 15% by weight, at least 17.5% by weight, at least 20% by weight, at least 22.5% by weight, at least 25% by weight, at least 30% by weight, at least 35% by weight, at least 40% by weight, at least 50% by weight, at least 60% by weight, at least 70% by weight, or at least 75% by weight. In some embodiments, a pharmaceutical composition disclosed herein may comprising or consisting essentially of or consisting of one or more free $C_{14-24}$ fatty acids in an amount of, e.g., at most 1% by weight, at most 2.5% by weight, at most 5% by weight, at most 7.5% by weight, at most 10% by weight, at most 12.5% by weight, at most 15% by weight, at most 17.5% by weight, at most 20% by weight, at most 22.5% by weight, at most 25% by weight, at most 30% by weight, at most 35% by weight, at most 40% by weight, at most 50% by weight, at most 60% by weight, at most 70% by weight, or at most 75% by weight.

In some embodiments, a pharmaceutical composition disclosed herein may comprising or consisting essentially of or consisting of one or more free $C_{14-24}$ fatty acids in an amount of, e.g., about 1% to about 2.5% by weight, about 1% to about 5% by weight, about 1% to about 10% by weight, about 1% to about 15% by weight, about 1% to about 20% by weight, about 1% to about 25% by weight, about 2.5% to about 5% by weight, about 2.5% to about 10% by weight, about 2.5% to about 15% by weight, about 2.5% to about 20% by weight, about 2.5% to about 25% by weight, about 2.5% to about 30% by weight, about 5% to about 10% by weight, about 5% to about 15% by weight, about 5% to about 20% by weight, about 5% to about 25% by weight, about 5% to about 30% by weight, about 10% to about 15% by weight, about 10% to about 20% by weight, about 10% to about 25% by weight, about 10% to about 30% by weight, about 10% to about 40% by weight, about 10% to about 45% by weight, about 10% to about 50% by weight, about 10% to about 60% by weight, about 10% to about 70% by weight, about 15% to about 20% by weight, about 15% to about 25% by weight, about 15% to about 30% by weight, about 15% to about 40% by weight, about 15% to about 45% by weight, about 15% to about 50% by weight, about 15% to about 60% by weight, about 15% to about 70% by weight, about 20% to about 25% by weight, about 20% to about 30% by weight, about 20% to about 40% by weight, about 20% to about 45% by weight, about 20% to about 50% by weight, about 20% to about 60% by weight, about 20% to about 70% by weight, about 30% to about 40% by weight, about 30% to about 50% by weight, about 30% to about 60% by weight, about 30% to about 70% by weight, about 30% to about 75% by weight, about 35% to about 40% by weight, about 35% to about 50% by weight, about 35% to about 60% by weight, about 35% to about 70% by weight, about 35% to about 75% by weight, about 40% to about 50% by weight, about 40% to about 60% by weight, about 40% to about 70% by weight, about 40% to about 75% by weight, about 50% to about 60% by weight, about 50% to about 70% by weight, or about 60% to about 70% by weight.

In some embodiments, a pharmaceutical composition disclosed herein may comprising or consisting essentially of or consisting of one or more free $C_{14-24}$ fatty acids in a concentration of, e.g., at most 0.01 mM, at most 0.025 mM, at most 0.05 mM, at most 0.075 mM, at most 0.1 mM, at most 0.25 mM, at most 0.5 mM, at most 0.75 mM, at most 1 mM, at most 1.25 mM, at most 1.5 mM, at most 1.75 mM, or at most 2 mM. In some embodiments, a pharmaceutical composition disclosed herein may comprising or consisting essentially of or consisting of one or more free $C_{14-24}$ fatty acids in a concentration of, e.g., about 0.01 mM to about 0.05 mM, about 0.01 mM to about 0.1 mM, about 0.01 mM to about 0.5 mM, about 0.01 mM to about 1 mM, about 0.01 mM to about 1.25 mM, about 0.01 mM to about 1.5 mM, about 0.01 mM to about 1.75 mM, about 0.01 mM to about 2 mM, about 0.05 mM to about 0.1 mM, about 0.05 mM to about 0.5 mM, about 0.05 mM to about 1 mM, about 0.05 mM to about 1.25 mM, about 0.05 mM to about 1.5 mM, about 0.05 mM to about 1.75 mM, about 0.05 mM to about 2 mM, about 0.1 mM to about 0.5 mM, about 0.1 mM to about 1 mM, about 0.1 mM to about 1.25 mM, about 0.1 mM to about 1.5 mM, about 0.1 mM to about 1.75 mM, about 0.1 mM to about 2 mM, about 0.5 mM to about 1 mM, about 0.5 mM to about 1.25 mM, about 0.5 mM to about 1.5 mM, about 0.5 mM to about 1.75 mM, about 0.5 mM to about 2 mM, about 1 mM to about 1.25 mM, about 1 mM to about 1.5 mM, about 1 mM to about 1.75 mM, or about 15 mM to about 2 mM.

Phospholipids

A pharmaceutical composition disclosed herein may comprises one or more phospholipids. Like bile acids disclosed herein, phospholipids disclosed herein to break apart the lipid component of a pharmaceutical composition disclosed herein via its surfactant properties into smaller lipid structures that mimic emulsion droplets, thereby facilitating the emulsification process. The "emulsion droplets" recruit colipase and create a greater surface area for which pancreatic lipase can digest the hard fat glycerolipids present therewithin. In addition phospholipids disclosed herein, along with free fatty acid surfactants disclosed herein, facilitate formation of micelles by associating with the lipid digestion products of triglycerides, and then enhancing association of the triglyceride digestion products with fatty acid transporters, thereby enhancing absorption lipid molecules and the associated therapeutic compound into enterocytes.

The structure of the phospholipid generally comprises a hydrophobic tail of one or more fatty acids and a hydrophilic head containing phosphoric acid functional group and is amphipathic in nature and having an HLB of greater than 12. Phospholipids include, without limitation, phosphoglycerides and phosphosphingolipids. Phosphoglycerides have a general structure comprising a glycerol backbone with two fatty acids esterified to the first and second hydroxyl groups of glycerol and a phosphoric acid group esterified to the third hydroxyl group of glycerol. An alcohol group is esterified to the phosphoric acid group of a phosphoglyceride. Phosphoglycerides always have two fatty acids usually with one fatty acid being saturated and the other being unsaturated. Phosphoglycerides are generally typed according to the particular alcohol group present on the phosphortic acid group, such as, e.g., ethanolamine, choline, serine or inositol. Non-limiting examples of phosphoglycerides include a phosphatidic acid (phosphatidate) (PA), a phosphatidylethanolamine (PE), a phosphatidylcholine (PC), a phosphatidylserine (PS), a cardiolipin, and a phosphoinositide including phosphatidylinositol (PI), phosphatidylinositol phosphate (PIP), phosphatidylinositol bisphosphate (PIP2), and phosphatidylinositol triphosphate (PIP3).

Although structurally different, phosphosphingolipids also have a polar head and two nonpolar tails. Phosphosphingolipids have a general structure comprising a long-chain amino alcohol sphingosine backbone with a fatty acid forming an amide linkage to the amino group of to the sphingosine backbone and a phosphoric acid group esterified to the hydroxyl group of the sphingosine backbone. Non-limiting examples of phosphosphingolipids include a ceramide phosphorylethanolamine (Cer-PE), and ceramide phosphorylcholine (Cer-PC), and ceramide phosphorylglycerol (Cer-PG).

In addition to its amphipathic nature, a phospholipid can be a zwitterionic phospholipids. A zwitterionic phospholipid is a fully ionized molecule that contains an equal number of positively charged and negatively charged functional groups and is electrically neutral. Non-limiting examples of a zwitterionic phospholipid include phosphatidylethanolamine (PE), phosphatidylcholine (PC), ceramide phosphorylethanolamine (Cer-PE), and ceramide phosphorylcholine (Cer-PC).

Phospholipids disclosed herein include lecthins. Lecthins are amphiphilic mixtures of glycerophospholipids. In some embodiments, a lecthin comprises a mixture of phosphatidylcholine, phosphatidylethanolamine, phosphatidylinositol, phosphatidylserine, and phosphatidic acid. In some embodiments, a lecthin comprises 19% to 21% phosphatidylcholine, 8% to 20% phosphatidylethanolamine, 20% to 21% phosphatidylinositol, and 5% to 11% phospholipids comprising phosphatidylserine, and phosphatidic acid.

In some embodiments, a pharmaceutical composition disclosed herein may comprising or consisting essentially of or consisting of one or more phospholipids in an amount of, e.g., about 1.0% by weight, about 1.5% by weight, about 2.0% by weight, about 2.5% by weight, about 3.0% by weight, about 3.5% by weight, about 4.0% by weight, about 4.5% by weight, about 5.0% by weight, about 5.5% by weight, about 6.0% by weight, about 6.5% by weight, about 7.0% by weight, about 7.5% by weight, about 8.0% by weight, about 8.5% by weight, about 9.0% by weight, about 9.5% by weight, or about 10.0% by weight. In some embodiments, a pharmaceutical composition disclosed herein may comprising or consisting essentially of or consisting of one or more phospholipids in an amount of, e.g., at least 1.0% by weight, at least 1.5% by weight, at least 2.0% by weight, at least 2.5% by weight, at least 3.0% by weight, at least 3.5% by weight, at least 4.0% by weight, at least 4.5% by weight, at least 5.0% by weight, at least 5.5% by weight, at least 6.0% by weight, at least 6.5% by weight, at least 7.0% by weight, at least 7.5% by weight, at least 8.0% by weight, at least 8.5% by weight, at least 9.0% by weight, at least 9.5% by weight, or at least 10.0% by weight. In some embodiments, a pharmaceutical composition disclosed herein may comprising or consisting essentially of or consisting of one or more phospholipids in an amount of, e.g., at most 1.0% by weight, at most 1.5% by weight, at most 2.0% by weight, at most 2.5% by weight, at most 3.0% by weight, at most 3.5% by weight, at most 4.0% by weight, at most 4.5% by weight, at most 5.0% by weight, at most 5.5% by weight, at most 6.0% by weight, at most 6.5% by weight, at most 7.0% by weight, at most 7.5% by weight, at most 8.0% by weight, at most 8.5% by weight, at most 9.0% by weight, at most 9.5% by weight, or at most 10.0% by weight.

In some embodiments, a pharmaceutical composition disclosed herein may comprising or consisting essentially of or consisting of one or more phospholipids in an amount of, e.g., about 1.0% to about 2.0%, about 1.0% to about 3.0%, about 1.0% to about 4.0%, about 1.0% to about 5.0%, about 1.0% to about 6.0%, about 1.0% to about 7.0%, about 1.0% to about 8.0%, about 1.0% to about 9.0%, about 1.0% to about 10.0%, about 2.0% to about 3.0%, about 2.0% to about 4.0%, about 2.0% to about 5.0%, about 2.0% to about 6.0%, about 2.0% to about 7.0%, about 2.0% to about 8.0%, about 2.0% to about 9.0%, about 2.0% to about 10.0%, about 3.0% to about 4.0%, about 3.0% to about 5.0%, about 3.0% to about 6.0%, about 3.0% to about 7.0%, about 3.0% to about 8.0%, about 3.0% to about 9.0%, about 3.0% to about 10.0%, about 4.0% to about 5.0%, about 4.0% to about 6.0%, about 4.0% to about 7.0%, about 4.0% to about 8.0%, about 4.0% to about 9.0%, about 4.0% to about 10.0%, about 5.0% to about 6.0%, about 5.0% to about 7.0%, about 5.0% to about 8.0%, about 5.0% to about 9.0%, about 5.0% to about 10.0%, about 6.0% to about 7.0%, about 6.0% to about 8.0%, about 6.0% to about 9.0%, about 6.0% to about 10.0%, about 7.0% to about 8.0%, about 7.0% to about 9.0%, about 7.0% to about 10.0%, about 8.0% to about 9.0%, about 8.0% to about 10.0%, or about 9.0% to about 10.0% by weight.

$C_{14-24}$ Fatty Acid Surfactants

A pharmaceutical composition disclosed herein may comprises one or more free $C_{14-24}$ fatty acid surfactants. A fatty acid surfactant comprises a carboxylic acid with a long unbranched hydrocarbon chain which may be either saturated or unsaturated associated with an alkali metal or other metal ion and are hydrophobic molecules amphipathic molecules having a HLB of greater than 12. The primary purpose of free $C_{14-24}$ fatty acid surfactants are to enhance solubility of a therapeutic compound disclosed herein with the glycerolipid admixture and to enhance absorption of a therapeutic compound disclosed herein thereby improving the pharmacokinetics of the compound. The improved solubility properties are achieved by the free $C_{14-24}$ fatty acid surfactants through the interaction of its carboxylic acid functional group with sodium ions present on a therapeutic compound which neutralizes the charge and facilitating the compounds interaction with the hydrophobic glycolipid admixture. The improved absorption properties are achieved by the free $C_{14-24}$ fatty acid surfactants by facilitating and increasing the formation of mixed micelles by breaking up larger emulsion droplets, thereby mimicking the lipid digestion products of triglycerides, namely free fatty acids. As such, a $C_{14-24}$ fatty acid surfactant disclosed herein increases the uptake of micelles comprising one or more therapeutic compounds into enterocytes. A free $C_{14-24}$ fatty acid surfactant disclosed herein is a free $C_{14-24}$ fatty acid that is associated with an alkali metal, such as, e.g., lithium (Li), sodium (Na), potassium (K), rubidium (Rb), cesium (Cs), and francium (Fr), or alkaline earth metal, such as, e.g., beryllium (Be), magnesium (Mg), calcium (Ca), strontium (Sr), barium (Ba), and radium (Ra).

In some embodiments, pharmaceutical composition disclosed herein may include one or more free $C_{14-24}$ fatty acid surfactants comprising, or consisting essentially of or consisting of unsaturated free $C_{14}$-$C_{16}$ fatty acid surfactants, unsaturated free $C_{14}$-$C_{18}$ fatty acid surfactants, unsaturated free $C_{14}$-$C_{20}$ fatty acid surfactants, unsaturated free $C_{14}$-$C_{22}$ fatty acid surfactants, unsaturated free $C_{14}$-$C_{24}$ fatty acid surfactants, unsaturated free $C_{16}$-$C_{18}$ fatty acid surfactants, unsaturated free $C_{16}$-$C_{20}$ fatty acid surfactants, unsaturated free $C_{16}$-$C_{22}$ fatty acid surfactants, unsaturated free $C_{16}$-$C_{24}$ fatty acid surfactants, unsaturated free $C_{18}$-$C_{20}$ fatty acid surfactants, unsaturated free $C_{18}$-$C_{22}$ fatty acid surfactants, unsaturated free $C_{18}$-$C_{24}$ fatty acid surfactants, unsaturated free $C_{20}$-$C_{22}$ fatty acid surfactants, or unsaturated free $C_{22}$-$C_{24}$ fatty acid surfactants. In some embodiments, pharmaceutical composition disclosed herein may include one or more free $C_{14-24}$ fatty acid surfactants comprising, or consisting essentially of or consisting of ω-3 unsaturated free $C_{18}$-$C_{22}$ fatty acid surfactants, ω-5 unsaturated free $C_{18}$-$C_{22}$ fatty acid surfactants, ω-6 unsaturated free $C_{18}$-$C_{22}$ fatty acid surfactants, ω-7 unsaturated free $C_{18}$-$C_{22}$ fatty acid surfactants, ω-9 unsaturated free $C_{18}$-$C_{22}$ fatty acid surfactants, ω-10 unsaturated free $C_{18}$-$C_{22}$ fatty acid surfactants, ω-11 unsaturated free $C_{18}$-$C_{22}$ fatty acid surfactants, or ω-12 unsaturated free $C_{18}$-$C_{22}$ fatty acid surfactants.

In some embodiments, pharmaceutical composition disclosed herein may include one or more free $C_{14-24}$ fatty acid surfactants comprising, or consisting essentially of or consisting of saturated free $C_{14}$-$C_{16}$ fatty acid surfactants, saturated free $C_{14}$-$C_{18}$ fatty acid surfactants, saturated free $C_{14}$-$C_{20}$ fatty acid surfactants, saturated free $C_{14}$-$C_{22}$ fatty acid surfactants, saturated free $C_{14}$-$C_{24}$ fatty acid surfactants, saturated free $C_{16}$-$C_{18}$ fatty acid surfactants, saturated free $C_{16}$-$C_{20}$ fatty acid surfactants, saturated free $C_{16}$-$C_{22}$ fatty acid surfactants, saturated free $C_{16}$-$C_{24}$ fatty acid surfactants, saturated free $C_{18}$-$C_{20}$ fatty acid surfactants, saturated free $C_{18}$-$C_{22}$ fatty acid surfactants, saturated free $C_{18}$-$C_{24}$ fatty acid surfactants, saturated free $C_{20}$-$C_{22}$ fatty acid surfactants, or saturated free $C_{22}$-$C_{24}$ fatty acid surfactants.

In some embodiments, a pharmaceutical composition disclosed herein may include one or more free $C_{14-24}$ fatty acid surfactants comprising, or consisting essentially of or consisting of a mixture of saturated and unsaturated free $C_{14}$-$C_{16}$ fatty acid surfactants, a mixture of saturated and unsaturated free $C_{14}$-$C_{18}$ fatty acid surfactants, a mixture of saturated and unsaturated free $C_{14}$-$C_{20}$ fatty acid surfactants, a mixture of saturated and unsaturated free $C_{14}$-$C_{22}$ fatty acid surfactants, a mixture of saturated and unsaturated free $C_{14}$-$C_{24}$ fatty acid surfactants, a mixture of saturated and unsaturated free $C_{16}$-$C_{18}$ fatty acid surfactants, a mixture of saturated and unsaturated free $C_{16}$-$C_{20}$ fatty acid surfactants, a mixture of saturated and unsaturated free $C_{16}$-$C_{22}$ fatty acid surfactants, a mixture of saturated and unsaturated free $C_{16}$-$C_{24}$ fatty acid surfactants, a mixture of saturated and unsaturated free $C_{18}$-$C_{20}$ fatty acid surfactants, a mixture of saturated and unsaturated free $C_{18}$-$C_{22}$ fatty acid surfactants, a mixture of saturated and unsaturated free $C_{18}$-$C_{24}$ fatty acid surfactants, a mixture of saturated and unsaturated free $C_{20}$-$C_{22}$ fatty acid surfactants, or a mixture of saturated and unsaturated free $C_{22}$-$C_{24}$ fatty acid surfactants.

Non-limiting examples of a free $C_{14-24}$ fatty acid surfactant include sodium palmitate (hexadecanoate), sodium palmitolinolenate, sodium palmitidonate, sodium palmitovaccenate, sodium palmitoleate, sodium sapienate, sodium 4-Hexadecenoate, sodium stearate (octadecenoate), sodium α-linolenate, sodium stearidonate, sodium α-eleostearate, sodium β-eleostearate, sodium pumicate, sodium 7,10,13-octadecatrienoate, sodium 12-octadecenoate, sodium linoleate, sodium linolelaidate. Sodium γ-linolenate, sodium calendate, sodium pinolenate, sodium vaccinate, sodium ruminate, sodium oleate, sodium elaidate, sodium petroselinate, sodium arachidate (eicosanoate), sodium dihomo-α-linolenate, sodium eicosatetraenoate, sodium eicosapentaenoate, sodium 9,12,15-eicosatrienoate, sodium β-eicosatetraenoate, sodium dihomo-linoleate, sodium dihomo-γ-linolenate, sodium arachidonate, sodium paullinate, sodium 7,10,13-eicosatrienoate, sodium gondoate, Sodium 8,11-eicosadienoate, sodium meadate, sodium gadoleate, sodium 8-eicosenoate, sodium behenate (docosanoate), sodium clupanodonate, sodium docosahexaenoate, sodium adrenate, sodium osbondate, sodium erucate, sodium lignocerate (tetracosanate), sodium 9,12,15,18,21-Tetracosapentaenoate, sodium 6,9,12,15,18,21-Tetracosahexaenoate, and sodium nervonate.

The lower limit of one or more free $C_{14-24}$ fatty acid surfactants that can be included in a pharmaceutical composition disclosed herein is an amount sufficient to solubilize a therapeutic compound and confer its improved absorption properties. The upper limit of one or more free $C_{14-24}$ fatty acid surfactants that can be included in a pharmaceutical composition disclosed herein is its micellar concentration (CMC).

The amount of one or more free $C_{14-24}$ fatty acid surfactants useful in a pharmaceutical composition disclosed herein is an amount below its CMC. In some embodiments, a pharmaceutical composition disclosed herein may comprising or consisting essentially of or consisting of one or more free $C_{14-24}$ fatty acid surfactants in an amount of, e.g., about 0.1% by weight, about 0.5% by weight, about 1.0% by weight, about 1.0% by weight, about 1.5% by weight, about 2.0% by weight, about 2.5% by weight, about 3.0% by weight, about 3.5% by weight, about 4.0% by weight, about 4.5% by weight, about 5.0% by weight, about 5.5% by weight, about 6.0% by weight, about 6.5% by weight, about 7.0% by weight, about 7.5% by weight, about 8.0% by weight, about 8.5% by weight, about 9.0% by weight, about 9.5% by weight, or about 10.0% by weight. In some embodiments, a pharmaceutical composition disclosed herein may comprising or consisting essentially of or consisting of one or more free $C_{14-24}$ fatty acid surfactants in an amount of, e.g., at least 0.5% by weight, at least 1.0% by weight, at least 1.5% by weight, at least 2.0% by weight, at least 2.5% by weight, at least 3.0% by weight, at least 3.5% by weight, at least 4.0% by weight, at least 4.5% by weight, at least 5.0% by weight, at least 5.5% by weight, at least 6.0% by weight, at least 6.5% by weight, at least 7.0% by weight, at least 7.5% by weight, at least 8.0% by weight, at least 8.5% by weight, at least 9.0% by weight, at least 9.5% by weight, or at least 10.0% by weight. In some embodiments, a pharmaceutical composition disclosed herein may comprising or consisting essentially of or consisting of one or more free $C_{14-24}$ fatty acid surfactants in an amount of, e.g., at most 0.1% by weight, at most 0.5% by weight, at most 1.0% by weight, at most 1.5% by weight, at most 2.0% by weight, at most 2.5% by weight, at most 3.0% by weight, at most 3.5% by weight, at most 4.0% by weight, at most 4.5% by weight, at most 5.0% by weight, at most 5.5% by weight, at most 6.0% by weight, at most 6.5% by weight, at most 7.0% by weight, at most 7.5% by weight, at most 8.0% by weight, at most 8.5% by weight, at most 9.0% by weight, at most 9.5% by weight, or at most 10.0% by weight.

In some embodiments, a pharmaceutical composition disclosed herein may comprising or consisting essentially of or consisting of one or more free $C_{14-24}$ fatty acid surfactants in an amount of, e.g., about 0.1% to about 0.5%, about 0.1% to about 1.0%, about 0.1% to about 2.0%, about 0.1% to about 3.0%, about 0.1% to about 4.0%, about 0.1% to about 5.0%, about 0.1% to about 6.0%, about 0.1% to about 7.0%, about 0.1% to about 8.0%, about 0.1% to about 9.0%, about 0.1% to about 10.0%, about 0.5% to about 1.0%, about 0.5% to about 2.0%, about 0.5% to about 3.0%, about 0.5% to about 4.0%, about 0.5% to about 5.0%, about 0.5% to about 6.0%, about 0.5% to about 7.0%, about 0.5% to about 8.0%, about 0.5% to about 9.0%, about 0.5% to about 10.0%, about 1.0% to about 2.0%, about 1.0% to about 3.0%, about 1.0% to about 4.0%, about 1.0% to about 5.0%, about 1.0% to about 6.0%, about 1.0% to about 7.0%, about 1.0% to about 8.0%, about 1.0% to about 9.0%, about 1.0% to about 10.0%, about 2.0% to about 3.0%, about 2.0% to about 4.0%, about 2.0% to about 5.0%, about 2.0% to about 6.0%, about 2.0% to about 7.0%, about 2.0% to about 8.0%, about 2.0% to about 9.0%, about 2.0% to about 10.0%, about 3.0% to about 4.0%, about 3.0% to about 5.0%, about 3.0% to about 6.0%, about 3.0% to about 7.0%, about 3.0% to about 8.0%, about 3.0% to about 9.0%, about 3.0% to about 10.0%, about 4.0% to about 5.0%, about 4.0% to about 6.0%, about 4.0% to about 7.0%, about 4.0% to about 8.0%, about 4.0% to about 9.0%, about 4.0% to about 10.0%, about 5.0% to about 6.0%, about 5.0% to about 7.0%, about 5.0% to about 8.0%, about 5.0% to about 9.0%, about 5.0% to about 10.0%, about 6.0% to about 7.0%, about 6.0% to about 8.0%, about 6.0% to about 9.0%, about 6.0% to about 10.0%, about 7.0% to about 8.0%, about 7.0% to about 9.0%, about 7.0% to about 10.0%, about 8.0% to about 9.0%, about 8.0% to about 10.0%, or about 9.0% to about 10.0% by weight.

In some embodiments, a pharmaceutical composition disclosed herein may comprising or consisting essentially of or consisting of one or more free $C_{14-24}$ fatty acid surfactants in a concentration of, e.g., at most 5 μM, at most 10 μM, at most 15 μM, at most 20 μM, at most 25 μM, at most μM, or at most 35 μM. In some embodiments, a pharmaceutical composition disclosed herein may comprising or consisting essentially of or consisting of one or more free $C_{14-24}$ fatty acid surfactants in a concentration of, e.g., about 1 μM to about 5 μM, about 1 μM to about 10 μM, about 1 μM to about 15 μM, about 1 μM to about 20 μM, about 1 μM to about 25 μM, about 1 μM to about 30 μM, about 1 μM to about 35 μM, about 5 μM to about 10 μM, about 5 μM to about 15 μM, about 5 μM to about 20 μM, about 5 μM to about 25 μM, about 5 μM to about 30 μM, about 5 μM to about 35 μM, about 10 μM to about 15 μM, about 10 μM to about 20 μM, about 10 μM to about 25 μM, about 10 μM to about 30 μM, about 10 μM to about 35 μM, about 15 μM to about 20 μM, about 15 μM to about 25 μM, about 15 μM to about 30 μM, about 15 μM to about 35 μM, about 20 μM to about 25 μM, about 20 μM to about 30 μM, about 20 μM to about 35 μM, about 25 μM to about 30 μM, about 25 μM to about 35 μM, or about 30 μM to about 35 μM.

Curcumin

Aspects of the present specification disclose, in part, a curcumin. In some embodiments, a pharmaceutical composition disclosed herein may include a curcumin. Curcumin is a pigment of phenolic nature extracted from *Curcuma longa*. Although a pharmacologically bioactive molecule, curcumin is able to facilitate gall bladder contraction, making this compound useful as a digestion enhancer disclosed herein. Gall bladder contraction is an important process in the absorption of fat and thus provide an important benefit increase the formation of mixed micelles by breaking up larger emulsion droplets, thereby increasing the uptake of micelles comprising one or more therapeutic compounds into enterocytes. While a highly insoluble compound, as shown in Example 3, curcumin is soluble using a formulation disclosed herein.

The amount of a curcumin useful in a pharmaceutical composition disclosed herein is a therapeutically effective amount or an amount effective in facilitating gall bladder contraction. In some embodiments, a pharmaceutical composition disclosed herein may comprising or consisting essentially of or consisting of curcumin in an amount of, e.g., about 0.1%, about 0.5%, about 1% by weight, about 1.5% by weight, about 2% by weight, about 2.5% by weight, about 3% by weight, about 4% by weight, about 5% by weight, about 7.5% by weight, or about 10% by weight. In some embodiments, a pharmaceutical composition disclosed herein may comprising or consisting essentially of or consisting of curcumin in an amount of, e.g., at least 0.1%, at least 0.5%, at least 1% by weight, at least 1.5% by weight, at least 2% by weight, at least 2.5% by weight, at least 3% by weight, at least 4% by weight, at least 5% by weight, at least 7.5% by weight, or at least 10% by weight. In some embodiments, a pharmaceutical composition disclosed herein may comprising or consisting essentially of or consisting of curcumin in an amount of, e.g., at most 0.1%, at most 0.5%, at most 1% by weight, at most 1.5% by weight, at most 2% by weight, at most 1% by weight, at most 1.5% by weight, at most 2% by weight, at most 2.5% by weight, at most 3% by weight, at most 4% by weight, at most 5% by weight, at most 7.5% by weight, or at most 10% by weight.

In some embodiments, a pharmaceutical composition disclosed herein may comprising or consisting essentially of or consisting of curcumin in an amount of, e.g., about 0.1% to about 1% by weight, about 0.1% to about 1.5% by weight, about 0.1% to about 2% by weight, about 0.1% to about 2.5% by weight, about 0.1% to about 5% by weight, about 0.1% to about 7.5% by weight, about 0.1% to about 10% by weight, about 0.5% to about 1% by weight, about 0.5% to about 1.5% by weight, about 0.5% to about 2% by weight, about 0.5% to about 2.5% by weight, about 0.5% to about 5% by weight, about 0.5% to about 7.5% by weight, about 0.5% to about 10% by weight, about 1% to about 1.5% by weight, about 1% to about 2% by weight, about 1% to about 2.5% by weight, about 1% to about 5% by weight, about 1% to about 7.5% by weight, or about 1% to about 10% by weight.

Glycol Polymers

Aspects of the present specification disclose, in part, a glycol polymer. In some embodiments, a pharmaceutical composition disclosed herein may include one or more glycol polymers.

A pharmaceutical composition disclosed herein may comprise a stabilizing agent in an amount sufficient to stabilize the free acid or base present in a therapeutic compound disclosed herein. In other aspects of this embodiment, a pharmaceutical composition disclosed herein may comprise a stabilizing agent in an amount of, e.g., less than about 40% by weight, less than about 35% by weight, less than about 30% by weight, less than about 25% by weight, less than about 20% by weight, less than about 19% by weight, less than about 18% by weight, less than about 17% by weight, less than about 16% by weight, less than about 15% by weight, less than about 14% by weight, less than about 13% by weight, less than about 12% by weight, less than about 11% by weight, less than about 10% by weight, less than about 9% by weight, less than about 8% by weight, less than about 7% by weight, less than about 6% by weight, less than about 5% by weight, less than about 4% by weight, less than about 3% by weight, less than about 2% by weight, or less than about 1%. In other aspects of this embodiment, a pharmaceutical composition disclosed herein may comprise a stabilizing agent in an amount of, e.g., about 1% to about 5% by weight, about 1% to about 7% by weight, about 1% to about 10% by weight, about 1% to about 12% by weight, about 1% to about 15% by weight, about 1% to about 18% by weight, about 1% to about 20% by weight, about 2% to about 5% by weight, about 2% to about 7% by weight, about 2% to about 10% by weight, about 2% to about 12% by weight, about 2% to about 15% by weight, about 2% to about 18% by weight, about 2% to about 20% by weight, about 3% to about 5% by weight, about 3% to about 7% by weight, about 3% to about 10% by weight, about 3% to about 12% by weight, about 3% to about 15% by weight, about 3% to about 18% by weight, about 3% to about 20% by weight, about 4% to about 5% by weight, about 4% to about 7% by weight, about 4% to about 10% by weight, about 4% to about 12% by weight, about 4% to about 15% by weight, about 4% to about 18% by weight, about 4% to about 20% by weight, about 5% to about 7% by weight, about 5% to about 10% by weight, about 5% to about 12% by weight, about 5% to about 15% by weight, about 5% to about 18% by weight, about 5% to about 20% by weight, about 6% to about 7% by weight, about 6% to about 10% by weight, about 6% to about 12% by weight, about 6% to about 15% by weight, about 6% to about 18% by weight, about 6% to about 20% by weight, about 7% to about 10% by weight, about 7% to about 12% by weight, about 7% to about 15% by weight, about 7% to about 18% by weight, about 7% to about 20% by weight, about 8% to about 10% by weight, about 8% to about 12% by weight, about 8% to about 15% by weight, about 8% to about 18% by weight, about 8% to about 20% by weight, about 9% to about 10% by weight, about 9% to about 12% by weight, about 9% to about 15% by weight, about 9% to about 18% by weight, about 9% to about 20% by weight, about 10% to about 12% by weight, about 10% to about 15% by weight, about 10% to about 18% by weight, or about 10% to about 20% by weight.

A stability agent as disclosed herein is not a solvent as it is used in an amount that does not result in substantial dissolving of a solute. As such, the amount stability agent used in a solid solution composition disclosed herein results in no more than 85% dissolution of a therapeutic compound disclosed herein. In aspects of this embodiment, he amount stability agent used in a solid solution composition disclosed herein results in. e.g., no more than 80%, no more than 75%, no more than 70%, no more than 65%, no more than 60%, no more than 55%, no more than 50%, no more than 45%, no more than 40%, no more than 35%, no more than 30%, no more than 25%, no more than 20%, no more than 15%, no more than 10%, or no more than 5% dissolution of a therapeutic compound disclosed herein.

In an embodiment, a glycol polymer may comprise a pharmaceutically-acceptable PEG polymer. PEG polymers, also known as polyethylene oxide (PEO) polymers or polyoxyethylene (POE) polymers, are prepared by polymerization of ethylene oxide and are commercially available over a wide range of molecular weights from 100 g/mol to 10,000,000 g/mol. PEG polymers with a low molecular mass are liquids or low-melting solids, whereas PEG polymers of a higher molecular mass are solids. In an aspect of this embodiment, a PEG polymer used as a stability agent is a liquid PEG polymer. In aspects of this embodiment, a PEG polymer has a molecular weight of, e.g., no more than 100 g/mol, no more than 200 g/mol, no more than 300 g/mol, no more than 400 g/mol, no more than 500 g/mol, no more than 600 g/mol, no more than 700 g/mol, no more than 800 g/mol, no more than 900 g/mol, or no more than 1000 g/mol.

A PEG polymer include, without limitation, PEG 100, PEG 200, PEG 300, PEG 400, PEG 500, PEG 600, PEG 700, PEG 800, PEG 900, PEG 1000, PEG 1100, PEG 1200, PEG 1300, PEG 1400, PEG 1500, PEG 1600, PEG 1700, PEG 1800, PEG 1900, PEG 2000, PEG 2100, PEG 2200, PEG 2300, PEG 2400, PEG 2500, PEG 2600, PEG 2700, PEG 2800, PEG 2900, PEG 3000, PEG 3250, PEG 3350, PEG 3500, PEG 3750, PEG 4000, PEG 4250, PEG 4500, PEG 4750, PEG 5000, PEG 5500, PEG 6000, PEG 6500, PEG 7000, PEG 7500, PEG 8000, PEG 8500, PEG 9000, PEG 9500, PEG 10,000, PEG 11,000, PEG 12,000, PEG 13,000, PEG 14,000, PEG 15,000, PEG 16,000, PEG 17,000, PEG 18,000, PEG 19,000, or PEG 20,000.

In another embodiment, a glycol polymer may comprise a pharmaceutically-acceptable polypropylene glycol (PPG) polymer. PPG polymers, also known as polypropylene oxide (PPO) polymers or polyoxypropylene (POP) polymers, are prepared by polymerization of propylene oxide and are commercially available over a wide range of molecular weights from 100 g/mol to 10,000,000 g/mol. PPG polymers with a low molecular mass are liquids or low-melting solids, whereas PPG polymers of a higher molecular mass are solids. In an aspect of this embodiment, a PPG polymer used as a stability agent is a liquid PPG polymer. In aspects of this embodiment, a PPG polymer has a molecular weight of, e.g., no more than 100 g/mol, no more than 200 g/mol, no more than 300 g/mol, no more than 400 g/mol, no more than 500 g/mol, no more than 600 g/mol, no more than 700 g/mol, no more than 800 g/mol, no more than 900 g/mol, or no more than 1000 g/mol.

A PPG polymer include, without limitation, PPG 100, PPG 200, PPG 300, PPG 400, PPG 500, PPG 600, PPG 700, PPG 800, PPG 900, PPG 1000, PPG 1100, PPG 1200, PPG 1300, PPG 1400, PPG 1500, PPG 1600, PPG 1700, PPG 1800, PPG 1900, PPG 2000, PPG 2100, PPG 2200, PPG 2300, PPG 2400, PPG 2500, PPG 2600, PPG 2700, PPG 2800, PPG 2900, PPG 3000, PPG 3250, PPG 3350, PPG 3500, PPG 3750, PPG 4000, PPG 4250, PPG 4500, PPG 4750, PPG 5000, PPG 5500, PPG 6000, PPG 6500, PPG 7000, PPG 7500, PPG 8000, PPG 8500, PPG 9000, PPG 9500, PPG 10,000, PPG 11,000, PPG 12,000, PPG 13,000, PPG 14,000, PPG 15,000, PPG 16,000, PPG 17,000, PPG 18,000, PPG 19,000, or PPG 20,000.

In some embodiments, a pharmaceutical composition disclosed herein does not include a glycol polymer. In aspects of these embodiments, a pharmaceutical composition disclosed herein does not include a PEG polymer. In other aspects of these embodiments, a pharmaceutical composition disclosed herein does not include a PGG polymer. In yet other aspects of these embodiments, a pharmaceutical composition disclosed herein does not include both a PEG polymer and a PGG polymer.

Release Effects

In an embodiment, a substantial amount of a therapeutic compound present in a pharmaceutical composition disclosed herein is delivered to or enters a lipid digestion and/or absorption pathway. In aspects of this embodiment, about 10%, about 20%, about 30%, about 40%, about 50%, about 60%, about 70%, about 80% about 90%, or about 95% of a therapeutic compound present in a pharmaceutical composition disclosed herein is delivered to or enters a lipid digestion and/or absorption pathway. In other aspects of this embodiment, at least 10%, at least 20%, at least 30%, at least 40%, at least 50%, at least 60%, at least 70%, at least 80% at least 90%, or at least 95% of a therapeutic compound present in a pharmaceutical composition disclosed herein is delivered to or enters a lipid digestion and/or absorption pathway. In yet other aspects of this embodiment, at most 10%, at most 20%, at most 30%, at most 40%, at most 50%, at most 60%, at most 70%, at most 80% at most 90%, or at most 95% of a therapeutic compound present in a pharmaceutical composition disclosed herein is delivered to or enters a lipid digestion and/or absorption pathway.

In yet other aspects of this embodiment, about 10% to about 20%, about 10% to about 30%, about 10% to about 40%, about 10% to about 50%, about 10% to about 60%, about 10% to about 70%, about 10% to about 80%, about 10% to about 90%, about 10% to about 100%, about 20% to about 30%, about 20% to about 40%, about 20% to about 50%, about 20% to about 60%, about 20% to about 70%, about 20% to about 80%, about 20% to about 90%, about 20% to about 100%, about 30% to about 40%, about 30% to about 50%, about 30% to about 60%, about 30% to about 70%, about 30% to about 80%, about 30% to about 90%, about 30% to about 100%, about 40% to about 50%, about 40% to about 60%, about 40% to about 70%, about 40% to about 80%, about 40% to about 90%, about 40% to about 100%, about 50% to about 60%, about 50% to about 70%, about 50% to about 80%, about 50% to about 90%, about 50% to about 100%, about 60% to about 70%, about 60% to about 80%, about 60% to about 90%, about 60% to about 100%, about 70% to about 80%, about 70% to about 90%, about 70% to about 100%, about 80% to about 90%, about 80% to about 100%, or about 90% to about 100%, of a therapeutic compound present in a pharmaceutical composition disclosed herein is delivered to or enters a lipid digestion and/or absorption pathway.

In an embodiment, an insubstantial amount of a therapeutic compound present in a pharmaceutical composition disclosed herein is absorbed by blood capillaries and enters directly into the blood. In aspects of this embodiment, at most 1%, at most 5%, at most 10%, at most 20%, at most 30%, at most 40%, at most 50%, at most 60%, at most 70%, at most 80% at most 90%, or at most 95% of a therapeutic compound present in a pharmaceutical composition disclosed herein is absorbed by blood capillaries and enters directly into the blood. In aspects of this embodiment, about 1% to about 10%, about 1% to about 20%, about 1% to about 30%, about 1% to about 40%, about 1% to about 50%, about 1% to about 60%, about 1% to about 70%, about 1% to about 80%, about 1% to about 90%, about 1% to about 95%, about 10% to about 20%, about 10% to about 30%, about 10% to about 40%, about 10% to about 50%, about 10% to about 60%, about 10% to about 70%, about 10% to about 80%, about 10% to about 90%, about 10% to about 95%, about 20% to about 30%, about 20% to about 40%, about 20% to about 50%, about 20% to about 60%, about 20% to about 70%, about 20% to about 80%, about 20% to about 90%, about 20% to about 95%, about 30% to about 40%, about 30% to about 50%, about 30% to about 60%, about 30% to about 70%, about 30% to about 80%, about 30% to about 90%, about 30% to about 95%, about 40% to about 50%, about 40% to about 60%, about 40% to about 70%, about 40% to about 80%, about 40% to about 90%, about 40% to about 95%, about 50% to about 60%, about 50% to about 70%, about 50% to about 80%, about 50% to about 90%, about 50% to about 95%, about 60% to about 70%, about 60% to about 80%, about 60% to about 90%, about 60% to about 95%, about 70% to about 80%, about 70% to about 90%, about 70% to about 95%, about 80% to about 90%, about 80% to about 95%, or about 90% to about 95%, of a therapeutic compound present in a pharmaceutical composition disclosed herein is absorbed by blood capillaries and enters directly into the blood.

Formulating Procedure

The inclusion of one or more digestion enhancers to one or more therapeutic compounds to a pharmaceutical composition disclosed herein is applicable to any therapeutic compound administered by a route of administration where uptake of the compound is achieved by absorption through the gastrointestinal tract, such as, e.g., oral delivery. However, formulation of a pharmaceutical composition disclosed herein is dependent on the solubility of a therapeutic compound in the one or more glycerolipid used in formulating the pharmaceutical composition. As such, formulation of any one particular therapeutic compound disclosed herein is achieved by the process described below.

As a first step, it is first determined whether a selected therapeutic compound can be formulated using 1) glycerolipids including at least one liquid fat (glycerolipid that is liquid at 18° C.) and at least one hard fat (glycerolipid that is solid at 18° C.) and 2) one or more digestion enhancers. In some embodiments, the one or more liquid and hard fats are first heated and the one or more digestion enhancers are solubilized in the glycerolipid admixture. Upon completion of solubility of the digestion enhancers, and if appropriate, the temperature of the admixture can be adjusted and a selected therapeutic compound is then dissolved in this heated admixture to incorporate the compound. Such manufacturing procedure is useful when formulating a therapeutic compound that is easily solubilized in lipid admixtures. In some embodiments, the one or more liquid fats are first heated and the one or more digestion enhancers are solubilized in the liquid fats. Upon completion of solubility of the digestion enhancers, and if appropriate, the temperature of the admixture can be adjusted and a selected therapeutic compound is then dissolved in this heated admixture to incorporate the compound. Upon complete dissolution of the therapeutic compound, one or more hard fats are then added to this heated admixture. Such manufacturing procedure is useful when formulating a lipophilic therapeutic compound. In some embodiments, one or more digestion enhancers are first heated and a selected therapeutic compound is then dissolved to this heated admixture to incorporate the compound. Upon completion dissolution of the therapeutic compound, and if appropriate, the temperature of the admixture can be adjusted and one or more liquid fats are then added and incorporated into this admixture. Upon completion of solubility of the one or more liquid fats, one or more hard fats are then added and incorporated into this admixture. Such manufacturing procedure is useful when formulating a therapeutic compound that is highly insoluble in lipid admixtures. The initial heating step in all procedures is performed at a temperature sufficient to dissolve the one or more digestion enhancers and selected therapeutic compound and can be empirically determined based on the melting point of the selected components. Generally, this temperature range is about 60° C. to about 170° C. Any subsequent adjustment to the heat when one or more liquid fats and/or one or more hart fats are being added to the admixture is performed at a temperature sufficient to melt the hard fats and can be empirically determined based on the melting point of the hard fat used in the formulation. Generally, this temperature range is about 40° C. to about 60° C.

This incorporated mixture is then allowed to cool to room temperature, at which time stirring is ceased and the mixture is transferred to suitable containers where it will solidify. Once cooled, the pharmaceutical composition can be optionally stability tested by reheating the composition to a temperature sufficient to cause it to melt. The reheating step is performed at a temperature sufficient to melt the glycerolipid components and can be empirically determined based on the melting point of the hard fat used in the formulation. Generally, this temperature range is 40° C. to 50° C. The selection of the one or more digestion enhancers is generally not a critical component in this process, as a bile acid, free fatty acid, phospholipid, or free fatty acid surfactant can all be used in any combination to achieve a pharmaceutical composition disclosed herein. A successful formulation is achieved if this selected therapeutic compound remains stably incorporated in the glycerolipid mixture. However, if the selected therapeutic compound fails to incorporate into the heated glycerolipid admixture or precipitates out during the cooling process, the reheating step, or during storage at room temperature, then the compound cannot be formulated according to this process. As shown in Example 2, the preparative methods all include a complete dissolution phase that upon cooling nano-crystallization of some components occurs and this is described in the XRPD spectra.

Examples 4-11 exemplify therapeutic compounds formulated according to this process. These examples also reveal two formulary subgroups. In one subgroup, the presence of one or more digestion enhancers does not appreciable enhance the solubility of the therapeutic compound in a glycerolipid matrix. Instead, the presence of digestion enhancers serves to improve bioavailability of the therapeutic compound. Example 4 pertaining to fenofibrate and Example 5 pertaining to Cannabidiol exemplify therapeutic compounds of this formulary subgroup. In one subgroup, the presence of one or more digestion enhancers is necessary to achieve solubility of the therapeutic compound in a glycerolipid matrix as well as improve bioavailability of the compound. Example 3 pertaining to Curcumin and Examples δ-11 exemplify therapeutic compounds of this formulary subgroup.

If a therapeutic compound cannot be formulated by the above process, then the therapeutic compound is assessed for the presence of an ionic functional group, such as, e.g., an organic acid functional group (such as, e.g., a carboxylic acid functional group or sulfonic acid functional group), or an organic base functional group (such as, e.g., an amine functional group). In some embodiments, if a therapeutic compound includes an organic acid functional group, then a component including an organic base functional group is mixed with the therapeutic compound to form an anhydrous salt form of the therapeutic compound. In some embodiments, if a therapeutic compound includes an organic base functional group, then a simple an organic acid functional group is employed to form an anhydrous salt form of the therapeutic compound. In these preparative methods, formation of an anhydrous salt of the therapeutic compound enable formulation of a pharmaceutical composition disclosed herein and as such, is a prerequisite to formation of the glycerolipid matrix. The ionic bonding which must occur in order to form an anhydrous salt is an unexpected result because no dissolution of ions can occur since the components are not in an aqueous environment. The presence of one or more hard fats in the admixture before the formation of an anhydrous salt of the therapeutic compound will prevent dissolution of the therapeutic compound and cause the compound to precipitate from the admixture.

Alternatively, therapeutic compounds comprising an ionic functional group can be formulated by neutralizing the compound into its non-ionic form. Many therapeutic compounds are presented in ionic form. For example an organic acid such as an NSAID is often presented as a salt such as, but not limited to, an alkali or alkaline earth metal salt. Other therapeutic compounds such as, but not limited to amines are often presented as mineral acid salts such as hydrochlorides for example amitriptyline and ketamine. Such therapeutic compounds can also be used in their neutral non-ionic form by releasing the carboxylic acid or the amine from its salt.

For example, as exemplified in Example 12 for Naproxen, a therapeutic compound including a carboxylic acid function group can exist either in a free carboxylic acid form or a carboxylate salt form. The present process has found that although either ionic form alone is insoluble in a glycerolipid admixture, mixing the free carboxylic acid form of Naproxen with carboxylate salt form of Naproxen results in dissolution of the anhydrous salt of Naproxen and subsequent stable incorporation into the glycerolipid matrix (see Table 24, Naproxen formulation NAPF3). Similarly, mixing the free carboxylic acid form of Naproxen with $C_{14-24}$ fatty acid surfactant results in formation and dissolution of the anhydrous salt of Naproxen and subsequent stable incorporation into the glycerolipid matrix (see Table 24, Naproxen formulation NAPF2). These findings for Naproxen have been extended to other therapeutic compounds comprising an organic acid where mixture with a component including an organic base functional group forms an anhydrous salt of the therapeutic compound and subsequent incorporation into the glycerolipid matrix (see Examples 12-17). A component including an organic base, whether present as a therapeutic component or additional component, can be an alkali metal or alkali earth metal salt and functions as a crystalline inhibitor that slows the rate of crystallization.

Similarly, as disclosed in Example 12, mixing the carboxylate salt form of Naproxen with a $C_{14-24}$ fatty acids results in formation and dissolution of the anhydrous salt of Naproxen and subsequent stable incorporation into the glycerolipid matrix (see Table 24, Naproxen formulation NAPF1 and NAPF4). The findings for Naproxen have been extended to other therapeutic compounds comprising an organic base where mixture with a component including an organic acid functional group forms an anhydrous salt form (see Examples 18-20). For example, Example 18 describes seven formulations for aprepitant (APRF1-APRF7). In each case, formation of an anhydrous salt of the therapeutic compound first resulted in the dissolution of the anhydrous salt of Naproxen and subsequent stable incorporation into the glycerolipid matrix.

Based on these findings, if a therapeutic compound includes an organic acid functional group, one of the following processes can be employed to formulate a pharmaceutical composition disclosed herein. In some embodiments, one or more one liquid fat (glycerolipid that is liquid at 18° C.) and one or more digestion enhancers comprising an organic base are first heated and a selected therapeutic compound including an organic acid functional group is then dissolved in this heated admixture to incorporate the compound and form an anhydrous salt of the therapeutic compound. Upon complete dissolution of the therapeutic compound, one or more hard fats are then added to this heated admixture. In some embodiments, one or more digestion enhancers comprising an organic base are first heated and a selected therapeutic compound including an organic acid functional group is then dissolved in this heated admixture to incorporate the compound and form an anhydrous salt of the therapeutic compound. Upon complete dissolution of the therapeutic compound, one or more hard fats are then added to this heated admixture. In some embodiments, one or more digestion enhancers comprising an organic base are first heated and a selected therapeutic compound including an organic acid functional group is then dissolved in this heated admixture to incorporate the compound and form an anhydrous salt of the therapeutic compound. Upon completion dissolution of the therapeutic compound, and if appropriate, the temperature of the admixture can be adjusted and one or more liquid fats are then added and incorporated into this admixture. Upon completion of solubility of the one or more liquid fats, one or more hard fats are then added and incorporated into this admixture. The initial heating step in all procedures is performed at a temperature sufficient to dissolve the one or more digestion enhancers and selected therapeutic compound and can be empirically determined based on the melting point of the selected components. Generally, this temperature range is about 60° C. to about 170° C. Any subsequent adjustment to the heat when one or more liquid fats and/or one or more hart fats are being added to the admixture is performed at a temperature sufficient to melt the hard fats and can be empirically determined based on the melting point of the hard fat used in the formulation. Generally, this temperature range is about 40° C. to about 60° C.

Regardless of which process is employed, the incorporated mixture is then allowed to cool to room temperature at which time stirring is ceased and the mixture is transferred to suitable containers where it will solidify. Additionally, once cooled, the pharmaceutical composition can be optionally stability tested by reheating the composition to a temperature sufficient to cause it to melt. The reheating step is performed at a temperature sufficient to melt the glycerolipid components and can be empirically determined based on the melting point of the hard fat used in the formulation. Generally, this temperature range is 40° C. to 50° C. Although, as discussed above, depending on the process a carboxylic acid or carboxylate salt form may be required, the selection of the one or more digestion enhancers is generally not a critical component in this process, as a bile acid, free fatty acid, phospholipid, or free fatty acid surfactant in its appropriate ionic form can all be used in any combination to achieve a pharmaceutical composition disclosed herein. A successful formulation is achieved if this selected therapeutic compound remains stably incorporated in the glycerolipid mixture.

Based on these findings, if a therapeutic compound includes an organic base functional group, one of the following processes can be employed to formulate a pharmaceutical composition disclosed herein. In some embodiments, one or more one liquid fat (glycerolipid that is liquid at 18° C.) and one or more digestion enhancers comprising an organic acid are first heated and a selected therapeutic compound including an organic base functional group is then dissolved in this heated admixture to incorporate the compound and form an anhydrous salt of the therapeutic compound. Upon complete dissolution of the therapeutic compound, one or more hard fats are then added to this heated admixture. In some embodiments, one or more digestion enhancers comprising an organic acid are first heated and a selected therapeutic compound including an organic base functional group is then dissolved in this heated admixture to incorporate the compound and form an anhydrous salt of the therapeutic compound. Upon complete dissolution of the therapeutic compound, one or more hard fats are then added to this heated admixture. In some embodiments, one or more digestion enhancers comprising an organic acid are first heated and a selected therapeutic compound including an organic base functional group is then dissolved in this heated admixture to incorporate the compound and form an anhydrous salt of the therapeutic compound. Upon completion dissolution of the therapeutic compound, and if appropriate, the temperature of the admixture can be adjusted and one or more liquid fats are then added and incorporated into this admixture. Upon completion of solubility of the one or more liquid fats, one or more hard fats are then added and incorporated into this admixture. The initial heating step in all procedures is performed at a temperature sufficient to dissolve the one or more digestion enhancers and selected therapeutic compound and can be empirically determined based on the melting point of the selected components. Generally, this temperature range is about 60° C. to about 170° C. Any subsequent adjustment to the heat when one or more liquid fats and/or one or more hart fats are being added to the admixture is performed at a temperature sufficient to melt the hard fats and can be empirically determined based on the melting point of the hard fat used in the formulation. Generally, this temperature range is about 40° C. to about 60° C.

Regardless of which process is employed, the incorporated mixture is then allowed to cool to room temperature at which time stirring is ceased and the mixture is transferred to suitable containers where it will solidify. Additionally, once cooled, the pharmaceutical composition can be optionally stability tested by reheating the composition to a temperature sufficient to cause it to melt. The reheating step is performed at a temperature sufficient to melt the glycerolipid components and can be empirically determined based on the melting point of the hard fat used in the formulation. Generally, this temperature range is 40° C. to 50° C. The selection of the one or more digestion enhancers is generally not a critical component in this process, as a bile acid, free fatty acid, phospholipid, or free fatty acid surfactant can all be used in any combination to achieve a pharmaceutical composition disclosed herein. A successful formulation is achieved if this selected therapeutic compound remains stably incorporated in the glycerolipid mixture. Example 11 exemplifies therapeutic compounds formulated according to this process.

In some embodiments, a pharmaceutical comprises one or more therapeutic compounds, one or more glycerolipids, and one or more digestion enhancers. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof. In some embodiments, the one or more digestion enhancers comprises one or more bile acids, one or more one or more free $C_{14\text{-}24}$ fatty acids, one or more one or more free $C_{14\text{-}24}$ fatty acid surfactants, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more digestion enhancers comprises one or more bile acids, one or more one or more free $C_{14\text{-}24}$ fatty acids, one or more one or more free $C_{14\text{-}24}$ fatty acid surfactants, or any combination thereof.

In some embodiments, a pharmaceutical comprises about 0.1% to about 20% by weight of one or more therapeutic compounds, about 80% to about 99% by weight of one or more glycerolipids, and about 0.1% to about 10% by weight of one or more digestion enhancers. In some embodiments, a pharmaceutical comprises about 25 mg/mL to about 600 mg/mL of one or more therapeutic compounds, about 80% to about 99% by weight of one or more glycerolipids, and about 0.1% to about 10% by weight of one or more digestion enhancers. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof. In some embodiments, the one or more digestion enhancers comprises one or more bile acids, one or more one or more free $C_{14-24}$ fatty acids, one or more one or more free $C_{14-24}$ fatty acid surfactants, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more digestion enhancers comprises one or more bile acids, one or more one or more free $C_{14-24}$ fatty acids, one or more one or more free $C_{14-24}$ fatty acid surfactants, or any combination thereof.

In some embodiments, a pharmaceutical comprises about 0.1% to about 20% by weight of one or more therapeutic compounds, about 75% to about 95% by weight of one or more glycerolipids, and about 5% to about 30% by weight of one or more digestion enhancers. In some embodiments, a pharmaceutical comprises about 25 mg/mL to about 600 mg/mL of one or more therapeutic compounds, about 75% to about 95% by weight of one or more glycerolipids, and about 5% to about 30% by weight of one or more digestion enhancers. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof. In some embodiments, the one or more digestion enhancers comprises one or more bile acids, one or more one or more free $C_{14-24}$ fatty acids, one or more one or more free $C_{14-24}$ fatty acid surfactants, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more digestion enhancers comprises one or more bile acids, one or more one or more free $C_{14-24}$ fatty acids, one or more one or more free $C_{14-24}$ fatty acid surfactants, or any combination thereof.

In some embodiments, a pharmaceutical comprises about 0.1% to about 30% by weight of one or more therapeutic compounds, about 50% to about 85% by weight of one or more glycerolipids, and about 5% to about 25% of one or more digestion enhancers. In some embodiments, a pharmaceutical comprises about 25 mg/mL to about 600 mg/mL of one or more therapeutic compounds, about 50% to about 85% by weight of one or more glycerolipids, and about 5% to about 25% by weight of one or more digestion enhancers. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof. In some embodiments, the one or more digestion enhancers comprises one or more bile acids, one or more one or more free $C_{14-24}$ fatty acids, one or more one or more free $C_{14-24}$ fatty acid surfactants, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more digestion enhancers comprises one or more bile acids, one or more one or more free $C_{14-24}$ fatty acids, one or more one or more free $C_{14-24}$ fatty acid surfactants, or any combination thereof.

In some embodiments, a pharmaceutical comprises about 0.1% to about 30% by weight of one or more therapeutic compounds, about 45% to about 80% by weight of one or more glycerolipids, and about 20% to about 45% by weight of one or more digestion enhancers. In some embodiments, a pharmaceutical comprises about 25 mg/mL to about 600 mg/mL of one or more therapeutic compounds, about 45% to about 80% by weight of one or more glycerolipids, and about 20% to about 45% by weight of one or more digestion enhancers. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof. In some embodiments, the one or more digestion enhancers comprises one or more bile acids, one or more one or more free $C_{14-24}$ fatty acids, one or more one or more free $C_{14-24}$ fatty acid surfactants, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more digestion enhancers comprises one or more bile acids, one or more one or more free $C_{14-24}$ fatty acids, one or more one or more free $C_{14-24}$ fatty acid surfactants, or any combination thereof.

In some embodiments, a pharmaceutical comprises about 0.1% to about 30% by weight of one or more therapeutic compounds, about 30% to about 55% by weight of one or more glycerolipids, and about 40% to about 80% by weight of one or more digestion enhancers. In some embodiments, a pharmaceutical comprises about 25 mg/mL to about 600 mg/mL of one or more therapeutic compounds, about 30% to about 55% by weight of one or more glycerolipids, and about 40% to about 80% by weight of one or more digestion enhancers. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof. In some embodiments, the one or more digestion enhancers comprises one or more bile acids, one or more one or more free $C_{14-24}$ fatty acids, one or more one or more free $C_{14-24}$ fatty acid surfactants, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more digestion enhancers comprises one or more bile acids, one or more one or more free $C_{14-24}$ fatty acids, one or more one or more free $C_{14-24}$ fatty acid surfactants, or any combination thereof.

In some embodiments, a pharmaceutical comprises one or more therapeutic compounds, one or more hard fats, one or more liquid fats, and one or more digestion enhancers. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof. In some embodiments, the one or more digestion enhancers comprises one or more bile acids, one or more one or more free $C_{14-24}$ fatty acids, one or more one or more free $C_{14-24}$ fatty acid surfactants, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more digestion enhancers comprises one or more bile acids, one or more one or more free $C_{14-24}$ fatty acids, one or more one or more free $C_{14-24}$ fatty acid surfactants, or any combination thereof.

In some embodiments, a pharmaceutical comprises about 0.1% to about 20% by weight of one or more therapeutic compounds, about 25% to about 70% by weight of one or more hard fats, about 25% to about 70% by weight of one or more liquid fats, and about 0.1% to about 10% by weight of one or more digestion enhancers. In some embodiments, a pharmaceutical comprises about 25 mg/mL to about 600 mg/mL of one or more therapeutic compounds, about 25% to about 70% by weight of one or more hard fats, about 25% to about 70% by weight of one or more liquid fats, and about 0.1% to about 10% by weight of one or more digestion enhancers. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof. In some embodiments, the one or more digestion enhancers comprises one or more bile acids, one or more one or more free $C_{14-24}$ fatty acids, one or more one or more free $C_{14-24}$ fatty acid surfactants, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more digestion enhancers comprises one or more bile acids, one or more one or more free $C_{14-24}$ fatty acids, one or more one or more free $C_{14-24}$ fatty acid surfactants, or any combination thereof.

In some embodiments, a pharmaceutical comprises about 0.1% to about 20% by weight of one or more therapeutic compounds, about 25% to about 70% by weight of one or more hard fats comprising glycerolipids, about 25% to about 70% by weight of one or more liquid fats comprising partially hydrolyzed glycerolipids including a mixture of mono-, di- and triglycerides, and about 0.1% to about 10% by weight of one or more digestion enhancers. In some embodiments, a pharmaceutical comprises about 25 mg/mL to about 600 mg/mL of one or more therapeutic compounds, about 25% to about 70% by weight of one or more hard fats comprising glycerolipids, about 25% to about 70% by weight of one or more liquid fats comprising partially hydrolyzed glycerolipids including a mixture of mono-, di- and triglycerides, and about 0.1% to about 10% by weight of one or more digestion enhancers. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof. In some embodiments, the one or more digestion enhancers comprises one or more bile acids, one or more one or more free $C_{14-24}$ fatty acids, one or more one or more free $C_{14-24}$ fatty acid surfactants, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more digestion enhancers comprises one or more bile acids, one or more one or more free $C_{14-24}$ fatty acids, one or more one or more free $C_{14-24}$ fatty acid surfactants, or any combination thereof.

In some embodiments, a pharmaceutical comprises about 0.1% to about 20% by weight of one or more therapeutic compounds, about 25% to about 70% by weight of one or more hard fats comprising $C_{10}$-$C_{24}$ triglycerides, about 25% to about 70% by weight of one or more liquid fats comprising partially hydrolyzed triglycerides including a mixture of $C_{10}$-$C_{24}$ mono-, $C_{10}$-$C_{24}$ di- and $C_{10}$-$C_{24}$ triglycerides, and about 0.1% to about 10% by weight of one or more digestion enhancers. In some embodiments, a pharmaceutical comprises about 25 mg/mL to about 600 mg/mL of one or more therapeutic compounds, about 25% to about 70% by weight of one or more hard fats comprising $C_{10}$-$C_{24}$ triglycerides, about 25% to about 70% by weight of one or more liquid fats comprising partially hydrolyzed triglycerides including a mixture of $C_{10}$-$C_{24}$ mono-, $C_{10}$-$C_{24}$ di- and $C_{10}$-$C_{24}$ triglycerides, and about 0.1% to about 10% by weight of one or more digestion enhancers. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof. In some embodiments, the one or more digestion enhancers comprises one or more bile acids, one or more one or more free $C_{14\text{-}24}$ fatty acids, one or more one or more free $C_{14\text{-}24}$ fatty acid surfactants, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more digestion enhancers comprises one or more bile acids, one or more one or more free $C_{14\text{-}24}$ fatty acids, one or more one or more free $C_{14\text{-}24}$ fatty acid surfactants, or any combination thereof.

In some embodiments, a pharmaceutical comprises about 0.1% to about 20% by weight of one or more therapeutic compounds, about 25% to about 70% by weight of one or more hard fats comprising a mixture of saturated $C_{10}$-$C_{18}$ triglycerides and/or saturated $C_{12}$-$C_{18}$ triglycerides, about 25% to about 70% by weight of one or more liquid fats comprising partially hydrolyzed triglycerides including a mixture of $C_{16}$-$C_{18}$ mono-, $C_{16}$-$C_{18}$ di- and $C_{16}$-$C_{18}$ triglycerides, and about 0.1% to about 10% by weight of one or more digestion enhancers. In some embodiments, a pharmaceutical comprises about 25 mg/mL to about 600 mg/mL of one or more therapeutic compounds, about 25% to about 70% by weight of one or more hard fats comprising a mixture of saturated $C_{10}$-$C_{18}$ triglycerides and/or saturated $C_{12}$-$C_{18}$ triglycerides, about 25% to about 70% by weight of one or more liquid fats comprising partially hydrolyzed triglycerides including a mixture of $C_{16}$-$C_{18}$ mono-, $C_{16}$-$C_{18}$ di- and $C_{16}$-$C_{18}$ triglycerides, and about 0.1% to about 10% by weight of one or more digestion enhancers. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof. In some embodiments, the one or more digestion enhancers comprises one or more bile acids, one or more one or more free $C_{14\text{-}24}$ fatty acids, one or more one or more free $C_{14\text{-}24}$ fatty acid surfactants, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more digestion enhancers comprises one or more bile acids, one or more one or more free $C_{14\text{-}24}$ fatty acids, one or more one or more free $C_{14\text{-}24}$ fatty acid surfactants, or any combination thereof.

In some embodiments, a pharmaceutical comprises about 0.1% to about 20% by weight of one or more therapeutic compounds, about 35% to about 55% by weight of one or more hard fats, about 25% to about 50% by weight of one or more liquid fats, and about 5% to about 30% by weight of one or more digestion enhancers. In some embodiments, a pharmaceutical comprises about 25 mg/mL to about 600 mg/mL of one or more therapeutic compounds, about 35% to about 55% by weight of one or more hard fats, about 25% to about 50% by weight of one or more liquid fats, and about 5% to about 30% by weight of one or more digestion enhancers. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof. In some embodiments, the one or more digestion enhancers comprises one or more bile acids, one or more one or more free $C_{14\text{-}24}$ fatty acids, one or more one or more free $C_{14\text{-}24}$ fatty acid surfactants, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more digestion enhancers comprises one or more bile acids, one or more one or more free $C_{14\text{-}24}$ fatty acids, one or more one or more free $C_{14\text{-}24}$ fatty acid surfactants, or any combination thereof.

In some embodiments, a pharmaceutical comprises about 0.1% to about 20% by weight of one or more therapeutic compounds, about 35% to about 55% by weight of one or more hard fats comprising glycerolipids, about 25% to about 50% by weight of one or more liquid fats comprising partially hydrolyzed glycerolipids including a mixture of mono-, di- and triglycerides, and about 5% to about 30% by weight of one or more digestion enhancers. In some embodiments, a pharmaceutical comprises about 25 mg/mL to about 600 mg/mL of one or more therapeutic compounds, about 35% to about 55% by weight of one or more hard fats comprising glycerolipids, about 25% to about 50% by weight of one or more liquid fats comprising partially hydrolyzed glycerolipids including a mixture of mono-, di- and triglycerides, and about 5% to about 30% by weight of one or more digestion enhancers. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof. In some embodiments, the one or more digestion enhancers comprises one or more bile acids, one or more one or more free $C_{14\text{-}24}$ fatty acids, one or more one or more free $C_{14\text{-}24}$ fatty acid surfactants, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more digestion enhancers comprises one or more bile acids, one or more one or more free $C_{14-24}$ fatty acids, one or more one or more free $C_{14-24}$ fatty acid surfactants, or any combination thereof.

In some embodiments, a pharmaceutical comprises about 0.1% to about 20% by weight of one or more therapeutic compounds, about 35% to about 55% by weight of one or more hard fats comprising $C_{10}$-$C_{24}$ triglycerides, about 25% to about 50% by weight of one or more liquid fats comprising partially hydrolyzed triglycerides including a mixture of $C_{10}$-$C_{24}$ mono-, $C_{10}$-$C_{24}$ di- and $C_{10}$-$C_{24}$ triglycerides, and about 5% to about 30% by weight of one or more digestion enhancers. In some embodiments, a pharmaceutical comprises about 25 mg/mL to about 600 mg/mL of one or more therapeutic compounds, about 35% to about 55% by weight of one or more hard fats comprising $C_{10}$-$C_{24}$ triglycerides, about 25% to about 50% by weight of one or more liquid fats comprising partially hydrolyzed triglycerides including a mixture of $C_{10}$-$C_{24}$ mono-, $C_{10}$-$C_{24}$ di- and $C_{10}$-$C_{24}$ triglycerides, and about 5% to about 30% by weight of one or more digestion enhancers. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof. In some embodiments, the one or more digestion enhancers comprises one or more bile acids, one or more one or more free $C_{14-24}$ fatty acids, one or more one or more free $C_{14-24}$ fatty acid surfactants, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more digestion enhancers comprises one or more bile acids, one or more one or more free $C_{14-24}$ fatty acids, one or more one or more free $C_{14-24}$ fatty acid surfactants, or any combination thereof.

In some embodiments, a pharmaceutical comprises about 0.1% to about 20% by weight of one or more therapeutic compounds, about 35% to about 55% by weight of one or more hard fats comprising a mixture of saturated $C_{10}$-$C_{18}$ triglycerides and/or saturated $C_{12}$-$C_{18}$ triglycerides, about 25% to about 50% by weight of one or more liquid fats comprising partially hydrolyzed triglycerides including a mixture of $C_{16}$-$C_{18}$ mono-, $C_{16}$-$C_{18}$ di- and $C_{16}$-$C_{18}$ triglycerides, and about 5% to about 30% by weight of one or more digestion enhancers. In some embodiments, a pharmaceutical comprises about 25 mg/mL to about 600 mg/mL of one or more therapeutic compounds, about 35% to about 55% by weight of one or more hard fats comprising a mixture of saturated $C_{10}$-$C_{18}$ triglycerides and/or saturated $C_{12}$-$C_{18}$ triglycerides, about 25% to about 50% by weight of one or more liquid fats comprising partially hydrolyzed triglycerides including a mixture of $C_{16}$-$C_{18}$ mono-, $C_{16}$-$C_{18}$ di- and $C_{16}$-$C_{18}$ triglycerides, and about 5% to about 30% by weight of one or more digestion enhancers. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof. In some embodiments, the one or more digestion enhancers comprises one or more bile acids, one or more one or more free $C_{14-24}$ fatty acids, one or more one or more free $C_{14-24}$ fatty acid surfactants, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more digestion enhancers comprises one or more bile acids, one or more one or more free $C_{14-24}$ fatty acids, one or more one or more free $C_{14-24}$ fatty acid surfactants, or any combination thereof.

In some embodiments, a pharmaceutical comprises about 0.1% to about 30% by weight of one or more therapeutic compounds, about 15% to about 65% by weight of one or more hard fats, about 15% to about 50% by weight of one or more liquid fats, and about 5% to about 25% by weight of one or more digestion enhancers. In some embodiments, a pharmaceutical comprises about 25 mg/mL to about 600 mg/mL of one or more therapeutic compounds, about 15% to about 65% by weight of one or more hard fats, about 15% to about 50% by weight of one or more liquid fats, and about 5% to about 25% by weight of one or more digestion enhancers. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof. In some embodiments, the one or more digestion enhancers comprises one or more bile acids, one or more one or more free $C_{14-24}$ fatty acids, one or more one or more free $C_{14-24}$ fatty acid surfactants, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more digestion enhancers comprises one or more bile acids, one or more one or more free $C_{14-24}$ fatty acids, one or more one or more free $C_{14-24}$ fatty acid surfactants, or any combination thereof.

In some embodiments, a pharmaceutical comprises about 0.1% to about 30% by weight of one or more therapeutic compounds, about 15% to about 65% by weight of one or more hard fats comprising glycerolipids, about 15% to about 50% by weight of one or more liquid fats comprising partially hydrolyzed glycerolipids including a mixture of mono-, di- and triglycerides, and about 5% to about 25% by weight of one or more digestion enhancers. In some embodiments, a pharmaceutical comprises about 25 mg/mL to about 600 mg/mL of one or more therapeutic compounds, about 15% to about 65% by weight of one or more hard fats comprising glycerolipids, about 15% to about 50% by weight of one or more liquid fats comprising partially hydrolyzed glycerolipids including a mixture of mono-, di- and triglycerides, and about 5% to about 25% by weight of one or more digestion enhancers. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof. In some embodiments, the one or more digestion enhancers comprises one or more bile acids, one or more one or more free $C_{14-24}$ fatty acids, one or more one or more free $C_{14-24}$ fatty acid surfactants, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more digestion enhancers comprises one or more bile acids, one or more one or more free $C_{14-24}$ fatty acids, one or more one or more free $C_{14-24}$ fatty acid surfactants, or any combination thereof.

In some embodiments, a pharmaceutical comprises about 0.1% to about 30% by weight of one or more therapeutic compounds, about 15% to about 65% by weight of one or more hard fats comprising $C_{10}$-$C_{24}$ triglycerides, about 15% to about 50% by weight of one or more liquid fats comprising partially hydrolyzed triglycerides including a mixture of $C_{10}$-$C_{24}$ mono-, $C_{10}$-$C_{24}$ di- and $C_{10}$-$C_{24}$ triglycerides, and about 5% to about 25% by weight of one or more digestion enhancers. In some embodiments, a pharmaceutical comprises about 25 mg/mL to about 600 mg/mL of one or more therapeutic compounds, about 15% to about 65% by weight of one or more hard fats comprising $C_{10}$-$C_{24}$ triglycerides, about 15% to about 50% by weight of one or more liquid fats comprising partially hydrolyzed triglycerides including a mixture of $C_{10}$-$C_{24}$ mono-, $C_{10}$-$C_{24}$ di- and $C_{10}$-$C_{24}$ triglycerides, and about 5% to about 25% by weight of one or more digestion enhancers. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof. In some embodiments, the one or more digestion enhancers comprises one or more bile acids, one or more one or more free $C_{14-24}$ fatty acids, one or more one or more free $C_{14-24}$ fatty acid surfactants, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more digestion enhancers comprises one or more bile acids, one or more one or more free $C_{14-24}$ fatty acids, one or more one or more free $C_{14-24}$ fatty acid surfactants, or any combination thereof.

In some embodiments, a pharmaceutical comprises about 0.1% to about 30% by weight of one or more therapeutic compounds, about 15% to about 65% by weight of one or more hard fats comprising a mixture of saturated $C_{10}$-$C_{18}$ triglycerides and/or saturated $C_{12}$-$C_{18}$ triglycerides, about 15% to about 50% by weight of one or more liquid fats comprising partially hydrolyzed triglycerides including a mixture of $C_{16}$-$C_{18}$ mono-, $C_{16}$-$C_{18}$ di- and $C_{16}$-$C_{18}$ triglycerides, and about 5% to about 25% by weight of one or more digestion enhancers. In some embodiments, a pharmaceutical comprises about 25 mg/mL to about 600 mg/mL of one or more therapeutic compounds, about 15% to about 65% by weight of one or more hard fats comprising a mixture of saturated $C_{10}$-$C_{18}$ triglycerides and/or saturated $C_{12}$-$C_{18}$ triglycerides, about 15% to about 50% by weight of one or more liquid fats comprising partially hydrolyzed triglycerides including a mixture of $C_{16}$-$C_{18}$ mono-, $C_{16}$-$C_{18}$ di- and $C_{16}$-$C_{18}$ triglycerides, and about 5% to about 25% by weight of one or more digestion enhancers. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof. In some embodiments, the one or more digestion enhancers comprises one or more bile acids, one or more one or more free $C_{14-24}$ fatty acids, one or more one or more free $C_{14-24}$ fatty acid surfactants, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more digestion enhancers comprises one or more bile acids, one or more one or more free $C_{14-24}$ fatty acids, one or more one or more free $C_{14-24}$ fatty acid surfactants, or any combination thereof.

In some embodiments, a pharmaceutical comprises about 0.1% to about 30% by weight of one or more therapeutic compounds, about 20% to about 55% by weight of one or more hard fats, about 15% to about 45% by weight of one or more liquid fats, and about 20% to about 45% by weight of one or more digestion enhancers. In some embodiments, a pharmaceutical comprises about 25 mg/mL to about 600 mg/mL of one or more therapeutic compounds, about 20% to about 55% by weight of one or more hard fats, about 15% to about 45% by weight of one or more liquid fats, and about 20% to about 45% by weight of one or more digestion enhancers. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof. In some embodiments, the one or more digestion enhancers comprises one or more bile acids, one or more one or more free $C_{14-24}$ fatty acids, one or more one or more free $C_{14-24}$ fatty acid surfactants, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more digestion enhancers comprises one or more bile acids, one or more one or more free $C_{14-24}$ fatty acids, one or more one or more free $C_{14-24}$ fatty acid surfactants, or any combination thereof.

In some embodiments, a pharmaceutical comprises about 0.1% to about 30% by weight of one or more therapeutic compounds, about 20% to about 55% by weight of one or more hard fats comprising glycerolipids, about 15% to about 45% by weight of one or more liquid fats comprising partially hydrolyzed glycerolipids including a mixture of mono-, di- and triglycerides, and about 20% to about 45% by weight of one or more digestion enhancers. In some embodiments, a pharmaceutical comprises about 25 mg/mL to about 600 mg/mL of one or more therapeutic compounds, about 20% to about 55% by weight of one or more hard fats comprising glycerolipids, about 15% to about 45% by weight of one or more liquid fats comprising partially hydrolyzed glycerolipids including a mixture of mono-, di- and triglycerides, and about 20% to about 45% by weight of one or more digestion enhancers. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof. In some embodiments, the one or more digestion enhancers comprises one or more bile acids, one or more one or more free $C_{14-24}$ fatty acids, one or more one or more free $C_{14-24}$ fatty acid surfactants, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more digestion enhancers comprises one or more bile acids, one or more one or more free $C_{14-24}$ fatty acids, one or more one or more free $C_{14-24}$ fatty acid surfactants, or any combination thereof.

In some embodiments, a pharmaceutical comprises about 0.1% to about 30% by weight of one or more therapeutic compounds, about 20% to about 55% by weight of one or more hard fats comprising $C_{10}$-$C_{24}$ triglycerides, about 15% to about 45% by weight of one or more liquid fats comprising partially hydrolyzed triglycerides including a mixture of $C_{10}$-$C_{24}$ mono-, $C_{10}$-$C_{24}$ di- and $C_{10}$-$C_{24}$ triglycerides, and about 20% to about 45% by weight of one or more digestion enhancers. In some embodiments, a pharmaceutical comprises about 25 mg/mL to about 600 mg/mL of one or more therapeutic compounds, about 20% to about 55% by weight of one or more hard fats comprising $C_{10}$-$C_{24}$ triglycerides, about 15% to about 45% by weight of one or more liquid fats comprising partially hydrolyzed triglycerides including a mixture of $C_{10}$-$C_{24}$ mono-, $C_{10}$-$C_{24}$ di- and $C_{10}$-$C_{24}$ triglycerides, and about 20% to about 45% by weight of one or more digestion enhancers. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof. In some embodiments, the one or more digestion enhancers comprises one or more bile acids, one or more one or more free $C_{14-24}$ fatty acids, one or more one or more free $C_{14-24}$ fatty acid surfactants, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more digestion enhancers comprises one or more bile acids, one or more one or more free $C_{14-24}$ fatty acids, one or more one or more free $C_{14-24}$ fatty acid surfactants, or any combination thereof.

In some embodiments, a pharmaceutical comprises about 0.1% to about 30% by weight of one or more therapeutic compounds, about 20% to about 55% by weight of one or more hard fats comprising a mixture of saturated $C_{10}$-$C_{18}$ triglycerides and/or saturated $C_{12}$-$C_{18}$ triglycerides, about 15% to about 45% by weight of one or more liquid fats comprising partially hydrolyzed triglycerides including a mixture of $C_{16}$-$C_{18}$ mono-, $C_{16}$-$C_{18}$ di- and $C_{16}$-$C_{18}$ triglycerides, and about 20% to about 45% by weight of one or more digestion enhancers. In some embodiments, a pharmaceutical comprises about 25 mg/mL to about 600 mg/mL of one or more therapeutic compounds, about 20% to about 55% by weight of one or more hard fats comprising a mixture of saturated $C_{10}$-$C_{18}$ triglycerides and/or saturated $C_{12}$-$C_{18}$ triglycerides, about 15% to about 45% by weight of one or more liquid fats comprising partially hydrolyzed triglycerides including a mixture of $C_{16}$-$C_{18}$ mono-, $C_{16}$-$C_{18}$ di- and $C_{16}$-$C_{18}$ triglycerides, and about 20% to about 45% by weight of one or more digestion enhancers. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof. In some embodiments, the one or more digestion enhancers comprises one or more bile acids, one or more one or more free $C_{14-24}$ fatty acids, one or more one or more free $C_{14-24}$ fatty acid surfactants, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more digestion enhancers comprises one or more bile acids, one or more one or more free $C_{14-24}$ fatty acids, one or more one or more free $C_{14-24}$ fatty acid surfactants, or any combination thereof.

In some embodiments, a pharmaceutical comprises one or more therapeutic compounds, one or more hard fats, one or more liquid fats, and one or more bile acids. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof. In some embodiments, the one or more bile acids in the above embodiments comprises cholic acid. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more bile acids in the above embodiments comprises cholic acid.

In some embodiments, a pharmaceutical comprises about 0.1% to about 20% by weight of one or more therapeutic compounds, about 25% to about 70% by weight of one or more hard fats, about 25% to about 70% by weight of one or more liquid fats, and about 0.1% to about 10% by weight of one or more bile acids. In some embodiments, a pharmaceutical comprises about 25 mg/mL to about 600 mg/mL of one or more therapeutic compounds, about 25% to about 70% by weight of one or more hard fats, about 25% to about 70% by weight of one or more liquid fats, and about 0.1% to about 10% by weight of one or more bile acids. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof. In some embodiments, the one or more bile acids in the above embodiments comprises cholic acid. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more bile acids in the above embodiments comprises cholic acid.

In some embodiments, a pharmaceutical comprises about 0.1% to about 20% by weight of one or more therapeutic compounds, about 25% to about 70% by weight of one or more hard fats comprising glycerolipids, about 25% to about 70% by weight of one or more liquid fats comprising partially hydrolyzed glycerolipids including a mixture of mono-, di- and triglycerides, and about 0.1% to about 10% by weight of one or more bile acids. In some embodiments, a pharmaceutical comprises about 25 mg/mL to about 600 mg/mL of one or more therapeutic compounds, about 25% to about 70% by weight of one or more hard fats comprising glycerolipids, about 25% to about 70% by weight of one or more liquid fats comprising partially hydrolyzed glycerolipids including a mixture of mono-, di- and triglycerides, and about 0.1% to about 10% by weight of one or more bile acids. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof. In some embodiments, the one or more bile acids in the above embodiments comprises cholic acid. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more bile acids in the above embodiments comprises cholic acid.

In some embodiments, a pharmaceutical comprises about 0.1% to about 20% by weight of one or more therapeutic compounds, about 25% to about 70% by weight of one or more hard fats comprising $C_{10}$-$C_{24}$ triglycerides, about 25% to about 70% by weight of one or more liquid fats comprising partially hydrolyzed triglycerides including a mixture of $C_{10}$-$C_{24}$ mono-, $C_{10}$-$C_{24}$ di- and $C_{10}$-$C_{24}$ triglycerides, and about 0.1% to about 10% by weight of one or more bile acids. In some embodiments, a pharmaceutical comprises about 25 mg/mL to about 600 mg/mL of one or more therapeutic compounds, about 25% to about 70% by weight of one or more hard fats comprising $C_{10}$-$C_{24}$ triglycerides, about 25% to about 70% by weight of one or more liquid fats comprising partially hydrolyzed triglycerides including a mixture of $C_{10}$-$C_{24}$ mono-, $C_{10}$-$C_{24}$ di- and $C_{10}$-$C_{24}$ triglycerides, and about 0.1% to about 10% by weight of one or more bile acids. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof. In some embodiments, the one or more bile acids in the above embodiments comprises cholic acid. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more bile acids in the above embodiments comprises cholic acid.

In some embodiments, a pharmaceutical comprises about 0.1% to about 20% by weight of one or more therapeutic compounds, about 25% to about 70% by weight of one or more hard fats comprising a mixture of saturated $C_{10}$-$C_{18}$ triglycerides and/or saturated $C_{12}$-$C_{18}$ triglycerides, about 25% to about 70% by weight of one or more liquid fats comprising partially hydrolyzed triglycerides including a mixture of $C_{16}$-$C_{18}$ mono-, $C_{16}$-$C_{18}$ di- and $C_{16}$-$C_{18}$ triglycerides, and about 0.1% to about 10% by weight of one or more bile acids. In some embodiments, a pharmaceutical comprises about 25 mg/mL to about 600 mg/mL of one or more therapeutic compounds, about 25% to about 70% by weight of one or more hard fats comprising a mixture of saturated $C_{10}$-$C_{18}$ triglycerides and/or saturated $C_{12}$-$C_{18}$ triglycerides, about 25% to about 70% by weight of one or more liquid fats comprising partially hydrolyzed triglycerides including a mixture of $C_{16}$-$C_{18}$ mono-, $C_{16}$-$C_{18}$ di- and $C_{16}$-$C_{18}$ triglycerides, and about 0.1% to about 10% by weight of one or more bile acids. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof. In some embodiments, the one or more bile acids in the above embodiments comprises cholic acid. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more bile acids in the above embodiments comprises cholic acid.

In some embodiments, a pharmaceutical comprises about 0.1% to about 20% by weight of one or more therapeutic compounds, about 35% to about 55% by weight of one or more hard fats, about 25% to about 50% by weight of one or more liquid fats, and about 0.1% to about 10% by weight of one or more bile acids. In some embodiments, a pharmaceutical comprises about 25 mg/mL to about 600 mg/mL of one or more therapeutic compounds, about 35% to about 55% by weight of one or more hard fats, about 25% to about 50% by weight of one or more liquid fats, and about 0.1% to about 10% by weight of one or more bile acids. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof. In some embodiments, the one or more bile acids in the above embodiments comprises cholic acid. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more bile acids in the above embodiments comprises cholic acid.

In some embodiments, a pharmaceutical comprises about 0.1% to about 20% by weight of one or more therapeutic compounds, about 35% to about 55% by weight of one or more hard fats comprising glycerolipids, about 25% to about 50% by weight of one or more liquid fats comprising partially hydrolyzed glycerolipids including a mixture of mono-, di- and triglycerides, and about 0.1% to about 10% by weight of one or more bile acids. In some embodiments, a pharmaceutical comprises about 25 mg/mL to about 600 mg/mL of one or more therapeutic compounds, about 35% to about 55% by weight of one or more hard fats comprising glycerolipids, about 25% to about 50% by weight of one or more liquid fats comprising partially hydrolyzed glycerolipids including a mixture of mono-, di- and triglycerides, and about 0.1% to about 10% by weight of one or more bile acids. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof. In some embodiments, the one or more bile acids in the above embodiments comprises cholic acid. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more bile acids in the above embodiments comprises cholic acid.

In some embodiments, a pharmaceutical comprises about 0.1% to about 20% by weight of one or more therapeutic compounds, about 35% to about 55% by weight of one or more hard fats comprising $C_{10}$-$C_{24}$ triglycerides, about 25% to about 50% by weight of one or more liquid fats comprising partially hydrolyzed triglycerides including a mixture of $C_{10}$-$C_{24}$ mono-, $C_{10}$-$C_{24}$ di- and $C_{10}$-$C_{24}$ triglycerides, and about 0.1% to about 10% by weight of one or more bile acids. In some embodiments, a pharmaceutical comprises about 25 mg/mL to about 600 mg/mL of one or more therapeutic compounds, about 35% to about 55% by weight of one or more hard fats comprising $C_{10}$-$C_{24}$ triglycerides, about 25% to about 50% by weight of one or more liquid fats comprising partially hydrolyzed triglycerides including a mixture of $C_{10}$-$C_{24}$ mono-, $C_{10}$-$C_{24}$ di- and $C_{10}$-$C_{24}$ triglycerides, and about 0.1% to about 10% by weight of one or more bile acids. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof. In some embodiments, the one or more bile acids in the above embodiments comprises cholic acid. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more bile acids in the above embodiments comprises cholic acid.

In some embodiments, a pharmaceutical comprises about 0.1% to about 20% by weight of one or more therapeutic compounds, about 35% to about 55% by weight of one or more hard fats comprising a mixture of saturated $C_{10}$-$C_{18}$ triglycerides and/or saturated $C_{12}$-$C_{18}$ triglycerides, about 25% to about 50% by weight of one or more liquid fats comprising partially hydrolyzed triglycerides including a mixture of $C_{18}$-$C_{18}$ mono-, $C_{16}$-$C_{18}$ di- and $C_{16}$-$C_{18}$ triglycerides, and about 0.1% to about 10% by weight of one or more bile acids. In some embodiments, a pharmaceutical comprises about 25 mg/mL to about 600 mg/mL of one or more therapeutic compounds, about 35% to about 55% by weight of one or more hard fats comprising a mixture of saturated $C_{10}$-$C_{18}$ triglycerides and/or saturated $C_{12}$-$C_{18}$ triglycerides, about 25% to about 50% by weight of one or more liquid fats comprising partially hydrolyzed triglycerides including a mixture of $C_{16}$-$C_{18}$ mono-, $C_{16}$-$C_{18}$ di- and $C_{16}$-$C_{18}$ triglycerides, and about 0.1% to about 10% by weight of one or more bile acids. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof. In some embodiments, the one or more bile acids in the above embodiments comprises cholic acid. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more bile acids in the above embodiments comprises cholic acid.

In some embodiments, a pharmaceutical comprises about 0.1% to about 30% by weight of one or more therapeutic compounds, about 15% to about 65% by weight of one or more hard fats, about 15% to about 50% by weight of one or more liquid fats, and about 0.1% to about 10% by weight of one or more bile acids. In some embodiments, a pharmaceutical comprises about 25 mg/mL to about 600 mg/mL of one or more therapeutic compounds, about 15% to about 65% by weight of one or more hard fats, about 15% to about 50% by weight of one or more liquid fats, and about 0.1% to about 10% by weight of one or more bile acids. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof. In some embodiments, the one or more bile acids in the above embodiments comprises cholic acid. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more bile acids in the above embodiments comprises cholic acid.

In some embodiments, a pharmaceutical comprises about 0.1% to about 30% by weight of one or more therapeutic compounds, about 15% to about 65% by weight of one or more hard fats comprising glycerolipids, about 15% to about 50% by weight of one or more liquid fats comprising partially hydrolyzed glycerolipids including a mixture of mono-, di- and triglycerides, and about 0.1% to about 10% by weight of one or more bile acids. In some embodiments, a pharmaceutical comprises about 25 mg/mL to about 600 mg/mL of one or more therapeutic compounds, about 15% to about 65% by weight of one or more hard fats comprising glycerolipids, about 15% to about 50% by weight of one or more liquid fats comprising partially hydrolyzed glycerolipids including a mixture of mono-, di- and triglycerides, and about 0.1% to about 10% by weight of one or more bile acids. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof. In some embodiments, the one or more bile acids in the above embodiments comprises cholic acid. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more bile acids in the above embodiments comprises cholic acid.

In some embodiments, a pharmaceutical comprises about 0.1% to about 30% by weight of one or more therapeutic compounds, about 15% to about 65% by weight of one or more hard fats comprising $C_{10}$-$C_{24}$ triglycerides, about 15% to about 50% by weight of one or more liquid fats comprising partially hydrolyzed triglycerides including a mixture of $C_{10}$-$C_{24}$ mono-, $C_{10}$-$C_{24}$ di- and $C_{10}$-$C_{24}$ triglycerides, and about 0.1% to about 10% by weight of one or more bile acids. In some embodiments, a pharmaceutical comprises about 25 mg/mL to about 600 mg/mL of one or more therapeutic compounds, about 15% to about 65% by weight of one or more hard fats comprising $C_{10}$-$C_{24}$ triglycerides, about 15% to about 50% by weight of one or more liquid fats comprising partially hydrolyzed triglycerides including a mixture of $C_{10}$-$C_{24}$ mono-, $C_{10}$-$C_{24}$ di- and $C_{10}$-$C_{24}$ triglycerides, and about 0.1% to about 10% by weight of one or more bile acids. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof. In some embodiments, the one or more bile acids in the above embodiments comprises cholic acid. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more bile acids in the above embodiments comprises cholic acid.

In some embodiments, a pharmaceutical comprises about 0.1% to about 30% by weight of one or more therapeutic compounds, about 15% to about 65% by weight of one or more hard fats comprising a mixture of saturated $C_{10}$-$C_{18}$ triglycerides and/or saturated $C_{12}$-$C_{18}$ triglycerides, about 15% to about 50% by weight of one or more liquid fats comprising partially hydrolyzed triglycerides including a mixture of $C_{18}$-$C_{18}$ mono-, $C_{16}$-$C_{18}$ di- and $C_{16}$-$C_{18}$ triglycerides, and about 0.1% to about 10% by weight of one or more bile acids. In some embodiments, a pharmaceutical comprises about 25 mg/mL to about 600 mg/mL of one or more therapeutic compounds, about 15% to about 65% by weight of one or more hard fats comprising a mixture of saturated $C_{10}$-$C_{18}$ triglycerides and/or saturated $C_{12}$-$C_{18}$ triglycerides, about 15% to about 50% by weight of one or more liquid fats comprising partially hydrolyzed triglycerides including a mixture of $C_{16}$-$C_{18}$ mono-, $C_{16}$-$C_{18}$ di- and $C_{16}$-$C_{18}$ triglycerides, and about 0.1% to about 10% by weight of one or more bile acids. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof. In some embodiments, the one or more bile acids in the above embodiments comprises cholic acid. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more bile acids in the above embodiments comprises cholic acid.

In some embodiments, a pharmaceutical comprises about 0.1% to about 30% by weight of one or more therapeutic compounds, about 20% to about 55% by weight of one or more hard fats, about 15% to about 45% by weight of one or more liquid fats, and about 0.1% to about 10% by weight of one or more bile acids. In some embodiments, a pharmaceutical comprises about 25 mg/mL to about 600 mg/mL of one or more therapeutic compounds, about 20% to about 55% by weight of one or more hard fats, about 15% to about 45% by weight of one or more liquid fats, and about 0.1% to about 10% by weight of one or more bile acids. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof. In some embodiments, the one or more bile acids in the above embodiments comprises cholic acid. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more bile acids in the above embodiments comprises cholic acid.

In some embodiments, a pharmaceutical comprises about 0.1% to about 30% by weight of one or more therapeutic compounds, about 20% to about 55% by weight of one or more hard fats comprising glycerolipids, about 15% to about 45% by weight of one or more liquid fats comprising partially hydrolyzed glycerolipids including a mixture of mono-, di- and triglycerides, and about 0.1% to about 10% by weight of one or more bile acids. In some embodiments, a pharmaceutical comprises about 25 mg/mL to about 600 mg/mL of one or more therapeutic compounds, about 20% to about 55% by weight of one or more hard fats comprising glycerolipids, about 15% to about 45% by weight of one or more liquid fats comprising partially hydrolyzed glycerolipids including a mixture of mono-, di- and triglycerides, and about 0.1% to about 10% by weight of one or more bile acids. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof. In some embodiments, the one or more bile acids in the above embodiments comprises cholic acid. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more bile acids in the above embodiments comprises cholic acid.

In some embodiments, a pharmaceutical comprises about 0.1% to about 30% by weight of one or more therapeutic compounds, about 20% to about 55% by weight of one or more hard fats comprising $C_{10}$-$C_{24}$ triglycerides, about 15% to about 45% by weight of one or more liquid fats comprising partially hydrolyzed triglycerides including a mixture of $C_{10}$-$C_{24}$ mono-, $C_{10}$-$C_{24}$ di- and $C_{10}$-$C_{24}$ triglycerides, and about 0.1% to about 10% by weight of one or more bile acids. In some embodiments, a pharmaceutical comprises about 25 mg/mL to about 600 mg/mL of one or more therapeutic compounds, about 20% to about 55% by weight of one or more hard fats comprising $C_{10}$-$C_{24}$ triglycerides, about 15% to about 45% by weight of one or more liquid fats comprising partially hydrolyzed triglycerides including a mixture of $C_{10}$-$C_{24}$ mono-, $C_{10}$-$C_{24}$ di- and $C_{10}$-$C_{24}$ triglycerides, and about 0.1% to about 10% by weight of one or more bile acids. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof. In some embodiments, the one or more bile acids in the above embodiments comprises cholic acid. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more bile acids in the above embodiments comprises cholic acid.

In some embodiments, a pharmaceutical comprises about 0.1% to about 30% by weight of one or more therapeutic compounds, about 20% to about 55% by weight of one or more hard fats comprising a mixture of saturated $C_{10}$-$C_{18}$ triglycerides and/or saturated $C_{12}$-$C_{18}$ triglycerides, about 15% to about 45% by weight of one or more liquid fats comprising partially hydrolyzed triglycerides including a mixture of $C_{18}$-$C_{18}$ mono-, $C_{16}$-$C_{18}$ di- and $C_{16}$-$C_{18}$ triglycerides, and about 0.1% to about 10% by weight of one or more bile acids. In some embodiments, a pharmaceutical comprises about 25 mg/mL to about 600 mg/mL of one or more therapeutic compounds, about 20% to about 55% by weight of one or more hard fats comprising a mixture of saturated $C_{10}$-$C_{18}$ triglycerides and/or saturated $C_{12}$-$C_{18}$ triglycerides, about 15% to about 45% by weight of one or more liquid fats comprising partially hydrolyzed triglycerides including a mixture of $C_{16}$-$C_{18}$ mono-, $C_{16}$-$C_{18}$ di- and $C_{16}$-$C_{18}$ triglycerides, and about 0.1% to about 10% by weight of one or more bile acids. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof. In some embodiments, the one or more bile acids in the above embodiments comprises cholic acid. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more bile acids in the above embodiments comprises cholic acid.

In some embodiments, a pharmaceutical comprises one or more therapeutic compounds, one or more hard fats, one or more liquid fats, one or more bile acids and one or more free $C_{14-24}$ fatty acids. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof. In some embodiments, the one or more bile acids in the above embodiments comprises cholic acid. In some embodiments, the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more bile acids in the above embodiments comprises cholic acid. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof, the one or more bile acids in the above embodiments comprises cholic acid, and the one or more free $C_{14-24}$ fatty acids in the above embodiments comprises one or more free $C_{14-18}$ fatty acids, preferably oleic acid, steric acid, linoleic acid, or any combination thereof.

In some embodiments, a pharmaceutical comprises about 0.1% to about 20% by weight of one or more therapeutic compounds, about 25% to about 70% by weight of one or more hard fats, about 25% to about 70% by weight of one or more liquid fats, about 0.1% to about 10% by weight of one or more bile acids, and about 1% to about 10% by weight of one or more free $C_{14-24}$ fatty acids. In some embodiments, a pharmaceutical comprises about 25 mg/mL to about 600 mg/mL of one or more therapeutic compounds, about 25% to about 70% by weight of one or more hard fats, about 25% to about 70% by weight of one or more liquid fats, about 0.1% to about 10% by weight of one or more bile acids, and about 1% to about 10% by weight of one or more free $C_{14-24}$ fatty acids. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof. In some embodiments, the one or more bile acids in the above embodiments comprises cholic acid. In some embodiments, the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more bile acids in the above embodiments comprises cholic acid. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof, the one or more bile acids in the above embodiments comprises cholic acid, and the one or more free $C_{14-24}$ fatty acids in the above embodiments comprises one or more free $C_{14-18}$ fatty acids, preferably oleic acid, steric acid, linoleic acid, or any combination thereof.

In some embodiments, a pharmaceutical comprises about 0.1% to about 20% by weight of one or more therapeutic compounds, about 25% to about 70% by weight of one or more hard fats comprising glycerolipids, about 25% to about 70% by weight of one or more liquid fats comprising partially hydrolyzed glycerolipids including a mixture of mono-, di- and triglycerides, about 0.1% to about 10% by weight of one or more bile acids, and about 1% to about 10% by weight of one or more free $C_{14-24}$ fatty acids. In some embodiments, a pharmaceutical comprises about 25 mg/mL to about 600 mg/mL of one or more therapeutic compounds, about 25% to about 70% by weight of one or more hard fats comprising glycerolipids, about 25% to about 70% by weight of one or more liquid fats comprising partially hydrolyzed glycerolipids including a mixture of mono-, di- and triglycerides, about 0.1% to about 10% by weight of one or more bile acids, and about 1% to about 10% by weight of one or more free $C_{14-24}$ fatty acids. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof. In some embodiments, the one or more bile acids in the above embodiments comprises cholic acid. In some embodiments, the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more bile acids in the above embodiments comprises cholic acid. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof, the one or more bile acids in the above embodiments comprises cholic acid, and the one or more free $C_{14-24}$ fatty acids in the above embodiments comprises one or more free $C_{14-18}$ fatty acids, preferably oleic acid, steric acid, linoleic acid, or any combination thereof.

In some embodiments, a pharmaceutical comprises about 0.1% to about 20% by weight of one or more therapeutic compounds, about 25% to about 70% by weight of one or more hard fats comprising $C_{10}$-$C_{24}$ triglycerides, about 25% to about 70% by weight of one or more liquid fats comprising partially hydrolyzed triglycerides including a mixture of $C_{10}$-$C_{24}$ mono-, $C_{10}$-$C_{24}$ di- and $C_{10}$-$C_{24}$ triglycerides, about 0.1% to about 10% by weight of one or more bile acids, and about 1% to about 10% by weight of one or more free $C_{14-24}$ fatty acids. In some embodiments, a pharmaceutical comprises about 25 mg/mL to about 600 mg/mL of one or more therapeutic compounds, about 25% to about 70% by weight of one or more hard fats comprising $C_{10}$-$C_{24}$ triglycerides, about 25% to about 70% by weight of one or more liquid fats comprising partially hydrolyzed triglycerides including a mixture of $C_{10}$-$C_{24}$ mono-, $C_{10}$-$C_{24}$ di- and $C_{10}$-$C_{24}$ triglycerides, about 0.1% to about 10% by weight of one or more bile acids, and about 1% to about 10% by weight of one or more free $C_{14-24}$ fatty acids. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof. In some embodiments, the one or more bile acids in the above embodiments comprises cholic acid. In some embodiments, the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more bile acids in the above embodiments comprises cholic acid. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof, the one or more bile acids in the above embodiments comprises cholic acid, and the one or more free $C_{14-24}$ fatty acids in the above embodiments comprises one or more free $C_{14-18}$ fatty acids, preferably oleic acid, steric acid, linoleic acid, or any combination thereof.

In some embodiments, a pharmaceutical comprises about 0.1% to about 20% by weight of one or more therapeutic compounds, about 25% to about 70% by weight of one or more hard fats comprising a mixture of saturated $C_{10}$-$C_{18}$ triglycerides and/or saturated $C_{12}$-$C_{18}$ triglycerides, about 25% to about 70% by weight of one or more liquid fats comprising partially hydrolyzed triglycerides including a mixture of $C_{18}$-$C_{18}$ mono-, $C_{16}$-$C_{18}$ di- and $C_{16}$-$C_{18}$ triglycerides, about 0.1% to about 10% by weight of one or more bile acids, and about 1% to about 10% by weight of one or more free $C_{14-24}$ fatty acids. In some embodiments, a pharmaceutical comprises about 25 mg/mL to about 600 mg/mL of one or more therapeutic compounds, about 25% to about 70% by weight of one or more hard fats comprising a mixture of saturated $C_{10}$-$C_{18}$ triglycerides and/or saturated $C_{12}$-$C_{18}$ triglycerides, about 25% to about 70% by weight of one or more liquid fats comprising partially hydrolyzed triglycerides including a mixture of $C_{16}$-$C_{18}$ mono-, $C_{16}$-$C_{18}$ di- and $C_{16}$-$C_{18}$ triglycerides, about 0.1% to about 10% by weight of one or more bile acids, and about 1% to about 10% by weight of one or more free $C_{14-24}$ fatty acids. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof. In some embodiments, the one or more bile acids in the above embodiments comprises cholic acid. In some embodiments, the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more bile acids in the above embodiments comprises cholic acid. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof, the one or more bile acids in the above embodiments comprises cholic acid, and the one or more free $C_{14-24}$ fatty acids in the above embodiments comprises one or more free $C_{14-18}$ fatty acids, preferably oleic acid, steric acid, linoleic acid, or any combination thereof.

In some embodiments, a pharmaceutical comprises about 0.1% to about 20% by weight of one or more therapeutic compounds, about 35% to about 55% by weight of one or more hard fats, about 25% to about 50% by weight of one or more liquid fats, about 0.1% to about 10% by weight of one or more bile acids, and about 1% to about 30% by weight of one or more free $C_{14-24}$ fatty acids. In some embodiments, a pharmaceutical comprises about 25 mg/mL to about 600 mg/mL of one or more therapeutic compounds, about 35% to about 55% by weight of one or more hard fats, about 25% to about 50% by weight of one or more liquid fats, about 0.1% to about 10% by weight of one or more bile acids, and about 1% to about 30% by weight of one or more free $C_{14-24}$ fatty acids. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof. In some embodiments, the one or more bile acids in the above embodiments comprises cholic acid. In some embodiments, the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more bile acids in the above embodiments comprises cholic acid. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof, the one or more bile acids in the above embodiments comprises cholic acid, and the one or more free $C_{14-24}$ fatty acids in the above embodiments comprises one or more free $C_{14-18}$ fatty acids, preferably oleic acid, steric acid, linoleic acid, or any combination thereof.

In some embodiments, a pharmaceutical comprises about 0.1% to about 20% by weight of one or more therapeutic compounds, about 35% to about 55% by weight of one or more hard fats comprising glycerolipids, about 25% to about 50% by weight of one or more liquid fats comprising partially hydrolyzed glycerolipids including a mixture of mono-, di- and triglycerides, about 0.1% to about 10% by weight of one or more bile acids, and about 1% to about 30% by weight of one or more free $C_{14-24}$ fatty acids. In some embodiments, a pharmaceutical comprises about 25 mg/mL to about 600 mg/mL of one or more therapeutic compounds, about 35% to about 55% by weight of one or more hard fats comprising glycerolipids, about 25% to about 50% by weight of one or more liquid fats comprising partially hydrolyzed glycerolipids including a mixture of mono-, di- and triglycerides, about 0.1% to about 10% by weight of one or more bile acids, and about 1% to about 30% by weight of one or more free $C_{14-24}$ fatty acids. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof. In some embodiments, the one or more bile acids in the above embodiments comprises cholic acid. In some embodiments, the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more bile acids in the above embodiments comprises cholic acid. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more free $C_{14\text{-}24}$ fatty acids in the above embodiments comprises one or more free $C_{14\text{-}18}$ fatty acids, preferably oleic acid, steric acid, linoleic acid, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof, the one or more bile acids in the above embodiments comprises cholic acid, and the one or more free $C_{14\text{-}24}$ fatty acids in the above embodiments comprises one or more free $C_{14\text{-}18}$ fatty acids, preferably oleic acid, steric acid, linoleic acid, or any combination thereof.

In some embodiments, a pharmaceutical comprises about 0.1% to about 20% by weight of one or more therapeutic compounds, about 35% to about 55% by weight of one or more hard fats comprising $C_{10}$-$C_{24}$ triglycerides, about 25% to about 50% by weight of one or more liquid fats comprising partially hydrolyzed triglycerides including a mixture of $C_{10}$-$C_{24}$ mono-, $C_{10}$-$C_{24}$ di- and $C_{10}$-$C_{24}$ triglycerides, about 0.1% to about 10% by weight of one or more bile acids, and about 1% to about 30% by weight of one or more free $C_{14\text{-}24}$ fatty acids. In some embodiments, a pharmaceutical comprises about 25 mg/mL to about 600 mg/mL of one or more therapeutic compounds, about 35% to about 55% by weight of one or more hard fats comprising $C_{10}$-$C_{24}$ triglycerides, about 25% to about 50% by weight of one or more liquid fats comprising partially hydrolyzed triglycerides including a mixture of $C_{10}$-$C_{24}$ mono-, $C_{10}$-$C_{24}$ di- and $C_{10}$-$C_{24}$ triglycerides, about 0.1% to about 10% by weight of one or more bile acids, and about 1% to about 30% by weight of one or more free $C_{14\text{-}24}$ fatty acids. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof. In some embodiments, the one or more bile acids in the above embodiments comprises cholic acid. In some embodiments, the one or more free $C_{14\text{-}24}$ fatty acids in the above embodiments comprises one or more free $C_{14\text{-}18}$ fatty acids, preferably oleic acid, steric acid, linoleic acid, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more bile acids in the above embodiments comprises cholic acid. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more free $C_{14\text{-}24}$ fatty acids in the above embodiments comprises one or more free $C_{14\text{-}18}$ fatty acids, preferably oleic acid, steric acid, linoleic acid, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof, the one or more bile acids in the above embodiments comprises cholic acid, and the one or more free $C_{14\text{-}24}$ fatty acids in the above embodiments comprises one or more free $C_{14\text{-}18}$ fatty acids, preferably oleic acid, steric acid, linoleic acid, or any combination thereof.

In some embodiments, a pharmaceutical comprises about 0.1% to about 20% by weight of one or more therapeutic compounds, about 35% to about 55% by weight of one or more hard fats comprising a mixture of saturated $C_{10}$-$C_{18}$ triglycerides and/or saturated $C_{12}$-$C_{18}$ triglycerides, about 25% to about 50% by weight of one or more liquid fats comprising partially hydrolyzed triglycerides including a mixture of $C_{18}$-$C_{18}$ mono-, $C_{16}$-$C_{18}$ di- and $C_{16}$-$C_{18}$ triglycerides, about 0.1% to about 10% by weight of one or more bile acids, and about 1% to about 30% by weight of one or more free $C_{14\text{-}24}$ fatty acids. In some embodiments, a pharmaceutical comprises about 25 mg/mL to about 600 mg/mL of one or more therapeutic compounds, about 35% to about 55% by weight of one or more hard fats comprising a mixture of saturated $C_{10}$-$C_{18}$ triglycerides and/or saturated $C_{12}$-$C_{18}$ triglycerides, about 25% to about 50% by weight of one or more liquid fats comprising partially hydrolyzed triglycerides including a mixture of $C_{16}$-$C_{18}$ mono-, $C_{16}$-$C_{18}$ di- and $C_{16}$-$C_{18}$ triglycerides, about 0.1% to about 10% by weight of one or more bile acids, and about 1% to about 30% by weight of one or more free $C_{14\text{-}24}$ fatty acids. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof. In some embodiments, the one or more bile acids in the above embodiments comprises cholic acid. In some embodiments, the one or more free $C_{14\text{-}24}$ fatty acids in the above embodiments comprises one or more free $C_{14\text{-}18}$ fatty acids, preferably oleic acid, steric acid, linoleic acid, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more bile acids in the above embodiments comprises cholic acid. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more free $C_{14\text{-}24}$ fatty acids in the above embodiments comprises one or more free $C_{14\text{-}18}$ fatty acids, preferably oleic acid, steric acid, linoleic acid, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof, the one or more bile acids in the above embodiments comprises cholic acid, and the one or more free $C_{14\text{-}24}$ fatty acids in the above embodiments comprises one or more free $C_{14\text{-}18}$ fatty acids, preferably oleic acid, steric acid, linoleic acid, or any combination thereof.

In some embodiments, a pharmaceutical comprises about 0.1% to about 30% by weight of one or more therapeutic compounds, about 15% to about 65% by weight of one or more hard fats, about 15% to about 50% by weight of one or more liquid fats, about 0.1% to about 10% by weight of one or more bile acids, and about 1% to about 25% by weight of one or more free $C_{14\text{-}24}$ fatty acids. In some embodiments, a pharmaceutical comprises about 25 mg/mL to about 600 mg/mL of one or more therapeutic compounds, about 15% to about 65% by weight of one or more hard fats, about 15% to about 50% by weight of one or more liquid fats, about 0.1% to about 10% by weight of one or more bile acids, and about 1% to about 25% by weight of one or more free $C_{14\text{-}24}$ fatty acids. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof. In some embodiments, the one or more bile acids in the above embodiments comprises cholic acid. In some embodiments, the one or more free $C_{14\text{-}24}$ fatty acids in the above embodiments comprises one or more free $C_{14\text{-}18}$ fatty acids, preferably oleic acid, steric acid, linoleic acid, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more bile acids in the above embodiments comprises cholic acid. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more free $C_{14\text{-}24}$ fatty acids in the above embodiments comprises one or more free $C_{14\text{-}18}$ fatty acids, preferably oleic acid, steric acid, linoleic acid, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof, the one or more bile acids in the above embodiments comprises cholic acid, and the one or more free $C_{14\text{-}24}$ fatty acids in the above embodiments comprises one or more free $C_{14\text{-}18}$ fatty acids, preferably oleic acid, steric acid, linoleic acid, or any combination thereof.

In some embodiments, a pharmaceutical comprises about 0.1% to about 30% by weight of one or more therapeutic compounds, about 15% to about 65% by weight of one or more hard fats comprising glycerolipids, about 15% to about 50% by weight of one or more liquid fats comprising partially hydrolyzed glycerolipids including a mixture of mono-, di- and triglycerides, about 0.1% to about 10% by weight of one or more bile acids, and about 1% to about 25% by weight of one or more free $C_{14\text{-}24}$ fatty acids. In some embodiments, a pharmaceutical comprises about 25 mg/mL to about 600 mg/mL of one or more therapeutic compounds, about 15% to about 65% by weight of one or more hard fats comprising glycerolipids, about 15% to about 50% by weight of one or more liquid fats comprising partially hydrolyzed glycerolipids including a mixture of mono-, di- and triglycerides, about 0.1% to about 10% by weight of one or more bile acids, and about 1% to about 25% by weight of one or more free $C_{14\text{-}24}$ fatty acids. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof. In some embodiments, the one or more bile acids in the above embodiments comprises cholic acid. In some embodiments, the one or more free $C_{14\text{-}24}$ fatty acids in the above embodiments comprises one or more free $C_{14\text{-}18}$ fatty acids, preferably oleic acid, steric acid, linoleic acid, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more bile acids in the above embodiments comprises cholic acid. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more free $C_{14\text{-}24}$ fatty acids in the above embodiments comprises one or more free $C_{14\text{-}18}$ fatty acids, preferably oleic acid, steric acid, linoleic acid, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof, the one or more bile acids in the above embodiments comprises cholic acid, and the one or more free $C_{14\text{-}24}$ fatty acids in the above embodiments comprises one or more free $C_{14\text{-}18}$ fatty acids, preferably oleic acid, steric acid, linoleic acid, or any combination thereof.

In some embodiments, a pharmaceutical comprises about 0.1% to about 30% by weight of one or more therapeutic compounds, about 15% to about 65% by weight of one or more hard fats comprising $C_{10}$-$C_{24}$ triglycerides, about 15% to about 50% by weight of one or more liquid fats comprising partially hydrolyzed triglycerides including a mixture of $C_{10}$-$C_{24}$ mono-, $C_{10}$-$C_{24}$ di- and $C_{10}$-$C_{24}$ triglycerides, about 0.1% to about 10% by weight of one or more bile acids, and about 1% to about 25% by weight of one or more free $C_{14\text{-}24}$ fatty acids. In some embodiments, a pharmaceutical comprises about 25 mg/mL to about 600 mg/mL of one or more therapeutic compounds, about 15% to about 65% by weight of one or more hard fats comprising $C_{10}$-$C_{24}$ triglycerides, about 15% to about 50% by weight of one or more liquid fats comprising partially hydrolyzed triglycerides including a mixture of $C_{10}$-$C_{24}$ mono-, $C_{10}$-$C_{24}$ di- and $C_{10}$-$C_{24}$ triglycerides, about 0.1% to about 10% by weight of one or more bile acids, and about 1% to about 25% by weight of one or more free $C_{14\text{-}24}$ fatty acids. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof. In some embodiments, the one or more bile acids in the above embodiments comprises cholic acid. In some embodiments, the one or more free $C_{14\text{-}24}$ fatty acids in the above embodiments comprises one or more free $C_{14\text{-}18}$ fatty acids, preferably oleic acid, steric acid, linoleic acid, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more bile acids in the above embodiments comprises cholic acid. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more free $C_{14\text{-}24}$ fatty acids in the above embodiments comprises one or more free $C_{14\text{-}18}$ fatty acids, preferably oleic acid, steric acid, linoleic acid, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof, the one or more bile acids in the above embodiments comprises cholic acid, and the one or more free $C_{14\text{-}24}$ fatty acids in the above embodiments comprises one or more free $C_{14\text{-}18}$ fatty acids, preferably oleic acid, steric acid, linoleic acid, or any combination thereof.

In some embodiments, a pharmaceutical comprises about 0.1% to about 30% by weight of one or more therapeutic compounds, about 15% to about 65% by weight of one or more hard fats comprising a mixture of saturated $C_{10}$-$C_{18}$ triglycerides and/or saturated $C_{12}$-$C_{18}$ triglycerides, about 15% to about 50% by weight of one or more liquid fats comprising partially hydrolyzed triglycerides including a mixture of $C_{16}$-$C_{18}$ mono-, $C_{16}$-$C_{18}$ di- and $C_{16}$-$C_{18}$ triglycerides, about 0.1% to about 10% by weight of one or more bile acids, and about 1% to about 25% by weight of one or more free $C_{14\text{-}24}$ fatty acids. In some embodiments, a pharmaceutical comprises about 25 mg/mL to about 600 mg/mL of one or more therapeutic compounds, about 15% to about 65% by weight of one or more hard fats comprising a mixture of saturated $C_{10}$-$C_{18}$ triglycerides and/or saturated $C_{12}$-$C_{18}$ triglycerides, about 15% to about 50% by weight of one or more liquid fats comprising partially hydrolyzed triglycerides including a mixture of $C_{16}$-$C_{18}$ mono-, $C_{16}$-$C_{18}$ di- and $C_{16}$-$C_{18}$ triglycerides, about 0.1% to about 10% by weight of one or more bile acids, and about 1% to about 25% by weight of one or more free $C_{14\text{-}24}$ fatty acids. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof. In some embodiments, the one or more bile acids in the above embodiments comprises cholic acid. In some embodiments, the one or more free $C_{14\text{-}24}$ fatty acids in the above embodiments comprises one or more free $C_{14\text{-}18}$ fatty acids, preferably oleic acid, steric acid, linoleic acid, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more bile acids in the above embodiments comprises cholic acid. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more free $C_{14\text{-}24}$ fatty acids in the above embodiments comprises one or more free $C_{14\text{-}18}$ fatty acids, preferably oleic acid, steric acid, linoleic acid, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof, the one or more bile acids in the above embodiments comprises cholic acid, and the one or more free $C_{14\text{-}24}$ fatty acids in the above embodiments comprises one or more free $C_{14\text{-}18}$ fatty acids, preferably oleic acid, steric acid, linoleic acid, or any combination thereof.

In some embodiments, a pharmaceutical comprises about 0.1% to about 30% by weight of one or more therapeutic compounds, about 20% to about 55% by weight of one or more hard fats, about 15% to about 45% by weight of one or more liquid fats, about 0.1% to about 10% by weight of one or more bile acids, and about 10% to about 45% by weight of one or more free $C_{14-24}$ fatty acids. In some embodiments, a pharmaceutical comprises about 25 mg/mL to about 600 mg/mL of one or more therapeutic compounds, about 20% to about 55% by weight of one or more hard fats, about 15% to about 45% by weight of one or more liquid fats, about 0.1% to about 10% by weight of one or more bile acids, and about 10% to about 45% by weight of one or more free $C_{14-24}$ fatty acids. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof. In some embodiments, the one or more bile acids in the above embodiments comprises cholic acid. In some embodiments, the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more bile acids in the above embodiments comprises cholic acid. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof, the one or more bile acids in the above embodiments comprises cholic acid, and the one or more free $C_{14-24}$ fatty acids in the above embodiments comprises one or more free $C_{14-18}$ fatty acids, preferably oleic acid, steric acid, linoleic acid, or any combination thereof.

In some embodiments, a pharmaceutical comprises about 0.1% to about 30% by weight of one or more therapeutic compounds, about 20% to about 55% by weight of one or more hard fats comprising glycerolipids, about 15% to about 45% by weight of one or more liquid fats comprising partially hydrolyzed glycerolipids including a mixture of mono-, di- and triglycerides, about 0.1% to about 10% by weight of one or more bile acids, and about 10% to about 45% by weight of one or more free $C_{14-24}$ fatty acids. In some embodiments, a pharmaceutical comprises about 25 mg/mL to about 600 mg/mL of one or more therapeutic compounds, about 20% to about 55% by weight of one or more hard fats comprising glycerolipids, about 15% to about 45% by weight of one or more liquid fats comprising partially hydrolyzed glycerolipids including a mixture of mono-, di- and triglycerides, about 0.1% to about 10% by weight of one or more bile acids, and about 10% to about 45% by weight of one or more free $C_{14-24}$ fatty acids. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof. In some embodiments, the one or more bile acids in the above embodiments comprises cholic acid. In some embodiments, the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more bile acids in the above embodiments comprises cholic acid. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof, the one or more bile acids in the above embodiments comprises cholic acid, and the one or more free $C_{14-24}$ fatty acids in the above embodiments comprises one or more free $C_{14-18}$ fatty acids, preferably oleic acid, steric acid, linoleic acid, or any combination thereof.

In some embodiments, a pharmaceutical comprises about 0.1% to about 30% by weight of one or more therapeutic compounds, about 20% to about 55% by weight of one or more hard fats comprising $C_{10}$-$C_{24}$ triglycerides, about 15% to about 45% by weight of one or more liquid fats comprising partially hydrolyzed triglycerides including a mixture of $C_{10}$-$C_{24}$ mono-, $C_{10}$-$C_{24}$ di- and $C_{10}$-$C_{24}$ triglycerides, about 0.1% to about 10% by weight of one or more bile acids, and about 10% to about 45% by weight of one or more free $C_{14-24}$ fatty acids. In some embodiments, a pharmaceutical comprises about 25 mg/mL to about 600 mg/mL of one or more therapeutic compounds, about 20% to about 55% by weight of one or more hard fats comprising $C_{10}$-$C_{24}$ triglycerides, about 15% to about 45% by weight of one or more liquid fats comprising partially hydrolyzed triglycerides including a mixture of $C_{10}$-$C_{24}$ mono-, $C_{10}$-$C_{24}$ di- and $C_{10}$-$C_{24}$ triglycerides, about 0.1% to about 10% by weight of one or more bile acids, and about 10% to about 45% by weight of one or more free $C_{14-24}$ fatty acids. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof. In some embodiments, the one or more bile acids in the above embodiments comprises cholic acid. In some embodiments, the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more bile acids in the above embodiments comprises cholic acid. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof, the one or more bile acids in the above embodiments comprises cholic acid, and the one or more free $C_{14-24}$ fatty acids in the above embodiments comprises one or more free $C_{14-18}$ fatty acids, preferably oleic acid, steric acid, linoleic acid, or any combination thereof.

In some embodiments, a pharmaceutical comprises about 0.1% to about 30% by weight of one or more therapeutic compounds, about 20% to about 55% by weight of one or more hard fats comprising a mixture of saturated $C_{16}$-$C_{18}$ triglycerides and/or saturated $C_{12}$-$C_{18}$ triglycerides, about 15% to about 45% by weight of one or more liquid fats comprising partially hydrolyzed triglycerides including a mixture of $C_{16}$-$C_{18}$ mono-, $C_{16}$-$C_{18}$ di- and $C_{16}$-$C_{18}$ triglycerides, about 0.1% to about 10% by weight of one or more bile acids, and about 10% to about 45% by weight of one or more free $C_{14-24}$ fatty acids. In some embodiments, a pharmaceutical comprises about 25 mg/mL to about 600 mg/mL of one or more therapeutic compounds, about 20% to about 55% by weight of one or more hard fats comprising a mixture of saturated $C_{10}$-$C_{18}$ triglycerides and/or saturated $C_{12}$-$C_{18}$ triglycerides, about 15% to about 45% by weight of one or more liquid fats comprising partially hydrolyzed triglycerides including a mixture of $C_{16}$-$C_{18}$ mono-, $C_{16}$-$C_{18}$ di- and $C_{16}$-$C_{18}$ triglycerides, about 0.1% to about 10% by weight of one or more bile acids, and about 10% to about 45% by weight of one or more free $C_{14-24}$ fatty acids. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof. In some embodiments, the one or more bile acids in the above embodiments comprises cholic acid. In some embodiments, the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more bile acids in the above embodiments comprises cholic acid. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof, the one or more bile acids in the above embodiments comprises cholic acid, and the one or more free $C_{14-24}$ fatty acids in the above embodiments comprises one or more free $C_{14-18}$ fatty acids, preferably oleic acid, steric acid, linoleic acid, or any combination thereof.

In some embodiments, a pharmaceutical comprises one or more therapeutic compounds, one or more hard fats, one or more liquid fats, one or more bile acids, and one or more free $C_{14-24}$ fatty acid surfactants. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof. In some embodiments, the one or more bile acids in the above embodiments comprises cholic acid. In some embodiments, the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more bile acids in the above embodiments comprises cholic acid. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more free $C_{14\text{-}24}$ fatty acid surfactants in the above embodiments comprises one or more free $C_{14\text{-}18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more bile acids in the above embodiments comprises cholic acid and the one or more free $C_{14\text{-}24}$ fatty acid surfactants in the above embodiments comprises one or more free $C_{14\text{-}18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof, the one or more bile acids in the above embodiments comprises cholic acid, and the one or more free $C_{14\text{-}24}$ fatty acid surfactants in the above embodiments comprises one or more free $C_{14\text{-}18}$ fatty acid surfactants, preferably an oleate alkali metal or alkali earth metal salt, a stearate alkali metal or alkali earth metal salt, a linoleate alkali metal or alkali earth metal salt, or any combination thereof.

In some embodiments, a pharmaceutical comprises about 0.1% to about 20% by weight of one or more therapeutic compounds, about 25% to about 70% by weight of one or more hard fats, about 25% to about 70% by weight of one or more liquid fats, about 0.1% to about 10% by weight of one or more bile acids, and about 0.1% to about 5% by weight of one or more free $C_{14\text{-}24}$ fatty acid surfactants. In some embodiments, a pharmaceutical comprises about 25 mg/mL to about 600 mg/mL of one or more therapeutic compounds, about 25% to about 70% by weight of one or more hard fats, about 25% to about 70% by weight of one or more liquid fats, about 0.1% to about 10% by weight of one or more bile acids, and about 0.1% to about 5% by weight of one or more free $C_{14\text{-}24}$ fatty acid surfactants. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof. In some embodiments, the one or more bile acids in the above embodiments comprises cholic acid. In some embodiments, the one or more free $C_{14\text{-}24}$ fatty acid surfactants in the above embodiments comprises one or more free $C_{14\text{-}18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more bile acids in the above embodiments comprises cholic acid. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more free $C_{14\text{-}24}$ fatty acid surfactants in the above embodiments comprises one or more free $C_{14\text{-}18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more bile acids in the above embodiments comprises cholic acid and the one or more free $C_{14\text{-}24}$ fatty acid surfactants in the above embodiments comprises one or more free $C_{14\text{-}18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof, the one or more bile acids in the above embodiments comprises cholic acid, and the one or more free $C_{14\text{-}24}$ fatty acid surfactants in the above embodiments comprises one or more free $C_{14\text{-}18}$ fatty acid surfactants, preferably an oleate alkali metal or alkali earth metal salt, a stearate alkali metal or alkali earth metal salt, a linoleate alkali metal or alkali earth metal salt, or any combination thereof.

In some embodiments, a pharmaceutical comprises about 0.1% to about 20% by weight of one or more therapeutic compounds, about 25% to about 70% by weight of one or more hard fats comprising glycerolipids, about 25% to about 70% by weight of one or more liquid fats comprising partially hydrolyzed glycerolipids including a mixture of mono-, di- and triglycerides, about 0.1% to about 10% by weight of one or more bile acids, and about 0.1% to about 5% by weight of one or more free $C_{14\text{-}24}$ fatty acid surfactants. In some embodiments, a pharmaceutical comprises about 25 mg/mL to about 600 mg/mL of one or more therapeutic compounds, about 25% to about 70% by weight of one or more hard fats comprising glycerolipids, about 25% to about 70% by weight of one or more liquid fats comprising partially hydrolyzed glycerolipids including a mixture of mono-, di- and triglycerides, about 0.1% to about 10% by weight of one or more bile acids, and about 0.1% to about 5% by weight of one or more free $C_{14\text{-}24}$ fatty acid surfactants. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof. In some embodiments, the one or more bile acids in the above embodiments comprises cholic acid. In some embodiments, the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more bile acids in the above embodiments comprises cholic acid. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more bile acids in the above embodiments comprises cholic acid and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof, the one or more bile acids in the above embodiments comprises cholic acid, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof.

In some embodiments, a pharmaceutical comprises about 0.1% to about 20% by weight of one or more therapeutic compounds, about 25% to about 70% by weight of one or more hard fats comprising $C_{10}$-$C_{24}$ triglycerides, about 25% to about 70% by weight of one or more liquid fats comprising partially hydrolyzed triglycerides including a mixture of $C_{10}$-$C_{24}$ mono-, $C_{10}$-$C_{24}$ di- and $C_{10}$-$C_{24}$ triglycerides, about 0.1% to about 10% by weight of one or more bile acids, and about 0.1% to about 5% by weight of one or more free $C_{14-24}$ fatty acid surfactants. In some embodiments, a pharmaceutical comprises about 25 mg/mL to about 600 mg/mL of one or more therapeutic compounds, about 25% to about 70% by weight of one or more hard fats comprising $C_{10}$-$C_{24}$ triglycerides, about 25% to about 70% by weight of one or more liquid fats comprising partially hydrolyzed triglycerides including a mixture of $C_{10}$-$C_{24}$ mono-, $C_{10}$-$C_{24}$ di- and $C_{10}$-$C_{24}$ triglycerides, about 0.1% to about 10% by weight of one or more bile acids, about 0.1% to about 5% by weight of one or more free $C_{14-24}$ fatty acid surfactants. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof. In some embodiments, the one or more bile acids in the above embodiments comprises cholic acid. In some embodiments, the one or more free $C_{14}$-24 fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more bile acids in the above embodiments comprises cholic acid. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more bile acids in the above embodiments comprises cholic acid and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof, the one or more bile acids in the above embodiments comprises cholic acid, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof.

In some embodiments, a pharmaceutical comprises about 0.1% to about 20% by weight of one or more therapeutic compounds, about 25% to about 70% by weight of one or more hard fats comprising a mixture of saturated $C_{10}$-$C_{18}$ triglycerides and/or saturated $C_{12}$-$C_{18}$ triglycerides, about 25% to about 70% by weight of one or more liquid fats comprising partially hydrolyzed triglycerides including a mixture of $C_{18}$-$C_{18}$ mono-, $C_{16}$-$C_{18}$ di- and $C_{16}$-$C_{18}$ triglycerides, about 0.1% to about 10% by weight of one or more bile acids, and about 0.1% to about 5% by weight of one or more free $C_{14-24}$ fatty acid surfactants. In some embodiments, a pharmaceutical comprises about 25 mg/mL to about 600 mg/mL of one or more therapeutic compounds, about 25% to about 70% by weight of one or more hard fats comprising a mixture of saturated $C_{10}$-$C_{18}$ triglycerides and/or saturated $C_{12}$-$C_{18}$ triglycerides, about 25% to about 70% by weight of one or more liquid fats comprising partially hydrolyzed triglycerides including a mixture of $C_{16}$-$C_{18}$ mono-, $C_{16}$-$C_{18}$ di- and $C_{16}$-$C_{18}$ triglycerides, about 0.1% to about 10% by weight of one or more bile acids, and about 0.1% to about 5% by weight of one or more free $C_{14-24}$ fatty acid surfactants. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof. In some embodiments, the one or more bile acids in the above embodiments comprises cholic acid. In some embodiments, the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more bile acids in the above embodiments comprises cholic acid. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more bile acids in the above embodiments comprises cholic acid and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof, the one or more bile acids in the above embodiments comprises cholic acid, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof.

In some embodiments, a pharmaceutical comprises about 0.1% to about 20% by weight of one or more therapeutic compounds, about 35% to about 55% by weight of one or more hard fats, about 25% to about 50% by weight of one or more liquid fats, about 0.1% to about 10% by weight of one or more bile acids, and about 0.1% to about 5% by weight of one or more free $C_{14-24}$ fatty acid surfactants. In some embodiments, a pharmaceutical comprises about 25 mg/mL to about 600 mg/mL of one or more therapeutic compounds, about 35% to about 55% by weight of one or more hard fats, about 25% to about 50% by weight of one or more liquid fats, about 0.1% to about 10% by weight of one or more bile acids, and about 0.1% to about 5% by weight of one or more free $C_{14-24}$ fatty acid surfactants. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof. In some embodiments, the one or more bile acids in the above embodiments comprises cholic acid. In some embodiments, the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more bile acids in the above embodiments comprises cholic acid. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more bile acids in the above embodiments comprises cholic acid and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof, the one or more bile acids in the above embodiments comprises cholic acid, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof.

In some embodiments, a pharmaceutical comprises about 0.1% to about 20% by weight of one or more therapeutic compounds, about 35% to about 55% by weight of one or more hard fats comprising glycerolipids, about 25% to about 50% by weight of one or more liquid fats comprising partially hydrolyzed glycerolipids including a mixture of mono-, di- and triglycerides, about 0.1% to about 10% by weight of one or more bile acids, and about 0.1% to about 5% by weight of one or more free $C_{14-24}$ fatty acid surfactants. In some embodiments, a pharmaceutical comprises about 25 mg/mL to about 600 mg/mL of one or more therapeutic compounds, about 35% to about 55% by weight of one or more hard fats comprising glycerolipids, about 25% to about 50% by weight of one or more liquid fats comprising partially hydrolyzed glycerolipids including a mixture of mono-, di- and triglycerides, about 0.1% to about 10% by weight of one or more bile acids, and about 0.1% to about 5% by weight of one or more free $C_{14-24}$ fatty acid surfactants. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof. In some embodiments, the one or more bile acids in the above embodiments comprises cholic acid. In some embodiments, the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more bile acids in the above embodiments comprises cholic acid. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more bile acids in the above embodiments comprises cholic acid and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof, the one or more bile acids in the above embodiments comprises cholic acid, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof.

In some embodiments, a pharmaceutical comprises about 0.1% to about 20% by weight of one or more therapeutic compounds, about 35% to about 55% by weight of one or more hard fats comprising $C_{10}$-$C_{24}$ triglycerides, about 25% to about 50% by weight of one or more liquid fats comprising partially hydrolyzed triglycerides including a mixture of $C_{10}$-$C_{24}$ mono-, $C_{10}$-$C_{24}$ di- and $C_{10}$-$C_{24}$ triglycerides, about 0.1% to about 10% by weight of one or more bile acids, and about 0.1% to about 5% by weight of one or more free $C_{14-24}$ fatty acid surfactants. In some embodiments, a pharmaceutical comprises about 25 mg/mL to about 600 mg/mL of one or more therapeutic compounds, about 35% to about 55% by weight of one or more hard fats comprising $C_{10}$-$C_{24}$ triglycerides, about 25% to about 50% by weight of one or more liquid fats comprising partially hydrolyzed triglycerides including a mixture of $C_{10}$-$C_{24}$ mono-, $C_{10}$-$C_{24}$ di- and $C_{10}$-$C_{24}$ triglycerides, about 0.1% to about 10% by weight of one or more bile acids, about 0.1% to about 5% by weight of one or more free $C_{14-24}$ fatty acid surfactants. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof. In some embodiments, the one or more bile acids in the above embodiments comprises cholic acid. In some embodiments, the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more bile acids in the above embodiments comprises cholic acid. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more bile acids in the above embodiments comprises cholic acid and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof, the one or more bile acids in the above embodiments comprises cholic acid, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof.

In some embodiments, a pharmaceutical comprises about 0.1% to about 20% by weight of one or more therapeutic compounds, about 35% to about 55% by weight of one or more hard fats comprising a mixture of saturated $C_{10}$-$C_{18}$ triglycerides and/or saturated $C_{12}$-$C_{18}$ triglycerides, about 25% to about 50% by weight of one or more liquid fats comprising partially hydrolyzed triglycerides including a mixture of $C_{18}$-$C_{18}$ mono-, $C_{16}$-$C_{18}$ di- and $C_{16}$-$C_{18}$ triglycerides, about 0.1% to about 10% by weight of one or more bile acids, and about 0.1% to about 5% by weight of one or more free $C_{14-24}$ fatty acid surfactants. In some embodiments, a pharmaceutical comprises about 25 mg/mL to about 600 mg/mL of one or more therapeutic compounds, about 35% to about 55% by weight of one or more hard fats comprising a mixture of saturated $C_{10}$-$C_{18}$ triglycerides and/or saturated $C_{12}$-$C_{18}$ triglycerides, about 25% to about 50% by weight of one or more liquid fats comprising partially hydrolyzed triglycerides including a mixture of $C_{16}$-$C_{18}$ mono-, $C_{16}$-$C_{18}$ di- and $C_{16}$-$C_{18}$ triglycerides, about 0.1% to about 10% by weight of one or more bile acids, and about 0.1% to about 5% by weight of one or more free $C_{14-24}$ fatty acid surfactants. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof. In some embodiments, the one or more bile acids in the above embodiments comprises cholic acid. In some embodiments, the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more bile acids in the above embodiments comprises cholic acid. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more bile acids in the above embodiments comprises cholic acid and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof, the one or more bile acids in the above embodiments comprises cholic acid, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof.

In some embodiments, a pharmaceutical comprises about 0.1% to about 30% by weight of one or more therapeutic compounds, about 15% to about 65% by weight of one or more hard fats, about 15% to about 50% by weight of one or more liquid fats, about 0.1% to about 10% by weight of one or more bile acids, and about 0.1% to about 5% by weight of one or more free $C_{14-24}$ fatty acid surfactants. In some embodiments, a pharmaceutical comprises about 25 mg/mL to about 600 mg/mL of one or more therapeutic compounds, about 15% to about 65% by weight of one or more hard fats, about 15% to about 50% by weight of one or more liquid fats, about 0.1% to about 10% by weight of one or more bile acids, and about 0.1% to about 5% by weight of one or more free $C_{14-24}$ fatty acid surfactants. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof. In some embodiments, the one or more bile acids in the above embodiments comprises cholic acid. In some embodiments, the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more bile acids in the above embodiments comprises cholic acid. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more bile acids in the above embodiments comprises cholic acid and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof, the one or more bile acids in the above embodiments comprises cholic acid, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof.

In some embodiments, a pharmaceutical comprises about 0.1% to about 30% by weight of one or more therapeutic compounds, about 15% to about 65% by weight of one or more hard fats comprising glycerolipids, about 15% to about 50% by weight of one or more liquid fats comprising partially hydrolyzed glycerolipids including a mixture of mono-, di- and triglycerides, about 0.1% to about 10% by weight of one or more bile acids, and about 0.1% to about 5% by weight of one or more free $C_{14-24}$ fatty acid surfactants. In some embodiments, a pharmaceutical comprises about 25 mg/mL to about 600 mg/mL of one or more therapeutic compounds, about 15% to about 65% by weight of one or more hard fats comprising glycerolipids, about 15% to about 50% by weight of one or more liquid fats comprising partially hydrolyzed glycerolipids including a mixture of mono-, di- and triglycerides, about 0.1% to about 10% by weight of one or more bile acids, and about 0.1% to about 5% by weight of one or more free $C_{14-24}$ fatty acid surfactants. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof. In some embodiments, the one or more bile acids in the above embodiments comprises cholic acid. In some embodiments, the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more bile acids in the above embodiments comprises cholic acid. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more bile acids in the above embodiments comprises cholic acid and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof, the one or more bile acids in the above embodiments comprises cholic acid, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof.

In some embodiments, a pharmaceutical comprises about 0.1% to about 30% by weight of one or more therapeutic compounds, about 15% to about 65% by weight of one or more hard fats comprising $C_{10}$-$C_{24}$ triglycerides, about 15% to about 50% by weight of one or more liquid fats comprising partially hydrolyzed triglycerides including a mixture of $C_{10}$-$C_{24}$ mono-, $C_{10}$-$C_{24}$ di- and $C_{10}$-$C_{24}$ triglycerides, about 0.1% to about 10% by weight of one or more bile acids, and about 0.1% to about 5% by weight of one or more free $C_{14-24}$ fatty acid surfactants. In some embodiments, a pharmaceutical comprises about 25 mg/mL to about 600 mg/mL of one or more therapeutic compounds, about 15% to about 65% by weight of one or more hard fats comprising $C_{10}$-$C_{24}$ triglycerides, about 15% to about 50% by weight of one or more liquid fats comprising partially hydrolyzed triglycerides including a mixture of $C_{10}$-$C_{24}$ mono-, $C_{10}$-$C_{24}$ di- and $C_{10}$-$C_{24}$ triglycerides, about 0.1% to about 10% by weight of one or more bile acids, about 0.1% to about 5% by weight of one or more free $C_{14-24}$ fatty acid surfactants. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof. In some embodiments, the one or more bile acids in the above embodiments comprises cholic acid. In some embodiments, the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more bile acids in the above embodiments comprises cholic acid. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more bile acids in the above embodiments comprises cholic acid and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof, the one or more bile acids in the above embodiments comprises cholic acid, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof.

In some embodiments, a pharmaceutical comprises about 0.1% to about 30% by weight of one or more therapeutic compounds, about 15% to about 65% by weight of one or more hard fats comprising a mixture of saturated $C_{10}$-$C_{18}$ triglycerides and/or saturated $C_{12}$-$C_{18}$ triglycerides, about 15% to about 50% by weight of one or more liquid fats comprising partially hydrolyzed triglycerides including a mixture of $C_{16}$-$C_{18}$ mono-, $C_{16}$-$C_{18}$ di- and $C_{16}$-$C_{18}$ triglycerides, about 0.1% to about 10% by weight of one or more bile acids, and about 0.1% to about 5% by weight of one or more free $C_{14-24}$ fatty acid surfactants. In some embodiments, a pharmaceutical comprises about 25 mg/mL to about 600 mg/mL of one or more therapeutic compounds, about 15% to about 65% by weight of one or more hard fats comprising a mixture of saturated $C_{10}$-$C_{18}$ triglycerides and/or saturated $C_{12}$-$C_{18}$ triglycerides, about 15% to about 50% by weight of one or more liquid fats comprising partially hydrolyzed triglycerides including a mixture of $C_{16}$-$C_{18}$ mono-, $C_{16}$-$C_{18}$ di- and $C_{16}$-$C_{18}$ triglycerides, about 0.1% to about 10% by weight of one or more bile acids, and about 0.1% to about 5% by weight of one or more free $C_{14-24}$ fatty acid surfactants. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof. In some embodiments, the one or more bile acids in the above embodiments comprises cholic acid. In some embodiments, the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more bile acids in the above embodiments comprises cholic acid. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more bile acids in the above embodiments comprises cholic acid and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof, the one or more bile acids in the above embodiments comprises cholic acid, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof.

In some embodiments, a pharmaceutical comprises about 0.1% to about 30% by weight of one or more therapeutic compounds, about 20% to about 55% by weight of one or more hard fats, about 15% to about 45% by weight of one or more liquid fats, about 0.1% to about 10% by weight of one or more bile acids, and about 0.1% to about 5% by weight of one or more free $C_{14-24}$ fatty acid surfactants. In some embodiments, a pharmaceutical comprises about 25 mg/mL to about 600 mg/mL of one or more therapeutic compounds, about 20% to about 55% by weight of one or more hard fats, about 15% to about 45% by weight of one or more liquid fats, about 0.1% to about 10% by weight of one or more bile acids, and about 0.1% to about 5% by weight of one or more free $C_{14-24}$ fatty acid surfactants. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof. In some embodiments, the one or more bile acids in the above embodiments comprises cholic acid. In some embodiments, the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more bile acids in the above embodiments comprises cholic acid. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more bile acids in the above embodiments comprises cholic acid and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof, the one or more bile acids in the above embodiments comprises cholic acid, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof.

In some embodiments, a pharmaceutical comprises about 0.1% to about 30% by weight of one or more therapeutic compounds, about 20% to about 55% by weight of one or more hard fats comprising glycerolipids, about 15% to about 45% by weight of one or more liquid fats comprising partially hydrolyzed glycerolipids including a mixture of mono-, di- and triglycerides, about 0.1% to about 10% by weight of one or more bile acids, and about 0.1% to about 5% by weight of one or more free $C_{14-24}$ fatty acid surfactants. In some embodiments, a pharmaceutical comprises about 25 mg/mL to about 600 mg/mL of one or more therapeutic compounds, about 20% to about 55% by weight of one or more hard fats comprising glycerolipids, about 15% to about 45% by weight of one or more liquid fats comprising partially hydrolyzed glycerolipids including a mixture of mono-, di- and triglycerides, about 0.1% to about 10% by weight of one or more bile acids, and about 0.1% to about 5% by weight of one or more free $C_{14-24}$ fatty acid surfactants. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof. In some embodiments, the one or more bile acids in the above embodiments comprises cholic acid. In some embodiments, the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more bile acids in the above embodiments comprises cholic acid. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more bile acids in the above embodiments comprises cholic acid and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof, the one or more bile acids in the above embodiments comprises cholic acid, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof.

In some embodiments, a pharmaceutical comprises about 0.1% to about 30% by weight of one or more therapeutic compounds, about 20% to about 55% by weight of one or more hard fats comprising $C_{10}$-$C_{24}$ triglycerides, about 15% to about 45% by weight of one or more liquid fats comprising partially hydrolyzed triglycerides including a mixture of $C_{10}$-$C_{24}$ mono-, $C_{10}$-$C_{24}$ di- and $C_{10}$-$C_{24}$ triglycerides, about 0.1% to about 10% by weight of one or more bile acids, and about 0.1% to about 5% by weight of one or more free $C_{14-24}$ fatty acid surfactants. In some embodiments, a pharmaceutical comprises about 25 mg/mL to about 600 mg/mL of one or more therapeutic compounds, about 20% to about 55% by weight of one or more hard fats comprising $C_{10}$-$C_{24}$ triglycerides, about 15% to about 45% by weight of one or more liquid fats comprising partially hydrolyzed triglycerides including a mixture of $C_{10}$-$C_{24}$ mono-, $C_{10}$-$C_{24}$ di- and $C_{10}$-$C_{24}$ triglycerides, about 0.1% to about 10% by weight of one or more bile acids, about 0.1% to about 5% by weight of one or more free $C_{14-24}$ fatty acid surfactants. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof. In some embodiments, the one or more bile acids in the above embodiments comprises cholic acid. In some embodiments, the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more bile acids in the above embodiments comprises cholic acid. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more bile acids in the above embodiments comprises cholic acid and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof, the one or more bile acids in the above embodiments comprises cholic acid, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof.

In some embodiments, a pharmaceutical comprises about 0.1% to about 30% by weight of one or more therapeutic compounds, about 20% to about 55% by weight of one or more hard fats comprising a mixture of saturated $C_{10}$-$C_{18}$ triglycerides and/or saturated $C_{12}$-$C_{18}$ triglycerides, about 15% to about 45% by weight of one or more liquid fats comprising partially hydrolyzed triglycerides including a mixture of $C_{18}$-$C_{18}$ mono-, $C_{16}$-$C_{18}$ di- and $C_{16}$-$C_{18}$ triglycerides, about 0.1% to about 10% by weight of one or more bile acids, and about 0.1% to about 5% by weight of one or more free $C_{14-24}$ fatty acid surfactants. In some embodiments, a pharmaceutical comprises about 25 mg/mL to about 600 mg/mL of one or more therapeutic compounds, about 20% to about 55% by weight of one or more hard fats comprising a mixture of saturated $C_{10}$-$C_{18}$ triglycerides and/or saturated $C_{12}$-$C_{18}$ triglycerides, about 15% to about 45% by weight of one or more liquid fats comprising partially hydrolyzed triglycerides including a mixture of $C_{16}$-$C_{18}$ mono-, $C_{16}$-$C_{18}$ di- and $C_{16}$-$C_{18}$ triglycerides, about 0.1% to about 10% by weight of one or more bile acids, and about 0.1% to about 5% by weight of one or more free $C_{14-24}$ fatty acid surfactants. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof. In some embodiments, the one or more bile acids in the above embodiments comprises cholic acid. In some embodiments, the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more bile acids in the above embodiments comprises cholic acid. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more bile acids in the above embodiments comprises cholic acid and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof, the one or more bile acids in the above embodiments comprises cholic acid, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof.

In some embodiments, a pharmaceutical comprises one or more therapeutic compounds, one or more hard fats, one or more liquid fats, one or more bile acids, one or more free $C_{14-24}$ fatty acids, and one or more free $C_{14-24}$ fatty acid surfactants. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof. In some embodiments, the one or more bile acids in the above embodiments comprises cholic acid. In some embodiments, the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more bile acids in the above embodiments comprises cholic acid. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more bile acids in the above embodiments comprises cholic acid and the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more bile acids in the above embodiments comprises cholic acid and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more free $C_{14-24}$ fatty acids in the above embodiments comprises one or more free $C_{14-18}$ fatty acids, preferably oleic acid, steric acid, linoleic acid, or any combination thereof, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof, the one or more bile acids in the above embodiments comprises cholic acid, and the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof, the one or more bile acids in the above embodiments comprises cholic acid, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof, the one or more free $C_{14-24}$ fatty acids in the above embodiments comprises one or more free $C_{14-18}$ fatty acids, preferably oleic acid, steric acid, linoleic acid, or any combination thereof, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more bile acids in the above embodiments comprises cholic acid, the one or more free $C_{14-24}$ fatty acids in the above embodiments comprises one or more free $C_{14-18}$ fatty acids, preferably oleic acid, steric acid, linoleic acid, or any combination thereof, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof, the one or more bile acids in the above embodiments comprises cholic acid, the one or more free $C_{14-24}$ fatty acids in the above embodiments comprises one or more free $C_{14-18}$ fatty acids, preferably oleic acid, steric acid, linoleic acid, or any combination thereof, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof.

In some embodiments, a pharmaceutical comprises about 0.1% to about 20% by weight of one or more therapeutic compounds, about 25% to about 70% by weight of one or more hard fats, about 25% to about 70% by weight of one or more liquid fats, about 0.1% to about 10% by weight of one or more bile acids, about 10% to about 25% by weight of one or more free $C_{14-24}$ fatty acids, and about 0.1% to about 5% by weight of one or more free $C_{14-24}$ fatty acid surfactants. In some embodiments, a pharmaceutical comprises about 25 mg/mL to about 600 mg/mL of one or more therapeutic compounds, about 25% to about 70% by weight of one or more hard fats, about 25% to about 70% by weight of one or more liquid fats, about 0.1% to about 10% by weight of one or more bile acids, about 10% to about 25% by weight of one or more free $C_{14-24}$ fatty acids, and about 0.1% to about 5% by weight of one or more free $C_{14-24}$ fatty acid surfactants. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof. In some embodiments, the one or more bile acids in the above embodiments comprises cholic acid. In some embodiments, the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more bile acids in the above embodiments comprises cholic acid. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more bile acids in the above embodiments comprises cholic acid and the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more bile acids in the above embodiments comprises cholic acid and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more free $C_{14-24}$ fatty acids in the above embodiments comprises one or more free $C_{14-18}$ fatty acids, preferably oleic acid, steric acid, linoleic acid, or any combination thereof, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof, the one or more bile acids in the above embodiments comprises cholic acid, and the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof, the one or more bile acids in the above embodiments comprises cholic acid, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof, the one or more free $C_{14-24}$ fatty acids in the above embodiments comprises one or more free $C_{14-18}$ fatty acids, preferably oleic acid, steric acid, linoleic acid, or any combination thereof, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more bile acids in the above embodiments comprises cholic acid, the one or more free $C_{14-24}$ fatty acids in the above embodiments comprises one or more free $C_{14-18}$ fatty acids, preferably oleic acid, steric acid, linoleic acid, or any combination thereof, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof, the one or more bile acids in the above embodiments comprises cholic acid, the one or more free $C_{14-24}$ fatty acids in the above embodiments comprises one or more free $C_{14-18}$ fatty acids, preferably oleic acid, steric acid, linoleic acid, or any combination thereof, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof.

In some embodiments, a pharmaceutical comprises about 0.1% to about 20% by weight of one or more therapeutic compounds, about 25% to about 70% by weight of one or more hard fats comprising glycerolipids, about 25% to about 70% by weight of one or more liquid fats comprising partially hydrolyzed glycerolipids including a mixture of mono-, di- and triglycerides, about 0.1% to about 10% by weight of one or more bile acids, about 10% to about 25% by weight of one or more free $C_{14-24}$ fatty acids, and about 0.1% to about 5% by weight of one or more free $C_{14-24}$ fatty acid surfactants. In some embodiments, a pharmaceutical comprises about 25 mg/mL to about 600 mg/mL of one or more therapeutic compounds, about 25% to about 70% by weight of one or more hard fats comprising glycerolipids, about 25% to about 70% by weight of one or more liquid fats comprising partially hydrolyzed glycerolipids including a mixture of mono-, di- and triglycerides, about 0.1% to about 10% by weight of one or more bile acids, about 10% to about 25% by weight of one or more free $C_{14-24}$ fatty acids, and about 0.1% to about 5% by weight of one or more free $C_{14-24}$ fatty acid surfactants. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof. In some embodiments, the one or more bile acids in the above embodiments comprises cholic acid. In some embodiments, the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more bile acids in the above embodiments comprises cholic acid. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more bile acids in the above embodiments comprises cholic acid and the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more bile acids in the above embodiments comprises cholic acid and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more free $C_{14-24}$ fatty acids in the above embodiments comprises one or more free $C_{14-18}$ fatty acids, preferably oleic acid, steric acid, linoleic acid, or any combination thereof, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof, the one or more bile acids in the above embodiments comprises cholic acid, and the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof, the one or more bile acids in the above embodiments comprises cholic acid, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof, the one or more free $C_{14-24}$ fatty acids in the above embodiments comprises one or more free $C_{14-18}$ fatty acids, preferably oleic acid, steric acid, linoleic acid, or any combination thereof, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more bile acids in the above embodiments comprises cholic acid, the one or more free $C_{14-24}$ fatty acids in the above embodiments comprises one or more free $C_{14-18}$ fatty acids, preferably oleic acid, steric acid, linoleic acid, or any combination thereof, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof, the one or more bile acids in the above embodiments comprises cholic acid, the one or more free $C_{14-24}$ fatty acids in the above embodiments comprises one or more free $C_{14-18}$ fatty acids, preferably oleic acid, steric acid, linoleic acid, or any combination thereof, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof.

In some embodiments, a pharmaceutical comprises about 0.1% to about 20% by weight of one or more therapeutic compounds, about 25% to about 70% by weight of one or more hard fats comprising $C_{10}$-$C_{24}$ triglycerides, about 25% to about 70% by weight of one or more liquid fats comprising partially hydrolyzed triglycerides including a mixture of $C_{10}$-$C_{24}$ mono-, $C_{10}$-$C_{24}$ di- and $C_{10}$-$C_{24}$ triglycerides, about 0.1% to about 10% by weight of one or more bile acids, about 10% to about 25% by weight of one or more free $C_{14-24}$ fatty acids, and about 0.1% to about 5% by weight of one or more free $C_{14-24}$ fatty acid surfactants. In some embodiments, a pharmaceutical comprises about 25 mg/mL to about 600 mg/mL of one or more therapeutic compounds, about 25% to about 70% by weight of one or more hard fats comprising $C_{10}$-$C_{24}$ triglycerides, about 25% to about 70% by weight of one or more liquid fats comprising partially hydrolyzed triglycerides including a mixture of $C_{10}$-$C_{24}$ mono-, $C_{10}$-$C_{24}$ di- and $C_{10}$-$C_{24}$ triglycerides, about 0.1% to about 10% by weight of one or more bile acids, and about 10% to about 25% by weight of one or more free $C_{14-24}$ fatty acids, about 0.1% to about 5% by weight of one or more free $C_{14-24}$ fatty acid surfactants. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof. In some embodiments, the one or more bile acids in the above embodiments comprises cholic acid. In some embodiments, the one or more free $C_{14\text{-}24}$ fatty acids in the above embodiments comprises one or more free $C_{14\text{-}18}$ fatty acids, preferably oleic acid, steric acid, linoleic acid, or any combination thereof. In some embodiments, the one or more free $C_{14\text{-}24}$ fatty acid surfactants in the above embodiments comprises one or more free $C_{14\text{-}18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more bile acids in the above embodiments comprises cholic acid. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more free $C_{14\text{-}24}$ fatty acids in the above embodiments comprises one or more free $C_{14\text{-}18}$ fatty acids, preferably oleic acid, steric acid, linoleic acid, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more free $C_{14\text{-}24}$ fatty acid surfactants in the above embodiments comprises one or more free $C_{14\text{-}18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more bile acids in the above embodiments comprises cholic acid and the one or more free $C_{14\text{-}24}$ fatty acids in the above embodiments comprises one or more free $C_{14\text{-}18}$ fatty acids, preferably oleic acid, steric acid, linoleic acid, or any combination thereof. In some embodiments, the one or more bile acids in the above embodiments comprises cholic acid and the one or more free $C_{14\text{-}24}$ fatty acid surfactants in the above embodiments comprises one or more free $C_{14\text{-}18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more free $C_{14\text{-}24}$ fatty acids in the above embodiments comprises one or more free $C_{14\text{-}18}$ fatty acids, preferably oleic acid, steric acid, linoleic acid, or any combination thereof, and the one or more free $C_{14\text{-}24}$ fatty acid surfactants in the above embodiments comprises one or more free $C_{14\text{-}18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof, the one or more bile acids in the above embodiments comprises cholic acid, and the one or more free $C_{14\text{-}24}$ fatty acids in the above embodiments comprises one or more free $C_{14\text{-}18}$ fatty acids, preferably oleic acid, steric acid, linoleic acid, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof, the one or more bile acids in the above embodiments comprises cholic acid, and the one or more free $C_{14\text{-}24}$ fatty acid surfactants in the above embodiments comprises one or more free $C_{14\text{-}18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof, the one or more free $C_{14\text{-}24}$ fatty acids in the above embodiments comprises one or more free $C_{14\text{-}18}$ fatty acids, preferably oleic acid, steric acid, linoleic acid, or any combination thereof, and the one or more free $C_{14\text{-}24}$ fatty acid surfactants in the above embodiments comprises one or more free $C_{14\text{-}18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more bile acids in the above embodiments comprises cholic acid, the one or more free $C_{14\text{-}24}$ fatty acids in the above embodiments comprises one or more free $C_{14\text{-}18}$ fatty acids, preferably oleic acid, steric acid, linoleic acid, or any combination thereof, and the one or more free $C_{14\text{-}24}$ fatty acid surfactants in the above embodiments comprises one or more free $C_{14\text{-}18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof, the one or more bile acids in the above embodiments comprises cholic acid, the one or more free $C_{14\text{-}24}$ fatty acids in the above embodiments comprises one or more free $C_{14\text{-}18}$ fatty acids, preferably oleic acid, steric acid, linoleic acid, or any combination thereof, and the one or more free $C_{14\text{-}24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof.

In some embodiments, a pharmaceutical comprises about 0.1% to about 20% by weight of one or more therapeutic compounds, about 25% to about 70% by weight of one or more hard fats comprising a mixture of saturated $C_{10}$-$C_{18}$ triglycerides and/or saturated $C_{12}$-$C_{18}$ triglycerides, about 25% to about 70% by weight of one or more liquid fats comprising partially hydrolyzed triglycerides including a mixture of $C_{18}$-$C_{18}$ mono-, $C_{16}$-$C_{18}$ di- and $C_{16}$-$C_{18}$ triglycerides, about 0.1% to about 10% by weight of one or more bile acids, about 10% to about 25% by weight of one or more free $C_{14-24}$ fatty acids, and about 0.1% to about 5% by weight of one or more free $C_{14-24}$ fatty acid surfactants. In some embodiments, a pharmaceutical comprises about 25 mg/mL to about 600 mg/mL of one or more therapeutic compounds, about 25% to about 70% by weight of one or more hard fats comprising a mixture of saturated $C_{10}$-$C_{18}$ triglycerides and/or saturated $C_{12}$-$C_{18}$ triglycerides, about 25% to about 70% by weight of one or more liquid fats comprising partially hydrolyzed triglycerides including a mixture of $C_{16}$-$C_{18}$ mono-, $C_{16}$-$C_{18}$ di- and $C_{16}$-$C_{18}$ triglycerides, about 0.1% to about 10% by weight of one or more bile acids, about 10% to about 25% by weight of one or more free $C_{14-24}$ fatty acids, and about 0.1% to about 5% by weight of one or more free $C_{14-24}$ fatty acid surfactants. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof. In some embodiments, the one or more bile acids in the above embodiments comprises cholic acid. In some embodiments, the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more bile acids in the above embodiments comprises cholic acid. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more bile acids in the above embodiments comprises cholic acid and the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more bile acids in the above embodiments comprises cholic acid and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more free $C_{14-24}$ fatty acids in the above embodiments comprises one or more free $C_{14-18}$ fatty acids, preferably oleic acid, steric acid, linoleic acid, or any combination thereof, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof, the one or more bile acids in the above embodiments comprises cholic acid, and the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof, the one or more bile acids in the above embodiments comprises cholic acid, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof, the one or more free $C_{14-24}$ fatty acids in the above embodiments comprises one or more free $C_{14-18}$ fatty acids, preferably oleic acid, steric acid, linoleic acid, or any combination thereof, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more bile acids in the above embodiments comprises cholic acid, the one or more free $C_{14-24}$ fatty acids in the above embodiments comprises one or more free $C_{14-18}$ fatty acids, preferably oleic acid, steric acid, linoleic acid, or any combination thereof, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof, the one or more bile acids in the above embodiments comprises cholic acid, the one or more free $C_{14-24}$ fatty acids in the above embodiments comprises one or more free $C_{14-18}$ fatty acids, preferably oleic acid, steric acid, linoleic acid, or any combination thereof, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof.

In some embodiments, a pharmaceutical comprises about 0.1% to about 20% by weight of one or more therapeutic compounds, about 35% to about 55% by weight of one or more hard fats, about 25% to about 50% by weight of one or more liquid fats, about 0.1% to about 10% by weight of one or more bile acids, about 1% to about 30% by weight of one or more free $C_{14-24}$ fatty acids, and about 0.1% to about 5% by weight of one or more free $C_{14-24}$ fatty acid surfactants. In some embodiments, a pharmaceutical comprises about 25 mg/mL to about 600 mg/mL of one or more therapeutic compounds, about 35% to about 55% by weight of one or more hard fats, about 25% to about 50% by weight of one or more liquid fats, about 0.1% to about 10% by weight of one or more bile acids, about 1% to about 30% by weight of one or more free $C_{14-24}$ fatty acids, and about 0.1% to about 5% by weight of one or more free $C_{14-24}$ fatty acid surfactants. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof. In some embodiments, the one or more bile acids in the above embodiments comprises cholic acid. In some embodiments, the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more bile acids in the above embodiments comprises cholic acid. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more bile acids in the above embodiments comprises cholic acid and the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more bile acids in the above embodiments comprises cholic acid and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more free $C_{14-24}$ fatty acids in the above embodiments comprises one or more free $C_{14-18}$ fatty acids, preferably oleic acid, steric acid, linoleic acid, or any combination thereof, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof, the one or more bile acids in the above embodiments comprises cholic acid, and the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof, the one or more bile acids in the above embodiments comprises cholic acid, and the one or more free $C_{14\text{-}24}$ fatty acid surfactants in the above embodiments comprises one or more free $C_{14\text{-}18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof, the one or more free $C_{14\text{-}24}$ fatty acids in the above embodiments comprises one or more free $C_{14\text{-}18}$ fatty acids, preferably oleic acid, steric acid, linoleic acid, or any combination thereof, and the one or more free $C_{14\text{-}24}$ fatty acid surfactants in the above embodiments comprises one or more free $C_{14\text{-}18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more bile acids in the above embodiments comprises cholic acid, the one or more free $C_{14\text{-}24}$ fatty acids in the above embodiments comprises one or more free $C_{14\text{-}18}$ fatty acids, preferably oleic acid, steric acid, linoleic acid, or any combination thereof, and the one or more free $C_{14\text{-}24}$ fatty acid surfactants in the above embodiments comprises one or more free $C_{14\text{-}18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof, the one or more bile acids in the above embodiments comprises cholic acid, the one or more free $C_{14\text{-}24}$ fatty acids in the above embodiments comprises one or more free $C_{14\text{-}18}$ fatty acids, preferably oleic acid, steric acid, linoleic acid, or any combination thereof, and the one or more free $C_{14\text{-}24}$ fatty acid surfactants in the above embodiments comprises one or more free $C_{14\text{-}18}$ fatty acid surfactants, preferably an oleate alkali metal or alkali earth metal salt, a stearate alkali metal or alkali earth metal salt, a linoleate alkali metal or alkali earth metal salt, or any combination thereof.

In some embodiments, a pharmaceutical comprises about 0.1% to about 20% by weight of one or more therapeutic compounds, about 35% to about 55% by weight of one or more hard fats comprising glycerolipids, about 25% to about 50% by weight of one or more liquid fats comprising partially hydrolyzed glycerolipids including a mixture of mono-, di- and triglycerides, about 0.1% to about 10% by weight of one or more bile acids, about 1% to about 30% by weight of one or more free $C_{14\text{-}24}$ fatty acids, and about 0.1% to about 5% by weight of one or more free $C_{14\text{-}24}$ fatty acid surfactants. In some embodiments, a pharmaceutical comprises about 25 mg/mL to about 600 mg/mL of one or more therapeutic compounds, about 35% to about 55% by weight of one or more hard fats comprising glycerolipids, about 25% to about 50% by weight of one or more liquid fats comprising partially hydrolyzed glycerolipids including a mixture of mono-, di- and triglycerides, about 0.1% to about 10% by weight of one or more bile acids, about 1% to about 30% by weight of one or more free $C_{14\text{-}24}$ fatty acids, and about 0.1% to about 5% by weight of one or more free $C_{14\text{-}24}$ fatty acid surfactants. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof. In some embodiments, the one or more bile acids in the above embodiments comprises cholic acid. In some embodiments, the one or more free $C_{14\text{-}24}$ fatty acids in the above embodiments comprises one or more free $C_{14\text{-}18}$ fatty acids, preferably oleic acid, steric acid, linoleic acid, or any combination thereof. In some embodiments, the one or more free $C_{14\text{-}24}$ fatty acid surfactants in the above embodiments comprises one or more free $C_{14\text{-}18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more bile acids in the above embodiments comprises cholic acid. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more free $C_{14\text{-}24}$ fatty acids in the above embodiments comprises one or more free $C_{14\text{-}18}$ fatty acids, preferably oleic acid, steric acid, linoleic acid, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more free $C_{14\text{-}24}$ fatty acid surfactants in the above embodiments comprises one or more free $C_{14\text{-}18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more bile acids in the above embodiments comprises cholic acid and the one or more free $C_{14\text{-}24}$ fatty acids in the above embodiments comprises one or more free $C_{14\text{-}18}$ fatty acids, preferably oleic acid, steric acid, linoleic acid, or any combination thereof. In some embodiments, the one or more bile acids in the above embodiments comprises cholic acid and the one or more free $C_{14\text{-}24}$ fatty acid surfactants in the above embodiments comprises one or more free $C_{14\text{-}18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more free $C_{14\text{-}24}$ fatty acids in the above embodiments comprises one or more free $C_{14\text{-}18}$ fatty acids, preferably oleic acid, steric acid, linoleic acid, or any combination thereof, and the one or more free $C_{14\text{-}24}$ fatty acid surfactants in the above embodiments comprises one or more free $C_{14\text{-}18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof, the one or more bile acids in the above embodiments comprises cholic acid, and the one or more free $C_{14\text{-}24}$ fatty acids in the above embodiments comprises one or more free $C_{14\text{-}18}$ fatty acids, preferably oleic acid, steric acid, linoleic acid, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof, the one or more bile acids in the above embodiments comprises cholic acid, and the one or more free $C_{14\text{-}24}$ fatty acid surfactants in the above embodiments comprises one or more free $C_{14\text{-}18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof, the one or more free $C_{14\text{-}24}$ fatty acids in the above embodiments comprises one or more free $C_{14\text{-}18}$ fatty acids, preferably oleic acid, steric acid, linoleic acid, or any combination thereof, and the one or more free $C_{14\text{-}24}$ fatty acid surfactants in the above embodiments comprises one or more free $C_{14\text{-}18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more bile acids in the above embodiments comprises cholic acid, the one or more free $C_{14\text{-}24}$ fatty acids in the above embodiments comprises one or more free $C_{14\text{-}18}$ fatty acids, preferably oleic acid, steric acid, linoleic acid, or any combination thereof, and the one or more free $C_{14\text{-}24}$ fatty acid surfactants in the above embodiments comprises one or more free $C_{14\text{-}18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof, the one or more bile acids in the above embodiments comprises cholic acid, the one or more free $C_{14\text{-}24}$ fatty acids in the above embodiments comprises one or more free $C_{14\text{-}18}$ fatty acids, preferably oleic acid, steric acid, linoleic acid, or any combination thereof, and the one or more free $C_{14\text{-}24}$ fatty acid surfactants in the above embodiments comprises one or more free $C_{14\text{-}18}$ fatty acid surfactants, preferably an oleate alkali metal or alkali earth metal salt, a stearate alkali metal or alkali earth metal salt, a linoleate alkali metal or alkali earth metal salt, or any combination thereof.

In some embodiments, a pharmaceutical comprises about 0.1% to about 20% by weight of one or more therapeutic compounds, about 35% to about 55% by weight of one or more hard fats comprising $C_{10}$-$C_{24}$ triglycerides, about 25% to about 50% by weight of one or more liquid fats comprising partially hydrolyzed triglycerides including a mixture of $C_{10}$-$C_{24}$ mono-, $C_{10}$-$C_{24}$ di- and $C_{10}$-$C_{24}$ triglycerides, about 0.1% to about 10% by weight of one or more bile acids, about 1% to about 30% by weight of one or more free $C_{14\text{-}24}$ fatty acids, and about 0.1% to about 5% by weight of one or more free $C_{14\text{-}24}$ fatty acid surfactants. In some embodiments, a pharmaceutical comprises about 25 mg/mL to about 600 mg/mL of one or more therapeutic compounds, about 35% to about 55% by weight of one or more hard fats comprising $C_{10}$-$C_{24}$ triglycerides, about 25% to about 50% by weight of one or more liquid fats comprising partially hydrolyzed triglycerides including a mixture of $C_{10}$-$C_{24}$ mono-, $C_{10}$-$C_{24}$ di- and $C_{10}$-$C_{24}$ triglycerides, about 0.1% to about 10% by weight of one or more bile acids, and about 1% to about 30% by weight of one or more free $C_{14\text{-}24}$ fatty acids, about 0.1% to about 5% by weight of one or more free $C_{14\text{-}24}$ fatty acid surfactants. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof. In some embodiments, the one or more bile acids in the above embodiments comprises cholic acid. In some embodiments, the one or more free $C_{14\text{-}24}$ fatty acids in the above embodiments comprises one or more free $C_{14\text{-}18}$ fatty acids, preferably oleic acid, steric acid, linoleic acid, or any combination thereof. In some embodiments, the one or more free $C_{14\text{-}24}$ fatty acid surfactants in the above embodiments comprises one or more free $C_{14\text{-}18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more bile acids in the above embodiments comprises cholic acid. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more bile acids in the above embodiments comprises cholic acid and the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more bile acids in the above embodiments comprises cholic acid and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more free $C_{14-24}$ fatty acids in the above embodiments comprises one or more free $C_{14-18}$ fatty acids, preferably oleic acid, steric acid, linoleic acid, or any combination thereof, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof, the one or more bile acids in the above embodiments comprises cholic acid, and the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof, the one or more bile acids in the above embodiments comprises cholic acid, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof, the one or more free $C_{14-24}$ fatty acids in the above embodiments comprises one or more free $C_{14-18}$ fatty acids, preferably oleic acid, steric acid, linoleic acid, or any combination thereof, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more bile acids in the above embodiments comprises cholic acid, the one or more free $C_{14-24}$ fatty acids in the above embodiments comprises one or more free $C_{14-18}$ fatty acids, preferably oleic acid, steric acid, linoleic acid, or any combination thereof, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof, the one or more bile acids in the above embodiments comprises cholic acid, the one or more free $C_{14-24}$ fatty acids in the above embodiments comprises one or more free $C_{14-18}$ fatty acids, preferably oleic acid, steric acid, linoleic acid, or any combination thereof, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof.

In some embodiments, a pharmaceutical comprises about 0.1% to about 20% by weight of one or more therapeutic compounds, about 35% to about 55% by weight of one or more hard fats comprising a mixture of saturated $C_{10}$-$C_{18}$ triglycerides and/or saturated $C_{12}$-$C_{18}$ triglycerides, about 25% to about 50% by weight of one or more liquid fats comprising partially hydrolyzed triglycerides including a mixture of $C_{18}$-$C_{18}$ mono-, $C_{16}$-$C_{18}$ di- and $C_{16}$-$C_{18}$ triglycerides, about 0.1% to about 10% by weight of one or more bile acids, about 1% to about 30% by weight of one or more free $C_{14-24}$ fatty acids, and about 0.1% to about 5% by weight of one or more free $C_{14-24}$ fatty acid surfactants. In some embodiments, a pharmaceutical comprises about 25 mg/mL to about 600 mg/mL of one or more therapeutic compounds, about 35% to about 55% by weight of one or more hard fats comprising a mixture of saturated $C_{10}$-$C_{18}$ triglycerides and/or saturated $C_{12}$-$C_{18}$ triglycerides, about 25% to about 50% by weight of one or more liquid fats comprising partially hydrolyzed triglycerides including a mixture of $C_{16}$-$C_{18}$ mono-, $C_{16}$-$C_{18}$ di- and $C_{16}$-$C_{18}$ triglycerides, about 0.1% to about 10% by weight of one or more bile acids, about 1% to about 30% by weight of one or more free $C_{14-24}$ fatty acids, and about 0.1% to about 5% by weight of one or more free $C_{14-24}$ fatty acid surfactants. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof. In some embodiments, the one or more bile acids in the above embodiments comprises cholic acid. In some embodiments, the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more bile acids in the above embodiments comprises cholic acid. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more bile acids in the above embodiments comprises cholic acid and the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more bile acids in the above embodiments comprises cholic acid and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more free $C_{14-24}$ fatty acids in the above embodiments comprises one or more free $C_{14-18}$ fatty acids, preferably oleic acid, steric acid, linoleic acid, or any combination thereof, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof, the one or more bile acids in the above embodiments comprises cholic acid, and the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof, the one or more bile acids in the above embodiments comprises cholic acid, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof, the one or more free $C_{14-24}$ fatty acids in the above embodiments comprises one or more free $C_{14-18}$ fatty acids, preferably oleic acid, steric acid, linoleic acid, or any combination thereof, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more bile acids in the above embodiments comprises cholic acid, the one or more free $C_{14-24}$ fatty acids in the above embodiments comprises one or more free $C_{14-18}$ fatty acids, preferably oleic acid, steric acid, linoleic acid, or any combination thereof, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof, the one or more bile acids in the above embodiments comprises cholic acid, the one or more free $C_{14-24}$ fatty acids in the above embodiments comprises one or more free $C_{14-18}$ fatty acids, preferably oleic acid, steric acid, linoleic acid, or any combination thereof, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof.

In some embodiments, a pharmaceutical comprises about 0.1% to about 30% by weight of one or more therapeutic compounds, about 15% to about 65% by weight of one or more hard fats, about 15% to about 50% by weight of one or more liquid fats, about 0.1% to about 10% by weight of one or more bile acids, about 1% to about 25% by weight of one or more free $C_{14-24}$ fatty acids, and about 0.1% to about 5% by weight of one or more free $C_{14-24}$ fatty acid surfactants. In some embodiments, a pharmaceutical comprises about 25 mg/mL to about 600 mg/mL of one or more therapeutic compounds, about 15% to about 65% by weight of one or more hard fats, about 15% to about 50% by weight of one or more liquid fats, about 0.1% to about 10% by weight of one or more bile acids, about 1% to about 25% by weight of one or more free $C_{14-24}$ fatty acids, and about 0.1% to about 5% by weight of one or more free $C_{14-24}$ fatty acid surfactants. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof. In some embodiments, the one or more bile acids in the above embodiments comprises cholic acid. In some embodiments, the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more bile acids in the above embodiments comprises cholic acid. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more bile acids in the above embodiments comprises cholic acid and the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more bile acids in the above embodiments comprises cholic acid and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more free $C_{14-24}$ fatty acids in the above embodiments comprises one or more free $C_{14-18}$ fatty acids, preferably oleic acid, steric acid, linoleic acid, or any combination thereof, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof, the one or more bile acids in the above embodiments comprises cholic acid, and the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof, the one or more bile acids in the above embodiments comprises cholic acid, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof, the one or more free $C_{14-24}$ fatty acids in the above embodiments comprises one or more free $C_{14-18}$ fatty acids, preferably oleic acid, steric acid, linoleic acid, or any combination thereof, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more bile acids in the above embodiments comprises cholic acid, the one or more free $C_{14-24}$ fatty acids in the above embodiments comprises one or more free $C_{14-18}$ fatty acids, preferably oleic acid, steric acid, linoleic acid, or any combination thereof, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof, the one or more bile acids in the above embodiments comprises cholic acid, the one or more free $C_{14-24}$ fatty acids in the above embodiments comprises one or more free $C_{14-18}$ fatty acids, preferably oleic acid, steric acid, linoleic acid, or any combination thereof, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof.

In some embodiments, a pharmaceutical comprises about 0.1% to about 30% by weight of one or more therapeutic compounds, about 15% to about 65% by weight of one or more hard fats comprising glycerolipids, about 15% to about 50% by weight of one or more liquid fats comprising partially hydrolyzed glycerolipids including a mixture of mono-, di- and triglycerides, about 0.1% to about 10% by weight of one or more bile acids, about 1% to about 25% by weight of one or more free $C_{14-24}$ fatty acids, and about 0.1% to about 5% by weight of one or more free $C_{14-24}$ fatty acid surfactants. In some embodiments, a pharmaceutical comprises about 25 mg/mL to about 600 mg/mL of one or more therapeutic compounds, about 15% to about 65% by weight of one or more hard fats comprising glycerolipids, about 15% to about 50% by weight of one or more liquid fats comprising partially hydrolyzed glycerolipids including a mixture of mono-, di- and triglycerides, about 0.1% to about 10% by weight of one or more bile acids, about 1% to about 25% by weight of one or more free $C_{14-24}$ fatty acids, and about 0.1% to about 5% by weight of one or more free $C_{14-24}$ fatty acid surfactants. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof. In some embodiments, the one or more bile acids in the above embodiments comprises cholic acid. In some embodiments, the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more bile acids in the above embodiments comprises cholic acid. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more bile acids in the above embodiments comprises cholic acid and the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more bile acids in the above embodiments comprises cholic acid and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more free $C_{14-24}$ fatty acids in the above embodiments comprises one or more free $C_{14-18}$ fatty acids, preferably oleic acid, steric acid, linoleic acid, or any combination thereof, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof, the one or more bile acids in the above embodiments comprises cholic acid, and the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof, the one or more bile acids in the above embodiments comprises cholic acid, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof, the one or more free $C_{14-24}$ fatty acids in the above embodiments comprises one or more free $C_{14-18}$ fatty acids, preferably oleic acid, steric acid, linoleic acid, or any combination thereof, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more bile acids in the above embodiments comprises cholic acid, the one or more free $C_{14-24}$ fatty acids in the above embodiments comprises one or more free $C_{14-18}$ fatty acids, preferably oleic acid, steric acid, linoleic acid, or any combination thereof, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof, the one or more bile acids in the above embodiments comprises cholic acid, the one or more free $C_{14-24}$ fatty acids in the above embodiments comprises one or more free $C_{14-18}$ fatty acids, preferably oleic acid, steric acid, linoleic acid, or any combination thereof, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof.

In some embodiments, a pharmaceutical comprises about 0.1% to about 30% by weight of one or more therapeutic compounds, about 15% to about 65% by weight of one or more hard fats comprising $C_{10}$-$C_{24}$ triglycerides, about 15% to about 50% by weight of one or more liquid fats comprising partially hydrolyzed triglycerides including a mixture of $C_{10}$-$C_{24}$ mono-, $C_{10}$-$C_{24}$ di- and $C_{10}$-$C_{24}$ triglycerides, about 0.1% to about 10% by weight of one or more bile acids, about 1% to about 25% by weight of one or more free $C_{14-24}$ fatty acids, and about 0.1% to about 5% by weight of one or more free $C_{14-24}$ fatty acid surfactants. In some embodiments, a pharmaceutical comprises about 25 mg/mL to about 600 mg/mL of one or more therapeutic compounds, about 15% to about 65% by weight of one or more hard fats comprising $C_{10}$-$C_{24}$ triglycerides, about 15% to about 50% by weight of one or more liquid fats comprising partially hydrolyzed triglycerides including a mixture of $C_{10}$-$C_{24}$ mono-, $C_{10}$-$C_{24}$ di- and $C_{10}$-$C_{24}$ triglycerides, about 0.1% to about 10% by weight of one or more bile acids, and about 1% to about 25% by weight of one or more free $C_{14-24}$ fatty acids, about 0.1% to about 5% by weight of one or more free $C_{14-24}$ fatty acid surfactants. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof. In some embodiments, the one or more bile acids in the above embodiments comprises cholic acid. In some embodiments, the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more bile acids in the above embodiments comprises cholic acid. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more bile acids in the above embodiments comprises cholic acid and the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more bile acids in the above embodiments comprises cholic acid and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more free $C_{14-24}$ fatty acids in the above embodiments comprises one or more free $C_{14-18}$ fatty acids, preferably oleic acid, steric acid, linoleic acid, or any combination thereof, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof, the one or more bile acids in the above embodiments comprises cholic acid, and the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof, the one or more bile acids in the above embodiments comprises cholic acid, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof, the one or more free $C_{14-24}$ fatty acids in the above embodiments comprises one or more free $C_{14-18}$ fatty acids, preferably oleic acid, steric acid, linoleic acid, or any combination thereof, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more bile acids in the above embodiments comprises cholic acid, the one or more free $C_{14-24}$ fatty acids in the above embodiments comprises one or more free $C_{14-18}$ fatty acids, preferably oleic acid, steric acid, linoleic acid, or any combination thereof, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof, the one or more bile acids in the above embodiments comprises cholic acid, the one or more free $C_{14-24}$ fatty acids in the above embodiments comprises one or more free $C_{14-18}$ fatty acids, preferably oleic acid, steric acid, linoleic acid, or any combination thereof, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof.

In some embodiments, a pharmaceutical comprises about 0.1% to about 30% by weight of one or more therapeutic compounds, about 15% to about 65% by weight of one or more hard fats comprising a mixture of saturated $C_{10}$-$C_{18}$ triglycerides and/or saturated $C_{12}$-$C_{18}$ triglycerides, about 15% to about 50% by weight of one or more liquid fats comprising partially hydrolyzed triglycerides including a mixture of $C_{18}$-$C_{18}$ mono-, $C_{16}$-$C_{18}$ di- and $C_{16}$-$C_{18}$ triglycerides, about 0.1% to about 10% by weight of one or more bile acids, about 1% to about 25% by weight of one or more free $C_{14-24}$ fatty acids, and about 0.1% to about 5% by weight of one or more free $C_{14-24}$ fatty acid surfactants. In some embodiments, a pharmaceutical comprises about 25 mg/mL to about 600 mg/mL of one or more therapeutic compounds, about 15% to about 65% by weight of one or more hard fats comprising a mixture of saturated $C_{10}$-$C_{18}$ triglycerides and/or saturated $C_{12}$-$C_{18}$ triglycerides, about 15% to about 50% by weight of one or more liquid fats comprising partially hydrolyzed triglycerides including a mixture of $C_{16}$-$C_{18}$ mono-, $C_{16}$-$C_{18}$ di- and $C_{16}$-$C_{18}$ triglycerides, about 0.1% to about 10% by weight of one or more bile acids, about 1% to about 25% by weight of one or more free $C_{14-24}$ fatty acids, and about 0.1% to about 5% by weight of one or more free $C_{14-24}$ fatty acid surfactants. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof. In some embodiments, the one or more bile acids in the above embodiments comprises cholic acid. In some embodiments, the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more bile acids in the above embodiments comprises cholic acid. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more bile acids in the above embodiments comprises cholic acid and the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more bile acids in the above embodiments comprises cholic acid and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more free $C_{14-24}$ fatty acids in the above embodiments comprises one or more free $C_{14-18}$ fatty acids, preferably oleic acid, steric acid, linoleic acid, or any combination thereof, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof, the one or more bile acids in the above embodiments comprises cholic acid, and the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound comprising an organic acid functional group, a therapeutic compound comprising an organic base functional group, or any combination thereof, the one or more bile acids in the above embodiments comprises cholic acid, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof, the one or more free $C_{14-24}$ fatty acids in the above embodiments comprises one or more free $C_{14-18}$ fatty acids, preferably oleic acid, steric acid, linoleic acid, or any combination thereof, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more bile acids in the above embodiments comprises cholic acid, the one or more free $C_{14-24}$ fatty acids in the above embodiments comprises one or more free $C_{14-18}$ fatty acids, preferably oleic acid, steric acid, linoleic acid, or any combination thereof, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof, the one or more bile acids in the above embodiments comprises cholic acid, the one or more free $C_{14-24}$ fatty acids in the above embodiments comprises one or more free $C_{14-18}$ fatty acids, preferably oleic acid, steric acid, linoleic acid, or any combination thereof, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof.

In some embodiments, a pharmaceutical comprises about 0.1% to about 30% by weight of one or more therapeutic compounds, about 20% to about 55% by weight of one or more hard fats, about 15% to about 45% by weight of one or more liquid fats, about 0.1% to about 10% by weight of one or more bile acids, about 10% to about 45% by weight of one or more free $C_{14-24}$ fatty acids, and about 0.1% to about 5% by weight of one or more free $C_{14-24}$ fatty acid surfactants. In some embodiments, a pharmaceutical comprises about 25 mg/mL to about 600 mg/mL of one or more therapeutic compounds, about 20% to about 55% by weight of one or more hard fats, about 15% to about 45% by weight of one or more liquid fats, about 0.1% to about 10% by weight of one or more bile acids, about 10% to about 45% by weight of one or more free $C_{14-24}$ fatty acids, and about 0.1% to about 5% by weight of one or more free $C_{14-24}$ fatty acid surfactants. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof. In some embodiments, the one or more bile acids in the above embodiments comprises cholic acid. In some embodiments, the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more bile acids in the above embodiments comprises cholic acid. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more bile acids in the above embodiments comprises cholic acid and the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more bile acids in the above embodiments comprises cholic acid and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more free $C_{14-24}$ fatty acids in the above embodiments comprises one or more free $C_{14-18}$ fatty acids, preferably oleic acid, steric acid, linoleic acid, or any combination thereof, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof, the one or more bile acids in the above embodiments comprises cholic acid, and the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof, the one or more bile acids in the above embodiments comprises cholic acid, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof, the one or more free $C_{14-24}$ fatty acids in the above embodiments comprises one or more free $C_{14-18}$ fatty acids, preferably oleic acid, steric acid, linoleic acid, or any combination thereof, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more bile acids in the above embodiments comprises cholic acid, the one or more free $C_{14-24}$ fatty acids in the above embodiments comprises one or more free $C_{14-18}$ fatty acids, preferably oleic acid, steric acid, linoleic acid, or any combination thereof, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof, the one or more bile acids in the above embodiments comprises cholic acid, the one or more free $C_{14-24}$ fatty acids in the above embodiments comprises one or more free $C_{14-18}$ fatty acids, preferably oleic acid, steric acid, linoleic acid, or any combination thereof, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof.

In some embodiments, a pharmaceutical comprises about 0.1% to about 30% by weight of one or more therapeutic compounds, about 20% to about 55% by weight of one or more hard fats comprising glycerolipids, about 15% to about 45% by weight of one or more liquid fats comprising partially hydrolyzed glycerolipids including a mixture of mono-, di- and triglycerides, about 0.1% to about 10% by weight of one or more bile acids, about 10% to about 45% by weight of one or more free $C_{14-24}$ fatty acids, and about 0.1% to about 5% by weight of one or more free $C_{14-24}$ fatty acid surfactants. In some embodiments, a pharmaceutical comprises about 25 mg/mL to about 600 mg/mL of one or more therapeutic compounds, about 20% to about 55% by weight of one or more hard fats comprising glycerolipids, about 15% to about 45% by weight of one or more liquid fats comprising partially hydrolyzed glycerolipids including a mixture of mono-, di- and triglycerides, about 0.1% to about 10% by weight of one or more bile acids, about 10% to about 45% by weight of one or more free $C_{14-24}$ fatty acids, and about 0.1% to about 5% by weight of one or more free $C_{14-24}$ fatty acid surfactants. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof. In some embodiments, the one or more bile acids in the above embodiments comprises cholic acid. In some embodiments, the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more bile acids in the above embodiments comprises cholic acid. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more bile acids in the above embodiments comprises cholic acid and the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more bile acids in the above embodiments comprises cholic acid and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more free $C_{14-24}$ fatty acids in the above embodiments comprises one or more free $C_{14-18}$ fatty acids, preferably oleic acid, steric acid, linoleic acid, or any combination thereof, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof, the one or more bile acids in the above embodiments comprises cholic acid, and the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof, the one or more bile acids in the above embodiments comprises cholic acid, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof, the one or more free $C_{14\text{-}24}$ fatty acids in the above embodiments comprises one or more free $C_{14\text{-}18}$ fatty acids, preferably oleic acid, steric acid, linoleic acid, or any combination thereof, and the one or more free $C_{14\text{-}24}$ fatty acid surfactants in the above embodiments comprises one or more free $C_{14\text{-}18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more bile acids in the above embodiments comprises cholic acid, the one or more free $C_{14\text{-}24}$ fatty acids in the above embodiments comprises one or more free $C_{14\text{-}18}$ fatty acids, preferably oleic acid, steric acid, linoleic acid, or any combination thereof, and the one or more free $C_{14\text{-}24}$ fatty acid surfactants in the above embodiments comprises one or more free $C_{14\text{-}18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof, the one or more bile acids in the above embodiments comprises cholic acid, the one or more free $C_{14\text{-}24}$ fatty acids in the above embodiments comprises one or more free $C_{14\text{-}18}$ fatty acids, preferably oleic acid, steric acid, linoleic acid, or any combination thereof, and the one or more free $C_{14\text{-}24}$ fatty acid surfactants in the above embodiments comprises one or more free $C_{14\text{-}18}$ fatty acid surfactants, preferably an oleate alkali metal or alkali earth metal salt, a stearate alkali metal or alkali earth metal salt, a linoleate alkali metal or alkali earth metal salt, or any combination thereof.

In some embodiments, a pharmaceutical comprises about 0.1% to about 30% by weight of one or more therapeutic compounds, about 20% to about 55% by weight of one or more hard fats comprising $C_{10}$-$C_{24}$ triglycerides, about 15% to about 45% by weight of one or more liquid fats comprising partially hydrolyzed triglycerides including a mixture of $C_{10}$-$C_{24}$ mono-, $C_{10}$-$C_{24}$ di- and $C_{10}$-$C_{24}$ triglycerides, about 0.1% to about 10% by weight of one or more bile acids, about 10% to about 45% by weight of one or more free $C_{14\text{-}24}$ fatty acids, and about 0.1% to about 5% by weight of one or more free $C_{14\text{-}24}$ fatty acid surfactants. In some embodiments, a pharmaceutical comprises about 25 mg/mL to about 600 mg/mL of one or more therapeutic compounds, about 20% to about 55% by weight of one or more hard fats comprising $C_{10}$-$C_{24}$ triglycerides, about 15% to about 45% by weight of one or more liquid fats comprising partially hydrolyzed triglycerides including a mixture of $C_{10}$-$C_{24}$ mono-, $C_{10}$-$C_{24}$ di- and $C_{10}$-$C_{24}$ triglycerides, about 0.1% to about 10% by weight of one or more bile acids, and about 10% to about 45% by weight of one or more free $C_{14\text{-}24}$ fatty acids, about 0.1% to about 5% by weight of one or more free $C_{14\text{-}24}$ fatty acid surfactants. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof. In some embodiments, the one or more bile acids in the above embodiments comprises cholic acid. In some embodiments, the one or more free $C_{14\text{-}24}$ fatty acids in the above embodiments comprises one or more free $C_{14\text{-}18}$ fatty acids, preferably oleic acid, steric acid, linoleic acid, or any combination thereof. In some embodiments, the one or more free $C_{14\text{-}24}$ fatty acid surfactants in the above embodiments comprises one or more free $C_{14\text{-}18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more bile acids in the above embodiments comprises cholic acid. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more free $C_{14\text{-}24}$ fatty acids in the above embodiments comprises one or more free $C_{14\text{-}18}$ fatty acids, preferably oleic acid, steric acid, linoleic acid, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more free $C_{14\text{-}24}$ fatty acid surfactants in the above embodiments comprises one or more free $C_{14\text{-}18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more bile acids in the above embodiments comprises cholic acid and the one or more free $C_{14\text{-}24}$ fatty acids in the above embodiments comprises one or more free $C_{14\text{-}18}$ fatty acids, preferably oleic acid, steric acid, linoleic acid, or any combination thereof. In some embodiments, the one or more bile acids in the above embodiments comprises cholic acid and the one or more free $C_{14\text{-}24}$ fatty acid surfactants in the above embodiments comprises one or more free $C_{14\text{-}18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more free $C_{14\text{-}24}$ fatty acids in the above embodiments comprises one or more free $C_{14\text{-}18}$ fatty acids, preferably oleic acid, steric acid, linoleic acid, or any combination thereof, and the one or more free $C_{14\text{-}24}$ fatty acid surfactants in the above embodiments comprises one or more free $C_{14\text{-}18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof, the one or more bile acids in the above embodiments comprises cholic acid, and the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof, the one or more bile acids in the above embodiments comprises cholic acid, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof, the one or more free $C_{14-24}$ fatty acids in the above embodiments comprises one or more free $C_{14-18}$ fatty acids, preferably oleic acid, steric acid, linoleic acid, or any combination thereof, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more bile acids in the above embodiments comprises cholic acid, the one or more free $C_{14-24}$ fatty acids in the above embodiments comprises one or more free $C_{14-18}$ fatty acids, preferably oleic acid, steric acid, linoleic acid, or any combination thereof, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof, the one or more bile acids in the above embodiments comprises cholic acid, the one or more free $C_{14-24}$ fatty acids in the above embodiments comprises one or more free $C_{14-18}$ fatty acids, preferably oleic acid, steric acid, linoleic acid, or any combination thereof, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof.

In some embodiments, a pharmaceutical comprises about 0.1% to about 30% by weight of one or more therapeutic compounds, about 20% to about 55% by weight of one or more hard fats comprising a mixture of saturated $C_{10}$-$C_{18}$ triglycerides and/or saturated $C_{12}$-$C_{18}$ triglycerides, about 15% to about 45% by weight of one or more liquid fats comprising partially hydrolyzed triglycerides including a mixture of $C_{18}$-$C_{18}$ mono-, $C_{16}$-$C_{18}$ di- and $C_{16}$-$C_{18}$ triglycerides, about 0.1% to about 10% by weight of one or more bile acids, about 10% to about 45% by weight of one or more free $C_{14-24}$ fatty acids, and about 0.1% to about 5% by weight of one or more free $C_{14-24}$ fatty acid surfactants. In some embodiments, a pharmaceutical comprises about 25 mg/mL to about 600 mg/mL of one or more therapeutic compounds, about 20% to about 55% by weight of one or more hard fats comprising a mixture of saturated $C_{10}$-$C_{18}$ triglycerides and/or saturated $C_{12}$-$C_{18}$ triglycerides, about 15% to about 45% by weight of one or more liquid fats comprising partially hydrolyzed triglycerides including a mixture of $C_{16}$-$C_{18}$ mono-, $C_{16}$-$C_{18}$ di- and $C_{16}$-$C_{18}$ triglycerides, about 0.1% to about 10% by weight of one or more bile acids, about 10% to about 45% by weight of one or more free $C_{14-24}$ fatty acids, and about 0.1% to about 5% by weight of one or more free $C_{14-24}$ fatty acid surfactants. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof. In some embodiments, the one or more bile acids in the above embodiments comprises cholic acid. In some embodiments, the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more bile acids in the above embodiments comprises cholic acid. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more bile acids in the above embodiments comprises cholic acid and the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more bile acids in the above embodiments comprises cholic acid and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more free $C_{14-24}$ fatty acids in the above embodiments comprises one or more free $C_{14-18}$ fatty acids, preferably oleic acid, steric acid, linoleic acid, or any combination thereof, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof, the one or more bile acids in the above embodiments comprises cholic acid, and the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof, the one or more bile acids in the above embodiments comprises cholic acid, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof, the one or more free $C_{14-24}$ fatty acids in the above embodiments comprises one or more free $C_{14-18}$ fatty acids, preferably oleic acid, steric acid, linoleic acid, or any combination thereof, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more bile acids in the above embodiments comprises cholic acid, the one or more free $C_{14-24}$ fatty acids in the above embodiments comprises one or more free $C_{14-18}$ fatty acids, preferably oleic acid, steric acid, linoleic acid, or any combination thereof, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof, the one or more bile acids in the above embodiments comprises cholic acid, the one or more free $C_{14-24}$ fatty acids in the above embodiments comprises one or more free $C_{14-18}$ fatty acids, preferably oleic acid, steric acid, linoleic acid, or any combination thereof, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof.

In some embodiments, a pharmaceutical comprises one or more therapeutic compounds, one or more hard fats, and one or more digestion enhancers. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof. In some embodiments, the one or more digestion enhancers comprises one or more bile acids, one or more one or more free $C_{14-24}$ fatty acids, one or more one or more free $C_{14-24}$ fatty acid surfactants, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more digestion enhancers comprises one or more bile acids, one or more one or more free $C_{14-24}$ fatty acids, one or more one or more free $C_{14-24}$ fatty acid surfactants, or any combination thereof.

In some embodiments, a pharmaceutical comprises about 0.1% to about 30% by weight of one or more therapeutic compounds, about 20% to about 55% by weight of one or more hard fats, and about 40% to about 80% by weight of one or more digestion enhancers. In some embodiments, a pharmaceutical comprises about 25 mg/mL to about 600 mg/mL of one or more therapeutic compounds, about 20% to about 55% by weight of one or more hard fats, and about 40% to about 80% by weight of one or more digestion enhancers. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof. In some embodiments, the one or more digestion enhancers comprises one or more bile acids, one or more one or more free $C_{14-24}$ fatty acids, one or more one or more free $C_{14-24}$ fatty acid surfactants, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more digestion enhancers comprises one or more bile acids, one or more one or more free $C_{14-24}$ fatty acids, one or more one or more free $C_{14-24}$ fatty acid surfactants, or any combination thereof.

In some embodiments, a pharmaceutical comprises about 0.1% to about 30% by weight of one or more therapeutic compounds, about 20% to about 55% by weight of one or more hard fats comprising glycerolipids, and about 40% to about 80% by weight of one or more digestion enhancers. In some embodiments, a pharmaceutical comprises about 25 mg/mL to about 600 mg/mL of one or more therapeutic compounds, about 20% to about 55% by weight of one or more hard fats comprising glycerolipids, and about 40% to about 80% by weight of one or more digestion enhancers. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof. In some embodiments, the one or more digestion enhancers comprises one or more bile acids, one or more one or more free $C_{14-24}$ fatty acids, one or more one or more free $C_{14-24}$ fatty acid surfactants, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more digestion enhancers comprises one or more bile acids, one or more one or more free $C_{14-24}$ fatty acids, one or more one or more free $C_{14-24}$ fatty acid surfactants, or any combination thereof.

In some embodiments, a pharmaceutical comprises about 0.1% to about 30% by weight of one or more therapeutic compounds, about 20% to about 55% by weight of one or more hard fats comprising $C_{10}$-$C_{24}$ triglycerides, and about 40% to about 80% by weight of one or more digestion enhancers. In some embodiments, a pharmaceutical comprises about 25 mg/mL to about 600 mg/mL of one or more therapeutic compounds, about 20% to about 55% by weight of one or more hard fats comprising $C_{10}$-$C_{24}$ triglycerides, and about 40% to about 80% by weight of one or more digestion enhancers. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof. In some embodiments, the one or more digestion enhancers comprises one or more bile acids, one or more one or more free $C_{14-24}$ fatty acids, one or more one or more free $C_{14-24}$ fatty acid surfactants, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more digestion enhancers comprises one or more bile acids, one or more one or more free $C_{14-24}$ fatty acids, one or more one or more free $C_{14-24}$ fatty acid surfactants, or any combination thereof.

In some embodiments, a pharmaceutical comprises about 0.1% to about 30% by weight of one or more therapeutic compounds, about 20% to about 55% by weight of one or more hard fats comprising a mixture of saturated $C_{10}$-$C_{18}$ triglycerides and/or saturated $C_{12}$-$C_{18}$ triglycerides, and about 40% to about 80% by weight of one or more digestion enhancers. In some embodiments, a pharmaceutical comprises about 25 mg/mL to about 600 mg/mL of one or more therapeutic compounds, about 20% to about 55% by weight of one or more hard fats comprising a mixture of saturated $C_{10}$-$C_{18}$ triglycerides and/or saturated $C_{12}$-$C_{18}$ triglycerides, and about 40% to about 80% by weight of one or more digestion enhancers. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof. In some embodiments, the one or more digestion enhancers comprises one or more bile acids, one or more one or more free $C_{14-24}$ fatty acids, one or more one or more free $C_{14-24}$ fatty acid surfactants, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more digestion enhancers comprises one or more bile acids, one or more one or more free $C_{14-24}$ fatty acids, one or more one or more free $C_{14-24}$ fatty acid surfactants, or any combination thereof.

In some embodiments, a pharmaceutical comprises one or more therapeutic compounds, one or more hard fats, and one or more bile acids. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof. In some embodiments, the one or more bile acids in the above embodiments comprises cholic acid. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more bile acids in the above embodiments comprises cholic acid.

In some embodiments, a pharmaceutical comprises about 0.1% to about 30% by weight of one or more therapeutic compounds, about 20% to about 55% by weight of one or more hard fats, and about 0.1% to about 10% by weight of one or more bile acids. In some embodiments, a pharmaceutical comprises about 25 mg/mL to about 600 mg/mL of one or more therapeutic compounds, about 20% to about 55% by weight of one or more hard fats, and about 0.1% to about 10% by weight of one or more bile acids. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof. In some embodiments, the one or more bile acids in the above embodiments comprises cholic acid. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more bile acids in the above embodiments comprises cholic acid.

In some embodiments, a pharmaceutical comprises about 0.1% to about 30% by weight of one or more therapeutic compounds, about 20% to about 55% by weight of one or more hard fats comprising glycerolipids, and about 0.1% to about 10% by weight of one or more bile acids. In some embodiments, a pharmaceutical comprises about 25 mg/mL to about 600 mg/mL of one or more therapeutic compounds, about 20% to about 55% by weight of one or more hard fats comprising glycerolipids, and about 0.1% to about 10% by weight of one or more bile acids. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof. In some embodiments, the one or more bile acids in the above embodiments comprises cholic acid. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more bile acids in the above embodiments comprises cholic acid.

In some embodiments, a pharmaceutical comprises about 0.1% to about 30% by weight of one or more therapeutic compounds, about 20% to about 55% by weight of one or more hard fats comprising $C_{10}$-$C_{24}$ triglycerides, and about 0.1% to about 10% by weight of one or more bile acids. In some embodiments, a pharmaceutical comprises about 25 mg/mL to about 600 mg/mL of one or more therapeutic compounds, about 20% to about 55% by weight of one or more hard fats comprising $C_{10}$-$C_{24}$ triglycerides, and about 0.1% to about 10% by weight of one or more bile acids. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof. In some embodiments, the one or more bile acids in the above embodiments comprises cholic acid. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more bile acids in the above embodiments comprises cholic acid.

In some embodiments, a pharmaceutical comprises about 0.1% to about 30% by weight of one or more therapeutic compounds, about 20% to about 55% by weight of one or more hard fats comprising a mixture of saturated $C_{10}$-$C_{18}$ triglycerides and/or saturated $C_{12}$-$C_{18}$ triglycerides, and about 0.1% to about 10% by weight of one or more bile acids. In some embodiments, a pharmaceutical comprises about 25 mg/mL to about 600 mg/mL of one or more therapeutic compounds, about 20% to about 55% by weight of one or more hard fats comprising a mixture of saturated $C_{10}$-$C_{18}$ triglycerides and/or saturated $C_{12}$-$C_{18}$ triglycerides, and about 0.1% to about 10% by weight of one or more bile acids. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof. In some embodiments, the one or more bile acids in the above embodiments comprises cholic acid. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more bile acids in the above embodiments comprises cholic acid.

In some embodiments, a pharmaceutical comprises one or more therapeutic compounds, one or more hard fats, one or more bile acids and one or more free $C_{14-24}$ fatty acids. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof. In some embodiments, the one or more bile acids in the above embodiments comprises cholic acid. In some embodiments, the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more bile acids in the above embodiments comprises cholic acid. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof, the one or more bile acids in the above embodiments comprises cholic acid, and the one or more free $C_{14-24}$ fatty acids in the above embodiments comprises one or more free $C_{14-18}$ fatty acids, preferably oleic acid, steric acid, linoleic acid, or any combination thereof.

In some embodiments, a pharmaceutical comprises about 0.1% to about 30% by weight of one or more therapeutic compounds, about 20% to about 55% by weight of one or more hard fats, about 0.1% to about 10% by weight of one or more bile acids, and about 35% to about 75% by weight of one or more free $C_{14-24}$ fatty acids. In some embodiments, a pharmaceutical comprises about 25 mg/mL to about 600 mg/mL of one or more therapeutic compounds, about 20% to about 55% by weight of one or more hard fats, about 0.1% to about 10% by weight of one or more bile acids, and about 35% to about 75% by weight of one or more free $C_{14-24}$ fatty acids. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof. In some embodiments, the one or more bile acids in the above embodiments comprises cholic acid. In some embodiments, the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more bile acids in the above embodiments comprises cholic acid. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the comprising an organic acid functional group, a therapeutic compound comprising an organic base functional group, or any combination thereof and the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof, the one or more bile acids in the above embodiments comprises cholic acid, and the one or more free $C_{14-24}$ fatty acids in the above embodiments comprises one or more free $C_{14-18}$ fatty acids, preferably oleic acid, steric acid, linoleic acid, or any combination thereof.

In some embodiments, a pharmaceutical comprises about 0.1% to about 30% by weight of one or more therapeutic compounds, about 20% to about 55% by weight of one or more hard fats comprising glycerolipids, about 0.1% to about 10% by weight of one or more bile acids, and about 35% to about 75% by weight of one or more free $C_{14-24}$ fatty acids. In some embodiments, a pharmaceutical comprises about 25 mg/mL to about 600 mg/mL of one or more therapeutic compounds, about 20% to about 55% by weight of one or more hard fats comprising glycerolipids, about 0.1% to about 10% by weight of one or more bile acids, and about 35% to about 75% by weight of one or more free $C_{14-24}$ fatty acids. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof. In some embodiments, the one or more bile acids in the above embodiments comprises cholic acid. In some embodiments, the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more bile acids in the above embodiments comprises cholic acid. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof, the one or more bile acids in the above embodiments comprises cholic acid, and the one or more free $C_{14-24}$ fatty acids in the above embodiments comprises one or more free $C_{14-18}$ fatty acids, preferably oleic acid, steric acid, linoleic acid, or any combination thereof.

In some embodiments, a pharmaceutical comprises about 0.1% to about 30% by weight of one or more therapeutic compounds, about 20% to about 55% by weight of one or more hard fats comprising $C_{10}$-$C_{24}$ triglycerides, about 0.1% to about 10% by weight of one or more bile acids, and about 35% to about 75% by weight of one or more free $C_{14-24}$ fatty acids. In some embodiments, a pharmaceutical comprises about 25 mg/mL to about 600 mg/mL of one or more therapeutic compounds, about 20% to about 55% by weight of one or more hard fats comprising $C_{10}$-$C_{24}$ triglycerides, about 0.1% to about 10% by weight of one or more bile acids, and about 35% to about 75% by weight of one or more free $C_{14-24}$ fatty acids. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof. In some embodiments, the one or more bile acids in the above embodiments comprises cholic acid. In some embodiments, the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more bile acids in the above embodiments comprises cholic acid. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof, the one or more bile acids in the above embodiments comprises cholic acid, and the one or more free $C_{14-24}$ fatty acids in the above embodiments comprises one or more free $C_{14-18}$ fatty acids, preferably oleic acid, steric acid, linoleic acid, or any combination thereof.

In some embodiments, a pharmaceutical comprises about 0.1% to about 30% by weight of one or more therapeutic compounds, about 20% to about 55% by weight of one or more hard fats comprising a mixture of saturated $C_{10}$-$C_{18}$ triglycerides and/or saturated $C_{12}$-$C_{18}$ triglycerides, about 0.1% to about 10% by weight of one or more bile acids, and about 35% to about 75% by weight of one or more free $C_{14-24}$ fatty acids. In some embodiments, a pharmaceutical comprises about 25 mg/mL to about 600 mg/mL of one or more therapeutic compounds, about 20% to about 55% by weight of one or more hard fats comprising a mixture of saturated $C_{10}$-$C_{18}$ triglycerides and/or saturated $C_{12}$-$C_{18}$ triglycerides, about 0.1% to about 10% by weight of one or more bile acids, and about 35% to about 75% by weight of one or more free $C_{14-24}$ fatty acids. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof. In some embodiments, the one or more bile acids in the above embodiments comprises cholic acid. In some embodiments, the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more bile acids in the above embodiments comprises cholic acid. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof, the one or more bile acids in the above embodiments comprises cholic acid, and the one or more free $C_{14-24}$ fatty acids in the above embodiments comprises one or more free $C_{14-18}$ fatty acids, preferably oleic acid, steric acid, linoleic acid, or any combination thereof.

In some embodiments, a pharmaceutical comprises one or more therapeutic compounds, one or more hard fats, one or more bile acids, and one or more free $C_{14-24}$ fatty acid surfactants. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof. In some embodiments, the one or more bile acids in the above embodiments comprises cholic acid. In some embodiments, the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more bile acids in the above embodiments comprises cholic acid. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more bile acids in the above embodiments comprises cholic acid and the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more bile acids in the above embodiments comprises cholic acid and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more free $C_{14-24}$ fatty acids in the above embodiments comprises one or more free $C_{14-18}$ fatty acids, preferably oleic acid, steric acid, linoleic acid, or any combination thereof, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof, the one or more bile acids in the above embodiments comprises cholic acid, and the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof, the one or more bile acids in the above embodiments comprises cholic acid, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof, the one or more free $C_{14-24}$ fatty acids in the above embodiments comprises one or more free $C_{14-18}$ fatty acids, preferably oleic acid, steric acid, linoleic acid, or any combination thereof, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more bile acids in the above embodiments comprises cholic acid, the one or more free $C_{14-24}$ fatty acids in the above embodiments comprises one or more free $C_{14-18}$ fatty acids, preferably oleic acid, steric acid, linoleic acid, or any combination thereof, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof, the one or more bile acids in the above embodiments comprises cholic acid, the one or more free $C_{14-24}$ fatty acids in the above embodiments comprises one or more free $C_{14-18}$ fatty acids, preferably oleic acid, steric acid, linoleic acid, or any combination thereof, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof.

In some embodiments, a pharmaceutical comprises about 0.1% to about 30% by weight of one or more therapeutic compounds, about 20% to about 55% by weight of one or more hard fats, about 0.1% to about 10% by weight of one or more bile acids, and about 0.1% to about 5% by weight of one or more free $C_{14-24}$ fatty acid surfactants. In some embodiments, a pharmaceutical comprises about 25 mg/mL to about 600 mg/mL of one or more therapeutic compounds, about 20% to about 55% by weight of one or more hard fats, about 0.1% to about 10% by weight of one or more bile acids, and about 0.1% to about 5% by weight of one or more free $C_{14-24}$ fatty acid surfactants. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof. In some embodiments, the one or more bile acids in the above embodiments comprises cholic acid. In some embodiments, the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more bile acids in the above embodiments comprises cholic acid. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more bile acids in the above embodiments comprises cholic acid and the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more bile acids in the above embodiments comprises cholic acid and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more free $C_{14-24}$ fatty acids in the above embodiments comprises one or more free $C_{14-18}$ fatty acids, preferably oleic acid, steric acid, linoleic acid, or any combination thereof, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof, the one or more bile acids in the above embodiments comprises cholic acid, and the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof, the one or more bile acids in the above embodiments comprises cholic acid, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof, the one or more free $C_{14-24}$ fatty acids in the above embodiments comprises one or more free $C_{14-18}$ fatty acids, preferably oleic acid, steric acid, linoleic acid, or any combination thereof, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more bile acids in the above embodiments comprises cholic acid, the one or more free $C_{14-24}$ fatty acids in the above embodiments comprises one or more free $C_{14-18}$ fatty acids, preferably oleic acid, steric acid, linoleic acid, or any combination thereof, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof, the one or more bile acids in the above embodiments comprises cholic acid, the one or more free $C_{14-24}$ fatty acids in the above embodiments comprises one or more free $C_{14-18}$ fatty acids, preferably oleic acid, steric acid, linoleic acid, or any combination thereof, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof.

In some embodiments, a pharmaceutical comprises about 0.1% to about 30% by weight of one or more therapeutic compounds, about 20% to about 55% by weight of one or more hard fats comprising glycerolipids, about 0.1% to about 10% by weight of one or more bile acids, and about 0.1% to about 5% by weight of one or more free $C_{14-24}$ fatty acid surfactants. In some embodiments, a pharmaceutical comprises about 25 mg/mL to about 600 mg/mL of one or more therapeutic compounds, about 20% to about 55% by weight of one or more hard fats comprising glycerolipids, about 0.1% to about 10% by weight of one or more bile acids, and about 0.1% to about 5% by weight of one or more free $C_{14-24}$ fatty acid surfactants. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof. In some embodiments, the one or more bile acids in the above embodiments comprises cholic acid. In some embodiments, the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more bile acids in the above embodiments comprises cholic acid. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more bile acids in the above embodiments comprises cholic acid and the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more bile acids in the above embodiments comprises cholic acid and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more free $C_{14-24}$ fatty acids in the above embodiments comprises one or more free $C_{14-18}$ fatty acids, preferably oleic acid, steric acid, linoleic acid, or any combination thereof, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof, the one or more bile acids in the above embodiments comprises cholic acid, and the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof, the one or more bile acids in the above embodiments comprises cholic acid, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof, the one or more free $C_{14-24}$ fatty acids in the above embodiments comprises one or more free $C_{14-18}$ fatty acids, preferably oleic acid, steric acid, linoleic acid, or any combination thereof, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more bile acids in the above embodiments comprises cholic acid, the one or more free $C_{14-24}$ fatty acids in the above embodiments comprises one or more free $C_{14-18}$ fatty acids, preferably oleic acid, steric acid, linoleic acid, or any combination thereof, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof, the one or more bile acids in the above embodiments comprises cholic acid, the one or more free $C_{14-24}$ fatty acids in the above embodiments comprises one or more free $C_{14-18}$ fatty acids, preferably oleic acid, steric acid, linoleic acid, or any combination thereof, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof.

In some embodiments, a pharmaceutical comprises about 0.1% to about 30% by weight of one or more therapeutic compounds, about 20% to about 55% by weight of one or more hard fats comprising $C_{10}$-$C_{24}$ triglycerides, about 0.1% to about 10% by weight of one or more bile acids, and about 0.1% to about 5% by weight of one or more free $C_{14-24}$ fatty acid surfactants. In some embodiments, a pharmaceutical comprises about 25 mg/mL to about 600 mg/mL of one or more therapeutic compounds, about 20% to about 55% by weight of one or more hard fats comprising $C_{10}$-$C_{24}$ triglycerides, about 0.1% to about 10% by weight of one or more bile acids, about 0.1% to about 5% by weight of one or more free $C_{14-24}$ fatty acid surfactants. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof. In some embodiments, the one or more bile acids in the above embodiments comprises cholic acid. In some embodiments, the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more bile acids in the above embodiments comprises cholic acid. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more bile acids in the above embodiments comprises cholic acid and the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more bile acids in the above embodiments comprises cholic acid and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more free $C_{14-24}$ fatty acids in the above embodiments comprises one or more free $C_{14-18}$ fatty acids, preferably oleic acid, steric acid, linoleic acid, or any combination thereof, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof, the one or more bile acids in the above embodiments comprises cholic acid, and the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof, the one or more bile acids in the above embodiments comprises cholic acid, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof, the one or more free $C_{14-24}$ fatty acids in the above embodiments comprises one or more free $C_{14-18}$ fatty acids, preferably oleic acid, steric acid, linoleic acid, or any combination thereof, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more bile acids in the above embodiments comprises cholic acid, the one or more free $C_{14-24}$ fatty acids in the above embodiments comprises one or more free $C_{14-18}$ fatty acids, preferably oleic acid, steric acid, linoleic acid, or any combination thereof, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof, the one or more bile acids in the above embodiments comprises cholic acid, the one or more free $C_{14-24}$ fatty acids in the above embodiments comprises one or more free $C_{14-18}$ fatty acids, preferably oleic acid, steric acid, linoleic acid, or any combination thereof, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof.

In some embodiments, a pharmaceutical comprises about 0.1% to about 30% by weight of one or more therapeutic compounds, about 20% to about 55% by weight of one or more hard fats comprising a mixture of saturated $C_{10}$-$C_{18}$ triglycerides and/or saturated $C_{12}$-$C_{18}$ triglycerides, about 0.1% to about 10% by weight of one or more bile acids, and about 0.1% to about 5% by weight of one or more free $C_{14-24}$ fatty acid surfactants. In some embodiments, a pharmaceutical comprises about 25 mg/mL to about 600 mg/mL of one or more therapeutic compounds, about 20% to about 55% by weight of one or more hard fats comprising a mixture of saturated $C_{10}$-$C_{18}$ triglycerides and/or saturated $C_{12}$-$C_{18}$ triglycerides, about 0.1% to about 10% by weight of one or more bile acids, and about 0.1% to about 5% by weight of one or more free $C_{14-24}$ fatty acid surfactants. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof. In some embodiments, the one or more bile acids in the above embodiments comprises cholic acid. In some embodiments, the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more bile acids in the above embodiments comprises cholic acid. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more bile acids in the above embodiments comprises cholic acid and the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more bile acids in the above embodiments comprises cholic acid and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more free $C_{14-24}$ fatty acids in the above embodiments comprises one or more free $C_{14-18}$ fatty acids, preferably oleic acid, steric acid, linoleic acid, or any combination thereof, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof, the one or more bile acids in the above embodiments comprises cholic acid, and the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof, the one or more bile acids in the above embodiments comprises cholic acid, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof, the one or more free $C_{14-24}$ fatty acids in the above embodiments comprises one or more free $C_{14-18}$ fatty acids, preferably oleic acid, steric acid, linoleic acid, or any combination thereof, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more bile acids in the above embodiments comprises cholic acid, the one or more free $C_{14-24}$ fatty acids in the above embodiments comprises one or more free $C_{14-18}$ fatty acids, preferably oleic acid, steric acid, linoleic acid, or any combination thereof, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof, the one or more bile acids in the above embodiments comprises cholic acid, the one or more free $C_{14-24}$ fatty acids in the above embodiments comprises one or more free $C_{14-18}$ fatty acids, preferably oleic acid, steric acid, linoleic acid, or any combination thereof, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof.

In some embodiments, a pharmaceutical comprises one or more therapeutic compounds, one or more hard fats, one or more bile acids, one or more free $C_{14-24}$ fatty acids, and one or more free $C_{14-24}$ fatty acid surfactants. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof. In some embodiments, the one or more bile acids in the above embodiments comprises cholic acid. In some embodiments, the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more bile acids in the above embodiments comprises cholic acid. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more bile acids in the above embodiments comprises cholic acid and the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more bile acids in the above embodiments comprises cholic acid and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more free $C_{14-24}$ fatty acids in the above embodiments comprises one or more free $C_{14-18}$ fatty acids, preferably oleic acid, steric acid, linoleic acid, or any combination thereof, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof, the one or more bile acids in the above embodiments comprises cholic acid, and the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof, the one or more bile acids in the above embodiments comprises cholic acid, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof, the one or more free $C_{14-24}$ fatty acids in the above embodiments comprises one or more free $C_{14-18}$ fatty acids, preferably oleic acid, steric acid, linoleic acid, or any combination thereof, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more bile acids in the above embodiments comprises cholic acid, the one or more free $C_{14-24}$ fatty acids in the above embodiments comprises one or more free $C_{14-18}$ fatty acids, preferably oleic acid, steric acid, linoleic acid, or any combination thereof, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof, the one or more bile acids in the above embodiments comprises cholic acid, the one or more free $C_{14-24}$ fatty acids in the above embodiments comprises one or more free $C_{14-18}$ fatty acids, preferably oleic acid, steric acid, linoleic acid, or any combination thereof, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof.

In some embodiments, a pharmaceutical comprises about 0.1% to about 30% by weight of one or more therapeutic compounds, about 20% to about 55% by weight of one or more hard fats, about 0.1% to about 10% by weight of one or more bile acids, about 35% to about 75% by weight of one or more free $C_{14-24}$ fatty acids, and about 0.1% to about 5% by weight of one or more free $C_{14-24}$ fatty acid surfactants. In some embodiments, a pharmaceutical comprises about 25 mg/mL to about 600 mg/mL of one or more therapeutic compounds, about 20% to about 55% by weight of one or more hard fats, about 0.1% to about 10% by weight of one or more bile acids, about 35% to about 75% by weight of one or more free $C_{14-24}$ fatty acids, and about 0.1% to about 5% by weight of one or more free $C_{14-24}$ fatty acid surfactants. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof. In some embodiments, the one or more bile acids in the above embodiments comprises cholic acid. In some embodiments, the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more bile acids in the above embodiments comprises cholic acid. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more bile acids in the above embodiments comprises cholic acid and the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more bile acids in the above embodiments comprises cholic acid and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more free $C_{14-24}$ fatty acids in the above embodiments comprises one or more free $C_{14-18}$ fatty acids, preferably oleic acid, steric acid, linoleic acid, or any combination thereof, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof, the one or more bile acids in the above embodiments comprises cholic acid, and the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof, the one or more bile acids in the above embodiments comprises cholic acid, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof, the one or more free $C_{14-24}$ fatty acids in the above embodiments comprises one or more free $C_{14-18}$ fatty acids, preferably oleic acid, steric acid, linoleic acid, or any combination thereof, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more bile acids in the above embodiments comprises cholic acid, the one or more free $C_{14-24}$ fatty acids in the above embodiments comprises one or more free $C_{14-18}$ fatty acids, preferably oleic acid, steric acid, linoleic acid, or any combination thereof, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof, the one or more bile acids in the above embodiments comprises cholic acid, the one or more free $C_{14-24}$ fatty acids in the above embodiments comprises one or more free $C_{14-18}$ fatty acids, preferably oleic acid, steric acid, linoleic acid, or any combination thereof, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof.

In some embodiments, a pharmaceutical comprises about 0.1% to about 30% by weight of one or more therapeutic compounds, about 20% to about 55% by weight of one or more hard fats comprising glycerolipids, about 0.1% to about 10% by weight of one or more bile acids, about 35% to about 75% by weight of one or more free $C_{14-24}$ fatty acids, and about 0.1% to about 5% by weight of one or more free $C_{14}$-24 fatty acid surfactants. In some embodiments, a pharmaceutical comprises about 25 mg/mL to about 600 mg/mL of one or more therapeutic compounds, about 20% to about 55% by weight of one or more hard fats comprising glycerolipids, about 0.1% to about 10% by weight of one or more bile acids, about 35% to about 75% by weight of one or more free $C_{14-24}$ fatty acids, and about 0.1% to about 5% by weight of one or more free $C_{14-24}$ fatty acid surfactants. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof. In some embodiments, the one or more bile acids in the above embodiments comprises cholic acid. In some embodiments, the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more bile acids in the above embodiments comprises cholic acid. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more bile acids in the above embodiments comprises cholic acid and the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more bile acids in the above embodiments comprises cholic acid and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more free $C_{14-24}$ fatty acids in the above embodiments comprises one or more free $C_{14-18}$ fatty acids, preferably oleic acid, steric acid, linoleic acid, or any combination thereof, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof, the one or more bile acids in the above embodiments comprises cholic acid, and the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof, the one or more bile acids in the above embodiments comprises cholic acid, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof, the one or more free $C_{14-24}$ fatty acids in the above embodiments comprises one or more free $C_{14-18}$ fatty acids, preferably oleic acid, steric acid, linoleic acid, or any combination thereof, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more bile acids in the above embodiments comprises cholic acid, the one or more free $C_{14-24}$ fatty acids in the above embodiments comprises one or more free $C_{14-18}$ fatty acids, preferably oleic acid, steric acid, linoleic acid, or any combination thereof, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof, the one or more bile acids in the above embodiments comprises cholic acid, the one or more free $C_{14-24}$ fatty acids in the above embodiments comprises one or more free $C_{14-18}$ fatty acids, preferably oleic acid, steric acid, linoleic acid, or any combination thereof, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof.

In some embodiments, a pharmaceutical comprises about 0.1% to about 30% by weight of one or more therapeutic compounds, about 20% to about 55% by weight of one or more hard fats comprising $C_{10}$-$C_{24}$ triglycerides, about 0.1% to about 10% by weight of one or more bile acids, about 35% to about 75% by weight of one or more free $C_{14-24}$ fatty acids, and about 0.1% to about 5% by weight of one or more free $C_{14-24}$ fatty acid surfactants. In some embodiments, a pharmaceutical comprises about 25 mg/mL to about 600 mg/mL of one or more therapeutic compounds, about 20% to about 55% by weight of one or more hard fats comprising $C_{10}$-$C_{24}$ triglycerides, about 0.1% to about 10% by weight of one or more bile acids, and about 35% to about 75% by weight of one or more free $C_{14-24}$ fatty acids, about 0.1% to about 5% by weight of one or more free $C_{14-24}$ fatty acid surfactants. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof. In some embodiments, the one or more bile acids in the above embodiments comprises cholic acid. In some embodiments, the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more bile acids in the above embodiments comprises cholic acid. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more bile acids in the above embodiments comprises cholic acid and the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more bile acids in the above embodiments comprises cholic acid and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more free $C_{14-24}$ fatty acids in the above embodiments comprises one or more free $C_{14-18}$ fatty acids, preferably oleic acid, steric acid, linoleic acid, or any combination thereof, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof, the one or more bile acids in the above embodiments comprises cholic acid, and the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof, the one or more bile acids in the above embodiments comprises cholic acid, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof, the one or more free $C_{14-24}$ fatty acids in the above embodiments comprises one or more free $C_{14-18}$ fatty acids, preferably oleic acid, steric acid, linoleic acid, or any combination thereof, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more bile acids in the above embodiments comprises cholic acid, the one or more free $C_{14-24}$ fatty acids in the above embodiments comprises one or more free $C_{14-18}$ fatty acids, preferably oleic acid, steric acid, linoleic acid, or any combination thereof, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof, the one or more bile acids in the above embodiments comprises cholic acid, the one or more free $C_{14-24}$ fatty acids in the above embodiments comprises one or more free $C_{14-18}$ fatty acids, preferably oleic acid, steric acid, linoleic acid, or any combination thereof, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof.

In some embodiments, a pharmaceutical comprises about 0.1% to about 30% by weight of one or more therapeutic compounds, about 20% to about 55% by weight of one or more hard fats comprising a mixture of saturated $C_{10}$-$C_{18}$ triglycerides and/or saturated $C_{12}$-$C_{18}$ triglycerides, about 0.1% to about 10% by weight of one or more bile acids, about 35% to about 75% by weight of one or more free $C_{14-24}$ fatty acids, and about 0.1% to about 5% by weight of one or more free $C_{14-24}$ fatty acid surfactants. In some embodiments, a pharmaceutical comprises about 25 mg/mL to about 600 mg/mL of one or more therapeutic compounds, about 20% to about 55% by weight of one or more hard fats comprising a mixture of saturated $C_{10}$-$C_{18}$ triglycerides and/or saturated $C_{12}$-$C_{18}$ triglycerides, about 0.1% to about 10% by weight of one or more bile acids, about 35% to about 75% by weight of one or more free $C_{14-24}$ fatty acids, and about 0.1% to about 5% by weight of one or more free $C_{14-24}$ fatty acid surfactants. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof. In some embodiments, the one or more bile acids in the above embodiments comprises cholic acid. In some embodiments, the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more bile acids in the above embodiments comprises cholic acid. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more bile acids in the above embodiments comprises cholic acid and the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more bile acids in the above embodiments comprises cholic acid and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more free $C_{14-24}$ fatty acids in the above embodiments comprises one or more free $C_{14-18}$ fatty acids, preferably oleic acid, steric acid, linoleic acid, or any combination thereof, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof, the one or more bile acids in the above embodiments comprises cholic acid, and the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof, the one or more bile acids in the above embodiments comprises cholic acid, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof, the one or more free $C_{14-24}$ fatty acids in the above embodiments comprises one or more free $C_{14-18}$ fatty acids, preferably oleic acid, steric acid, linoleic acid, or any combination thereof, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more bile acids in the above embodiments comprises cholic acid, the one or more free $C_{14-24}$ fatty acids in the above embodiments comprises one or more free $C_{14-18}$ fatty acids, preferably oleic acid, steric acid, linoleic acid, or any combination thereof, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more therapeutic compounds in the above embodiments comprises a hydrophilic therapeutic compound, an amphipathic therapeutic compound, a hydrophobic therapeutic compound, a lipophilic therapeutic compound, a therapeutic compound comprising an organic acid functional group, a therapeutic compound comprising an organic base functional group, or any combination thereof, the one or more bile acids in the above embodiments comprises cholic acid, the one or more free $C_{14-24}$ fatty acids in the above embodiments comprises one or more free $C_{14-18}$ fatty acids, preferably oleic acid, steric acid, linoleic acid, or any combination thereof, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof.

In some embodiments, a pharmaceutical comprises abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, one or more glycerolipids, and one or more digestion enhancers. In some embodiments, the one or more digestion enhancers comprises one or more bile acids, one or more one or more free $C_{14-24}$ fatty acids, one or more one or more free $C_{14-24}$ fatty acid surfactants, or any combination thereof.

In some embodiments, a pharmaceutical comprises about 0.1% to about 20% by weight of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 80% to about 99% by weight of one or more glycerolipids, and about 0.1% to about 10% by weight of one or more digestion enhancers. In some embodiments, a pharmaceutical comprises about 25 mg/mL to about 600 mg/mL of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 80% to about 99% by weight of one or more glycerolipids, and about 0.1% to about 10% by weight of one or more digestion enhancers. In some embodiments, the one or more digestion enhancers comprises one or more bile acids, one or more one or more free $C_{14-24}$ fatty acids, one or more one or more free $C_{14-24}$ fatty acid surfactants, or any combination thereof.

In some embodiments, a pharmaceutical comprises about 0.1% to about 20% by weight of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 75% to about 95% by weight of one or more glycerolipids, and about 5% to about 30% by weight of one or more digestion enhancers. In some embodiments, a pharmaceutical comprises about 25 mg/mL to about 600 mg/mL of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 75% to about 95% by weight of one or more glycerolipids, and about 5% to about 30% by weight of one or more digestion enhancers. In some embodiments, the one or more digestion enhancers comprises one or more bile acids, one or more one or more free $C_{14-24}$ fatty acids, one or more one or more free $C_{14-24}$ fatty acid surfactants, or any combination thereof.

In some embodiments, a pharmaceutical comprises about 0.1% to about 30% by weight of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 50% to about 85% by weight of one or more glycerolipids, and about 5% to about 25% of one or more digestion enhancers. In some embodiments, a pharmaceutical comprises about 25 mg/mL to about 600 mg/mL of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 50% to about 85% by weight of one or more glycerolipids, and about 5% to about 25% by weight of one or more digestion enhancers. In some embodiments, the one or more digestion enhancers comprises one or more bile acids, one or more one or more free $C_{14-24}$ fatty acids, one or more one or more free $C_{14-24}$ fatty acid surfactants, or any combination thereof.

In some embodiments, a pharmaceutical comprises about 0.1% to about 30% by weight of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 45% to about 80% by weight of one or more glycerolipids, and about 20% to about 45% by weight of one or more digestion enhancers. In some embodiments, a pharmaceutical comprises about 25 mg/mL to about 600 mg/mL of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 45% to about 80% by weight of one or more glycerolipids, and about 20% to about 45% by weight of one or more digestion enhancers. In some embodiments, the one or more digestion enhancers comprises one or more bile acids, one or more one or more free $C_{14-24}$ fatty acids, one or more one or more free $C_{14-24}$ fatty acid surfactants, or any combination thereof.

In some embodiments, a pharmaceutical comprises about 0.1% to about 30% by weight of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 30% to about 55% by weight of one or more glycerolipids, and about 40% to about 80% by weight of one or more digestion enhancers. In some embodiments, a pharmaceutical comprises about 25 mg/mL to about 600 mg/mL of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 30% to about 55% by weight of one or more glycerolipids, and about 40% to about 80% by weight of one or more digestion enhancers. In some embodiments, the one or more digestion enhancers comprises one or more bile acids, one or more one or more free $C_{14-24}$ fatty acids, one or more one or more free $C_{14-24}$ fatty acid surfactants, or any combination thereof.

In some embodiments, a pharmaceutical comprises abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, one or more hard fats, one or more liquid fats, and one or more digestion enhancers. In some embodiments, the one or more digestion enhancers comprises one or more bile acids, one or more one or more free $C_{14-24}$ fatty acids, one or more one or more free $C_{14-24}$ fatty acid surfactants, or any combination thereof.

In some embodiments, a pharmaceutical comprises about 0.1% to about 20% by weight of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 25% to about 70% by weight of one or more hard fats, about 25% to about 70% by weight of one or more liquid fats, and about 0.1% to about 10% by weight of one or more digestion enhancers. In some embodiments, a pharmaceutical comprises about 25 mg/mL to about 600 mg/mL of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 25% to about 70% by weight of one or more hard fats, about 25% to about 70% by weight of one or more liquid fats, and about 0.1% to about 10% by weight of one or more digestion enhancers. In some embodiments, the one or more digestion enhancers comprises one or more bile acids, one or more one or more free $C_{14-24}$ fatty acids, one or more one or more free $C_{14-24}$ fatty acid surfactants, or any combination thereof.

In some embodiments, a pharmaceutical comprises about 0.1% to about 20% by weight of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 25% to about 70% by weight of one or more hard fats comprising glycerolipids, about 25% to about 70% by weight of one or more liquid fats comprising partially hydrolyzed glycerolipids including a mixture of mono-, di- and triglycerides, and about 0.1% to about 10% by weight of one or more digestion enhancers. In some embodiments, a pharmaceutical comprises about 25 mg/mL to about 600 mg/mL of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 25% to about 70% by weight of one or more hard fats comprising glycerolipids, about 25% to about 70% by weight of one or more liquid fats comprising partially hydrolyzed glycerolipids including a mixture of mono-, di- and triglycerides, and about 0.1% to about 10% by weight of one or more digestion enhancers. In some embodiments, the one or more digestion enhancers comprises one or more bile acids, one or more one or more free $C_{14-24}$ fatty acids, one or more one or more free $C_{14-24}$ fatty acid surfactants, or any combination thereof.

In some embodiments, a pharmaceutical comprises about 0.1% to about 20% by weight of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 25% to about 70% by weight of one or more hard fats comprising $C_{10}$-$C_{24}$ triglycerides, about 25% to about 70% by weight of one or more liquid fats comprising partially hydrolyzed triglycerides including a mixture of $C_{10}$-$C_{24}$ mono-, $C_{10}$-$C_{24}$ di- and $C_{10}$-$C_{24}$ triglycerides, and about 0.1% to about 10% by weight of one or more digestion enhancers. In some embodiments, a pharmaceutical comprises about 25 mg/mL to about 600 mg/mL of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 25% to about 70% by weight of one or more hard fats comprising $C_{10}$-$C_{24}$ triglycerides, about 25% to about 70% by weight of one or more liquid fats comprising partially hydrolyzed triglycerides including a mixture of $C_{10}$-$C_{24}$ mono-, $C_{10}$-$C_{24}$ di- and $C_{10}$-$C_{24}$ triglycerides, and about 0.1% to about 10% by weight of one or more digestion enhancers. In some embodiments, the one or more digestion enhancers comprises one or more bile acids, one or more one or more free $C_{14-24}$ fatty acids, one or more one or more free $C_{14-24}$ fatty acid surfactants, or any combination thereof.

In some embodiments, a pharmaceutical comprises about 0.1% to about 20% by weight of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 25% to about 70% by weight of one or more hard fats comprising a mixture of saturated $C_{10}$-$C_{18}$ triglycerides and/or saturated $C_{12}$-$C_{18}$ triglycerides, about 25% to about 70% by weight of one or more liquid fats comprising partially hydrolyzed triglycerides including a mixture of $C_{16}$-$C_{18}$ mono-, $C_{16}$-$C_{18}$ di- and $C_{16}$-$C_{18}$ triglycerides, and about 0.1% to about 10% by weight of one or more digestion enhancers. In some embodiments, a pharmaceutical comprises about 25 mg/mL to about 600 mg/mL of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 25% to about 70% by weight of one or more hard fats comprising a mixture of saturated $C_{10}$-$C_{18}$ triglycerides and/or saturated $C_{12}$-$C_{18}$ triglycerides, about 25% to about 70% by weight of one or more liquid fats comprising partially hydrolyzed triglycerides including a mixture of $C_{16}$-$C_{18}$ mono-, $C_{16}$-$C_{18}$ di- and $C_{16}$-$C_{18}$ triglycerides, and about 0.1% to about 10% by weight of one or more digestion enhancers. In some embodiments, the one or more digestion enhancers comprises one or more bile acids, one or more one or more free $C_{14-24}$ fatty acids, one or more one or more free $C_{14-24}$ fatty acid surfactants, or any combination thereof.

In some embodiments, a pharmaceutical comprises about 0.1% to about 20% by weight of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 35% to about 55% by weight of one or more hard fats, about 25% to about 50% by weight of one or more liquid fats, and about 5% to about 30% by weight of one or more digestion enhancers. In some embodiments, a pharmaceutical comprises about 25 mg/mL to about 600 mg/mL of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 35% to about 55% by weight of one or more hard fats, about 25% to about 50% by weight of one or more liquid fats, and about 5% to about 30% by weight of one or more digestion enhancers. In some embodiments, the one or more digestion enhancers comprises one or more bile acids, one or more one or more free $C_{14-24}$ fatty acids, one or more one or more free $C_{14-24}$ fatty acid surfactants, or any combination thereof.

In some embodiments, a pharmaceutical comprises about 0.1% to about 20% by weight of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 35% to about 55% by weight of one or more hard fats comprising glycerolipids, about 25% to about 50% by weight of one or more liquid fats comprising partially hydrolyzed glycerolipids including a mixture of mono-, di- and triglycerides, and about 5% to about 30% by weight of one or more digestion enhancers. In some embodiments, a pharmaceutical comprises about 25 mg/mL to about 600 mg/mL of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 35% to about 55% by weight of one or more hard fats comprising glycerolipids, about 25% to about 50% by weight of one or more liquid fats comprising partially hydrolyzed glycerolipids including a mixture of mono-, di- and triglycerides, and about 5% to about 30% by weight of one or more digestion enhancers. In some embodiments, the one or more digestion enhancers comprises one or more bile acids, one or more one or more free $C_{14-24}$ fatty acids, one or more one or more free $C_{14-24}$ fatty acid surfactants, or any combination thereof.

In some embodiments, a pharmaceutical comprises about 0.1% to about 20% by weight of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 35% to about 55% by weight of one or more hard fats comprising $C_{10}$-$C_{24}$ triglycerides, about 25% to about 50% by weight of one or more liquid fats comprising partially hydrolyzed triglycerides including a mixture of $C_{10}$-$C_{24}$ mono-, $C_{10}$-$C_{24}$ di- and $C_{10}$-$C_{24}$ triglycerides, and about 5% to about 30% by weight of one or more digestion enhancers. In some embodiments, a pharmaceutical comprises about 25 mg/mL to about 600 mg/mL of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 35% to about 55% by weight of one or more hard fats comprising $C_{10}$-$C_{24}$ triglycerides, about 25% to about 50% by weight of one or more liquid fats comprising partially hydrolyzed triglycerides including a mixture of $C_{10}$-$C_{24}$ mono-, $C_{10}$-$C_{24}$ di- and $C_{10}$-$C_{24}$ triglycerides, and about 5% to about 30% by weight of one or more digestion enhancers. In some embodiments, the one or more digestion enhancers comprises one or more bile acids, one or more one or more free $C_{14-24}$ fatty acids, one or more one or more free $C_{14-24}$ fatty acid surfactants, or any combination thereof.

In some embodiments, a pharmaceutical comprises about 0.1% to about 20% by weight of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 35% to about 55% by weight of one or more hard fats comprising a mixture of saturated $C_{10}$-$C_{18}$ triglycerides and/or saturated $C_{12}$-$C_{18}$ triglycerides, about 25% to about 50% by weight of one or more liquid fats comprising partially hydrolyzed triglycerides including a mixture of $C_{16}$-$C_{18}$ mono-, $C_{16}$-$C_{18}$ di- and $C_{16}$-$C_{18}$ triglycerides, and about 5% to about 30% by weight of one or more digestion enhancers. In some embodiments, a pharmaceutical comprises about 25 mg/mL to about 600 mg/mL of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 35% to about 55% by weight of one or more hard fats comprising a mixture of saturated $C_{10}$-$C_{18}$ triglycerides and/or saturated $C_{12}$-$C_{18}$ triglycerides, about 25% to about 50% by weight of one or more liquid fats comprising partially hydrolyzed triglycerides including a mixture of $C_{16}$-$C_{18}$ mono-, $C_{16}$-$C_{18}$ di- and $C_{16}$-$C_{18}$ triglycerides, and about 5% to about 30% by weight of one or more digestion enhancers. In some embodiments, the one or more digestion enhancers comprises one or more bile acids, one or more one or more free $C_{14-24}$ fatty acids, one or more one or more free $C_{14-24}$ fatty acid surfactants, or any combination thereof.

In some embodiments, a pharmaceutical comprises about 0.1% to about 30% by weight of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 15% to about 65% by weight of one or more hard fats, about 15% to about 50% by weight of one or more liquid fats, and about 5% to about 25% by weight of one or more digestion enhancers. In some embodiments, a pharmaceutical comprises about 25 mg/mL to about 600 mg/mL of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 15% to about 65% by weight of one or more hard fats, about 15% to about 50% by weight of one or more liquid fats, and about 5% to about 25% by weight of one or more digestion enhancers. In some embodiments, the one or more digestion enhancers comprises one or more bile acids, one or more one or more free $C_{14-24}$ fatty acids, one or more one or more free $C_{14-24}$ fatty acid surfactants, or any combination thereof.

In some embodiments, a pharmaceutical comprises about 0.1% to about 30% by weight of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 15% to about 65% by weight of one or more hard fats comprising glycerolipids, about 15% to about 50% by weight of one or more liquid fats comprising partially hydrolyzed glycerolipids including a mixture of mono-, di- and triglycerides, and about 5% to about 25% by weight of one or more digestion enhancers. In some embodiments, a pharmaceutical comprises about 25 mg/mL to about 600 mg/mL of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 15% to about 65% by weight of one or more hard fats comprising glycerolipids, about 15% to about 50% by weight of one or more liquid fats comprising partially hydrolyzed glycerolipids including a mixture of mono-, di- and triglycerides, and about 5% to about 25% by weight of one or more digestion enhancers. In some embodiments, the one or more digestion enhancers comprises one or more bile acids, one or more one or more free $C_{14-24}$ fatty acids, one or more one or more free $C_{14-24}$ fatty acid surfactants, or any combination thereof.

In some embodiments, a pharmaceutical comprises about 0.1% to about 30% by weight of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 15% to about 65% by weight of one or more hard fats comprising $C_{10}$-$C_{24}$ triglycerides, about 15% to about 50% by weight of one or more liquid fats comprising partially hydrolyzed triglycerides including a mixture of $C_{10}$-$C_{24}$ mono-, $C_{10}$-$C_{24}$ di- and $C_{10}$-$C_{24}$ triglycerides, and about 5% to about 25% by weight of one or more digestion enhancers. In some embodiments, a pharmaceutical comprises about 25 mg/mL to about 600 mg/mL of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 15% to about 65% by weight of one or more hard fats comprising $C_{10}$-$C_{24}$ triglycerides, about 15% to about 50% by weight of one or more liquid fats comprising partially hydrolyzed triglycerides including a mixture of $C_{10}$-$C_{24}$ mono-, $C_{10}$-$C_{24}$ di- and $C_{10}$-$C_{24}$ triglycerides, and about 5% to about 25% by weight of one or more digestion enhancers. In some embodiments, the one or more digestion enhancers comprises one or more bile acids, one or more one or more free $C_{14-24}$ fatty acids, one or more one or more free $C_{14-24}$ fatty acid surfactants, or any combination thereof.

In some embodiments, a pharmaceutical comprises about 0.1% to about 30% by weight of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 15% to about 65% by weight of one or more hard fats comprising a mixture of saturated $C_{10}$-$C_{18}$ triglycerides and/or saturated $C_{12}$-$C_{18}$ triglycerides, about 15% to about 50% by weight of one or more liquid fats comprising partially hydrolyzed triglycerides including a mixture of $C_{16}$-$C_{18}$ mono-, $C_{16}$-$C_{18}$ di- and $C_{16}$-$C_{18}$ triglycerides, and about 5% to about 25% by weight of one or more digestion enhancers. In some embodiments, a pharmaceutical comprises about 25 mg/mL to about 600 mg/mL of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 15% to about 65% by weight of one or more hard fats comprising a mixture of saturated $C_{10}$-$C_{18}$ triglycerides and/or saturated $C_{12}$-$C_{18}$ triglycerides, about 15% to about 50% by weight of one or more liquid fats comprising partially hydrolyzed triglycerides including a mixture of $C_{16}$-$C_{18}$ mono-, $C_{16}$-$C_{18}$ di- and $C_{16}$-$C_{18}$ triglycerides, and about 5% to about 25% by weight of one or more digestion enhancers. In some embodiments, the one or more digestion enhancers comprises one or more bile acids, one or more one or more free $C_{14-24}$ fatty acids, one or more one or more free $C_{14-24}$ fatty acid surfactants, or any combination thereof.

In some embodiments, a pharmaceutical comprises about 0.1% to about 30% by weight of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 20% to about 55% by weight of one or more hard fats, about 15% to about 45% by weight of one or more liquid fats, and about 20% to about 45% by weight of one or more digestion enhancers. In some embodiments, a pharmaceutical comprises about 25 mg/mL to about 600 mg/mL of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 20% to about 55% by weight of one or more hard fats, about 15% to about 45% by weight of one or more liquid fats, and about 20% to about 45% by weight of one or more digestion enhancers. In some embodiments, the one or more digestion enhancers comprises one or more bile acids, one or more one or more free $C_{14-24}$ fatty acids, one or more one or more free $C_{14-24}$ fatty acid surfactants, or any combination thereof.

In some embodiments, a pharmaceutical comprises about 0.1% to about 30% by weight of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 20% to about 55% by weight of one or more hard fats comprising glycerolipids, about 15% to about 45% by weight of one or more liquid fats comprising partially hydrolyzed glycerolipids including a mixture of mono-, di- and triglycerides, and about 20% to about 45% by weight of one or more digestion enhancers. In some embodiments, a pharmaceutical comprises about 25 mg/mL to about 600 mg/mL of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 20% to about 55% by weight of one or more hard fats comprising glycerolipids, about 15% to about 45% by weight of one or more liquid fats comprising partially hydrolyzed glycerolipids including a mixture of mono-, di- and triglycerides, and about 20% to about 45% by weight of one or more digestion enhancers. In some embodiments, the one or more digestion enhancers comprises one or more bile acids, one or more one or more free $C_{14-24}$ fatty acids, one or more one or more free $C_{14-24}$ fatty acid surfactants, or any combination thereof.

In some embodiments, a pharmaceutical comprises about 0.1% to about 30% by weight of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 20% to about 55% by weight of one or more hard fats comprising $C_{10}$-$C_{24}$ triglycerides, about 15% to about 45% by weight of one or more liquid fats comprising partially hydrolyzed triglycerides including a mixture of $C_{10}$-$C_{24}$ mono-, $C_{10}$-$C_{24}$ di- and $C_{10}$-$C_{24}$ triglycerides, and about 20% to about 45% by weight of one or more digestion enhancers. In some embodiments, a pharmaceutical comprises about 25 mg/mL to about 600 mg/mL of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 20% to about 55% by weight of one or more hard fats comprising $C_{10}$-$C_{24}$ triglycerides, about 15% to about 45% by weight of one or more liquid fats comprising partially hydrolyzed triglycerides including a mixture of $C_{10}$-$C_{24}$ mono-, $C_{10}$-$C_{24}$ di- and $C_{10}$-$C_{24}$ triglycerides, and about 20% to about 45% by weight of one or more digestion enhancers. In some embodiments, the one or more digestion enhancers comprises one or more bile acids, one or more one or more free $C_{14-24}$ fatty acids, one or more one or more free $C_{14-24}$ fatty acid surfactants, or any combination thereof.

In some embodiments, a pharmaceutical comprises about 0.1% to about 30% by weight of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 20% to about 55% by weight of one or more hard fats comprising a mixture of saturated $C_{10}$-$C_{18}$ triglycerides and/or saturated $C_{12}$-$C_{18}$ triglycerides, about 15% to about 45% by weight of one or more liquid fats comprising partially hydrolyzed triglycerides including a mixture of $C_{16}$-$C_{18}$ mono-, $C_{16}$-$C_{18}$ di- and $C_{16}$-$C_{18}$ triglycerides, and about 20% to about 45% by weight of one or more digestion enhancers. In some embodiments, a pharmaceutical comprises about 25 mg/mL to about 600 mg/mL of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 20% to about 55% by weight of one or more hard fats comprising a mixture of saturated $C_{10}$-$C_{18}$ triglycerides and/or saturated $C_{12}$-$C_{18}$ triglycerides, about 15% to about 45% by weight of one or more liquid fats comprising partially hydrolyzed triglycerides including a mixture of $C_{16}$-$C_{18}$ mono-, $C_{16}$-$C_{18}$ di- and $C_{16}$-$C_{18}$ triglycerides, and about 20% to about 45% by weight of one or more digestion enhancers. In some embodiments, the one or more digestion enhancers comprises one or more bile acids, one or more one or more free $C_{14-24}$ fatty acids, one or more one or more free $C_{14-24}$ fatty acid surfactants, or any combination thereof.

In some embodiments, a pharmaceutical comprises abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, one or more hard fats, one or more liquid fats, and one or more bile acids. In some embodiments, the one or more bile acids in the above embodiments comprises cholic acid.

In some embodiments, a pharmaceutical comprises about 0.1% to about 20% by weight of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 25% to about 70% by weight of one or more hard fats, about 25% to about 70% by weight of one or more liquid fats, and about 0.1% to about 10% by weight of one or more bile acids. In some embodiments, a pharmaceutical comprises about 25 mg/mL to about 600 mg/mL of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 25% to about 70% by weight of one or more hard fats, about 25% to about 70% by weight of one or more liquid fats, and about 0.1% to about 10% by weight of one or more bile acids. In some embodiments, the one or more bile acids in the above embodiments comprises cholic acid.

In some embodiments, a pharmaceutical comprises about 0.1% to about 20% by weight of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 25% to about 70% by weight of one or more hard fats comprising glycerolipids, about 25% to about 70% by weight of one or more liquid fats comprising partially hydrolyzed glycerolipids including a mixture of mono-, di- and triglycerides, and about 0.1% to about 10% by weight of one or more bile acids. In some embodiments, a pharmaceutical comprises about 25 mg/mL to about 600 mg/mL of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 25% to about 70% by weight of one or more hard fats comprising glycerolipids, about 25% to about 70% by weight of one or more liquid fats comprising partially hydrolyzed glycerolipids including a mixture of mono-, di- and triglycerides, and about 0.1% to about 10% by weight of one or more bile acids. In some embodiments, the one or more bile acids in the above embodiments comprises cholic acid.

In some embodiments, a pharmaceutical comprises about 0.1% to about 20% by weight of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 25% to about 70% by weight of one or more hard fats comprising $C_{10}$-$C_{24}$ triglycerides, about 25% to about 70% by weight of one or more liquid fats comprising partially hydrolyzed triglycerides including a mixture of $C_{10}$-$C_{24}$ mono-, $C_{10}$-$C_{24}$ di- and $C_{10}$-$C_{24}$ triglycerides, and about 0.1% to about 10% by weight of one or more bile acids. In some embodiments, a pharmaceutical comprises about 25 mg/mL to about 600 mg/mL of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 25% to about 70% by weight of one or more hard fats comprising $C_{10}$-$C_{24}$ triglycerides, about 25% to about 70% by weight of one or more liquid fats comprising partially hydrolyzed triglycerides including a mixture of $C_{10}$-$C_{24}$ mono-, $C_{10}$-$C_{24}$ di- and $C_{10}$-$C_{24}$ triglycerides, and about 0.1% to about 10% by weight of one or more bile acids. In some embodiments, the one or more bile acids in the above embodiments comprises cholic acid.

In some embodiments, a pharmaceutical comprises about 0.1% to about 20% by weight of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 25% to about 70% by weight of one or more hard fats comprising a mixture of saturated $C_{10}$-$C_{18}$ triglycerides and/or saturated $C_{12}$-$C_{18}$ triglycerides, about 25% to about 70% by weight of one or more liquid fats comprising partially hydrolyzed triglycerides including a mixture of $C_{16}$-$C_{18}$ mono-, $C_{16}$-$C_{18}$ di- and $C_{16}$-$C_{18}$ triglycerides, and about 0.1% to about 10% by weight of one or more bile acids. In some embodiments, a pharmaceutical comprises about 25 mg/mL to about 600 mg/mL of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 25% to about 70% by weight of one or more hard fats comprising a mixture of saturated $C_{10}$-$C_{18}$ triglycerides and/or saturated $C_{12}$-$C_{18}$ triglycerides, about 25% to about 70% by weight of one or more liquid fats comprising partially hydrolyzed triglycerides including a mixture of $C_{16}$-$C_{18}$ mono-, $C_{16}$-$C_{18}$ di- and $C_{16}$-$C_{18}$ triglycerides, and about 0.1% to about 10% by weight of one or more bile acids. In some embodiments, the one or more bile acids in the above embodiments comprises cholic acid.

In some embodiments, a pharmaceutical comprises about 0.1% to about 20% by weight of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 35% to about 55% by weight of one or more hard fats, about 25% to about 50% by weight of one or more liquid fats, and about 0.1% to about 10% by weight of one or more bile acids. In some embodiments, a pharmaceutical comprises about 25 mg/mL to about 600 mg/mL of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 35% to about 55% by weight of one or more hard fats, about 25% to about 50% by weight of one or more liquid fats, and about 0.1% to about 10% by weight of one or more bile acids. In some embodiments, the one or more bile acids in the above embodiments comprises cholic acid.

In some embodiments, a pharmaceutical comprises about 0.1% to about 20% by weight of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 35% to about 55% by weight of one or more hard fats comprising glycerolipids, about 25% to about 50% by weight of one or more liquid fats comprising partially hydrolyzed glycerolipids including a mixture of mono-, di- and triglycerides, and about 0.1% to about 10% by weight of one or more bile acids. In some embodiments, a pharmaceutical comprises about 25 mg/mL to about 600 mg/mL of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 35% to about 55% by weight of one or more hard fats comprising glycerolipids, about 25% to about 50% by weight of one or more liquid fats comprising partially hydrolyzed glycerolipids including a mixture of mono-, di- and triglycerides, and about 0.1% to about 10% by weight of one or more bile acids. In some embodiments, the one or more bile acids in the above embodiments comprises cholic acid.

In some embodiments, a pharmaceutical comprises about 0.1% to about 20% by weight of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 35% to about 55% by weight of one or more hard fats comprising $C_{10}$-$C_{24}$ triglycerides, about 25% to about 50% by weight of one or more liquid fats comprising partially hydrolyzed triglycerides including a mixture of $C_{10}$-$C_{24}$ mono-, $C_{10}$-$C_{24}$ di- and $C_{10}$-$C_{24}$ triglycerides, and about 0.1% to about 10% by weight of one or more bile acids. In some embodiments, a pharmaceutical comprises about 25 mg/mL to about 600 mg/mL of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 35% to about 55% by weight of one or more hard fats comprising $C_{10}$-$C_{24}$ triglycerides, about 25% to about 50% by weight of one or more liquid fats comprising partially hydrolyzed triglycerides including a mixture of $C_{10}$-$C_{24}$ mono-, $C_{10}$-$C_{24}$ di- and $C_{10}$-$C_{24}$ triglycerides, and about 0.1% to about 10% by weight of one or more bile acids. In some embodiments, the one or more bile acids in the above embodiments comprises cholic acid.

In some embodiments, a pharmaceutical comprises about 0.1% to about 20% by weight of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 35% to about 55% by weight of one or more hard fats comprising a mixture of saturated $C_{10}$-$C_{18}$ triglycerides and/or saturated $C_{12}$-$C_{18}$ triglycerides, about 25% to about 50% by weight of one or more liquid fats comprising partially hydrolyzed triglycerides including a mixture of $C_{16}$-$C_{18}$ mono-, $C_{16}$-$C_{18}$ di- and $C_{16}$-$C_{18}$ triglycerides, and about 0.1% to about 10% by weight of one or more bile acids. In some embodiments, a pharmaceutical comprises about 25 mg/mL to about 600 mg/mL of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 35% to about 55% by weight of one or more hard fats comprising a mixture of saturated $C_{10}$-$C_{18}$ triglycerides and/or saturated $C_{12}$-$C_{18}$ triglycerides, about 25% to about 50% by weight of one or more liquid fats comprising partially hydrolyzed triglycerides including a mixture of $C_{16}$-$C_{18}$ mono-, $C_{16}$-$C_{18}$ di- and $C_{16}$-$C_{18}$ triglycerides, and about 0.1% to about 10% by weight of one or more bile acids. In some embodiments, the one or more bile acids in the above embodiments comprises cholic acid.

In some embodiments, a pharmaceutical comprises about 0.1% to about 30% by weight of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 15% to about 65% by weight of one or more hard fats, about 15% to about 50% by weight of one or more liquid fats, and about 0.1% to about 10% by weight of one or more bile acids. In some embodiments, a pharmaceutical comprises about 25 mg/mL to about 600 mg/mL of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 15% to about 65% by weight of one or more hard fats, about 15% to about 50% by weight of one or more liquid fats, and about 0.1% to about 10% by weight of one or more bile acids.

In some embodiments, a pharmaceutical comprises about 0.1% to about 30% by weight of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 15% to about 65% by weight of one or more hard fats comprising glycerolipids, about 15% to about 50% by weight of one or more liquid fats comprising partially hydrolyzed glycerolipids including a mixture of mono-, di- and triglycerides, and about 0.1% to about 10% by weight of one or more bile acids. In some embodiments, a pharmaceutical comprises about 25 mg/mL to about 600 mg/mL of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 15% to about 65% by weight of one or more hard fats comprising glycerolipids, about 15% to about 50% by weight of one or more liquid fats comprising partially hydrolyzed glycerolipids including a mixture of mono-, di- and triglycerides, and about 0.1% to about 10% by weight of one or more bile acids. In some embodiments, the one or more bile acids in the above embodiments comprises cholic acid.

In some embodiments, a pharmaceutical comprises about 0.1% to about 30% by weight of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 15% to about 65% by weight of one or more hard fats comprising $C_{10}$-$C_{24}$ triglycerides, about 15% to about 50% by weight of one or more liquid fats comprising partially hydrolyzed triglycerides including a mixture of $C_{10}$-$C_{24}$ mono-, $C_{10}$-$C_{24}$ di- and $C_{10}$-$C_{24}$ triglycerides, and about 0.1% to about 10% by weight of one or more bile acids. In some embodiments, a pharmaceutical comprises about 25 mg/mL to about 600 mg/mL of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 15% to about 65% by weight of one or more hard fats comprising $C_{10}$-$C_{24}$ triglycerides, about 15% to about 50% by weight of one or more liquid fats comprising partially hydrolyzed triglycerides including a mixture of $C_{10}$-$C_{24}$ mono-, $C_{10}$-$C_{24}$ di- and $C_{10}$-$C_{24}$ triglycerides, and about 0.1% to about 10% by weight of one or more bile acids. In some embodiments, the one or more bile acids in the above embodiments comprises cholic acid.

In some embodiments, a pharmaceutical comprises about 0.1% to about 30% by weight of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 15% to about 65% by weight of one or more hard fats comprising a mixture of saturated $C_{10}$-$C_{18}$ triglycerides and/or saturated $C_{12}$-$C_{18}$ triglycerides, about 15% to about 50% by weight of one or more liquid fats comprising partially hydrolyzed triglycerides including a mixture of $C_{16}$-$C_{18}$ mono-, $C_{16}$-$C_{18}$ di- and $C_{16}$-$C_{18}$ triglycerides, and about 0.1% to about 10% by weight of one or more bile acids. In some embodiments, a pharmaceutical comprises about 25 mg/mL to about 600 mg/mL of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 15% to about 65% by weight of one or more hard fats comprising a mixture of saturated $C_{10}$-$C_{18}$ triglycerides and/or saturated $C_{12}$-$C_{18}$ triglycerides, about 15% to about 50% by weight of one or more liquid fats comprising partially hydrolyzed triglycerides including a mixture of $C_{16}$-$C_{18}$ mono-, $C_{16}$-$C_{18}$ di- and $C_{16}$-$C_{18}$ triglycerides, and about 0.1% to about 10% by weight of one or more bile acids. In some embodiments, the one or more bile acids in the above embodiments comprises cholic acid.

In some embodiments, a pharmaceutical comprises about 0.1% to about 30% by weight of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 20% to about 55% by weight of one or more hard fats, about 15% to about 45% by weight of one or more liquid fats, and about 0.1% to about 10% by weight of one or more bile acids. In some embodiments, a pharmaceutical comprises about 25 mg/mL to about 600 mg/mL of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 20% to about 55% by weight of one or more hard fats, about 15% to about 45% by weight of one or more liquid fats, and about 0.1% to about 10% by weight of one or more bile acids. In some embodiments, the one or more bile acids in the above embodiments comprises cholic acid.

In some embodiments, a pharmaceutical comprises about 0.1% to about 30% by weight of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 20% to about 55% by weight of one or more hard fats comprising glycerolipids, about 15% to about 45% by weight of one or more liquid fats comprising partially hydrolyzed glycerolipids including a mixture of mono-, di- and triglycerides, and about 0.1% to about 10% by weight of one or more bile acids. In some embodiments, a pharmaceutical comprises about 25 mg/mL to about 600 mg/mL of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 20% to about 55% by weight of one or more hard fats comprising glycerolipids, about 15% to about 45% by weight of one or more liquid fats comprising partially hydrolyzed glycerolipids including a mixture of mono-, di- and triglycerides, and about 0.1% to about 10% by weight of one or more bile acids. In some embodiments, the one or more bile acids in the above embodiments comprises cholic acid.

In some embodiments, a pharmaceutical comprises about 0.1% to about 30% by weight of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 20% to about 55% by weight of one or more hard fats comprising $C_{10}$-$C_{24}$ triglycerides, about 15% to about 45% by weight of one or more liquid fats comprising partially hydrolyzed triglycerides including a mixture of $C_{10}$-$C_{24}$ mono-, $C_{10}$-$C_{24}$ di- and $C_{10}$-$C_{24}$ triglycerides, and about 0.1% to about 10% by weight of one or more bile acids. In some embodiments, a pharmaceutical comprises about 25 mg/mL to about 600 mg/mL of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 20% to about 55% by weight of one or more hard fats comprising $C_{10}$-$C_{24}$ triglycerides, about 15% to about 45% by weight of one or more liquid fats comprising partially hydrolyzed triglycerides including a mixture of $C_{10}$-$C_{24}$ mono-, $C_{10}$-$C_{24}$ di- and $C_{10}$-$C_{24}$ triglycerides, and about 0.1% to about 10% by weight of one or more bile acids. In some embodiments, the one or more bile acids in the above embodiments comprises cholic acid.

In some embodiments, a pharmaceutical comprises about 0.1% to about 30% by weight of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 20% to about 55% by weight of one or more hard fats comprising a mixture of saturated $C_{10}$-$C_{18}$ triglycerides and/or saturated $C_{12}$-$C_{18}$ triglycerides, about 15% to about 45% by weight of one or more liquid fats comprising partially hydrolyzed triglycerides including a mixture of $C_{16}$-$C_{18}$ mono-, $C_{16}$-$C_{18}$ di- and $C_{16}$-$C_{18}$ triglycerides, and about 0.1% to about 10% by weight of one or more bile acids. In some embodiments, a pharmaceutical comprises about 25 mg/mL to about 600 mg/mL of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 20% to about 55% by weight of one or more hard fats comprising a mixture of saturated $C_{10}$-$C_{18}$ triglycerides and/or saturated $C_{12}$-$C_{18}$ triglycerides, about 15% to about 45% by weight of one or more liquid fats comprising partially hydrolyzed triglycerides including a mixture of $C_{16}$-$C_{18}$ mono-, $C_{16}$-$C_{18}$ di- and $C_{16}$-$C_{18}$ triglycerides, and about 0.1% to about 10% by weight of one or more bile acids. In some embodiments, the one or more bile acids in the above embodiments comprises cholic acid.

In some embodiments, a pharmaceutical comprises abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, one or more hard fats, one or more liquid fats, one or more bile acids and one or more free $C_{14\text{-}24}$ fatty acids. In some embodiments, the one or more bile acids in the above embodiments comprises cholic acid. In some embodiments, the one or more free $C_{14\text{-}24}$ fatty acids in the above embodiments comprises one or more free $C_{14\text{-}18}$ fatty acids, preferably oleic acid, steric acid, linoleic acid, or any combination thereof. In some embodiments, the one or more bile acids in the above embodiments comprises cholic acid, and the one or more free $C_{14\text{-}24}$ fatty acids in the above embodiments comprises one or more free $C_{14\text{-}18}$ fatty acids, preferably oleic acid, steric acid, linoleic acid, or any combination thereof.

In some embodiments, a pharmaceutical comprises about 0.1% to about 20% by weight of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 25% to about 70% by weight of one or more hard fats, about 25% to about 70% by weight of one or more liquid fats, about 0.1% to about 10% by weight of one or more bile acids, and about 1% to about 10% by weight of one or more free $C_{14\text{-}24}$ fatty acids. In some embodiments, a pharmaceutical comprises about 25 mg/mL to about 600 mg/mL of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 25% to about 70% by weight of one or more hard fats, about 25% to about 70% by weight of one or more liquid fats, about 0.1% to about 10% by weight of one or more bile acids, and about 1% to about 10% by weight of one or more free $C_{14\text{-}24}$ fatty acids. In some embodiments, the one or more bile acids in the above embodiments comprises cholic acid. In some embodiments, the one or more free $C_{14\text{-}24}$ fatty acids in the above embodiments comprises one or more free $C_{14\text{-}18}$ fatty acids, preferably oleic acid, steric acid, linoleic acid, or any combination thereof. In some embodiments, the one or more bile acids in the above embodiments comprises cholic acid, and the one or more free $C_{14\text{-}24}$ fatty acids in the above embodiments comprises one or more free $C_{14\text{-}18}$ fatty acids, preferably oleic acid, steric acid, linoleic acid, or any combination thereof.

In some embodiments, a pharmaceutical comprises about 0.1% to about 20% by weight of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 25% to about 70% by weight of one or more hard fats comprising glycerolipids, about 25% to about 70% by weight of one or more liquid fats comprising partially hydrolyzed glycerolipids including a mixture of mono-, di- and triglycerides, about 0.1% to about 10% by weight of one or more bile acids, and about 1% to about 10% by weight of one or more free $C_{14\text{-}24}$ fatty acids. In some embodiments, a pharmaceutical comprises about 25 mg/mL to about 600 mg/mL of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 25% to about 70% by weight of one or more hard fats comprising glycerolipids, about 25% to about 70% by weight of one or more liquid fats comprising partially hydrolyzed glycerolipids including a mixture of mono-, di- and triglycerides, about 0.1% to about 10% by weight of one or more bile acids, and about 1% to about 10% by weight of one or more free $C_{14\text{-}24}$ fatty acids. In some embodiments, the one or more bile acids in the above embodiments comprises cholic acid. In some embodiments, the one or more free $C_{14\text{-}24}$ fatty acids in the above embodiments comprises one or more free $C_{14\text{-}18}$ fatty acids, preferably oleic acid, steric acid, linoleic acid, or any combination thereof. In some embodiments, the one or more bile acids in the above embodiments comprises cholic acid, and the one or more free $C_{14\text{-}24}$ fatty acids in the above embodiments comprises one or more free $C_{14\text{-}18}$ fatty acids, preferably oleic acid, steric acid, linoleic acid, or any combination thereof.

In some embodiments, a pharmaceutical comprises about 0.1% to about 20% by weight of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 25% to about 70% by weight of one or more hard fats comprising $C_{10}$-$C_{24}$ triglycerides, about 25% to about 70% by weight of one or more liquid fats comprising partially hydrolyzed triglycerides including a mixture of $C_{10}$-$C_{24}$ mono-, $C_{10}$-$C_{24}$ di- and $C_{10}$-$C_{24}$ triglycerides, about 0.1% to about 10% by weight of one or more bile acids, and about 1% to about 10% by weight of one or more free $C_{14-24}$ fatty acids. In some embodiments, a pharmaceutical comprises about 25 mg/mL to about 600 mg/mL of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 25% to about 70% by weight of one or more hard fats comprising $C_{10}$-$C_{24}$ triglycerides, about 25% to about 70% by weight of one or more liquid fats comprising partially hydrolyzed triglycerides including a mixture of $C_{10}$-$C_{24}$ mono-, $C_{10}$-$C_{24}$ di- and $C_{10}$-$C_{24}$ triglycerides, about 0.1% to about 10% by weight of one or more bile acids, and about 1% to about 10% by weight of one or more free $C_{14-24}$ fatty acids. In some embodiments, the one or more bile acids in the above embodiments comprises cholic acid. In some embodiments, the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more bile acids in the above embodiments comprises cholic acid, and the one or more free $C_{14-24}$ fatty acids in the above embodiments comprises one or more free $C_{14-18}$ fatty acids, preferably oleic acid, steric acid, linoleic acid, or any combination thereof.

In some embodiments, a pharmaceutical comprises about 0.1% to about 20% by weight of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 25% to about 70% by weight of one or more hard fats comprising a mixture of saturated $C_{10}$-$C_{18}$ triglycerides and/or saturated $C_{12}$-$C_{18}$ triglycerides, about 25% to about 70% by weight of one or more liquid fats comprising partially hydrolyzed triglycerides including a mixture of $C_{16}$-$C_{18}$ mono-, $C_{16}$-$C_{18}$ di- and $C_{16}$-$C_{18}$ triglycerides, about 0.1% to about 10% by weight of one or more bile acids, and about 1% to about 10% by weight of one or more free $C_{14-24}$ fatty acids. In some embodiments, a pharmaceutical comprises about 25 mg/mL to about 600 mg/mL of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 25% to about 70% by weight of one or more hard fats comprising a mixture of saturated $C_{10}$-$C_{18}$ triglycerides and/or saturated $C_{12}$-$C_{18}$ triglycerides, about 25% to about 70% by weight of one or more liquid fats comprising partially hydrolyzed triglycerides including a mixture of $C_{16}$-$C_{18}$ mono-, $C_{16}$-$C_{18}$ di- and $C_{16}$-$C_{18}$ triglycerides, about 0.1% to about 10% by weight of one or more bile acids, and about 1% to about 10% by weight of one or more free $C_{14-24}$ fatty acids. In some embodiments, the one or more bile acids in the above embodiments comprises cholic acid. In some embodiments, the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more bile acids in the above embodiments comprises cholic acid, and the one or more free $C_{14-24}$ fatty acids in the above embodiments comprises one or more free $C_{14-18}$ fatty acids, preferably oleic acid, steric acid, linoleic acid, or any combination thereof.

In some embodiments, a pharmaceutical comprises about 0.1% to about 20% by weight of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 35% to about 55% by weight of one or more hard fats, about 25% to about 50% by weight of one or more liquid fats, about 0.1% to about 10% by weight of one or more bile acids, and about 1% to about 30% by weight of one or more free $C_{14-24}$ fatty acids. In some embodiments, a pharmaceutical comprises about 25 mg/mL to about 600 mg/mL of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 35% to about 55% by weight of one or more hard fats, about 25% to about 50% by weight of one or more liquid fats, about 0.1% to about 10% by weight of one or more bile acids, and about 1% to about 30% by weight of one or more free $C_{14-24}$ fatty acids. In some embodiments, the one or more bile acids in the above embodiments comprises cholic acid. In some embodiments, the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more bile acids in the above embodiments comprises cholic acid, and the one or more free $C_{14-24}$ fatty acids in the above embodiments comprises one or more free $C_{14-18}$ fatty acids, preferably oleic acid, steric acid, linoleic acid, or any combination thereof.

In some embodiments, a pharmaceutical comprises about 0.1% to about 20% by weight of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 35% to about 55% by weight of one or more hard fats comprising glycerolipids, about 25% to about 50% by weight of one or more liquid fats comprising partially hydrolyzed glycerolipids including a mixture of mono-, di- and triglycerides, about 0.1% to about 10% by weight of one or more bile acids, and about 1% to about 30% by weight of one or more free $C_{14-24}$ fatty acids. In some embodiments, a pharmaceutical comprises about 25 mg/mL to about 600 mg/mL of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 35% to about 55% by weight of one or more hard fats comprising glycerolipids, about 25% to about 50% by weight of one or more liquid fats comprising partially hydrolyzed glycerolipids including a mixture of mono-, di- and triglycerides, about 0.1% to about 10% by weight of one or more bile acids, and about 1% to about 30% by weight of one or more free $C_{14-24}$ fatty acids. In some embodiments, the one or more bile acids in the above embodiments comprises cholic acid. In some embodiments, the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more bile acids in the above embodiments comprises cholic acid, and the one or more free $C_{14-24}$ fatty acids in the above embodiments comprises one or more free $C_{14-18}$ fatty acids, preferably oleic acid, steric acid, linoleic acid, or any combination thereof.

In some embodiments, a pharmaceutical comprises about 0.1% to about 20% by weight of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 35% to about 55% by weight of one or more hard fats comprising $C_{10}$-$C_{24}$ triglycerides, about 25% to about 50% by weight of one or more liquid fats comprising partially hydrolyzed triglycerides including a mixture of $C_{10}$-$C_{24}$ mono-, $C_{10}$-$C_{24}$ di- and $C_{10}$-$C_{24}$ triglycerides, about 0.1% to about 10% by weight of one or more bile acids, and about 1% to about 30% by weight of one or more free $C_{14-24}$ fatty acids. In some embodiments, a pharmaceutical comprises about 25 mg/mL to about 600 mg/mL of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 35% to about 55% by weight of one or more hard fats comprising $C_{10}$-$C_{24}$ triglycerides, about 25% to about 50% by weight of one or more liquid fats comprising partially hydrolyzed triglycerides including a mixture of $C_{10}$-$C_{24}$ mono-, $C_{10}$-$C_{24}$ di- and $C_{10}$-$C_{24}$ triglycerides, about 0.1% to about 10% by weight of one or more bile acids, and about 1% to about 30% by weight of one or more free $C_{14-24}$ fatty acids. In some embodiments, the one or more bile acids in the above embodiments comprises cholic acid. In some embodiments, the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more bile acids in the above embodiments comprises cholic acid, and the one or more free $C_{14-24}$ fatty acids in the above embodiments comprises one or more free $C_{14-18}$ fatty acids, preferably oleic acid, steric acid, linoleic acid, or any combination thereof.

In some embodiments, a pharmaceutical comprises about 0.1% to about 20% by weight of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 35% to about 55% by weight of one or more hard fats comprising a mixture of saturated $C_{10}$-$C_{18}$ triglycerides and/or saturated $C_{12}$-$C_{18}$ triglycerides, about 25% to about 50% by weight of one or more liquid fats comprising partially hydrolyzed triglycerides including a mixture of $C_{16}$-$C_{18}$ mono-, $C_{16}$-$C_{18}$ di- and $C_{16}$-$C_{18}$ triglycerides, about 0.1% to about 10% by weight of one or more bile acids, and about 1% to about 30% by weight of one or more free $C_{14-24}$ fatty acids. In some embodiments, a pharmaceutical comprises about 25 mg/mL to about 600 mg/mL of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 35% to about 55% by weight of one or more hard fats comprising a mixture of saturated $C_{10}$-$C_{18}$ triglycerides and/or saturated $C_{12}$-$C_{18}$ triglycerides, about 25% to about 50% by weight of one or more liquid fats comprising partially hydrolyzed triglycerides including a mixture of $C_{16}$-$C_{18}$ mono-, $C_{16}$-$C_{18}$ di- and $C_{16}$-$C_{18}$ triglycerides, about 0.1% to about 10% by weight of one or more bile acids, and about 1% to about 30% by weight of one or more free $C_{14-24}$ fatty acids. In some embodiments, the one or more bile acids in the above embodiments comprises cholic acid. In some embodiments, the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more bile acids in the above embodiments comprises cholic acid, and the one or more free $C_{14-24}$ fatty acids in the above embodiments comprises one or more free $C_{14-18}$ fatty acids, preferably oleic acid, steric acid, linoleic acid, or any combination thereof.

In some embodiments, a pharmaceutical comprises about 0.1% to about 30% by weight of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 15% to about 65% by weight of one or more hard fats, about 15% to about 50% by weight of one or more liquid fats, about 0.1% to about 10% by weight of one or more bile acids, and about 1% to about 25% by weight of one or more free $C_{14-24}$ fatty acids. In some embodiments, a pharmaceutical comprises about 25 mg/mL to about 600 mg/mL of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 15% to about 65% by weight of one or more hard fats, about 15% to about 50% by weight of one or more liquid fats, about 0.1% to about 10% by weight of one or more bile acids, and about 1% to about 25% by weight of one or more free $C_{14-24}$ fatty acids. In some embodiments, the one or more bile acids in the above embodiments comprises cholic acid. In some embodiments, the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more bile acids in the above embodiments comprises cholic acid, and the one or more free $C_{14-24}$ fatty acids in the above embodiments comprises one or more free $C_{14-18}$ fatty acids, preferably oleic acid, steric acid, linoleic acid, or any combination thereof.

In some embodiments, a pharmaceutical comprises about 0.1% to about 30% by weight of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 15% to about 65% by weight of one or more hard fats comprising glycerolipids, about 15% to about 50% by weight of one or more liquid fats comprising partially hydrolyzed glycerolipids including a mixture of mono-, di- and triglycerides, about 0.1% to about 10% by weight of one or more bile acids, and about 1% to about 25% by weight of one or more free $C_{14-24}$ fatty acids. In some embodiments, a pharmaceutical comprises about 25 mg/mL to about 600 mg/mL of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 15% to about 65% by weight of one or more hard fats comprising glycerolipids, about 15% to about 50% by weight of one or more liquid fats comprising partially hydrolyzed glycerolipids including a mixture of mono-, di- and triglycerides, about 0.1% to about 10% by weight of one or more bile acids, and about 1% to about 25% by weight of one or more free $C_{14-24}$ fatty acids. In some embodiments, the one or more bile acids in the above embodiments comprises cholic acid. In some embodiments, the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more bile acids in the above embodiments comprises cholic acid, and the one or more free $C_{14-24}$ fatty acids in the above embodiments comprises one or more free $C_{14-18}$ fatty acids, preferably oleic acid, steric acid, linoleic acid, or any combination thereof.

In some embodiments, a pharmaceutical comprises about 0.1% to about 30% by weight of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 15% to about 65% by weight of one or more hard fats comprising $C_{10}$-$C_{24}$ triglycerides, about 15% to about 50% by weight of one or more liquid fats comprising partially hydrolyzed triglycerides including a mixture of $C_{10}$-$C_{24}$ mono-, $C_{10}$-$C_{24}$ di- and $C_{10}$-$C_{24}$ triglycerides, about 0.1% to about 10% by weight of one or more bile acids, and about 1% to about 25% by weight of one or more free $C_{14-24}$ fatty acids. In some embodiments, a pharmaceutical comprises about 25 mg/mL to about 600 mg/mL of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 15% to about 65% by weight of one or more hard fats comprising $C_{10}$-$C_{24}$ triglycerides, about 15% to about 50% by weight of one or more liquid fats comprising partially hydrolyzed triglycerides including a mixture of $C_{10}$-$C_{24}$ mono-, $C_{10}$-$C_{24}$ di- and $C_{10}$-$C_{24}$ triglycerides, about 0.1% to about 10% by weight of one or more bile acids, and about 1% to about 25% by weight of one or more free $C_{14-24}$ fatty acids. In some embodiments, the one or more bile acids in the above embodiments comprises cholic acid. In some embodiments, the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more bile acids in the above embodiments comprises cholic acid, and the one or more free $C_{14-24}$ fatty acids in the above embodiments comprises one or more free $C_{14-18}$ fatty acids, preferably oleic acid, steric acid, linoleic acid, or any combination thereof.

In some embodiments, a pharmaceutical comprises about 0.1% to about 30% by weight of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 15% to about 65% by weight of one or more hard fats comprising a mixture of saturated $C_{10}$-$C_{18}$ triglycerides and/or saturated $C_{12}$-$C_{18}$ triglycerides, about 15% to about 50% by weight of one or more liquid fats comprising partially hydrolyzed triglycerides including a mixture of $C_{16}$-$C_{18}$ mono-, $C_{16}$-$C_{18}$ di- and $C_{16}$-$C_{18}$ triglycerides, about 0.1% to about 10% by weight of one or more bile acids, and about 1% to about 25% by weight of one or more free $C_{14-24}$ fatty acids. In some embodiments, a pharmaceutical comprises about 25 mg/mL to about 600 mg/mL of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 15% to about 65% by weight of one or more hard fats comprising a mixture of saturated $C_{10}$-$C_{18}$ triglycerides and/or saturated $C_{12}$-$C_{18}$ triglycerides, about 15% to about 50% by weight of one or more liquid fats comprising partially hydrolyzed triglycerides including a mixture of $C_{16}$-$C_{18}$ mono-, $C_{16}$-$C_{18}$ di- and $C_{16}$-$C_{18}$ triglycerides, about 0.1% to about 10% by weight of one or more bile acids, and about 1% to about 25% by weight of one or more free $C_{14-24}$ fatty acids. In some embodiments, the one or more bile acids in the above embodiments comprises cholic acid. In some embodiments, the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more bile acids in the above embodiments comprises cholic acid, and the one or more free $C_{14-24}$ fatty acids in the above embodiments comprises one or more free $C_{14-18}$ fatty acids, preferably oleic acid, steric acid, linoleic acid, or any combination thereof.

In some embodiments, a pharmaceutical comprises about 0.1% to about 30% by weight of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 20% to about 55% by weight of one or more hard fats, about 15% to about 45% by weight of one or more liquid fats, about 0.1% to about 10% by weight of one or more bile acids, and about 10% to about 45% by weight of one or more free $C_{14-24}$ fatty acids. In some embodiments, a pharmaceutical comprises about 25 mg/mL to about 600 mg/mL of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 20% to about 55% by weight of one or more hard fats, about 15% to about 45% by weight of one or more liquid fats, about 0.1% to about 10% by weight of one or more bile acids, and about 10% to about 45% by weight of one or more free $C_{14-24}$ fatty acids. In some embodiments, the one or more bile acids in the above embodiments comprises cholic acid. In some embodiments, the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more bile acids in the above embodiments comprises cholic acid, and the one or more free $C_{14-24}$ fatty acids in the above embodiments comprises one or more free $C_{14-18}$ fatty acids, preferably oleic acid, steric acid, linoleic acid, or any combination thereof.

In some embodiments, a pharmaceutical comprises about 0.1% to about 30% by weight of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 20% to about 55% by weight of one or more hard fats comprising glycerolipids, about 15% to about 45% by weight of one or more liquid fats comprising partially hydrolyzed glycerolipids including a mixture of mono-, di- and triglycerides, about 0.1% to about 10% by weight of one or more bile acids, and about 10% to about 45% by weight of one or more free $C_{14-24}$ fatty acids. In some embodiments, a pharmaceutical comprises about 25 mg/mL to about 600 mg/mL of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 20% to about 55% by weight of one or more hard fats comprising glycerolipids, about 15% to about 45% by weight of one or more liquid fats comprising partially hydrolyzed glycerolipids including a mixture of mono-, di- and triglycerides, about 0.1% to about 10% by weight of one or more bile acids, and about 10% to about 45% by weight of one or more free $C_{14-24}$ fatty acids. In some embodiments, the one or more bile acids in the above embodiments comprises cholic acid. In some embodiments, the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more bile acids in the above embodiments comprises cholic acid, and the one or more free $C_{14-24}$ fatty acids in the above embodiments comprises one or more free $C_{14-18}$ fatty acids, preferably oleic acid, steric acid, linoleic acid, or any combination thereof.

In some embodiments, a pharmaceutical comprises about 0.1% to about 30% by weight of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 20% to about 55% by weight of one or more hard fats comprising $C_{10}$-$C_{24}$ triglycerides, about 15% to about 45% by weight of one or more liquid fats comprising partially hydrolyzed triglycerides including a mixture of $C_{10}$-$C_{24}$ mono-, $C_{10}$-$C_{24}$ di- and $C_{10}$-$C_{24}$ triglycerides, about 0.1% to about 10% by weight of one or more bile acids, and about 10% to about 45% by weight of one or more free $C_{14-24}$ fatty acids. In some embodiments, a pharmaceutical comprises about 25 mg/mL to about 600 mg/mL of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 20% to about 55% by weight of one or more hard fats comprising $C_{10}$-$C_{24}$ triglycerides, about 15% to about 45% by weight of one or more liquid fats comprising partially hydrolyzed triglycerides including a mixture of $C_{10}$-$C_{24}$ mono-, $C_{10}$-$C_{24}$ di- and $C_{10}$-$C_{24}$ triglycerides, about 0.1% to about 10% by weight of one or more bile acids, and about 10% to about 45% by weight of one or more free $C_{14-24}$ fatty acids. In some embodiments, the one or more bile acids in the above embodiments comprises cholic acid. In some embodiments, the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more bile acids in the above embodiments comprises cholic acid, and the one or more free $C_{14-24}$ fatty acids in the above embodiments comprises one or more free $C_{14-18}$ fatty acids, preferably oleic acid, steric acid, linoleic acid, or any combination thereof.

In some embodiments, a pharmaceutical comprises about 0.1% to about 30% by weight of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 20% to about 55% by weight of one or more hard fats comprising a mixture of saturated $C_{10}$-$C_{18}$ triglycerides and/or saturated $C_{12}$-$C_{18}$ triglycerides, about 15% to about 45% by weight of one or more liquid fats comprising partially hydrolyzed triglycerides including a mixture of $C_{16}$-$C_{18}$ mono-, $C_{16}$-$C_{18}$ di- and $C_{16}$-$C_{18}$ triglycerides, about 0.1% to about 10% by weight of one or more bile acids, and about 10% to about 45% by weight of one or more free $C_{14-24}$ fatty acids. In some embodiments, a pharmaceutical comprises about 25 mg/mL to about 600 mg/mL of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 20% to about 55% by weight of one or more hard fats comprising a mixture of saturated $C_{10}$-$C_{18}$ triglycerides and/or saturated $C_{12}$-$C_{18}$ triglycerides, about 15% to about 45% by weight of one or more liquid fats comprising partially hydrolyzed triglycerides including a mixture of $C_{16}$-$C_{18}$ mono-, $C_{16}$-$C_{18}$ di- and $C_{16}$-$C_{18}$ triglycerides, about 0.1% to about 10% by weight of one or more bile acids, and about 10% to about 45% by weight of one or more free $C_{14-24}$ fatty acids. In some embodiments, the one or more bile acids in the above embodiments comprises cholic acid. In some embodiments, the one or more free $C_{14-24}$ fatty acids in the above embodiments comprises one or more free $C_{14-18}$ fatty acids, preferably oleic acid, steric acid, linoleic acid, or any combination thereof.

In some embodiments, the one or more bile acids in the above embodiments comprises cholic acid, and the one or more free $C_{14-24}$ fatty acids in the above embodiments comprises one or more free $C_{14-18}$ fatty acids, preferably oleic acid, steric acid, linoleic acid, or any combination thereof.

In some embodiments, a pharmaceutical comprises abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, one or more hard fats, one or more liquid fats, one or more bile acids, and one or more free $C_{14-24}$ fatty acid surfactants. In some embodiments, the one or more bile acids in the above embodiments comprises cholic acid. In some embodiments, the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more bile acids in the above embodiments comprises cholic acid, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof.

In some embodiments, a pharmaceutical comprises about 0.1% to about 20% by weight of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 25% to about 70% by weight of one or more hard fats, about 25% to about 70% by weight of one or more liquid fats, about 0.1% to about 10% by weight of one or more bile acids, and about 0.1% to about 5% by weight of one or more free $C_{14-24}$ fatty acid surfactants. In some embodiments, a pharmaceutical comprises about 25 mg/mL to about 600 mg/mL of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 25% to about 70% by weight of one or more hard fats, about 25% to about 70% by weight of one or more liquid fats, about 0.1% to about 10% by weight of one or more bile acids, and about 0.1% to about 5% by weight of one or more free $C_{14-24}$ fatty acid surfactants. In some embodiments, the one or more bile acids in the above embodiments comprises cholic acid. In some embodiments, the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more bile acids in the above embodiments comprises cholic acid, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof.

In some embodiments, a pharmaceutical comprises about 0.1% to about 20% by weight of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 25% to about 70% by weight of one or more hard fats comprising glycerolipids, about 25% to about 70% by weight of one or more liquid fats comprising partially hydrolyzed glycerolipids including a mixture of mono-, di- and triglycerides, about 0.1% to about 10% by weight of one or more bile acids, and about 0.1% to about 5% by weight of one or more free $C_{14-24}$ fatty acid surfactants. In some embodiments, a pharmaceutical comprises about 25 mg/mL to about 600 mg/mL of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 25% to about 70% by weight of one or more hard fats comprising glycerolipids, about 25% to about 70% by weight of one or more liquid fats comprising partially hydrolyzed glycerolipids including a mixture of mono-, di- and triglycerides, about 0.1% to about 10% by weight of one or more bile acids, and about 0.1% to about 5% by weight of one or more free $C_{14-24}$ fatty acid surfactants. In some embodiments, the one or more bile acids in the above embodiments comprises cholic acid. In some embodiments, the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more bile acids in the above embodiments comprises cholic acid, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof.

In some embodiments, a pharmaceutical comprises about 0.1% to about 20% by weight of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 25% to about 70% by weight of one or more hard fats comprising $C_{10}$-$C_{24}$ triglycerides, about 25% to about 70% by weight of one or more liquid fats comprising partially hydrolyzed triglycerides including a mixture of $C_{10}$-$C_{24}$ mono-, $C_{10}$-$C_{24}$ di- and $C_{10}$-$C_{24}$ triglycerides, about 0.1% to about 10% by weight of one or more bile acids, and about 0.1% to about 5% by weight of one or more free $C_{14-24}$ fatty acid surfactants. In some embodiments, a pharmaceutical comprises about 25 mg/mL to about 600 mg/mL of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 25% to about 70% by weight of one or more hard fats comprising $C_{10}$-$C_{24}$ triglycerides, about 25% to about 70% by weight of one or more liquid fats comprising partially hydrolyzed triglycerides including a mixture of $C_{10}$-$C_{24}$ mono-, $C_{10}$-$C_{24}$ di- and $C_{10}$-$C_{24}$ triglycerides, about 0.1% to about 10% by weight of one or more bile acids, about 0.1% to about 5% by weight of one or more free $C_{14-24}$ fatty acid surfactants. In some embodiments, the one or more bile acids in the above embodiments comprises cholic acid. In some embodiments, the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more bile acids in the above embodiments comprises cholic acid, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof.

In some embodiments, a pharmaceutical comprises about 0.1% to about 20% by weight of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 25% to about 70% by weight of one or more hard fats comprising a mixture of saturated $C_{10}$-$C_{18}$ triglycerides and/or saturated $C_{12}$-$C_{18}$ triglycerides, about 25% to about 70% by weight of one or more liquid fats comprising partially hydrolyzed triglycerides including a mixture of $C_{16}$-$C_{18}$ mono-, $C_{16}$-$C_{18}$ di- and $C_{16}$-$C_{18}$ triglycerides, about 0.1% to about 10% by weight of one or more bile acids, and about 0.1% to about 5% by weight of one or more free $C_{14-24}$ fatty acid surfactants. In some embodiments, a pharmaceutical comprises about 25 mg/mL to about 600 mg/mL of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 25% to about 70% by weight of one or more hard fats comprising a mixture of saturated $C_{10}$-$C_{18}$ triglycerides and/or saturated $C_{12}$-$C_{18}$ triglycerides, about 25% to about 70% by weight of one or more liquid fats comprising partially hydrolyzed triglycerides including a mixture of $C_{16}$-$C_{18}$ mono-, $C_{16}$-$C_{18}$ di- and $C_{16}$-$C_{18}$ triglycerides, about 0.1% to about 10% by weight of one or more bile acids, and about 0.1% to about 5% by weight of one or more free $C_{14-24}$ fatty acid surfactants. In some embodiments, the one or more bile acids in the above embodiments comprises cholic acid. In some embodiments, the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more bile acids in the above embodiments comprises cholic acid, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof.

In some embodiments, a pharmaceutical comprises about 0.1% to about 20% by weight of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 35% to about 55% by weight of one or more hard fats, about 25% to about 50% by weight of one or more liquid fats, about 0.1% to about 10% by weight of one or more bile acids, and about 0.1% to about 5% by weight of one or more free $C_{14-24}$ fatty acid surfactants. In some embodiments, a pharmaceutical comprises about 25 mg/mL to about 600 mg/mL of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 35% to about 55% by weight of one or more hard fats, about 25% to about 50% by weight of one or more liquid fats, about 0.1% to about 10% by weight of one or more bile acids, and about 0.1% to about 5% by weight of one or more free $C_{14-24}$ fatty acid surfactants. In some embodiments, the one or more bile acids in the above embodiments comprises cholic acid. In some embodiments, the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more bile acids in the above embodiments comprises cholic acid, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof.

In some embodiments, a pharmaceutical comprises about 0.1% to about 20% by weight of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 35% to about 55% by weight of one or more hard fats comprising glycerolipids, about 25% to about 50% by weight of one or more liquid fats comprising partially hydrolyzed glycerolipids including a mixture of mono-, di- and triglycerides, about 0.1% to about 10% by weight of one or more bile acids, and about 0.1% to about 5% by weight of one or more free $C_{14-24}$ fatty acid surfactants. In some embodiments, a pharmaceutical comprises about 25 mg/mL to about 600 mg/mL of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 35% to about 55% by weight of one or more hard fats comprising glycerolipids, about 25% to about 50% by weight of one or more liquid fats comprising partially hydrolyzed glycerolipids including a mixture of mono-, di- and triglycerides, about 0.1% to about 10% by weight of one or more bile acids, and about 0.1% to about 5% by weight of one or more free $C_{14-24}$ fatty acid surfactants. In some embodiments, the one or more bile acids in the above embodiments comprises cholic acid. In some embodiments, the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more bile acids in the above embodiments comprises cholic acid, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof.

In some embodiments, a pharmaceutical comprises about 0.1% to about 20% by weight of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 35% to about 55% by weight of one or more hard fats comprising $C_{10}$-$C_{24}$ triglycerides, about 25% to about 50% by weight of one or more liquid fats comprising partially hydrolyzed triglycerides including a mixture of $C_{10}$-$C_{24}$ mono-, $C_{10}$-$C_{24}$ di- and $C_{10}$-$C_{24}$ triglycerides, about 0.1% to about 10% by weight of one or more bile acids, and about 0.1% to about 5% by weight of one or more free $C_{14-24}$ fatty acid surfactants. In some embodiments, a pharmaceutical comprises about 25 mg/mL to about 600 mg/mL of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 35% to about 55% by weight of one or more hard fats comprising $C_{10}$-$C_{24}$ triglycerides, about 25% to about 50% by weight of one or more liquid fats comprising partially hydrolyzed triglycerides including a mixture of $C_{10}$-$C_{24}$ mono-, $C_{10}$-$C_{24}$ di- and $C_{10}$-$C_{24}$ triglycerides, about 0.1% to about 10% by weight of one or more bile acids, about 0.1% to about 5% by weight of one or more free $C_{14-24}$ fatty acid surfactants. In some embodiments, the one or more bile acids in the above embodiments comprises cholic acid. In some embodiments, the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more bile acids in the above embodiments comprises cholic acid, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof.

In some embodiments, a pharmaceutical comprises about 0.1% to about 20% by weight of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 35% to about 55% by weight of one or more hard fats comprising a mixture of saturated $C_{10}$-$C_{18}$ triglycerides and/or saturated $C_{12}$-$C_{18}$ triglycerides, about 25% to about 50% by weight of one or more liquid fats comprising partially hydrolyzed triglycerides including a mixture of $C_{16}$-$C_{18}$ mono-, $C_{16}$-$C_{18}$ di- and $C_{16}$-$C_{18}$ triglycerides, about 0.1% to about 10% by weight of one or more bile acids, and about 0.1% to about 5% by weight of one or more free $C_{14-24}$ fatty acid surfactants. In some embodiments, a pharmaceutical comprises about 25 mg/mL to about 600 mg/mL of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 35% to about 55% by weight of one or more hard fats comprising a mixture of saturated $C_{10}$-$C_{18}$ triglycerides and/or saturated $C_{12}$-$C_{18}$ triglycerides, about 25% to about 50% by weight of one or more liquid fats comprising partially hydrolyzed triglycerides including a mixture of $C_{16}$-$C_{18}$ mono-, $C_{16}$-$C_{18}$ di- and $C_{16}$-$C_{18}$ triglycerides, about 0.1% to about 10% by weight of one or more bile acids, and about 0.1% to about 5% by weight of one or more free $C_{14-24}$ fatty acid surfactants. In some embodiments, the one or more bile acids in the above embodiments comprises cholic acid. In some embodiments, the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more bile acids in the above embodiments comprises cholic acid, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof.

In some embodiments, a pharmaceutical comprises about 0.1% to about 30% by weight of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 15% to about 65% by weight of one or more hard fats, about 15% to about 50% by weight of one or more liquid fats, about 0.1% to about 10% by weight of one or more bile acids, and about 0.1% to about 5% by weight of one or more free $C_{14-24}$ fatty acid surfactants. In some embodiments, a pharmaceutical comprises about 25 mg/mL to about 600 mg/mL of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 15% to about 65% by weight of one or more hard fats, about 15% to about 50% by weight of one or more liquid fats, about 0.1% to about 10% by weight of one or more bile acids, and about 0.1% to about 5% by weight of one or more free $C_{14-24}$ fatty acid surfactants. In some embodiments, the one or more bile acids in the above embodiments comprises cholic acid. In some embodiments, the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more bile acids in the above embodiments comprises cholic acid, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof.

In some embodiments, a pharmaceutical comprises about 0.1% to about 30% by weight of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 15% to about 65% by weight of one or more hard fats comprising glycerolipids, about 15% to about 50% by weight of one or more liquid fats comprising partially hydrolyzed glycerolipids including a mixture of mono-, di- and triglycerides, about 0.1% to about 10% by weight of one or more bile acids, and about 0.1% to about 5% by weight of one or more free $C_{14-24}$ fatty acid surfactants. In some embodiments, a pharmaceutical comprises about 25 mg/mL to about 600 mg/mL of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 15% to about 65% by weight of one or more hard fats comprising glycerolipids, about 15% to about 50% by weight of one or more liquid fats comprising partially hydrolyzed glycerolipids including a mixture of mono-, di- and triglycerides, about 0.1% to about 10% by weight of one or more bile acids, and about 0.1% to about 5% by weight of one or more free $C_{14-24}$ fatty acid surfactants. In some embodiments, the one or more bile acids in the above embodiments comprises cholic acid. In some embodiments, the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more bile acids in the above embodiments comprises cholic acid, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof.

In some embodiments, a pharmaceutical comprises about 0.1% to about 30% by weight of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 15% to about 65% by weight of one or more hard fats comprising $C_{10}$-$C_{24}$ triglycerides, about 15% to about 50% by weight of one or more liquid fats comprising partially hydrolyzed triglycerides including a mixture of $C_{10}$-$C_{24}$ mono-, $C_{10}$-$C_{24}$ di- and $C_{10}$-$C_{24}$ triglycerides, about 0.1% to about 10% by weight of one or more bile acids, and about 0.1% to about 5% by weight of one or more free $C_{14-24}$ fatty acid surfactants. In some embodiments, a pharmaceutical comprises about 25 mg/mL to about 600 mg/mL of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 15% to about 65% by weight of one or more hard fats comprising $C_{10}$-$C_{24}$ triglycerides, about 15% to about 50% by weight of one or more liquid fats comprising partially hydrolyzed triglycerides including a mixture of $C_{10}$-$C_{24}$ mono-, $C_{10}$-$C_{24}$ di- and $C_{10}$-$C_{24}$ triglycerides, about 0.1% to about 10% by weight of one or more bile acids, about 0.1% to about 5% by weight of one or more free $C_{14-24}$ fatty acid surfactants. In some embodiments, the one or more bile acids in the above embodiments comprises cholic acid. In some embodiments, the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more bile acids in the above embodiments comprises cholic acid, and the one or more free $C_{14\text{-}24}$ fatty acid surfactants in the above embodiments comprises one or more free $C_{14\text{-}18}$ fatty acid surfactants, preferably an oleate alkali metal or alkali earth metal salt, a stearate alkali metal or alkali earth metal salt, a linoleate alkali metal or alkali earth metal salt, or any combination thereof.

In some embodiments, a pharmaceutical comprises about 0.1% to about 30% by weight of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 15% to about 65% by weight of one or more hard fats comprising a mixture of saturated $C_{10}\text{-}C_{18}$ triglycerides and/or saturated $C_{12}\text{-}C_{18}$ triglycerides, about 15% to about 50% by weight of one or more liquid fats comprising partially hydrolyzed triglycerides including a mixture of $C_{16}\text{-}C_{18}$ mono-, $C_{16}\text{-}C_{18}$ di- and $C_{16}\text{-}C_{18}$ triglycerides, about 0.1% to about 10% by weight of one or more bile acids, and about 0.1% to about 5% by weight of one or more free $C_{14\text{-}24}$ fatty acid surfactants. In some embodiments, a pharmaceutical comprises about 25 mg/mL to about 600 mg/mL of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 15% to about 65% by weight of one or more hard fats comprising a mixture of saturated $C_{10}\text{-}C_{18}$ triglycerides and/or saturated $C_{12}\text{-}C_{18}$ triglycerides, about 15% to about 50% by weight of one or more liquid fats comprising partially hydrolyzed triglycerides including a mixture of $C_{16}\text{-}C_{18}$ mono-, $C_{16}\text{-}C_{18}$ di- and $C_{16}\text{-}C_{18}$ triglycerides, about 0.1% to about 10% by weight of one or more bile acids, and about 0.1% to about 5% by weight of one or more free $C_{14\text{-}24}$ fatty acid surfactants. In some embodiments, the one or more bile acids in the above embodiments comprises cholic acid. In some embodiments, the one or more free $C_{14\text{-}24}$ fatty acid surfactants in the above embodiments comprises one or more free $C_{14\text{-}18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more bile acids in the above embodiments comprises cholic acid, and the one or more free $C_{14\text{-}24}$ fatty acid surfactants in the above embodiments comprises one or more free $C_{14\text{-}18}$ fatty acid surfactants, preferably an oleate alkali metal or alkali earth metal salt, a stearate alkali metal or alkali earth metal salt, a linoleate alkali metal or alkali earth metal salt, or any combination thereof.

In some embodiments, a pharmaceutical comprises about 0.1% to about 30% by weight of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 20% to about 55% by weight of one or more hard fats, about 15% to about 45% by weight of one or more liquid fats, about 0.1% to about 10% by weight of one or more bile acids, and about 0.1% to about 5% by weight of one or more free $C_{14\text{-}24}$ fatty acid surfactants. In some embodiments, a pharmaceutical comprises about 25 mg/mL to about 600 mg/mL of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 20% to about 55% by weight of one or more hard fats, about 15% to about 45% by weight of one or more liquid fats, about 0.1% to about 10% by weight of one or more bile acids, and about 0.1% to about 5% by weight of one or more free $C_{14\text{-}24}$ fatty acid surfactants. In some embodiments, the one or more bile acids in the above embodiments comprises cholic acid. In some embodiments, the one or more free $C_{14\text{-}24}$ fatty acid surfactants in the above embodiments comprises one or more free $C_{14\text{-}18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more bile acids in the above embodiments comprises cholic acid, and the one or more free $C_{14\text{-}24}$ fatty acid surfactants in the above embodiments comprises one or more free $C_{14\text{-}18}$ fatty acid surfactants, preferably an oleate alkali metal or alkali earth metal salt, a stearate alkali metal or alkali earth metal salt, a linoleate alkali metal or alkali earth metal salt, or any combination thereof.

In some embodiments, a pharmaceutical comprises about 0.1% to about 30% by weight of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 20% to about 55% by weight of one or more hard fats comprising glycerolipids, about 15% to about 45% by weight of one or more liquid fats comprising partially hydrolyzed glycerolipids including a mixture of mono-, di- and triglycerides, about 0.1% to about 10% by weight of one or more bile acids, and about 0.1% to about 5% by weight of one or more free $C_{14\text{-}24}$ fatty acid surfactants. In some embodiments, a pharmaceutical comprises about 25 mg/mL to about 600 mg/mL of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 20% to about 55% by weight of one or more hard fats comprising glycerolipids, about 15% to about 45% by weight of one or more liquid fats comprising partially hydrolyzed glycerolipids including a mixture of mono-, di- and triglycerides, about 0.1% to about 10% by weight of one or more bile acids, and about 0.1% to about 5% by weight of one or more free $C_{14\text{-}24}$ fatty acid surfactants. In some embodiments, the one or more bile acids in the above embodiments comprises cholic acid. In some embodiments, the one or more free $C_{14\text{-}24}$ fatty acid surfactants in the above embodiments comprises one or more free $C_{14\text{-}18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more bile acids in the above embodiments comprises cholic acid, and the one or more free $C_{14\text{-}24}$ fatty acid surfactants in the above embodiments comprises one or more free $C_{14\text{-}18}$ fatty acid surfactants, preferably an oleate alkali metal or alkali earth metal salt, a stearate alkali metal or alkali earth metal salt, a linoleate alkali metal or alkali earth metal salt, or any combination thereof.

In some embodiments, a pharmaceutical comprises about 0.1% to about 30% by weight of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 20% to about 55% by weight of one or more hard fats comprising $C_{10}\text{-}C_{24}$ triglycerides, about 15% to about 45% by weight of one or more liquid fats comprising partially hydrolyzed triglycerides including a mixture of $C_{10}$-$C_{24}$ mono-, $C_{10}$-$C_{24}$ di- and $C_{10}$-$C_{24}$ triglycerides, about 0.1% to about 10% by weight of one or more bile acids, and about 0.1% to about 5% by weight of one or more free $C_{14-24}$ fatty acid surfactants. In some embodiments, a pharmaceutical comprises about 25 mg/mL to about 600 mg/mL of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 20% to about 55% by weight of one or more hard fats comprising $C_{10}$-$C_{24}$ triglycerides, about 15% to about 45% by weight of one or more liquid fats comprising partially hydrolyzed triglycerides including a mixture of $C_{10}$-$C_{24}$ mono-, $C_{10}$-$C_{24}$ di- and $C_{10}$-$C_{24}$ triglycerides, about 0.1% to about 10% by weight of one or more bile acids, about 0.1% to about 5% by weight of one or more free $C_{14-24}$ fatty acid surfactants. In some embodiments, the one or more bile acids in the above embodiments comprises cholic acid. In some embodiments, the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more bile acids in the above embodiments comprises cholic acid, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof.

In some embodiments, a pharmaceutical comprises about 0.1% to about 30% by weight of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 20% to about 55% by weight of one or more hard fats comprising a mixture of saturated $C_{10}$-$C_{18}$ triglycerides and/or saturated $C_{12}$-$C_{18}$ triglycerides, about 15% to about 45% by weight of one or more liquid fats comprising partially hydrolyzed triglycerides including a mixture of $C_{16}$-$C_{18}$ mono-, $C_{16}$-$C_{18}$ di- and $C_{16}$-$C_{18}$ triglycerides, about 0.1% to about 10% by weight of one or more bile acids, and about 0.1% to about 5% by weight of one or more free $C_{14-24}$ fatty acid surfactants. In some embodiments, a pharmaceutical comprises about 25 mg/mL to about 600 mg/mL of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 20% to about 55% by weight of one or more hard fats comprising a mixture of saturated $C_{10}$-$C_{18}$ triglycerides and/or saturated $C_{12}$-$C_{18}$ triglycerides, about 15% to about 45% by weight of one or more liquid fats comprising partially hydrolyzed triglycerides including a mixture of $C_{16}$-$C_{18}$ mono-, $C_{16}$-$C_{18}$ di- and $C_{16}$-$C_{18}$ triglycerides, about 0.1% to about 10% by weight of one or more bile acids, and about 0.1% to about 5% by weight of one or more free $C_{14-24}$ fatty acid surfactants. In some embodiments, the one or more bile acids in the above embodiments comprises cholic acid. In some embodiments, the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more bile acids in the above embodiments comprises cholic acid, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof.

In some embodiments, a pharmaceutical comprises abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, one or more hard fats, one or more liquid fats, one or more bile acids, one or more free $C_{14-24}$ fatty acids, and one or more free $C_{14-24}$ fatty acid surfactants. In some embodiments, the one or more bile acids in the above embodiments comprises cholic acid. In some embodiments, the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more bile acids in the above embodiments comprises cholic acid and the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more bile acids in the above embodiments comprises cholic acid and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more free $C_{14-24}$ fatty acids in the above embodiments comprises one or more free $C_{14-18}$ fatty acids, preferably oleic acid, steric acid, linoleic acid, or any combination thereof, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more bile acids in the above embodiments comprises cholic acid, the one or more free $C_{14-24}$ fatty acids in the above embodiments comprises one or more free $C_{14-18}$ fatty acids, preferably oleic acid, steric acid, linoleic acid, or any combination thereof, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof.

In some embodiments, a pharmaceutical comprises about 0.1% to about 20% by weight of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 25% to about 70% by weight of one or more hard fats, about 25% to about 70% by weight of one or more liquid fats, about 0.1% to about 10% by weight of one or more bile acids, about 10% to about 25% by weight of one or more free $C_{14-24}$ fatty acids, and about 0.1% to about 5% by weight of one or more free $C_{14-24}$ fatty acid surfactants. In some embodiments, a pharmaceutical comprises about 25 mg/mL to about 600 mg/mL of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 25% to about 70% by weight of one or more hard fats, about 25% to about 70% by weight of one or more liquid fats, about 0.1% to about 10% by weight of one or more bile acids, about 10% to about 25% by weight of one or more free $C_{14-24}$ fatty acids, and about 0.1% to about 5% by weight of one or more free $C_{14-24}$ fatty acid surfactants. In some embodiments, the one or more bile acids in the above embodiments comprises cholic acid. In some embodiments, the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more bile acids in the above embodiments comprises cholic acid and the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more bile acids in the above embodiments comprises cholic acid and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more free $C_{14-24}$ fatty acids in the above embodiments comprises one or more free $C_{14-18}$ fatty acids, preferably oleic acid, steric acid, linoleic acid, or any combination thereof, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more bile acids in the above embodiments comprises cholic acid, the one or more free $C_{14-24}$ fatty acids in the above embodiments comprises one or more free $C_{14-18}$ fatty acids, preferably oleic acid, steric acid, linoleic acid, or any combination thereof, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof.

In some embodiments, a pharmaceutical comprises about 0.1% to about 20% by weight of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 25% to about 70% by weight of one or more hard fats comprising glycerolipids, about 25% to about 70% by weight of one or more liquid fats comprising partially hydrolyzed glycerolipids including a mixture of mono-, di- and triglycerides, about 0.1% to about 10% by weight of one or more bile acids, about 10% to about 25% by weight of one or more free $C_{14-24}$ fatty acids, and about 0.1% to about 5% by weight of one or more free $C_{14-24}$ fatty acid surfactants. In some embodiments, a pharmaceutical comprises about 25 mg/mL to about 600 mg/mL of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 25% to about 70% by weight of one or more hard fats comprising glycerolipids, about 25% to about 70% by weight of one or more liquid fats comprising partially hydrolyzed glycerolipids including a mixture of mono-, di- and triglycerides, about 0.1% to about 10% by weight of one or more bile acids, about 10% to about 25% by weight of one or more free $C_{14-24}$ fatty acids, and about 0.1% to about 5% by weight of one or more free $C_{14-24}$ fatty acid surfactants. In some embodiments, the one or more bile acids in the above embodiments comprises cholic acid. In some embodiments, the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more bile acids in the above embodiments comprises cholic acid and the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more bile acids in the above embodiments comprises cholic acid and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more free $C_{14-24}$ fatty acids in the above embodiments comprises one or more free $C_{14-18}$ fatty acids, preferably oleic acid, steric acid, linoleic acid, or any combination thereof, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more bile acids in the above embodiments comprises cholic acid, the one or more free $C_{14-24}$ fatty acids in the above embodiments comprises one or more free $C_{14-18}$ fatty acids, preferably oleic acid, steric acid, linoleic acid, or any combination thereof, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof.

In some embodiments, a pharmaceutical comprises about 0.1% to about 20% by weight of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 25% to about 70% by weight of one or more hard fats comprising $C_{10}$-$C_{24}$ triglycerides, about 25% to about 70% by weight of one or more liquid fats comprising partially hydrolyzed triglycerides including a mixture of $C_{10}$-$C_{24}$ mono-, $C_{10}$-$C_{24}$ di- and $C_{10}$-$C_{24}$ triglycerides, about 0.1% to about 10% by weight of one or more bile acids, about 10% to about 25% by weight of one or more free $C_{14\text{-}24}$ fatty acids, and about 0.1% to about 5% by weight of one or more free $C_{14\text{-}24}$ fatty acid surfactants. In some embodiments, a pharmaceutical comprises about 25 mg/mL to about 600 mg/mL of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 25% to about 70% by weight of one or more hard fats comprising $C_{10}$-$C_{24}$ triglycerides, about 25% to about 70% by weight of one or more liquid fats comprising partially hydrolyzed triglycerides including a mixture of $C_{10}$-$C_{24}$ mono-, $C_{10}$-$C_{24}$ di- and $C_{10}$-$C_{24}$ triglycerides, about 0.1% to about 10% by weight of one or more bile acids, and about 10% to about 25% by weight of one or more free $C_{14\text{-}24}$ fatty acids, about 0.1% to about 5% by weight of one or more free $C_{14\text{-}24}$ fatty acid surfactants. In some embodiments, the one or more bile acids in the above embodiments comprises cholic acid. In some embodiments, the one or more free $C_{14\text{-}24}$ fatty acids in the above embodiments comprises one or more free $C_{14\text{-}18}$ fatty acids, preferably oleic acid, steric acid, linoleic acid, or any combination thereof. In some embodiments, the one or more free $C_{14\text{-}24}$ fatty acid surfactants in the above embodiments comprises one or more free $C_{14\text{-}18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more bile acids in the above embodiments comprises cholic acid and the one or more free $C_{14\text{-}24}$ fatty acids in the above embodiments comprises one or more free $C_{14\text{-}18}$ fatty acids, preferably oleic acid, steric acid, linoleic acid, or any combination thereof. In some embodiments, the one or more bile acids in the above embodiments comprises cholic acid and the one or more free $C_{14\text{-}24}$ fatty acid surfactants in the above embodiments comprises one or more free $C_{14\text{-}18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more free $C_{14\text{-}24}$ fatty acids in the above embodiments comprises one or more free $C_{14\text{-}18}$ fatty acids, preferably oleic acid, steric acid, linoleic acid, or any combination thereof, and the one or more free $C_{14\text{-}24}$ fatty acid surfactants in the above embodiments comprises one or more free $C_{14\text{-}18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more bile acids in the above embodiments comprises cholic acid, the one or more free $C_{14\text{-}24}$ fatty acids in the above embodiments comprises one or more free $C_{14\text{-}18}$ fatty acids, preferably oleic acid, steric acid, linoleic acid, or any combination thereof, and the one or more free $C_{14\text{-}24}$ fatty acid surfactants in the above embodiments comprises one or more free $C_{14\text{-}18}$ fatty acid surfactants, preferably an oleate alkali metal or alkali earth metal salt, a stearate alkali metal or alkali earth metal salt, a linoleate alkali metal or alkali earth metal salt, or any combination thereof.

In some embodiments, a pharmaceutical comprises about 0.1% to about 20% by weight of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 25% to about 70% by weight of one or more hard fats comprising a mixture of saturated $C_{10}$-$C_{18}$ triglycerides and/or saturated $C_{12}$-$C_{18}$ triglycerides, about 25% to about 70% by weight of one or more liquid fats comprising partially hydrolyzed triglycerides including a mixture of $C_{16}$-$C_{18}$ mono-, $C_{16}$-$C_{18}$ di- and $C_{16}$-$C_{18}$ triglycerides, about 0.1% to about 10% by weight of one or more bile acids, about 10% to about 25% by weight of one or more free $C_{14\text{-}24}$ fatty acids, and about 0.1% to about 5% by weight of one or more free $C_{14\text{-}24}$ fatty acid surfactants. In some embodiments, a pharmaceutical comprises about 25 mg/mL to about 600 mg/mL of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 25% to about 70% by weight of one or more hard fats comprising a mixture of saturated $C_{10}$-$C_{18}$ triglycerides and/or saturated $C_{12}$-$C_{18}$ triglycerides, about 25% to about 70% by weight of one or more liquid fats comprising partially hydrolyzed triglycerides including a mixture of $C_{16}$-$C_{18}$ mono-, $C_{16}$-$C_{18}$ di- and $C_{16}$-$C_{18}$ triglycerides, about 0.1% to about 10% by weight of one or more bile acids, about 10% to about 25% by weight of one or more free $C_{14\text{-}24}$ fatty acids, and about 0.1% to about 5% by weight of one or more free $C_{14\text{-}24}$ fatty acid surfactants. In some embodiments, the one or more bile acids in the above embodiments comprises cholic acid. In some embodiments, the one or more free $C_{14\text{-}24}$ fatty acids in the above embodiments comprises one or more free $C_{14\text{-}18}$ fatty acids, preferably oleic acid, steric acid, linoleic acid, or any combination thereof. In some embodiments, the one or more free $C_{14\text{-}24}$ fatty acid surfactants in the above embodiments comprises one or more free $C_{14\text{-}18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more bile acids in the above embodiments comprises cholic acid and the one or more free $C_{14\text{-}24}$ fatty acids in the above embodiments comprises one or more free $C_{14\text{-}18}$ fatty acids, preferably oleic acid, steric acid, linoleic acid, or any combination thereof. In some embodiments, the one or more bile acids in the above embodiments comprises cholic acid and the one or more free $C_{14\text{-}24}$ fatty acid surfactants in the above embodiments comprises one or more free $C_{14\text{-}18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more free $C_{14\text{-}24}$ fatty acids in the above embodiments comprises one or more free $C_{14\text{-}18}$ fatty acids, preferably oleic acid, steric acid, linoleic acid, or any combination thereof, and the one or more free $C_{14\text{-}24}$ fatty acid surfactants in the above embodiments comprises one or more free $C_{14\text{-}18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more bile acids in the above embodiments comprises cholic acid, the one or more free $C_{14\text{-}24}$ fatty acids in the above embodiments comprises one or more free $C_{14\text{-}18}$ fatty acids, preferably oleic acid, steric acid, linoleic acid, or any combination thereof, and the one or more free $C_{14\text{-}24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof.

In some embodiments, a pharmaceutical comprises about 0.1% to about 20% by weight of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 35% to about 55% by weight of one or more hard fats, about 25% to about 50% by weight of one or more liquid fats, about 0.1% to about 10% by weight of one or more bile acids, about 1% to about 30% by weight of one or more free $C_{14-24}$ fatty acids, and about 0.1% to about 5% by weight of one or more free $C_{14-24}$ fatty acid surfactants. In some embodiments, a pharmaceutical comprises about 25 mg/mL to about 600 mg/mL of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 35% to about 55% by weight of one or more hard fats, about 25% to about 50% by weight of one or more liquid fats, about 0.1% to about 10% by weight of one or more bile acids, about 1% to about 30% by weight of one or more free $C_{14-24}$ fatty acids, and about 0.1% to about 5% by weight of one or more free $C_{14-24}$ fatty acid surfactants. In some embodiments, the one or more bile acids in the above embodiments comprises cholic acid. In some embodiments, the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more bile acids in the above embodiments comprises cholic acid and the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more bile acids in the above embodiments comprises cholic acid and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more free $C_{14-24}$ fatty acids in the above embodiments comprises one or more free $C_{14-18}$ fatty acids, preferably oleic acid, steric acid, linoleic acid, or any combination thereof, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more bile acids in the above embodiments comprises cholic acid, the one or more free $C_{14-24}$ fatty acids in the above embodiments comprises one or more free $C_{14-18}$ fatty acids, preferably oleic acid, steric acid, linoleic acid, or any combination thereof, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof.

In some embodiments, a pharmaceutical comprises about 0.1% to about 20% by weight of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 35% to about 55% by weight of one or more hard fats comprising glycerolipids, about 25% to about 50% by weight of one or more liquid fats comprising partially hydrolyzed glycerolipids including a mixture of mono-, di- and triglycerides, about 0.1% to about 10% by weight of one or more bile acids, about 1% to about 30% by weight of one or more free $C_{14-24}$ fatty acids, and about 0.1% to about 5% by weight of one or more free $C_{14-24}$ fatty acid surfactants. In some embodiments, a pharmaceutical comprises about 25 mg/mL to about 600 mg/mL of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 35% to about 55% by weight of one or more hard fats comprising glycerolipids, about 25% to about 50% by weight of one or more liquid fats comprising partially hydrolyzed glycerolipids including a mixture of mono-, di- and triglycerides, about 0.1% to about 10% by weight of one or more bile acids, about 1% to about 30% by weight of one or more free $C_{14-24}$ fatty acids, and about 0.1% to about 5% by weight of one or more free $C_{14-24}$ fatty acid surfactants. In some embodiments, the one or more bile acids in the above embodiments comprises cholic acid. In some embodiments, the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more bile acids in the above embodiments comprises cholic acid and the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more bile acids in the above embodiments comprises cholic acid and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more free $C_{14-24}$ fatty acids in the above embodiments comprises one or more free $C_{14-18}$ fatty acids, preferably oleic acid, steric acid, linoleic acid, or any combination thereof, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more bile acids in the above embodiments comprises cholic acid, the one or more free $C_{14-24}$ fatty acids in the above embodiments comprises one or more free $C_{14-18}$ fatty acids, preferably oleic acid, steric acid, linoleic acid, or any combination thereof, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof.

In some embodiments, a pharmaceutical comprises about 0.1% to about 20% by weight of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 35% to about 55% by weight of one or more hard fats comprising $C_{10}$-$C_{24}$ triglycerides, about 25% to about 50% by weight of one or more liquid fats comprising partially hydrolyzed triglycerides including a mixture of $C_{10}$-$C_{24}$ mono-, $C_{10}$-$C_{24}$ di- and $C_{10}$-$C_{24}$ triglycerides, about 0.1% to about 10% by weight of one or more bile acids, about 1% to about 30% by weight of one or more free $C_{14-24}$ fatty acids, and about 0.1% to about 5% by weight of one or more free $C_{14-24}$ fatty acid surfactants. In some embodiments, a pharmaceutical comprises about 25 mg/mL to about 600 mg/mL of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 35% to about 55% by weight of one or more hard fats comprising $C_{10}$-$C_{24}$ triglycerides, about 25% to about 50% by weight of one or more liquid fats comprising partially hydrolyzed triglycerides including a mixture of $C_{10}$-$C_{24}$ mono-, $C_{10}$-$C_{24}$ di- and $C_{10}$-$C_{24}$ triglycerides, about 0.1% to about 10% by weight of one or more bile acids, and about 1% to about 30% by weight of one or more free $C_{14-24}$ fatty acids, about 0.1% to about 5% by weight of one or more free $C_{14-24}$ fatty acid surfactants. In some embodiments, the one or more bile acids in the above embodiments comprises cholic acid. In some embodiments, the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more bile acids in the above embodiments comprises cholic acid and the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more bile acids in the above embodiments comprises cholic acid and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more free $C_{14-24}$ fatty acids in the above embodiments comprises one or more free $C_{14-18}$ fatty acids, preferably oleic acid, steric acid, linoleic acid, or any combination thereof, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more bile acids in the above embodiments comprises cholic acid, the one or more free $C_{14-24}$ fatty acids in the above embodiments comprises one or more free $C_{14-18}$ fatty acids, preferably oleic acid, steric acid, linoleic acid, or any combination thereof, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof.

In some embodiments, a pharmaceutical comprises about 0.1% to about 20% by weight of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 35% to about 55% by weight of one or more hard fats comprising a mixture of saturated $C_{10}$-$C_{18}$ triglycerides and/or saturated $C_{12}$-$C_{18}$ triglycerides, about 25% to about 50% by weight of one or more liquid fats comprising partially hydrolyzed triglycerides including a mixture of $C_{16}$-$C_{18}$ mono-, $C_{16}$-$C_{18}$ di- and $C_{16}$-$C_{18}$ triglycerides, about 0.1% to about 10% by weight of one or more bile acids, about 1% to about 30% by weight of one or more free $C_{14-24}$ fatty acids, and about 0.1% to about 5% by weight of one or more free $C_{14-24}$ fatty acid surfactants. In some embodiments, a pharmaceutical comprises about 25 mg/mL to about 600 mg/mL of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 35% to about 55% by weight of one or more hard fats comprising a mixture of saturated $C_{10}$-$C_{18}$ triglycerides and/or saturated $C_{12}$-$C_{18}$ triglycerides, about 25% to about 50% by weight of one or more liquid fats comprising partially hydrolyzed triglycerides including a mixture of $C_{16}$-$C_{18}$ mono-, $C_{16}$-$C_{18}$ di- and $C_{16}$-$C_{18}$ triglycerides, about 0.1% to about 10% by weight of one or more bile acids, about 1% to about 30% by weight of one or more free $C_{14-24}$ fatty acids, and about 0.1% to about 5% by weight of one or more free $C_{14-24}$ fatty acid surfactants. In some embodiments, the one or more bile acids in the above embodiments comprises cholic acid. In some embodiments, the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more bile acids in the above embodiments comprises cholic acid and the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more bile acids in the above embodiments comprises cholic acid and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more free $C_{14-24}$ fatty acids in the above embodiments comprises one or more free $C_{14-18}$ fatty acids, preferably oleic acid, steric acid, linoleic acid, or any combination thereof, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more bile acids in the above embodiments comprises cholic acid, the one or more free $C_{14-24}$ fatty acids in the above embodiments comprises one or more free $C_{14-18}$ fatty acids, preferably oleic acid, steric acid, linoleic acid, or any combination thereof, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof.

In some embodiments, a pharmaceutical comprises about 0.1% to about 30% by weight of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 15% to about 65% by weight of one or more hard fats, about 15% to about 50% by weight of one or more liquid fats, about 0.1% to about 10% by weight of one or more bile acids, about 1% to about 25% by weight of one or more free $C_{14-24}$ fatty acids, and about 0.1% to about 5% by weight of one or more free $C_{14-24}$ fatty acid surfactants. In some embodiments, a pharmaceutical comprises about 25 mg/mL to about 600 mg/mL of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 15% to about 65% by weight of one or more hard fats, about 15% to about 50% by weight of one or more liquid fats, about 0.1% to about 10% by weight of one or more bile acids, about 1% to about 25% by weight of one or more free $C_{14-24}$ fatty acids, and about 0.1% to about 5% by weight of one or more free $C_{14-24}$ fatty acid surfactants. In some embodiments, the one or more bile acids in the above embodiments comprises cholic acid. In some embodiments, the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more bile acids in the above embodiments comprises cholic acid and the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more bile acids in the above embodiments comprises cholic acid and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more free $C_{14-24}$ fatty acids in the above embodiments comprises one or more free $C_{14-18}$ fatty acids, preferably oleic acid, steric acid, linoleic acid, or any combination thereof, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more bile acids in the above embodiments comprises cholic acid, the one or more free $C_{14-24}$ fatty acids in the above embodiments comprises one or more free $C_{14-18}$ fatty acids, preferably oleic acid, steric acid, linoleic acid, or any combination thereof, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof.

In some embodiments, a pharmaceutical comprises about 0.1% to about 30% by weight of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 15% to about 65% by weight of one or more hard fats comprising glycerolipids, about 15% to about 50% by weight of one or more liquid fats comprising partially hydrolyzed glycerolipids including a mixture of mono-, di- and triglycerides, about 0.1% to about 10% by weight of one or more bile acids, about 1% to about 25% by weight of one or more free $C_{14-24}$ fatty acids, and about 0.1% to about 5% by weight of one or more free $C_{14-24}$ fatty acid surfactants. In some embodiments, a pharmaceutical comprises about 25 mg/mL to about 600 mg/mL of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 15% to about 65% by weight of one or more hard fats comprising glycerolipids, about 15% to about 50% by weight of one or more liquid fats comprising partially hydrolyzed glycerolipids including a mixture of mono-, di- and triglycerides, about 0.1% to about 10% by weight of one or more bile acids, about 1% to about 25% by weight of one or more free $C_{14-24}$ fatty acids, and about 0.1% to about 5% by weight of one or more free $C_{14-24}$ fatty acid surfactants. In some embodiments, the one or more bile acids in the above embodiments comprises cholic acid. In some embodiments, the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more bile acids in the above embodiments comprises cholic acid and the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more bile acids in the above embodiments comprises cholic acid and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more free $C_{14-24}$ fatty acids in the above embodiments comprises one or more free $C_{14-18}$ fatty acids, preferably oleic acid, steric acid, linoleic acid, or any combination thereof, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more bile acids in the above embodiments comprises cholic acid, the one or more free $C_{14-24}$ fatty acids in the above embodiments comprises one or more free $C_{14-18}$ fatty acids, preferably oleic acid, steric acid, linoleic acid, or any combination thereof, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof.

In some embodiments, a pharmaceutical comprises about 0.1% to about 30% by weight of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 15% to about 65% by weight of one or more hard fats comprising $C_{10}$-$C_{24}$ triglycerides, about 15% to about 50% by weight of one or more liquid fats comprising partially hydrolyzed triglycerides including a mixture of $C_{10}$-$C_{24}$ mono-, $C_{10}$-$C_{24}$ di- and $C_{10}$-$C_{24}$ triglycerides, about 0.1% to about 10% by weight of one or more bile acids, about 1% to about 25% by weight of one or more free $C_{14-24}$ fatty acids, and about 0.1% to about 5% by weight of one or more free $C_{14-24}$ fatty acid surfactants. In some embodiments, a pharmaceutical comprises about 25 mg/mL to about 600 mg/mL of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 15% to about 65% by weight of one or more hard fats comprising $C_{10}$-$C_{24}$ triglycerides, about 15% to about 50% by weight of one or more liquid fats comprising partially hydrolyzed triglycerides including a mixture of $C_{10}$-$C_{24}$ mono-, $C_{10}$-$C_{24}$ di- and $C_{10}$-$C_{24}$ triglycerides, about 0.1% to about 10% by weight of one or more bile acids, and about 1% to about 25% by weight of one or more free $C_{14-24}$ fatty acids, about 0.1% to about 5% by weight of one or more free $C_{14-24}$ fatty acid surfactants. In some embodiments, the one or more bile acids in the above embodiments comprises cholic acid. In some embodiments, the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more bile acids in the above embodiments comprises cholic acid and the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more bile acids in the above embodiments comprises cholic acid and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more free $C_{14-24}$ fatty acids in the above embodiments comprises one or more free $C_{14-18}$ fatty acids, preferably oleic acid, steric acid, linoleic acid, or any combination thereof, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more bile acids in the above embodiments comprises cholic acid, the one or more free $C_{14-24}$ fatty acids in the above embodiments comprises one or more free $C_{14-18}$ fatty acids, preferably oleic acid, steric acid, linoleic acid, or any combination thereof, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof.

In some embodiments, a pharmaceutical comprises about 0.1% to about 30% by weight of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 15% to about 65% by weight of one or more hard fats comprising a mixture of saturated $C_{10}$-$C_{18}$ triglycerides and/or saturated $C_{12}$-$C_{18}$ triglycerides, about 15% to about 50% by weight of one or more liquid fats comprising partially hydrolyzed triglycerides including a mixture of $C_{16}$-$C_{18}$ mono-, $C_{16}$-$C_{18}$ di- and $C_{16}$-$C_{18}$ triglycerides, about 0.1% to about 10% by weight of one or more bile acids, about 1% to about 25% by weight of one or more free $C_{14-24}$ fatty acids, and about 0.1% to about 5% by weight of one or more free $C_{14-24}$ fatty acid surfactants. In some embodiments, a pharmaceutical comprises about 25 mg/mL to about 600 mg/mL of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 15% to about 65% by weight of one or more hard fats comprising a mixture of saturated $C_{10}$-$C_{18}$ triglycerides and/or saturated $C_{12}$-$C_{18}$ triglycerides, about 15% to about 50% by weight of one or more liquid fats comprising partially hydrolyzed triglycerides including a mixture of $C_{16}$-$C_{18}$ mono-, $C_{16}$-$C_{18}$ di- and $C_{16}$-$C_{18}$ triglycerides, about 0.1% to about 10% by weight of one or more bile acids, about 1% to about 25% by weight of one or more free $C_{14-24}$ fatty acids, and about 0.1% to about 5% by weight of one or more free $C_{14-24}$ fatty acid surfactants. In some embodiments, the one or more bile acids in the above embodiments comprises cholic acid. In some embodiments, the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more bile acids in the above embodiments comprises cholic acid and the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more bile acids in the above embodiments comprises cholic acid and the one or more free $C_{14\text{-}24}$ fatty acid surfactants in the above embodiments comprises one or more free $C_{14\text{-}18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more free $C_{14\text{-}24}$ fatty acids in the above embodiments comprises one or more free $C_{14\text{-}18}$ fatty acids, preferably oleic acid, steric acid, linoleic acid, or any combination thereof, and the one or more free $C_{14\text{-}24}$ fatty acid surfactants in the above embodiments comprises one or more free $C_{14\text{-}18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more bile acids in the above embodiments comprises cholic acid, the one or more free $C_{14\text{-}24}$ fatty acids in the above embodiments comprises one or more free $C_{14\text{-}18}$ fatty acids, preferably oleic acid, steric acid, linoleic acid, or any combination thereof, and the one or more free $C_{14\text{-}24}$ fatty acid surfactants in the above embodiments comprises one or more free $C_{14\text{-}18}$ fatty acid surfactants, preferably an oleate alkali metal or alkali earth metal salt, a stearate alkali metal or alkali earth metal salt, a linoleate alkali metal or alkali earth metal salt, or any combination thereof.

In some embodiments, a pharmaceutical comprises about 0.1% to about 30% by weight of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 20% to about 55% by weight of one or more hard fats, about 15% to about 45% by weight of one or more liquid fats, about 0.1% to about 10% by weight of one or more bile acids, about 10% to about 45% by weight of one or more free $C_{14\text{-}24}$ fatty acids, and about 0.1% to about 5% by weight of one or more free $C_{14\text{-}24}$ fatty acid surfactants. In some embodiments, a pharmaceutical comprises about 25 mg/mL to about 600 mg/mL of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 20% to about 55% by weight of one or more hard fats, about 15% to about 45% by weight of one or more liquid fats, about 0.1% to about 10% by weight of one or more bile acids, about 10% to about 45% by weight of one or more free $C_{14\text{-}24}$ fatty acids, and about 0.1% to about 5% by weight of one or more free $C_{14\text{-}24}$ fatty acid surfactants. In some embodiments, the one or more bile acids in the above embodiments comprises cholic acid. In some embodiments, the one or more free $C_{14\text{-}24}$ fatty acids in the above embodiments comprises one or more free $C_{14\text{-}18}$ fatty acids, preferably oleic acid, steric acid, linoleic acid, or any combination thereof. In some embodiments, the one or more free $C_{14\text{-}24}$ fatty acid surfactants in the above embodiments comprises one or more free $C_{14\text{-}18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more bile acids in the above embodiments comprises cholic acid and the one or more free $C_{14\text{-}24}$ fatty acids in the above embodiments comprises one or more free $C_{14\text{-}18}$ fatty acids, preferably oleic acid, steric acid, linoleic acid, or any combination thereof. In some embodiments, the one or more bile acids in the above embodiments comprises cholic acid and the one or more free $C_{14\text{-}24}$ fatty acid surfactants in the above embodiments comprises one or more free $C_{14\text{-}18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more free $C_{14\text{-}24}$ fatty acids in the above embodiments comprises one or more free $C_{14\text{-}18}$ fatty acids, preferably oleic acid, steric acid, linoleic acid, or any combination thereof, and the one or more free $C_{14\text{-}24}$ fatty acid surfactants in the above embodiments comprises one or more free $C_{14\text{-}18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more bile acids in the above embodiments comprises cholic acid, the one or more free $C_{14\text{-}24}$ fatty acids in the above embodiments comprises one or more free $C_{14\text{-}18}$ fatty acids, preferably oleic acid, steric acid, linoleic acid, or any combination thereof, and the one or more free $C_{14\text{-}24}$ fatty acid surfactants in the above embodiments comprises one or more free $C_{14\text{-}18}$ fatty acid surfactants, preferably an oleate alkali metal or alkali earth metal salt, a stearate alkali metal or alkali earth metal salt, a linoleate alkali metal or alkali earth metal salt, or any combination thereof.

In some embodiments, a pharmaceutical comprises about 0.1% to about 30% by weight of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 20% to about 55% by weight of one or more hard fats comprising glycerolipids, about 15% to about 45% by weight of one or more liquid fats comprising partially hydrolyzed glycerolipids including a mixture of mono-, di- and triglycerides, about 0.1% to about 10% by weight of one or more bile acids, about 10% to about 45% by weight of one or more free $C_{14\text{-}24}$ fatty acids, and about 0.1% to about 5% by weight of one or more free $C_{14\text{-}24}$ fatty acid surfactants. In some embodiments, a pharmaceutical comprises about 25 mg/mL to about 600 mg/mL of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 20% to about 55% by weight of one or more hard fats comprising glycerolipids, about 15% to about 45% by weight of one or more liquid fats comprising partially hydrolyzed glycerolipids including a mixture of mono-, di- and triglycerides, about 0.1% to about 10% by weight of one or more bile acids, about 10% to about 45% by weight of one or more free $C_{14\text{-}24}$ fatty acids, and about 0.1% to about 5% by weight of one or more free $C_{14\text{-}24}$ fatty acid surfactants.

In some embodiments, the one or more bile acids in the above embodiments comprises cholic acid. In some embodiments, the one or more free $C_{14\text{-}24}$ fatty acids in the above embodiments comprises one or more free $C_{14\text{-}18}$ fatty acids, preferably oleic acid, steric acid, linoleic acid, or any combination thereof. In some embodiments, the one or more free $C_{14\text{-}24}$ fatty acid surfactants in the above embodiments comprises one or more free $C_{14\text{-}18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more bile acids in the above embodiments comprises cholic acid and the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more bile acids in the above embodiments comprises cholic acid and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more free $C_{14-24}$ fatty acids in the above embodiments comprises one or more free $C_{14-18}$ fatty acids, preferably oleic acid, steric acid, linoleic acid, or any combination thereof, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more bile acids in the above embodiments comprises cholic acid, the one or more free $C_{14-24}$ fatty acids in the above embodiments comprises one or more free $C_{14-18}$ fatty acids, preferably oleic acid, steric acid, linoleic acid, or any combination thereof, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof.

In some embodiments, a pharmaceutical comprises about 0.1% to about 30% by weight of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 20% to about 55% by weight of one or more hard fats comprising $C_{10}$-$C_{24}$ triglycerides, about 15% to about 45% by weight of one or more liquid fats comprising partially hydrolyzed triglycerides including a mixture of $C_{10}$-$C_{24}$ mono-, $C_{10}$-$C_{24}$ di- and $C_{10}$-$C_{24}$ triglycerides, about 0.1% to about 10% by weight of one or more bile acids, about 10% to about 45% by weight of one or more free $C_{14-24}$ fatty acids, and about 0.1% to about 5% by weight of one or more free $C_{14-24}$ fatty acid surfactants. In some embodiments, a pharmaceutical comprises about 25 mg/mL to about 600 mg/mL of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 20% to about 55% by weight of one or more hard fats comprising $C_{10}$-$C_{24}$ triglycerides, about 15% to about 45% by weight of one or more liquid fats comprising partially hydrolyzed triglycerides including a mixture of $C_{10}$-$C_{24}$ mono-, $C_{10}$-$C_{24}$ di- and $C_{10}$-$C_{24}$ triglycerides, about 0.1% to about 10% by weight of one or more bile acids, and about 10% to about 45% by weight of one or more free $C_{14-24}$ fatty acids, about 0.1% to about 5% by weight of one or more free $C_{14-24}$ fatty acid surfactants. In some embodiments, the one or more bile acids in the above embodiments comprises cholic acid. In some embodiments, the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more bile acids in the above embodiments comprises cholic acid and the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more bile acids in the above embodiments comprises cholic acid and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more free $C_{14-24}$ fatty acids in the above embodiments comprises one or more free $C_{14-18}$ fatty acids, preferably oleic acid, steric acid, linoleic acid, or any combination thereof, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more bile acids in the above embodiments comprises cholic acid, the one or more free $C_{14-24}$ fatty acids in the above embodiments comprises one or more free $C_{14-18}$ fatty acids, preferably oleic acid, steric acid, linoleic acid, or any combination thereof, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof.

In some embodiments, a pharmaceutical comprises about 0.1% to about 30% by weight of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 20% to about 55% by weight of one or more hard fats comprising a mixture of saturated $C_{10}$-$C_{18}$ triglycerides and/or saturated $C_{12}$-$C_{18}$ triglycerides, about 15% to about 45% by weight of one or more liquid fats comprising partially hydrolyzed triglycerides including a mixture of $C_{16}$-$C_{18}$ mono-, $C_{16}$-$C_{18}$ di- and $C_{16}$-$C_{18}$ triglycerides, about 0.1% to about 10% by weight of one or more bile acids, about 10% to about 45% by weight of one or more free $C_{14-24}$ fatty acids, and about 0.1% to about 5% by weight of one or more free $C_{14-24}$ fatty acid surfactants. In some embodiments, a pharmaceutical comprises about 25 mg/mL to about 600 mg/mL of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 20% to about 55% by weight of one or more hard fats comprising a mixture of saturated $C_{10}$-$C_{18}$ triglycerides and/or saturated $C_{12}$-$C_{18}$ triglycerides, about 15% to about 45% by weight of one or more liquid fats comprising partially hydrolyzed triglycerides including a mixture of $C_{16}$-$C_{18}$ mono-, $C_{16}$-$C_{18}$ di- and $C_{16}$-$C_{18}$ triglycerides, about 0.1% to about 10% by weight of one or more bile acids, about 10% to about 45% by weight of one or more free $C_{14-24}$ fatty acids, and about 0.1% to about 5% by weight of one or more free $C_{14-24}$ fatty acid surfactants. In some embodiments, the one or more bile acids in the above embodiments comprises cholic acid. In some embodiments, the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more bile acids in the above embodiments comprises cholic acid and the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more bile acids in the above embodiments comprises cholic acid and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more free $C_{14-24}$ fatty acids in the above embodiments comprises one or more free $C_{14-18}$ fatty acids, preferably oleic acid, steric acid, linoleic acid, or any combination thereof, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more bile acids in the above embodiments comprises cholic acid, the one or more free $C_{14-24}$ fatty acids in the above embodiments comprises one or more free $C_{14-18}$ fatty acids, preferably oleic acid, steric acid, linoleic acid, or any combination thereof, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof.

In some embodiments, a pharmaceutical comprises abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, one or more hard fats, and one or more digestion enhancers. In some embodiments, the one or more digestion enhancers comprises one or more bile acids, one or more one or more free $C_{14-24}$ fatty acids, one or more one or more free $C_{14-24}$ fatty acid surfactants, or any combination thereof.

In some embodiments, a pharmaceutical comprises about 0.1% to about 30% by weight of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 20% to about 55% by weight of one or more hard fats, and about 40% to about 80% by weight of one or more digestion enhancers. In some embodiments, a pharmaceutical comprises about 25 mg/mL to about 600 mg/mL of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 20% to about 55% by weight of one or more hard fats, and about 40% to about 80% by weight of one or more digestion enhancers. In some embodiments, the one or more digestion enhancers comprises one or more bile acids, one or more one or more free $C_{14-24}$ fatty acids, one or more one or more free $C_{14-24}$ fatty acid surfactants, or any combination thereof.

acids, one or more one or more free $C_{14-24}$ fatty acids, one or more one or more free $C_{14-24}$ fatty acid surfactants, or any combination thereof.

In some embodiments, a pharmaceutical comprises about 0.1% to about 30% by weight of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 20% to about 55% by weight of one or more hard fats comprising glycerolipids, and about 40% to about 80% by weight of one or more digestion enhancers. In some embodiments, a pharmaceutical comprises about 25 mg/mL to about 600 mg/mL of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 20% to about 55% by weight of one or more hard fats comprising glycerolipids, and about 40% to about 80% by weight of one or more digestion enhancers. In some embodiments, the one or more digestion enhancers comprises one or more bile acids, one or more one or more free $C_{14-24}$ fatty acids, one or more one or more free $C_{14-24}$ fatty acid surfactants, or any combination thereof.

In some embodiments, a pharmaceutical comprises about 0.1% to about 30% by weight of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 20% to about 55% by weight of one or more hard fats comprising $C_{10}$-$C_{24}$ triglycerides, and about 40% to about 80% by weight of one or more digestion enhancers. In some embodiments, a pharmaceutical comprises about 25 mg/mL to about 600 mg/mL of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 20% to about 55% by weight of one or more hard fats comprising $C_{10}$-$C_{24}$ triglycerides, and about 40% to about 80% by weight of one or more digestion enhancers. In some embodiments, the one or more digestion enhancers comprises one or more bile acids, one or more one or more free $C_{14-24}$ fatty acids, one or more one or more free $C_{14-24}$ fatty acid surfactants, or any combination thereof.

In some embodiments, a pharmaceutical comprises about 0.1% to about 30% by weight of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 20% to about 55% by weight of one or more hard fats comprising a mixture of saturated $C_{10}$-$C_{18}$ triglycerides and/or saturated $C_{12}$-$C_{18}$ triglycerides, and about 40% to about 80% by weight of one or more digestion enhancers. In some embodiments, a pharmaceutical comprises about 25 mg/mL to about 600 mg/mL of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 20% to about 55% by weight of one or more hard fats comprising a mixture of saturated $C_{10}$-$C_{18}$ triglycerides and/or saturated $C_{12}$-$C_{18}$ triglycerides, and about 40% to about 80% by weight of one or more digestion enhancers. In some embodiments, the one or more digestion enhancers comprises one or more bile acids, one or more one or more free $C_{14-24}$ fatty acids, one or more one or more free $C_{14-24}$ fatty acid surfactants, or any combination thereof.

In some embodiments, a pharmaceutical comprises abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, one or more hard fats, and one or more bile acids. In some embodiments, the one or more bile acids in the above embodiments comprises cholic acid.

In some embodiments, a pharmaceutical comprises about 0.1% to about 30% by weight of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 20% to about 55% by weight of one or more hard fats, and about 0.1% to about 10% by weight of one or more bile acids. In some embodiments, a pharmaceutical comprises about 25 mg/mL to about 600 mg/mL of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 20% to about 55% by weight of one or more hard fats, and about 0.1% to about 10% by weight of one or more bile acids. In some embodiments, the one or more bile acids in the above embodiments comprises cholic acid.

In some embodiments, a pharmaceutical comprises about 0.1% to about 30% by weight of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 20% to about 55% by weight of one or more hard fats comprising glycerolipids, and about 0.1% to about 10% by weight of one or more bile acids. In some embodiments, a pharmaceutical comprises about 25 mg/mL to about 600 mg/mL of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 20% to about 55% by weight of one or more hard fats comprising glycerolipids, and about 0.1% to about 10% by weight of one or more bile acids. In some embodiments, the one or more bile acids in the above embodiments comprises cholic acid.

In some embodiments, a pharmaceutical comprises about 0.1% to about 30% by weight of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 20% to about 55% by weight of one or more hard fats comprising $C_{10}$-$C_{24}$ triglycerides, and about 0.1% to about 10% by weight of one or more bile acids. In some embodiments, a pharmaceutical comprises about 25 mg/mL to about 600 mg/mL of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 20% to about 55% by weight of one or more hard fats comprising $C_{10}$-$C_{24}$ triglycerides, and about 0.1% to about 10% by weight of one or more bile acids. In some embodiments, the one or more bile acids in the above embodiments comprises cholic acid.

In some embodiments, a pharmaceutical comprises about 0.1% to about 30% by weight of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 20% to about 55% by weight of one or more hard fats comprising a mixture of saturated $C_{10}$-$C_{18}$ triglycerides and/or saturated $C_{12}$-$C_{18}$ triglycerides, and about 0.1% to about 10% by weight of one or more bile acids. In some embodiments, a pharmaceutical comprises about 25 mg/mL to about 600 mg/mL of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 20% to about 55% by weight of one or more hard fats comprising a mixture of saturated $C_{10}$-$C_{18}$ triglycerides and/or saturated $C_{12}$-$C_{18}$ triglycerides, and about 0.1% to about 10% by weight of one or more bile acids. In some embodiments, the one or more bile acids in the above embodiments comprises cholic acid.

In some embodiments, a pharmaceutical comprises abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, one or more hard fats, one or more bile acids and one or more free $C_{14-24}$ fatty acids. In some embodiments, the one or more bile acids in the above embodiments comprises cholic acid. In some embodiments, the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more bile acids in the above embodiments comprises cholic acid, and the one or more free $C_{14-24}$ fatty acids in the above embodiments comprises one or more free $C_{14-18}$ fatty acids, preferably oleic acid, steric acid, linoleic acid, or any combination thereof.

In some embodiments, a pharmaceutical comprises about 0.1% to about 30% by weight of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 20% to about 55% by weight of one or more hard fats, about 0.1% to about 10% by weight of one or more bile acids, and about 35% to about 75% by weight of one or more free $C_{14-24}$ fatty acids. In some embodiments, a pharmaceutical comprises about 25 mg/mL to about 600 mg/mL of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 20% to about 55% by weight of one or more hard fats, about 0.1% to about 10% by weight of one or more bile acids, and about 35% to about 75% by weight of one or more free $C_{14-24}$ fatty acids. In some embodiments, the one or more bile acids in the above embodiments comprises cholic acid. In some embodiments, the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more bile acids in the above embodiments comprises cholic acid, and the one or more free $C_{14-24}$ fatty acids in the above embodiments comprises one or more free $C_{14-18}$ fatty acids, preferably oleic acid, steric acid, linoleic acid, or any combination thereof.

In some embodiments, a pharmaceutical comprises about 0.1% to about 30% by weight of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 20% to about 55% by weight of one or more hard fats comprising glycerolipids, about 0.1% to about 10% by weight of one or more bile acids, and about 35% to about 75% by weight of one or more free $C_{14-24}$ fatty acids. In some embodiments, a pharmaceutical comprises about 25 mg/mL to about 600 mg/mL of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 20% to about 55% by weight of one or more hard fats comprising glycerolipids, about 0.1% to about 10% by weight of one or more bile acids, and about 35% to about 75% by weight of one or more free $C_{14-24}$ fatty acids. In some embodiments, the one or more bile acids in the above embodiments comprises cholic acid. In some embodiments, the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more bile acids in the above embodiments comprises cholic acid, and the one or more free $C_{14-24}$ fatty acids in the above embodiments comprises one or more free $C_{14-18}$ fatty acids, preferably oleic acid, steric acid, linoleic acid, or any combination thereof.

In some embodiments, a pharmaceutical comprises about 0.1% to about 30% by weight of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 20% to about 55% by weight of one or more hard fats comprising $C_{10}$-$C_{24}$ triglycerides, about 0.1% to about 10% by weight of one or more bile acids, and about 35% to about 75% by weight of one or more free $C_{14-24}$ fatty acids. In some embodiments, a pharmaceutical comprises about 25 mg/mL to about 600 mg/mL of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 20% to about 55% by weight of one or more hard fats comprising $C_{10}$-$C_{24}$ triglycerides, about 0.1% to about 10% by weight of one or more bile acids, and about 35% to about 75% by weight of one or more free $C_{14-24}$ fatty acids. In some embodiments, the one or more bile acids in the above embodiments comprises cholic acid. In some embodiments, the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more bile acids in the above embodiments comprises cholic acid, and the one or more free $C_{14-24}$ fatty acids in the above embodiments comprises one or more free $C_{14-18}$ fatty acids, preferably oleic acid, steric acid, linoleic acid, or any combination thereof.

In some embodiments, a pharmaceutical comprises about 0.1% to about 30% by weight of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 20% to about 55% by weight of one or more hard fats comprising a mixture of saturated $C_{10}$-$C_{18}$ triglycerides and/or saturated $C_{12}$-$C_{18}$ triglycerides, about 0.1% to about 10% by weight of one or more bile acids, and about 35% to about 75% by weight of one or more free $C_{14-24}$ fatty acids. In some embodiments, a pharmaceutical comprises about 25 mg/mL to about 600 mg/mL of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 20% to about 55% by weight of one or more hard fats comprising a mixture of saturated $C_{10}$-$C_{18}$ triglycerides and/or saturated $C_{12}$-$C_{18}$ triglycerides, about 0.1% to about 10% by weight of one or more bile acids, and about 35% to about 75% by weight of one or more free $C_{14-24}$ fatty acids. In some embodiments, the one or more bile acids in the above embodiments comprises cholic acid. In some embodiments, the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more bile acids in the above embodiments comprises cholic acid, and the one or more free $C_{14-24}$ fatty acids in the above embodiments comprises one or more free $C_{14-18}$ fatty acids, preferably oleic acid, steric acid, linoleic acid, or any combination thereof.

In some embodiments, a pharmaceutical comprises abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, one or more hard fats, one or more bile acids, and one or more free $C_{14-24}$ fatty acid surfactants. In some embodiments, the one or more bile acids in the above embodiments comprises cholic acid. In some embodiments, the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more bile acids in the above embodiments comprises cholic acid and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof.

In some embodiments, a pharmaceutical comprises about 0.1% to about 30% by weight of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 20% to about 55% by weight of one or more hard fats, about 0.1% to about 10% by weight of one or more bile acids, and about 0.1% to about 5% by weight of one or more free $C_{14-24}$ fatty acid surfactants. In some embodiments, a pharmaceutical comprises about 25 mg/mL to about 600 mg/mL of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 20% to about 55% by weight of one or more hard fats, about 0.1% to about 10% by weight of one or more bile acids, and about 0.1% to about 5% by weight of one or more free $C_{14-24}$ fatty acid surfactants. In some embodiments, the one or more bile acids in the above embodiments comprises cholic acid. In some embodiments, the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more bile acids in the above embodiments comprises cholic acid and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof.

In some embodiments, a pharmaceutical comprises about 0.1% to about 30% by weight of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 20% to about 55% by weight of one or more hard fats comprising glycerolipids, about 0.1% to about 10% by weight of one or more bile acids, and about 0.1% to about 5% by weight of one or more free $C_{14-24}$ fatty acid surfactants. In some embodiments, a pharmaceutical comprises about 25 mg/mL to about 600 mg/mL of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 20% to about 55% by weight of one or more hard fats comprising glycerolipids, about 0.1% to about 10% by weight of one or more bile acids, and about 0.1% to about 5% by weight of one or more free $C_{14-24}$ fatty acid surfactants. In some embodiments, the one or more bile acids in the above embodiments comprises cholic acid. In some embodiments, the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more bile acids in the above embodiments comprises cholic acid and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof.

In some embodiments, a pharmaceutical comprises about 0.1% to about 30% by weight of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 20% to about 55% by weight of one or more hard fats comprising $C_{10}$-$C_{24}$ triglycerides, about 0.1% to about 10% by weight of one or more bile acids, and about 0.1% to about 5% by weight of one or more free $C_{14-24}$ fatty acid surfactants. In some embodiments, a pharmaceutical comprises about 25 mg/mL to about 600 mg/mL of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 20% to about 55% by weight of one or more hard fats comprising $C_{10}$-$C_{24}$ triglycerides, about 0.1% to about 10% by weight of one or more bile acids, about 0.1% to about 5% by weight of one or more free $C_{14-24}$ fatty acid surfactants. In some embodiments, the one or more bile acids in the above embodiments comprises cholic acid. In some embodiments, the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more bile acids in the above embodiments comprises cholic acid and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof.

In some embodiments, a pharmaceutical comprises about 0.1% to about 30% by weight of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 20% to about 55% by weight of one or more hard fats comprising a mixture of saturated $C_{10}$-$C_{18}$ triglycerides and/or saturated $C_{12}$-$C_{18}$ triglycerides, about 0.1% to about 10% by weight of one or more bile acids, and about 0.1% to about 5% by weight of one or more free $C_{14-24}$ fatty acid surfactants. In some embodiments, a pharmaceutical comprises about 25 mg/mL to about 600 mg/mL of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 20% to about 55% by weight of one or more hard fats comprising a mixture of saturated $C_{10}$-$C_{18}$ triglycerides and/or saturated $C_{12}$-$C_{18}$ triglycerides, about 0.1% to about 10% by weight of one or more bile acids, and about 0.1% to about 5% by weight of one or more free $C_{14-24}$ fatty acid surfactants. In some embodiments, the one or more bile acids in the above embodiments comprises cholic acid. In some embodiments, the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more bile acids in the above embodiments comprises cholic acid and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof.

In some embodiments, a pharmaceutical comprises abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, one or more hard fats, one or more bile acids, one or more free $C_{14-24}$ fatty acids, and one or more free $C_{14-24}$ fatty acid surfactants. In some embodiments, the one or more bile acids in the above embodiments comprises cholic acid. In some embodiments, the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more bile acids in the above embodiments comprises cholic acid and the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more bile acids in the above embodiments comprises cholic acid and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more free $C_{14-24}$ fatty acids in the above embodiments comprises one or more free $C_{14-18}$ fatty acids, preferably oleic acid, steric acid, linoleic acid, or any combination thereof, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more bile acids in the above embodiments comprises cholic acid, the one or more free $C_{14-24}$ fatty acids in the above embodiments comprises one or more free $C_{14-18}$ fatty acids, preferably oleic acid, steric acid, linoleic acid, or any combination thereof, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof.

In some embodiments, a pharmaceutical comprises about 0.1% to about 30% by weight of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 20% to about 55% by weight of one or more hard fats, about 0.1% to about 10% by weight of one or more bile acids, about 35% to about 75% by weight of one or more free $C_{14-24}$ fatty acids, and about 0.1% to about 5% by weight of one or more free $C_{14-24}$ fatty acid surfactants. In some embodiments, a pharmaceutical comprises about 25 mg/mL to about 600 mg/mL of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 20% to about 55% by weight of one or more hard fats, about 0.1% to about 10% by weight of one or more bile acids, about 35% to about 75% by weight of one or more free $C_{14-24}$ fatty acids, and about 0.1% to about 5% by weight of one or more free $C_{14-24}$ fatty acid surfactants. In some embodiments, the one or more bile acids in the above embodiments comprises cholic acid. In some embodiments, the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more bile acids in the above embodiments comprises cholic acid and the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more bile acids in the above embodiments comprises cholic acid and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more free $C_{14-24}$ fatty acids in the above embodiments comprises one or more free $C_{14-18}$ fatty acids, preferably oleic acid, steric acid, linoleic acid, or any combination thereof, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more bile acids in the above embodiments comprises cholic acid, the one or more free $C_{14-24}$ fatty acids in the above embodiments comprises one or more free $C_{14-18}$ fatty acids, preferably oleic acid, steric acid, linoleic acid, or any combination thereof, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof.

In some embodiments, a pharmaceutical comprises about 0.1% to about 30% by weight of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 20% to about 55% by weight of one or more hard fats comprising glycerolipids, about 0.1% to about 10% by weight of one or more bile acids, about 35% to about 75% by weight of one or more free $C_{14-24}$ fatty acids, and about 0.1% to about 5% by weight of one or more free $C_{14-24}$ fatty acid surfactants. In some embodiments, a pharmaceutical comprises about 25 mg/mL to about 600 mg/mL of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 20% to about 55% by weight of one or more hard fats comprising glycerolipids, about 0.1% to about 10% by weight of one or more bile acids, about 35% to about 75% by weight of one or more free $C_{14-24}$ fatty acids, and about 0.1% to about 5% by weight of one or more free $C_{14-24}$ fatty acid surfactants. In some embodiments, the one or more bile acids in the above embodiments comprises cholic acid. In some embodiments, the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more bile acids in the above embodiments comprises cholic acid and the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more bile acids in the above embodiments comprises cholic acid and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more free $C_{14-24}$ fatty acids in the above embodiments comprises one or more free $C_{14-18}$ fatty acids, preferably oleic acid, steric acid, linoleic acid, or any combination thereof, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more bile acids in the above embodiments comprises cholic acid, the one or more free $C_{14-24}$ fatty acids in the above embodiments comprises one or more free $C_{14-18}$ fatty acids, preferably oleic acid, steric acid, linoleic acid, or any combination thereof, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof.

In some embodiments, a pharmaceutical comprises about 0.1% to about 30% by weight of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 20% to about 55% by weight of one or more hard fats comprising $C_{10}$-$C_{24}$ triglycerides, about 0.1% to about 10% by weight of one or more bile acids, about 35% to about 75% by weight of one or more free $C_{14-24}$ fatty acids, and about 0.1% to about 5% by weight of one or more free $C_{14-24}$ fatty acid surfactants. In some embodiments, a pharmaceutical comprises about 25 mg/mL to about 600 mg/mL of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 20% to about 55% by weight of one or more hard fats comprising $C_{10}$-$C_{24}$ triglycerides, about 0.1% to about 10% by weight of one or more bile acids, and about 35% to about 75% by weight of one or more free $C_{14-24}$ fatty acids, about 0.1% to about 5% by weight of one or more free $C_{14-24}$ fatty acid surfactants. In some embodiments, the one or more bile acids in the above embodiments comprises cholic acid. In some embodiments, the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more bile acids in the above embodiments comprises cholic acid and the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more bile acids in the above embodiments comprises cholic acid and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more free $C_{14-24}$ fatty acids in the above embodiments comprises one or more free $C_{14-18}$ fatty acids, preferably oleic acid, steric acid, linoleic acid, or any combination thereof, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more bile acids in the above embodiments comprises cholic acid, the one or more free $C_{14-24}$ fatty acids in the above embodiments comprises one or more free $C_{14-18}$ fatty acids, preferably oleic acid, steric acid, linoleic acid, or any combination thereof, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof.

In some embodiments, a pharmaceutical comprises about 0.1% to about 30% by weight of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 20% to about 55% by weight of one or more hard fats comprising a mixture of saturated $C_{10}$-$C_{18}$ triglycerides and/or saturated $C_{12}$-$C_{18}$ triglycerides, about 0.1% to about 10% by weight of one or more bile acids, about 35% to about 75% by weight of one or more free $C_{14-24}$ fatty acids, and about 0.1% to about 5% by weight of one or more free $C_{14-24}$ fatty acid surfactants. In some embodiments, a pharmaceutical comprises about 25 mg/mL to about 600 mg/mL of abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, or telmisartan, about 20% to about 55% by weight of one or more hard fats comprising a mixture of saturated $C_{10}$-$C_{18}$ triglycerides and/or saturated $C_{12}$-$C_{18}$ triglycerides, about 0.1% to about 10% by weight of one or more bile acids, about 35% to about 75% by weight of one or more free $C_{14-24}$ fatty acids, and about 0.1% to about 5% by weight of one or more free $C_{14-24}$ fatty acid surfactants. In some embodiments, the one or more bile acids in the above embodiments comprises cholic acid. In some embodiments, the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more bile acids in the above embodiments comprises cholic acid and the one or more free $C_{14-24}$ fatty acids in the above embodiments comprises one or more free $C_{14-18}$ fatty acids, preferably oleic acid, steric acid, linoleic acid, or any combination thereof. In some embodiments, the one or more bile acids in the above embodiments comprises cholic acid and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more free $C_{14-24}$ fatty acids in the above embodiments comprises one or more free $C_{14-18}$ fatty acids, preferably oleic acid, steric acid, linoleic acid, or any combination thereof, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof. In some embodiments, the one or more bile acids in the above embodiments comprises cholic acid, the one or more free $C_{14-24}$ fatty acids in the above embodiments comprises one or more free $C_{14-18}$ fatty acids, preferably oleic acid, steric acid, linoleic acid, or any combination thereof, and the one or more free $C_{14-24}$ fatty acid surfactants in the above embodiments comprises one or more free $C_{14-18}$ fatty acid surfactants, preferably an oleate alkali metal or alkali earth metal salt, a stearate alkali metal or alkali earth metal salt, a linoleate alkali metal or alkali earth metal salt, or any combination thereof.

Aspects of the present specification can also be described by the following embodiments:

1. A pharmaceutical composition disclosed herein comprises a) one or more therapeutic compounds, b) one or more glycerolipids, and c) one or more digestion enhancers.

2. The pharmaceutical composition of embodiment 1, wherein the one or more therapeutic compounds comprise one or more pharmaceutical active agents or ingredients, one or more diagnostic agents or ingredients, one or more cosmeceutical active agents or ingredients, one or more nutriceutical active agents or ingredients, or any combination thereof 3. The pharmaceutical composition of any one of embodiments 1-2, wherein the one or more therapeutic compounds comprise: a) one or more BCS Class I therapeutic compounds, one or more BCS Class II therapeutic compounds, one or more BCS Class III therapeutic compounds, one or more BCS Class IV therapeutic compounds, or any combination thereof; or b) one or more hydrophilic therapeutic compounds, one or more amphipathic therapeutic compounds, one or more hydrophobic therapeutic compounds, one or more lipophilic therapeutic compounds, one or more therapeutic compounds comprising an organic acid functional group, one or more therapeutic compounds comprising an organic base functional group, or any combination thereof; or c) one or more analgesics, one or more anesthetics, one or more antibacterials, one or more anticoagulants, one or more anticonvulsants, one or more antidementia agents, one or more antidepressants, one or more antidotes and antitoxins, one or more antiemetics, one or more antifungals, one or more anti-inflammatory agents, one or more antimigraine agents, one or more antimyasthenic agents, one or more antimycobacterials, one or more antineoplastics, one or more antiparasitics, one or more antiparkinson agents, one or more antipsychotics, one or more antivirals, one or more anxiolytic agents, one or more bipolar agents, one or more blood glucose regulators, one or more blood products, one or more cardiovascular agents, one or more central nervous system agents, one or more dental and oral agents, one or more dermatological agents, one or more enzyme replacement agent, one or more gastrointestinal agents, one or more genitourinary agents, one or more hormonal agents, one or more hormone suppressant, one or more immunological agents, one or more inflammatory bowel disease agents, one or more metabolic bone disease agents, one or more nootropic agents, one or more ophthalmic agents, one or more otic agents, one or more respiratory tract agents, one or more sedatives and hypnotics, one or more skeletal muscle relaxants, one or more and therapeutic nutrients, one or more minerals, one or more electrolytes, or any combination thereof; or d) one or more 5-alpha-reductase inhibitors, one or more 5-aminosalicylates, one or more 5HT3 receptor antagonists, one or more adamantane, one or more adrenal cortical steroids, one or more adrenal corticosteroid inhibitors, one or more agents for hypertensive emergencies, one or more agents for pulmonary hypertension, one or more aldosterone receptor antagonists, one or more alkylating agents, one or more allergenics, one or more alpha-glucosidase inhibitors, one or more alternative medicines, one or more amebicides, one or more aminoglycosides, one or more aminopenicillins, one or more aminosalicylates, one or more AMPA receptor antagonists, one or more amphetamines, one or more amylin analogs, one or more analgesics, one or more androgens, one or more anabolic steroids, one or more Angiotensin Converting Enzyme (ACE) inhibitors, one or more angiotensin II inhibitors, one or more angiotensin receptor blockers, one or more anorexiants, one or more antacids, one or more antiadrenergic agents, one or more antiandrogens, one or more antianginal agents, one or more antiarrhythmic agents, one or more antiasthmatic agents, one or more antianxiety agents, one or more antibiotics, one or more anticholinergic agents, one or more anticoagulants, one or more anticoagulant reversal agents, one or more anticonvulsants, one or more antidepressants, one or more antidiabetic agents, one or more antidiarrheals, one or more antidotes, one or more antiemetic agents, one or more antifungals, one or more antigonadotropic agents, one or more antigout agents, one or more antihelmintic agents, one or more antihistamines, one or more antihyperlipidemic agents, one or more antihypertensive agents, one or more antihyperuricemic agents, one or more antiinfective agents, one or more antimalarial agents, one or more antimanic agents, one or more antimetabolites, one or more antimigraine agents, one or more antineoplastic agents, one or more antineoplastic detoxifying agents, one or more antineoplastic interferons, one or more antiparkinson agents, one or more antiplatelet agents, one or more antipseudomonal penicillins, one or more antipsoriatics, one or more antipsychotics, one or more antirheumatics, one or more antirosacea agents, one or more antiseptic and germicides, one or more antispasmodics, one or more antithyroid agents, one or more antitoxins and antivenins, one or more antituberculosis agents, one or more antitussive agents, one or more antivertigo agents, one or more antiviral agents, one or more antiviral boosters, one or more anxiolytics, one or more sedatives, one or more and hypnotics, one or more aromatase inhibitors, one or more astringents, one or more atypical antipsychotics, one or more azole, one or more barbiturates, one or more BCR-ABL tyrosine kinase inhibitors, one or more benzodiazepines, one or more beta blockers, one or more beta-adrenergic blocking agents, one or more beta-lactamase inhibitors, one or more bile acid sequestrants, one or more bisphosphonates, one or more bone morphogenetic proteins, one or more bone resorption inhibitors, one or more bronchodilator combinations, one or more bronchodilators, one or more BTK inhibitors, one or more calcimimetics, one or more calcineurin inhibitors, one or more calcitonin, one or more calcium channel blocking agents, one or more carbapenems, one or more carbonic anhydrase inhibitors, one or more cardiac stressing agents, one or more cardioselective beta blockers, one or more cardiovascular agents, one or more catecholamines, one or more CDK 4/6 inhibitors, one or more central nervous system agents, one or more cephalosporins, one or more cerumenolytics, one or more CFTR potentiators, one or more CGRP inhibitors, one or more chelating agents, one or more chemokine receptor antagonist, one or more chloride channel activators, one or more cholesterol absorption inhibitors, one or more cholinergic agonists, one or more cholinergic muscle stimulants, one or more cholinesterase inhibitors, one or more chronotropic agents, one or more CNS agents, one or more CNS stimulants, one or more coagulation modifiers, one or more colony stimulating factors, one or more corticosteroids, one or more corticotropin, one or more coumarins and indandiones, one or more cox-2 inhibitors, one or more decongestants, one or more diarylquinolines, one or more dibenzazepine, one or more diagnostic dyes, one or more dipeptidyl peptidase 4 inhibitors, one or more disease-modifying antirheumatic drugs (DMARDs), one or more diuretics, one or more echinocandins, one or more EGFR inhibitors, one or more erythropoiesis agents, one or more estrogen receptor antagonists, one or more estrogens, one or more expectorants, one or more factor Xa inhibitors, one or more fibric acid derivatives, one or more first generation cephalosporins, one or more fourth generation cephalosporins, one or more functional bowel disorder agents, one or more gallstone solubilizing agents, one or more gamma-aminobutyric acid analogs, one or more gamma-aminobutyric acid reuptake inhibitors. gastrointestinal agents, one or more genitourinary tract agents, one or more GI stimulants, one or more glucocorticoids, one or more glucose elevating agents, one or more glycoprotein platelet inhibitors, one or more glycylcyclines, one or more gonadotropin releasing hormones, one or more gonadotropin-releasing hormone antagonists, one or more gonadotropins, one or more group I antiarrhythmics, one or more group II antiarrhythmics, one or more group III antiarrhythmics, one or more group IV antiarrhythmics, one or more group V antiarrhythmics, one or more growth hormone receptor blockers, one or more growth hormones, one or more guanylate cyclase-C agonists, one or more *H. pylori* eradication agents, one or more H2 antagonists, one or more hedgehog pathway inhibitors, one or more hematopoietic stem cell mobilizer, one or more heparin antagonists, one or more heparins, one or more HER2 inhibitors, one or more herbal products, one or more histone deacetylase inhibitors, one or more hormones, one or more hydantoin, one or more hydrazide derivatives, one or more immunologic agents, one or more immunostimulants, one or more immunosuppressive agents, one or more impotence agents, one or more incretin mimetics, one or more inotropic agents, one or more insulin, one or more insulin-like growth factors, one or more integrase strand transfer inhibitor, one or more interferons, one or more interleukin inhibitors, one or more interleukins, one or more intravenous nutritional products, one or more investigational drugs, one or more iodinated contrast media, one or more iron products, one or more ketolides, one or more leprostatics, one or more leukotriene modifiers, one or more lincomycin derivatives, one or more local injectable anesthetics, one or more lymphatic staining agents, one or more macrolide derivatives, one or more macrolides, one or more magnetic resonance imaging contrast media, one or more malignancy photosensitizers, one or more mast cell stabilizers, one or more meglitinides, one or more melanocortin receptor agonists, one or more metabolic agents, one or more methylxanthines, one or more mineralocorticoids, one or more minerals and electrolytes, one or more mitotic inhibitors, one or more monoamine oxidase inhibitors, one or more mTOR inhibitors, one or more mucolytics, one or more multikinase inhibitors, one or more muscle relaxants, one or more mydriatics, one or more neprilysin inhibitors, one or more neuraminidase inhibitors, one or more neuromuscular blocking agents, one or more neuronal potassium channel openers, one or more NHE3 inhibitors, one or more nicotinic acid derivatives, one or more NK1 receptor antagonists, one or more non-opioids, one or more NNRTIs, one or more non-cardioselective beta blockers, one or more non-sulfonylureas, one or more nonsteroidal anti-inflammatory drugs, one or more nootropic agents, one or more NS5A inhibitors, one or more nucleoside reverse transcriptase inhibitors (NRTIs), one or more nutraceutical products, one or more nutritional products, one or more ophthalmic agents, one or more opioids, one or more otic agents, one or more oxazolidinedione, one or more parathyroid hormone and analogs, one or more PARP inhibitors, one or more PCSK9 inhibitors, one or more penicillins, one or more peripheral opioid receptor antagonists, one or more peripheral opioid receptor mixed agonists/antagonists, one or more peripheral vasodilators, one or more peripherally acting antiobesity agents, one or more phenothiazine, one or more phenylpiperazine, one or more phosphate binders, one or more PI3K inhibitors, one or more plasma expanders, one or more platelet aggregation inhibitors, one or more platelet-stimulating agents, one or more polyenes, one or more probiotics, one or more progesterone receptor modulators, one or more progestins, one or more prolactin inhibitors, one or more prostaglandin $D_2$ antagonists, one or more protease inhibitors, one or more protease-activated receptor-1 antagonists, one or more proteasome inhibitors, one or more proton pump inhibitors, one or more PPAR agonists, one or more psoralens, one or more psychotherapeutic agents, one or more purine nucleosides, one or more pyrrolidine, one or more quinolones, one or more radiocontrast agents, one or more radiologic adjuncts, one or more radiologic agents, one or more radiologic conjugating agents, one or more radiopharmaceuticals, one or more renal replacement solutions, one or more renin inhibitors, one or more respiratory agents, one or more rifamycin derivatives, one or more salicylates, one or more sclerosing agents, one or more second generation cephalosporins, one or more selective estrogen receptor modulators, one or more selective immunosuppressants, one or more selective phosphodiesterase-4 inhibitors, one or more selective serotonin reuptake inhibitors, one or more serotonin-norepinephrine reuptake inhibitors, one or more serotoninergic neuroenteric modulators, one or more sex hormones, one or more SGLT-2 inhibitors, one or more skeletal muscle relaxants, one or more smoking cessation agents, one or more somatostatin and somatostatin analogs, one or more spermicides, one or more statins, one or more streptogramins, one or more *streptomyces* derivatives, one or more succinimide, one or more sulfonamides, one or more sulfonylureas, one or more sympathomimetic amines, one or more synthetic ovulation stimulants, one or more tetracyclines, one or more therapeutic radiopharmaceuticals, one or more thiazide, one or more thiazolidinediones, one or more thioxanthenes, one or more third generation cephalosporins, one or more thrombin inhibitors, one or more thrombolytics, one or more thyroid drugs, one or more TNFα inhibitors, one or more tocolytic agents, one or more transthyretin stabilizers, one or more triazines, one or more urea cycle disorder agents, one or more urinary pH modifiers, one or more uterotonic agents, one or more vasodilators, one or more vasopressin antagonists, one or more vasopressors, one or more VEGF/VEGFR inhibitors, one or more viscosupplementation agents, one or more vitamin, one or more VMAT2 inhibitors, or any combination thereof; or e) an alkylating agent, an anti-metabolite, a cytotoxic antibiotic, a NSAID, a paracetamol-type therapeutic compound, a plant alkaloid and terpenoid, a PPARα agonist, a PPARγ agonist, a PPARγ agonist, a duel PPAR-α/γ agonist, a PPAR-13 agonist, a topoisomerase inhibitor, amphetamines, anticholinergic agents, anticonvulsant agents, antidementia agents, antidepressant agents, antispasticity agents, antiemetic agents, antimigraine agents, anti-obesity agents, antiparkinson agents, antipsychotic agents, anxiolytic agents, attention deficit hyperactivity disorder agents, benzodiazepines, bipolar agents, calcitonin gene-related peptide (CGRP) receptor antagonists, calcium channel modifying agents, cholinesterase inhibitors, dopamine agonists, dopamine precursors and/or I-amino acid decarboxylase inhibitors, emetogenic therapy adjuncts, ergot alkaloids, fibromyalgia agents, gamma-aminobutyric acid (GABA) augmenting agents, monoamine oxidase inhibitors, monoamine oxidase B inhibitors, multiple sclerosis agents, N-methyl-D-aspartate (NMDA) receptor antagonist, selective serotonin reuptake inhibitors/serotonin and norepinephrine reuptake inhibitors (SSRI/SNRI), serotonin (5-HT) receptor agonists, sleep disorder agents, sleep promoting agents, sodium channel modifying agents, tricyclic agents, and wakefulness promoting agents, a fibrate, a statin, a tocotrienol, a niacin, a bile acid sequestrants (resin), a cholesterol absorption inhibitor, a pancreatic lipase inhibitor, an α-adrenergic agonist, a β-adrenergic agonist, a dopaminergic agonist, a monoamine oxidase (MAO) inhibitor, a COMT inhibitor, a retinoid, a vitamin, a cannabinoid, a cannabinoid receptor modulator, a 5-HT3 serotonin ion channel antagonist, a 5-HT serotonin G-protein receptor antagonist, a CB1 agonist, a $D_2/D_3$ antagonist, a H1 antagonist, a mACh antagonist, a NK1 antagonist, or any combination thereof; or f) abiraterone, amlexanox, aprepitant, auranofin, cannibidiol, curcumin, diclofenac, eliglustat, fenofibrate, ibuprofen, mebendazole, midastaurin, naproxen, niflumic acid, nintedanib, olaparib, pirfenidone, pitolosant, telmisartan, or any combination thereof.

4. The pharmaceutical composition of any one of embodiments 1-3, wherein the one or more therapeutic compounds are in an amount of about 0.1% to about 1%, about 0.1% to about 2.5%, about 0.1% to about 5%, about 0.1% to about 7.5%, about 0.1% to about 10%, about 0.1% to about 12.5%, about 0.1% to about 15%, about 0.1% to about 17.5%, about 0.1% to about 20%, about 0.1% to about 22.5%, about 0.1% to about 25%, about 0.1% to about 30%, about 0.1% to about 40%, about 0.1% to about 50%, about 1% to about 2.5%, about 1% to about 5%, about 1% to about 7.5%, about 1% to about 10%, about 1% to about 12.5%, about 1% to about 15%, about 1% to about 17.5%, about 1% to about 20%, about 1% to about 22.5%, about 1% to about 25%, about 1% to about 30%, about 1% to about 40%, about 1% to about 50%, about 5% to about 10%, about 5% to about 15%, about 5% to about 20%, about 5% to about 25%, about 5% to about 30%, about 5% to about 40%, about 5% to about 50%, about 10% to about 15%, about 10% to about 20%, about 10% to about 25%, about 10% to about 30%, about 10% to about 40%, about 10% to about 50%, about 15% to about 20%, about 15% to about 25%, about 15% to about 30%, about 15% to about 40%, about 15% to about 50%, about 20% to about 30%, about 20% to about 40%, about 20% to about 50%, about 30% to about 40%, about 30% to about 50%, or about 40% to about 50% by weight.

5. The pharmaceutical composition of any one of embodiments 1-4, wherein the one or more therapeutic compounds are in an amount of about 25 mg/mL to about 50 mg/mL, about 25 mg/mL to about 75 mg/mL, about 25 mg/mL to about 100 mg/mL, about 25 mg/mL to about 125 mg/mL, about 25 mg/mL to about 150 mg/mL, about 25 mg/mL to about 200 mg/mL, about 25 mg/mL to about 250 mg/mL, about 25 mg/mL to about 300 mg/mL, about 25 mg/mL to about 350 mg/mL, about 25 mg/mL to about 400 mg/mL, about 25 mg/mL to about 450 mg/mL, about 25 mg/mL to about 500 mg/mL, about 25 mg/mL to about 550 mg/mL, about 25 mg/mL to about 600 mg/mL, about 50 mg/mL to about 100 mg/mL, about 50 mg/mL to about 150 mg/mL, about 50 mg/mL to about 200 mg/mL, about 50 mg/mL to about 250 mg/mL, about 50 mg/mL to about 300 mg/mL, about 50 mg/mL to about 350 mg/mL, about 50 mg/mL to about 400 mg/mL, about 50 mg/mL to about 450 mg/mL, about 50 mg/mL to about 500 mg/mL, about 50 mg/mL to about 550 mg/mL, about 50 mg/mL to about 600 mg/mL, about 75 mg/mL to about 100 mg/mL, about 75 mg/mL to about 150 mg/mL, about 75 mg/mL to about 200 mg/mL, about 75 mg/mL to about 250 mg/mL, about 75 mg/mL to about 300 mg/mL, about 75 mg/mL to about 350 mg/mL, about 75 mg/mL to about 400 mg/mL, about 75 mg/mL to about 450 mg/mL, about 75 mg/mL to about 500 mg/mL, about 75 mg/mL to about 550 mg/mL, about 75 mg/mL to about 600 mg/mL, about 100 mg/mL to about 150 mg/mL, about 100 mg/mL to about 200 mg/mL, about 100 mg/mL to about 250 mg/mL, about 100 mg/mL to about 300 mg/mL, about 100 mg/mL to about 350 mg/mL, about 100 mg/mL to about 400 mg/mL, about 100 mg/mL to about 450 mg/mL, about 100 mg/mL to about 500 mg/mL, about 100 mg/mL to about 550 mg/mL, or about 100 mg/mL to about 600 mg/mL.

6. The pharmaceutical composition of any one of embodiments 1-5, wherein the one or more glycerolipids are in an amount of at least 20% by weight, at least 25% by weight, at least 30% by weight, at least 35% by weight, at least 40% by weight, at least 45% by weight, at least 50% by weight, at least 55% by weight, at least 60% by weight, at least 65% by weight, at least 70% by weight, at least 75% by weight, at least 80% by weight, at least 85% by weight, at least 90% by weight, or at least 95% by weight and/or at most 40% by weight, at most 45% by weight, at most 50% by weight, at most 55% by weight, at most 60% by weight, at most 65% by weight, at most 70% by weight, at most 75% by weight, at most 80% by weight, at most 85% by weight, at most 90% by weight, at most 95% by weight, or at most 99% by weight or between about 20% to about 30%, about 20% to about 40%, about 20% to about 50%, about 20% to about 55%, about 20% to about 60%, about 20% to about 70%, about 20% to about 80%, about 20% to about 90%, about 25% to about 30%, about 25% to about 40%, about 25% to about 50%, about 25% to about 55%, about 25% to about 60%, about 25% to about 70%, about 25% to about 80%, about 25% to about 90%, about 30% to about 40%, about 30% to about 50%, about 30% to about 55%, about 30% to about 60%, about 30% to about 70%, about 30% to about 80%, about 30% to about 90%, about 40% to about 50%, about 40% to about 55%, about 40% to about 60%, about 40% to about 65%, about 40% to about 70%, about 40% to about 75%, about 40% to about 80%, about 40% to about 85%, about 40% to about 90%, about 40% to about 95%, about 45% to about 55%, about 45% to about 60%, about 45% to about 65%, about 45% to about 70%, about 45% to about 75%, about 45% to about 80%, about 45% to about 85%, about 45% to about 90%, about 45% to about 95%, about 50% to about 55%, about 50% to about 60%, about 50% to about 65%, about 50% to about 70%, about 50% to about 75%, about 50% to about 80%, about 50% to about 85%, about 50% to about 90%, about 50% to about 95%, about 55% to about 60%, about 55% to about 65%, about 55% to about 70%, about 55% to about 75%, about 55% to about 85%, about 55% to about 95%, about 60% to about 65%, about 60% to about 70%, about 60% to about 75%, about 60% to about 80%, about 60% to about 85%, about 60% to about 90%, about 60% to about 95%, about 65% to about 70%, about 65% to about 75%, about 65% to about 80%, about 65% to about 90%, about 65% to about 95%, about 70% to about 75%, about 70% to about 80%, about 70% to about 85%, about 70% to about 90%, about 70% to about 95%, about 75% to about 80%, about 75% to about 85%, about 75% to about 95%, about 80% to about 90%, about 80% to about 95%, about 80% to about 99%, about 85% to about 90%, about 85% to about 95%, about 85% to about 99%, about 90% to about 95%, or about 90% to about 99% by weight.

7. The pharmaceutical composition of any one of embodiments 1-6, wherein the one or more glycerolipids comprises one or more hard fats, one or more liquid fats, or any combination thereof.

8. The pharmaceutical composition of embodiment 7, wherein the one or more hard fats include one or more triglycerides.

9. The pharmaceutical composition of embodiment 8, wherein the one or more triglycerides include a mixture of saturated $C_{10}$-$C_{18}$ triglycerides, a mixture of saturated $C_{18}$-$C_{20}$ triglycerides, a mixture of saturated $C_{18}$-$C_{22}$ triglycerides, a mixture of saturated $C_{18}$-$C_{24}$ triglycerides, a mixture of saturated $C_{12}$-$C_{18}$ triglycerides, a mixture of saturated $C_{12}$-$C_{20}$ triglycerides, a mixture of saturated $C_{12}$-$C_{22}$ triglycerides, a mixture of saturated $C_{12}$-$C_{24}$ triglycerides, a mixture of saturated $C_{14}$-$C_{18}$ triglycerides, a mixture of saturated $C_{14}$-$C_{20}$ triglycerides, a mixture of saturated $C_{14}$-$C_{22}$ triglycerides, a mixture of saturated $C_{14}$-$C_{24}$ triglycerides, a mixture of saturated $C_{16}$-$C_{18}$ triglycerides, a mixture of saturated $C_{18}$-$C_{20}$ triglycerides, a mixture of saturated $C_{16}$-$C_{22}$ triglycerides, a mixture of saturated $C_{16}$-$C_{24}$ triglycerides, a mixture of saturated $C_{18}$-$C_{20}$ triglycerides, a mixture of saturated $C_{18}$-$C_{22}$ triglycerides, a mixture of saturated $C_{18}$-$C_{24}$ triglycerides, a mixture of saturated $C_{20}$-$C_{22}$ triglycerides, or a mixture of saturated $C_{22}$-$C_{24}$ triglycerides.

10. The pharmaceutical composition of embodiment 8, wherein the one or more triglycerides include a mixture of unsaturated $C_{16}$-$C_{18}$ triglycerides, a mixture of unsaturated $C_{18}$-$C_{20}$ triglycerides, a mixture of unsaturated $C_{18}$-$C_{22}$ triglycerides, a mixture of unsaturated $C_{18}$-$C_{24}$ triglycerides, a mixture of unsaturated $C_{12}$-$C_{18}$ triglycerides, a mixture of unsaturated $C_{12}$-$C_{20}$ triglycerides, a mixture of unsaturated $C_{12}$-$C_{22}$ triglycerides, a mixture of unsaturated $C_{12}$-$C_{24}$ triglycerides, a mixture of unsaturated $C_{14}$-$C_{18}$ triglycerides, a mixture of unsaturated $C_{14}$-$C_{20}$ triglycerides, a mixture of unsaturated $C_{14}$-$C_{22}$ triglycerides, a mixture of unsaturated $C_{14}$-$C_{24}$ triglycerides, a mixture of unsaturated $C_{16}$-$C_{18}$ triglycerides, a mixture of unsaturated $C_{16}$-$C_{20}$ triglycerides, a mixture of unsaturated $C_{16}$-$C_{22}$ triglycerides, a mixture of unsaturated $C_{16}$-$C_{24}$ triglycerides, a mixture of unsaturated $C_{18}$-$C_{20}$ triglycerides, a mixture of unsaturated $C_{18}$-$C_{22}$ triglycerides, a mixture of unsaturated $C_{18}$-$C_{24}$ triglycerides, a mixture of unsaturated $C_{20}$-$C_{22}$ triglycerides, or a mixture of unsaturated $C_{22}$-$C_{24}$ triglycerides.

11. The pharmaceutical composition of embodiment 8, wherein the one or more triglycerides include a mixture of saturated and unsaturated $C_{16}$-$C_{18}$ triglycerides, a mixture of saturated and unsaturated $C_{18}$-$C_{20}$ triglycerides, a mixture of saturated and unsaturated $C_{18}$-$C_{22}$ triglycerides, a mixture of saturated and unsaturated $C_{18}$-$C_{24}$ triglycerides, a mixture of saturated and unsaturated $C_{12}$-$C_{18}$ triglycerides, a mixture of saturated and unsaturated $C_{12}$-$C_{20}$ triglycerides, a mixture of saturated and unsaturated $C_{12}$-$C_{22}$ triglycerides, a mixture of saturated and unsaturated $C_{12}$-$C_{24}$ triglycerides, a mixture of saturated and unsaturated $C_{14}$-$C_{18}$ triglycerides, a mixture of saturated and unsaturated $C_{14}$-$C_{20}$ triglycerides, a mixture of saturated and unsaturated $C_{14}$-$C_{22}$ triglycerides, a mixture of saturated and unsaturated $C_{14}$-$C_{24}$ triglycerides, a mixture of saturated and unsaturated $C_{16}$-$C_{18}$ triglycerides, a mixture of saturated and unsaturated $C_{16}$-$C_{20}$ triglycerides, a mixture of saturated and unsaturated $C_{16}$-$C_{22}$ triglycerides, a mixture of saturated and unsaturated $C_{16}$-$C_{24}$ triglycerides, a mixture of saturated and unsaturated $C_{18}$-$C_{20}$ triglycerides, a mixture of saturated and unsaturated $C_{18}$-$C_{22}$ triglycerides, a mixture of saturated and unsaturated $C_{18}$-$C_{24}$ triglycerides, a mixture of saturated and unsaturated $C_{20}$-$C_{22}$ triglycerides, or a mixture of saturated and unsaturated $C_{22}$-$C_{24}$ triglycerides.

12. The pharmaceutical composition of any one of embodiments 8-11, wherein the one or more hard fats are in an amount of at least 10% by weight, at least 15% by weight, at least 20% by weight, at least 25% by weight, at least 30% by weight, at least 35% by weight, at least 40% by weight, at least 45% by weight, at least 50% by weight, at least 55% by weight, at least 60% by weight, at least 65% by weight, at least 70% by weight, at least 75% by weight, and/or at most 10% by weight, at most 15% by weight, at most 20% by weight, at most 25% by weight, at most 30% by weight, at most 35% by weight, at most 40% by weight, at most 45% by weight, at most 50% by weight, at most 55% by weight, at most 60% by weight, at most 65% by weight, at most 70% by weight, at most 75% by weight, or between about 10% to about 20%, about 10% to about 25%, about 10% to about 30%, about 10% to about 35%, about 10% to about 40%, about 10% to about 45%, about 10% to about 50%, about 10% to about 55%, about 10% to about 60%, about 10% to about 65%, about 10% to about 70%, about 15% to about 20%, about 15% to about 25%, about 15% to about 30%, about 15% to about 35%, about 15% to about 40%, about 15% to about 45%, about 15% to about 50%, about 15% to about 55%, about 15% to about 60%, about 15% to about 65%, about 15% to about 70%, about 20% to about 25%, about 20% to about 30%, about 20% to about 35%, about 20% to about 40%, about 20% to about 45%, about 20% to about 50%, about 20% to about 55%, about 20% to about 60%, about 20% to about 65%, about 20% to about 70%, about 25% to about 30%, about 25% to about 35%, about 25% to about 40%, about 25% to about 45%, about 25% to about 50%, about 25% to about 55%, about 25% to about 60%, about 25% to about 65%, about 25% to about 70%, about 30% to about 35%, about 30% to about 40%, about 30% to about 45%, about 30% to about 50%, about 30% to about 55%, about 30% to about 60%, about 30% to about 65%, about 30% to about 70%, about 35% to about 40%, about 35% to about 45%, about 35% to about 50%, about 35% to about 55%, about 35% to about 60%, about 35% to about 65%, about 35% to about 70%, about 40% to about 45%, about 40% to about 50%, about 40% to about 55%, about 40% to about 60%, about 40% to about 65%, about 40% to about 70%, about 45% to about 50%, about 45% to about 55%, about 45% to about 60%, about 45% to about 65%, about 45% to about 70%, about 50% to about 55%, about 50% to about 60%, about 50% to about 65%, about 50% to about 70%, about 55% to about 60%, about 55% to about 65%, about 55% to about 70%, about 60% to about 65%, about 60% to about 70%, or about 65% to about 70% by weight.

13. The pharmaceutical composition of any one of embodiments 7-12, wherein the one or more liquid fats include one or more partially hydrolyzed glycerolipids, one or more monoglycerides, or a combination thereof.

14. The pharmaceutical composition of embodiment 13, wherein the one or more partially hydrolyzed glycerolipids comprise a mixture of mono-, di- and triglycerides.

15. The pharmaceutical composition of embodiment 13, wherein the one or more partially hydrolyzed glycerolipids comprise a mixture of unsaturated $C_{10}$-$C_{18}$ monoglycerides, $C_{10}$-$C_{18}$ diglycerides, and $C_{10}$-$C_{18}$ triglycerides, a mixture of unsaturated $C_{10}$-$C_{20}$ monoglycerides, $C_{10}$-$C_{20}$ diglycerides, and $C_{10}$-$C_{20}$ triglycerides, a mixture of unsaturated $C_{10}$-$C_{22}$ monoglycerides, $C_{10}$-$C_{22}$ diglycerides, and $C_{10}$-$C_{22}$ triglycerides, a mixture of unsaturated $C_{10}$-$C_{24}$ monoglycerides, $C_{10}$-$C_{24}$ diglycerides, and $C_{10}$-$C_{24}$ triglycerides, a mixture of unsaturated $C_{12}$-$C_{18}$ monoglycerides, $C_{12}$-$C_{18}$ diglycerides, and $C_{12}$-$C_{18}$ triglycerides, a mixture of unsaturated $C_{12}$-$C_{20}$ monoglycerides, $C_{12}$-$C_{20}$ diglycerides, and $C_{12}$-$C_{20}$ triglycerides, a mixture of unsaturated $C_{12}$-$C_{22}$ monoglycerides, $C_{12}$-$C_{22}$ diglycerides, and $C_{12}$-$C_{22}$ triglycerides, a mixture of unsaturated $C_{12}$-$C_{24}$ monoglycerides, $C_{12}$-$C_{24}$ diglycerides, and $C_{12}$-$C_{24}$ triglycerides, a mixture of unsaturated $C_{14}$-$C_{18}$ monoglycerides, $C_{14}$-$C_{18}$ diglycerides, and $C_{14}$-$C_{18}$ triglycerides, a mixture of unsaturated $C_{14}$-$C_{20}$ monoglycerides, $C_{14}$-$C_{20}$ diglycerides, and $C_{14}$-$C_{20}$ triglycerides, a mixture of unsaturated $C_{14}$-$C_{22}$ monoglycerides, $C_{14}$-$C_{22}$ diglycerides, and $C_{14}$-$C_{22}$ triglycerides, a mixture of unsaturated $C_{14}$-$C_{24}$ monoglycerides, $C_{14}$-$C_{24}$ diglycerides, and $C_{14}$-$C_{24}$ triglycerides, a mixture of unsaturated $C_{16}$-$C_{18}$ monoglycerides, $C_{16}$-$C_{18}$ diglycerides, and $C_{16}$-$C_{18}$ triglycerides, a mixture of unsaturated $C_{16}$-$C_{20}$ monoglycerides, $C_{16}$-$C_{20}$ diglycerides, and $C_{16}$-$C_{20}$ triglycerides, a mixture of unsaturated $C_{16}$-$C_{22}$ monoglycerides, $C_{16}$-$C_{22}$ diglycerides, and $C_{16}$-$C_{22}$ triglycerides, a mixture of unsaturated $C_{16}$-$C_{24}$ monoglycerides, $C_{16}$-$C_{24}$ diglycerides, and $C_{16}$-$C_{24}$ triglycerides, a mixture of unsaturated $C_{18}$-$C_{20}$ monoglycerides, $C_{18}$-$C_{20}$ diglycerides, and $C_{18}$-$C_{20}$ triglycerides, a mixture of unsaturated $C_{18}$-$C_{22}$ monoglycerides, $C_{18}$-$C_{22}$ diglycerides, and $C_{18}$-$C_{22}$ triglycerides, a mixture of unsaturated $C_{18}$-$C_{24}$ monoglycerides, $C_{18}$-$C_{24}$ diglycerides, and $C_{18}$-$C_{24}$ triglycerides, a mixture of unsaturated $C_{20}$-$C_{22}$ monoglycerides, $C_{20}$-$C_{22}$ diglycerides, $C_{20}$-$C_{22}$ triglycerides, or a mixture of unsaturated $C_{22}$-$C_{24}$ monoglycerides, $C_{22}$-$C_{24}$ diglycerides, and $C_{22}$-$C_{24}$ triglycerides.

16. The pharmaceutical composition of embodiment 13, wherein the one or more partially hydrolyzed glycerolipids comprise a mixture of saturated $C_{10}$-$C_{18}$ monoglycerides, $C_{10}$-$C_{18}$ diglycerides, and $C_{10}$-$C_{18}$ triglycerides, a mixture of saturated $C_{10}$-$C_{20}$ monoglycerides, $C_{10}$-$C_{20}$ diglycerides, and $C_{10}$-$C_{20}$ triglycerides, a mixture of saturated $C_{10}$-$C_{22}$ monoglycerides, $C_{10}$-$C_{22}$ diglycerides, and $C_{10}$-$C_{22}$ triglycerides, a mixture of saturated $C_{10}$-$C_{24}$ monoglycerides, $C_{10}$-$C_{24}$ diglycerides, and $C_{10}$-$C_{24}$ triglycerides, a mixture of saturated $C_{12}$-$C_{18}$ monoglycerides, $C_{12}$-$C_{18}$ diglycerides, and $C_{12}$-$C_{18}$ triglycerides, a mixture of saturated $C_{12}$-$C_{20}$ monoglycerides, $C_{12}$-$C_{20}$ diglycerides, and $C_{12}$-$C_{20}$ triglycerides, a mixture of saturated $C_{12}$-$C_{22}$ monoglycerides, $C_{12}$-$C_{22}$ diglycerides, and $C_{12}$-$C_{22}$ triglycerides, a mixture of saturated $C_{12}$-$C_{24}$ monoglycerides, $C_{12}$-$C_{24}$ diglycerides, and $C_{12}$-$C_{24}$ triglycerides, a mixture of saturated $C_{14}$-$C_{18}$ monoglycerides, $C_{14}$-$C_{18}$ diglycerides, and $C_{14}$-$C_{18}$ triglycerides, a mixture of saturated $C_{14}$-$C_{20}$ monoglycerides, $C_{14}$-$C_{20}$ diglycerides, and $C_{14}$-$C_{20}$ triglycerides, a mixture of saturated $C_{14}$-$C_{22}$ monoglycerides, $C_{14}$-$C_{22}$ diglycerides, and $C_{14}$-$C_{22}$ triglycerides, a mixture of saturated $C_{14}$-$C_{24}$ monoglycerides, $C_{14}$-$C_{24}$ diglycerides, and $C_{14}$-$C_{24}$ triglycerides, a mixture of saturated $C_{16}$-$C_{18}$ monoglycerides, $C_{16}$-

C$_{18}$ diglycerides, and C$_{16}$-C$_{18}$ triglycerides, a mixture of saturated C$_{16}$-C$_{20}$ monoglycerides, C$_{16}$-C$_{20}$ diglycerides, and C$_{16}$-C$_{20}$ triglycerides, a mixture of saturated C$_{16}$-C$_{22}$ monoglycerides, C$_{16}$-C$_{22}$ diglycerides, and C$_{16}$-C$_{22}$ triglycerides, a mixture of saturated C$_{16}$-C$_{24}$ monoglycerides, C$_{16}$-C$_{24}$ diglycerides, and C$_{16}$-C$_{24}$ triglycerides, a mixture of saturated C$_{18}$-C$_{20}$ monoglycerides, C$_{18}$-C$_{20}$ diglycerides, and C$_{18}$-C$_{20}$ triglycerides, a mixture of saturated C$_{18}$-C$_{22}$ monoglycerides, C$_{18}$-C$_{22}$ diglycerides, and C$_{18}$-C$_{22}$ triglycerides, a mixture of saturated C$_{18}$-C$_{24}$ monoglycerides, C$_{18}$-C$_{24}$ diglycerides, and C$_{18}$-C$_{24}$ triglycerides, a mixture of saturated C$_{20}$-C$_{22}$ monoglycerides, C$_{20}$-C$_{22}$ diglycerides, C$_{20}$-C$_{22}$ triglycerides, or a mixture of saturated C$_{22}$-C$_{24}$ monoglycerides, C$_{22}$-C$_{24}$ diglycerides, and C$_{22}$-C$_{24}$ triglycerides.

17. The pharmaceutical composition of embodiment 13, wherein the one or more partially hydrolyzed glycerolipids comprise a mixture of saturated and unsaturated C$_{10}$-C$_{18}$ monoglycerides, C$_{10}$-C$_{18}$ diglycerides, and C$_{10}$-C$_{18}$ triglycerides, a mixture of saturated and unsaturated C$_{10}$-C$_{20}$ monoglycerides, C$_{10}$-C$_{20}$ diglycerides, and C$_{10}$-C$_{20}$ triglycerides, a mixture of saturated and unsaturated C$_{10}$-C$_{22}$ monoglycerides, C$_{10}$-C$_{22}$ diglycerides, and C$_{10}$-C$_{22}$ triglycerides, a mixture of saturated and unsaturated C$_{10}$-C$_{24}$ monoglycerides, C$_{10}$-C$_{24}$ diglycerides, and C$_{10}$-C$_{24}$ triglycerides, a mixture of saturated and unsaturated C$_{12}$-C$_{18}$ monoglycerides, C$_{12}$-C$_{18}$ diglycerides, and C$_{12}$-C$_{18}$ triglycerides, a mixture of saturated and unsaturated C$_{12}$-C$_{20}$ monoglycerides, C$_{12}$-C$_{20}$ diglycerides, and C$_{12}$-C$_{20}$ triglycerides, a mixture of saturated and unsaturated C$_{12}$-C$_{22}$ monoglycerides, C$_{12}$-C$_{22}$ diglycerides, and C$_{12}$-C$_{22}$ triglycerides, a mixture of saturated and unsaturated C$_{12}$-C$_{24}$ monoglycerides, C$_{12}$-C$_{24}$ diglycerides, and C$_{12}$-C$_{24}$ triglycerides, a mixture of saturated and unsaturated C$_{14}$-C$_{18}$ monoglycerides, C$_{14}$-C$_{18}$ diglycerides, and C$_{14}$-C$_{18}$ triglycerides, a mixture of saturated and unsaturated C$_{14}$-C$_{20}$ monoglycerides, C$_{14}$-C$_{20}$ diglycerides, and C$_{14}$-C$_{20}$ triglycerides, a mixture of saturated and unsaturated C$_{14}$-C$_{22}$ monoglycerides, C$_{14}$-C$_{22}$ diglycerides, and C$_{14}$-C$_{22}$ triglycerides, a mixture of saturated and unsaturated C$_{14}$-C$_{24}$ monoglycerides, C$_{14}$-C$_{24}$ diglycerides, and C$_{14}$-C$_{24}$ triglycerides, a mixture of saturated and unsaturated C$_{16}$-C$_{18}$ monoglycerides, C$_{16}$-C$_{18}$ diglycerides, and C$_{16}$-C$_{18}$ triglycerides, a mixture of saturated and unsaturated C$_{16}$-C$_{20}$ monoglycerides, C$_{16}$-C$_{20}$ diglycerides, and C$_{16}$-C$_{20}$ triglycerides, a mixture of saturated and unsaturated C$_{16}$-C$_{22}$ monoglycerides, C$_{16}$-C$_{22}$ diglycerides, and C$_{16}$-C$_{22}$ triglycerides, a mixture of saturated and unsaturated C$_{16}$-C$_{24}$ monoglycerides, C$_{16}$-C$_{24}$ diglycerides, and C$_{16}$-C$_{24}$ triglycerides, a mixture of saturated and unsaturated C$_{18}$-C$_{20}$ monoglycerides, C$_{18}$-C$_{20}$ diglycerides, and C$_{18}$-C$_{20}$ triglycerides, a mixture of saturated and unsaturated C$_{18}$-C$_{22}$ monoglycerides, C$_{18}$-C$_{22}$ diglycerides, and C$_{18}$-C$_{22}$ triglycerides, a mixture of saturated and unsaturated C$_{18}$-C$_{24}$ monoglycerides, C$_{18}$-C$_{24}$ diglycerides, and C$_{18}$-C$_{24}$ triglycerides, a mixture of saturated and unsaturated C$_{20}$-C$_{22}$ monoglycerides, C$_{20}$-C$_{22}$ diglycerides, C$_{20}$-C$_{22}$ triglycerides, or a mixture of saturated and unsaturated C$_{22}$-C$_{24}$ monoglycerides, C$_{22}$-C$_{24}$ diglycerides, and C$_{22}$-C$_{24}$ triglycerides.

18. The pharmaceutical composition of any one or embodiments 13-17, wherein the one or more partially hydrolyzed glycerolipids are in an amount of at least 10% by weight, at least 15% by weight, at least 20% by weight, at least 25% by weight, at least 30% by weight, at least 35% by weight, at least 40% by weight, at least 45% by weight, at least 50% by weight, at least 55% by weight, at least 60% by weight, at least 65% by weight, at least 70% by weight, at least 75% by weight, and/or at most 10% by weight, at most 15% by weight, at most 20% by weight, at most 25% by weight, at most 30% by weight, at most 35% by weight, at most 40% by weight, at most 45% by weight, at most 50% by weight, at most 55% by weight, at most 60% by weight, at most 65% by weight, at most 70% by weight, at most 75% by weight, or between about 10% to about 20%, about 10% to about 25%, about 10% to about 30%, about 10% to about 35%, about 10% to about 40%, about 10% to about 45%, about 10% to about 50%, about 10% to about 55%, about 10% to about 60%, about 10% to about 65%, about 10% to about 70%, about 15% to about 20%, about 15% to about 25%, about 15% to about 30%, about 15% to about 35%, about 15% to about 40%, about 15% to about 45%, about 15% to about 50%, about 15% to about 55%, about 15% to about 60%, about 15% to about 65%, about 15% to about 70%, about 20% to about 25%, about 20% to about 30%, about 20% to about 35%, about 20% to about 40%, about 20% to about 45%, about 20% to about 50%, about 20% to about 55%, about 20% to about 60%, about 20% to about 65%, about 20% to about 70%, about 25% to about 30%, about 25% to about 35%, about 25% to about 40%, about 25% to about 45%, about 25% to about 50%, about 25% to about 55%, about 25% to about 60%, about 25% to about 65%, about 25% to about 70%, about 30% to about 35%, about 30% to about 40%, about 30% to about 45%, about 30% to about 50%, about 30% to about 55%, about 30% to about 60%, about 30% to about 65%, about 30% to about 70%, about 35% to about 40%, about 35% to about 45%, about 35% to about 50%, about 35% to about 55%, about 35% to about 60%, about 35% to about 65%, about 35% to about 70%, about 40% to about 45%, about 40% to about 50%, about 40% to about 55%, about 40% to about 60%, about 40% to about 65%, about 40% to about 70%, about 45% to about 50%, about 45% to about 55%, about 45% to about 60%, about 45% to about 65%, about 45% to about 70%, about 50% to about 55%, about 50% to about 60%, about 50% to about 65%, about 50% to about 70%, about 55% to about 60%, about 55% to about 65%, about 55% to about 70%, about 60% to about 65%, about 60% to about 70%, or about 65% to about 70% by weight.

19. The pharmaceutical composition of any one of embodiments 13-18, wherein the one or more monoglycerides comprise unsaturated C$_{10}$-C$_{18}$ monoglycerides, unsaturated C$_{10}$-C$_{20}$ monoglycerides, unsaturated C$_{10}$-C$_{22}$ monoglycerides, unsaturated C$_{10}$-C$_{24}$ monoglycerides, unsaturated C$_{12}$-C$_{18}$ monoglycerides, unsaturated C$_{12}$-C$_{20}$ monoglycerides, unsaturated C$_{12}$-C$_{22}$ monoglycerides, unsaturated C$_{12}$-C$_{24}$ monoglycerides, unsaturated C$_{14}$-C$_{18}$ monoglycerides, unsaturated C$_{14}$-C$_{20}$ monoglycerides, unsaturated C$_{14}$-C$_{22}$ monoglycerides, unsaturated C$_{14}$-C$_{24}$ monoglycerides, unsaturated C$_{16}$-C$_{18}$ monoglycerides, unsaturated C$_{16}$-C$_{20}$ monoglycerides, unsaturated C$_{16}$-C$_{22}$ monoglycerides, unsaturated C$_{16}$-C$_{24}$ monoglycerides, unsaturated C$_{18}$-C$_{20}$ monoglycerides, unsaturated C$_{18}$-C$_{22}$ monoglycerides, unsaturated $C_{18}$-$C_{24}$ monoglycerides, unsaturated $C_{20}$-$C_{22}$ monoglycerides, or unsaturated $C_{22}$-$C_{24}$ monoglycerides.

20. The pharmaceutical composition of any one of embodiments 13-18, wherein the one or more mono- glycerides comprise saturated $C_{10}$-$C_{18}$ monoglycerides, saturated $C_{10}$-$C_{20}$ monoglycerides, saturated $C_{10}$-$C_{22}$ monoglycerides, saturated $C_{10}$-$C_{24}$ monoglycerides, saturated $C_{12}$-$C_{18}$ monoglycerides, saturated $C_{12}$-$C_{20}$ monoglycerides, saturated $C_{12}$-$C_{22}$ monoglycerides, saturated $C_{12}$-$C_{24}$ monoglycerides, saturated $C_{14}$-$C_{18}$ monoglycerides, saturated $C_{14}$-$C_{20}$ monoglycerides, saturated $C_{14}$-$C_{22}$ monoglycerides, saturated $C_{14}$-$C_{24}$ monoglycerides, saturated $C_{16}$-$C_{18}$ monoglycerides, saturated $C_{16}$-$C_{20}$ monoglycerides, saturated $C_{16}$-$C_{22}$ monoglycerides, saturated $C_{16}$-$C_{24}$ monoglycerides, saturated $C_{18}$-$C_{20}$ monoglycerides, saturated $C_{18}$-$C_{22}$ monoglycerides, saturated $C_{18}$-$C_{24}$ monoglycerides, saturated $C_{20}$-$C_{22}$ monoglycerides, or saturated $C_{22}$-$C_{24}$ monoglycerides.

21. The pharmaceutical composition of any one of embodiments 13-18, wherein the one or more mono- glycerides comprise a mixture of saturated and unsatu- rated $C_{10}$-$C_{18}$ monoglycerides, a mixture of saturated and unsaturated $C_{10}$-$C_{20}$ monoglycerides, a mixture of saturated and unsaturated $C_{10}$-$C_{22}$ monoglycerides, a mixture of saturated and unsaturated $C_{10}$-$C_{24}$ mono- glycerides, a mixture of saturated and unsaturated $C_{12}$- $C_{18}$ monoglycerides, a mixture of saturated and unsatu- rated $C_{12}$-$C_{20}$ monoglycerides, a mixture of saturated and unsaturated $C_{12}$-$C_{22}$ monoglycerides, a mixture of saturated and unsaturated $C_{12}$-$C_{24}$ monoglycerides, a mixture of saturated and unsaturated $C_{14}$-$C_{18}$ mono- glycerides, a mixture of saturated and unsaturated $C_{14}$- $C_{20}$ monoglycerides, a mixture of saturated and unsatu- rated $C_{14}$-$C_{22}$ monoglycerides, a mixture of saturated and unsaturated $C_{14}$-$C_{24}$ monoglycerides, a mixture of saturated and unsaturated $C_{16}$-$C_{18}$ monoglycerides, a mixture of saturated and unsaturated $C_{16}$-$C_{20}$ mono- glycerides, a mixture of saturated and unsaturated $C_{16}$- $C_{22}$ monoglycerides, a mixture of saturated and unsatu- rated $C_{16}$-$C_{24}$ monoglycerides, a mixture of saturated and unsaturated $C_{18}$-$C_{20}$ monoglycerides, a mixture of saturated and unsaturated $C_{18}$-$C_{22}$ monoglycerides, a mixture of saturated and unsaturated $C_{18}$-$C_{24}$ mono- glycerides, a mixture of saturated and unsaturated $C_{20}$- $C_{22}$ monoglycerides, or a mixture of saturated and unsaturated $C_{22}$-$C_{24}$ monoglycerides.

22. The pharmaceutical composition of any one or embodiments 19-21, wherein the one or more mono- glycerides are in an amount of at least 10% by weight, at least 15% by weight, at least 20% by weight, at least 25% by weight, at least 30% by weight, at least 35% by weight, at least 40% by weight, at least 45% by weight, at least 50% by weight, at least 55% by weight, at least 60% by weight, at least 65% by weight, at least 70% by weight, at least 75% by weight, and/or at most 10% by weight, at most 15% by weight, at most 20% by weight, at most 25% by weight, at most 30% by weight, at most 35% by weight, at most 40% by weight, at most 45% by weight, at most 50% by weight, at most 55% by weight, at most 60% by weight, at most 65% by weight, at most 70% by weight, at most 75% by weight, or between about 10% to about 20%, about 10% to about 25%, about 10% to about 30%, about 10% to about 35%, about 10% to about 40%, about 10% to about 45%, about 10% to about 50%, about 10% to about 55%, about 10% to about 60%, about 10% to about 65%, about 10% to about 70%, about 15% to about 20%, about 15% to about 25%, about 15% to about 30%, about 15% to about 35%, about 15% to about 40%, about 15% to about 45%, about 15% to about 50%, about 15% to about 55%, about 15% to about 60%, about 15% to about 65%, about 15% to about 70%, about 20% to about 25%, about 20% to about 30%, about 20% to about 35%, about 20% to about 40%, about 20% to about 45%, about 20% to about 50%, about 20% to about 55%, about 20% to about 60%, about 20% to about 65%, about 20% to about 70%, about 25% to about 30%, about 25% to about 35%, about 25% to about 40%, about 25% to about 45%, about 25% to about 50%, about 25% to about 55%, about 25% to about 60%, about 25% to about 65%, about 25% to about 70%, about 30% to about 35%, about 30% to about 40%, about 30% to about 45%, about 30% to about 50%, about 30% to about 55%, about 30% to about 60%, about 30% to about 65%, about 30% to about 70%, about 35% to about 40%, about 35% to about 45%, about 35% to about 50%, about 35% to about 55%, about 35% to about 60%, about 35% to about 65%, about 35% to about 70%, about 40% to about 45%, about 40% to about 50%, about 40% to about 55%, about 40% to about 60%, about 40% to about 65%, about 40% to about 70%, about 45% to about 50%, about 45% to about 55%, about 45% to about 60%, about 45% to about 65%, about 45% to about 70%, about 50% to about 55%, about 50% to about 60%, about 50% to about 65%, about 50% to about 70%, about 55% to about 60%, about 55% to about 65%, about 55% to about 70%, about 60% to about 65%, about 60% to about 70%, or about 65% to about 70% by weight.

23. The pharmaceutical composition of any one or embodiments 7-22, wherein the one or more hard fats and the one or more liquid fats are in a hard fat to liquid fat ratio of about 5:1 to about 4:1, about 5:1 to about 3:1, about 5:1 to about 2:1, about 5:1 to about 1:1, about 4:1 to about 3:1, about 4:1 to about 2:1, about 4:1 to about 1:1, about 3:1 to about 2:1, about 3:1 to about 1:1, or about 2:1 to about 1:1.

24. The pharmaceutical composition of any one or embodiments 7-22, wherein the one or more hard fats and the one or more liquid fats are in a hard fat to liquid fat ratio of about 1:5 to about 1:4, about 1:5 to about 1:3, about 1:5 to about 1:2, about 1:5 to about 1:1, about 1:4 to about 1:3, about 1:4 to about 1:2, about 1:4 to about 1:1, about 1:3 to about 1:2, about 1:3 to about 1:1, or about 1:2 to about 1:1.

25. The pharmaceutical composition of any one of embodiments 1-24, wherein the one or more digestion enhancers include one or more bile acids, one or more phospholipids, one or more free $C_{14-24}$ fatty acids, one or more free $C_{14-24}$ fatty acid surfactants, or any com- bination thereof.

26. The pharmaceutical composition of embodiment 25, wherein the one or more digestion enhancers are in an amount of at least 1% by weight, at least 2.5% by weight, at least 5% by weight, at least 7.5% by weight, at least 10% by weight, at least 12.5% by weight, at least 15% by weight, at least 17.5% by weight, at least 20% by weight, at least 22.5% by weight, at least 25% by weight, at least 30% by weight, at least 35% by weight, at least 40% by weight, at least 45% by weight, at least 50% by weight, at least 55% by weight, at least 60% by weight, at least 65% by weight, at least 70% by weight, at least 75% by weight, at least 75% by weight and/or at most 1% by weight, at most 2.5% by weight, at most 5% by weight, at most 7.5% by weight, at most 10% by weight, at most 12.5% by weight, at most 15% by weight, at most 17.5% by weight, at most 20% by weight, at most 22.5% by weight, at most 25% by weight, at most 30% by weight, at most 35% by weight, at most 40% by weight, at most 45% by weight, at most 50% by weight, at most 55% by weight, at most 60% by weight, at most 65% by weight, at most 70% by weight, at most 75% by weight, or at most 80% by weight, or between about 1% to about 2.5% by weight, about 1% to about 5% by weight, about 1% to about 10% by weight, about 1% to about 15% by weight, about 1% to about 20% by weight, about 1% to about 25% by weight, about 2.5% to about 5% by weight, about 2.5% to about 10% by weight, about 2.5% to about 15% by weight, about 2.5% to about 20% by weight, about 2.5% to about 25% by weight, about 5% to about 10% by weight, about 5% to about 15% by weight, about 5% to about 20% by weight, about 5% to about 25% by weight, about 10% to about 20%, about 10% to about 25%, about 10% to about 30%, about 10% to about 35%, about 10% to about 40%, about 10% to about 45%, about 10% to about 50%, about 10% to about 55%, about 10% to about 60%, about 10% to about 65%, about 10% to about 70%, about 15% to about 20%, about 15% to about 25%, about 15% to about 30%, about 15% to about 35%, about 15% to about 40%, about 15% to about 45%, about 15% to about 50%, about 15% to about 55%, about 15% to about 60%, about 15% to about 65%, about 15% to about 70%, about 20% to about 25%, about 20% to about 30%, about 20% to about 35%, about 20% to about 40%, about 20% to about 45%, about 20% to about 50%, about 20% to about 55%, about 20% to about 60%, about 20% to about 65%, about 20% to about 70%, about 25% to about 30%, about 25% to about 35%, about 25% to about 40%, about 25% to about 45%, about 25% to about 50%, about 25% to about 55%, about 25% to about 60%, about 25% to about 65%, about 25% to about 70%, about 30% to about 35%, about 30% to about 40%, about 30% to about 45%, about 30% to about 50%, about 30% to about 55%, about 30% to about 60%, about 30% to about 65%, about 30% to about 70%, about 35% to about 40%, about 35% to about 45%, about 35% to about 50%, about 35% to about 55%, about 35% to about 60%, about 35% to about 65%, about 35% to about 70%, about 40% to about 45%, about 40% to about 50%, about 40% to about 55%, about 40% to about 60%, about 40% to about 65%, about 40% to about 70%, about 40% to about 75%, about 40% to about 80%, about 45% to about 50%, about 45% to about 55%, about 45% to about 60%, about 45% to about 65%, about 45% to about 70%, about 45% to about 75%, about 45% to about 80%, about 50% to about 55%, about 50% to about 60%, about 50% to about 65%, about 50% to about 70%, about 50% to about 75%, about 50% to about 80%, about 55% to about 60%, about 55% to about 65%, about 55% to about 70%, about 55% to about 75%, about 55% to about 80%, about 60% to about 65%, about 60% to about 70%, about 60% to about 75%, about 60% to about 80%, about 65% to about 70% by weight, about 65% to about 75%, about 65% to about 80%, about 70% to about 75%, about 70% to about 80%, or about 75% to about 80% by weight.

27. The pharmaceutical composition of embodiment 25, wherein the one or more bile acids includes cholic acid, chenodeoxycholic acid, dafachronic acid, deoxycholic acid, glycocholic acid, glycohenodeoxycholic acid, lithocholic acid, taurochenodeoxycholic acid, taurocholic acid, any stereoisomer thereof, and any combination thereof.

28. The pharmaceutical composition of embodiment 25 or 27, wherein the one or more bile acids are in an amount of at least 0.1% by weight, at least 0.5% by weight, at least 1.0% by weight, at least 1.5% by weight, at least 2.0% by weight, at least 2.5% by weight, at least 3.0% by weight, at least 3.5% by weight, at least 4.0% by weight, at least 4.5% by weight, at least 5.0% by weight, at least 5.5% by weight, at least 6.0% by weight, at least 6.5% by weight, at least 7.0% by weight, at least 7.5% by weight, at least 8.0% by weight, at least 8.5% by weight, at least 9.0% by weight, at least 9.5% by weight, at least 10.0% by weight and/or at most 0.1% by weight, at most 0.5% by weight, at most 1.0% by weight, at most 1.5% by weight, at most 2.0% by weight, at most 2.5% by weight, at most 3.0% by weight, at most 3.5% by weight, at most 4.0% by weight, at most 4.5% by weight, at most 5.0% by weight, at most 5.5% by weight, at most 6.0% by weight, at most 6.5% by weight, at most 7.0% by weight, at most 7.5% by weight, at most 8.0% by weight, at most 8.5% by weight, at most 9.0% by weight, at most 9.5% by weight, at most 10.0% by weight or between about 0.1% to about 0.5%, about 0.1% to about 1.0%, about 0.1% to about 2.0%, about 0.1% to about 3.0%, about 0.1% to about 4.0%, about 0.1% to about 5.0%, about 0.1% to about 6.0%, about 0.1% to about 7.0%, about 0.1% to about 8.0%, about 0.1% to about 9.0%, about 0.1% to about 10.0%, about 0.5% to about 1.0%, about 0.5% to about 2.0%, about 0.5% to about 3.0%, about 0.5% to about 4.0%, about 0.5% to about 5.0%, about 0.5% to about 6.0%, about 0.5% to about 7.0%, about 0.5% to about 8.0%, about 0.5% to about 9.0%, about 0.5% to about 10.0%, about 1.0% to about 2.0%, about 1.0% to about 3.0%, about 1.0% to about 4.0%, about 1.0% to about 5.0%, about 1.0% to about 6.0%, about 1.0% to about 7.0%, about 1.0% to about 8.0%, about 1.0% to about 9.0%, about 1.0% to about 10.0%, about 2.0% to about 3.0%, about 2.0% to about 4.0%, about 2.0% to about 5.0%, about 2.0% to about 6.0%, about 2.0% to about 7.0%, about 2.0% to about 8.0%, about 2.0% to about 9.0%, about 2.0% to about 10.0%, about 3.0% to about 4.0%, about 3.0% to about 5.0%, about 3.0% to about 6.0%, about 3.0% to about 7.0%, about 3.0% to about 8.0%, about 3.0% to about 9.0%, about 3.0% to about 10.0%, about 4.0% to about 5.0%, about 4.0% to about 6.0%, about 4.0% to about 7.0%, about 4.0% to about 8.0%, about 4.0% to about 9.0%, about 4.0% to about 10.0%, about 5.0% to about 6.0%, about 5.0% to about 7.0%, about 5.0% to about 8.0%, about 5.0% to about 9.0%, about 5.0% to about 10.0%, about 6.0% to about 7.0%, about 6.0% to about 8.0%, about 6.0% to about 9.0%, about 6.0% to about 10.0%, about 7.0% to about 8.0%, about 7.0% to about 9.0%, about 7.0% to about 10.0%, about 8.0% to about 9.0%, about 8.0% to about 10.0%, or about 9.0% to about 10.0% by weight.

29. The pharmaceutical composition of any one of embodiments 25, 27, or 28, wherein the one or more phospholipids include one or more phosphoglycerides, one or more phosphosphingolipids, one or more lecithins, or any combination thereof.

30. The pharmaceutical composition of embodiment 29, wherein the one or more phosphoglycerides include a phosphatidic acid (phosphatidate) (PA), a phosphatidylethanolamine (PE), a phosphatidylcholine (PC), a phosphatidylserine (PS), a cardiolipin, a phosphoinositide, or any combination thereof.

31. The pharmaceutical composition of embodiment 29, wherein the one or more phosphosphingolipids include phosphatidylethanolamine (PE), phosphatidylcholine (PC), ceramide phosphorylethanolamine (Cer-PE), ceramide phosphorylcholine (Cer-PC), or any combination thereof.

32. The pharmaceutical composition of embodiment 25 or 29-31, wherein the one or more phospholipids are in an amount of at least 1.0% by weight, at least 1.5% by weight, at least 2.0% by weight, at least 2.5% by weight, at least 3.0% by weight, at least 3.5% by weight, at least 4.0% by weight, at least 4.5% by weight, at least 5.0% by weight, at least 5.5% by weight, at least 6.0% by weight, at least 6.5% by weight, at least 7.0% by weight, at least 7.5% by weight, at least 8.0% by weight, at least 8.5% by weight, at least 9.0% by weight, at least 9.5% by weight, or at least 10.0% and/or at most 1.0% by weight, at most 1.5% by weight, at most 2.0% by weight, at most 2.5% by weight, at most 3.0% by weight, at most 3.5% by weight, at most 4.0% by weight, at most 4.5% by weight, at most 5.0% by weight, at most 5.5% by weight, at most 6.0% by weight, at most 6.5% by weight, at most 7.0% by weight, at most 7.5% by weight, at most 8.0% by weight, at most 8.5% by weight, at most 9.0% by weight, at most 9.5% by weight, or at most 10.0% by weight or between about 1.0% to about 2.0%, about 1.0% to about 3.0%, about 1.0% to about 4.0%, about 1.0% to about 5.0%, about 1.0% to about 6.0%, about 1.0% to about 7.0%, about 1.0% to about 8.0%, about 1.0% to about 9.0%, about 1.0% to about 10.0%, about 2.0% to about 3.0%, about 2.0% to about 4.0%, about 2.0% to about 5.0%, about 2.0% to about 6.0%, about 2.0% to about 7.0%, about 2.0% to about 8.0%, about 2.0% to about 9.0%, about 2.0% to about 10.0%, about 3.0% to about 4.0%, about 3.0% to about 5.0%, about 3.0% to about 6.0%, about 3.0% to about 7.0%, about 3.0% to about 8.0%, about 3.0% to about 9.0%, about 3.0% to about 10.0%, about 4.0% to about 5.0%, about 4.0% to about 6.0%, about 4.0% to about 7.0%, about 4.0% to about 8.0%, about 4.0% to about 9.0%, about 4.0% to about 10.0%, about 5.0% to about 6.0%, about 5.0% to about 7.0%, about 5.0% to about 8.0%, about 5.0% to about 9.0%, about 5.0% to about 10.0%, about 6.0% to about 7.0%, about 6.0% to about 8.0%, about 6.0% to about 9.0%, about 6.0% to about 10.0%, about 7.0% to about 8.0%, about 7.0% to about 9.0%, about 7.0% to about 10.0%, about 8.0% to about 9.0%, about 8.0% to about 10.0%, or about 9.0% to about 10.0% by weight.

33. The pharmaceutical composition of any one of embodiments 25 or 27-32, wherein the one or more free $C_{14-24}$ fatty acids include unsaturated free $C_{14}$-$C_{16}$ fatty acids, unsaturated free $C_{14}$-$C_{18}$ fatty acids, unsaturated free $C_{14}$-$C_{20}$ fatty acids, unsaturated free $C_{14}$-$C_{22}$ fatty acids, unsaturated free $C_{14}$-$C_{24}$ fatty acids, unsaturated free $C_{16}$-$C_{18}$ fatty acids, unsaturated free $C_{16}$-$C_{20}$ fatty acids, unsaturated free $C_{16}$-$C_{22}$ fatty acids, unsaturated free $C_{16}$-$C_{24}$ fatty acids, unsaturated free $C_{18}$-$C_{20}$ fatty acids, unsaturated free $C_{18}$-$C_{22}$ fatty acids, unsaturated free $C_{18}$-$C_{24}$ fatty acids, unsaturated free $C_{20}$-$C_{22}$ fatty acids, or unsaturated free $C_{22}$-$C_{24}$ fatty acids.

34. The pharmaceutical composition of any one of embodiments 25 or 27-32, wherein the one or more free $C_{14-24}$ fatty acids include ω-3 unsaturated free $C_{18}$-$C_{22}$ fatty acids, ω-5 unsaturated free $C_{18}$-$C_{22}$ fatty acids, ω-6 unsaturated free $C_{18}$-$C_{22}$ fatty acids, ω-7 unsaturated free $C_{18}$-$C_{22}$ fatty acids, ω-9 unsaturated free $C_{18}$-$C_{22}$ fatty acids, ω-10 unsaturated free $C_{18}$-$C_{22}$ fatty acids, ω-11 unsaturated free $C_{18}$-$C_{22}$ fatty acids, or ω-12 unsaturated free $C_{18}$-$C_{22}$ fatty acids.

35. The pharmaceutical composition of any one of embodiments 25 or 27-32, wherein the one or more free $C_{14-24}$ fatty acids include saturated free $C_{14}$-$C_{16}$ fatty acids, saturated free $C_{14}$-$C_{18}$ fatty acids, saturated free $C_{14}$-$C_{20}$ fatty acids, saturated free $C_{14}$-$C_{22}$ fatty acids, saturated free $C_{14}$-$C_{24}$ fatty acids, saturated free $C_{16}$-$C_{18}$ fatty acids, saturated free $C_{16}$-$C_{20}$ fatty acids, saturated free $C_{16}$-$C_{22}$ fatty acids, saturated free $C_{16}$-$C_{24}$ fatty acids, saturated free $C_{18}$-$C_{20}$ fatty acids, saturated free $C_{18}$-$C_{22}$ fatty acids, saturated free $C_{18}$-$C_{24}$ fatty acids, saturated free $C_{20}$-$C_{22}$ fatty acids, or saturated free $C_{22}$-$C_{24}$ fatty acids.

36. The pharmaceutical composition of any one of embodiments 25 or 27-32, wherein the one or more free $C_{14-24}$ fatty acids include a mixture of saturated and unsaturated free $C_{14}$-$C_{16}$ fatty acids, a mixture of saturated and unsaturated free $C_{14}$-$C_{18}$ fatty acids, a mixture of saturated and unsaturated free $C_{14}$-$C_{20}$ fatty acids, a mixture of saturated and unsaturated free $C_{14}$-$C_{22}$ fatty acids, a mixture of saturated and unsaturated free $C_{14}$-$C_{24}$ fatty acids, a mixture of saturated and unsaturated free $C_{16}$-$C_{18}$ fatty acids, a mixture of saturated and unsaturated free $C_{16}$-$C_{20}$ fatty acids, a mixture of saturated and unsaturated free $C_{16}$-$C_{22}$ fatty acids, a mixture of saturated and unsaturated free $C_{16}$-$C_{24}$ fatty acids, a mixture of saturated and unsaturated free $C_{18}$-$C_{20}$ fatty acids, a mixture of saturated and unsaturated free $C_{18}$-$C_{22}$ fatty acids, a mixture of saturated and unsaturated free $C_{18}$-$C_{24}$ fatty acids, a mixture of saturated and unsaturated free $C_{20}$-$C_{22}$ fatty acids, or a mixture of saturated and unsaturated free $C_{22}$-$C_{24}$ fatty acids.

37. The pharmaceutical composition of any one of embodiments 25 or 27-32, wherein the one or more free $C_{14-24}$ fatty acids include palmitic acid (hexadecenoic acid), palmitolinolenic acid, palmitidonic acid, palmitovaccenic acid, palmitoleic acid, sapienic acid, 4-Hexadecenoic acid, stearic acid (octadecenoic acid), α-linolenic acid, stearidonic acid, α-eleostearic acid, β-eleostearic acid, pumicic acid, 7,10,13-octadecatrienoic acid, 12-octadecenoic acid, linoleic acid, linolelaidic acid. γ-linolenic acid, calendic acid, pinolenic acid, vaccinic acid, ruminic acid, oleic acid, elaidic acid, petroselinic acid, arachidic acid (eicosanoic acid), dihomo-α-linolenic acid, eicosic acidtraenoic acid, eicosapentaenoic acid, 9,12,15-eicosatrienoic acid, β-eicosic acidtraenoic acid, dihomo-linoleic acid, dihomo-γ-linolenic acid, arachidonic acid, paullinic acid, 7,10,13-eicosatrienoic acid, gondoic acid, 8,11-eicosadienoic acid, meadic acid, gadoleic acid, 8-eicosenoic acid, behenic acid (docosanoic acid), clupanodonic acid, docosahexaenoic acid, adrenic acid, osbondic acid, erucic acid, lignoceric acid (tetracosanic acid), 9,12,15,18,21-Tetracosapentaenoic acid, 6,9,12, 15,18,21-Tetracosahexaenoic acid, and nervonic acid.

38. The pharmaceutical composition of any one of embodiments 25 or 33-37, wherein the one or more free $C_{14-24}$ fatty acids are in an amount of at least 1% by weight, at least 2.5% by weight, at least 5% by weight, at least 7.5% by weight, at least 10% by weight, at least 12.5% by weight, at least 15% by weight, at least 17.5% by weight, at least 20% by weight, at least 22.5% by weight, at least 25% by weight, at least 30% by weight, at least 35% by weight, at least 40% by weight, at least 50% by weight, at least 60% by weight, at least 70% by weight, at least 75% by weight and/or at most 1% by weight, at most 2.5% by weight, at most 5% by weight, at most 7.5% by weight, at most 10% by weight, at most 12.5% by weight, at most 15% by weight, at most 17.5% by weight, at most 20% by weight, at most 22.5% by weight, at most 25% by weight, at most 30% by weight, at most 35% by weight, at most 40% by weight, at most 50% by weight, at most 60% by weight, at most 70% by weight, at most 75% by weight or between about 1% to about 2.5% by weight, about 1% to about 5% by weight, about 1% to about 10% by weight, about 1% to about 15% by weight, about 1% to about 20% by weight, about 1% to about 25% by weight, about 2.5% to about 5% by weight, about 2.5% to about 10% by weight, about 2.5% to about 15% by weight, about 2.5% to about 20% by weight, about 2.5% to about 25% by weight, about 2.5% to about 30% by weight, about 5% to about 10% by weight, about 5% to about 15% by weight, about 5% to about 20% by weight, about 5% to about 25% by weight, about 5% to about 30% by weight, about 10% to about 15% by weight, about 10% to about 20% by weight, about 10% to about 25% by weight, about 10% to about 30% by weight, about 10% to about 40% by weight, about 10% to about 45% by weight, about 10% to about 50% by weight, about 10% to about 60% by weight, about 10% to about 70% by weight, about 15% to about 20% by weight, about 15% to about 25% by weight, about 15% to about 30% by weight, about 15% to about 40% by weight, about 15% to about 45% by weight, about 15% to about 50% by weight, about 15% to about 60% by weight, about 15% to about 70% by weight, about 20% to about 25% by weight, about 20% to about 30% by weight, about 20% to about 40% by weight, about 20% to about 45% by weight, about 20% to about 50% by weight, about 20% to about 60% by weight, about 20% to about 70% by weight, about 30% to about 40% by weight, about 30% to about 50% by weight, about 30% to about 60% by weight, about 30% to about 70% by weight, about 30% to about 75% by weight, about 35% to about 40% by weight, about 35% to about 50% by weight, about 35% to about 60% by weight, about 35% to about 70% by weight, about 35% to about 75% by weight, about 40% to about 50% by weight, about 40% to about 60% by weight, about 40% to about 70% by weight, about 40% to about 75% by weight, about 50% to about 60% by weight, about 50% to about 70% by weight, or about 60% to about 70% by weight.

39. The pharmaceutical composition of any one of embodiments 25 or 27-38, wherein the one or more free $C_{14-24}$ fatty acid surfactants include unsaturated free $C_{14}$-$C_{16}$ fatty acid surfactants, unsaturated free $C_{14}$-$C_{18}$ fatty acid surfactants, unsaturated free $C_{14}$-$C_{20}$ fatty acid surfactants, unsaturated free $C_{14}$-$C_{22}$ fatty acid surfactants, unsaturated free $C_{14}$-$C_{24}$ fatty acid surfactants, unsaturated free $C_{16}$-$C_{18}$ fatty acid surfactants, unsaturated free $C_{16}$-$C_{20}$ fatty acid surfactants, unsaturated free $C_{16}$-$C_{22}$ fatty acid surfactants, unsaturated free $C_{16}$-$C_{24}$ fatty acid surfactants, unsaturated free $C_{18}$-$C_{20}$ fatty acid surfactants, unsaturated free $C_{18}$-$C_{22}$ fatty acid surfactants, unsaturated free $C_{18}$-$C_{24}$ fatty acid surfactants, unsaturated free $C_{20}$-$C_{22}$ fatty acid surfactants, or unsaturated free $C_{22}$-$C_{24}$ fatty acid surfactants.

40. The pharmaceutical composition of any one of embodiments 25 or 27-38, wherein the one or more free $C_{14-24}$ fatty acid surfactants include ω-3 unsaturated free $C_{18}$-$C_{22}$ fatty acid surfactants, ω-5 unsaturated free $C_{18}$-$C_{22}$ fatty acid surfactants, ω-6 unsaturated free $C_{18}$-$C_{22}$ fatty acid surfactants, ω-7 unsaturated free $C_{18}$-$C_{22}$ fatty acid surfactants, ω-9 unsaturated free $C_{18}$-$C_{22}$ fatty acid surfactants, ω-10 unsaturated free $C_{18}$-$C_{22}$ fatty acid surfactants, ω-11 unsaturated free $C_{18}$-$C_{22}$ fatty acid surfactants, or ω-12 unsaturated free $C_{18}$-$C_{22}$ fatty acid surfactants.

41. The pharmaceutical composition of any one of embodiments 25 or 27-38, wherein the one or more free $C_{14-24}$ fatty acid surfactants include saturated free $C_{14}$-$C_{16}$ fatty acid surfactants, saturated free $C_{14}$-$C_{18}$ fatty acid surfactants, saturated free $C_{14}$-$C_{20}$ fatty acid surfactants, saturated free $C_{14}$-$C_{22}$ fatty acid surfactants, saturated free $C_{14}$-$C_{24}$ fatty acid surfactants, saturated free $C_{16}$-$C_{18}$ fatty acid surfactants, saturated free $C_{16}$-$C_{20}$ fatty acid surfactants, saturated free $C_{16}$-$C_{22}$ fatty acid surfactants, saturated free $C_{16}$-$C_{24}$ fatty acid surfactants, saturated free $C_{18}$-$C_{20}$ fatty acid surfactants, saturated free $C_{18}$-$C_{22}$ fatty acid surfactants, saturated free $C_{18}$-$C_{24}$ fatty acid surfactants, saturated free $C_{20}$-$C_{22}$ fatty acid surfactants, or saturated free $C_{22}$-$C_{24}$ fatty acid surfactants.

42. The pharmaceutical composition of any one of embodiments 25 or 27-38, wherein the one or more free $C_{14-24}$ fatty acid surfactants include a mixture of saturated and unsaturated free $C_{14}$-$C_{16}$ fatty acid surfactants, a mixture of saturated and unsaturated free $C_{14}$-$C_{18}$ fatty acid surfactants, a mixture of saturated and unsaturated free $C_{14}$-$C_{20}$ fatty acid surfactants, a mixture of saturated and unsaturated free $C_{14}$-$C_{22}$ fatty acid surfactants, a mixture of saturated and unsaturated free $C_{14}$-$C_{24}$ fatty acid surfactants, a mixture of saturated and unsaturated free $C_{16}$-$C_{18}$ fatty acid surfactants, a mixture of saturated and unsaturated free $C_{16}$-$C_{20}$ fatty acid surfactants, a mixture of saturated and unsaturated free $C_{16}$-$C_{22}$ fatty acid surfactants, a mixture of saturated and unsaturated free $C_{16}$-$C_{24}$ fatty acid surfactants, a mixture of saturated and unsaturated free $C_{18}$-$C_{20}$ fatty acid surfactants, a mixture of saturated and unsaturated free $C_{18}$-$C_{22}$ fatty acid surfactants, a mixture of saturated and unsaturated free $C_{18}$-$C_{24}$ fatty acid surfactants, a mixture of saturated and unsaturated free $C_{20}$-$C_{22}$ fatty acid surfactants, or a mixture of saturated and unsaturated free $C_{22}$-$C_{24}$ fatty acid surfactants.

43. The pharmaceutical composition of any one of embodiments 25 or 27-38, wherein the one or more free $C_{14-24}$ fatty acid surfactants include sodium palmitate (hexadecanoate), sodium palmitolinolenate, sodium palmitidonate, sodium palmitovaccenate, sodium palmitoleate, sodium sapienate, sodium 4-Hexadecenoate, sodium stearate (octadecenoate), sodium α-linolenate, sodium stearidonate, sodium α-eleostearate, sodium β-eleostearate, sodium pumicate, sodium 7,10, 13-octadecatrienoate, sodium 12-octadecenoate, sodium linoleate, sodium linolelaidate. Sodium γ-linolenate, sodium calendate, sodium pinolenate, sodium vaccinate, sodium ruminate, sodium oleate, sodium elaidate, sodium petroselinate, sodium arachidate (eicosanoate), sodium di homo-α-linolenate, sodium eicosatetraenoate, sodium eicosapentaenoate, sodium 9,12,15-eicosatrienoate, sodium β-eicosatetraenoate, sodium dihomo-linoleate, sodium dihomo-γ-linolenate, sodium arachidonate, sodium paullinate, sodium 7,10, 13-eicosatrienoate, sodium gondoate, Sodium 8,11-eicosadienoate, sodium meadate, sodium gadoleate, sodium 8-eicosenoate, sodium behenate (docosanoate), sodium clupanodonate, sodium docosahexaenoate, sodium adrenate, sodium osbondate, sodium erucate, sodium lignocerate (tetracosanate), sodium 9,12,15,18, 21-Tetracosapentaenoate, sodium 6,9,12,15,18,21-Tetracosahexaenoate, and sodium nervonate.

44. The pharmaceutical composition of any one of embodiments 25 or 33-43, wherein the one or more free $C_{14-24}$ fatty acid surfactants are in an amount of at least 0.5% by weight, at least 1.0% by weight, at least 1.5% by weight, at least 2.0% by weight, at least 2.5% by weight, at least 3.0% by weight, at least 3.5% by weight, at least 4.0% by weight, at least 4.5% by weight, at least 5.0% by weight, at least 5.5% by weight, at least 6.0% by weight, at least 6.5% by weight, at least 7.0% by weight, at least 7.5% by weight, at least 8.0% by weight, at least 8.5% by weight, at least 9.0% by weight, at least 9.5% by weight, at least 10.0% by weight and/or at most 0.1% by weight, at most 0.5% by weight, at most 1.0% by weight, at most 1.5% by weight, at most 2.0% by weight, at most 2.5% by weight, at most 3.0% by weight, at most 3.5% by weight, at most 4.0% by weight, at most 4.5% by weight, at most 5.0% by weight, at most 5.5% by weight, at most 6.0% by weight, at most 6.5% by weight, at most 7.0% by weight, at most 7.5% by weight, at most 8.0% by weight, at most 8.5% by weight, at most 9.0% by weight, at most 9.5% by weight, at most 10.0% by weight or between about 0.1% to about 0.5%, about 0.1% to about 1.0%, about 0.1% to about 2.0%, about 0.1% to about 3.0%, about 0.1% to about 4.0%, about 0.1% to about 5.0%, about 0.1% to about 6.0%, about 0.1% to about 7.0%, about 0.1% to about 8.0%, about 0.1% to about 9.0%, about 0.1% to about 10.0%, about 0.5% to about 1.0%, about 0.5% to about 2.0%, about 0.5% to about 3.0%, about 0.5% to about 4.0%, about 0.5% to about 5.0%, about 0.5% to about 6.0%, about 0.5% to about 7.0%, about 0.5% to about 8.0%, about 0.5% to about 9.0%, about 0.5% to about 10.0%, about 1.0% to about 2.0%, about 1.0% to about 3.0%, about 1.0% to about 4.0%, about 1.0% to about 5.0%, about 1.0% to about 6.0%, about 1.0% to about 7.0%, about 1.0% to about 8.0%, about 1.0% to about 9.0%, about 1.0% to about 10.0%, about 2.0% to about 3.0%, about 2.0% to about 4.0%, about 2.0% to about 5.0%, about 2.0% to about 6.0%, about 2.0% to about 7.0%, about 2.0% to about 8.0%, about 2.0% to about 9.0%, about 2.0% to about 10.0%, about 3.0% to about 4.0%, about 3.0% to about 5.0%, about 3.0% to about 6.0%, about 3.0% to about 7.0%, about 3.0% to about 8.0%, about 3.0% to about 9.0%, about 3.0% to about 10.0%, about 4.0% to about 5.0%, about 4.0% to about 6.0%, about 4.0% to about 7.0%, about 4.0% to about 8.0%, about 4.0% to about 9.0%, about 4.0% to about 10.0%, about 5.0% to about 6.0%, about 5.0% to about 7.0%, about 5.0% to about 8.0%, about 5.0% to about 9.0%, about 5.0% to about 10.0%, about 6.0% to about 7.0%, about 6.0% to about 8.0%, about 6.0% to about 9.0%, about 6.0% to about 10.0%, about 7.0% to about 8.0%, about 7.0% to about 9.0%, about 7.0% to about 10.0%, about 8.0% to about 9.0%, about 8.0% to about 10.0%, or about 9.0% to about 10.0% by weight.

45. The pharmaceutical composition of any one of embodiments 1-44, wherein the pharmaceutical composition is not an emulsion or self-emulsifying formulation.

EXAMPLES

The following non-limiting examples are provided for illustrative purposes only in order to facilitate a more complete understanding of representative embodiments now contemplated. These examples should not be construed to limit any of the embodiments described in the present specification, including those pertaining to the compounds, pharmaceutical compositions, or methods and uses disclosed herein.

Example 1 Assessing Critical Micellar Concentration Parameters

One of the key features of the disclosed pharmaceutical compositions is that they are incapable of self-emulsifying. A compound can self-emulsify to form micelles when its concentration reaches its critical micellar concentration (CMC). The lipid components GELUCIRE® 43/01 and MAISINE™ CC have no recorded CMC values, cannot form micelles, and as such are not self-emulsifying compounds. Similarly, while cholic acid is reported to have a CMC of 14.7 mM, below the 0.25 mM or less of cholic acid used in the disclosed pharmaceutical compositions. Likewise sodium stearate is reported to have a CMC of 71 μM, below the 35 μM or less of sodium stearate used in the disclosed pharmaceutical compositions. As such, cholic acid and sodium stearate cannot self-emulsify because their concentrations are insufficient to form micelles. On the other hand, oleic acid is reported to have a CMC of 2.3 mM which is near the up to 2 mM of oleic acid is used in the disclosed pharmaceutical compositions. As such, it was not clear whether oleic acid could act as a self-emulsifying agent as it could conceivably form micelles at the concentrations used in the disclosed pharmaceutical compositions.

To assess whether oleic acid could self-emulsify at the concentrations used in the disclosed pharmaceutical compositions, experiments was performed that were designed to model dissolution testing according to International Council for Harmonisation (ICH) guidelines. One liter of a dissolution media comprising phosphate buffered saline (PBS) and 2.5% curcumin was warmed to 37° C. and constant stirring at 300 rpm maintained. Curcumin was added as a coloring agent and was very effective at visualizing the distribution of lipids through the dissolution media. Miscibility experiments were performed using two concentrations of oleic acid nominally above the CMC concentration for this fatty acid. In one series of experiments, 1 g of 100% oleic acid was added to the dissolution media. The control compound was 1 g of 100% MAISINE™ CC. In a second series of experiments 1 g of 75% oleic acid (diluted with 250 mg of MAISINE™ CC) was added to the dissolution media. The control compound was 1 g of 75% MAISINE™ CC. The miscibility of oleic acid and MAISINE™ CC was assessed by observing the dissolution media for 10 minutes with constant stirring and then 10 minutes without stirring. Photographs were taken at time 0, 1, 2, 3, 4, 5 and 10 minutes during the stirring phase and 2, 4 and 10 minutes after stirring ceased.

Both oleic acid preparations quickly distributed throughout the PBS in small but clearly defined lipid droplets which were still observable after 10 minutes of stirring. On cessation of stirring, the lipid droplets either adhered to the stirrer or floated to the top of the PBS, with the bulk of the PBS clearing. In contrast, the MAISINE™ CC preparations rapidly dispersed in the dissolution media and this dispersion was maintained after the 10-minute period of no stirring. These results demonstrate that 1 gram of 100% oleic acid and 75% oleic acid were not miscible in the dissolution media, despite being at a concentration that is high enough to theoretically reach the critical micellar concentration. These experiment, modelling ICH dissolution conditions, demonstrate that oleic acid did not form emulsions and shown that this fatty acid cannot self-emulsify into micelles. Moreover, oleic acid is even less likely to self-emulsify, when combined with other lipid components which have no CMC concentration, such as MAISINE™ CC and GELUCIRE® 43/01.

Example 2 Assessing Cholic Acid Parameters

During the course of developing the disclosed pharmaceutical compositions, it became clear that there was a direct correlation between having cholic acid in the formulation and improved performance. For many drugs, cholic acid is required for solubility in the lipid matrix. As such we wanted to assess the effect of having increased concentrations of cholic in the lipid matrix.

Unless stated otherwise X-ray powder diffraction patterns for the samples were acquired on a Bruker D8 diffractometer using Cu Ka radiation (40 kV, 40 mA) and a θ-2θ goniometer. The incident beam passes through a 2.0 mm divergence slit followed by a 0.2 mm antiscatter slit and knife edge. The diffracted beam passes through an 8.0 mm receiving slit with 2.5° Soller slits followed by the Lynxeye Detector. The software used for data collection and analysis was Diffrac Plus XRD Commander and Diffrac Plus EVA respectively. Samples were run under ambient conditions over an angular range of 2° to 42° 2θ (using a step size of 0.05° 2θ and a step time of 0.5 seconds) as flat plate specimens using powder as received. The sample was prepared on a polished, zero-background (510) silicon wafer by gently pressing onto the flat surface or packed into a cut cavity. The sample was rotated in its own plane. Small $D_8$ disc recess holders were used to prepare sample. Pharmaceutical composition analyzed were 1) a fenofibrate composition disclosed herein comprising 36.5% MAISINE™ CC, 36.5% GELUCIRE® 43/01, 20.3% oleic acid, 6.1% cholic acid, 1.4% sodium stearate, and 0.6% fenofibrate; and 2) an aprepitant composition disclosed herein comprising 31.7% MAISINE™ CC, 26.1% GELUCIRE® 43/01, 31.7% oleic acid, 4.7% cholic acid, and 5.85% aprepitant. In addition, the following vehicles was also analyzed: 1) a vehicle comprising 36.5% MAISINE™ CC, 36.5% GELUCIRE® 43/01, 20.3% oleic acid, 6.1% cholic acid, and 1.4% sodium stearate; and 2) a vehicle comprising 31.7% MAISINE™ CC, 26.1% GELUCIRE® 43/01, 31.7% oleic acid, and 4.7% cholic acid. Controls for both experiments included GELUCIRE® 43/01, cholic acid, and the appropriate therapeutic com pound, namely fenofibrate or aprepitant. Controls for MAISINE™ CC, oleic acid, and sodium stearate were not performed as these compounds are liquid at room temperature, and as such, cannot be analyzed using X-ray powder diffraction.

Figure 1B:
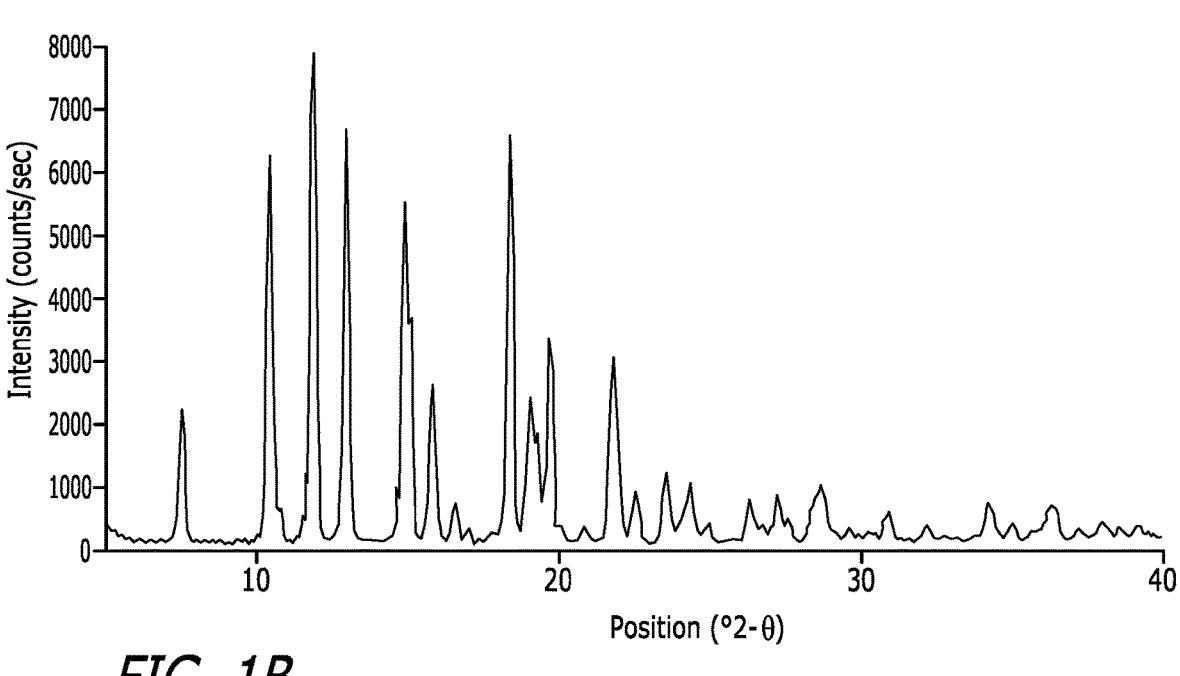
Figure 1C:
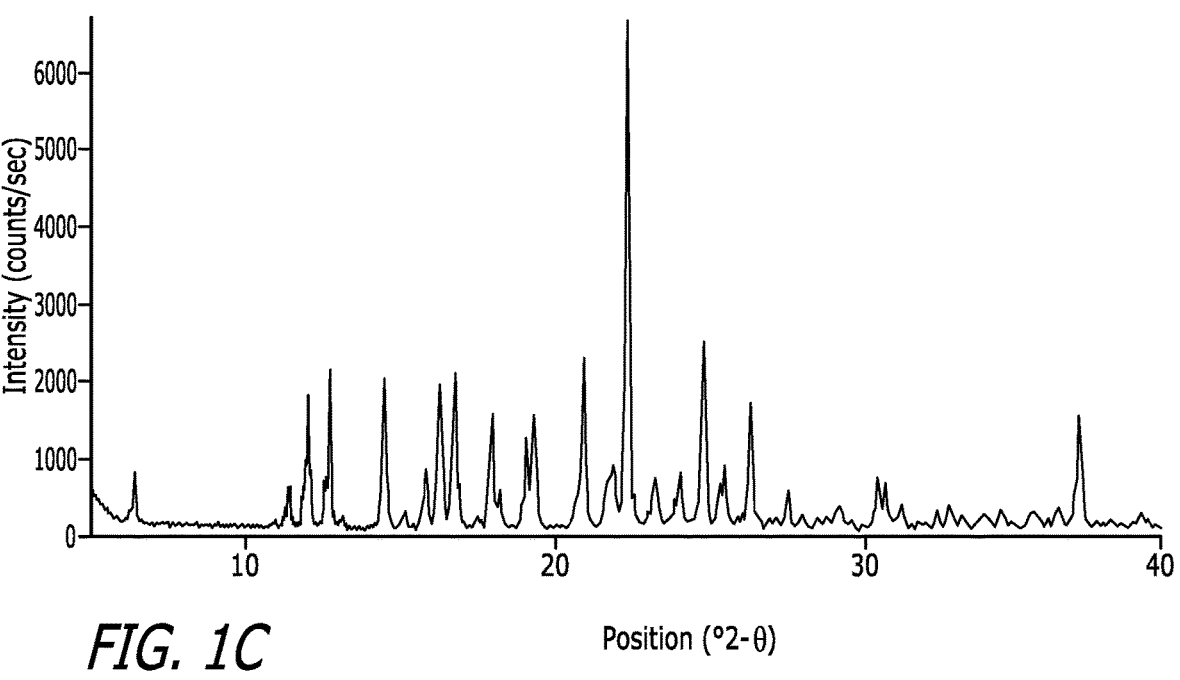
Figure 1D:
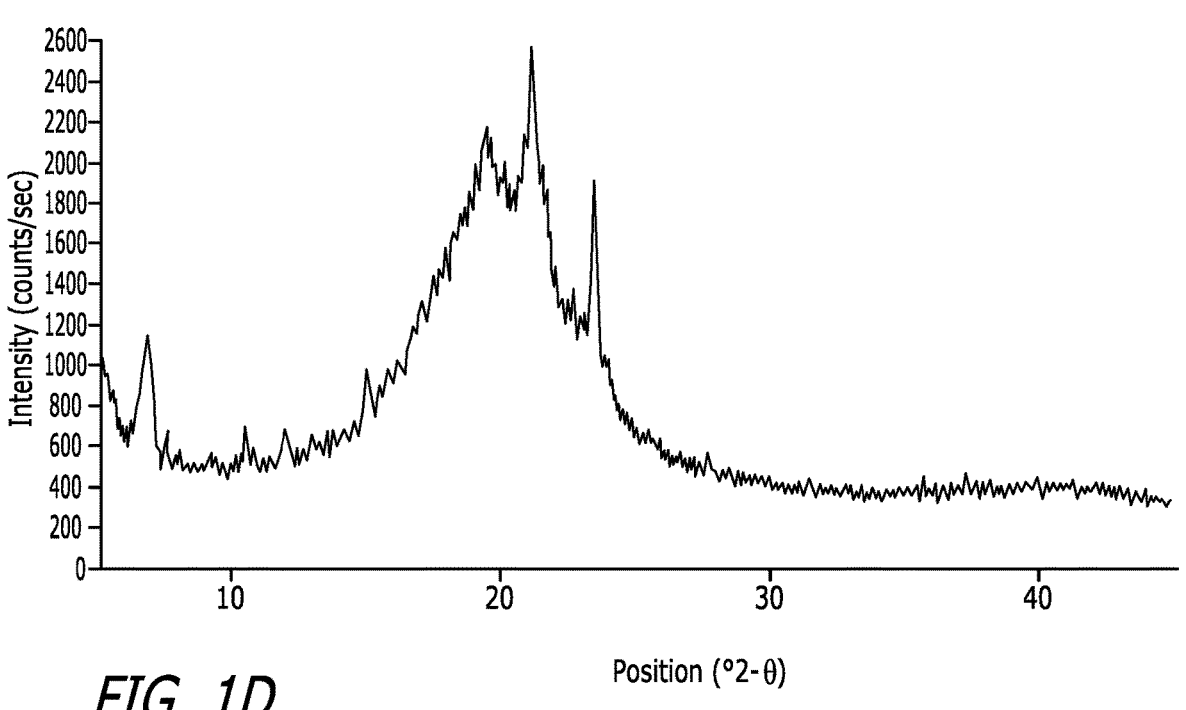
Figure 1E:
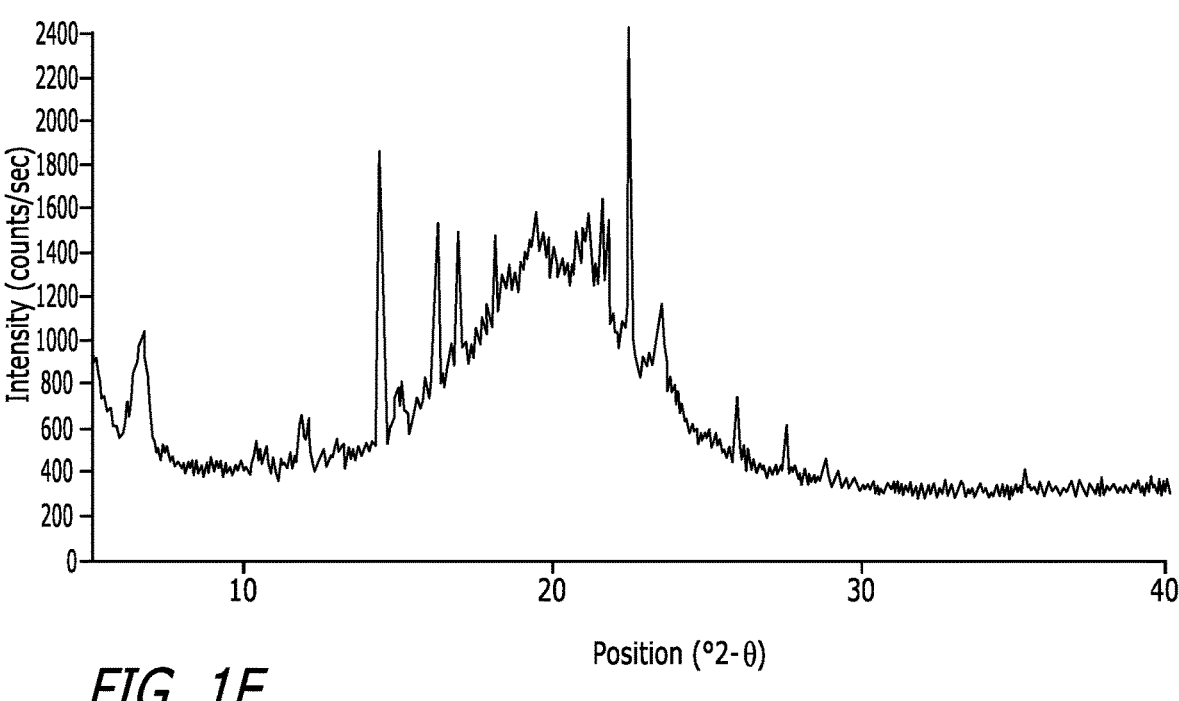
Figure 1F:
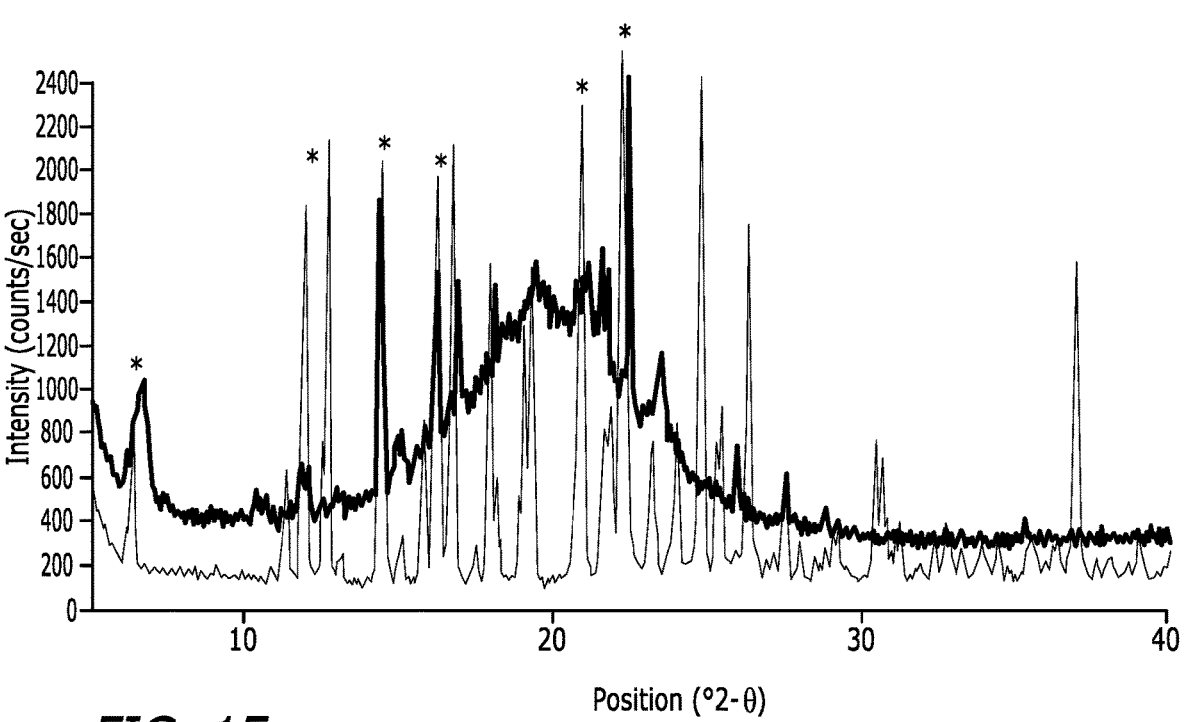

With respect to pharmaceutical compositions comprising fenofibrate, representative PXRD spectra of GELUCIRE® 43/01 (FIG. 1A), cholic acid (FIG. 1B), and fenofibrate (FIG. 1C), as well as the vehicle (FIG. 10) and the pharmaceutical composition (FIG. 1E), each show a distinctive pattern of peaks. Interestingly, when control PXRD spectra are superimposed over the vehicle and pharmaceutical composition PXRD spectra, there is a high degree of coincidental peaks. For example, FIG. 1F, is a PXRD spectra of the pharmaceutical composition superimposed with a PXRD spectra of fenofibrate. As shown by the asterisks, the pharmaceutical composition exhibits a peak profile coincident with fenofibrate, indicating that the pharmaceutical composition contains crystalline fenofibrate. This finding is important as it illustrates that the pharmaceutical composition is not a solid solution (or molecular dispersion) transitional phase instead comprises some solid fenofibrate micro to nano-sized particles suspended within the lipid matrix formed during the cooling of the formulation from a fully solubilized state.

Figure 1G:
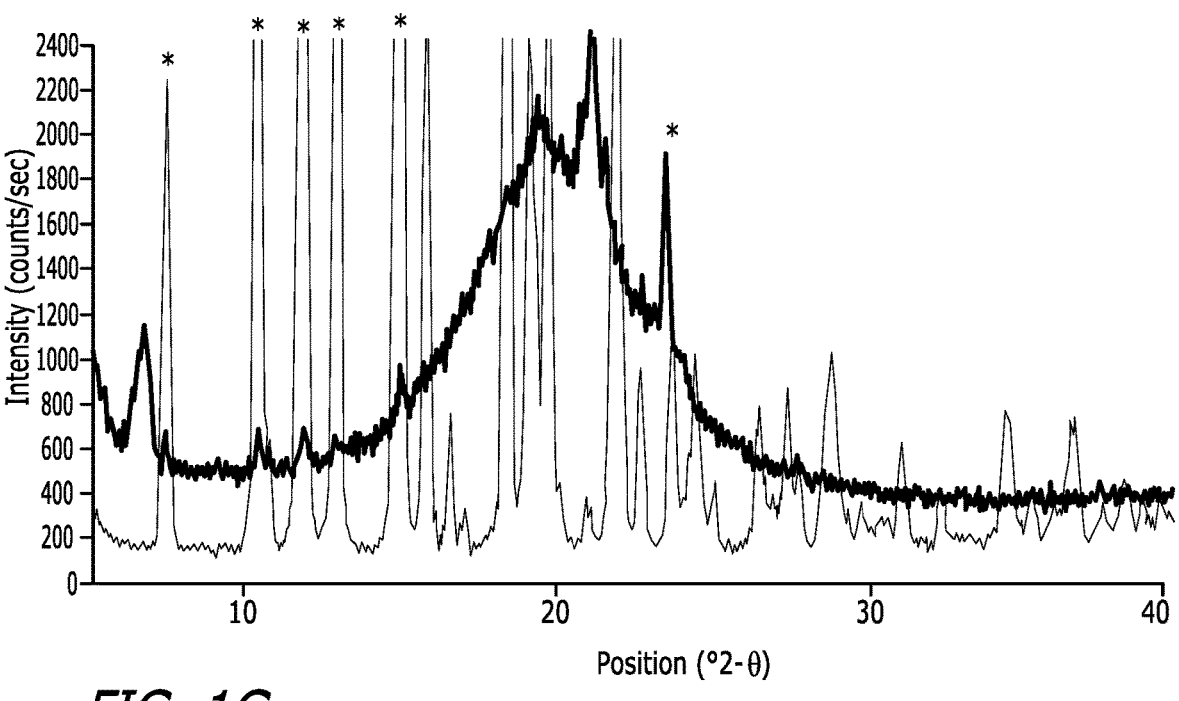
Figure 1H:
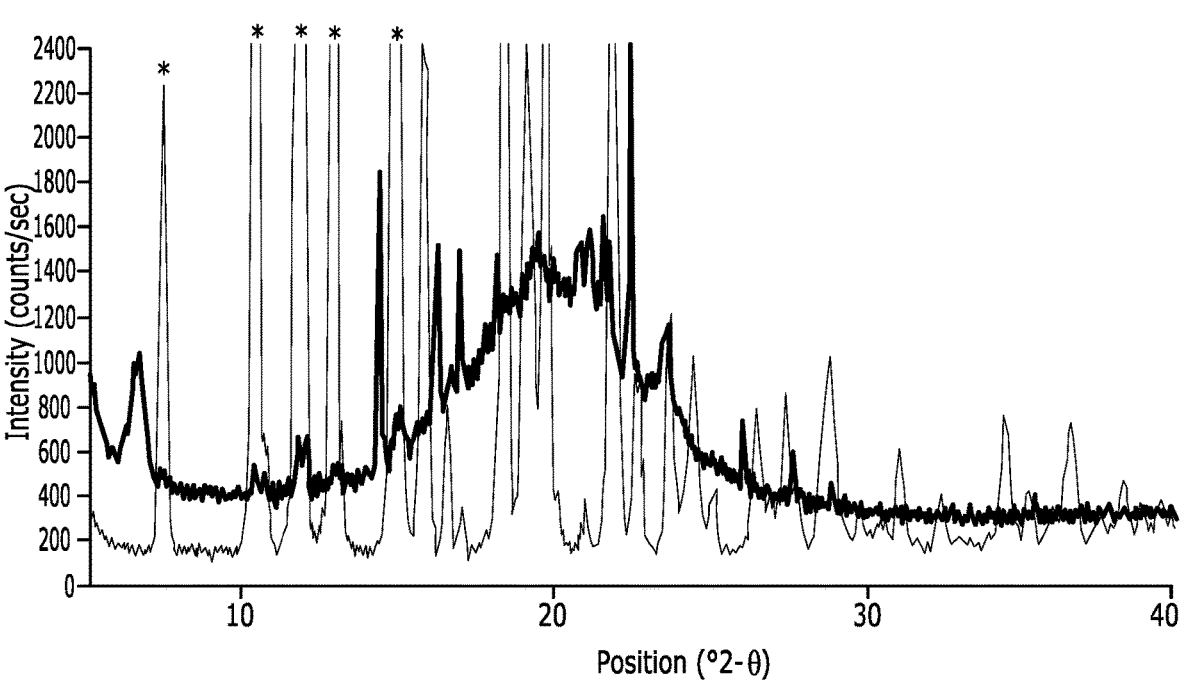

Even more surprising were the results obtained by analyzing the peak profile of cholic acid. FIG. 1G shows a PXRD spectra of the Vehicle superimposed with a PXRD spectra of cholic acid. As shown by the asterisks, the pharmaceutical composition exhibits a peak profile coincident with cholic acid, indicating that the pharmaceutical composition contains crystalline cholic acid. Similarly, FIG. 1H shows a PXRD spectra of the pharmaceutical composition superimposed with a PXRD spectra of cholic acid. As shown by the asterisks, the pharmaceutical composition exhibited a peak profile coincident with cholic acid, indicating that the pharmaceutical composition contained crystalline cholic acid. This finding was completely unexpected as it shows that pharmaceutical composition comprises solid cholic acid particles suspended within the lipid matrix. Additionally, as these particles were not observed during the formulation of the pharmaceutical composition, it was concluded that the crystalline cholic acid are present as micro to nano-sized particles formed during the cooling of the formulation.

Figure 2A:
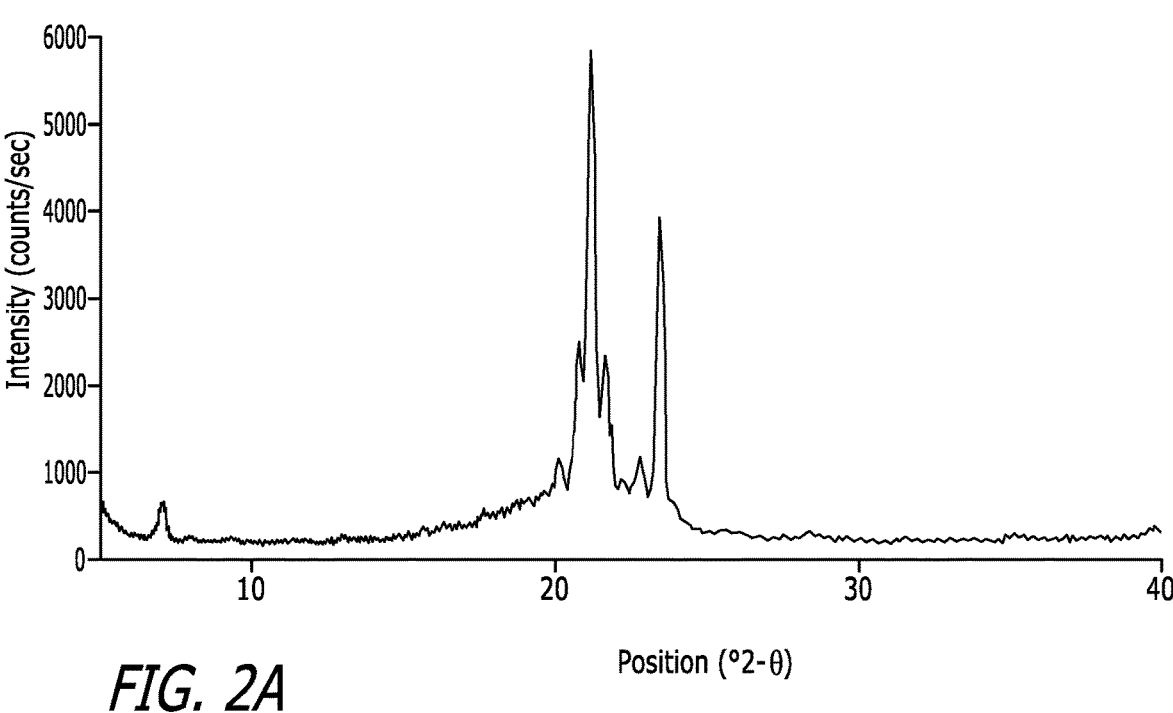
FIGS. 2A-2H show representative PXRD spectra analyzing a disclosed pharmaceutical composition comprising aprepitant with FIG. 2A showing a representative PXRD spectra of a GELCURE® 43/01 standard.
Figure 2B:
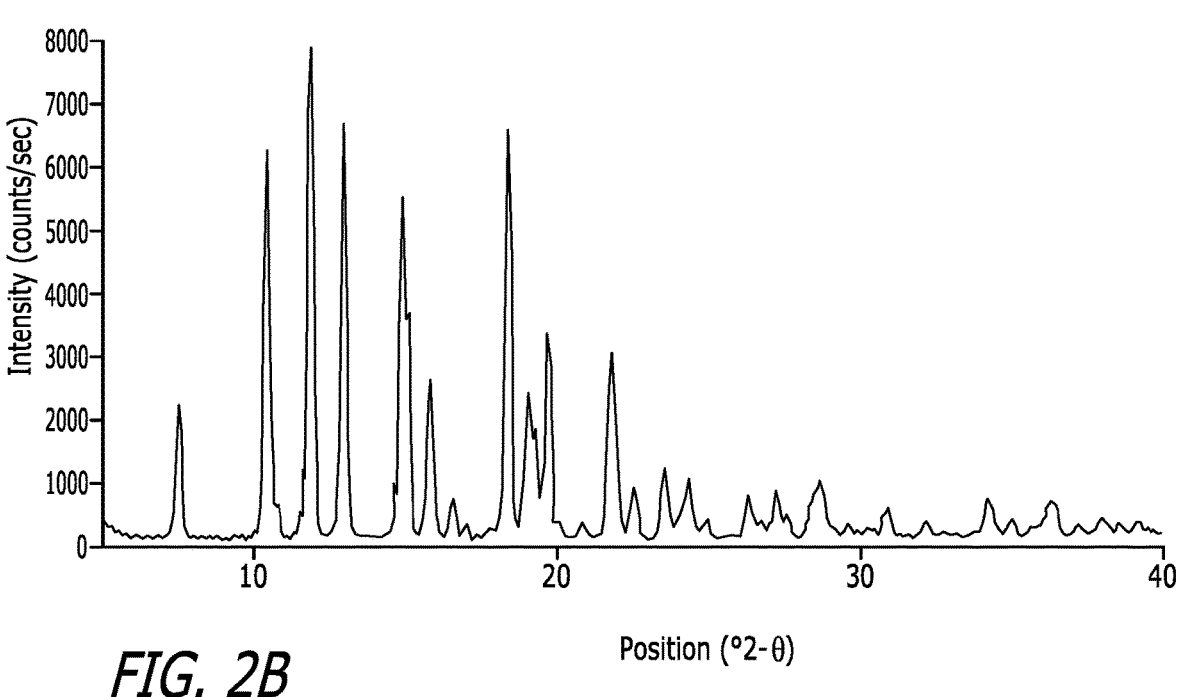
Figure 2C:
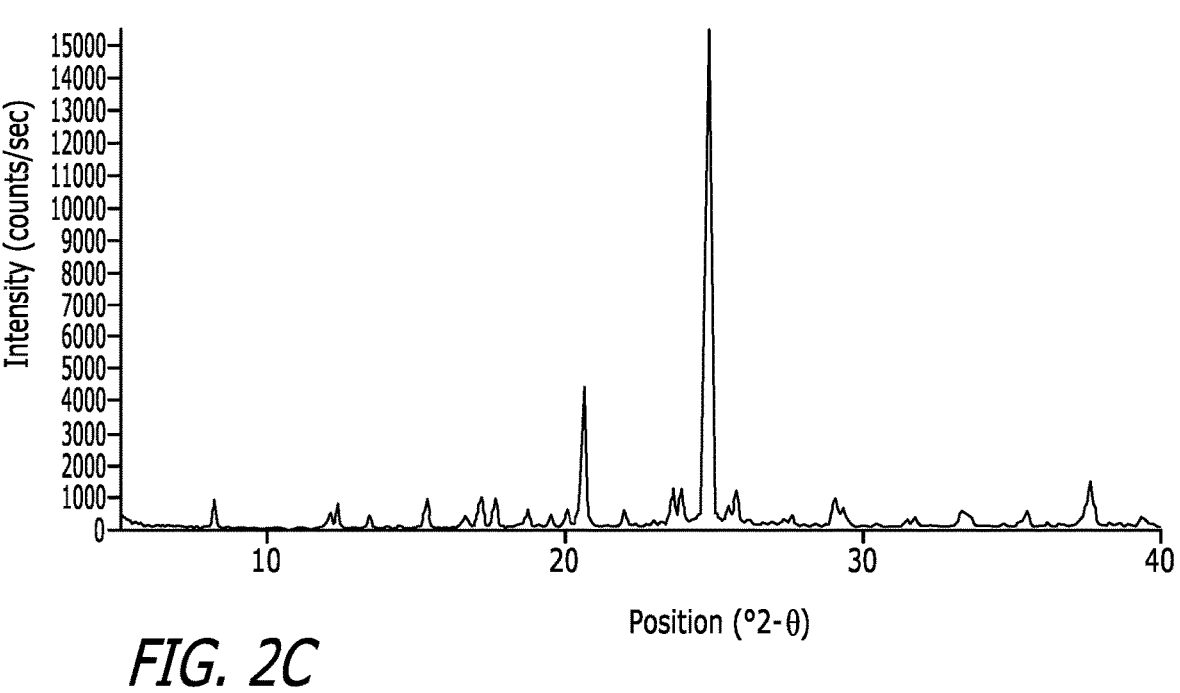
Figure 2D:
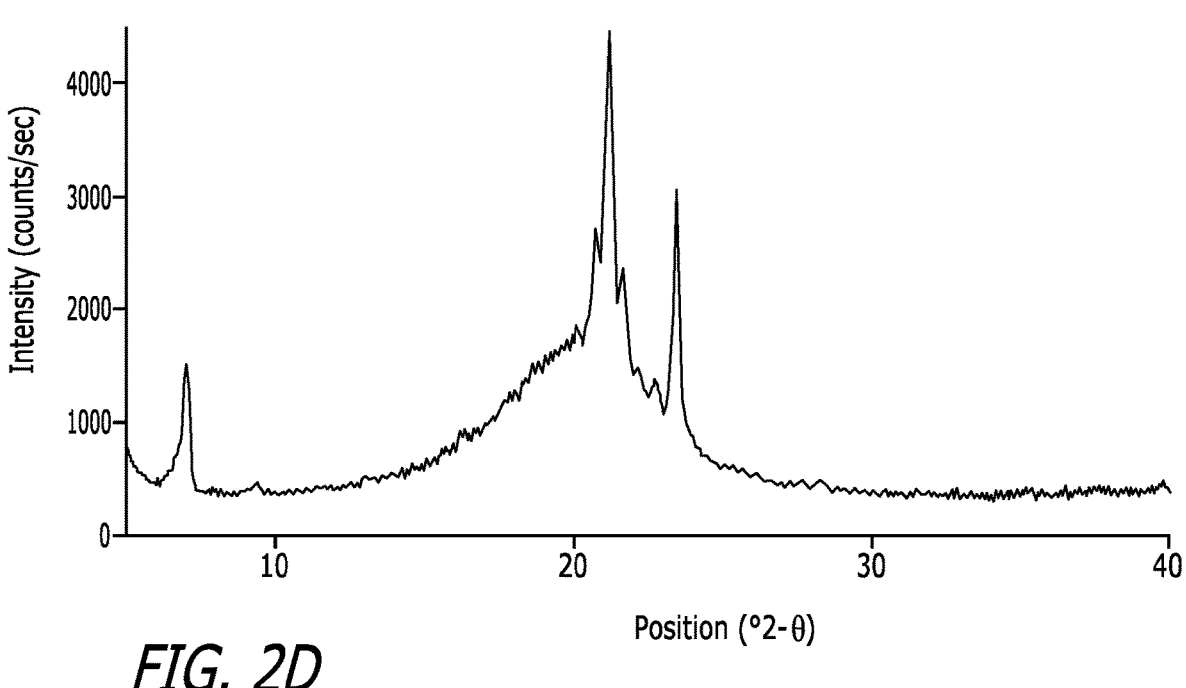
Figure 2E:
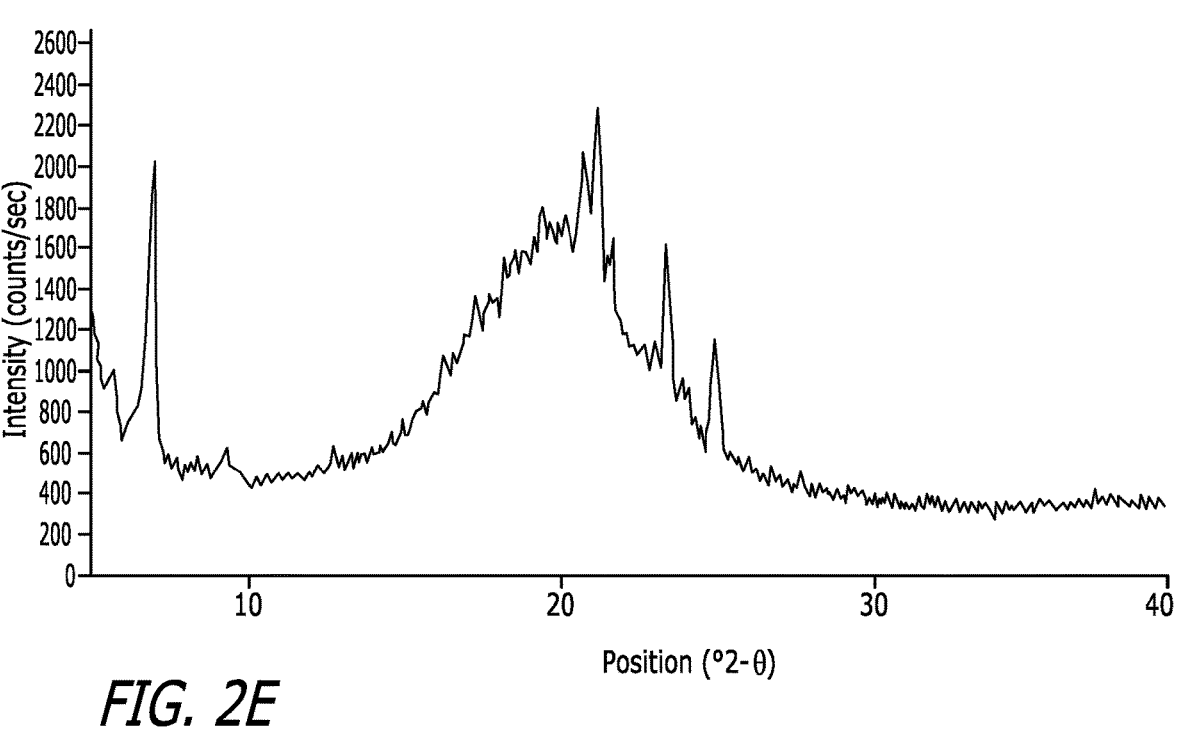
Figure 2F:
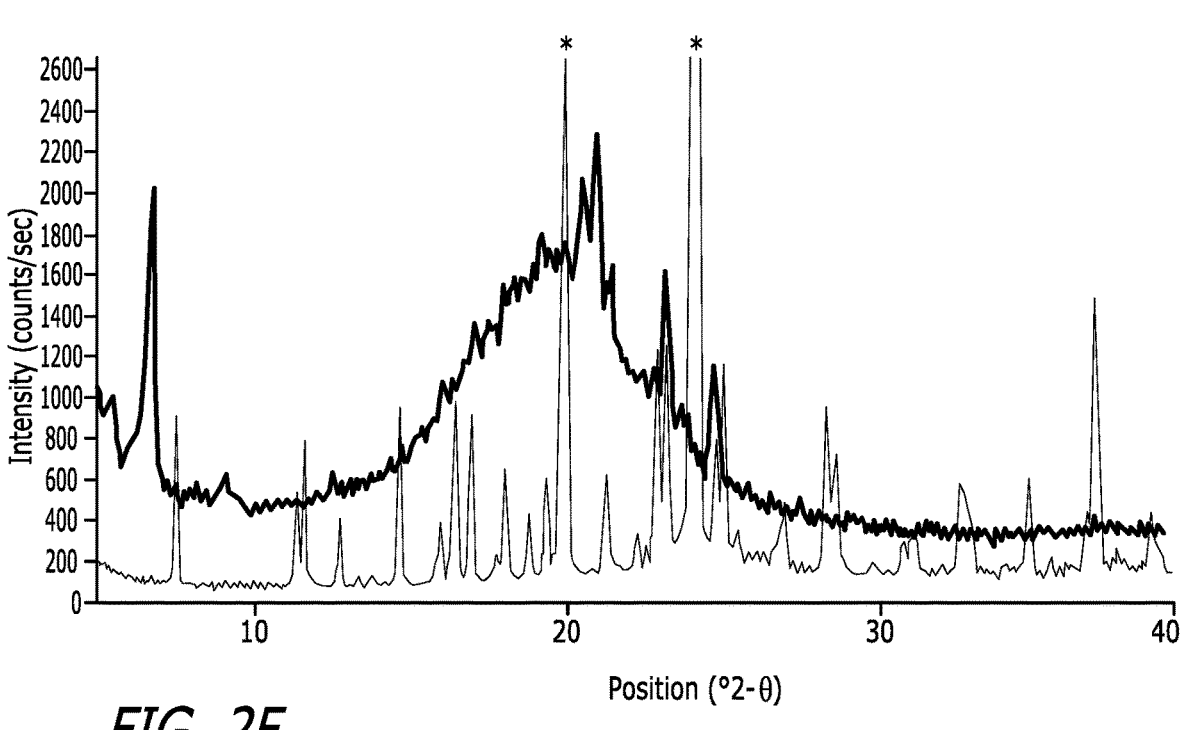

With respect to pharmaceutical compositions comprising aprepitant, representative PXRD spectra of GELUCIRE® 43/01 (FIG. 2A), cholic acid (FIG. 2B), and aprepitant (FIG. 2C), as well as the vehicle (FIG. 2D) and the pharmaceutical composition (FIG. 2E), each show a distinctive pattern of peaks. Interestingly, when control PXRD spectra are superimposed over the vehicle and pharmaceutical composition PXRD spectra, a high degree of coincidental peaks was only observed for aprepitant, but not cholic acid. For example, FIG. 2F, is a PXRD spectra of the pharmaceutical composition superimposed with a PXRD spectra of aprepitant. As shown by the asterisks, the pharmaceutical composition exhibited a peak profile coincident with fenofibrate, indicating that the pharmaceutical composition contained crystalline aprepitant. This finding is important as it illustrates that the pharmaceutical composition is not a solid solution (or molecular dispersion) transitional phase instead comprises some solid aprepitant micro to nano-sized particles suspended within the lipid matrix formed during the cooling of the formulation from a fully solubilized state.

Figure 2G:
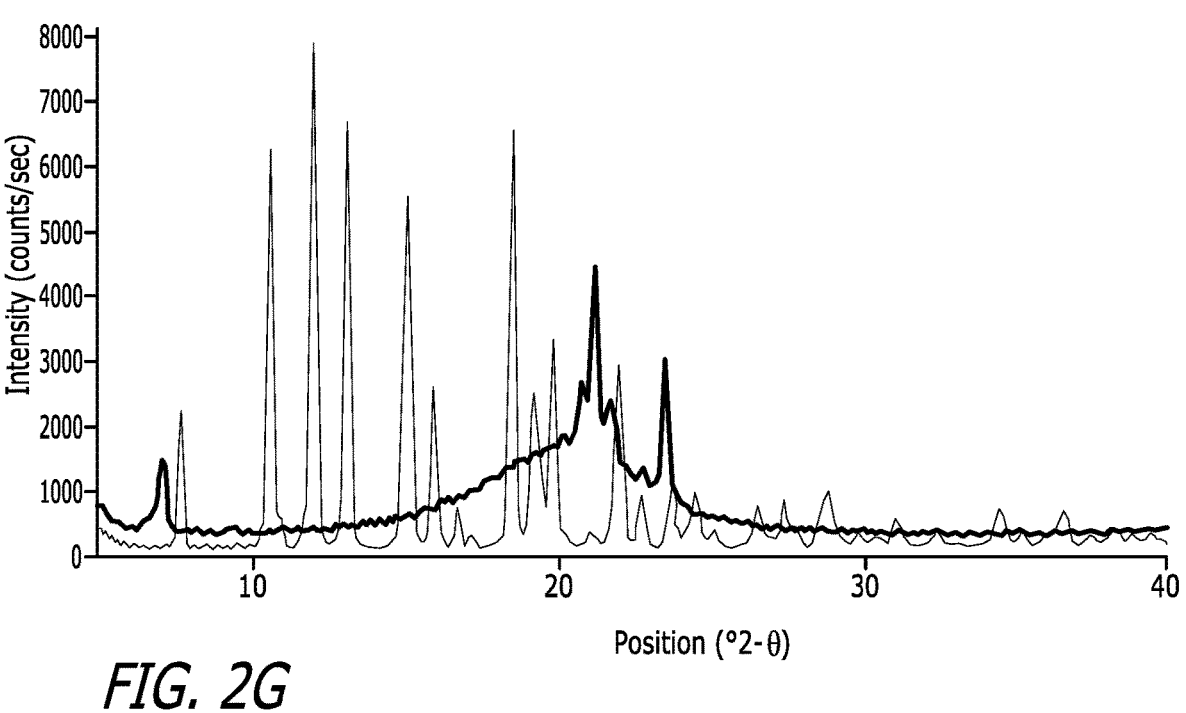
Figure 2H:
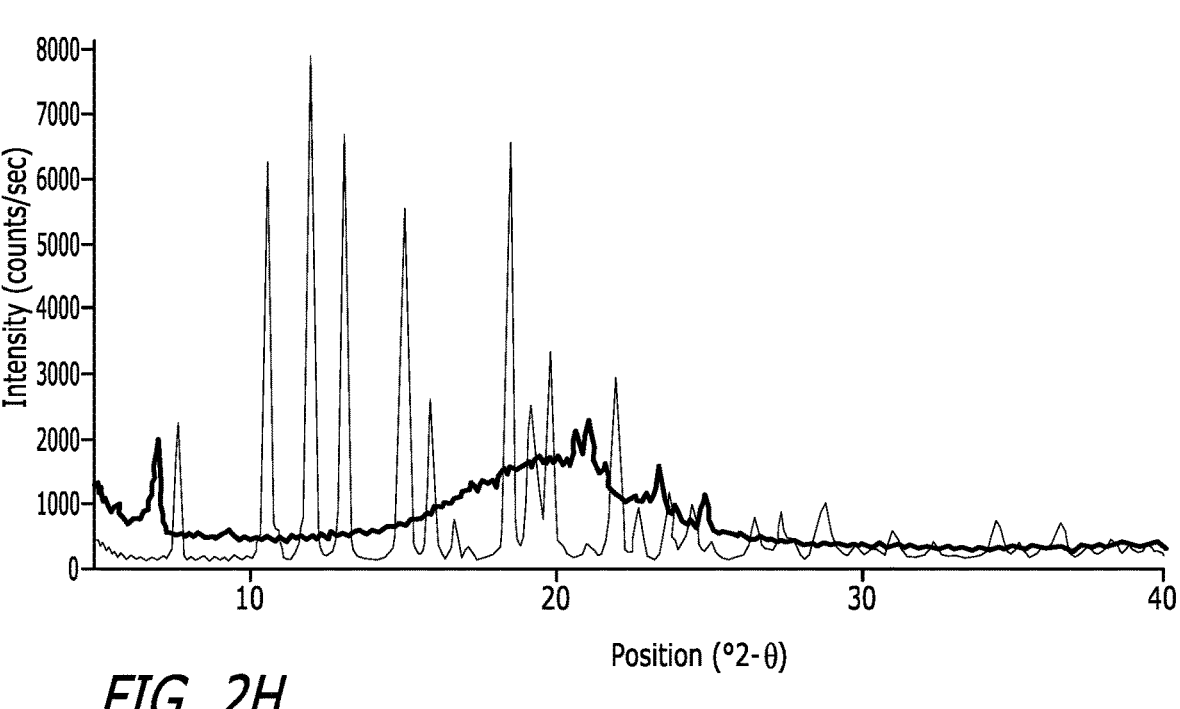

With respect to cholic acid, FIG. 2G shows a PXRD spectra of the Vehicle superimposed with a PXRD spectra of cholic acid. Unlike for fenofibrate formulations, the vehicle did not exhibit a peak profile coincident with cholic acid, indicating that the pharmaceutical composition contains does not appear to contain crystalline cholic acid. Similarly, FIG. 2H shows a PXRD spectra of the pharmaceutical composition superimposed with a PXRD spectra of cholic acid. Like the vehicle, the pharmaceutical composition did not exhibit a peak profile coincident with cholic acid, indicating that the pharmaceutical composition did not appear to contain crystalline cholic acid.

Taken together, the results of this analysis demonstrate that a pharmaceutical composition disclosed hereon is a mixed phase solid suspension of solid crystalline fenofibrate, aprepitant and solid crystalline cholic acid embedded within a solid lipid matrix.

Such mixed phase solid suspensions provide a unique formulation that offers several advantageous. For example, To assess whether the addition of one or more digestion enhancers could improve the solubility of curcumin when combined with glycerolipid components, pharmaceutical composition comprising curcumin was formulated according to Table 2 below. GELUCIRE® 43/01, oleic acid, cholic acid, and sodium stearate were combined heated to 110° C. to produce a clear yellow solution. While maintaining the temperature at 110° C., curcumin was then added to this heated admixture under constant stirring until a clear orange solution was produced. The resulting composition was then allowed to cool to room temperature (18-20° C.), at which time stirring ceased and the composition was transferred to suitable containers where it solidified. The resulting solid composition remelted at 40° C. to give a clear yellow solution with no precipitate formation and again solidified on cooling.

TABLE 2

| | Curcumin Formulation | | |
| Component | CURF1 | CURF2 | CURF3 |
| --- | --- | --- | --- |
| MAISINE ™ CC | 886 mg (43.8%) | 16.8 g (32.2%) | 16.8 g (30.6%) |
| GELUCIRE ® 43/01 | 886 mg (43.8%) | 16.8 g (32.2%) | 16.8 g (30.6%) |
| Oleic Acid | 48 mg (2.4%) | 16.8 g (32.2%) | 16.8 g (30.6%) |
| Sodium Stearate | 32 mg (1.6%) | — | — |
| Cholic Acid | 148 mg (7.3%) | 0.94 g (1.8%) | 3.74 g (6.8%) |
| Curcumin | 22 mg (1.1%) | 0.85 g (1.6%) | 0.85 g (1.5%) | in a single-phase composition, all the components are dissolved and digestion of the lipid matrix by pancreatic juices results in uniform processing of the composition into mixed micelles that are absorbed by the enterocytes. However, in mixed phase solid suspensions, while the dissolved components behave as in a single-phase composition, the solid crystalline compounds can solvent and interact with the aqueous environment of the small intestine to form bile salts. This dual processing scheme affords more opportunity for more complex processes to occur, that is faster, and produces more micellar formations.

Example 3 Curcumin Formulation

As a preliminary assessment, experiments were performed to assess whether curcumin could be formulated in the absence of cholic acid. In one series of experiments, 2 g of MAISINE™ CC was heated to 60° C., and 20 mg curcumin was then added and stirred for at least 60 minutes. However, undissolved curcumin particles remained clearly visible at all times indicating that this compound failed to completely dissolve in the heated liquid fat. In another series of experiments, 20 mg of GELUCIRE® 43/01 was heated to 60° C., and 20 g Curcumin was then added and stirred for at least 60 minutes. However, undissolved curcumin particles remained clearly visible at all times indicating that this compound failed to completely dissolve in heated GELU-CIRE® 43/01. In third series of experiments, 1 g of MAISINE™ CC and 1 g of GELUCIRE® 43/01 were combined and heated to 60° C., and 20 mg curcumin was then added and stirred for at least 60 minutes. However, undissolved curcumin particles remained clearly visible at all times indicating that this compound failed to completely dissolve in heated glycolipid mixture. These results show that curcumin remained insoluble in formulations containing only MAISINE™ CC, only GELUCIRE® 43/01. and an admixture of MAISINE™ CC and GELUCIRE® 43/01.

To assess whether the addition of one or more digestion enhancers to glycerolipid admixture comprising curcumin could improve the bioavailability of this therapeutic compound, the pharmacokinetics of these formulations were assessed. Pharmacokinetic analysis will include experiments designed to determine the amount of curcumin administer (dose), the peak concentration of curcumin achieved after administration (Cmax), the time it takes curcumin to reach its Cmax (Tmax), the time required for the concentration of curcumin to reach half its Cmax (T½), the integral of the concentration-time curve between from time zero to the time of last quantifiable measurement taken during the experiments (AUClast), and the integral of the concentration-time curve from time zero to infinity (AUCinf).

In one series of experiments, CURF1 and CURF3 were evaluated against Comparator Formulation 1 (CMF1) comprising 400 mg (95%) of Curcumin and 5 mg (5%) of piperine. Male wistar rats, each with an average weight of between 336 g to 566 g, were divided into three groups of 24 animals. Animals from each group were oral dosed by gavage as follows: Group 1 animals received a single dose of CURF2 administered at 1.5 mg/kg; Group 2 animals received a single dose of CURF3 administered at 1.5 mg/kg; and Group 3 animals received a single dose of CMF1 administered at 1.5 mg/kg. Samples of whole blood were taken just prior to administration, 0 h, and at the following 8 post-administration time points (n=3 per time point): 0.25 h, 1 h, 1.5 h, 2 h, 3 h, 4 h, 8 h, and 24 h. Samples of cerebral spinal fluid (CSF) and brain were taken at 8 post-administration time points (n=3 per time point): 0.25 h, 1 h, 1.5 h, 2 h, 3 h, 4 h, 8 h, and 24 h. Collected whole blood samples were processed using standard procedures and 20 µL of an internal standard solution and 100 µL of Acetonitrile were added to 20 µL of blood plasma and the resulting supernatants centrifuge at 13,000 rpm at 4° C. and 100 µL of this supernatant was stored at −80° C. for subsequent analysis. Collected brain samples were processed by homogenizing 1 g of brain in 4 mL of water, and 20 μL of an internal standard solution and 100 μL of Acetonitrile were added to 20 μL of brain homogenate and the resulting supernatants centrifuge at 13,000 rpm at 4° C. and 100 μL of this supernatant was stored at −80° C. for subsequent analysis. Processed blood and brain supernatants were sent for bioanalysis, utilizing UHLC-MS/MS with a reverse phase C18 column (3×50 mm), 1.7 μm 50° C. with a mobile phase gradient between: 10 mM ammonium formate in 0.1% formic acid and 0.1% formic acid in Acetonitrile, a flow rate of 0.5 mL/min and injection volume 1 μL. Pharmacokinetic parameters were calculated using the non-compartmental analysis tool of the Phoenix WinNonlin® software (Version 8.3) using the plasma or blood as data type (model 200-202) with Extravascular as Dose type. The area under the plasma concentration-time curve (AUClast) was calculated by the linear trapezoidal rule from time zero to the time of last quantifiable concentration. The AUCinf was obtained by adding AUClast and the extrapolated area determined by Clast/Kel. Peak plasma concentration (Cmax) and time for the peak plasma concentration (Tmax) were the observed values.

As shown in Table 3, CURF2 and CURF3, curcumin formulated with lipids and with digestion enhancers, exhibited superior pharmacokinetic properties for curcumin in blood relative to CMF1. In comparison to CMF1 (non-lipid comparator formulation), CURF2 demonstrated substantially higher absorption levels of curcumin in blood as indicated by a Cmax that was over 8 times greater versus CMF1, with lower clearance over time as indicated by an AUC that was 10.5 times higher versus CMF1. Although CURF3 exhibited only a slightly higher absorption level of curcumin in blood relative to CMF1, this formulation did demonstrate a lower clearance rate as indicated by an AUC that was over 4 times higher versus CMF1. Overall, CURF2 and CURF3 demonstrate pharmacokinetic improvements compared to the comparator formulation CMF1.

TABLE 3

| Mean Pharmacokinetics Parameter of Blood Curcumin by Formulation | | | |
|---|---|---|---|
| Parameter | CURF2 | CURF3 | CMF1 |
| T½ (hr) | 1 | 1 | 2 |
| Cmax (ng/g) | 10.27 | 1.58 | 1.26 |
| AUClast (hr*ng/mL) | 14.05 | 5.26 | 1.33 |

Additionally, as shown in Table 4, curcumin formulated with lipids and with digestion enhancers, exhibited superior pharmacokinetic properties for curcumin in brain relative to CMF1. In comparison to CMF1, CURF2 demonstrated substantially higher absorption levels of curcumin in brain as indicated by an Cmax that was over 2.4 times greater versus CMF1, with lower clearance over time as indicated by a AUC that was 4 times higher versus CMF1. Although CURF3 exhibited only a slightly higher absorption level of curcumin in blood relative to CMF1, this formulation did demonstrate a lower clearance rate as indicated by an AUC that was about 1.8 times higher versus CMF1. Overall, CURF2 and CURF3 demonstrate pharmacokinetic improvements compared to the comparator formulation CMF1. In addition, CURF2 and CURF3 achieved significantly greater bioavailability of curcumin in the brain when compared to the blood. For example, CURF2 demonstrated substantially higher absorption levels of curcumin in brain relative to the blood as indicated by an Cmax that was over 4 times greater in brain versus blood, with lower clearance over time as indicated by a AUC that was about 5.8 times higher in brain versus blood. Similarly, CURF3 demonstrated substantially higher absorption levels of curcumin in brain relative to the blood as indicated by an Cmax that was about 14.8 times greater in brain versus blood, with lower clearance over time as indicated by a AUC that was about 6.9 times higher in brain versus blood. Overall, CURF2 and CURF3 demonstrate pharmacokinetic improvements compared to the comparator formulation CMF1.

TABLE 4

| Mean Pharmacokinetics Parameter of Brain Curcumin by Formulation | | | |
|---|---|---|---|
| Parameter | CURF2 | CURF3 | CMF1 |
| T½ (hr) | 3 | 1 | 1.5 |
| Cmax (ng/g) | 44.90 | 23.38 | 18.48 |
| AUClast (hr*ng/mL) | 81.73 | 36.28 | 20.20 |

Taken together, these results show that CURF2 and CURF3 formulations exhibited significantly improved pharmacokinetic properties of curcumin relative to the CMF1 formulation. CURF2 demonstrated the best overall balance of pharmacokinetic parameters having both low T½ and Tmax values and high Cmax and AUC values, illustrating this formulation reaches maximum concentration in the shortest amount of time with the greatest amount of drug exposure over time. Overall, this data supports the proposition that the inclusion of digestion enhancers increases the extent and speed of absorption of drug, in both blood and brain, over a non-lipid-based comparator formulation of curcumin.

To assess whether the addition of one or more digestion enhancers to glycerolipid admixture comprising curcumin could improve the efficacy of this therapeutic compound, pharmacodynamic experiments will be conducted. Pharmacodynamic analysis will include experiments design to determine the efficacy of curcumin using an appropriate animal model system designed to mimic an indication or disease state for which this therapeutic compound is being used to alleviate. Initial experiments will ascertain whether a beneficial effect is obtained from a formulation comprising curcumin, followed by experiments designed to ascertain the dose-response relationship of curcumin and the beneficial effect associated with this compound.

Example 4 Fenofibrate Formulations

Pharmaceutical compositions comprising fenofibrate were formulated according to Tables 5 and 6 below. MAISINE™ CC, GELUCIRE® 43/01, and the fatty acid component or the surfactant component were combined and heated to 60° C. to produce a clear yellow solution. While maintaining the temperature at 60° C., fenofibrate was then added under constant stirring until a clear solution was produced. The resulting composition produced a clear yellow solution which was then allowed to cool to room temperature (18-20° C.) at which time stirring ceased and the composition was transferred to suitable containers where it solidified. The resulting solid composition remelted at 40° C. to give a clear yellow solution with no precipitate formation and again solidified on cooling.

TABLE 5

| Fenofibrate Formulations | | | | |
| --- | --- | --- | --- | --- |
| Component | FENF1 | FENF2 | FENF3 | FENF4 |
| MAISINE ™ CC | 2,020 mg (44.6%) | 2,100 mg (46.4%) | 300 mg (32.6%) | 3.65 g (36.5%) |
| GELUCIRE ® 43/01 | 2.020 mg (44.6%) | 2,250 mg (49.6%) | 300 mg (32.6%) | 3.65 g (36.5%) |
| Cholic Acid | 179 mg (4.0%) | 150 mg (3.3%) | — | 0.61 g (6.1%) |
| Linoleic acid | — | — | 110 mg (12.0%) | — |
| Oleic Acid | 279 mg (6.1%) | — | — | 2.03g (20.3%) |
| Sodium Stearate | — | — | 10 mg (1.1%) | 0.14 g (1.4%) |
| Fenofibrate | 30 mg (0.7%) | 30 mg (0.7%) | 200 mg (21.7%) | 0.06 g (0.6%) |

TABLE 6

| Fenofibrate Formulations | | | | |
| --- | --- | --- | --- | --- |
| Component | FENF5 | FENF6 | FENF7 | FENF8 |
| MAISINE ™ CC | 4.11 g (41.1%) | 4.42 g (44.2%) | 3.31 g (33.1%) | 4.44 g (44.4%) |
| GELUCIRE ® 43/01 | 2.81 g (28.1%) | 4.42 g (44.2%) | 4.42 g (44.2%) | 4.44 g (44.4%) |
| Cholic Acid | 0.9 g (9.0%) | — | — | 0.04 g (0.4%) |
| Linoleic acid | — | — | — | — |
| Oleic Acid | 2.01 g (20.1%) | 1.1 g (11.0%) | 2.21 g (22.1%) | 0.66 g (6.6%) |
| Sodium Stearate | 0.14 g (1.4%) | — | — | — |
| Fenofibrate | 0.07 g (0.7%) | 0.07 g (0.7%) | 0.07 g (0.7%) | 0.07 g (0.7%) |

Previous studies have shown that fenofibrate is soluble in a glycerolipid admixture of MAISINE™ CC and GELU-CIRE® 43/01. To assess whether the addition of one or more digestion enhancers to glycerolipid admixture comprising fenofibrate could improve the bioavailability of this therapeutic compound, both the pharmacokinetics and pharmacodynamics of these formulations were assessed. Pharmacokinetic analysis will ascertain how an organism affects the therapeutic compound being examined, whereas pharmacodynamics will determine how the therapeutic compound affects the organism. Pharmacokinetic analysis included experiments designed to determine the amount of a therapeutic compound administer (dose), the peak concentration of a therapeutic compound after administration (Cmax), the time it takes to reach Cmax (Tmax), the time required for the concentration of the therapeutic compound to reach half its Cmax (T½), and the integral of the concentration-time curve between the first and last sample points (AUClast).

In one series of experiments, FENF1 and FENF2 were evaluated against Comparator Formulation 1 (CMF1) comprising 2,250 mg (49.6%) of MAISINE™ CC, 2,250 mg (49.6%) of GELUCIRE® 43/01, and 30 mg (0.7%) of fenofibrate, and Comparator Formulation 2 (CMF2), a suspension comprising 1% carboxymethyl cellulose and 0.7% of fenofibrate. C57BL/6 male mice, each with an average weight of between 20 g to 25 g, were divided into four groups of nine animals. Animals from each group were oral dosed by gavage as follows: Group 1 animals received a single dose of FENF1 administered at 30 mg/kg; Group 2 animals received a single dose of FENF2 administered at 30 mg/kg; Group 3 animals received a single dose of CMF1 administered at 30 mg/kg; and Group 4 animals received a single dose of CMF2 administered at 30 mg/kg. Samples of whole blood were taken just prior to administration, 0 h, and at the following 7 post-administration time points: 0.5 hr, 1 hr, 2 hr, 4 hr, 8 hr, 12 hr, and 24 hr. Collected whole blood samples were processed by adding 200 μL of a tolbutamide internal standard solution (1 mg/mL tolbutamide in DMSO/water/acetonitrile) to 50 μL of whole blood and precipitating blood proteins from this admixture using standard procedures and the resulting supernatants were stored for analysis. Samples of brain were taken at 3 post-administration time points (n=3 per time point): 2 hr, 4 hr, and 24 hr. Collected brain samples were processed by homogenizing 1 g of brain in 1 mL of water, adding 200 μL of tolbutamide internal standard solution and 5 μL of 1:1 acetonitrile/water to 50 μL aliquots of sample brain homogenate, centrifuging this admixture, and adding 100 μL water to 50 μL of the resulting supernatant which was then stored for analysis. Processed blood and brain supernatants were sent for bioanalysis, utilizing UHPLC-MS/MS with a reverse phase C18 column (50×21 mm), 1.7 mm 50° C. with a mobile phase gradient between: 0.1% formic acid in water and 0.1% formic acid in acetonitrile, a flow rate of 0.4 mL/min and injection volume 2 mL. Blood samples were analyzed for various pharmacokinetic parameters including the amount of fenofibrate administer (dose), the peak concentration of fenofibrate and fenofibric acid achieved after administration (Cmax), the time required for fenofibrate and fenofibric acid to reach its Cmax (Tmax), the time required for the concentration of fenofibrate and fenofibric acid to reach half its Cmax (T½), the integral of the concentration-time curve between from time zero to the time of last quantifiable measurement taken during the experiments (AUClast), and the integral of the concentration-time curve from time zero to infinity (AUCinf). Since brain samples were limited to three time points only the pharmacokinetic parameters of amount of fenofibrate administer (dose) and the peak concentration of fenofibrate and fenofibric acid achieved after administration (Cmax) could be reliably defined.

Figure 3A:
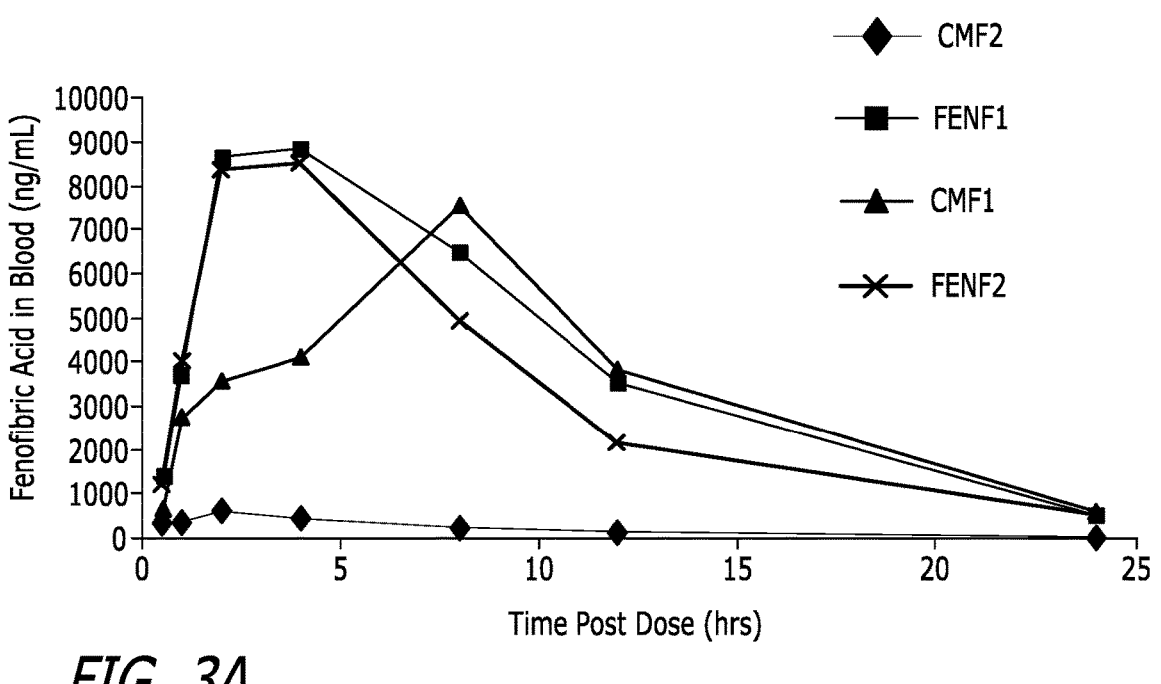
FIGS. 3A-3B show representative UHPLC tracings of fenofibric acid levels in blood and brain with FIG. 3A shows a UHPLC tracing of fenofibric acid levels in blood after oral administration of 30 mg/kg of disclosed pharmaceutical compositions comprising fenofibrate.

As shown in FIG. 3A and Table 7, FENF1 and FENF2, fenofibrate formulated with lipids and with digestion enhancers, exhibited superior pharmacokinetic properties for fenofibric acid relative to CMF1 and CMF2. In comparison to CMF1 (previous lipid formulation without digestion enhancers), FENF1 and FENF2 demonstrated higher absorption levels of fenofibric acid in blood as indicated by increased Cmax, with a shorter time to maximum concentration as shown by decreased Tmax, and lower clearance over time as indicated by a larger AUC versus CMF1. In comparison to CMF2 (non-lipid comparator formulation), FENF1 and FENF2 demonstrated substantially higher absorption levels of fenofibric acid in blood as indicated by increased Cmax, with lower clearance over time as indicated by a larger AUC versus CMF2. FENF1 had a higher Cmax and AUC than either FFEN2, CMF1 or CMF2 suggesting that FENF1 produces higher concentrations of fenofibric acid in blood with and the slowest clearance over time indicating greater drug exposure relative to the other formulations. Overall, FENF1 and FENF2 demonstrate pharmacokinetic improvements compared to the comparator formulations. CMF1 and CMF2.

TABLE 7

Mean Pharmacokinetic Parameters of Blood
Fenofibric Acid by Formulation

| Parameter | FENF1 | FENF2 | CMF1 | CMF2 |
|---|---|---|---|---|
| T½ (hr) | 4.4 | 5.1 | 4.4 | 3.3 |
| Tmax (hr) | 4.0 | 4.0 | 8.0 | 2.0 |
| Cmax (ng/mL) | 8875.7 | 8557.3 | 7586.0 | 611.9 |
| AUClast (hr*ng/mL) | 100664.4 | 82082.5 | 84882.6 | 4598.6 |
| AUCinf (hr*ng/mL) | 103969.7 | 85871.7 | 88625.7 | 4636.0 |

Figure 3B:
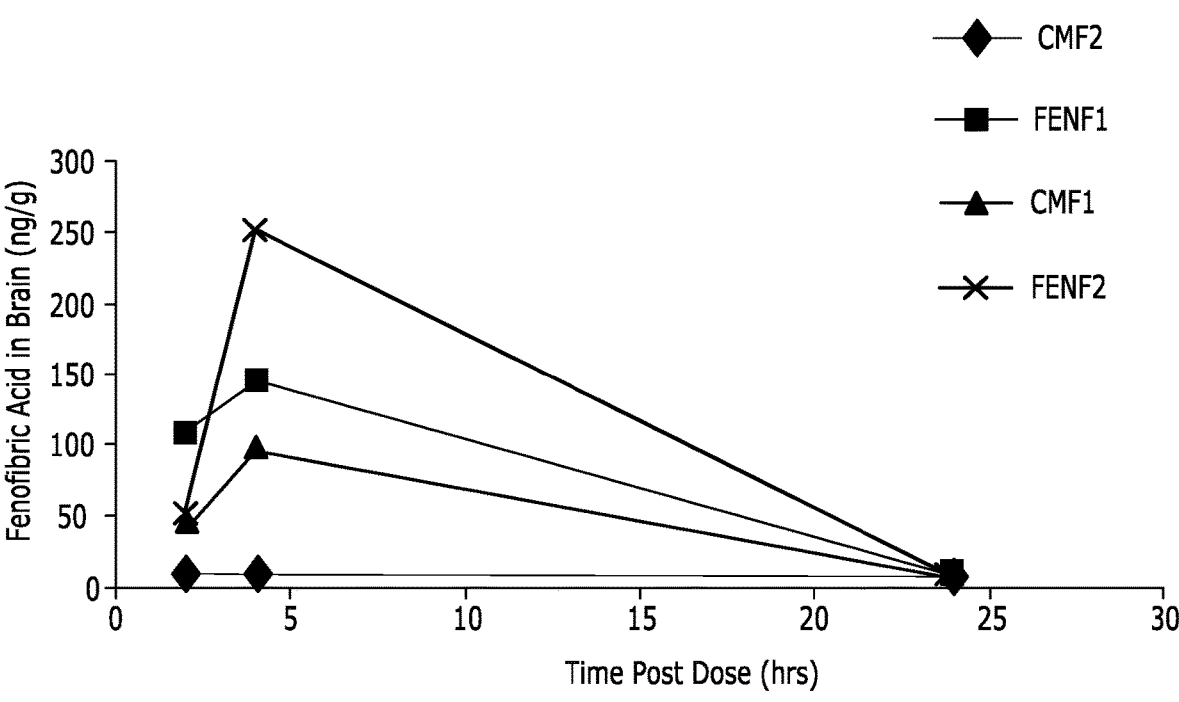

As shown in FIG. 3B and Table 8, FENF1 and FENF2 substantially increased the absorption level of fenofibric acid in brain over both CMF1 and CMF2. In comparison to CMF1, FENF1 and FENF2 exhibited higher absorption levels of fenofibric acid in brain as indicated by increased Cmax and larger AUC versus CMF1, with FENF1 being absorbed 1.5 times more than CMF1, and FENF2 being absorbed 2.5 times more than CMF1. In comparison to CMF2, FENF1 and FENF2 demonstrated substantially higher absorption levels of fenofibric acid in brain as indicated by increased Cmax and larger AUC versus CMF2, with FENF1 being absorbed 14 times more than CMF1, and FENF2 being absorbed 24 times more than CMF2. In addition, with respect to FENF2, the overall amount of fenofibric acid entering the brain as well as its proportion relative to blood concentration is great than FENF1 as well as CMF1 and CMF2. These results supports the pharmacokinetic advantages associated with FENF1 and FENF2, fenofibrate formulated with lipids and with digestion enhancers, by demonstrating enhanced concentration levels of fenofibric acid in brain, that are not achieved with previous lipid formulations without digestion enhancers (CMF1) and non-lipid comparators (CMF2).

TABLE 8

Fenofibric Acid Blood and Brain Ratios of Mean Cmax by Formulation

| Sample | FENF1 | FENF2 | CMF1 | CMF2 |
|---|---|---|---|---|
| Blood | 8875.7 ng/mL | 8557.3 ng/mL | 7586.0 ng/mL | 611.9 ng/mL |
| Brain | 145.9 ng/g | 253.9 ng/g | 98.8 ng/g | 10.4 ng/g |
| Brain:Blood Ratio | 0.016 | 0.030 | 0.013 | 0.17 |

Additionally, as shown in Table 9, fenofibrate formulated with lipids and with digestion enhancers, exhibited superior pharmacokinetic properties for fenofibrate itself relative to CMF1 and CMF2. Although no significant differences in measured pharmacokinetic parameters of fenofibrate was observed in blood, enhanced pharmacokinetic parameters of fenofibrate in brain were detected. For example, in comparison to CMF1, FENF1 and FENF2 exhibited higher absorption levels of fenofibrate in brain as indicated by increased Cmax versus CMF1, with FENF1 being absorbed 3.8 times more than CMF1, and FENF2 being absorbed 2.6 times more than CMF1. In comparison to CMF2, FENF1 and FENF2 exhibited higher absorption levels of fenofibrate in brain as indicated by increased Cmax versus CMF2, with FENF1 being absorbed 3.4 times more than CMF1, and FENF2 being absorbed 2.3 times more than CMF2. FENF1 and FENF2 produced higher concentrations of fenofibrate in both blood and brain compared to CMF2, providing pharmacokinetic support that the lipid formulations of fenofibrate achieve higher levels of drug in brain compared to non-lipid-based comparators. One explanation for these finding is that the lipid-formulations of FENF1 and FENF2 slow down the conversion rate of fenofibrate to fenofibric acid, and thus enabling fenofibrate survive in blood at levels high enough to facilitate its entry into the brain, i.e., the lipid-based formulations of FENF1 and FENF2 protect fenofibrate so that this compound can be transported into the brain. Although the levels of fenofibrate in the blood and brain were lower than those observed for fenofibric acid, this was expected based on the conversion rate of fenofibrate to fenofibric acid which can be slowed, but not prevented.

TABLE 9

Fenofibrate Blood and Brain Ratios of Mean Cmax by Formulation

| Sample | FENF1 | FENF2 | CMF1 | CMF2 |
|---|---|---|---|---|
| Blood | 5.9 ng/mL | 9.3 ng/mL | 12.8 ng/mL | 5.1 ng/mL |
| Brain | 33.9 ng/g | 23.0 ng/g | 8.9 ng/g | 10.0 ng/g |
| Brain:Blood Ratio | 5.7 | 2.5 | 0.7 | 2.0 |

Taken together, these results show that FENF1 and FENF2 formulations exhibited significantly improved pharmacokinetic properties of fenofibrate relative to either the CMF1 or CMF2 formulations. Overall, this data supports the proposition that the inclusion of digestion enhancers increases the extent and speed of absorption of drug, in both blood and brain, over previous lipid formulations (CMF1) and non-lipid based comparator formulations of fenofibrate (CMF2).

Figure 4A:
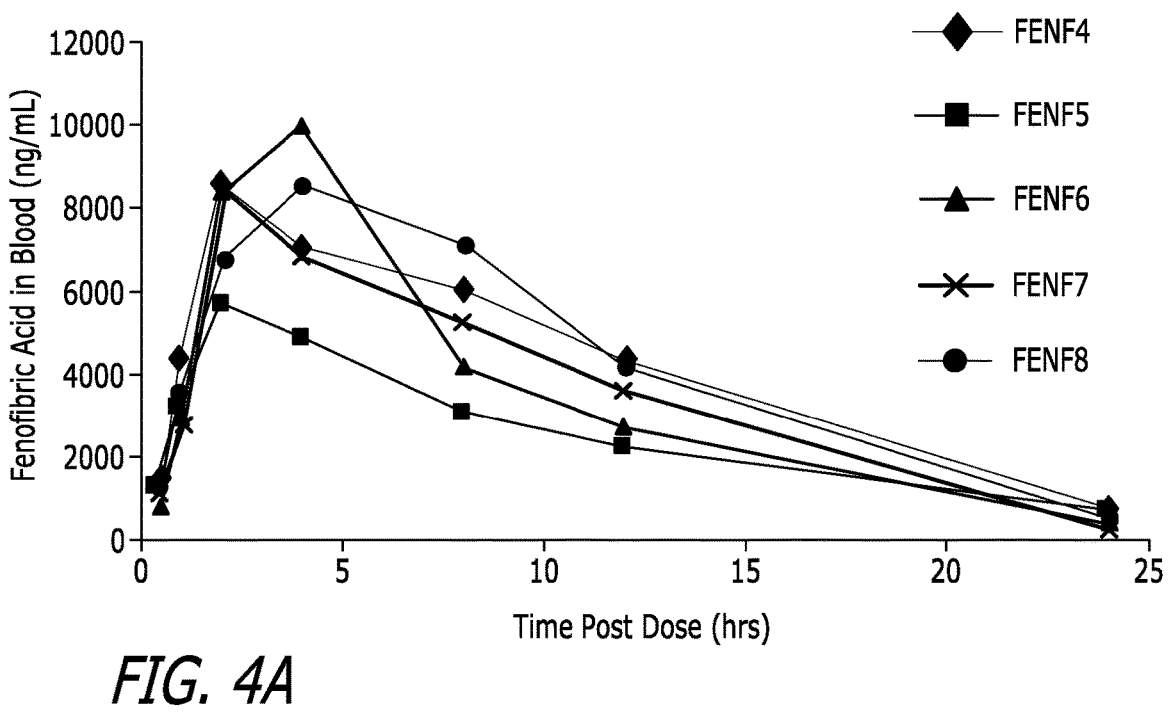
FIGS. 4A-4B show representative UHPLC tracings of fenofibric acid levels in blood and brain with FIG. 4A shows a UHPLC tracing of fenofibric acid levels in blood after oral administration of 30 mg/kg of disclosed pharmaceutical compositions comprising fenofibrate.

To extend this analysis, the pharmacokinetic properties of five further fenofibrate formulations were evaluated. In these experiments, C57BL/6 male mice were administered 30 mg/kg of fenofibrate formulated as FENF4, FENF5, FENF6, FENF7, or FENF8 using the experimental design described above. As shown in FIG. 4A and Table 10, FENF4, FENF6, FENF7, and FENF8, each a formulation of fenofibrate with lipids and with digestion enhancers, all demonstrated pharmacokinetic properties of fenofibric acid in blood that were comparable to the pharmacokinetic properties observed for FENF1 and FENF2. For example, absorption levels of fenofibric acid in blood as indicated by Cmax for FENF4, FENF6, FENF7, and FENF8 ranged between 8436.0 ng/mL to 10,010.0 ng/mL, levels comparable to the Cmax value of 8875.7 ng/mL for FENF1 and 8557.3 ng/mL for FENF2. Similarly, time to maximum fenofibric acid concentration as indicated by Tmax for FENF4, FENF6, FENF7, and FENF8 ranged between 3.6 hr to 4.8 hr, a time comparable to the Tmax of 4.0 for both FENF1 and FENF2. In terms of individual formulations, FENF6 demonstrated the highest Cmax (10,010.0 ng/mL), FENF7 demonstrated the lowest Tmax (3.6 hrs), and FENF4 demonstrated the lowest T½ (2.0 hrs). Overall, with the exception of FENF5, all fenofibrate formulations comprising lipids and digestion enhances demonstrated a similar absorption profile of fenofibric acid relative to FENF1 and FENF2. Compared to all other formulations, FENF4 demonstrated the best overall balance of pharmacokinetic parameters having both low T½ and Tmax values and high Cmax and AUC values, illustrating this formulation reaches maximum concentration in the shortest amount of time with the greatest amount of drug exposure over time in the blood.

TABLE 10

Mean Pharmacokinetic Parameters of Blood Fenofibric Acid by Formulation

| Parameter | FENF4 | FENF5 | FENF6 | FENF7 | FENF8 |
|---|---|---|---|---|---|
| T½ (hr) | 2.0 | 2.0 | 4.0 | 2.0 | 4.0 |
| Tmax (hr) | 4.8 | 6.8 | 4.5 | 3.6 | 3.9 |

TABLE 10-continued

| Mean Pharmacokinetic Parameters of Blood Fenofibric Acid by Formulation | | | | | |
|---|---|---|---|---|---|
| Parameter | FENF4 | FENF5 | FENF6 | FENF7 | FENF8 |
| Cmax (ng/mL) | 8575.0 | 5693.0 | 10010.0 | 8436.0 | 8574.0 |
| AUClast (hr*ng/mL) | 100600.0 | 60233.0 | 85889.0 | 87304.0 | 104221.0 |
| AUCinf (hr*ng/mL) | 105125.0 | 66248.0 | 88335.0 | 88764.0 | 106732.0 |

Figure 4B:
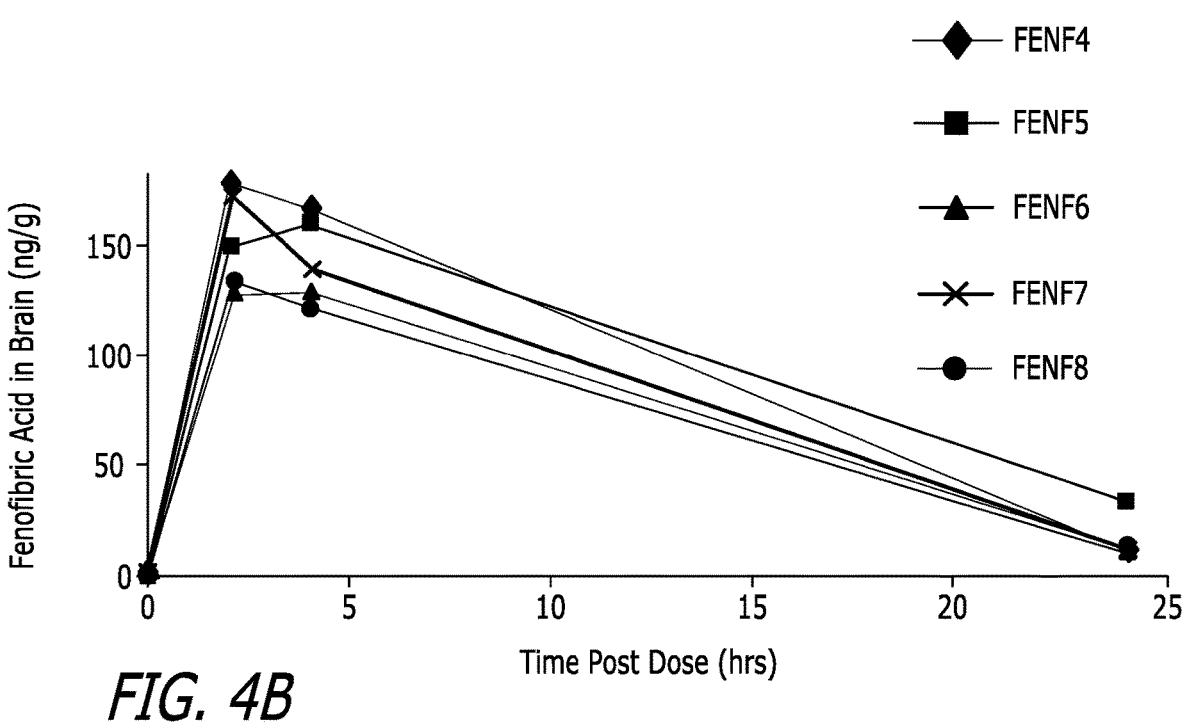

As shown in FIG. 4B and Table 11, FENF4, FENF5, FENF6, FENF7, and FENF8 all demonstrated pharmacokinetic properties of fenofibrate in blood that were superior to pharmacokinetic properties observed for FENF1 and FENF2. For example, absorption levels of fenofibrate in blood as indicated by Cmax for FENF4, FENF6, FENF7, and FENF8 ranged between 119.0 ng/mL to 548.0 ng/mL, levels significantly higher than the Cmax values of 5.9 ng/mL for FENF1 and 9.3 ng/mL for FENF2. In terms of individual formulations, FENF4 demonstrated the highest Cmax (548.0 ng/mL), FENF4, FENF5, and FENF8 all demonstrated the lowest Tmax (1.9 hrs), and FENF5 demonstrated the lowest T½ (0.5 hrs). Overall, all fenofibrate formulations comprising lipids and digestion enhances demonstrated a superior absorption profile of fenofibrate relative to FENF1 and FENF2. Compared to all other formulations, FENF4 again demonstrated the best overall balance of pharmacokinetic parameters having both low T½ and Tmax values and high Cmax and AUC values, illustrating this formulation reaches maximum concentration in the shortest amount of time with the greatest amount of drug exposure over time in the brain.

TABLE 11

| Mean Pharmacokinetic Parameters of Blood Fenofibrate by Formulation | | | | | |
|---|---|---|---|---|---|
| Parameter | FENF4 | FENF5 | FENF6 | FENF7 | FENF8 |
| T½ (hr) | 1.0 | 0.5 | 1.3 | 1.3 | 0.5 |
| Tmax (hr) | 1.9 | 1.9 | 2.0 | 2.0 | 1.9 |
| Cmax (ng/mL) | 548.0 | 154.8 | 131.8 | 119.0 | 195.0 |
| AUClast (hr*ng/mL) | 1520.0 | 580.0 | 282.9 | 269.0 | 576.0 |
| AUCinf (hr*ng/mL) | 1538.0 | 933.0 | NR | NR | NR |

NR: No result, insufficient data to reliably determine pharmacokinetic parameter.

Additionally, as shown in Table 12, FENF4, FENF5, FENF6, FENF7, and FENF8 all demonstrated pharmacokinetic properties of fenofibric acid that were comparable to pharmacokinetic properties observed for FENF1 and FENF2. For example, absorption levels of fenofibric acid in brain as indicated by $C_{max}$ for FENF4, FENF5, FENF6, FENF7, and FENF8 ranged between 130.0 ng/g to 178.0 ng/g, levels comparable to the Cmax values of 145.9 ng/g ng/mL for FENF1 and 253.9 ng/ng for FENF2. In terms of individual formulations, FENF4 demonstrated the highest Cmax (178.0 ng/g). Overall, all fenofibrate formulations comprising lipids and digestion enhances demonstrated a comparable absorption profile of fenofibric acid relative to FENF1 and FENF2. Compared to all other formulations, FENF4 again demonstrated the best overall balance of pharmacokinetic parameters having a high Cmax values, illustrating this formulation reaches maximum concentration in the shortest amount of time with the greatest amount of drug exposure over time in the brain.

TABLE 12

| Fenofibric Acid Blood and Brain Ratios of Mean Cmax by Formulation | | | | | |
|---|---|---|---|---|---|
| Sample | FENF4 | FENF5 | FENF6 | FENF7 | FENF8 |
| Blood | 8575.0 ng/mL | 5693.0 ng/mL | 10010.0 ng/mL | 8436.0 ng/mL | 8574.0 ng/mL |
| Brain | 178.0 ng/g | 159.3 ng/g | 130.0 ng/g | 173.0 ng/g | 133.0 ng/g |
| Brain:Blood Ratio | 0.021 | 0.028 | 0.013 | 0.021 | 0.016 |

Additionally, as shown in Table 13, FENF4, FENF5, FENF6, FENF7, and FENF8 all demonstrated pharmacokinetic properties of fenofibrate that were superior to pharmacokinetic properties observed for FENF1 and FENF2. For example, absorption levels of fenofibrate in brain as indicated by Cmax for FENF4, FENF5, FENF6, FENF7, and FENF8 ranged between 87.9 ng/g to 276.4 ng/g, levels significantly higher than the Cmax values of 33.9 ng/g ng/mL for FENF1 and 23.0 ng/ng for FENF2. In terms of individual formulations, FENF6 demonstrated the highest Cmax (276.4 ng/g). Overall, all fenofibrate formulations comprising lipids and digestion enhances demonstrated a superior absorption profile of fenofibrate relative to FENF1 and FENF2.

TABLE 13

| Fenofibrate Blood and Brain Ratios of Mean Cmax by Formulation | | | | | |
|---|---|---|---|---|---|
| Sample | FENF4 | FENF5 | FENF6 | FENF7 | FENF8 |
| Blood | 548.0 ng/mL | 154.8 ng/mL | 131.8 ng/mL | 119.0 ng/mL | 195.0 ng/mL |
| Brain | 195.8 ng/g | 199.5 ng/g | 276.4 ng/g | 257.7 ng/g | 87.9 ng/g |
| Brain:Blood Ratio | 0.357 | 1.289 | 2.097 | 2.174 | 0.451 |

Taken together, these results show that FENF4, FENF5, FENF6, FENF7, and FENF8 formulations exhibited significantly improved pharmacokinetic properties of fenofibric acid and fenofibrate that were largely equivalent to, and in many instances better than, FENF1 and FENF2. Of these formulations, FENF4 appeared to have the best pharmacokinetic properties of fenofibrate with demonstration of high Cmax, low Tmax and high AUC. Overall, this data supports the proposition that the inclusion of digestion enhancers increase the extent and speed of absorption of drug over a glycerolipid admixture alone, and over a non-lipid comparator formulation of fenofibrate.

Figure 5:
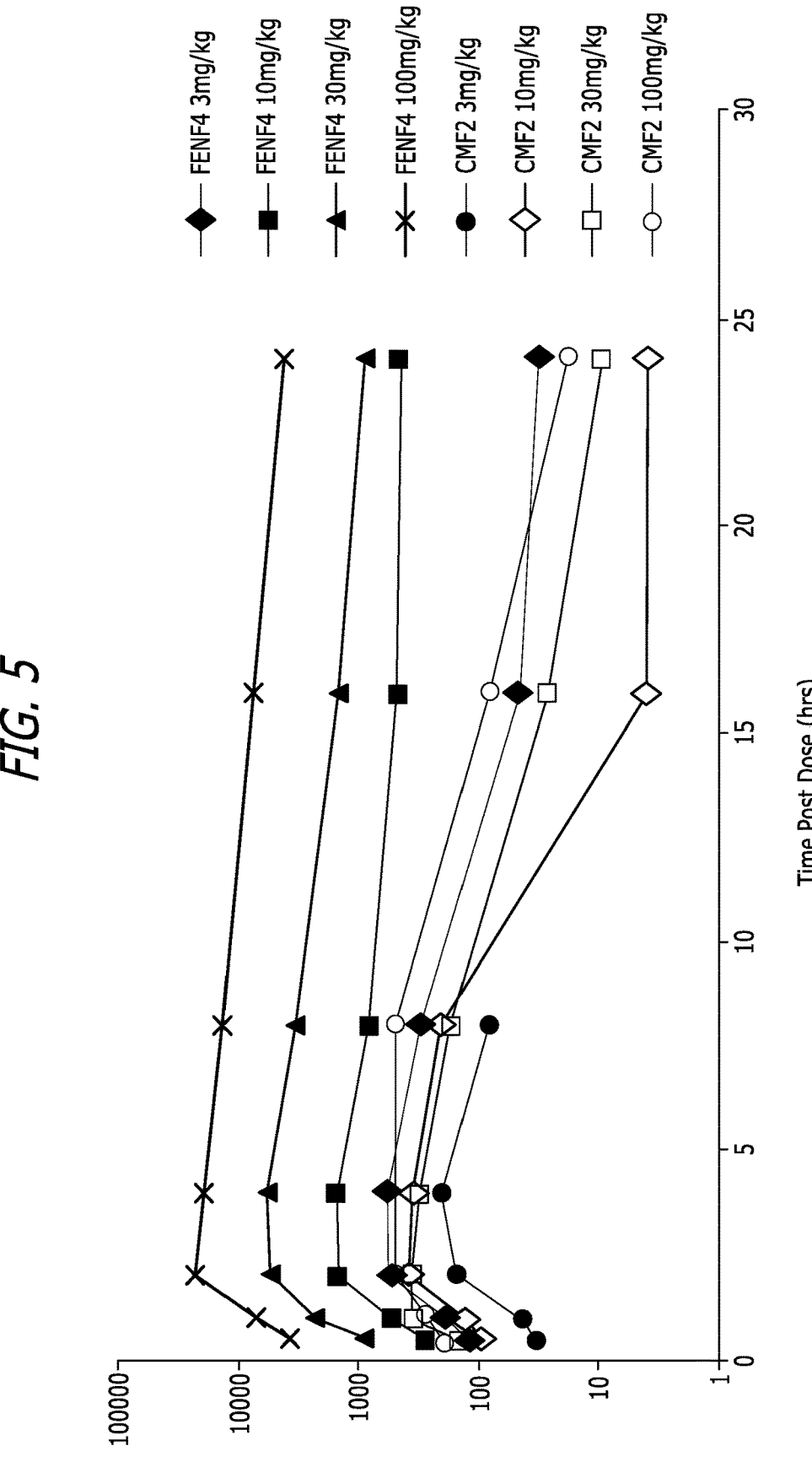
FIG. 5 show representative UHPLC tracings of fenofibric acid levels in blood after oral administration of 3 mg/kg, 10 mg/kg, 30 mg/kg and 100 mg/kg of disclosed pharmaceutical compositions comprising fenofibrate.
Figure 6A:
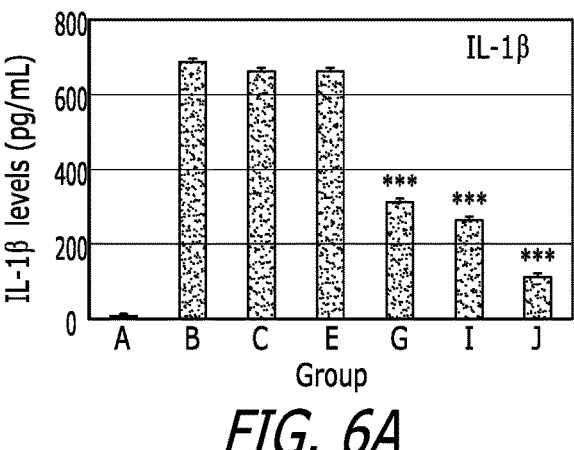
FIGS. 6A-6F show bar graphs of blood cytokine levels in animals undergoing 5 days of an LPS challenge with treatment occurring only on Day 1 of the LPS challenge with FIG. 6A showing IL-1β, levels.
Figure 6B:
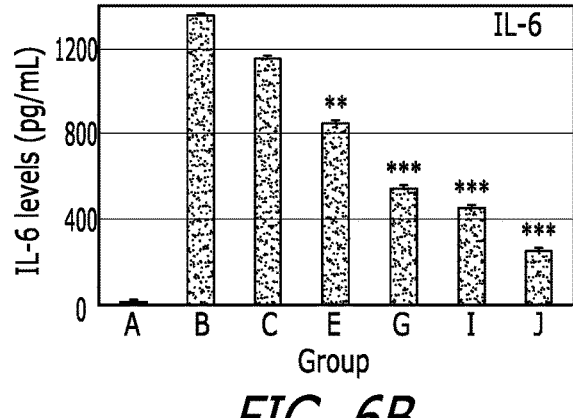
Figure 6C:
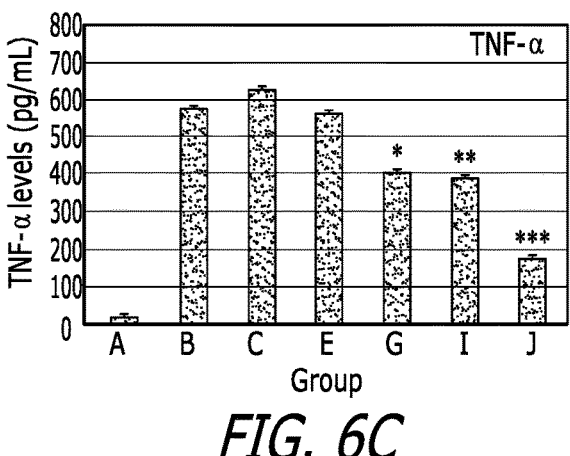
Figure 6D:
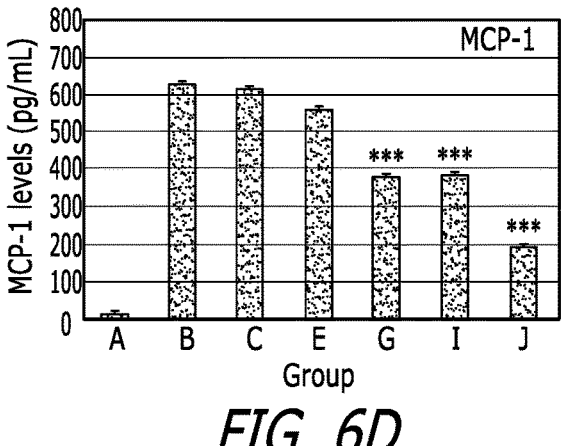
Figure 6E:
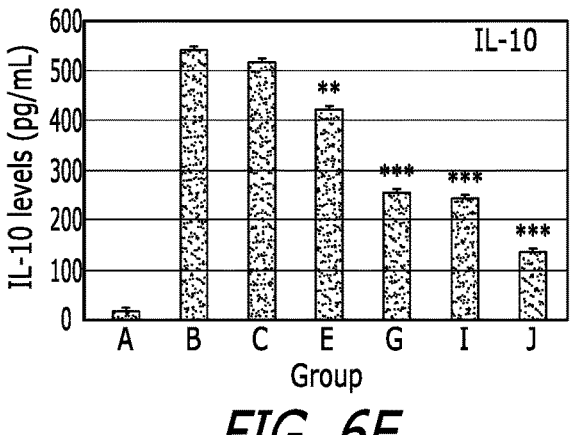
Figure 6F:
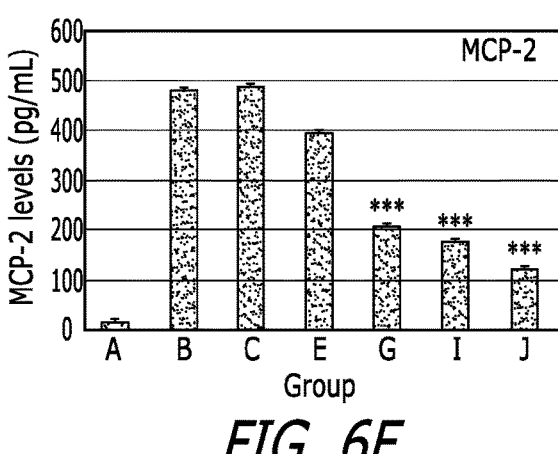
Figure 7A:
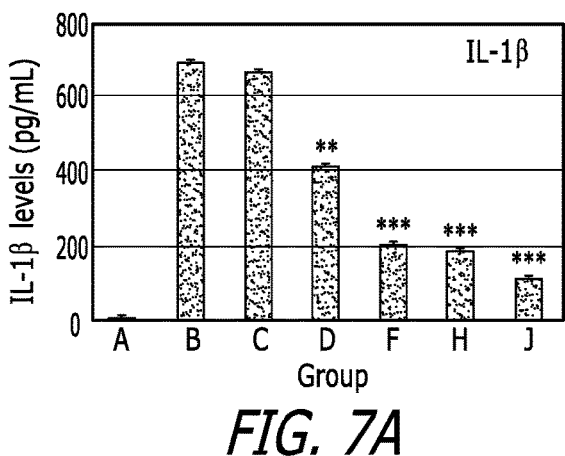
FIGS. 7A-7F show bar graphs of blood cytokine levels in animals undergoing 5 days of pre-treatment before 5 days of an LPS challenge with FIG. 7A showing IL-1β levels.
Figure 7B:
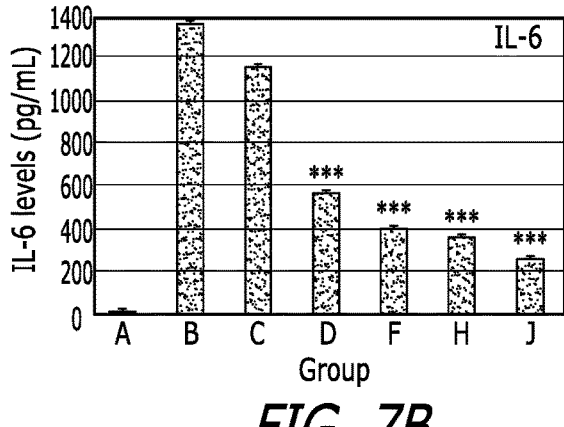
Figure 7C:
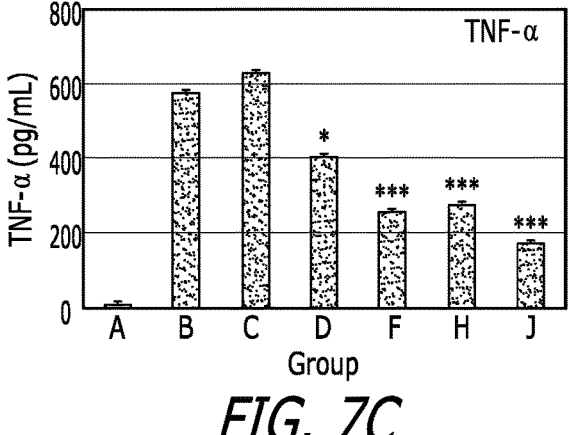
Figure 7D:
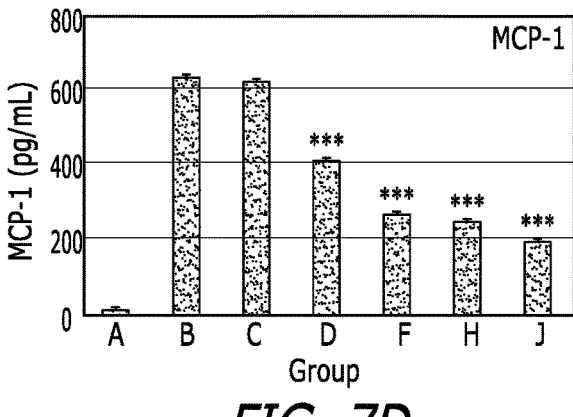
Figure 7E:
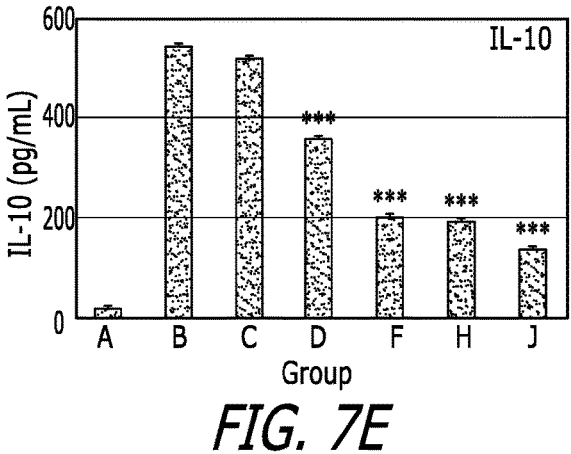
Figure 7F:
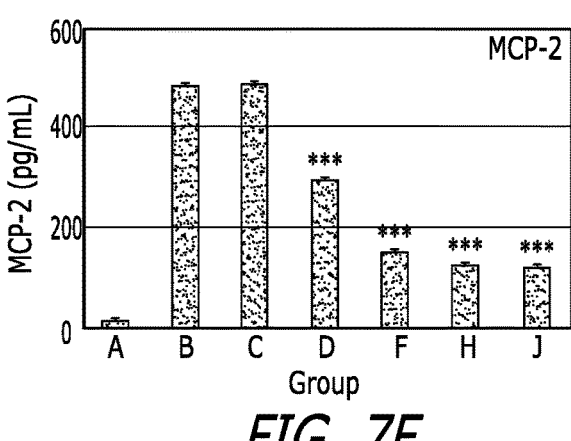
Figure 8A:
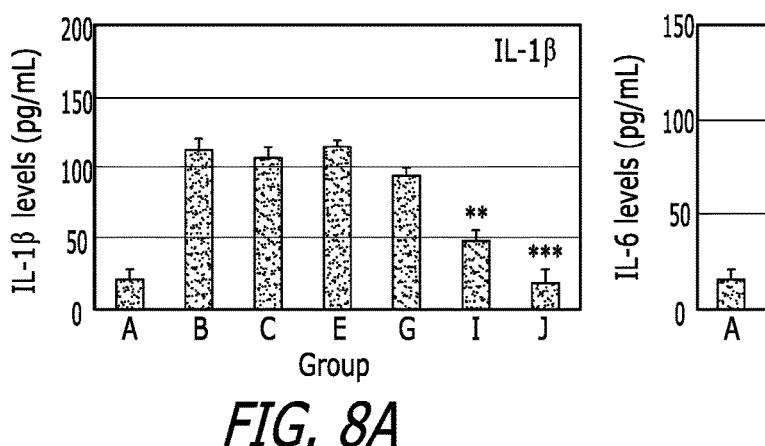
FIGS. 8A-8F show bar graphs of brain cytokine levels in animals undergoing 5 days of an LPS challenge with treatment occurring only on Day 1 of the LPS challenge with FIG. 8A showing IL-1β, levels.
Figure 8B:
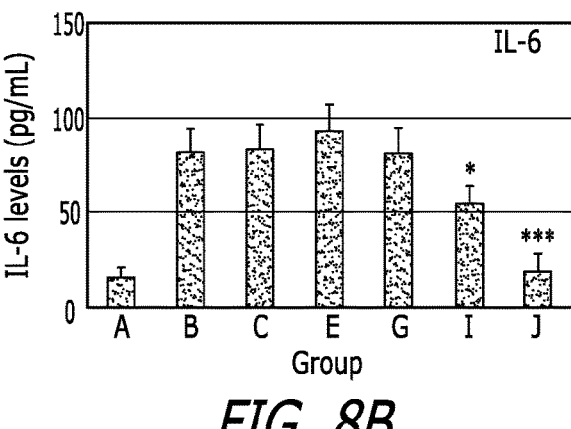
Figure 8C:
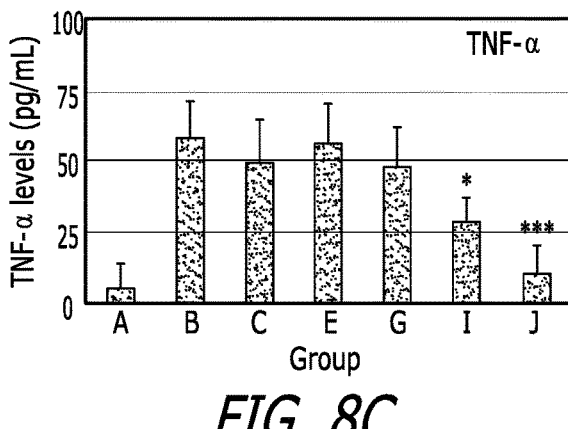
Figure 8D:
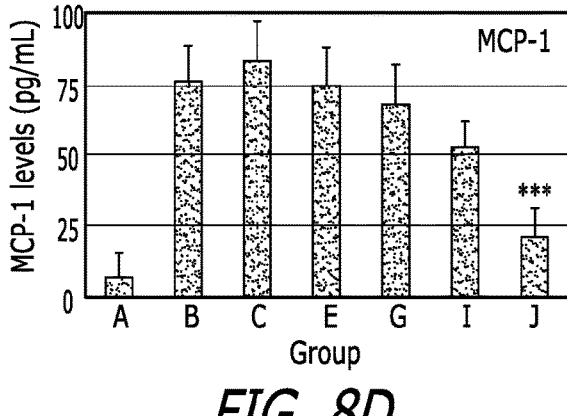
Figure 8E:
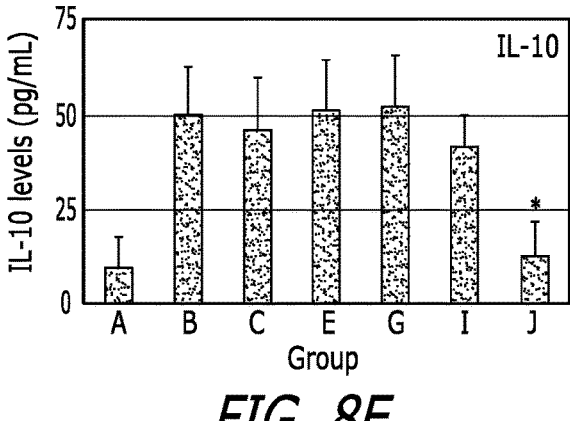
Figure 8F:
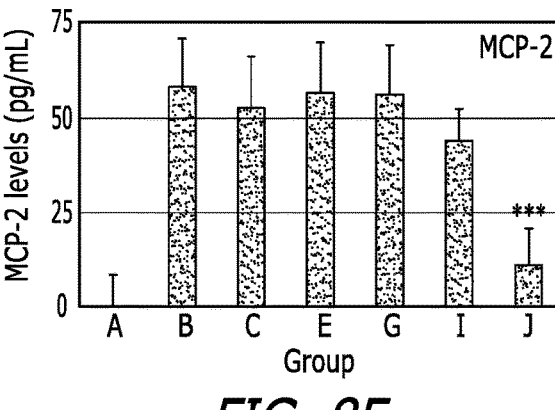

As FENF4 exhibited the best pharmacokinetic properties of all tested formulations, these studies were repeated using four different doses of fenofibrate. In these dose response experiments C57BL/6 male mice were administered 3 mg/kg, 10 mg/kg, 30 mg/kg, or 100 mg/kg of fenofibrate formulated as FENF4 using the experimental design described above. As comparator controls, C57BL/6 male mice were administered 3 mg/kg, 10 mg/kg, 30 mg/kg, or 100 mg/kg of fenofibrate formulated as CMF2 using the experimental design described above. As shown in FIG. 5, animals exhibited a significantly greater absorption level in blood of fenofibric acid formulated as FENF4 relative to the CMF2 controls. In fact, the lowest dose of FENF4 (3 mg/kg of fenofibrate) demonstrated equivalent absorption rates of fenofibric acid in blood as compared to the highest dose of CMF2 (100 mg/kg of fenofibrate), suggesting that only a low dose of FENF4 is required to meet systemic equivalence with a high dose of standard, non-lipid fenofibrate.

Additionally, as shown in FIG. 5 and Table 14, FENF4 revealed a dose-response effect on the absorption rate of fenofibric acid in blood with increasing doses producing progressively higher blood concentrations of fenofibric acid in animals and higher AUC. For example, the 3 mg/kg dose of FENF4 had a Cmax of 569.2 ng/mL of fenofibric acid in the blood, with the 10 mg/kg dose of FENF4 had a Cmax of 569.2 ng/mL of fenofibric acid in blood (representing a 2.6 times increase in Cmax versus the 3 mg/kg dose), the 30 mg/kg dose of FENF4 had a Cmax of 5690.6 ng/mL of fenofibric acid in the blood (representing a 3.8 times increase in Cmax versus the 10 mg/kg dose and a 10 times increase in Cmax versus the 3 mg/kg dose), and the 100 mg/kg dose of FENF4 had a Cmax of 22679.5 ng/mL of fenofibric acid in the blood (representing a 4 times increase in Cmax versus the 30 mg/kg dose, a 15.1 time increase in Cmax versus the 10 mg/kg dose, and a 39.8 times increase in Cmax versus the 3 mg/kg dose).

TABLE 14

| Mean Pharmacokinetic Parameters of Blood Fenofibric Acid by FENF4 Dose | | | | |
|---|---|---|---|---|
| | FENF4 Dosage | | | |
| Parameter | 3 mg/kg | 10 mg/kg | 30 mg/kg | 100 mg/kg |
| T½ (hr) | 4.8 | 17.7 | 8.5 | 9.3 |
| Tmax (hr) | 4.0 | 4.0 | 4.0 | 2.0 |
| Cmax (ng/mL) | 569.2 | 1498.9 | 5690.6 | 22679.5 |
| AUClast (hr*ng/mL) | 4986.6 | 17591.5 | 62571.5 | 259542.1 |
| AUCinf (hr*ng/mL) | 5196.1 | 28729.8 | 73503.6 | 316198.0 |

As shown in Table 15, FENF4 revealed a similar dose-response effect on the absorption rate of fenofibrate in blood with increasing doses producing progressively higher blood concentrations of fenofibrate in animals. For example, the 3 mg/kg dose of FENF4 had a Cmax of 10.3 ng/mL of fenofibrate in the blood, with the 10 mg/kg dose of FENF4 had a Cmax of 20.6 ng/mL of fenofibrate in blood (representing a 2.0 times increase versus the 3 mg/kg dose), the 30 mg/kg dose of FENF4 had a Cmax of 35.1 ng/mL of fenofibrate in the blood (representing a 1.7 times increase versus the 10 mg/kg dose and a 3.4 times increase versus the 3 mg/kg dose), and the 100 mg/kg dose of FENF4 had a Cmax of 117.9 ng/mL of fenofibrate in the blood (representing a 3.4 times increase in Cmax versus the 30 mg/kg dose, a 5.7 times increase in Cmax versus the 10 mg/kg dose, and a 11.4 times increase in Cmax versus the 3 mg/kg dose).

TABLE 15

Mean Pharmacokinetics Parameter of
Blood Fenofibrate by FENF4 Dose

| | FENF4 Dosage | | | |
| Parameter | 3 mg/kg | 10 mg/kg | 30 mg/kg | 100 mg/kg |
|---|---|---|---|---|
| T½ (hr) | NR | 1.7 | 9.4 | NR |
| Tmax (hr) | 0.5 | 0.5 | 1.0 | 0.5 |
| Cmax (ng/mL) | 10.3 | 20.6 | 35.1 | 117.9 |
| AUClast (hr*ng/mL) | NR | 32.6 | 175.2 | 507.9 |
| AUCinf (hr*ng/mL) | NR | 40.2 | 227.8 | NR |

NR: No result, insufficient data to reliably determine pharmacokinetic parameter.

As shown in Table 16, FENF4 revealed that the dose-response effect on the absorption rate of fenofibric acid and fenofibrate was maintained in brain, with increasing doses of fenofibrate formulated as FENF4 producing progressively higher brain concentrations of both fenofibric acid and fenofibrate in animals.

TABLE 16

Mean Cmax of Brain Fenofibric Acid
and Fenofibrate by FENF4 Dose

| | FENF4 Dosage | | | |
| Sample | 3 mg/kg | 10 mg/kg | 30 mg/kg | 100 mg/kg |
|---|---|---|---|---|
| Brain Fenofibric Acid | NR | 9 | 162 | 324 |
| Brain Fenofibrate | 6 | 9 | 182 | 324 |

NR: No result, insufficient data to reliably determine pharmacokinetic parameter.

Taken together, FENF4 demonstrated and improved pharmacokinetic profiled, compared to the non-lipid based CMF2 comparator formulation. In terms of fenofibric acid exposure in the blood, 3 mg/kg of FENF4 was equivalent to 100 mg/kg CMF2. In addition, fenofibrate formulated as FENF4 exhibited a dose-response curve for both fenofibric acid and fenofibrate with increasing doses of fenofibrate formulated as FENF4 producing progressively higher blood and brain concentrations of both fenofibric acid and fenofibrate in animals. With substantially improved pharmacokinetics over CMF1 and CMF2 with regards to both blood and brain exposure of fenofibrate and fenofibric acid, the 30 mg/kg dose of the FENF4 formulation was selected for pharmacodynamic analysis.

FENF4 was further evaluated for its pharmacodynamic properties. To evaluate the efficacy of FENF4 in treating an inflammatory response, lipopolysaccharide (LPS) challenge assays were performed in an animal model to measure the animal's ability to respond to an inflammatory stimulus by mounting an acute phase inflammatory response. Bacterial LPS is an endotoxin, a potent inducer of the acute phase response and systemic inflammation. This response is induced by the production of cytokines from activated monocytes and neutrophils in response to inflammatory stimuli, such as, e.g., IL-1β, IL-6; TNFα; MCP-1; IL-10; and MCP-2.

In one series of experiments, FENF4 were evaluated against CMF2 comprising carboxymethylcellulose and fenofibrate. C57BL/6 male mice, each with an average weight of between 15 g to 25 g, were divided into eight groups of ten animals. For FENF4 and CMF2 groups, half of the animals were administered a test composition 5 days prior to a LPS challenge, with dosing on Days −4, −3, −2, −1 and 1 while the remaining half were administered its test composition on Day 1 prior to a LPS challenge. Animals were intraperitoneally administered a single, daily, sub-lethal dose of LPS (1 mg/kg) for four consecutive days with the initial LPS dose being administered at a time that correlated with Tmax for the test composition (about 4 hours post dosing). Animals from each group were as follows: Group A animals received a single dose of saline administered intraperitoneally for four consecutive days in lieu of LPS and served as an LPS unchallenged control for inflammation; Group B animals received a single dose of non-lipid vehicle administered orally and served as a CMF2 vehicle control; Group C animals received a single dose of lipid vehicle administered orally and served as a FENF4 vehicle control; Group D animals received a single dose of CMF2 administered orally at 30 mg/kg for five consecutive days prior to the initial LPS challenge; Group E animals received a single dose of CMF2 administered orally at 30 mg/kg only on the same day as the LPS challenge; Group F animals received a single dose of CMF2 administered orally at 100 mg/kg for five consecutive days prior to the initial LPS challenge; Group G animals received a single dose of CMF2 administered orally at 100 mg/kg only on the same day as the LPS challenge; Group H animals received a single dose of FENF4 administered orally at 30 mg/kg for five consecutive days prior to the initial LPS challenge; Group I animals received a single dose of FENF4 administered orally at 30 mg/kg only on the same day as the LPS challenge; and Group J animals received a single dose of Dexamethasone administered orally at 3 mg/kg and served as a positive control for treatment.

Samples of whole blood were taken by venipuncture via lateral tail vein at Day 1, Day 2, Day 3, Day 4 immediately prior to and 4 hours after the LPS challenge and Day 5 immediately prior to sacrifice. Collected whole blood samples were processed by centrifugation at 1500 g for 10 min at 4° C. to extract plasma and the plasma aliquoted into 100 μL samples and stored at −80° C. for cytokine analysis. The brain of sacrificed animals was taken and processed by rinsing with saline, blotting dry and sectioning in half from the frontal anterior to the posterior to create two brain portions. The first brain portion was prepared for cytokine analysis by weighing the brain tissue and then snap freezing the tissue and storing at −80° C. for subsequent cytokine analysis. Frozen brain samples were processed by lysing samples by adding 5 uL of cell lysis buffer per mg of sample, homogenizing using a sonic probe, and incubating at room temperature with gentle agitation for 30 minutes. Resultant brain homogenates were centrifuged for 10 minutes and the decanted supernatant diluted 1:1 with PBS. Cytokines levels were evaluated using a customized multiplex assay (Bio-techne Ltd., UK) using a Magpix system (Luminex). Cytokines evaluated in both plasma and brain tissue were IL-1β, IL-6, TNFα, MCP-1, IL-10, and MCP-2.

The second brain portion was prepared for assessment of microglia activity by placing the brain tissue into a sterile container with 10% formalin for 48 hours before being immersed in ethanol for storage prior to immunohistochemistry. Fixed brain samples were processed in paraffin wax and 5 μM sections were transversely cut to encompass the cortex and hippocampus before being mounted on slides and stained using anti-IBA-1 antibodies and anti-CD68 antibodies. Cell counts and biomarker density were assessed via digital image analysis with cells staining positive IBA-1 (IBA-1+ cells) being indicative of microglia activation and cells staining positive for CD68 (CD68+ cells) being indicative of microglia accumulation. Statistical analyses for both the microglia and cytokine experiments were as follows: Inter-group deviations were statistically analyzed by a one-way analysis of variance (ANOVA). In the case of a significant difference in the mean values among the different levels of treatment, comparisons versus the vehicle group were carried out using the Dunnett's test. In case the equal variance test failed, a Kruskal-Wallis one-way analysis of variance on ranks followed by a Dunn's test was proposed. There was no failure of the equal variance test and other variance tests were not required. Dosing regimes of the Lipid formulation of Fenofibrate were also compared to the standard Fenofibrate formulation using unpaired t-test. For all tests, a p value <0.05 was considered statistically significant.

Analysis of blood cytokine levels in these experiments revealed that FENF4 exhibited significant anti-inflammatory activity being three-fold more effective than CMF2. FIGS. 6A-6F show blood cytokine levels in animals undergoing 5 days of an LPS challenge with treatment initiated on Day 1 prior to the initial LPS challenge. As expected, administration of the LPS unchallenged control resulted in no appreciable increase in any of the six cytokines assayed (see Group A in FIGS. 6A-6F). Similarly, administration of vehicle controls for CMF2 (see Group B in FIGS. 6A-6F) and FENF4 (see Group C in FIGS. 6A-6F) resulted, as expected, in significant increases of all cytokines measured. Likewise, administration of positive treatment control showed that dexamethasone significant reduced levels of all six cytokines assayed versus vehicle controls (p<0.001; see Group J in FIGS. 6A-6F). At the lower 30 mg/kg dose of fenofibrate, CMF2 exhibited marginal effects, with only IL-6 and IL-10 levels being lowered significantly versus its vehicle control (p<0.01; see Group E in FIGS. 6B & 6E); IL-1β, TNFα; MCP-1; and MCP-2 levels exhibited no statistically relevant lowering (see Group E in FIGS. 6A, 6C, 6D & 6F). At the higher 100 mg/kg dose of fenofibrate, CMF2 demonstrated significant lowering of all measured cytokines with IL-1β, IL-6, MCP-1, IL-10, and MCP-2 levels being reduced to a greater statistically significant level versus its vehicle control (p<0.001; see Group G in FIGS. 6A, 6B & 6D-6F) relative to TNFα (p<0.05; see Group G in FIG. 6C). FENF4 exhibited significant levels of reduction for all six cytokines assayed and the observed reduction was equivalent to both the higher 100 mg/kg dose of fenofibrate used in CMF2. For example, FENF4 demonstrated significant lowering of all measured cytokines with IL-1β, IL-6, MCP-1, IL-10, and MCP-2 levels being reduced to a greater statistically significant level versus its vehicle control (p<0.001; see Group I in FIGS. 6A, 6B & 6D-6F) relative to TNFα (p<0.01; see Group I in FIG. 6C). These results illustrate that a 30 mg/kg dose of fenofibrate formulated with lipids and with digestion enhancers (FENF4) achieved the same therapeutic potential for reducing systemic inflammation as the high 100 mg/kg dose of fenofibrate formulated in a non-lipid vehicle (CMF2).

FIGS. 7A-7F shows blood cytokine levels in animals undergoing 5 days of pre-treatment before initiation of an LPS challenge. As expected, administration of the LPS unchallenged control resulted in no appreciable increase in any of the six cytokines assayed (see Group A in FIGS. 7A-7F). Similarly, administration of vehicle controls for CMF2 (see Group B in FIGS. 7A-7F) and FENF4 (see Group C in FIGS. 7A-7F) resulted, as expected, in significant increases of all cytokines measured. Administration of positive treatment control showed that dexamethasone significant reduced levels of all six cytokines assayed versus vehicle controls (p<0.001; see Group J in FIGS. 7A-7F). At the lower 30 mg/kg dose of fenofibrate, CMF2 exhibited substantial effects, with IL-6, MCP-1, IL-10, and MCP-2 levels being reduced to a greater statistically significant level versus its vehicle control (p<0.001; see Group D in FIGS. 7B & 7D-7F) relative to IL-1β (p<0.01; see Group D in FIG. 7A) and TNFα (p<0.05; see Group D in FIG. 7C). At the higher 100 mg/kg dose of fenofibrate, CMF2 demonstrated significantly reduced levels of all six cytokines assayed versus vehicle controls (p<0.001; see Group F in FIGS. 7A-7F). As seen previously, a 30 mg/kg dose of fenofibrate formulated as FENF4 exhibited significant levels of reduction for all six cytokines assayed and the observed reduction was equivalent to both the higher 100 mg/kg dose of fenofibrate used in CMF2. Specifically, FENF4 demonstrated significantly reduced levels of all six cytokines assayed versus vehicle controls (p<0.001; see Group H in FIGS. 7A-7F).

Taken together, the FENF4 formulation of fenofibrate performed significantly better than the CMF2 formulation at the equivalent 30 mg/kg dose of fenofibrate and was equally as effective as the CMF2 formulation containing three times the amount of fenofibrate (100 mg/kg dose of CMF2). These results reveal that a 30 mg/kg dose of fenofibrate formulated with lipids and with digestion enhancers (FENF4) appeared to be three-fold more effective than non-lipid formulated CMF2 at inhibiting an inflammatory response. Interestingly, these results also indicate that the amount of anti-inflammatory activity achieved by FENF4 seemed enhanced with a 5-day pre-treatment dosing regimen versus dosing on the same day as LPS challenge commencement.

Analysis of brain cytokine levels in these experiments revealed that FENF4 exhibited significant anti-inflammatory activity, with such activity being entirely absent in CMF2. FIGS. 8A-8F shows brain cytokine levels in animals undergoing 5 days of an LPS challenge with treatment initiated on Day 1 prior to the initial LPS challenge. As expected, administration of the LPS unchallenged control resulted in no appreciable increase in any of the six cytokines assayed (see Group A in FIGS. 8A-8F). Similarly, administration of vehicle controls for CMF2 (see Group B in FIGS. 8A-8F) and FENF4 (see Group C in FIGS. 8A-8F) resulted, as expected, in significant increases of all cytokines measured. Administration of positive treatment control showed that dexamethasone significant reduced levels of all six cytokines assayed versus vehicle controls (p<0.001; see Group J in FIGS. 8A-8F). At both the lower 30 mg/kg dose of fenofibrate and higher 100 mg/kg dose of fenofibrate, CMF2 demonstrated no significant reduction in in any of the six cytokines assayed (see Group E and Group G in FIGS. 8A-8F). Only, a 30 mg/kg dose of fenofibrate formulated with lipids and with digestion enhancers (FENF4) exhibited significant levels of reduction for some of the cytokines assayed. Specifically, FENF4 demonstrated significant lowering of IL-1β levels versus its vehicle control (p<0.01; see Group I in FIG. 8A) as well as IL-6 and TNFα levels (p<0.05; see Group I in FIGS. 8B & 8C).

FIGS. 9A-9F shows brain cytokine levels in animals undergoing 5 days of pre-treatment before initiation of an LPS challenge. As expected, administration of the LPS unchallenged control resulted in no appreciable increase in any of the six cytokines assayed (see Group A in FIGS. 9A-9F). Similarly, administration of vehicle controls for CMF2 (see Group B in FIGS. 9A-9F) and FENF4 (see Group C in FIGS. 9A-9F) resulted, as expected, in significant increases of all cytokines measured. Likewise, administration of positive treatment control showed that dexamethasone significant reduced levels of all six cytokines assayed versus vehicle controls (p<0.001; see Group J in FIGS. 9A-9F). At both the lower 30 mg/kg dose of fenofibrate and higher 100 mg/kg dose of fenofibrate, CMF2 demonstrated no significant reduction in in any of the six cytokines assayed (see Group D and Group F in FIGS. 9A-9F). Only, a 30 mg/kg dose of fenofibrate formulated with lipids and with digestion enhancers (FENF4) exhibited significant levels of reduction for most of the cytokines assayed. Specifically, FENF4 demonstrated significant lowering of IL-1β, levels versus its vehicle control (p<0.001; see Group H in FIG. 9A), IL-6 and TNFα levels (p<0.01; see Group H in FIGS. 9B & 9C) as well as MCP-1 and IL-10 (p<0.01; see Group H in FIGS. 9D & 9E).

Taken together, the FENF4 formulation of fenofibrate performed significantly better than the CMF2 formulation at either dose. In fact, only FENF4 administration had any effect on cytokine levels in the brain compared to CMF2, suggesting that only FENF4 is effective at being able to reduce levels of brain related inflammation. Of note, levels of both MCP-1 and MCP-2 appeared more resistant to FENF4 administration relative to the other cytokines suggesting that monocytokine chemotaxis was not affected by FENF4 administration. Overall, FENF4 was effective at inhibiting the production of a wide range of cytokines in both the blood and the brain. In addition, both the broad anti-cytokine effect of FENF4 in the brain and the lack of chemotaxis effects, suggests that macrophage infiltration was not affected and that resident microglial cells could be the site of activity for FENF4 activity in the brain. As seen with blood cytokine levels, these brain results also indicate that the amount of anti-inflammatory activity achieved by FENF4 seemed enhanced with a 5-day pre-treatment dosing regimen versus dosing on the same day as LPS challenge commencement. This result suggests that prophylactic treatment with FENF4 could provide additional anti-inflammatory efficacy which will be considered in the design of clinical studies to follow.

To further extend the pharmacodynamic analysis of FENF4, experiments designed to ascertain the dose-response relationship of fenofibrate and the beneficial effect associated with this compound will be conducted. Additionally, the experiments described in this example can be repeated for other fibrates, such as, a bezafibrate, a ciprofibrate, a clinofibrate, a clofibrate, a clofibride, an etofibrate, a gemfibrozil, a nafenopin, a ronifibrate, a simfibrate.

Analysis of the percent level of IBA-1⁺ cells revealed that, regardless of the treatment protocol, FENF4 exhibited significant reduction of microglia activation in both hippocampal and cortical brain tissue, whereas CMF2 did not have any impact on the reduction of microglia activation. For example, FIG. 10A shows microglia activation in hippocampal brain tissue in animals undergoing 5 days of an LPS challenge with treatment initiated either on day one of the initial LPS challenge, or five days prior to the LPS challenge. As expected, administration of the LPS unchallenged control resulted in a no appreciable increase in the percent level of IBA-1⁺ cell indicating that hippocampal tissue did not undergo significant microglia activation (see Group A in FIG. 10A). In contrast, administration of vehicle controls for CMF2 (see Group B in FIG. 10A) and FENF4 (see Group C in FIG. 10A) to LPS challenged animals resulted, as expected, in significant increases in the percent level of IBA-1⁺ cell indicating that hippocampal tissue underwent significant microglia activation. Administration of positive treatment control to LPS challenged animals showed that dexamethasone significantly reduced the percent level of IBA-1⁺ cell indicating microglia activation versus vehicle controls (p<0.05; see Group J versus Groups B and C in FIG. 10A) indicating that dexamethasone significantly suppressed microglia activation in hippocampal tissue. At both the lower 30 mg/kg dose of fenofibrate and higher 100 mg/kg dose of fenofibrate, LPS challenged animals demonstrated no reduction in the percent level of IBA-1⁺ cell versus CMF2 vehicle controls (see Groups D, E, F and G versus B in FIG. 10A) indicating that CMF2 was ineffective at either dose in suppressing microglia activation in hippocampal tissue. In contrast, administration of the 30 mg/kg dose of fenofibrate formulated as FENF4 revealed that LPS challenged animals exhibited significant reduction in the percent level of IBA-1⁺ cell as compared to the FENF4 vehicle control (p<0.05; see Groups H and I versus Group C in FIG. 10A) indicating that FENF4 significantly suppressed microglia activation in hippocampal tissue. Additionally, FENF4 administration significant reduction in the percent level of IBA-1⁺ cells as compared to the 30 mg/kg of CMF2 administered for five consecutive days prior to the LPS challenge (p=0.01 for Group H or I versus Group E in FIG. 10A) or the 100 mg/kg of CMP2 administered by either dosing regimen (p=0.05 for Group H or I versus Group F or G in FIG. 10A). Overall, these results indicate that FENF4 significantly suppressed microglia activation in hippocampal tissue.

Referring to FIG. 10C, similar microglia activation results were observed in the analysis of cortical brain tissue. At both the lower 30 mg/kg dose of fenofibrate and higher 100 mg/kg dose of fenofibrate, LPS challenged animals demonstrated no reduction in the percent level of IBA-1⁺ cell versus CMF2 vehicle controls (see Groups D, E, F and G versus B in FIG. 10C) indicating that CMF2 was ineffective at either dose in suppressing microglia activation in cortical tissue. In contrast, administration of the 30 mg/kg dose of fenofibrate formulated as FENF4 revealed that LPS challenged animals exhibited significant reduction in the percent level of IBA-1⁺ cell as compared to the FENF4 vehicle control (see Groups H and I versus Group C in FIG. 10C). Furthermore, animals administered FENF4 five days prior to the LPS challenge demonstrated a more statistically significant reduction in microglia activation than animals administered FENF4 on Day 1 of the LPS challenge (see Group H versus Group I in FIG. 10C). Additionally, FENF4 administration significant reduction in the percent level of IBA-1⁺ cells as compared to either 30 mg/kg of CMF2 administered by either dosing regimen (p=0.01 for Group H or I versus Group D; p=0.05 for Group H or I versus Group E in FIG. 10C) or the 100 mg/kg of CMP2 administered by either dosing regimen (p=0.01 for Group H or I versus Group F; p=0.05 for Group H or I versus Group G in FIG. 10C). Overall, these results indicate that FENF4 significantly suppressed microglia activation in cortical tissue and are consistent with the findings that FENF4 suppressed microglia activation in hippocampal tissue.

Analysis of the percent level of CD68⁺ cells also revealed that, regardless of the treatment protocol, FENF4 e exhibited a significant reduction in microglia accumulation in both hippocampal and cortical brain tissue, whereas CMF2 did not have any impact on the reduction of microglia accumulation. For example, FIG. 10B shows microglia accumulation in hippocampal brain tissue in animals undergoing 5 days of an LPS challenge with treatment initiated either on day one of the initial LPS challenge or five days prior to the LPS challenge. As expected, administration of the LPS unchallenged control resulted in a no significant increase in the percent level of CD68⁺ cells indicating that hippocampal tissue did not undergo significant microglia accumulation (see Group A in FIG. 10B). In contrast, administration of vehicle controls for CMF2 (see Group B in FIG. 10B) and FENF4 (see Group C in FIG. 10B) to LPS challenged animals resulted, as expected, in significant increases in the percent level of CD68$^+$ cells indicating that hippocampal tissue underwent significant microglia accumulation. Administration of positive treatment control to LPS challenged animals showed that dexamethasone significantly reduced the percent level of CD68$^+$ cells indicating microglia accumulation versus vehicle controls (p<0.05; see Group J versus Groups B and C in FIG. 10B) indicating that dexamethasone significantly suppressed microglia accumulation in hippocampal tissue. At both the lower 30 mg/kg dose of fenofibrate and higher 100 mg/kg dose of fenofibrate, LPS challenged animals demonstrated no significant reduction in the percent level of CD68$^+$ cells versus CMF2 vehicle controls (see Groups D, E, F and G versus B in FIG. 10B) indicating that CMF2 was ineffective at either dose in suppressing microglia accumulation in hippocampal tissue. In contrast, administration of the 30 mg/kg dose of fenofibrate formulated as FENF4 revealed that LPS challenged animals exhibited significant reduction in the percent level of CD68$^+$ cells as compared to the FENF4 vehicle control (see Groups H and I versus Group C in FIG. 10B). Furthermore, animals administered FENF4 five days prior to the LPS challenge demonstrated a more statistically significant reduction in microglia accumulation than animals administered FENF4 on Day 1 of the LPS challenge (see Group H versus Group I in FIG. 10B). Additionally, FENF4 administration significant reduction in the percent level of CD68$^+$ cells as compared to either the 30 mg/kg or 100 mg/kg CMP2 administered only on the same day of the LPS challenge (p=0.01 for Group H or I versus Group D; p=0.05 for Group H or I versus Group G in FIG. 10B). Overall, these results indicate that FENF4 significantly suppressed microglia accumulation in hippocampal tissue and are consistent with the findings that FENF4 suppressed microglia activation in hippocampal tissue.

Referring to FIG. 10D, similar microglia accumulation results were observed for cortical brain tissue. At both the lower 30 mg/kg dose of fenofibrate and higher 100 mg/kg dose of fenofibrate, LPS challenged animals demonstrated no significant reduction in the percent level of CD68$^+$ cell versus CMF2 vehicle controls (see Groups D, E, F and G versus B in FIG. 10D) indicating that CMF2 was ineffective at either dose in suppressing microglia accumulation in cortical tissue. In contrast, administration of the 30 mg/kg dose of fenofibrate formulated as FENF4 revealed that LPS challenged animals exhibited significant reduction in the percent level of CD68$^+$ cell as compared to the FENF4 vehicle control (see Groups H and I versus Group C in FIG. 10D). Furthermore, animals administered FENF4 five days prior to the LPS challenge demonstrated a more statistically significant reduction in microglia accumulation than animals administered FENF4 on Day 1 of the LPS challenge (see Group H versus Group I in FIG. 10D). Additionally, FENF4 administration significant reduction in the percent level of CD68$^+$ cells as compared to either 30 mg/kg administered only on the same day of or for five consecutive days prior to the LPS challenge or 100 mg/kg CMP2 administered only on the same day of the LPS challenge (p=0.001 for Group H or I versus Group D or E; p=0.01 for Group H or I versus Group F in FIG. 10D). Overall, these results indicate that FENF4 significantly suppressed microglia accumulation in cortical tissue and are consistent with the findings that FENF4 suppressed microglia activation in cortical tissue.

Taken together, the FENF4 formulation of fenofibrate performed significantly better than the CMF2 formulation at either dose in terms of reducing both microglia activation and accumulation, as only FENF4 reduced microglia activation and accumulation in both hippocampal and cortical brain slices. These results are consistent with the cytokine analysis of FENF4 in brain tissue that also illustrate the anti-inflammatory properties of FENF4, that are not observed with CMF2. Comparable to the analysis of brain cytokine levels, these results associated with microglia activation and accumulation also indicate that the amount of anti-inflammatory activity achieved by FENF4 seemed enhanced with a 5-day pre-treatment dosing regimen versus treatment on day of the LPS challenge with FENF4. This result suggests that prophylactic treatment with FENF4 could provide additional anti-inflammatory efficacy which will be considered in the design of clinical studies to follow.

Overall, results from the present experiments demonstrate that lipid fenofibrate with digestion enhancers (FENF4) significantly increases the pharmacokinetic and pharmacodynamic profile of fenofibrate for the successful treatment of inflammation and neuroinflammation, compared to standard non-lipid based comparators (CMF2). Furthermore, the increased ability of FENF4 to deliver both fenofibric acid as well as fenofibrate to the brain, allows anti-inflammatory effects to be elicited that are mediated by PPARα, COX2 inhibition and CB2 activation, thereby increasing the ability of this lipid fenofibrate formulation to treat disorders of the CNS where the underlying pathological process is neuroinflammatory in nature.

Example 5 Cannabidiol Formulations

Pharmaceutical compositions comprising cannabidiol were formulated according to Tables 17 and 18 below. MAISINE™ CC, GELUCIRE® 43/01, the fatty acid component, and the surfactant component were combined and heated to 70° C. to produce a clear yellow solution. While maintaining the temperature at 70° C., cannabidiol was then added under constant stirring until a clear solution was produced. The resulting composition produced a clear yellow solution which was then allowed to cool to room temperature (18-20° C.) at which time stirring ceased and the composition was transferred to suitable containers where it solidified. The resulting solid composition remelted at 40° C. to give a clear yellow solution with no precipitate formation and again solidified on cooling.

TABLE 17

| | Cannabidiol Formulations | | | |
| Component | CBDF1 | CBDF2 | CBDF3 | CBDF4 |
| --- | --- | --- | --- | --- |
| MAISINE ™ CC | 220 mg (29.1%) | 214 mg (28.2%) | 300 mg (37.0%) | 6410 mg (65.7%) |
| GELUCIRE ® 43/01 | 220 mg (29.1%) | 214 mg (28.2%) | 300 mg (37.0%) | 3210 mg (32.8%) |
| Cholic Acid | 12 mg (1.6%) | — | — | 71.1 mg (0.7%) |
| Linoleic Acid | 105 mg (13.8%) | 120 mg (15.7%) | — | — |
| Sodium Stearate | — | 12 mg (1.6%) | — | — |
| Lecithin | — | — | 10 mg (1.2%) | — |

TABLE 17-continued

| | Cannabidiol Formulations | | | |
| --- | --- | --- | --- | --- |
| Component | CBDF1 | CBDF2 | CBDF3 | CBDF4 |
| α-pinene | — | — | — | 1 mg |
| limonene | — | — | — | 1 mg |
| β-pinene | — | — | — | 1 mg |
| Linalool | — | — | — | 3 mg |
| Cannabidiol | 200 mg (26.4%) | 200 mg (26.3%) | 200 mg (24.8%) | 71.0 mg (0.7%) |

TABLE 18

| | Cannabidiol Formulations | | |
| --- | --- | --- | --- |
| Component | CBDF5 | CBDF6 | CBDF7 |
| MAISINE ™ CC | — | 3500 mg (35.7%) | 6420 mg (65.1%) |
| GELUCIRE ® 43/01 | 3220 mg (32.8%) | 3500 mg (35.7%) | 3230 mg (32.7%) |
| Cholic Acid | 70.8 mg (0.7%) | 580.0 mg (5.9%) | 70.3 mg (0.7%) |
| Oleic Acid | 6420 mg (65.7%) | 2000 mg (20.4%) | — |
| Sodium Stearate | — | 140 mg (1.4%) | — |
| α-pinene | 1 mg | 1 mg | 1 mg |
| limonene | 1 mg | 1 mg | 1 mg |
| β-pinene | 1 mg | 1 mg | 1 mg |
| Linalool | 3 mg | 3 mg | 3 mg |
| Cholesterol | — | — | 71.1 mg (0.7%) |
| Cannabidiol | 70.9 mg (0.7%) | 70.6 (0.7%) | 70.8 mg (0.7%) |

Previous studies have shown that cannabidiol is soluble in a glycerolipid admixture of MAISINE™ CC and GELU-CIRE® 43/01. To assess whether the addition of one or more digestion enhancers to glycerolipid admixture comprising cannabidiol could improve the bioavailability of this therapeutic compound, the pharmacokinetics of these formulations will be assessed.

In one series of experiments, CBDF4, CBDF5, CBDF6, and CBDF7 were evaluated against Comparator Formulation 1 (CMF1) comprising a commercially relevant medium chain triglyceride (MCT) formulation. C57BL/6 male mice, each with an average weight of between 20 g to 25 g, were divided into four groups of six animals. Animals from each group were oral dosed by gavage as follows: Group 1 animals received a single dose of CBDF4 administered at 30 mg/kg; Group 2 animals received a single dose of CBDF5 administered at 30 mg/kg; Group 3 animals received a single dose of CBDF6 administered at 30 mg/kg; Group 4 animals received a single dose of CBDF7 administered at 30 mg/kg; and Group 5 animals received a single dose of CMF1 administered at 30 mg/kg. Samples of whole blood were taken just prior to administration, 0 h, and at the following 7 post-administration time points: 0.5 h, 1 h, 2 h, 4 h, 8 h, 12 h, and 24 h. Samples of brain were taken at 3 post-administration time points (n=3 per time point): 2 h, 4 h, and 24 h. Collected whole blood samples were processed by adding 200 μL of a Cannabidiol internal standard solution (100 μg/ml Cannabidiol-D$_3$ stock diluted down to 50 ng/ml with acetonitrile) and 20 μL of methanol to 20 μL of whole blood and precipitating blood proteins from this admixture using standard procedures and the resulting supernatants were stored for analysis. Collected brain samples were processed by homogenizing 1 g of brain in 1 mL of water, adding 200 μL of Cannabidiol internal standard solution and 5 μL of methanol to 50 μL aliquots of sample brain homogenate, centrifuging this admixture, and adding 100 μL water to 50 μL of the resulting supernatant which was then stored for analysis. Processed blood and brain supernatants were sent for bioanalysis, utilizing UHPLC-MS/MS with a reverse phase C$_{18}$ column (50×21 mm), 1.7 mm 50° C. with a mobile phase gradient between: 0.1% formic acid in water and 0.1% formic acid in acetonitrile, a flow rate of 0.4 mL/min and injection volume 5 μL.

Figure 11A:
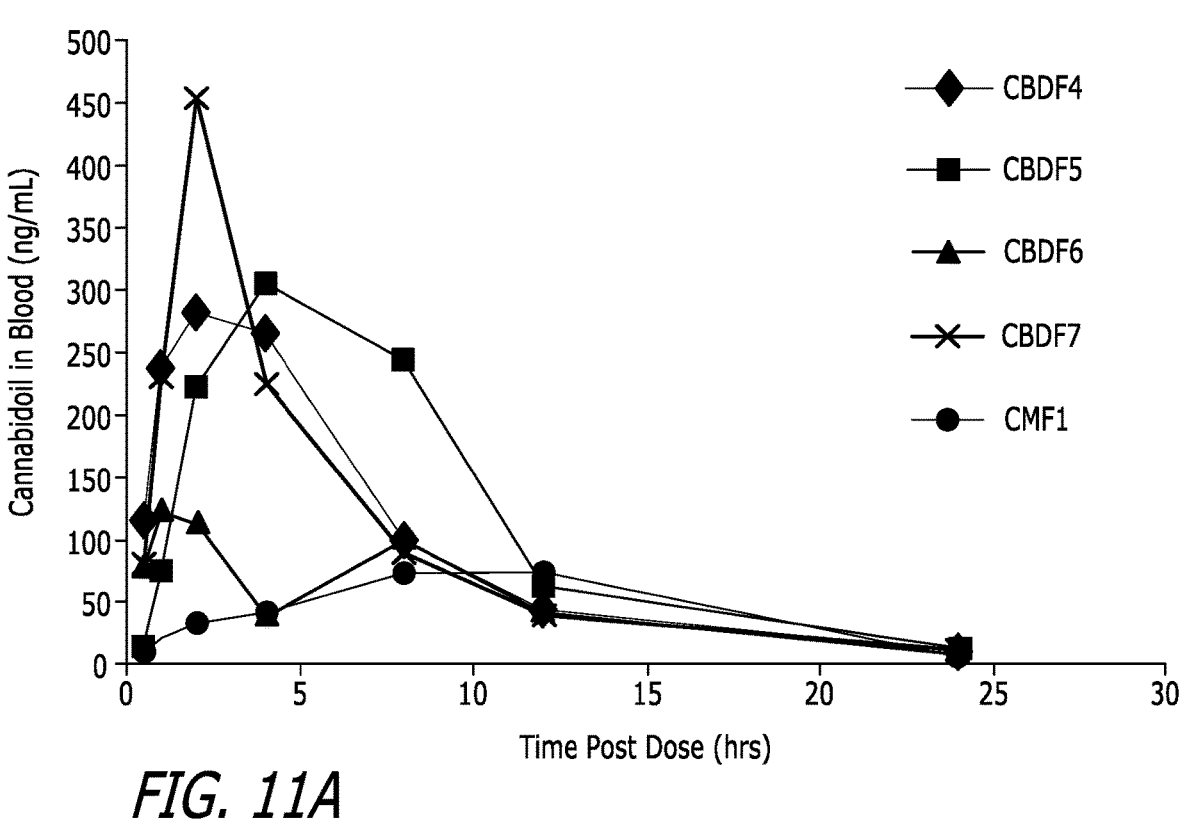
FIGS. 11A-11B show representative UHPLC tracings of cannabidiol levels in blood and brain with FIG. 11A shows a UHPLC tracing of cannabidiol levels in blood after oral administration of 30 mg/kg of disclosed pharmaceutical compositions comprising cannabidiol.

As shown in FIG. 11A and Table 19, CBDF4, CBDF5, and CBDF7, cannabidiol formulated with lipids and with digestion enhancers, exhibited superior pharmacokinetic properties for cannabidiol in blood relative to CMF1. In comparison to CMF1 (non-lipid comparator formulation: 1) CBDF4 demonstrated substantially higher absorption levels of cannabidiol in blood as indicated by a Cmax that was about 3.9 times greater versus CMF1, with lower clearance over time as indicated by an AUC that was 2 times higher versus CMF1; 2) CBDF5 demonstrated substantially higher absorption levels of cannabidiol in blood as indicated by a Cmax that was about 4.2 times greater versus CMF1, with lower clearance over time as indicated by an AUC that was about 2.6 times higher versus CMF1; and 3) CBDF7 demonstrated substantially higher absorption levels of cannabidiol in blood as indicated by a Cmax that was over 4.2 times greater versus CMF1, with lower clearance over time as indicated by an AUC that was about 1.4 times higher versus CMF1. Although CBDF6 exhibited only a higher absorption level of cannabidiol in blood relative to CMF1 as indicated by a Cmax that was about 1.7 times greater versus CMF1, this formulation demonstrated a faster clearance rate as indicated by an AUC that was lower versus CMF1. Interestingly, CBDF4, CBDF5, CBDF6, and CBDF7 each exhibited a significantly reduced absorbance rate compared to CMF1, showing Tmax values of between 1.0 hr and 4.0 hr, which was at least a third of the Tmax value of 12.0 hrs observed for CMF1. Overall, CBDF4, CBDF5, and CBDF7 demonstrated significant pharmacokinetic improvements compared to the comparator formulation CMF1.

TABLE 19

| | Mean Pharmacokinetics Parameter of Blood Cannabidiol by Formulation | | | | |
|---|---|---|---|---|---|
| Parameter | CBDF4 | CBDF5 | CBDF6 | CBDF7 | CMF1 |
| T½ (hr) | 5.2 | 4.2 | nr | 4.1 | nr |
| Tmax (hr) | 2.0 | 4.0 | 1.0 | 2.0 | 12.0 |
| Cmax (ng/mL) | 281.9 | 305.6 | 122.4 | 310.2 | 73.0 |
| AUClast (hr*ng/mL) | 2245.4 | 2866.6 | 911.4 | 1538.8 | 1103.3 |
| AUCinf (hr*ng/mL) | 2326.8 | 2949.4 | nr | 1776.4 | nr |

Figure 11B:
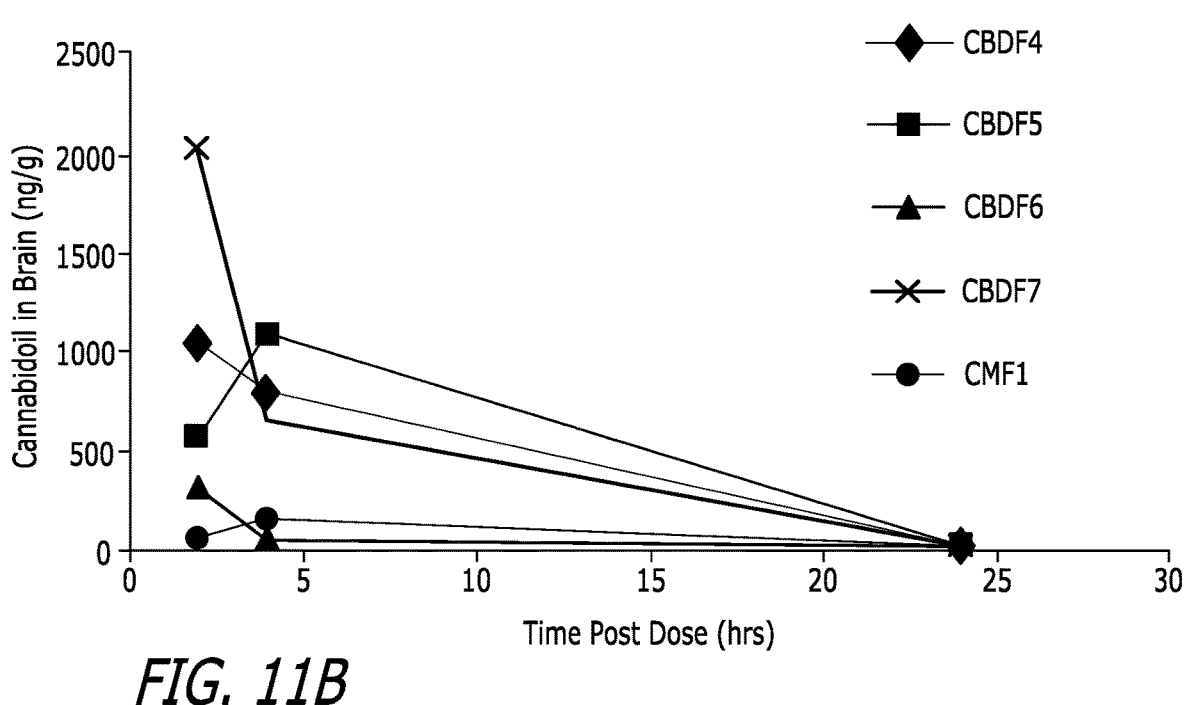

As shown in FIG. 11B and Table 20, CBDF4, CBDF5, and CBDF7 substantially increased the absorption rate of cannabidiol in brain over CMF1. In comparison to CMF1: 1) CBDF4 demonstrated substantially higher absorption levels of cannabidiol in blood as indicated by a Cmax that was about 6.9 times greater versus CMF1, with lower clearance over time as shown by a higher AUC versus CMF1 (see FIG. 11B); 2) CBDF5 demonstrated substantially higher absorption levels of cannabidiol in blood as indicated by a Cmax that was about 7.2 times greater versus CMF1, with lower clearance over time as shown by a higher AUC versus CMF1 (see FIG. 11B); and 3) CBDF7 demonstrated substantially higher absorption levels of cannabidiol in blood as indicated by a Cmax that was about 9.4 times greater versus CMF1, with lower clearance over time as shown by a higher AUC versus CMF1 (see FIG. 11B). Although CBDF6 exhibited only a higher absorption level of cannabidiol in blood relative to CMF1 as indicated by a Cmax that was about 2.1 times greater versus CMF1, this formulation demonstrated a faster clearance rate as shown by a higher AUC versus CMF1 (see FIG. 11B). Interestingly, formulations CBDF4, CBDF5, and CBDF7 all had significantly greater amounts cannabidiol in the brain as well as substantially higher brain to blood ratios that CMF1, indicating the cannabidiol is being preferentially delivered to the brain with these formulations (see Table 20).

codynamic analysis will include experiments design to determine the efficacy of cannabidiol using an inflammatory model such as the LPS induced cytokine release model, designed to mimic an indication or disease state for which this therapeutic compound is being used to alleviate. Initial experiments will ascertain whether a beneficial effect is obtained from a formulation comprising cannabidiol, followed by experiments designed to ascertain the dose-response relationship of cannabidiol and the beneficial effect associated with this compound.

Example 6 Abiraterone Formulation

As a preliminary assessment, experiments were performed to assess whether abiraterone could be formulated in the absence of cholic acid. On one series of experiments, 1 g of MAISINE™ CC was heated to 60° C., and 250 mg abiraterone was then added and stirred for at least 60 minutes. However, undissolved abiraterone particles remained clearly visible at all times indicating that this compound failed to completely dissolve in the heated liquid fat. To understand if additional lipid could affect solubility of abiraterone, GELUCIRE® 43/01 was added in a stepwise fashion of 0.5 g until the total amount reached 2 g. The mixture was maintaining at 60° C. for the entire experiment and for each addition of GELUCIRE® 43/01, the mixture was stirred for at least 60 minutes before the next addition of GELUCIRE® 43/01 was added. However, abiraterone crystals still remained clearly visible. These results show that abiraterone remained insoluble in formulations containing only MAISINE™ CC and MAISINE™ CC/GELUCIRE® 43/01 in ratios of 2:1 to 1:2.

TABLE 20

| | Cannabidiol Blood and Brain Ratios of Mean Cmax by Formulation | | | | |
|---|---|---|---|---|---|
| Sample | CBD4 | CBD5 | CBD6 | CBD7 | CMF1 |
| Blood | 281.9 ng/mL | 305.6 ng/mL | 122.4 ng/mL | 310.2 ng/mL | 73.0 ng/mL |
| Brain | 1049.5 ng/g | 1098.6 ng/g | 321.3 ng/g | 1435.0 ng/g | 152.7 ng/g |
| Brain:Blood Ratio | 3.7 | 3.6 | 2.6 | 4.6 | 2.1 |

Taken together, these results show that CBDF4, CBDF5, and CBDF7 exhibited significantly improved pharmacokinetic properties over CMF1, while CBDF6 underperformed. Compared to all other formulations, CBDF4 and CBDF5 demonstrated the best overall balance of pharmacokinetic parameters having both low T½ and Tmax values and high Cmax and AUC values, illustrating these formulation reaches maximum concentration in the shortest amount of time with the greatest amount of drug exposure over time. Overall, this data supports the proposition that the inclusion of digestion enhancers increases the extent and speed of absorption of drug, in both blood and brain, over a non-lipid based comparator formulation of cannabidiol.

To assess whether the addition of one or more digestion enhancers to glycerolipid admixture comprising cannabidiol could improve the efficacy of this therapeutic compound, pharmacodynamic experiments will be conducted. Pharma- To assess whether the addition of one or more digestion enhancers could improve the solubility of abiraterone when combined with glycerolipid components, a pharmaceutical composition comprising abiraterone was formulated according to Table 21 below. MAISINE™ CC, the fatty acid component, and the surfactant component were combined and heated to 60° C. to produce a clear yellow solution. While maintaining the temperature at 60° C., abiraterone was then added to this admixture under constant stirring until a clear solution was produced. GELUCIRE® 43/01 was added in a stepwise fashion until the final amount was reached. The resulting composition produced a clear yellow solution which was then allowed to cool to room temperature (18-20° C.) at which time stirring ceased and the composition was transferred to suitable containers where it solidified. The resulting solid composition remelted at 40° C. to give a clear yellow solution with no precipitate formation and again solidified on cooling.

TABLE 21

| Abiraterone Formulation | |
|---|---|
| Component | ABRF1 |
| MAISINE ™ CC | 443 mg (35.4%) |
| GELUCIRE ® 43/01 | 443 mg (35.4%) |
| Oleic Acid | 24 mg (1.9%) |
| Sodium Stearate | 16 mg (1.3%) |
| Cholic Acid | 74 mg (6.0%) |
| Abiraterone | 250 mg (20.0%) |

To assess whether the addition of one or more digestion enhancers to glycerolipid admixture comprising abiraterone could improve the bioavailability of abiraterone, the pharmacokinetics of these formulations will be assessed in a manner similar to the pharmacokinetic analysis described in Example 3 for curcumin, Example 4 for fenofibrate, or Example 5 for cannabidiol. Pharmacokinetic analysis will include experiments designed to determine the amount of abiraterone administer (dose), the peak concentration of abiraterone achieved after administration (Cmax), the time it takes abiraterone to reach its Cmax (Tmax), the time required for the concentration of abiraterone to reach half its Cmax (T½), the integral of the concentration-time curve between from time zero to the time of last quantifiable measurement taken during the experiments (AUClast), and the integral of the concentration-time curve from time zero to infinity (AUCinf).

To assess whether the addition of one or more digestion enhancers to glycerolipid admixture comprising abiraterone could improve the efficacy of this therapeutic compound, pharmacodynamic experiments will be conducted. Pharmacodynamic analysis will include experiments design to determine the efficacy of abiraterone using an appropriate animal model system such as a testicular cancer xenograft model designed to mimic an indication or disease state for which this therapeutic compound is being used to alleviate. Initial experiments will ascertain whether a beneficial effect is obtained from a formulation comprising abiraterone, followed by experiments designed to ascertain the dose-response relationship of abiraterone and the beneficial effect associated with this compound.

Example 7 Auranofin Formulation

As a preliminary assessment, experiments were performed to assess whether auranofin could be formulated in the absence of cholic acid. On one series of experiments, 500 mg of MAISINE™ CC was heated to 60° C., and 20 mg auranofin was then added and stirred for at least 60 minutes. However, undissolved auranofin particles remained clearly visible at all times indicating that this compound failed to completely dissolve in the heated liquid fat. To understand if additional lipid could affect solubility of abiraterone, GELUCIRE® 43/01 was added in a stepwise fashion of 125 mg until the total amount reached 500 mg. The mixture was maintaining at 60° C. for the entire experiment and for each addition of GELUCIRE® 43/01, the mixture was stirred for at least 60 minutes before the next addition of GELUCIRE® 43/01 was added. However, auranofin crystals still remained clearly visible. These results show that auranofin remained insoluble in formulations containing only MAISINE™ CC and MAISINE™ CC/GELUCIRE®43/01 in ratios of 2:1 to 1:2.

To assess whether the addition of one or more digestion enhancers could improve the solubility of auranofin when combined with glycerolipid components, a pharmaceutical composition comprising auranofin was formulated according to Table 22 below. MAISINE™ CC, the fatty acid component and the surfactant component were combined and heated to 130° C. to produce a clear yellow solution. While maintaining the temperature at 70° C., auranofin was then added to this admixture under constant stirring until a clear solution was produced. GELUCIRE® 43/01 was added in a stepwise fashion until the final amount was reached. The resulting composition produced a clear yellow solution which was then allowed to cool to room temperature (18-20° C.) at which time stirring ceased and the composition was transferred to suitable containers where it solidified. The resulting solid composition remelted at 40° C. to give a clear yellow solution with no precipitate formation and again solidified on cooling.

TABLE 22

| Auranofin Formulation | | | | |
|---|---|---|---|---|
| Component | AURF1 | AURF2 | AURF3 | AURF4 |
| MAISINE ™ CC | 443 mg (43.9%) | 1.5 g (37.1%) | 400 mg (47.62%) | — |
| GELUCIRE ® 43/01 | 443 mg (43.9%) | 2 g (49.5%) | 400 mg (47.62%) | 400 mg (47.62%) |
| Oleic Acid | 24 mg (2.4%) | 0.5 g (12.4%) | — | 400 mg (47.62%) |
| Sodium Stearate | 16 mg (1.5%) | — | — | — |
| Cholic Acid | 74 mg (7.3%) | — | 30 mg (3.57%) | 30 mg (3.57%) |
| Auranofin | 10 mg (1.0%) | 0.04 g (1.0%) | 10 mg (1.19%) | 10 mg (1.19%) |

To assess whether the addition of one or more digestion enhancers to glycerolipid admixture comprising auranofin could improve the bioavailability of auranofin, the pharmacokinetics of these formulations will be assessed in a manner similar to the pharmacokinetic analysis described in Example 3 for curcumin, Example 4 for fenofibrate, or Example 5 for cannabidiol. Pharmacokinetic analysis will include experiments designed to determine the amount of auranofin administer (dose), the peak concentration of auranofin achieved after administration (Cmax), the time it takes auranofin to reach its Cmax (Tmax), the time required for the concentration of auranofin to reach half its Cmax (T½), the integral of the concentration-time curve between from time zero to the time of last quantifiable measurement taken during the experiments (AUClast), and the integral of the concentration-time curve from time zero to infinity (AUCinf).

To assess whether the addition of one or more digestion enhancers to glycerolipid admixture comprising auranofin could improve the efficacy of this therapeutic compound, pharmacodynamic experiments will be conducted. Pharmacodynamic analysis will include experiments design to determine the efficacy of auranofin using an appropriate animal model system such as a hepatocellular carcinoma Hep3B xenograft cancer model designed to mimic an indication or disease state for which this therapeutic compound is being used to alleviate. Initial experiments will ascertain whether a beneficial effect is obtained from a formulation comprising auranofin, followed by experiments designed to ascertain the dose-response relationship of auranofin and the beneficial effect associated with this compound.

Example 8 Ibuprofen Formulation

As a preliminary assessment, experiments were performed to assess whether ibuprofen could be formulated in the absence of cholic acid. In one series of experiments, 20 g of MAISINE™ CC was heated to 100° C., and 3.925 g ibuprofen free and 0.56 g ibuprofen sodium were then added and stirred for at least 60 minutes. However, undissolved ibuprofen particles remained clearly visible at all times indicating that this compound failed to completely dissolve in the heated liquid fat. To understand if an additional lipid could affect solubility of ibuprofen, GELUCIRE® 43/01 was added in a stepwise fashion of 5 g until the total amount reached 20 g. The mixture was maintaining at 100° C. for the entire experiment and for each addition of GELUCIRE® 43/01, the mixture was stirred for at least 60 minutes before the next addition of GELUCIRE® 43/01 was added. However, ibuprofen particles still remained clearly visible. These results show that ibuprofen remained insoluble in formulations containing only MAISINE™ CC and MAISINE™ CC/GELUCIRE® 43/01 in ratios of 4:1 to 1:1.

To assess whether the addition of one or more digestion enhancers could improve the solubility of ibuprofen when combined with glycerolipid components, pharmaceutical composition comprising ibuprofen was formulated according to Table 23 below. MAISINE™ CC, and the fatty acid component or the surfactant component were combined and heated to 100° C. to produce a clear yellow solution. While maintaining the temperature at 100° C., ibuprofen was then added to this heated admixture under constant stirring until a clear solution was produced. GELUCIRE® 43/01 was added in a stepwise fashion of 5 g until the final amount was reached. The resulting composition produced a clear yellow solution which was then allowed to cool to room temperature (18-20° C.) at which time stirring ceased and the composition was transferred to suitable containers where it solidified. The resulting solid composition remelted at 50° C. to give a clear yellow solution with no precipitate formation and again solidified on cooling.

TABLE 23

| Ibuprofen Formulation | | |
| --- | --- | --- |
| Component | IBUF1 | IBUF2 |
| MAISINE ™ CC | 1,300 mg (15.3%) | 20.0 g (44.7%) |
| GELUCIRE ® 43/01 | 2,700 mg (31.8%) | 20.0 g (44.7%) |
| Oleic Acid | — | 0.28 g (0.6%) |
| Sodium Stearate | 500 mg (5.9%) | — |
| Ibuprofen (free) | 4,000 mg (47.0%) | 3.93 g (8.8%) |
| Ibuprofen sodium | — | 0.56 g (1.2%) |

To assess whether the addition of one or more digestion enhancers to glycerolipid admixture comprising ibuprofen could improve the bioavailability of ibuprofen, the pharmacokinetics of these formulations will be assessed in a manner similar to the pharmacokinetic analysis described in Example 3 for curcumin, Example 4 for fenofibrate, or Example 5 for cannabidiol. Pharmacokinetic analysis will include experiments designed to determine the amount of ibuprofen administer (dose), the peak concentration of ibuprofen achieved after administration (Cmax), the time it takes ibuprofen to reach its Cmax (Tmax), the time required for the concentration of ibuprofen to reach half its Cmax (T½), the integral of the concentration-time curve between from time zero to the time of last quantifiable measurement taken during the experiments (AUClast), and the integral of the concentration-time curve from time zero to infinity (AUCinf).

To assess whether the addition of one or more digestion enhancers to glycerolipid admixture comprising ibuprofen could improve the efficacy of this therapeutic compound, pharmacodynamic experiments will be conducted. Pharmacodynamic analysis will include experiments design to determine the efficacy of ibuprofen using a LPS challenge assay in a manner similar to the pharmacodynamic analysis described in Example 4 for fenofibrate. Initial experiments will ascertain whether a beneficial effect is obtained from a formulation comprising ibuprofen, followed by experiments designed to ascertain the dose-response relationship of ibuprofen and the beneficial effect associated with this compound.

Example 9 Midastaurin Formulation

As a preliminary assessment, experiments were performed to assess whether midastaurin could be formulated in the absence of cholic acid. On one series of experiments, 1 g of MAISINE™ CC was heated to 60° C., and 50 mg midastaurin was then added and stirred for at least 60 minutes. However, undissolved midastaurin particles remained clearly visible at all times indicating that this compound failed to completely dissolve in the heated liquid fat. To understand if additional lipid could affect solubility of midastaurin, GELUCIRE® 43/01 was added in a stepwise fashion of 0.5 g until the total amount reached 2 g. The mixture was maintaining at 60° C. for the entire experiment and for each addition of GELUCIRE® 43/01, the mixture was stirred for at least 60 minutes before the next addition of GELUCIRE® 43/01 was added. However, midastaurin crystals still remained clearly visible. These results show that midastaurin remained insoluble in formulations containing only MAISINE™ CC and MAISINE™ CC/GELUCIRE® 43/01 in ratios of 2:1 to 1:2.

To assess whether the addition of one or more digestion enhancers could improve the solubility of midastaurin when combined with glycerolipid components, a pharmaceutical composition comprising midastaurin was formulated according to Table 24 below. MAISINE™ CC, the fatty acid component, and the surfactant component were combined and heated to 60° C. to produce a clear yellow solution. While maintaining the temperature at 60° C., midastaurin was then added to this admixture under constant stirring until a clear solution was produced. GELUCIRE® 43/01 was added in a stepwise fashion until the final amount was reached. The resulting composition produced a clear yellow solution which was then allowed to cool to room temperature (18-20° C.) at which time stirring ceased and the composition was transferred to suitable containers where it solidified. The resulting solid composition remelted at 40° C. to give a clear yellow solution with no precipitate formation and again solidified on cooling.

TABLE 24

| Component | MIDF1 | MIDF2 | MIDF3 | MIDF4 | MIDF5 |
|---|---|---|---|---|---|
| | | | Midastaurin Formulation | | |
| MAISINE ™ CC | 0.3 g (33.0%) | 0.25 g (32.5%) | 0.4 g (44.4%) | — | 0.4 g (47.1%) |
| GELUCIRE ® 43/01 | 0.3 g (33.0%) | 0.3 g (39.0%) | 0.4 g (44.4%) | 0.4 g (44.4%) | 0.4 g (47.1%) |
| Oleic Acid | 0.2 g (21.9%) | 0.1 g (12.9%) | — | 0.4 g (44.4%) | — |
| Sodium Stearate | — | 10 mg (1.3%) | — | — | — |
| Cholic Acid | 0.06 g (6.6%) | 0.06 g (7.8%) | 0.05 g (5.6%) | 0.05 g (5.6%) | — |
| Midostaurin | 0.05 g (5.5%) | 0.05 g (6.5%) | 0.05 g (5.6%) | 0.05 g (5.6%) | 0.05 g (5.9%) |

To assess whether the addition of one or more digestion enhancers to glycerolipid admixture comprising midostaurin could improve the bioavailability of midostaurin, the pharmacokinetics of these formulations will be assessed in a manner similar to the pharmacokinetic analysis described in Example 3 for curcumin, Example 4 for fenofibrate, or Example 5 for cannabidiol. Pharmacokinetic analysis will include experiments designed to determine the amount of midostaurin administer (dose), the peak concentration of midostaurin achieved after administration (Cmax), the time it takes midostaurin to reach its Cmax (Tmax), the time required for the concentration of midostaurin to reach half its Cmax (T½), the integral of the concentration-time curve between from time zero to the time of last quantifiable measurement taken during the experiments (AUClast), and the integral of the concentration-time curve from time zero to infinity (AUCinf).

To assess whether the addition of one or more digestion enhancers to glycerolipid admixture comprising midostaurin could improve the efficacy of this therapeutic compound, pharmacodynamic experiments will be conducted. Pharmacodynamic analysis will include experiments design to determine the efficacy of midostaurin using an appropriate animal model system such as the leukemia MV4-11 xenograft cancer model, designed to mimic an indication or disease state for which this therapeutic compound is being used to alleviate. Initial experiments will ascertain whether a beneficial effect is obtained from a formulation comprising midostaurin, followed by experiments designed to ascertain the dose-response relationship of midostaurin and the beneficial effect associated with this compound.

Example 10 Pirfenidone Formulation

As a preliminary assessment, experiments were performed to assess whether pirfenidone could be formulated in the absence of cholic acid. On one series of experiments, 1 g of MAISINE™ CC was heated to 60° C., and 200 mg pirfenidone was then added and stirred for at least 60 minutes. However, undissolved pirfenidone particles remained clearly visible at all times indicating that this compound failed to completely dissolve in the heated liquid fat. To understand if additional lipid could affect solubility of pirfenidone, GELUCIRE® 43/01 was added in a stepwise fashion of 0.5 g until the total amount reached 2 g. The mixture was maintaining at 60° C. for the entire experiment and for each addition of GELUCIRE® 43/01, the mixture was stirred for at least 60 minutes before the next addition of GELUCIRE® 43/01 was added. However, pirfenidone crystals still remained clearly visible. These results show that pirfenidone remained insoluble in formulations containing only MAISINE™ CC and MAISINE™ CC/GELU-CIRE® 43/01 in ratios of 2:1 to 1:2.

To assess whether the addition of one or more digestion enhancers could improve the solubility of pirfenidone when combined with glycerolipid components, a pharmaceutical composition comprising pirfenidone was formulated according to Table 25 below. MAISINE™ CC, the fatty acid component, and the surfactant component were combined and heated to 60° C. to produce a clear yellow solution. While maintaining the temperature at 60° C., pirfenidone was then added to this admixture under constant stirring until a clear solution was produced. GELUCIRE® 43/01 was added in a stepwise fashion until the final amount was reached. The resulting composition produced a clear yellow solution which was then allowed to cool to room temperature (18-20° C.) at which time stirring ceased and the composition was transferred to suitable containers where it solidified. The resulting solid composition remelted at 40° C. to give a clear yellow solution with no precipitate formation and again solidified on cooling.

TABLE 25

| Component | PIRF1 |
|---|---|
| | Pirfenidone Formulation |
| MAISINE ™ CC | 443 mg (36.9%) |
| GELUCIRE ® 43/01 | 443 mg (36.9%) |
| Oleic Acid | 24 mg (2.0%) |
| Sodium Stearate | 16 mg (1.3%) |
| Cholic Acid | 74 mg (6.2%) |
| Pirfenidone | 200 mg (16.7%) |

To assess whether the addition of one or more digestion enhancers to glycerolipid admixture comprising pirfenidone could improve the bioavailability of pirfenidone, the pharmacokinetics of these formulations will be assessed in a manner similar to the pharmacokinetic analysis described in Example 3 for curcumin, Example 4 for fenofibrate, or Example 5 for cannabidiol. Pharmacokinetic analysis will include experiments designed to determine the amount of pirfenidone administer (dose), the peak concentration of pirfenidone achieved after administration (Cmax), the time it takes pirfenidone to reach its Cmax (Tmax), the time required for the concentration of pirfenidone to reach half its Cmax (T½), the integral of the concentration-time curve between from time zero to the time of last quantifiable measurement taken during the experiments (AUClast), and the integral of the concentration-time curve from time zero to infinity (AUCinf).

To assess whether the addition of one or more digestion enhancers to glycerolipid admixture comprising pirfenidone could improve the efficacy of this therapeutic compound, pharmacodynamic experiments will be conducted. Pharmacodynamic analysis will include experiments design to determine the efficacy of pirfenidone using an appropriate animal model system such as the murine bleomycin induced pulmonary fibrosis model, designed to mimic an indication or disease state for which this therapeutic compound is being used to alleviate. Initial experiments will ascertain whether a beneficial effect is obtained from a formulation comprising pirfenidone, followed by experiments designed to ascertain the dose-response relationship of pirfenidone and the beneficial effect associated with this compound.

Example 11 Pitolosant Formulation

As a preliminary assessment, experiments were performed to assess whether pitolosant could be formulated in the absence of cholic acid. On one series of experiments, 500 mg of MAISINE™ CC was heated to 60° C., and 20 mg pitolosant was then added and stirred for at least 60 minutes. However, undissolved pitolosant particles remained clearly visible at all times indicating that this compound failed to completely dissolve in the heated liquid fat. To understand if additional lipid could affect solubility of abiraterone, GELUCIRE® 43/01 was added in a stepwise fashion of 125 mg until the total amount reached 500 mg. The mixture was maintaining at 60° C. for the entire experiment and for each addition of GELUCIRE® 43/01, the mixture was stirred for at least 60 minutes before the next addition of GELUCIRE® 43/01 was added. However, pitolosant crystals still remained clearly visible. These results show that pitolosant remained insoluble in formulations containing only MAISINE™ CC and MAISINE™ CC/GELUCIRE®43/01 in ratios of 2:1 to 1:2.

To assess whether the addition of one or more digestion enhancers could improve the solubility of pitolosant when combined with glycerolipid components, a pharmaceutical composition comprising pitolosant was formulated according to Table 26 below. The fatty acid component and the surfactant component were combined and heated to 130° C. to produce a clear yellow solution. While maintaining the temperature at 70° C., pitolosant was then added to this admixture under constant stirring until a clear solution was produced. GELUCIRE® 43/01 was added in a stepwise fashion until the final amount was reached. The resulting composition produced a clear yellow solution which was then allowed to cool to room temperature (18-20° C.) at which time stirring ceased and the composition was transferred to suitable containers where it solidified. The resulting solid composition remelted at 40° C. to give a clear yellow solution with no precipitate formation and again solidified on cooling.

include experiments designed to determine the amount of pitolosant administer (dose), the peak concentration of pitolosant achieved after administration (Cmax), the time it takes pitolosant to reach its Cmax (Tmax), the time required for the concentration of pitolosant to reach half its Cmax (T½), the integral of the concentration-time curve between from time zero to the time of last quantifiable measurement taken during the experiments (AUClast), and the integral of the concentration-time curve from time zero to infinity (AUCinf).

To assess whether the addition of one or more digestion enhancers to glycerolipid admixture comprising pitolosant could improve the efficacy of this therapeutic compound, pharmacodynamic experiments will be conducted. Pharmacodynamic analysis will include experiments design to determine the efficacy of pitolosant using an appropriate animal model system such as the orexin knock out model of narcolepsy, designed to mimic an indication or disease state for which this therapeutic compound is being used to alleviate. Initial experiments will ascertain whether a beneficial effect is obtained from a formulation comprising pitolosant, followed by experiments designed to ascertain the dose-response relationship of pitolosant and the beneficial effect associated with this compound.

Example 12 Naproxen Formulation

As a preliminary assessment, experiments were performed to assess whether Naproxen could be formulated in the absence of cholic acid. On one series of experiments, 16.5 g of MAISINE™ CC was heated to 130° C., and 6.485 g naproxen sodium was then added and stirred for at least 60 minutes. However, undissolved Naproxen particles remained clearly visible at all times indicating that this compound failed to completely dissolve in the heated liquid fat. To understand if an additional lipid could affect solubility of Naproxen, GELUCIRE® 43/01 was added in a stepwise fashion of 4.125 g until the total amount reached 16.5 g. The mixture was maintaining at 130° C. for the entire experiment and for each addition of GELUCIRE® 43/01, the mixture was stirred for at least 60 minutes before the next addition of GELUCIRE® 43/01 was added. However, Naproxen particles still remained clearly visible. These results show that Naproxen remained insoluble in formulations containing only MAISINE™ CC and MAISINE™ CC/GELUCIRE® 43/01 in ratios of 4:1 to 1:1.

TABLE 26

| | Pitolosant Formulation | | | |
|---|---|---|---|---|
| Component | PITF1 | PITF1 | PITF1 | PITF1 |
| MAISINE ™ CC | — | 400 mg (44.4%) | 270 mg (31.8%) | 400 mg (48.8%) |
| GELUCIRE ® 43/01 | 500 mg (48.1%) | 400 mg (44.4%) | 270 mg (31.8%) | 400 mg (48.8%) |
| Oleic Acid | 500 mg (48.1%) | — | 270 mg (31.8%) | — |
| Sodium Stearate | — | — | — | — |
| Cholic Acid | 20 mg (1.9%) | 20 mg (5.6%) | 20 mg (2.4%) | — |
| Pitolosant | 20 mg (1.9%) | 20 mg (5.6%) | 20 mg (2.4%) | 20 mg (2.4%) |

To assess whether the addition of one or more digestion enhancers to glycerolipid admixture comprising pitolosant could improve the bioavailability of pitolosant, the pharmacokinetics of these formulations will be assessed in a manner similar to the pharmacokinetic analysis described in Example 3 for curcumin, Example 4 for fenofibrate, or Example 5 for cannabidiol. Pharmacokinetic analysis will As the above experiments illustrate, certain therapeutic compounds comprising an amine functional group that are extremely insoluble not only in water but also lipids despite the fact that these compounds have a high Log P value. When developing a lipid-based formulation which enhanced the solubility of naproxen, it was discovered that a certain process is required when formulating a pharmaceutical composition comprising such amine compounds. For example, one series of experiments when 393 mg of naproxen sodium was added to 500 mg of a liquid fat (MAISINE CC) and 1,000 mg of a hard fat (GELUCIRE® 43/01) heated to about 130° C., the naproxen sodium failed to incorporate into the heated glycerolipid mixture. Similarly, in a second series of experiments, when 393 mg of naproxen was added to 500 mg of a liquid fat (MAISINE CC) and 1,000 mg of a hard fat (GELUCIRE® 43/01) heated to about 130° C., the naproxen failed to incorporate into the heated glycerolipid mixture. In a third series of experiments, 450 mg of naproxen and 450 mg of naproxen sodium were added to 1,750 mg of a liquid fat (MAISINE CC) and 1,750 mg of a hard fat (GELUCIRE® 43/01) heated to about 130° C. to give a clear solution indicative of incorporation. This is a surprising result as both naproxen and naproxen sodium alone were insoluble in the heated glycerolipid admixture. Similarly, in a fourth series of experiments, 393 mg of naproxen sodium and 420 mg of oleic acid were added to 1,000 mg of a liquid fat (MAISINE CC) and 400 mg of a hard fat (GELUCIRE® 43/01) heated to about 130° C. to give a clear solution indicative of incorporation. Likewise, in a fifth series of experiments, 800 mg of naproxen and 500 mg of sodium sterate were added to 1,600 mg of a liquid fat (MAISINE CC) and 1,600 mg of a hard fat (GELUCIRE® 43/01) heated to about 130° C. to give a clear solution indicative of incorporation. Upon cooling to room temperature the formulations of experiments 3, 4, and 5 solidified into a solid or solid solution composition and the naproxen remained incorporated in the pharmaceutical compositions.

To assess whether the addition of one or more digestion enhancers could improve the solubility of naproxen when combined with glycerolipid components, pharmaceutical compositions comprising naproxen were formulated according to Table 27 below. MAISINE™ CC, and the fatty acid component or the surfactant component were combined and heated to 130° C. to produce a clear yellow solution. While maintaining the temperature at 130° C., naproxen was then added to this admixture under constant stirring until a clear solution was produced. GELUCIRE® 43/01 was added in a stepwise fashion until the final amount was reached. The resulting composition produced a clear yellow solution which was then allowed to cool to room temperature (18-20° C.) at which time stirring ceased and the composition was transferred to suitable containers where it solidified. The resulting solid composition remelted at 40° C. to give a clear yellow solution with no precipitate formation and again solidified on cooling.

TABLE 27

| Naproxen Formulations | | | | |
|---|---|---|---|---|
| Component | NAPF1 | NAPF2 | NAPF3 | NAPF4 |
| MAISINE CC | 1,000 mg (45.2%) | 1,600 mg (35.5%) | 1,750 mg (39.8%) | 16.5 g (35.6%) |
| GELUCIRE ® 43/01 | 400 mg (18.0%) | 1,600 mg (35.5%) | 1,750 mg (39.8%) | 16.5 g (35.6%) |
| Oleic Acid | 420 mg (19.0%) | — | — | 6.9 g (14.8%) |
| Sodium Stearate | — | 500 mg (11.0%) | — | — |
| Naproxen | — | 800 mg (17.8%) | 450 mg (10.2%) | — |
| Naproxen sodium | 393 mg (17.8%) | — | 450 mg (10.2%) | 6.5 g (14.0%) |

To assess whether the addition of one or more digestion enhancers to glycerolipid admixture comprising naproxen could improve the bioavailability of naproxen, the pharmacokinetics of these formulations will be assessed in a manner similar to the pharmacokinetic analysis described in Example 3 for curcumin, Example 4 for fenofibrate, or Example 5 for cannabidiol. Pharmacokinetic analysis will include experiments designed to determine the amount of naproxen administer (dose), the peak concentration of naproxen achieved after administration (Cmax), the time it takes naproxen to reach its Cmax (Tmax), the time required for the concentration of naproxen to reach half its Cmax (T½), the integral of the concentration-time curve between from time zero to the time of last quantifiable measurement taken during the experiments (AUClast), and the integral of the concentration-time curve from time zero to infinity (AUCinf).

To assess whether the addition of one or more digestion enhancers to glycerolipid admixture comprising naproxen could improve the efficacy of this therapeutic compound, pharmacodynamic experiments will be conducted. Pharmacodynamic analysis will include experiments design to determine the efficacy of naproxen using a LPS challenge assay in a manner similar to the pharmacodynamic analysis described in Example 4 for fenofibrate. Initial experiments GELUCIRE® 43/01, the mixture was stirred for at least 60 minutes before the next addition of GELUCIRE® 43/01 was added. However, Diclofenac particles still remained clearly visible. These results show that Diclofenac remained insoluble in formulations containing only oleic acid, a 1:1 ratio of oleic acid and MAISINE™ CC, and oleic acid/MAISINE™ CC to GELUCIRE® 43/01 in ratios of 2.6:1 to 0.67:1.

To assess whether the addition of one or more digestion enhancers could improve the solubility of diclofenac when combined with glycerolipid components, pharmaceutical compositions comprising diclofenac were formulated according to Table 28 below. MAISINE™ CC, and the fatty acid component or the surfactant component were combined and heated to 100° C. to produce a clear yellow solution. While maintaining the temperature at 100° C., diclofenac was then added to this admixture under constant stirring until a clear solution was produced. GELUCIRE® 43/01 was added in a stepwise fashion until the final amount was reached. The resulting composition produced a clear yellow solution which was then allowed to cool to room temperature (18-20° C.) at which time stirring ceased and the composition was transferred to suitable containers where it solidified. The resulting solid composition remelted at 40° C. to give a clear yellow solution with no precipitate formation and again solidified on cooling.

TABLE 28

| | Diclofenac Formulations | | | |
|---|---|---|---|---|
| Component | DICF1 | DICF2 | DICF3 | DICF4 |
| MAISINE ™ CC | 140 mg (20.3%) | 140 mg (20.3%) | 106 mg (19.1%) | 8.0 g (15.4%) |
| GELUCIRE ® 43/01 | 400 mg (58.0%) | 400 mg (58.0%) | 300 mg (53.9%) | 24.0 g (46.4) |
| Linoleic Acid | — | — | 100 mg (18.0%) | — |
| Oleic Acid | — | — | — | 8.0 g (15.4%) |
| Steric acid | — | 100 mg (14.5%) | — | — |
| Sodium Stearate | 100 mg (14.5%) | — | — | — |
| Cholic Acid | — | — | — | 6.8 g (13.1%) |
| Diclofenac calcium | — | 50 mg (7.2%%) | — | — |
| Diclofenac sodium | 50 mg (7.2%%) | — | 50 mg (9.0%) | 5.0 g (9.7%) | will ascertain whether a beneficial effect is obtained from a formulation comprising naproxen, followed by experiments designed to ascertain the dose-response relationship of naproxen and the beneficial effect associated with this compound.

Example 13 Diclofenac Formulations

As a preliminary assessment, experiments were performed to assess whether diclofenac could be formulated in the absence of cholic acid. On one series of experiments, 8 g of oleic acid was heated with stirring to 100° C. and 5 g diclofenac was then added and stirred for at least 60 minutes. However undissolved diclofenac particles remained clearly visible at all times indicating that this compound failed to completely dissolve in the heated liquid fat. To understand if an additional lipid could affect solubility of diclofenac, 8 g of MAISINE™ CC was added to the mixture under constant stirring for at least 60 minute and while maintaining the temperature at 100° C. Again, undissolved diclofenac particles remained clearly visible at all times indicating that this compound failed to completely dissolve in the heated lipid mixture. GELUCIRE® 43/01, was then added in a stepwise fashion of 6 g to this lipid mixture until the total amount reached 24 g. The mixture was maintaining at 100° C. for the entire experiment and for each addition of To assess whether the addition of one or more digestion enhancers to glycerolipid admixture comprising diclofenac could improve the bioavailability of diclofenac, the pharmacokinetics of these formulations will be assessed in a manner similar to the pharmacokinetic analysis described in Example 3 for curcumin, Example 4 for fenofibrate, or Example 5 for cannabidiol. Pharmacokinetic analysis will include experiments designed to determine the amount of diclofenac administer (dose), the peak concentration of diclofenac achieved after administration (Cmax), the time it takes diclofenac to reach its Cmax (Tmax), the time required for the concentration of diclofenac to reach half its Cmax (T½), the integral of the concentration-time curve between from time zero to the time of last quantifiable measurement taken during the experiments (AUClast), and the integral of the concentration-time curve from time zero to infinity (AUCinf).

To assess whether the addition of one or more digestion enhancers to glycerolipid admixture comprising diclofenac could improve the efficacy of this therapeutic compound, pharmacodynamic experiments will be conducted. Pharmacodynamic analysis will include experiments design to determine the efficacy of diclofenac using a LPS challenge assay in a manner similar to the pharmacodynamic analysis described in Example 4 for fenofibrate. Initial experiments will ascertain whether a beneficial effect is obtained from a formulation comprising diclofenac, followed by experiments designed to ascertain the dose-response relationship of diclofenac and the beneficial effect associated with this compound.

Example 14 Niflumic Acid Formulation

As a preliminary assessment, experiments were performed to assess whether niflumic acid could be formulated in the absence of cholic acid. On one series of experiments, 18.2 g of MAISINE™ CC was heated to 120° C., and 4.55 g niflumic acid were then added and stirred for at least 60 minutes. However, undissolved niflumic acid particles remained clearly visible at all times indicating that this compound failed to completely dissolve in the heated liquid fat. To understand if an additional lipid could affect solubility of niflumic acid, GELUCIRE® 43/01 was added in a stepwise fashion of 4.55 g until the total amount reached 18.2 g. The mixture was maintaining at 120° C. for the entire experiment and for each addition of GELUCIRE® 43/01, the mixture was stirred for at least 60 minutes before the next addition of GELUCIRE® 43/01 was added. However, niflumic acid particles still remained clearly visible. These results show that niflumic acid remained insoluble in formulations containing only MAISINE™ CC and MAISINE™ CC/GELUCIRE® 43/01 in ratios of 4:1 to 1:1.

To assess whether the addition of one or more digestion enhancers could improve the solubility of niflumic acid when combined with glycerolipid components, pharmaceutical composition comprising niflumic acid was formulated according to Table 29 below. MAISINE™ CC, and the fatty acid component or the surfactant component were combined and heated to 120° C. to produce a clear yellow solution. While maintaining the temperature at 120° C., diclofenac was then added to this admixture under constant stirring until a clear solution was produced. GELUCIRE® 43/01 was added in a stepwise fashion until the final amount was reached. The resulting composition produced a clear yellow solution which was then allowed to cool to room temperature (18-20° C.) at which time stirring ceased and the composition was transferred to suitable containers where it solidified. The resulting solid composition remelted at 50° C. to give a clear yellow solution with no precipitate formation and again solidified on cooling.

TABLE 29

| | Niflumic Acid Formulation | |
| Component | NFAF1 | NFAF2 |
| --- | --- | --- |
| MAISINE CC | 250 mg (33.3%) | 18.2 g (37.0%) |
| GELUCIRE ® 43/01 | 250 mg (33.3%) | 18.2 g (37.0%) |
| Sodium Stearate | 50 mg (6.8%) | 3.6 g (7.4%) |
| PEG 400 | 100 mg (13.3%) | 4.6 g (9.3%) |
| Niflumic acid | 100 mg (13.3%) | 4.6 g (9.3)% |

To assess whether the addition of one or more digestion enhancers to glycerolipid admixture comprising niflumic acid could improve the bioavailability of niflumic acid, the pharmacokinetics of these formulations will be assessed in a manner similar to the pharmacokinetic analysis described in Example 3 for curcumin, Example 4 for fenofibrate, or Example 5 for cannabidiol. Pharmacokinetic analysis will include experiments designed to determine the amount of niflumic acid administer (dose), the peak concentration of niflumic acid achieved after administration (Cmax), the time it takes niflumic acid to reach its $C_{max}$ (Tmax), the time required for the concentration of niflumic acid to reach half its Cmax (T½), the integral of the concentration-time curve between from time zero to the time of last quantifiable measurement taken during the experiments (AUClast), and the integral of the concentration-time curve from time zero to infinity (AUCinf).

To assess whether the addition of one or more digestion enhancers to glycerolipid admixture comprising niflumic acid could improve the efficacy of this therapeutic compound, pharmacodynamic experiments will be conducted. Pharmacodynamic analysis will include experiments design to determine the efficacy of niflumic acid using a LPS challenge assay in a manner similar to the pharmacodynamic analysis described in Example 4 for fenofibrate. Initial experiments will ascertain whether a beneficial effect is obtained from a formulation comprising niflumic acid, followed by experiments designed to ascertain the dose-response relationship of niflumic acid and the beneficial effect associated with this compound.

Example 15 Telmisartan Formulation

As a preliminary assessment, experiments were performed to assess whether telmisartan could be formulated in the absence of cholic acid. On one series of experiments, 20 g of MAISINE™ CC was heated to 100° C., and 2.5 g telmisartan was then added and stirred for at least 60 minutes. However, undissolved telmisartan particles remained clearly visible at all times indicating that this compound failed to completely dissolve in the heated liquid fat. To understand if additional lipid could affect solubility of telmisartan, GELUCIRE® 43/01 was added in a stepwise fashion of 5 g until the total amount reached 20 g. The mixture was maintaining at 100° C. for the entire experiment and for each addition of GELUCIRE® 43/01, the mixture was stirred for at least 60 minutes before the next addition of GELUCIRE® 43/01 was added. However, telmisartan crystals still remained clearly visible. These results show that telmisartan remained insoluble in formulations containing only MAISINE™ CC and MAISINE™ CC/GELUCIRE® 43/01 in ratios of 4:1 to 1:1.

To assess whether the addition of one or more digestion enhancers could improve the solubility of telmisartan when combined with glycerolipid components, pharmaceutical composition comprising telmisartan was formulated according to Table 30 below. MAISINE™ CC, and the surfactant component were combined and heated to 100° C. to produce a clear yellow solution. While maintaining the temperature at 100° C., telmisartan was then added to this admixture under constant stirring until a clear solution was produced. GELUCIRE® 43/01 was added in a stepwise fashion until the final amount was reached. The resulting composition produced a clear yellow solution which was then allowed to cool to room temperature (18-20° C.) at which time stirring ceased and the composition was transferred to suitable containers where it solidified. The resulting solid composition remelted at 50° C. to give a clear yellow solution with no precipitate formation and again solidified on cooling.

TABLE 30

| | Telmisartan Formulation | |
| Component | TELF1 | TELF2 |
| --- | --- | --- |
| MAISINE CC | 400 mg (40.8%) | 20 g (45.5%) |
| GELUCIRE ® 43/01 | 400 mg (40.8%) | 20 g (45.5%) |

TABLE 30-continued

| | Telmisartan Formulation | |
|---|---|---|
| Component | TELF1 | TELF2 |
| Sodium Stearate | 30 mg (3.1%) | 1.5 g (3.4%) |
| PEG 400 | 100 mg (10.2%) | — |
| Telmisartan | 50 mg (5.1%) | 2.5 g (5.6%) |

To assess whether the addition of one or more digestion enhancers to glycerolipid admixture comprising telmisartan could improve the bioavailability of telmisartan, the pharmacokinetics of these formulations will be assessed in a manner similar to the pharmacokinetic analysis described in Example 3 for curcumin, Example 4 for fenofibrate, or Example 5 for cannabidiol. Pharmacokinetic analysis will include experiments designed to determine the amount of telmisartan administer (dose), the peak concentration of telmisartan achieved after administration (Cmax), the time it takes telmisartan to reach its Cmax (Tmax), the time required for the concentration of telmisartan to reach half its Cmax (T½), the integral of the concentration-time curve between from time zero to the time of last quantifiable measurement taken during the experiments (AUClast), and the integral of the concentration-time curve from time zero to infinity (AUCinf).

To assess whether the addition of one or more digestion enhancers to glycerolipid admixture comprising telmisartan could improve the efficacy of this therapeutic compound, pharmacodynamic experiments will be conducted. Pharmacodynamic analysis will include experiments design to determine the efficacy of telmisartan using an appropriate animal model system such as the inhaled LPS model of pulmonary inflammation, designed to mimic an indication or disease state for which this therapeutic compound is being used to alleviate. Initial experiments will ascertain whether a beneficial effect is obtained from a formulation comprising telmisartan, followed by experiments designed to ascertain the dose-response relationship of telmisartan and the beneficial effect associated with this compound.

Example 16 Mebendazole Formulation

As a preliminary assessment, experiments were performed to assess whether mebendazole could be formulated in the absence of cholic acid. On one series of experiments, 20 g of MAISINE™ CC was heated with stirring to 100° C. and 1.375 g mebendazole was then added and stirred for at least 60 minutes. However undissolved mebendazole particles remained clearly visible at all times indicating that this compound failed to completely dissolve in the heated liquid fat. To understand if an additional lipid could improve solubility of mebendazole, GELUCIRE® 43/01 was added in a stepwise fashion of 5 g until the total amount reached 20 g. The mixture was maintaining at 80° C. for the entire experiment and for each addition of GELUCIRE® 43/01, and the mixture was stirred for at least 60 minutes before the next addition of GELUCIRE® 43/01 was added. However, mebendazole particles still remained clearly visible. These results show that mebendazole remained insoluble in formulations containing only MAISINE™ CC and MAISINE™ CC/GELUCIRE® 43/01 in ratios of 4:1 to 1:1.

To assess whether the addition of one or more digestion enhancers could improve the solubility of mebendazole when combined with glycerolipid components, pharmaceutical composition comprising mebendazole was formulated according to Tables 31 and 32 below. MAISINE™ CC, the fatty acid component, and the surfactant component were combined and heated to 130° C. to 140° C. to produce a clear yellow solution. The temperature of the admixture was then reduced to 100° C. and mebendazole was then added to this admixture under constant stirring until a clear solution was produced. The temperature of the admixture was then reduced to 80° C. and GELUCIRE® 43/01 was added in a stepwise fashion until the final amount was reached. The resulting composition produced a clear yellow solution which was then allowed to cool to room temperature (18-20° C.) at which time stirring ceased and the composition was transferred to suitable containers where it solidified. The resulting solid composition remelted at 50° C. to give a clear yellow solution with no precipitate formation and again solidified on cooling.

TABLE 31

| | Mebendazole Formulation | | | |
|---|---|---|---|---|
| Component | MEBF1 | MEBF2 | MEBF3 | MEBF4 |
| MAISINE CC | 400 mg (37.2%) | 10 g (23.4%) | 3 g (24.4%) | 1.5 g (24.8%) |
| GELUCIRE ® 43/01 | 400 mg (37.2%) | 20 g (46.8%) | 6 g (48.7%) | 3.0 g (49.7%) |
| oleic acid | 100 mg (9.3%) | 10 g (23.4%) | 3 g (24.4%) | 1.5 g (24.8%) |
| Sodium Stearate | 50 mg (4.7%) | — | — | — |
| cholic acid | — | 1.38 g (3.2%) | 0.19 g (1.5%) | — |
| PEG 400 | 70 mg (6.5%) | — | — | — |
| Mebendazole | 55 mg (5.1%) | 1.38 g (3.2%) | 0.13 g (1.0%) | 0.04 g (0.7%) |

TABLE 32

| | Mebendazole Formulation | | |
|---|---|---|---|
| Component | MEBF5 | MEBF6 | MEBF7 |
| MAISINE ™ CC | 1.5 g (24.1%) | 1.5 g (23.4%) | — |
| GELUCIRE ® 43/01 | 3.0 g (48.2%) | 3.0 g (46.9%) | 3.0 g (49.7%) |
| Oleic Acid | 1.5 g (24.1%) | 1.5 g (23.4%) | 3.0 g (49.7%) |
| Cholic Acid | 0.19 g (2.9%) | 0.36 g (5.6%) | — |
| Mebendazole | 0.06 g (0.7%) | 0.06 g (0.7%) | 0.04 g (0.7%) |

To assess whether the addition of one or more digestion enhancers to glycerolipid admixture comprising mebendazole could improve the bioavailability of mebendazole, the pharmacokinetics of these formulations was assessed in a manner similar to the pharmacokinetic analysis described in Example 3 for curcumin, Example 4 for fenofibrate, or Example 5 for cannabidiol.

In one series of experiments, MEBF4, MEBF5, MEBF6, and MEBF7 were evaluated against Comparator Formulation 1 (CMF1), a suspension comprising 0.5% carboxymethyl cellulose and 0.7% of mebendazole. Swiss CD1 male mice, each with an average weight of between 20 g to 25 g, were divided into five groups of six animals. Animals from each group were oral dosed by gavage as follows: Group 1 animals received a single dose of MEBF4 administered at 30 mg/kg; Group 2 animals received a single dose of MEB5 administered at 30 mg/kg; Group 3 animals received a single dose of MEB6 administered at 30 mg/kg; Group 4 animals received a single dose of MEBF7 administered at 30 mg/kg; and Group 5 animals received a single dose of CMF1 administered at 30 mg/kg. Samples of whole blood were taken just prior to administration, 0 h, and at the following 7 post-administration time points: 0.5 hr, 1 hr, 2 hr, 4 hr, 8 hr, 12 hr, and 24 hr. Samples of brain were taken at 2 post-administration time points (n=3 per time point): 2 hr and 24 hr. Collected whole blood samples were processed to obtain plasma by adding 100 μL of an internal standard solution (250 ng/ml tolbutamide in 0.1% formic acid in acetonitrile) and 20 μL of methanol to 20 μL of whole blood to precipitate blood proteins. After centrifugation at 13,000 rcf for 5 minutes, 50 μL of supernatant was transferred into 50 μL of 0.1% formic acid and stored until analyzed. Collected brain samples were processed by homogenizing 1 g of brain in 3 mL of PBS, and the resulting homogenate processed in the same manner as the blood samples. Processed blood and brain supernatants were sent for bioanalysis, utilizing UHPLC-MS/MS with a reverse phase $C_{18}$ column (50×21 mm), 1.7 mm 50° C. with a mobile phase gradient between: 0.1% formic acid in water and 0.1% formic acid in acetonitrile, a flow rate of 0.75 mL/min and injection volume 5 μL.

Figure 12:
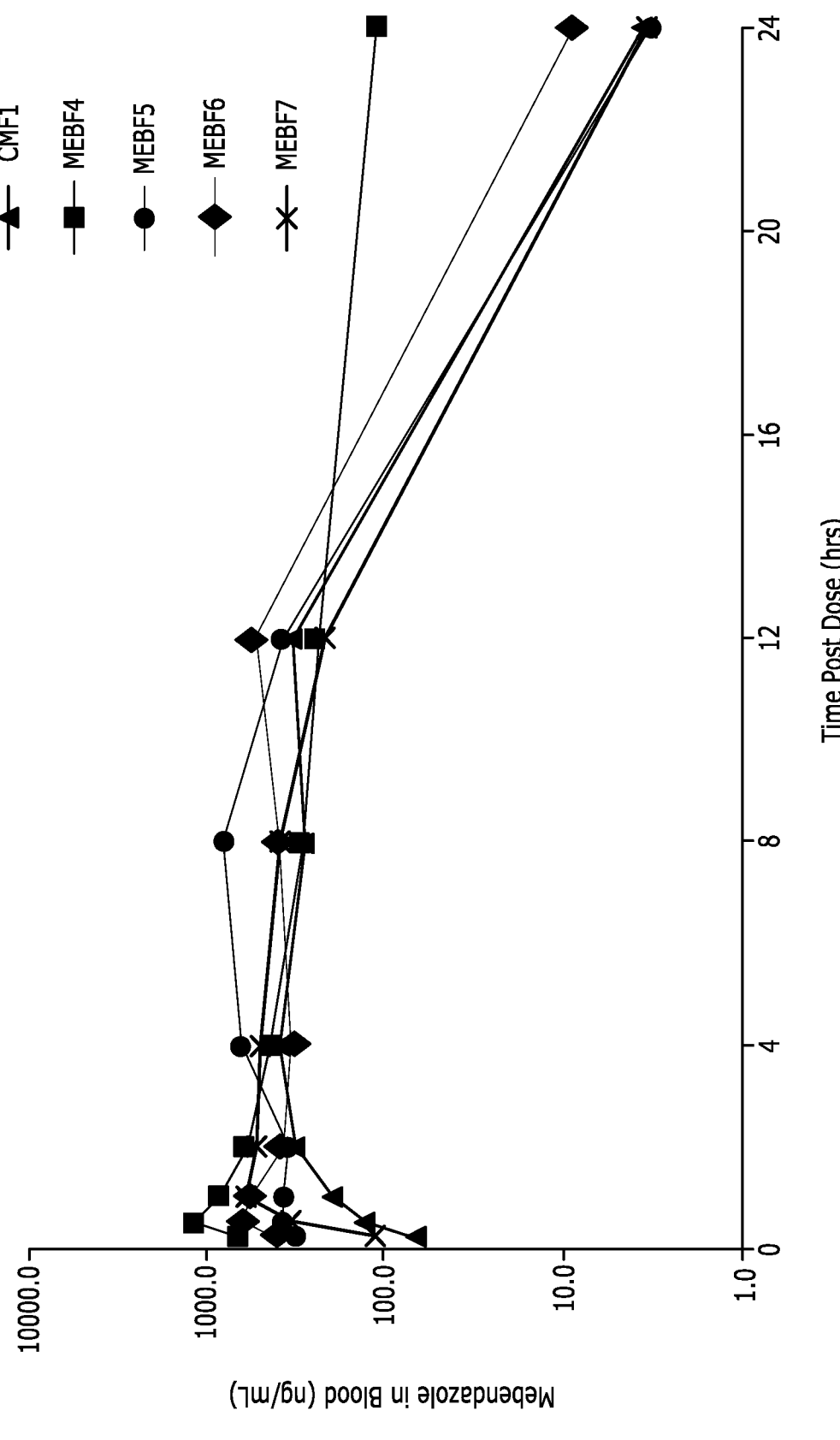
FIG. 12 shows a representative UHPLC tracing of mebendazole levels in blood after oral administration of 30 mg/kg of disclosed pharmaceutical compositions comprising mebendazole.

As shown in FIG. 12 and Table 33, MEBF4, MEBF5, MEBF6, and MEBF7, mebendazole formulated with lipids and with digestion enhancers, exhibited superior pharmacokinetic properties for mebendazole in blood relative to CMF1. In comparison to CMF1 (non-lipid comparator formulation: 1) MEBF4 demonstrated substantially higher absorption levels of mebendazole in blood as indicated by a Cmax that was about 3.0 times greater versus CMF1, with lower clearance over time as indicated by an AUC that was about 1.3 times higher versus CMF1; 2) MEBF5 demonstrated substantially higher absorption levels of mebendazole in blood as indicated by a Cmax that was about 2.1 times greater versus CMF1, with lower clearance over time as indicated by an AUC that was about 1.6 times higher versus CMF1; 3) MEBF6 demonstrated higher absorption levels of mebendazole in blood as indicated by a Cmax that was about 1.6 times greater versus CMF1, with lower clearance over time as indicated by an AUC that was about 1.4 times higher versus CMF1, and 4) MEBF7 demonstrated higher absorption levels of mebendazole in blood as indicated by a Cmax that was over 1.4 times greater versus CMF1, with lower clearance over time as indicated by an AUC that was about 1.1 times higher versus CMF1. Interestingly, MEBF4, MEBF6, and MEBF7 each exhibited a significantly increased absorbance rate compared to CMF1, showing Tmax values of between 0.5 hr and 1.0 hr, which was at least a quarter of the Tmax value of 4.0 hrs observed for CMF1. Conversely, MEBF5 exhibited a significantly reduced absorbance rate compared to CMF1, showing Tmax values of 8.0 hr, which was double the Tmax value of 4.0 hrs observed for CMF1. Overall, MEB4 and MEBF6 demonstrated the best pharmacokinetic improvements compared to the comparator formulation CMF1.

TABLE 33

| Mean Pharmacokinetics Parameter of Blood Mebendazole by Formulation | | | | | |
|---|---|---|---|---|---|
| Parameter | MEBF4 | MEBF5 | MEBF6 | MEBF7 | CMF1 |
| T½ (hr) | NR | NR | NR | NR | NR |
| Tmax (hr) | 0.5 | 8.0 | 0.5 | 1.0 | 4.0 |
| Cmax (ng/mL) | 1180 | 828 | 634 | 572 | 400 |
| AUClast (hr * ng/mL) | 7280 | 9310 | 8370 | 6330 | 5780 |
| AUCinf (hr * ng/mL) | 9200 | NC | 8410 | 6350 | 2800 |

NR: No result, insufficient data to reliably determine pharmacokinetic parameter.
NC: No calculation, insufficient data to reliably calculate pharmacokinetic parameter.

As shown in Table 34, MEBF4 and MEBF7 substantially increased the absorption rate of mebendazole in brain over CMF1. In comparison to CMF1: 1) MEBF4 demonstrated substantially higher absorption levels of mebendazole in brain as indicated by a Cmax that was about 1.3 times greater versus CMF1; and 2) MEBF7 demonstrated substantially higher absorption levels of cannabidiol in blood as indicated by a Cmax that was about 1.4 times greater versus CMF1. Both MEBF5 and MEBFF6 exhibited absorption levels of mebendazole in brain that were comparable the absorption level observed for CMF1.

TABLE 34

| Mebendazole Blood and Brain Ratios of Mean Cmax by Formulation | | | | | |
|---|---|---|---|---|---|
| Sample | MEBF4 | MEBF5 | MEBF6 | MEBF7 | CMF1 |
| Blood | 1180 ng/mL | 828 ng/mL | 634 ng/mL | 572 ng/mL | 400 ng/mL |
| Brain | 152 ng/mL | 111 ng/mL | 111 ng/mL | 170 ng/mL | 120 ng/mL |
| Brain:Blood Ratio | 0.13 | 0.13 | 0.18 | 0.30 | 0.30 |

Taken together, these results show that MEBF4 exhibited significantly improved pharmacokinetic properties over CMF1, with MEBF7 showing improved pharmacokinetic properties over CMF1 but to a lesser degree relative to MEBF4. MEBF6 showed slightly improved pharmacokinetic properties over CMF1. Although MEBF5 generally demonstrated improved pharmacokinetic properties over CMF1, the increase in time to achieve Tmax suggests a better use were delayed absorption is desired. Overall, MEBF4 appeared to have the best pharmacokinetic properties of all tested formulations. Compared to all other formulations, MEBF4 demonstrated the best overall balance of pharmacokinetic parameters having both low T½ and Tmax values and high Cmax and AUC values, illustrating this formulation reaches maximum concentration in the shortest amount of time with the greatest amount of drug exposure over time. In addition, this data supports the proposition that the inclusion of digestion enhancers increase the extent and speed of absorption of drug in both blood and brain over a non-lipid based comparator formulation of mebendazole.

To assess whether the addition of one or more digestion enhancers to glycerolipid admixture comprising mebendazole could improve the efficacy of this therapeutic compound, pharmacodynamic experiments will be conducted. Pharmacodynamic analysis will include experiments design to determine the efficacy of mebendazole using an appropriate animal model system, such as a glioblastoma multiforme xenograft model of cancer, designed to mimic an indication or disease state for which this therapeutic compound is being used to alleviate. Initial experiments will ascertain whether a beneficial effect is obtained from a formulation comprising mebendazole, followed by experiments designed to ascertain the dose-response relationship of mebendazole and the beneficial effect associated with this compound.

Example 17 Amlexanox Formulation

As a preliminary assessment, experiments were performed to assess whether amlexanox could be formulated in the absence of cholic acid. On one series of experiments, 20 g of MAISINE™ CC was heated to 130° C., and 333 mg amlexanox was then added and stirred for at least 60 minutes. However, undissolved amlexanox particles remained clearly visible at all times indicating that this compound failed to completely dissolve in the heated liquid fat. To understand if additional lipid could affect solubility of amlexanox, GELUCIRE® 43/01 was added in a stepwise fashion of 5 g until the total amount reached 20 g. The mixture was maintaining at 130° C. for the entire experiment and for each addition of GELUCIRE® 43/01, the mixture was stirred for at least 60 minutes before the next addition of GELUCIRE® 43/01 was added. However, amlexanox crystals still remained clearly visible. These results show that amlexanox remained insoluble in formulations containing only MAISINE™ CC and MAISINE™ CC/GELUCIRE® 43/01 in ratios of 4:1 to 1:1.

To assess whether the addition of one or more digestion enhancers could improve the solubility of amlexanox when combined with glycerolipid components, a pharmaceutical composition comprising amlexanox was formulated according to Table 35 below. MAISINE™ CC, the fatty acid component, and the surfactant component were combined and heated to 130° C. to produce a clear yellow solution. While maintaining the temperature at 130° C., amlexanox was then added to this admixture under constant stirring until a clear solution was produced. GELUCIRE® 43/01 was added in a stepwise fashion until the final amount was reached. The resulting composition produced a clear yellow solution which was then allowed to cool to room temperature (18-20° C.) at which time stirring ceased and the composition was transferred to suitable containers where it solidified. The resulting solid composition remelted at 50° C. to give a clear yellow solution with no precipitate formation and again solidified on cooling.

TABLE 35

| Amlexanox Formulation | |
| --- | --- |
| Component | AMLF1 |
| MAISINE ™ CC | 20 g (41.7%) |
| GELUCIRE ® 43/01 | 20 g (41.7%) |
| Oleic Acid | 6.7 g (14.0%) |
| Sodium Stearate | 0.33 g (0.7%) |
| Cholic Acid | 0.57 g (1.2%) |
| Amlexanox | 0.33 g (0.7%) |

To assess whether the addition of one or more digestion enhancers to glycerolipid admixture comprising amlexanox could improve the bioavailability of amlexanox, the pharmacokinetics of these formulations will be assessed in a manner similar to the pharmacokinetic analysis described in Example 3 for curcumin, Example 4 for fenofibrate, or Example 5 for cannabidiol. Pharmacokinetic analysis will include experiments designed to determine the amount of amlexanox administer (dose), the peak concentration of amlexanox achieved after administration (Cmax), the time it takes amlexanox to reach its Cmax (Tmax), the time required for the concentration of amlexanox to reach half its Cmax (T½), the integral of the concentration-time curve between from time zero to the time of last quantifiable measurement taken during the experiments (AUClast), and the integral of the concentration-time curve from time zero to infinity (AUCinf).

To assess whether the addition of one or more digestion enhancers to glycerolipid admixture comprising amlexanox could improve the efficacy of this therapeutic compound, pharmacodynamic experiments will be conducted. Pharmacodynamic analysis will include experiments design to determine the efficacy of amlexanox using an appropriate animal model system such as the dextran sulphate induced colitis model, designed to mimic an indication or disease state for which this therapeutic compound is being used to alleviate. Initial experiments will ascertain whether a beneficial effect is obtained from a formulation comprising amlexanox, followed by experiments designed to ascertain the dose-response relationship of amlexanox and the beneficial effect associated with this compound.

Example 18 Aprepitant Formulation

As a preliminary assessment, experiments were performed to assess whether aprepitant could be formulated in the absence of cholic acid. On one series of experiments, 30 g of oleic acid was heated with stirring to 130° C. and 1.250 g aprepitant was then added and stirred for at least 60 minutes. However undissolved aprepitant particles remained clearly visible at all times indicating that this compound failed to completely dissolve in the heated liquid fat. To understand if an additional lipid could affect solubility of aprepitant, GELUCIRE® 43/01 was added in a stepwise fashion of 2.5 g until the total amount reached 10 g. The mixture was maintaining at 130° C. for the entire experiment and for each addition of GELUCIRE® 43/01, the mixture was stirred for at least 60 minutes before the next addition of GELUCIRE® 43/01 was added. However, aprepitant crystals still remained clearly visible. These results show that aprepitant remained insoluble in formulations containing only oleic acid and oleic acid/GELUCIRE® 43/01 in ratios of 12:1 to 3:1.

Certain therapeutic compounds comprising an amine functional group that are extremely insoluble not only in water but also lipids despite the fact that these compounds have a high Log P value. It has been discovered that a certain process is required when formulating a pharmaceutical composition comprising such amine compounds. For example, one series of experiments when 50 mg of aprepitant and 40 mg of cholic acid were added to 500 mg of a liquid fat (MAISINE™ CC) and 1,000 mg of a hard fat (GELUCIRE® 43/01) heated to about 120° C. to about 160° C., the aprepitant failed to incorporate into the heated glycerolipid mixture. In a second series of experiments, 60 mg of aprepitant was added to 500 mg of a liquid fat (MAISINE™ CC) and heated to about 120° C. to about 160° C. to give a clear solution indicative of incorporation. However, when a hard fat (GELUCIRE® 43/01) was then slowly added in stepwise fashion up to 1,000 mg to this heated aprepitant admixture, the hard fat addition caused the aprepitant to precipitate with subsequent reheating failing to redissolve the aprepitant. In a third series of experiments, 50 mg of aprepitant and 40 mg of cholic acid were added to 500 mg of a liquid fat (MAISINE™ CC) and heated to about 120° C. to about 160° C. to give a clear solution indicative of incorporation. Surprisingly, when a hard fat (GELU-CIRE® 43/01) was then slowly added in stepwise fashion up to 1,000 mg to this heated aprepitant admixture, the aprepitant remained in solution. This reaction is indicative of the formation of an anhydrous salt since the ionic boding to form salts is in an anhydrous environment and as such there is no dissolution of ions since the components are not in an aqueous environment. In a fourth series of experiments, 40 mg of cholic acid was added to 500 mg of a liquid fat (MAISINE™ CC) and heated to about 120° C. to about 170° C. aprepitant (50 mg) was then added to this heated admixture to give a clear solution indicative of incorporation. Surprisingly, when a hard fat (GELUCIRE® 43/01) was then slowly added in stepwise fashion up to 1,000 mg to this heated aprepitant admixture, the aprepitant remained in solution. Upon cooling to room temperature the formulations of experiments 3 and 4 solidified into a solid or solid solution composition and the aprepitant remained incorporated in the pharmaceutical compositions.

Further analysis of the aprepitant in the of experiments 3 and 4. Upon heating to about 40° C., the solidified pharmaceutical composition melts to give a clear solution. However, when this solution is further heated to about 70° C. to about 100° C., the aprepitant and cholic acid precipitate out of solution. Further heating to about 120° C. to about 160° C. gives a clear solution where the precipitated components are once again incorporated into the glycerolipid admixture. Upon cooling to room temperature the incorporated mixture solidified into a solid or solid solution composition.

Although not wishing to be limited to any particular theory, the simplest explanation for these experiments results is as follows. The initial admixture of aprepitant, MAISINE™ CC and cholic acid formed when heated to about 120° C. to about 160° C. is a result of a dissolution process where cholic acid is first dissolved into the liquid fat, which once dissolved facilitates to dissolve the aprepitant to form a solution. The addition of GELUCIRE® 43/01 to this heated admixture is one where this hard fat merely acts as a diluent at this high temperature. When the heated admixture is cooled to below 40° C., the hard fat forms a matrix which prevents homo-crystallization of the aprepitant and cholic acid even though both components are insoluble in the liquid fat. As the admixture cools further to that approaching room temperature, the hard fat causes the admixture to solidify. Reheating the solidified admixture to 40° C. simply returns the admixture to hard fat matrix that prevents crystallization of the aprepitant and cholic acid. Increasing the temperature to about 70° C. to about 100° C. provides sufficient energy to break apart the hard fat matrix, thereby allowing both aprepitant and cholic acid to crystalize and precipitate out of solution. A further increase in temperature to about 120° C. to about 160° C. creates enough energy to break apart the crystalline structures and return aprepitant and cholic acid into solution. Cooling this solution to below 40° C. simply repeats the initial steps to produce a solidified admixture incorporated with aprepitant.

Using the procedure described in Example 10, pharmaceutical compositions comprising aprepitant were formulated according to Tables 36 and 37 below. The formulations produced a white, waxy solid comprising aprepitant dissolved in a lipid matrix. The resulting solid products remelted at 40° C. to give a clear solution.

TABLE 36

| Aprepitant Formulations | | | | |
|---|---|---|---|---|
| Component | APRF1 | APRF2 | APRF3 | APRF4 |
| MAISINE ™ CC | 500 mg (30.9%) | — | 1,650 mg (64.5%) | — |
| GELUCIRE ® 43/01 | 1,000 mg (61.7%) | 10 g (24.0%) | 815 mg (32.3%) | 818 mg (32.3%) |
| Cholic Acid | 60 mg (3.7%) | 0.48 g (1.2%) | 43.3 mg (1.6%) | 43.3 mg (1.6%) |
| Oleic Acid | — | 30 g (71.8%) | — | 1,610 mg (64.5%) |
| Aprepitant | 60 mg (3.7%) | 1.25 g (3.0%) | 43.1 mg (1.6%) | 43.2 mg (1.6%) |

TABLE 37

| Aprepitant Formulations | | | | |
| --- | --- | --- | --- | --- |
| Component | APRF5 | APRF6 | APRF7 | APRF8 |
| MAISINE ™ CC | — | — | — | 4.75 g (31.66%) |
| GELUCIRE ® 43/01 | 2.8 g (44.3%) | 2.8 g (47.0%) | 2.8 g (45.6%) | 3.92 g (26.1%) |
| Cholic Acid | 0.32 g (5.1%) | 0.16 g (2.7%) | 0.24 g (3.9%) | 0.71 g (4.74%) |
| Oleic Acid | 2.8 g (44.3%) | 2.8 g (47.0%) | 2.8 g (45.6%) | 4.75 g (31.66%) |
| Aprepitant | 0.4 g (6.3 g) | 0.2 g (3.3%) | 0.3 g (4.9%) | 0.88 g (5.85%) |

To assess whether the addition of one or more digestion enhancers to glycerolipid admixture comprising aprepitant could improve the bioavailability of this therapeutic compound, the pharmacokinetics of these formulations were assessed.

In one series of experiments, APRF3 and APRF4 were evaluated against Comparator Formulation 1 (CMF1) comprising a water-based suspension of Emend. C57BL/6 female mice, each with an average weight of between 15 g to 22 g, were divided into four groups of six animals. Animals from each group were oral dosed by gavage as follows: Group 1 animals received a single dose of APRF3 administered at 80 mg/kg; Group 2 animals received a single dose of APRF4 administered at 80 mg/kg; and Group 4 animals received a single dose of CMF1 administered at 80 mg/kg. Samples of whole blood were taken just prior to administration, 0 h, and at the following 8 post-administration time points: 0.25 hr, 0.5 hr, 1 hr, 2 hr, 4 hr, 8 hr, 12 hr, and 24 hr. Samples of brain were taken at 3 post-administration time points (n=3 per time point): 2 hr, 4 hr, and 24 hr. Collected whole blood samples were processed by adding 30 µL acetonitrile, 10 µl methanol, and 160 µL of an imipramine internal standard solution (25 ng/mL imipramine hydrochloride stock diluted down to 10 ng/mL with acetonitrile) to 20 µL and freezing at −20° C. for a minimum of 2 hours. Samples were then centrifuged and the resulting supernatant stored for analysis by LC-MS-MS. Collected brain samples were processed by homogenizing 1 g of brain in 1 mL of PBS, adding 150 µL of imipramine internal standard solution and 50 µL of acetonitrile to 50 µL aliquots of sample brain homogenate, and freezing at −20° C. for a minimum of 2 hours. Samples were then centrifuged and the resulting supernatant stored for analysis by LC-MS-MS. Processed blood and brain supernatants were sent for bioanalysis, utilizing UHPLC-MS/MS with a reverse phase $C_{18}$ column (50×21 mm), 1.6 µm 65° C. with a mobile phase gradient between: 0.1% formic acid in water and 0.1% formic acid in methanol, a flow rate of 0.8 mL/min and injection volume 1-2 µL.

Figure 13:
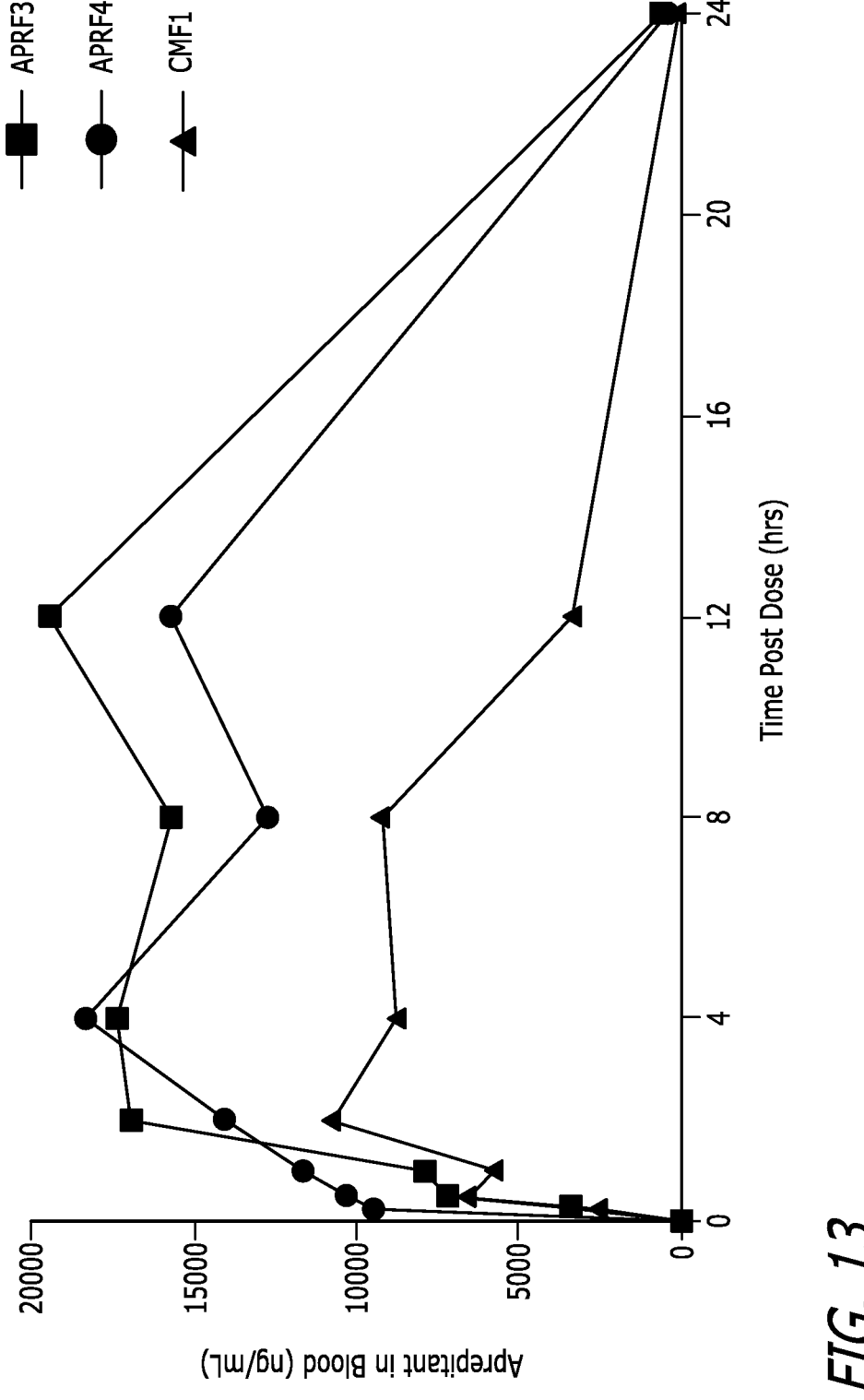
FIG. 13 shows a representative UHPLC tracing of aprepitant levels in blood after oral administration of 30 mg/kg of disclosed pharmaceutical compositions comprising aprepitant.

As shown in FIG. 13 and Table 38, APRF3 and APRF4, aprepitant formulated with lipids and with digestion enhancers, exhibited superior pharmacokinetic properties for aprepitant in blood relative to CMF1. In comparison to CMF1 (non-lipid comparator formulation: 1) APRF3 demonstrated substantially higher absorption levels of aprepitant in blood as indicated by a Cmax that was about 1.8 times greater versus CMF1, with lower clearance over time as indicated by an AUC that was about 2.7 times higher versus CMF1; and 2) APRF4 demonstrated substantially higher absorption levels of aprepitant in blood as indicated by a Cmax that was about 1.7 times greater versus CMF1, with lower clearance over time as indicated by an AUC that was about 2.3 times higher versus CMF1. Interestingly, the Tmax of the two lipid formulations were delayed compared to CMF1, although this is not therapeutically a disadvantage in the oncology setting, where AUC is the more important pharmacokinetic consideration.

TABLE 38

| Mean Pharmacokinetics Parameters of Blood Aprepitant by Formulation | | | |
| --- | --- | --- | --- |
| Parameter | APRF3 | APRF4 | CMF1 |
| T1/2 (hr) | 2.37 | 2.18 | 2.48 |
| Tmax (hr) | 12 | 4 | 2 |
| Cmax (ng/mL) | 19433 | 18302 | 10856 |
| AUClast (hr*ng/mL) | 308831 | 269581 | 115677 |

Taken together, these results show that APRF3 and APRF4 exhibited significantly improved pharmakinetic properties over CMF1. APRF4 demonstrated the best overall balance of pharmacokinetic parameters having both low T½ and Tmax values and high Cmax and AUC values, illustrating this formulation reaches maximum concentration in the shortest amount of time with the greatest amount of drug exposure over time. However, in application were a delay to reach Cmax is wanted, APRF3 demonstrated the best overall balance of pharmacokinetic parameters having both low T½ value and high Cmax and AUC values, illustrating this formulation reaches therapeutically effective concentration quickly and maintains this beneficial drug exposure over the longest period of time. Overall, this data supports the proposition that the inclusion of digestion enhancers increase the extent and speed of absorption of drug in blood over a non-lipid based comparator formulation of aprepitant.

To assess whether the addition of one or more digestion enhancers to glycerolipid admixture comprising aprepitant could improve the efficacy of this therapeutic compound, pharmacodynamic experiments will be conducted. Pharmacodynamic analysis will include experiments design to determine the efficacy of aprepitant using an appropriate animal model system, such as a triple negative breast xenograft cancer model, designed to mimic an indication or disease state for which this therapeutic compound is being used to alleviate. Initial experiments will ascertain whether a beneficial effect is obtained from a formulation comprising aprepitant, followed by experiments designed to ascertain the dose-response relationship of auranofin and the beneficial effect associated with this compound.

Example 19 Olaparib Formulation

As a preliminary assessment, experiments were performed to assess whether olaparib could be formulated in the absence of cholic acid. In one series of experiments, 1 g of MAISINE™ CC was heated to 130° C., and 55 mg olaparib was then added and stirred for at least 60 minutes. However, undissolved olaparib particles remained clearly visible at all times indicating that this compound failed to completely dissolve in the heated liquid fat. In another series of experiments, 1 g of GELUCIRE® 43/01 was heated to 130° C., and 55 mg olaparib was then added and stirred for at least 60 minutes. However, undissolved olaparib particles remained clearly visible at all times indicating that this compound failed to completely dissolve in heated GELU-CIRE® 43/01. In third series of experiments, 0.5 g of MAISINE™ CC and 0.5 g of GELUCIRE® 43/01 were combined and heated to 130° C., and 55 mg Olaparib was then added and stirred for at least 60 minutes. However, undissolved olaparib particles remained clearly visible at all times indicating that this compound failed to completely dissolve in heated glycolipid mixture. These results show that olaparib remained insoluble in formulations containing only MAISINE™ CC, only GELUCIRE® 43/01. and an admixture of MAISINE™ CC and GELUCIRE® 43/01.

To assess whether the addition of one or more digestion enhancers could improve the solubility of olaparib when combined with glycerolipid components, a pharmaceutical composition comprising olaparib was formulated according to Table 39 below. In one series of experiments, MAISINE™ CC and oleic acid were combined and heated to 130° C. to produce a clear yellow solution. While maintaining the temperature at 130° C., olaparib was then added to this admixture under constant stirring until a clear solution was produced. Molten GELUCIRE® 43/01 (130° C.) was added and stirred. The resulting composition produced a clear yellow solution which was then allowed to cool to room temperature (18-20° C.) at which time stirring ceased and the composition was transferred to suitable containers where it solidified. Upon solidification, it was noted that the resulting composition contained crystalline particles indicating that olaparib precipitated out of solution as the temperature cooled.

In another series of experiments, MAISINE™ CC, the fatty acid component, and the cholic acid were combined and heated to 130° C. to produce a clear yellow solution. While maintaining the temperature at 130° C., olaparib was then added to this admixture under constant stirring until a clear solution was produced. Molten GELUCIRE® 43/01 (130° C.) was added and stirred. The resulting composition produced a clear yellow solution which was then allowed to cool to room temperature (18-20° C.) at which time stirring ceased and the composition was transferred to suitable containers where it solidified. The resulting solid composition remelted at 50° C. to give a clear yellow solution with no precipitate formation and again solidified on cooling. These results show that the presence of cholic acid was required to maintain olaparib in solution and prevent this compound from precipitating out of the glycolipid matrix.

TABLE 39

| Component | Olaparib Formulation | | | | |
| | OLPF1 | OLPF2 | OLPF3 | OLPF4 | OLPF5 |
|---|---|---|---|---|---|
| MAISINE ™ CC | 1 g (26.2%) | 1.5 g (24.8%) | 1.5 g (24.1%) | 1.5 g (23.4%) | — |
| GELUCIRE ® 43/01 | 1 g (26.2%) | 3.0 g (49.7%) | 3.0 g (48.2%) | 3.0 g (46.9%) | 3.0 g (49.7%) |
| Oleic Acid | 1 g (26.2%) | 1.5 g (24.8%) | 1.5 g (24.1%) | 1.5 g (23.4%) | 3.0 g (49.7%) |
| Cholic Acid | 0.27 g (7.0%) | — | 0.19 g (2.9%) | 0.36 g (5.6%) | — |
| Olaparib | 0.55 g (14.4%) | 0.04 g (0.7%) | 0.06 g (0.7%) | 0.06 g (0.7%) | 0.04 g (0.7%) |

To assess whether the addition of one or more digestion enhancers to glycerolipid admixture comprising olaparib could improve the bioavailability of olaparib, the pharmacokinetics of these formulations will be assessed in a manner similar to the pharmacokinetic analysis described in Example 3 for curcumin, Example 4 for fenofibrate, or Example 5 for cannabidiol.

In one series of experiments, OLPF2, OLPF3, OLPF4, and OLPF5 were evaluated against Comparator Formulation 1 (CMF1), a suspension comprising 0.5% carboxymethyl cellulose and 0.7% of olaparib. Swiss CD1 male mice, each with an average weight of between 20 g to 25 g, were divided into five groups of six animals. Animals from each group were oral dosed by gavage as follows: Group 1 animals received a single dose of OLPF2 administered at 30 mg/kg; Group 2 animals received a single dose of OLPF3 administered at 30 mg/kg; Group 3 animals received a single dose of OLPF4 administered at 30 mg/kg; Group 4 animals received a single dose of OLPF5 administered at 30 mg/kg; and Group 5 animals received a single dose of CMF1 administered at 30 mg/kg. Samples of whole blood were taken just prior to administration, 0 h, and at the following 7 post-administration time points: 0.5 hr, 1 hr, 2 hr, 4 hr, 8 hr, 12 hr, and 24 hr. Samples of brain were taken at 2 post-administration time points (n=3 per time point): 2 hr and 24 hr. Collected whole blood samples were processed to obtain plasma by adding 100 μL of an internal standard solution (250 ng/ml tolbutamide in 0.1% formic acid in acetonitrile) and 20 μL of methanol to 20 μL of whole blood to precipitate blood proteins. After centrifugation at 13,000 rcf for 5 minutes, 50 μL of supernatant was transferred into 50 μL of 0.1% formic acid and stored until analyzed. Collected brain samples were processed by homogenizing 1 g of brain in 3 mL of PBS, and the resulting homogenate processed in the same manner as the blood samples. Processed blood and brain supernatants were sent for bioanalysis, utilizing UHPLC-MS/MS with a reverse phase C18 column (50×21 mm), 1.7 mm 50° C. with a mobile phase gradient between: 0.1% formic acid in water and 0.1% formic acid in acetonitrile, a flow rate of 0.75 mL/min and injection volume 5 μL.

Figure 14:
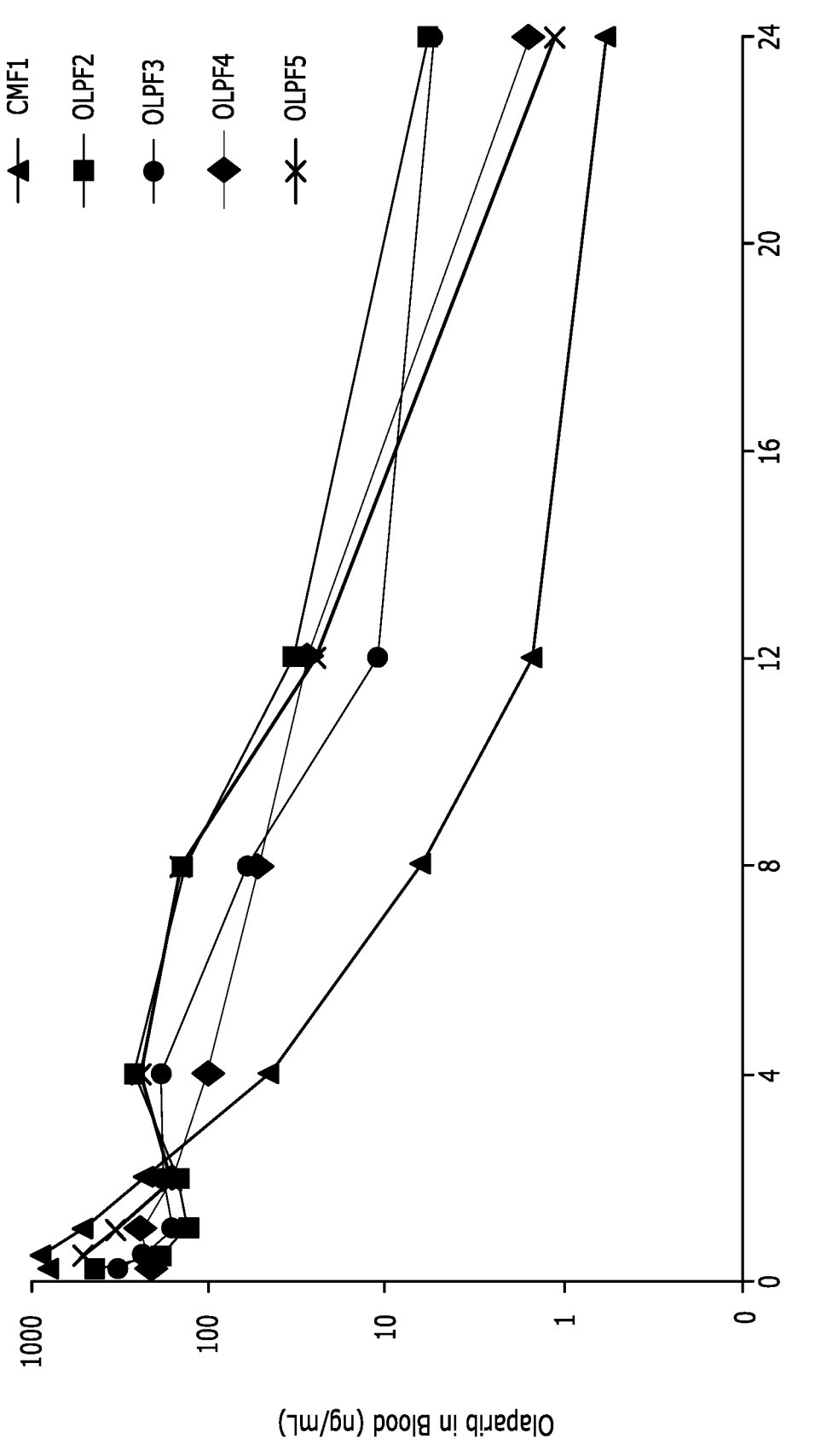
FIG. 14 shows a representative UHPLC tracing of olaparib levels in blood after oral administration of 30 mg/kg of disclosed pharmaceutical compositions comprising olaparib.

As shown in FIG. 14 and Table 40, OLPF2, OLPF3, OLPF4, and OLPF5, olaparib formulated with lipids and with digestion enhancers, exhibited superior pharmacokinetic properties for cannabidiol in blood relative to CMF1. In comparison to CMF1 (non-lipid comparator formulation: 1) OLPF2 demonstrated lower clearance of olaparib over time as indicated by an AUC that was 1.5 times higher versus CMF1; 2) OLPF3 demonstrated lower clearance of olaparib over time as indicated by an AUC that was about 1.1 times higher versus CMF1; and 3) OLPF5 demonstrated substantially lower clearance of olaparib over time as indicated by an AUC that was about 1.6 times higher versus CMF1. Additionally, as shown in FIG. 14, OLPF2, OLPF3, OLPF4, and OLPF5 each exhibited significantly increased exposure of Olaparib. For example, at 12 hours post-dose, mean olaparib concentrations in animals administered OLPF2, OLPF3, OLPF4, and OLPF5 were all over 10 ng/mL while that of CMF1 five-fold less (2 ng/mL). FIG. 14 also shows that while CMF1 demonstrated higher absorption levels of olaparib in blood, the concentration of Olaparib decreased rapidly in these animals relative to OLPF2, OLPF3, OLPF4, and OLPF5. Overall, OLPF2, OLPF3, OLPF4, and OLPF5 demonstrated significant pharmacokinetic improvements compared to the comparator formulation CMF1.

TABLE 40

| Parameter | Mean Pharmacokinetics Parameter of Blood Olaparib by Formulation | | | | |
| --- | --- | --- | --- | --- | --- |
| | OLPF2 | OLPF3 | OLPF4 | OLPF5 | CMF1 |
| T1/2 (hr) | NR | NR | NR | NR | NR |
| Tmax (hr) | 0.25 | 0.25 | 1 | 0.5 | 0.5 |
| Cmax (ng/mL) | 445 | 351 | 254 | 517 | 889 |
| AUClast (hr * ng/mL) | 2230 | 1560 | 1350 | 2410 | 1480 |
| AUCinf (hr * ng/mL) | 2260 | 1600 | 1360 | 2410 | 1490 |

NR: No result, insufficient data to reliably determine pharmacokinetic parameter.

As shown in Table 41, although the overall Olaparib absorption levels were not substantially higher in OLPF2, OLPF3, OLPF4, and OLPF5 relative to CMF1, the proportion of olaparib entering the brain, as shown by the brain to blood ratios, was equivalent to CMF1. For example, the Cmax value of OLPF2 in the blood was 445 ng/mL while in the brain maximum absorption level was 9.0 ng/mL, whereas the Cmax value of CMF1 in the blood was 889 ng/mL while in the brain maximum absorption level was 8.8 ng/mL. Thus, even though the overall amount of olaparib absorbed was higher in the blood using CMF1 versus OLPF2, the amount of olaparib absorbed in the brain using CMF1 was equivalent to that observed using OLPF2. Similar observations are seen with OLPF3, OLPF4, and OLPF5. One explanation for these finding is that the lipid-formulations of OLPF2, OLPF3, OLPF4, and OLPF5 slow down the clearance rate of Olaparib in the blood, and thus enabling olaparib remain in blood at levels high enough to facilitate its entry into the brain, i.e., the lipid-based formulations of OLPF2, OLPF3, OLPF4, and OLPF5 protect olaparib so that this compound can be transported into the brain.

TABLE 41

| Olaparib Blood and Brain Ratios of Mean Cmax by Formulation | | | | | |
| --- | --- | --- | --- | --- | --- |
| Sample | OLPF2 | OLPF3 | OLPF4 | OLPF5 | CMF1 |
| Blood | 445 ng/mL | 351 ng/mL | 254 ng/mL | 517 ng/mL | 889 ng/mL |
| Brain | 9.0 ng/mL | 4.4 ng/mL | 2.54 ng/mL | 4.8 ng/mL | 8.8 ng/mL |
| Brain:Blood Ratio | 0.02 | 0.01 | 0.01 | 0.01 | 0.01 |

Taken together, these results show that OLPF2, OLPF3, OLPF4, and OLPF5 exhibited significantly improved pharmacokinetic properties over CMF1 in terms of lower clearance levels, longer exposure drug exposure time, increased brain absorption levels. Compared to all other formulations, OLPF2 demonstrated the best overall balance of pharmacokinetic parameters having both low T½ and Tmax values and high AUC values, illustrating this formulation reaches maximum concentration in the shortest amount of time with the greatest amount of drug exposure over time. Overall, this data supports the proposition that the inclusion of digestion enhancers increase the extent and speed of absorption of drug in both blood and brain over a non-lipid based comparator formulation of olaparib.

To assess whether the addition of one or more digestion enhancers to glycerolipid admixture comprising olaparib could improve the efficacy of this therapeutic compound, pharmacodynamic experiments will be conducted. Pharmacodynamic analysis will include experiments design to determine the efficacy of olaparib using an appropriate animal model system, such as an ovarian xenograft cancer model, designed to mimic an indication or disease state for which this therapeutic compound is being used to alleviate. Initial experiments will ascertain whether a beneficial effect is obtained from a formulation comprising olaparib, followed by experiments designed to ascertain the dose-response relationship of olaparib and the beneficial effect associated with this compound.

Example 20 Nintedanib Formulation

As a preliminary assessment, experiments were performed to assess whether nintedanib could be formulated in the absence of cholic acid. On one series of experiments, 1 g of a liquid fat (MAISINE CC) was heated to 60° C., and 250 mg nintedanib was then added and stirred for at least 60 minutes. However, undissolved nintedanib particles remained clearly visible at all times indicating that this compound failed to completely dissolve in the heated liquid fat. To understand if additional lipid could affect solubility of nintedanib, a hard fat (GELUCIRE® 43/01) was added in a stepwise fashion of 0.5 g until the total amount reached 2 g. The mixture was maintaining at 60° C. for the entire experiment and for each addition of GELUCIRE® 43/01, the mixture was stirred for at least 60 minutes before the next addition of GELUCIRE® 43/01 was added. However, nintedanib crystals still remained clearly visible. These results show that nintedanib remained insoluble in formulations containing only MAISINE™ CC and MAISINE™ CC/GELUCIRE® 43/01 in ratios of 2:1 to 1:2.

In another series of experiments, 40 mg of nintedanib esylate was added to 1.0 g of a liquid fat (MAISINE CC) and one of the following combinations of digestion enhancers was added to the glycerolipid admixture: 1) 1.5 g oleic acid and 100 mg of sodium oleate; 2) 1.5 g oleic acid and 150 mg of sodium oleate; 3) 1.5 g oleic acid and 100 mg of sodium stearate; and 4) 1.5 g oleic acid and 150 mg of sodium stearate. After heating to about 130° C., the nintedanib esylate failed to incorporate into any of these four heated glycerolipid mixtures. In second series of experiments, 40 mg of nintedanib esylate was added to 1.0 g of a liquid fat (MAISINE CC) and one of the following combinations of digestion enhancers was added to the glycerolipid admixture: 1) 1.5 g oleic acid, 100 mg of sodium oleate, and 30 mg of cholic acid or 30 mg lecithin; 2) 1.5 g oleic acid, 150 mg of sodium oleate, and 30 mg of cholic acid or 30 mg lecithin; 3) 1.5 g oleic acid, 100 mg of sodium stearate, and 30 mg of cholic acid or 30 mg lecithin; and 4) 1.5 g oleic acid, 150 mg of sodium stearate, and 30 mg of cholic acid or 30 mg lecithin. Upon heating to about 130° C., all four glycerolipid mixtures containing cholic acid or lecithin produced a clear yellowish green solution indicating that nintedanib esylate became soluble and incorporated into these mixtures. The subsequent addition of 1.5 g of a hard fat (GELUCIRE® 43/01) still resulted in clear yellowish green solutions. The resulting solid composition remelted at 40° C. to give a clear yellowish green solution with no precipitate formation and again solidified on cooling.

To assess whether the addition of one or more digestion enhancers could improve the solubility of nintedanib when combined with glycerolipid components, a pharmaceutical composition comprising nintedanib was formulated according to Tables 42-45 below. Nintedanib (either organosulfonate salt or free base form) was added to MAISINE™ CC and the fatty acid component, and the surfactant component were then combined and heated to 130° C. to produce a clear yellowish green solution. While maintaining the temperature at 60° C., GELUCIRE® 43/01 was added in a stepwise fashion until the final amount was reached. The resulting composition produced a clear yellowish green solution which was then allowed to cool to room temperature (18-20° C.) at which time stirring ceased and the composition was transferred to suitable containers where it solidified. The resulting solid composition remelted at 40° C. to give a clear yellowish green solution with no precipitate formation and again solidified on cooling.

TABLE 42

Nintedanib Formulation

| Component | NINF1 | NINF2 | NINF3 | NINF4 |
|---|---|---|---|---|
| MAISINE ™ CC | 1.0 g | 1.0 g | 1.0 g | 1.0 g |
| GELUCIRE ® 43/01 | 1.5 g | 1.5 g | 1.5 g | 1.5 g |
| Oleic Acid | 1.5 g | 1.5 g | 1.5 g | 1.5 g |
| Cholic Acid | 30 mg | 30 mg | — | — |
| Deoxycholic Acid | — | — | — | — |
| Lecithin | — | — | 30 mg | 30 mg |
| Sodium Oleate | 100 mg | 150 mg | 100 mg | 150 mg |
| Sodium Stearate | — | — | 100 mg | — |
| Cholesterol | — | — | — | — |
| Nintedanib (salt) | 40 mg | 40 mg | 40 mg | 40 mg |
| Nintedanib (base) | — | — | — | — |

TABLE 43

Nintedanib Formulation

| Component | NINF5 | NINF6 | NINF7 | NINF8 |
|---|---|---|---|---|
| MAISINE ™ CC | 1.0 g | 1.0 g | 1.0 g | 1.0 g |
| GELUCIRE ® 43/01 | 1.5 g | 1.5 g | 1.5 g | 1.5 g |
| Oleic Acid | 1.5 g | 1.5 g | 1.5 g | 1.5 g |
| Cholic Acid | 30 mg | 30 mg | — | — |
| Deoxycholic Acid | — | — | — | — |
| Lecithin | — | — | 30 mg | 30 mg |
| Sodium Oleate | — | — | — | — |
| Sodium Stearate | 100 mg | 150 mg | 100 mg | 150 mg |
| Cholesterol | — | — | — | — |
| Nintedanib (salt) | 40 mg | 40 mg | 40 mg | 40 mg |
| Nintedanib (base) | — | — | — | — |

TABLE 44

Nintedanib Formulation

| Component | NINF9 | NINF10 | NINF11 | NINF12 |
|---|---|---|---|---|
| MAISINE ™ CC | 1.0 g (24.2 g) | 1.0 g | 1.0 g | 1.0 g |
| GELUCIRE ® 43/01 | 2.0 g (48.3%) | 1.5 g | 1.5 g | 1.5 g |
| Oleic Acid | 1.0 g (24.2 g) | 1.5 g | 1.5 g | 1.5 g |
| Cholic Acid | 0.04 g (1.0%) | 60 mg | — | — |
| Deoxycholic Acid | — | — | 60 mg | — |
| Lecithin | — | — | — | 30 mg |
| Sodium Oleate | — | — | — | — |
| Sodium Stearate | — | — | — | — |
| Cholesterol | — | — | — | — |
| Nintedanib (salt) | 0.1 g (2.3%) | — | — | — |
| Nintedanib (base) | — | 36 mg | 36 mg | 36 mg |

TABLE 45

Nintedanib Formulation

| Component | NINF13 | NINF14 |
|---|---|---|
| MAISINE ™ CC | 1.0 g | 1.0 g |
| GELUCIRE ® 43/01 | 1.5 g | 1.5 g |
| Oleic Acid | 1.5 g | 1.5 g |
| Cholic Acid | — | — |
| Deoxycholic Acid | — | — |
| Lecithin | — | — |
| Sodium Oleate | — | — |
| Sodium Stearate | 10 mg | — |
| Cholesterol | — | 100 mg |
| Nintedanib (salt) | — | — |
| Nintedanib (base) | 36 mg | 36 mg |

To assess whether the addition of one or more digestion enhancers to glycerolipid admixture comprising nintedanib could improve the bioavailability of nintedanib, the pharmacokinetics of these formulations will be assessed in a manner similar to the pharmacokinetic analysis described in Example 3 for curcumin, Example 4 for fenofibrate, or Example 5 for cannabidiol. Pharmacokinetic analysis will include experiments designed to determine the amount of nintedanib administer (dose), the peak concentration of nintedanib achieved after administration (Cmax), the time it takes nintedanib to reach its Cmax (Tmax), the time required for the concentration of nintedanib to reach half its Cmax (T½), the integral of the concentration-time curve between from time zero to the time of last quantifiable measurement taken during the experiments (AUClast), and the integral of the concentration-time curve from time zero to infinity (AUCinf).

To assess whether the addition of one or more digestion enhancers to glycerolipid admixture comprising nintedanib could improve the efficacy of this therapeutic compound, pharmacodynamic experiments will be conducted. Pharmacodynamic analysis will include experiments design to determine the efficacy of nintedanib using an appropriate animal model system, such as a bleomycin induced lung fibrosis model, designed to mimic an indication or disease state for which this therapeutic compound is being used to alleviate. Initial experiments will ascertain whether a beneficial effect is obtained from a formulation comprising nintedanib, followed by experiments designed to ascertain the dose-response relationship of nintedanib and the beneficial effect associated with this compound.

Example 21 Eliglustat Formulation

To assess whether the addition of one or more digestion enhancers could improve the solubility of eliglustat when combined with glycerolipid components, a pharmaceutical composition comprising eliglustat was formulated according to Tables 46-49 below. Eliglustat (either tartrate salt or free base form) was added to MAISINE™ CC and the fatty acid component, and the surfactant component were then combined and heated to 130° C. to produce a clear yellow solution. While maintaining the temperature at 60° C., GELUCIRE® 43/01 was added in a stepwise fashion until the final amount was reached. The resulting composition produced a clear yellow solution which was then allowed to cool to room temperature (18-20° C.) at which time stirring ceased and the composition was transferred to suitable containers where it solidified. The resulting solid composition remelted at 40° C. to give a clear yellow solution with no precipitate formation and again solidified on cooling.

TABLE 46

Eliglustat Formulation

| Component | ELGF1 | ELGF2 | ELGF3 | ELGF4 |
|---|---|---|---|---|
| MAISINE ™ CC | 1.75 g | 1.75 g | 1.75 g | 1.75 g |
| GELUCIRE ® 43/01 | 1.5 g | 1.5 g | 1.5 g | 1.5 g |
| Oleic Acid | 0.5 g | 1.5 g | 0.5 g | 1.5 g |
| Cholic Acid | — | — | 100 mg | 100 mg |
| Eliglustat (salt) | 85 mg | 85 mg | 85 mg | 85 mg |
| Eliglustat (base) | — | — | — | — |

TABLE 47

Eliglustat Formulation

| Component | ELGF5 | ELGF6 | ELGF7 | ELGF8 |
|---|---|---|---|---|
| MAISINE ™ CC | 2.25 g | 2.25 g | 2.25 g | 2.25 g |
| GELUCIRE ® 43/01 | 1.5 g | 1.5 g | 1.5 g | 1.5 g |
| Oleic Acid | 0.5 g | 1.5 g | 0.5 g | 1.5 g |
| Cholic Acid | — | — | 100 mg | 100 mg |
| Eliglustat (salt) | 85 mg | 85 mg | 85 mg | 85 mg |
| Eliglustat (base) | — | — | — | — |

TABLE 48

Eliglustat Formulation

| Component | ELGF9 | ELGF10 | ELGF11 | ELGF12 |
|---|---|---|---|---|
| MAISINE ™ CC | 1.75 g | 1.75 g | 1.75 g | 1.75 g |
| GELUCIRE ® 43/01 | 1.5 g | 1.5 g | 1.5 g | 1.5 g |
| Oleic Acid | 0.5 g | 1.5 g | 0.5 g | 1.5 g |
| Cholic Acid | — | — | 100 mg | 100 mg |
| Eliglustat (salt) | — | — | — | — |
| Eliglustat (base) | 70 mg | 70 mg | 70 mg | 70 mg |

TABLE 49

Eliglustat Formulation

| Component | ELGF13 | ELGF14 | ELGF15 | ELGF16 |
|---|---|---|---|---|
| MAISINE ™ CC | 2.25 g | 2.25 g | 2.25 g | 2.25 g |
| GELUCIRE ® 43/01 | 1.5 g | 1.5 g | 1.5 g | 1.5 g |
| Oleic Acid | 0.5 g | 1.5 g | 0.5 g | 1.5 g |
| Cholic Acid | — | — | 100 mg | 100 mg |
| Eliglustat (salt) | — | — | — | — |
| Eliglustat (base) | 70 mg | 70 mg | 70 mg | 70 mg |

To assess whether the addition of one or more digestion enhancers to glycerolipid admixture comprising eliglustat could improve the bioavailability of eliglustat, the pharmacokinetics of these formulations will be assessed in a manner similar to the pharmacokinetic analysis described in Example 3 for curcumin, Example 4 for fenofibrate, or Example 5 for cannabidiol. Pharmacokinetic analysis will include experiments designed to determine the amount of eliglustat administer (dose), the peak concentration of eliglustat achieved after administration (Cmax), the time it takes eliglustat to reach its Cmax (Tmax), the time required for the concentration of eliglustat to reach half its Cmax (T½), the integral of the concentration-time curve between from time zero to the time of last quantifiable measurement taken during the experiments (AUClast), and the integral of the concentration-time curve from time zero to infinity (AUCinf).

To assess whether the addition of one or more digestion enhancers to glycerolipid admixture comprising eliglustat could improve the efficacy of this therapeutic compound, pharmacodynamic experiments will be conducted. Pharmacodynamic analysis will include experiments design to determine the efficacy of eliglustat using an appropriate animal model system designed to mimic an indication or disease state for which this therapeutic compound is being used to alleviate. Initial experiments will ascertain whether a beneficial effect is obtained from a formulation comprising eliglustat, followed by experiments designed to ascertain the dose-response relationship of eliglustat and the beneficial effect associated with this compound.

Example 22 Therapeutic Peptide Formulation

To assess whether the addition of one or more digestion enhancers could improve the solubility of icatibant when combined with glycerolipid components, a pharmaceutical composition comprising icatibant was formulated according to one of the following two methods. In the first method, 500 mg of cholic acid will be added to 10 mL of an oleic acid solution comprising 90% oleic acid and 10% acetic acid and heated to 60° C. Upon complete dissolution of cholic acid, 10 mg of the therapeutic peptide icatibant is added to a 0.5 mL aliquot of this heated admixture. Upon dissolution of icatibant, this admixture is added to 5 mL of a MAISINE™ CC solution comprising 90% MAISINE™ CC and 10% oleic acid. Upon completion of solubility of this admixture in the MAISINE™ CC solution, 6 mL of a GELUCIRE® 43/01 solution comprising 90% GELUCIRE® 43/01 and 10% MAISINE™ CC is then added. The resulting composition will comprise 0.1% icatibant, 0.2% cholic acid, 0.4% acetic acid, 8.1% oleic acid, 44.3% MAISINE™ CC, and 46.9% GELUCIRE® 43/01 and will produce a clear yellow solution. The composition will then be allowed to cool to room temperature (18-20° C.) at which time stirring will cease and the composition will be transferred to suitable containers where it will solidify. The resulting solid composition will be remelted at 40° C. and it is expected to give a clear yellow solution with no solid components and again solidify on cooling. A similar result is expected when the therapeutic peptides semaglutide, oxytocin, or octreotide is substituted for icatibant.

In the second method, 15 mg of icatibant will be dissolved in 3 g of acetic acid. 0.5 ml of the peptide solution is added to 1.5 g of an oleic acid solution comprising 94% oleic acid and 6% cholic acid. Upon completion of solubility of this admixture, 2.5 g of a GELUCIRE® 43/01 solution comprising 60% GELUCIRE® 43/01 and 40% MAISINE™ CC is then added. The resulting composition will comprise 0.1% icatibant, 2% cholic acid, 10.0% acetic acid, 33.0% oleic acid, 33.0% MAISINE™ CC, and 22.0% GELUCIRE®

43/01 and will produce a clear yellow solution. The composition will then be allowed to cool to room temperature (18-20° C.) at which time stirring will cease and the composition will be transferred to suitable containers where it will solidify. The resulting solid composition will be remelted at 40° C. and it is expected to give a clear yellow solution with no solid components and again solidify on cooling. A similar result is expected when the therapeutic peptides semaglutide, oxytocin, or octreotide is substituted for icatibant.

To assess whether the addition of one or more digestion enhancers to glycerolipid admixture comprising icatibant could improve the bioavailability of icatibant, the pharmacokinetics of these formulations will be assessed in a manner similar to the pharmacokinetic analysis described in Example 3 for curcumin, Example 4 for fenofibrate, or Example 5 for cannabidiol. Pharmacokinetic analysis will include experiments designed to determine the amount of icatibant administer (dose), the peak concentration of icatibant achieved after administration (Cmax), the time it takes icatibant to reach its Cmax (Tmax), the time required for the concentration of icatibant to reach half its Cmax (T½), the integral of the concentration-time curve between from time zero to the time of last quantifiable measurement taken during the experiments (AUClast), and the integral of the concentration-time curve from time zero to infinity (AUCinf). Similar pharmacokinetic experiments will be performed for the therapeutic peptides semaglutide, oxytocin, an octreotide.

To assess whether the addition of one or more digestion enhancers to glycerolipid admixture comprising icatibant could improve the efficacy of this therapeutic compound, pharmacodynamic experiments will be conducted. Pharmacodynamic analysis will include experiments design to determine the efficacy of icatibant using an appropriate animal model system, such as specific gene knock out models of angioedema, designed to mimic an indication or disease state for which this therapeutic compound is being used to alleviate. Initial experiments will ascertain whether a beneficial effect is obtained from a formulation comprising icatibant, followed by experiments designed to ascertain the dose-response relationship of icatibant and the beneficial effect associated with this compound. Similar pharmacodynamic experiments will be performed for the therapeutic peptides semaglutide, oxytocin, an octreotide.

In closing, foregoing descriptions of embodiments of the present invention have been presented for the purposes of illustration and description. It is to be understood that, although aspects of the present invention are highlighted by referring to specific embodiments, one skilled in the art will readily appreciate that these described embodiments are only illustrative of the principles comprising the present invention. As such, the specific embodiments are not intended to be exhaustive or to limit the invention to the precise forms disclosed. Therefore, it should be understood that embodiments of the disclosed subject matter are in no way limited to a particular element, compound, composition, component, article, apparatus, methodology, use, protocol, step, and/or limitation described herein, unless expressly stated as such.

In addition, groupings of alternative embodiments, elements, steps and/or limitations of the present invention are not to be construed as limitations. Each such grouping may be referred to and claimed individually or in any combination with other groupings disclosed herein. It is anticipated that one or more alternative embodiments, elements, steps and/or limitations of a grouping may be included in, or deleted from, the grouping for reasons of convenience and/or patentability. When any such inclusion or deletion occurs, the specification is deemed to contain the grouping as modified, thus fulfilling the written description of all Markush groups used in the appended claims.

Furthermore, those of ordinary skill in the art will recognize that certain changes, modifications, permutations, alterations, additions, subtractions and sub-combinations thereof can be made in accordance with the teachings herein without departing from the spirit of the present invention. Furthermore, it is intended that the following appended claims and claims hereafter introduced are interpreted to include all such changes, modifications, permutations, alterations, additions, subtractions and sub-combinations as are within their true spirit and scope. Accordingly, the scope of the present invention is not to be limited to that precisely as shown and described by this specification.

Certain embodiments of the present invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the present invention to be practiced otherwise than specifically described herein. Accordingly, this invention includes all modifications and equivalents of the subject matter recited in the claims appended hereto as permitted by applicable law. Moreover, any combination of the above-described embodiments in all possible variations thereof is encompassed by the invention unless otherwise indicated herein or otherwise clearly contradicted by context.

The words, language, and terminology used in this specification is for the purpose of describing particular embodiments, elements, steps and/or limitations only and is not intended to limit the scope of the present invention, which is defined solely by the claims. In addition, such words, language, and terminology are to be understood not only in the sense of their commonly defined meanings, but to include by special definition in this specification structure, material or acts beyond the scope of the commonly defined meanings. Thus, if an element, step or limitation can be understood in the context of this specification as including more than one meaning, then its use in a claim must be understood as being generic to all possible meanings supported by the specification and by the word itself.

The definitions and meanings of the elements, steps or limitations recited in a claim set forth below are, therefore, defined in this specification to include not only the combination of elements, steps or limitations which are literally set forth, but all equivalent structure, material or acts for performing substantially the same function in substantially the same way to obtain substantially the same result. In this sense it is therefore contemplated that an equivalent substitution of two or more elements, steps and/or limitations may be made for any one of the elements, steps or limitations in a claim set forth below or that a single element, step or limitation may be substituted for two or more elements, steps and/or limitations in such a claim. Although elements, steps or limitations may be described above as acting in certain combinations and even initially claimed as such, it is to be expressly understood that one or more elements, steps and/or limitations from a claimed combination can in some cases be excised from the combination and that the claimed combination may be directed to a sub-combination or variation of a sub-combination. As such, notwithstanding the fact that the elements, steps and/or limitations of a claim are set forth below in a certain combination, it must be expressly understood that the invention includes other combinations of fewer, more or different elements, steps and/or limitations, which are disclosed in above combination even when not initially claimed in such combinations. Furthermore, insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements. Accordingly, the claims are thus to be understood to include what is specifically illustrated and described above, what is conceptually equivalent, what can be obviously substituted and also what essentially incorporates the essential idea of the invention.

Unless otherwise indicated, all numbers expressing a characteristic, item, quantity, parameter, property, term, and so forth used in the present specification and claims are to be understood as being modified in all instances by the term "about." As used herein, the term "about" means that the characteristic, item, quantity, parameter, property, or term so qualified encompasses a range of plus or minus ten percent above and below the value of the stated characteristic, item, quantity, parameter, property, or term. Accordingly, unless indicated to the contrary, the numerical parameters set forth in the specification and attached claims are approximations that may vary. For instance, as mass spectrometry instruments can vary slightly in determining the mass of a given analyte, the term "about" in the context of the mass of an ion or the mass/charge ratio of an ion refers to +/−0.50 atomic mass unit. At the very least, and not as an attempt to limit the application of the doctrine of equivalents to the scope of the claims, each numerical indication should at least be construed in light of the number of reported significant digits and by applying ordinary rounding techniques.

Notwithstanding that the numerical ranges and values setting forth the broad scope of the invention are approximations, the numerical ranges and values set forth in the specific examples are reported as precisely as possible. Any numerical range or value, however, inherently contains certain errors necessarily resulting from the standard deviation found in their respective testing measurements. Recitation of numerical ranges of values herein is merely intended to serve as a shorthand method of referring individually to each separate numerical value falling within the range. Unless otherwise indicated herein, each individual value of a numerical range is incorporated into the present specification as if it were individually recited herein.

Use of the terms "may" or "can" in reference to an embodiment or aspect of an embodiment also carries with it the alternative meaning of "may not" or "cannot." As such, if the present specification discloses that an embodiment or an aspect of an embodiment may be or can be included as part of the inventive subject matter, then the negative limitation or exclusionary proviso is also explicitly meant, meaning that an embodiment or an aspect of an embodiment may not be or cannot be included as part of the inventive subject matter. In a similar manner, use of the term "optionally" in reference to an embodiment or aspect of an embodiment means that such embodiment or aspect of the embodiment may be included as part of the inventive subject matter or may not be included as part of the inventive subject matter. Whether such a negative limitation or exclusionary proviso applies will be based on whether the negative limitation or exclusionary proviso is recited in the claimed subject matter.

The terms "a," "an," "the" and similar references used in the context of describing the present invention (especially in the context of the following claims) are to be construed to cover both the singular and the plural, unless otherwise indicated herein or clearly contradicted by context. Further, ordinal indicators—such as, e.g., "first," "second," "third," etc.—for identified elements are used to distinguish between the elements, and do not indicate or imply a required or limited number of such elements, and do not indicate a particular position or order of such elements unless otherwise specifically stated. All methods described herein can be performed in any suitable order unless otherwise indicated herein or otherwise clearly contradicted by context. The use of any and all examples or exemplary language (e.g., "such as") provided herein is intended merely to better illuminate the present invention and does not pose a limitation on the scope of the invention otherwise claimed. No language in the present specification should be construed as indicating any non-claimed element essential to the practice of the invention.

When used in the claims, whether as filed or added per amendment, the open-ended transitional term "comprising", variations thereof such as, e.g., "comprise" and "comprises", and equivalent open-ended transitional phrases thereof like "including", "containing" and "having", encompass all the expressly recited elements, limitations, steps, integers, and/or features alone or in combination with unrecited subject matter; the named elements, limitations, steps, integers, and/or features are essential, but other unnamed elements, limitations, steps, integers, and/or features may be added and still form a construct within the scope of the claim. Specific embodiments disclosed herein may be further limited in the claims using the closed-ended transitional phrases "consisting of" or "consisting essentially of" (or variations thereof such as, e.g., "consist of", "consists of", "consist essentially of", and "consists essentially of") in lieu of or as an amendment for "comprising." When used in the claims, whether as filed or added per amendment, the closed-ended transitional phrase "consisting of" excludes any element, limitation, step, integer, or feature not expressly recited in the claims. The closed-ended transitional phrase "consisting essentially of" limits the scope of a claim to the expressly recited elements, limitations, steps, integers, and/or features and any other elements, limitations, steps, integers, and/or features that do not materially affect the basic and novel characteristic(s) of the claimed subject matter. Thus, the meaning of the open-ended transitional phrase "comprising" is being defined as encompassing all the specifically recited elements, limitations, steps and/or features as well as any optional, additional unspecified ones. The meaning of the closed-ended transitional phrase "consisting of" is being defined as only including those elements, limitations, steps, integers, and/or features specifically recited in the claim, whereas the meaning of the closed-ended transitional phrase "consisting essentially of" is being defined as only including those elements, limitations, steps, integers, and/or features specifically recited in the claim and those elements, limitations, steps, integers, and/or features that do not materially affect the basic and novel characteristic(s) of the claimed subject matter. Therefore, the open-ended transitional phrase "comprising" (and equivalent open-ended transitional phrases thereof) includes within its meaning, as a limiting case, claimed subject matter specified by the closed-ended transitional phrases "consisting of" or "consisting essentially of." As such, the embodiments described herein or so claimed with the phrase "comprising" expressly and unambiguously provide description, enablement, and support for the phrases "consisting essentially of" and "consisting of."

Lastly, all patents, patent publications, and other references cited and identified in the present specification are individually and expressly incorporated herein by reference in their entirety for the purpose of describing and disclosing, for example, the compositions and methodologies described in such publications that might be used in connection with the present invention. These publications are provided solely for their disclosure prior to the filing date of the present application. The reference to any prior art in this specification is not, and should not be taken as, an acknowledgement or any form of suggestion that the prior art forms part of the common general knowledge from any country. In addition, nothing in this regard is or should be construed as an admission that the inventors are not entitled to antedate such disclosure by virtue of prior invention or for any other reason. All statements as to the date or representation as to the contents of these documents are based on the information available to the applicant and do not constitute any admission as to the correctness of the dates or contents of these documents.

The invention claimed is:

1. A pharmaceutical composition comprising:
   a) one or more pharmaceutically active agents selected from the group consisting of an abiraterone, an amlexanox, an aprepitant, an auranofin, a cannabidiol, a diclofenac, an eliglustat, an ezetimibe, a fenofibrate, an ibuprofen, an icatibant, a mebendazole, a mefenamic acid, a midostaurin, a naproxen, a niflumic acid, a nintedanib, an olaparib, a pirfenidone, a pitolisant, a telmisartan, tetrahydrocannabinol, and combinations thereof; and
   b) about 45% to about 95% by weight of the pharmaceutical composition of one or more glycerolipids, the one or more glycerolipids being one or more saturated $C_{10}$-$C_{22}$ triglycerides and a mixture of unsaturated $C_{14}$-$C_{22}$ monoglycerides, unsaturated $C_{14}$-$C_{22}$ diglycerides, and unsaturated $C_{14}$-$C_{22}$ triglycerides; and
   c) about 1.0% to about 8.0% by weight of the pharmaceutical composition of one or more free $C_{14\text{-}24}$ fatty acid surfactants, about 15% to about 40% by weight of the pharmaceutical composition of one or more free $C_{14\text{-}24}$ fatty acids, or both the one or more free $C_{14\text{-}24}$ fatty acid surfactants and the one or more free $C_{14\text{-}24}$ fatty acids; and
   wherein the pharmaceutical composition is an anhydrous formulation; and
   wherein the pharmaceutical composition is not an emulsion.

2. The pharmaceutical composition of claim 1, wherein the one or more pharmaceutically active agents are in an amount of about 0.1% to about 25% by weight of the pharmaceutical composition.

3. The pharmaceutical composition of claim 1, wherein the one or more pharmaceutically active agents are in an amount of about 25 mg/mL to about 600 mg/mL.

4. The pharmaceutical composition of claim 1, wherein the one or more glycerolipids are present in an amount of about 45% to about 75% by weight of the pharmaceutical composition.

5. The pharmaceutical composition of claim 1, wherein the one or more saturated $C_{10}$-$C_{22}$ triglycerides are present in an amount of about 10% to about 35% by weight of the pharmaceutical composition.

6. The pharmaceutical composition of claim 5, wherein the one or more saturated $C_{10}$-$C_{22}$ triglycerides are a mixture of saturated $C_{10}$-$C_{18}$ triglycerides.

7. The pharmaceutical composition of claim 5, wherein the one or more saturated $C_{10}$-$C_{22}$ triglycerides are present in an amount of about 15% to about 30% by weight of the pharmaceutical composition.

8. The pharmaceutical composition of claim 5, wherein the mixture of unsaturated $C_{14}$-$C_{22}$ monoglycerides, unsaturated $C_{14}$-$C_{22}$ diglycerides, and unsaturated $C_{14}$-$C_{22}$ triglycerides are present in an amount of about 20% to about 75% by weight of the pharmaceutical composition.

9. The pharmaceutical composition of claim 8, wherein the mixture of unsaturated $C_{14}$-$C_{22}$ monoglycerides, unsaturated $C_{14}$-$C_{22}$ diglycerides, and unsaturated $C_{14}$-$C_{22}$ triglycerides are a mixture of unsaturated $C_{16}$-$C_{20}$ monoglycerides, $C_{16}$-$C_{20}$ diglycerides, and $C_{16}$-$C_{20}$ triglycerides.

10. The pharmaceutical composition of claim 8, wherein the mixture of unsaturated $C_{14}$-$C_{22}$ monoglycerides, unsaturated $C_{14}$-$C_{22}$ diglycerides, and unsaturated $C_{14}$-$C_{22}$ triglycerides are present in an amount of about 20% to about 50% by weight of the pharmaceutical composition.

11. The pharmaceutical composition of claim 8, wherein the mixture of unsaturated $C_{14}$-$C_{22}$ monoglycerides, unsaturated $C_{14}$-$C_{22}$ diglycerides, and unsaturated $C_{14}$-$C_{22}$ triglycerides are present in an amount of about 50% to about 75% by weight of the pharmaceutical composition.

12. The pharmaceutical composition of claim 5, wherein the one or more saturated $C_{10}$-$C_{22}$ triglycerides and the mixture of unsaturated $C_{14}$-$C_{22}$ monoglycerides, unsaturated $C_{14}$-$C_{22}$ diglycerides, and unsaturated $C_{14}$-$C_{22}$ triglycerides are in a triglyceride to mixture weight ratio of about 1:1 to about 1:5.

13. The pharmaceutical composition of claim 1, wherein the one or more free $C_{14-24}$ fatty acid surfactants are present in an amount of about 2.0% to about 7.0% by weight of the pharmaceutical composition.

14. The pharmaceutical composition of claim 1, wherein the one or more free $C_{14-24}$ fatty acid surfactants are an oleate alkali metal or alkali earth metal salt, a stearate alkali metal or alkali earth metal salt, a linoleate alkali metal or alkali earth metal salt, or any combination thereof.

15. The pharmaceutical composition of claim 1, wherein the one or more free $C_{14-24}$ fatty acid surfactants are a sodium oleate, a sodium stearate, a sodium linoleate, or any combination thereof.

16. The pharmaceutical composition of claim 1, wherein the one or more free $C_{14-24}$ fatty acids are present in an amount of about 20% to about 35% by weight of the pharmaceutical composition.

17. The pharmaceutical composition of claim 14, wherein the one or more free $C_{14-24}$ fatty acids are an oleic acid, a stearic acid, a linoleic acid, or any combination thereof.

18. The pharmaceutical composition of claim 1, wherein the one or more saturated $C_{10}$-$C_{22}$ triglycerides are present in an amount of about 10% to about 25% by weight of the pharmaceutical composition, the mixture of unsaturated $C_{14}$-$C_{22}$ monoglycerides, unsaturated $C_{14}$-$C_{22}$ diglycerides, and unsaturated $C_{14}$-$C_{22}$ triglycerides are present in an amount of about 50% to about 75% by weight of the pharmaceutical composition, and the one or more free $C_{14-24}$ fatty acid surfactants are present in an amount of about 3.0% to about 7.0% by weight of the pharmaceutical composition.

19. The pharmaceutical composition of claim 1, wherein the one or more saturated $C_{10}$-$C_{22}$ triglycerides are present in an amount of about 15% to about 35% by weight of the pharmaceutical composition, the mixture of unsaturated $C_{14}$-$C_{22}$ monoglycerides, unsaturated $C_{14}$-$C_{22}$ diglycerides, and unsaturated $C_{14}$-$C_{22}$ triglycerides are present in an amount of about 20% to about 45% by weight of the pharmaceutical composition, and the one or more free $C_{14-24}$ fatty acids are present in an amount of about 20% to about 35% by weight of the pharmaceutical composition.

20. The pharmaceutical composition of claim 1, wherein the one or more glycerolipids are present in an amount of about 70% to about 95% by weight of the pharmaceutical composition.

21. The pharmaceutical composition of claim 1, wherein the one or more pharmaceutically active agents is an abiraterone, an amlexanox, an aprepitant, an auranofin, a diclofenac, an eliglustat, an ezetimibe, a fenofibrate, an ibuprofen, an icatibant, a mebendazole, a mefenamic acid, a midostaurin, a naproxen, a niflumic acid, a nintedanib, an olaparib, a pirfenidone, a pitolisant, a telmisartan, or a combination thereof.

* * * * *